US008058251B2

(12) United States Patent
Kaemmerer

(10) Patent No.: US 8,058,251 B2
(45) Date of Patent: Nov. 15, 2011

(54) DEVICES, SYSTEMS AND METHODS FOR IMPROVING MEMORY AND/OR COGNITIVE FUNCTION THROUGH BRAIN DELIVERY OF SIRNA

(76) Inventor: William F. Kaemmerer, Edina, MN (US)

( * ) Notice: Subject to any disclaimer, the term of this patent is extended or adjusted under 35 U.S.C. 154(b) by 0 days.

(21) Appl. No.: 11/930,939

(22) Filed: Oct. 31, 2007

(65) Prior Publication Data
US 2009/0060987 A1 Mar. 5, 2009

Related U.S. Application Data

(63) Continuation-in-part of application No. 11/253,393, filed on Oct. 19, 2005, now Pat. No. 7,618,948, which is a continuation-in-part of application No. 10/852,997, filed on May 25, 2004, now Pat. No. 7,829,694, which is a continuation-in-part of application No. 10/721,693, filed on Nov. 25, 2003, now Pat. No. 7,605,249, said application No. 11/253,393 is a continuation-in-part of application No. 11/157,608, filed on Jun. 21, 2005, and a continuation-in-part of application No. PCT/US2005/022156, filed on Jun. 21, 2005.

(60) Provisional application No. 60/444,614, filed on Feb. 3, 2003, provisional application No. 60/429,387, filed on Nov. 26, 2002, provisional application No. 60/581,730, filed on Jun. 21, 2004.

(51) Int. Cl.
*C12N 15/11* (2006.01)
*C07H 21/04* (2006.01)
*A61K 39/23* (2006.01)
*A61M 31/00* (2006.01)

(52) U.S. Cl. .................. 514/44 A; 514/44 R; 536/24.5; 424/93.2; 424/93.6; 424/233.1; 604/508

(58) Field of Classification Search ........................ None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,888,829 A | 12/1989 | Kleinerman et al. |
| 4,965,188 A | 10/1990 | Mullis et al. |
| 5,236,908 A | 8/1993 | Gruber et al. |
| 5,354,326 A | 10/1994 | Comben et al. |
| 5,534,350 A | 7/1996 | Liou |
| 5,624,803 A | 4/1997 | Noonberg et al. |
| 5,639,275 A | 6/1997 | Baetge et al. |
| 5,702,716 A | 12/1997 | Dunn et al. |
| 5,720,720 A | 2/1998 | Laske et al. |
| 5,735,814 A | 4/1998 | Elsberry et al. |
| 5,782,892 A | 7/1998 | Castle et al. |
| 5,800,390 A | 9/1998 | Hayakawa et al. |
| 5,814,014 A | 9/1998 | Elsberry et al. |
| 5,840,059 A | 11/1998 | March et al. |
| 5,882,561 A | 3/1999 | Barsoum et al. |
| 5,925,310 A | 7/1999 | Nakayama et al. |
| 5,942,455 A | 8/1999 | Barsoum et al. |
| 5,968,059 A | 10/1999 | Ellis et al. |
| 5,997,525 A | 12/1999 | March et al. |
| 6,042,579 A | 3/2000 | Elsberry et al. |
| 6,093,180 A | 7/2000 | Elsberry |
| 6,110,459 A | 8/2000 | Mickle et al. |
| 6,151,525 A | 11/2000 | Soykan et al. |
| 6,180,613 B1 | 1/2001 | Kaplitt et al. |
| 6,187,906 B1 | 2/2001 | Gluckman et al. |
| 6,231,969 B1 | 5/2001 | Knight et al. |
| 6,245,884 B1 | 6/2001 | Hook |
| 6,281,009 B1 | 8/2001 | Boyce |
| 6,291,243 B1 | 9/2001 | Fogarty et al. |
| 6,294,202 B1 | 9/2001 | Burns et al. |
| 6,300,539 B1 | 10/2001 | Morris |
| 6,309,634 B1 | 10/2001 | Bankiewicz et al. |
| 6,310,048 B1 | 10/2001 | Kumar |
| 6,313,268 B1 | 11/2001 | Hook |
| 6,319,905 B1 | 11/2001 | Mandel et al. |
| 6,343,233 B1 | 1/2002 | Werner et al. |
| 6,372,250 B1 * | 4/2002 | Pardridge ...................... 424/450 |
| 6,372,721 B1 | 4/2002 | Neuman et al. |

(Continued)

FOREIGN PATENT DOCUMENTS

| DE | 19938960 | 2/2001 |
| JP | 2004232811 | 8/2004 |
| WO | WO9220400 | 11/1992 |
| WO | WO93/23569 A1 | 11/1993 |
| WO | WO9323569 | 11/1993 |
| WO | WO94/02595 A1 | 2/1994 |
| WO | WO9402595 | 2/1994 |
| WO | WO96/18736 A2 | 6/1996 |
| WO | WO9618736 | 6/1996 |
| WO | WO97/40874 A1 | 11/1997 |

(Continued)

OTHER PUBLICATIONS

Cai et al. (2001) Nature Neuroscience 4:233-234.*

(Continued)

*Primary Examiner* — Richard Schnizer
(74) *Attorney, Agent, or Firm* — Mary P. Bauman; Gerard P. Norton; Fox Rothschild LLP

(57) ABSTRACT

The present invention relates to devices, systems, and methods for improving memory and/or cognitive function by brain delivery of compositions of small interfering RNA or vectors containing the DNA encoding for small interfering RNA. Such compositions can be administered using devices, systems and methods for direct delivery of the compositions to the brain, or using devices, methods of delivery, and compositions that deliver small interfering RNA or vectors containing the DNA encoding the small interfering RNA across the blood-brain barrier. The present invention also provides valuable small interfering RNA vectors, and methods for reduction of BACE1 levels in the hippocampus, cerebral cortex, or other regions of the brain that have beneficial effects on improving memory and/or cognitive function in a subject.

26 Claims, 7 Drawing Sheets

U.S. PATENT DOCUMENTS

| | | | |
|---|---|---|---|
| 6,376,471 B1 | 4/2002 | Lawrence, III et al. | |
| 6,436,392 B1 * | 8/2002 | Engelhardt et al. | 424/93.2 |
| 6,436,708 B1 * | 8/2002 | Leone et al. | 435/458 |
| 6,461,989 B1 | 10/2002 | El-Raghy et al. | |
| 6,468,524 B1 | 10/2002 | Chiorini et al. | |
| 6,551,290 B1 | 4/2003 | Elsberry et al. | |
| 6,594,880 B2 | 7/2003 | Elsberry | |
| 6,609,020 B2 | 8/2003 | Gill | |
| 6,632,671 B2 | 10/2003 | Unger | |
| 6,659,995 B1 | 12/2003 | Taheri | |
| 6,870,030 B2 | 3/2005 | Powell et al. | |
| 6,945,969 B1 | 9/2005 | Morris et al. | |
| 7,320,965 B2 | 1/2008 | Sah et al. | |
| 2001/0027309 A1 | 10/2001 | Elsberry | |
| 2001/0031947 A1 | 10/2001 | Heruth | |
| 2002/0004038 A1 | 1/2002 | Baugh et al. | |
| 2002/0068093 A1 | 6/2002 | Trogolo et al. | |
| 2002/0114780 A1 | 8/2002 | Bankiewicz | |
| 2002/0141980 A1 | 10/2002 | Bankiewicz | |
| 2002/0187127 A1 | 12/2002 | Bankiewicz | |
| 2003/0078229 A1 | 4/2003 | Cooper et al. | |
| 2003/0088236 A1 | 5/2003 | Johnson et al. | |
| 2003/0092003 A1 | 5/2003 | Blatt et al. | |
| 2003/0095958 A1 | 5/2003 | Bhisetti et al. | |
| 2003/0109476 A1 | 6/2003 | Kmiec et al. | |
| 2003/0120282 A1 | 6/2003 | Scouten et al. | |
| 2003/0143732 A1 | 7/2003 | Fosnaugh et al. | |
| 2003/0152947 A1 | 8/2003 | Crossman et al. | |
| 2003/0175772 A1 | 9/2003 | Wang | |
| 2003/0190635 A1 * | 10/2003 | McSwiggen | 435/6 |
| 2003/0224512 A1 | 12/2003 | Dobie | |
| 2004/0018520 A1 | 1/2004 | Thompson | |
| 2004/0023390 A1 | 2/2004 | Davidson | |
| 2004/0023855 A1 | 2/2004 | John et al. | |
| 2004/0186422 A1 | 9/2004 | Rioux | |
| 2004/0215164 A1 | 10/2004 | Abbott | |
| 2004/0220132 A1 | 11/2004 | Kaemmerer | |
| 2004/0258666 A1 | 12/2004 | Passini | |
| 2004/0259247 A1 | 12/2004 | Tuschl | |
| 2004/0265849 A1 | 12/2004 | Cargill | |
| 2004/0266707 A1 | 12/2004 | Leake | |
| 2005/0032733 A1 | 2/2005 | McSwiggen | |
| 2005/0042646 A1 | 2/2005 | Davidson | |
| 2005/0048641 A1 | 3/2005 | Hildebrand | |
| 2005/0096284 A1 | 5/2005 | McSwiggen | |
| 2005/0137134 A1 | 6/2005 | Gill | |
| 2005/0153353 A1 | 7/2005 | Meibohm | |
| 2005/0180955 A1 | 8/2005 | Bankiewicz | |
| 2005/0202075 A1 | 9/2005 | Pardridge | |
| 2005/0209179 A1 | 9/2005 | McSwiggen | |
| 2005/0255086 A1 | 11/2005 | Davidson | |
| 2005/0255487 A1 * | 11/2005 | Khvorova et al. | 435/6 |
| 2005/0282198 A1 | 12/2005 | Duff | |
| 2006/0009408 A1 | 1/2006 | Davidson et al. | |
| 2006/0014165 A1 | 1/2006 | Hakonarson | |
| 2006/0041242 A1 | 2/2006 | Stypulkowski | |
| 2006/0150747 A1 | 7/2006 | Mallett | |
| 2006/0210538 A1 | 9/2006 | Kaplitt et al. | |
| 2006/0224411 A1 | 10/2006 | Chang | |
| 2006/0257912 A1 | 11/2006 | Kaemmerer | |
| 2007/0031844 A1 | 2/2007 | Khvorova et al. | |
| 2007/0184029 A1 | 8/2007 | Mishra | |
| 2008/0113351 A1 | 5/2008 | Naito | |
| 2009/0022864 A1 | 1/2009 | Steenhof | |

FOREIGN PATENT DOCUMENTS

| | | |
|---|---|---|
| WO | WO9740847 | 11/1997 |
| WO | WO9846273 | 10/1998 |
| WO | WO9846740 | 10/1998 |
| WO | WO 9856361 A1 * | 12/1998 |
| WO | WO9939744 | 8/1999 |
| WO | WO99/50300 A1 | 10/1999 |
| WO | WO9950300 | 10/1999 |
| WO | WO00/30567 A2 | 6/2000 |
| WO | WO0030567 | 6/2000 |
| WO | WO00/64505 A1 | 11/2000 |
| WO | WO0004505 | 11/2000 |
| WO | WO01/16312 A2 | 3/2001 |
| WO | WO0116312 | 3/2001 |
| WO | WO01/49844 A1 | 7/2001 |
| WO | WO0149844 | 7/2001 |
| WO | WO01/60794 A2 | 8/2001 |
| WO | WO0160794 | 8/2001 |
| WO | WO0170276 | 9/2001 |
| WO | WO0180840 | 11/2001 |
| WO | WO01/91801 | 12/2001 |
| WO | WO0191801 | 12/2001 |
| WO | WO02/07810 A2 | 1/2002 |
| WO | WO0205804 | 1/2002 |
| WO | WO0207810 | 1/2002 |
| WO | WO0222177 | 3/2002 |
| WO | WO03042385 | 5/2003 |
| WO | WO03/047676 A1 | 6/2003 |
| WO | WO03047676 | 6/2003 |
| WO | WO03/053516 A1 | 7/2003 |
| WO | WO03053516 | 7/2003 |
| WO | WO 03/070895 A2 | 8/2003 |
| WO | WO03070895 | 8/2003 |
| WO | WO 03/099298 A1 | 12/2003 |
| WO | WO03099298 | 12/2003 |
| WO | WO03102131 | 12/2003 |
| WO | W2004007718 | 1/2004 |
| WO | WO 2004/010787 A1 | 2/2004 |
| WO | WO 2004/013280 A2 | 2/2004 |
| WO | WO2004010787 | 2/2004 |
| WO | WO2004013280 | 2/2004 |
| WO | WO2004013355 | 2/2004 |
| WO | WO 2004/041101 A2 | 5/2004 |
| WO | WO2004041101 | 5/2004 |
| WO | WO 2004/047872 A2 | 6/2004 |
| WO | WO2004047872 | 6/2004 |
| WO | WO 2004/058940 A2 | 7/2004 |
| WO | WO2004058940 | 7/2004 |
| WO | WO 2004/084955 A1 | 10/2004 |
| WO | WO2004084955 | 10/2004 |
| WO | WO 2004/101063 A1 | 11/2004 |
| WO | WO2004098648 | 11/2004 |
| WO | WO2004101063 | 11/2004 |
| WO | WO2005027980 | 3/2005 |
| WO | WO 2005/045034 A2 | 5/2005 |
| WO | WO2005045034 | 5/2005 |
| WO | WO2005116204 | 8/2005 |
| WO | WO2005120581 | 12/2005 |
| WO | WO200622639 | 3/2006 |
| WO | WO2007039721 | 4/2007 |
| WO | WO2008005562 | 7/2007 |
| WO | WO2007087451 | 8/2007 |
| WO | WO2007139811 | 12/2007 |
| WO | WO2008004260 | 1/2008 |
| WO | WO2008021157 | 2/2008 |
| WO | WO2008046273 | 4/2008 |
| WO | WO2008143774 | 11/2008 |

OTHER PUBLICATIONS

Ashe et al. (2001) "Learning and Memory in Transgenic Mice Modeling Alzheimer's Disease" Learning & Memory 8:301-308.*
Aebisher, Trends in Neurosci. 24(9) 553-540 (Sep. 2001).
Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 µg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.
Basi et al., "Antagonistic Effects of β-site Amyloid Precursor Protein-cleaving Enzymes 1 and 2 on β-Amyloid Peptide Production in Cells," J. Bio. Chem., Published, JBC Papers in Press, Jun. 2003; 278(34): 31512-31520.
Bass et al., Nature 411: 428-429 (2001).

Bertrand et al., Biochem Biophys Res Comm 296: 1000-1004 (2002).
Bodendorf et al., J. Neurochem. 80(5), 799-806 (Mar. 2002).
Boillee et al., "Gene therapy for ALS deliver," Trends in Neurosciences, May 2004; 27(5): 235-238.
Bortolin, Susan et al., "Analytical validation of the tag-it high-throughput microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; I2(12): 1587-1598.
ElBashir, EMBO J 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behay. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc © vectors), For the intracellular targeting of recombinant proteins and antibodies, Catalog Nos. V820-20, V821-20, V822-20, V823-20, Version E, copyright 1998-2001, 35 pgs.
Invitrogen, pTRACER™ -CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).

Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 12, 2005], Revised Dec. 2005. Retrieved from the Internet: <URL:http://www.ncbi.nlm.nih.gov>; 2 pgs.
National Center for Biotechnology Information, National Library of Medicine, National Institutes of Health, GenBank Locus AF163864, Accession No. AF163864, "Homo sapiens SNCA isoform (SNCA) gene, complete cds, alternatively spliced," [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.
National Center for Biotechnology Information, National Library of Medicine, National Institutes of Health, GenBank Locus AF163865, Accession No. AF163865, "Mus musculus alpha-synuclein (SNCA) gene, complete cds," [online]. Bethesda, MD [retrieved on Jun. 21, 2004]. Retrieved from the Internet: <URL:http://www.ncbi.nlm.nih.gov/entrez/viewer.fcgi?db=nucleotide&val=11118354>; 33 pgs.
National Center for Biotechnology Information, National Library of Medicine, National Institutes of Health, GenBank Locus AH003045, Accession No. AH003045, "Homo sapiens huntingtin (HD) gene, exon 1," [online]. Bethesda, MD [retrieved on Mar. 5, 2009]. Retrieved from the Internet:<URL:http://www.ncbi.nlm.nih.gov/entrez/viewer.fcgi?db=nucleotide&val=663286>; 42 pgs.
National Center for Biotechnology Information, National Library of Medicine, National Institutes of Health, GenBank Locus NM_000027, Accession No. NM_000027, "Homo sapiens aspartylglucosaminidase (AGA), mRNA," [online]. Bethesda, MD

[retrieved on Mar. 5, 2009]. Retrieved from the Internet:<URL:http://www.ncbi.nlm.nih.gov/entrez/viewer.fcgi?db=nucleotide&val=32313568>; 4 pgs.

National Center for Biotechnology Information, National Library of Medicine, National Institutes of Health, GenBank Locus NM_000046, Accession No. NM_000046, "*Homo sapiens* arylsulfatase B (ARSB), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=38569404>; 4 pgs.

National Center for Biotechnology Information, National Library of Medicine, National Institutes of Health, GenBank Locus NM_000049, Accession No. NM_000049, "*Homo sapiens* aspartoacylase (aminoacylase 1, Canavan disease) (ASPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557334>; 4 pgs.

National Center for Biotechnology Information, National Library of Medicine, National Institutes of Health, GenBank Locus NM_000147, Accession No. NM_000147, "*Homo sapiens* fucosidase, alpha-L1, tissue (FUCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24475878>; 3 pgs.

National Center for Biotechnology Information, National Library of Medicine, National Institutes of Health, GenBank Locus NM_000152, Accession No. NM_000152, "*Homo sapiens* glucosidase, alpha; acid (Pompe disease, glycogen storage disease type II) (GAA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=11496988>; 4 pgs.

National Center for Biotechnology Information, National Library of Medicine, National Institutes of Health, GenBank Locus NM_000153, Accession No. NM_000153, "*Homo sapiens* galactosylceramidase (Krabbe disease) (GALC), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557612>; 5 pgs.

National Center for Biotechnology Information, National Library of Medicine, National Institutes of Health, GenBank Locus NM_000157, Accession No. NM_000157, "*Homo sapiens* glucosidase, beta; acid (includes glucosylceramidase) (GBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4503934>; 7 pgs.

National Center for Biotechnology Information, National Library of Medicine, National Institutes of Health, GenBank Locus NM_000158, Accession No. NM_000158, "*Homo sapiens* glucan (1, 4-alpha-), branching enzyme 1 (glucogen branching enzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi? db=nucleotide&val=4557618>; 2 pgs.

National Center for Biotechnology Information, National Library of Medicine, National Institutes of Health, GenBank Locus NM_000181, Accession No. NM_000181, "*Homo sapiens* glucuronidase, beta (GUSB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504222>; 4 pgs.

National Center for Biotechnology Information, National Library of Medicine, National Institutes of Health, GenBank Locus NM_000199, Accession No. NM_000199, "*Homo sapiens* N-sulfoglucosamine sulfohydrolase (sulfamidase) (SGSH), mRNA," [online]. Bethesda, MD [retrieved on Mar. 5, 2009]. Retrieved from the Internet:<Url:http://www.ncbi.nlm.nih.gov/entrez/viewer.fcgi?db=nucleotide&val=31543619>; 3 pgs.

National Center for Biotechnology Information, National Library of Medicine, National Institutes of Health, GenBank Locus NM_000202, Accession No. NM_000202, "*Homo sapiens* iduronate 2-sulfatase (Hunter syndrome)(ID), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=5360215>; 8 pgs.

National Center for Biotechnology Information, National Library of Medicine, National Institutes of Health, GenBank Locus NM_000203, Accession No. NM_000203, "*Homo sapiens* iduronidase, alpha-L-(IDUA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40354208>; 6 pgs.

National Center for Biotechnology Information, National Library of Medicine, National Institutes of Health, GenBank Locus NM_000235, Accession No. NM_000235, "*Homo sapiens* lipase A, lysosomal acid, cholesterol esterase (Wolman disease) (LIPA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557720>; 4 pgs.

National Center for Biotechnology Information, National Library of Medicine, National Institutes of Health, GenBank Locus NM_000262, Accession No. NM_000262, "*Homo sapiens* N-acetylgalactosaminidase, alpha- (NAGA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557780>; 4 pgs.

National Center for Biotechnology Information, National Library of Medicine, National Institutes of Health, GenBank Locus NM_000263, Accession No. NM_000263, "*Homo sapiens* N-acetylglucosaminidase, alpha-(Sanfilippo disease) (IIIB)(NAGLU), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40548380>; 4 pgs.

National Center for Biotechnology Information, National Library of Medicine, National Institutes of Health, GenBank Locus NM_000310, Accession No. NM_000310, "*Homo sapiens* palmitoyl-protein thioesterase 1 (ceroid-lipofuscinosis, neuronal 1, infantile) (PPT1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4506030>; 4 pgs.

National Center for Biotechnology Information, National Library of Medicine, National Institutes of Health, GenBank Locus NM_000332, Accession No. NM_000332, "*Homo sapiens* spinocerebellar ataxia 1 (olivopontocerebellar ataxia 1, autosomal dominant, ataxin 1) (SCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4506792>: 7 pgs.

National Center for Biotechnology Information, National Library of Medicine, National Institutes of Health, GenBank Locus NM_000345, Accession No. NM_000345, "*Homo sapiens* synuclein, alpha (nonA4 component of amyloid precursor) (SNCA), transcript variant NACP140, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806896>; 6 pgs.

National Center for Biotechnology Information, National Library of Medicine, National Institutes of Health, GenBank Locus NM_000404, Accession No. NM_000404, "*Homo sapiens* glactosidase, beta 1 (GLB1), transcript variant 179423, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834965>; 5 pgs.

National Center for Biotechnology Information, National Library of Medicine, National Institutes of Health, GenBank Locus NM_000434, Accession No. NM_000434, "*Homo sapiens* sialidase 1 (lysosomal sialidase)(NEU1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40806202>; 5 pgs.

National Center for Biotechnology Information, National Library of Medicine, National Institutes of Health, GenBank Locus NM_000487, Accession No. NM_000487, "*Homo sapiens* arysulfatase A (ARSA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7262293>: 4 pgs.

National Center for Biotechnology Information, National Library of Medicine, National Institutes of Health, GenBank Locus NM_000512, Accession No. NM_000512, "*Homo sapiens* galactosamine (N-acetyl)-6-sulfate sulfatase (Morquio syndrome, mucopolysaccharidosis type IVA), (GALNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=9945384>; 4 pgs.

National Center for Biotechnology Information, National Library of Medicine, National Institutes of Health, GenBank Locus NM_000520, Accession No. NM_000520, "*Homo sapiens* hexosaminidase A (alpha polypeptide) (HEXA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13128865>; 5 pgs.

National Center for Biotechnology Information, National Library of Medicine, National Institutes of Health, GenBank Locus NM_000521, Accession No. NM_000521, "*Homo sapiens* hexosaminidase B (beta polypeptide) (HEXB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13128866>; 6 pgs.

National Center for Biotechnology Information, National Library of Medicine, National Institutes of Health, GenBank Locus NM_000528, Accession No. NM_000528, "*Homo sapiens* mannosidase, alpha, class 2B, member 1 (MAN2B1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "*Homo sapiens* sphingomyelin phosphodiesterase 1 acid lysosomal (acid sphingomyelinase) (SMPD1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40254417>; 5 pgs.

National Center for Biotechnology Information, National Library of Medicine, National Institutes of Health, GenBank Locus NM_002076, Accession No. NM_002076, "*Homo sapiens* glucosamine (N-acetyl)-6-sulfatase (Sanfilippo disease)(IIID)(GNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, Accession No. NM_000169, "*Homo sapiens* glactosidase, alpha (GLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504008>; 4 pgs.

National Center for Biotechnology Information, National Library of Medicine, National Institutes of Health, GenBank Locus NM_002778, Accession No. NM_002778, "*Homo sapiens*prosaposin (variant Gaucher disease and variant metachromatic leukodystrophy) (PSAP), mRNA," [online]. Bethesda, MD [retrieved on Mar. 5, 2009]. Retrieved from the Internet:<URL:http//www.ncbi.nlm.nih.gov/entrez/viewer.fcgi?db=nucleotide&val=11386146>; 8 pgs.

National Center for Biotechnology Information, National Library of Medicine, National Institutes of Health, GenBank Locus NM_004315, Accession No. NM_004315, "*Homo sapiens* N-acylsphingosine amidohydrolase (acid ceramidase) 1 (ASAHI), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=30089929>; 5 pgs.

National Center for Biotechnology Information, National Library of Medicine, National Institutes of Health, GenBank Locus NM_004993, Accession No. NM_004993, "*Homo sapiens* Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM_005908, Accession No. NM_005908, "*Homo sapiens* mannosidase, beta A, lyosomal (MANBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus NM_007308, Accession No. NM_007308, "*Homo sapiens* synuclein, alpha (nonA4 component of amyloid precursor) (SNCA), transcript variant NACP112, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "Definition," [online]. Bethesda, MD [retrieved on Mar. 5, 2009]. Retrieved from the Internet:<URL:http://www.ncbi.nlm.nih.gov/entrez/viewer.fcgi?db=nucleotide&val=33636695>; 5 pgs.

National Center for Biotechnology Information, National Library of Medicine, National Institutes of Health, GenBank Locus NM_011792, Accession No. NM_011792, Version NM_011792.2, "Mus musculus beta-site APP cleaving enzyme 1 (BACE 1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "Mus musculus beta-site APP cleaving enzyme (BACE), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "*Homo sapiens* beta-site APP-cleaving enzyme 1 (BACE1), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "*Homo sapiens* beta-site APP-cleaving enzyme (BACE), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040369>; 10 pgs.

National Center for Biotechnology Information, National Library of Medicine, National Institutes of Health, GenBank Locus NM_013995, Accession No. NM_013995, "*Homo sapiens* lysosomal-associated membrane protein 2 (LAMP2), transcript variant LAMP2B, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7669502>; 6 pgs.

National Center for Biotechnology Information, National Library of Medicine, National Institutes of Health, GenBank Locus NM_030660, Accession No. NM_030660, "*Homo sapiens* Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "*Homo sapiens* N-acetylglucosamine-1-phosphotransferase, gamma subunit (GNPTAG), mRNA," [online]. Bethesda, MD [retrieved on Mar. 5, 2009]. Retrieved from the Internet:<URL:http//www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "*Homo sapiens* beta-site APP-cleaving enzyme 1 (BACE1), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255012>; 8 pgs.

National Center for Biotechnology Information, National Library of Medicine, National Institutes of Health, GenBank Locus NM_138971, Accession No. NM_138971, Version NM_138971.1, "*Homo sapiens* beta-site APP-cleaving enzyme (BACE), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040363>; 10 pgs.

National Center for Biotechnology Information, National Library of Medicine, National Institutes of Health, GenBank Locus NM_138972, Accession No. NM_138972, "*Homo sapiens* beta-site APP-cleaving enzyme 1 (BACE1), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255013>; 8 pgs.

National Center for Biotechnology Information, National Library of Medicine, National Institutes of Health, GenBank Locus NM_138972, Accession No. NM_138972, Version NM_138972.1, "*Homo sapiens* beta-site APP-cleaving enzyme (BACE), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040365>; 10 pgs.

National Center for Biotechnology Information, National Library of Medicine, National Institutes of Health, GenBank Locus NM_138973, Accession No. NM_138973, "*Homo sapiens* beta-site APP-cleaving enzyme 1 (BACE1), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255014>; 8 pgs.

National Center for Biotechnology Information, National Library of Medicine, National Institutes of Health, GenBank Locus NM_138973, Accession No. NM_138973, Version NM_138973.1, "*Homo sapiens* beta-site APP-cleaving enzyme (BACE), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040367>; 10 pgs.

National Center for Biotechnology Information, National Library of Medicine, National Institutes of Health, GenBank Locus U24233, Accession No. 024233, "Mus musculus huntingtin (Hd) mRNA, complete cds," [online]. Bethesda, MD [retrieved on Mar. 5, 2009]. Retrieved from the Internet:<URL:http://www.ncbi.nlm.nih.gov/entrez/viewer.fcgi?db=nucleotide&val=902003>; 5 pgs.

National Center for Biotechnology Information, National Library of Medicine, National Institutes of Health, GenBank Locus XM_032588, Accession No. XM_032588, "*Homo sapiens* dentatorubral-pallidoluysian atrophy (artrophin-1) (DRPLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20555988>; 3 pgs.

National Center for Biotechnology Information, National Library of Medicine, National Institutes of Health, GenBank Locus XM_132846, Accession No. XM_132846, "*Mus musculus* dentatorubral pallidoluysian atrophy (DRPLA) mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20832263>; 3 pgs.

Noonberg et al., Nucl. Acid Res. 22(14) 2830-2836 (1994).
Noordmans et al., Soc. Neurosci. Abstr. 27, Program 572.14 (2001).
Ohkawa Nucl. Acid. Symp. Ser. 27, 15-16 (1992).

Ohno et al., "BACEI Deficiency Rescues Memory Deficits and Cholinergic Dysfunction in a Mouse Model of Alzheimer's Disease," Neuron, Jan. 2004; 41: 27-33.
Ojwang et al., Proc. Nat. Acad. Sci. 89 10802-10806.
Paxinos et al The Mouse Brain in Stereotactic Coordinates, Acad. Press 2nd Ed. (2001).
Potter, N. T. et al., "Technical standards and guidelines for huntington disease testing," Genetics in Medicine 6:61-65 (2004).
Promega Corporation, T4 DNA Ligase Blue/White Cloning Qualified, Part# 9PIM180, Revised Apr. 2005, 2 pgs.
Promega Corporation, T4 DNA Polymerase(a) , Part# 9PIM421, Revised May 2004, 2 pgs.
Qiagen, Qiaex II Handbook, Feb. 1999, 24 pgs.
Qiagen, Rneasy Mini Handbook, 3rd Edition, Jun. 2001, 116 pgs.
R&D Systems, β-Secretase Activity Kit, Catalog No. FP002, Aug. 2002, 2 pgs.
Roberds et al., "BACE knockout mice are healthy despite lacking the primary β-secretase activity in brain: implications for Alzheimer's disease therapeutics," Human Molecular Genetics, Jun. 2001; 10(12): 1317-1324.
Ryu, Biomaterials 26: 319-326 (2005).
Salehi et al., J. Neural Transm. 106 955-986 (1999).
Sapru et al., Annual Meeting Soc. Neurosci. Abstract 297.9, XP001204566 (2003).
Sarver et al., Science 247, 1222-1225 (1990).
Scanlon et al., Proc. Nat. Acad. Sci. 88, 10591-10595 (1995).
Schenk, "Amyloid-β immunotherapy for Alzheimer's disease: the end of the beginning," Nature Reviews—Neuroscience, Oct. 2002; 3: 824-828.
Scherr et al., Cell Cycle 2(3) 251-257 (2003).
Serra et at., Medical Image Analysis 1(4) 317-329 (1996).
Singer et al., Nat. Neurosci. 8(10) 1343-1349 (ePub Aug. 28, 2005).
Stackman et al., Experimental Neurology 184, 510-520 (2003).
Strategene, AAV Helper-Free System, Instruction Manual, Catalog #240071, #240074, #240075, Revision #084007i, Aug. 2004, 50 pgs.
Strategene, pBluescript® II Phagemid Vectors, Instruction Manual, Catalog #212205, #212206, #212207, #212208, Revision #083001m, Aug. 2003, 35 pgs.
Sullenger, Science 262, p. 1566 (Dec. 3, 1993).
Taira et al., Nucl. Acid. Res. 19(19) 5125-5130 (1991).
Thompson et al., Nucl. Acid. Res. 23(12), 2259 (1995).
Timson et al., Biochem J 363:515-520 (2002).
TuscjI Lab, "The siRNA user guide," Revised May 2004, [online]. Retrieved on Nov. 29, 2005. Retrieved from the Internet:<URL:rockefeller.edu/labheads/tuschl/sirna.html>; 6 pgs.
Valbonesi et al., Ttransf. And Apheresis Sci. 30: 153-156 (2004).
Van Bilsen et al., "Identification and allele-specific silencing of the mutant huntingtin allele in Huntington's disease patient-derived fibroblasts," Human Gene Therapy, vol. 19, pp. 710-718 (2008).
Vassar et al., Science 286 735-741 (1999).
Ventura et al., Nucl. Acid. Res. 21(14) 3249-3255 (1993).
Vickers, Journal of Bio. Chemistry, vol. 278, No. 9 7108-7118 (2003).
Watanabe et al., J. Mol. Cel. Card. 37 (3) 691-698 (2004).
Weerasinghe et al., J. Virol. 65(10), 5531-3334 (1991).
Whitesell et al., Proc. Nat. Acad. Sci. 90: 4665-4669 (1993).
Xia et al., Nat. Biotech. 20, 1006-1010 (2002).
Xia et al., Nat. Med. 10(8) 816-820 (2004).
Yamamoto et al., Cell 101, 57-66 (2000).
Yu et al., Proc. Nat. Acad. Sci. 90 6340-6344 (1993).
Yu et al., Proc. Nat. Acad. Sci. 99 6047-6052 (2002).
Zhang et al., "Global Non-Viral Gene Transfer to the Primate Brain Following Intravenous Administration," Molecular Therapy, Jan. 2003; 7(1): 11-18.
Zhang et al., "In vivo knockdown of gene expression in brain cancer with intravenous RNAi in adult rats," J. Gene Med., 2003; 5:1039-1045; published online Aug. 4, 2003.
Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.
Zhang et al., 1996 J. Mol. Neurosci. 7: 13-28 (1996).
Zhao et al., J. Biol. Chem. 271(49), 31407-31411 (Dec. 1996).

Zlokovic et al., Neurosurgery 40 805-813 (1997).

Aebischer, et al., "Recombinanat proteins for neurodegenerative disease: the delivery issue,"; Trends in Neurosciences (2001): vol. 24, No. 9; pp. 533-540.

Bass, Brenda L. "The Short Answer," Nature (May 2001), vol. 411 pp. 428-429.

Cahill et al., Atlas of Human Cross-Sectional Anatomy, Wiley-Liss, 3rd Ed. (1995).

Callahan, et al., "Augmented senile plaque load in aged female β-amyloid precursor protein-transgenic mice," American Journal of Pathology (Mar. 2001); vol. 158, No. 3 pp. 1173-1177.

Caplen, et al., "Rescue of polyglutamine-mediated cytotoxicity by double-stranded RNA-mediated RNA interference," Human Molecular Genetics (2002), vol. 11, No. 2, pp. 175-184.

Chen, et al., "Multitarget-ribozyme directed to cleave at up to nine highly conserved HIV-1 env RNA regions inhibits HIV-1 replication-potential effectiveness against most presently sequenced HIV-1 isolates," Nucleic Acids Research, vol. 20, No. 17 pp. 4581-4589.

Chowrira, et al., "In vitro and in vivo comparison of hammerhead, hairpin, and hepatitis delta virus self-processign ribozyme cassettes," The Journal of Biological Chemistry (1994), vol. 269, No. 41 pp. 25856-25864.

Clark et al., "Purkinje cell expression of a mutant allele of SCA1 in transgenic mice leads to disparate effects on motor behaviors, followed by a progressive cerebellar dysfunction and hitological alterations," The Journal of Neuroscience, (Oct. 1, 1997), vol. 17, No. 19 pp. 7385-7395.

Coutoure et al., "Anti-gene therapy: the use of ribozymes to inhibit gene function," TIG (Dec. 1996): vol. 12, No. 12 pp. 510-515.

Davidson, et al., "Molecular medicine for the brain: silencing of disease genes with RNA interference," The Lancet (2004) pp. 145-149.

Dineley et al., "Accelerated plaque accumulation, associative learning deficits, and up-regulation of α7 nicotinic receptor protein in transgenic mice co-expressing mutant human presenilin 1 and amyloid precursor proteins," The Journal of Biological Chemistry (Jun. 21, 2002), vol. 277, No. 25 pp. 22768-22780.

Dorri et al., "Douwn-regulation of mglur5 by antisense deoxynucleotides alters pharmacological responses to applications of ACPD in the rat hippocampus," Experimental Neurology vol. 147, Article No. EN976567, pp. 48-54.

Dropulic, et al., "Functional characterization of a U5 ribozyme: intracellular suppression of human immunodeficiency virus type 1 expression," Journal of Virology (Mar. 1992) vol. 66, No. 3 pp. 1432-1441.

Ezrin-Waters, et al., "The nucleus basalis of meynert," The Canadian Journal of Neurological Sciences (Feb. 1986), vol. 13, No. 1 pp. 8-14.

Gau et al., "Stable β-secretase activity and presynaptic cholinergic markers durign progressive central nervous system amyloidogenesis in Tg2576 mice," American Journal of Pathology (Feb. 2002), vol. 160, No. 2 pp. 731-738.

Glorioso et al., "Use of hsv vectors to moidfy the nervous system," Current Opinion in Drug Discovery & Development (2002), PharmaPress Ltd. ISSN 1367-6733.

Good et al., "Expression of small, therapeutic RNAs in human cell nuclei," Gene Therapy (1997) vol. 4, pp. 45-54.

Goto et al., "Suppression of huntingtin gene expression by sirna: a possible therapeutic tool for huntington's disease," Neurology (Mar. 2003).

Heale et al., " siRNA target site secondary structure predictions using local stable substructures," Nucleic Acids Research (2005), vol. 33 No. 3 pp. 1-10.

Hommel et al., "Local gene knockdown in the brain using viral—mediated RNA interference," Society For Neuroscience Abstract (2003), Abstract 325.14.

Hooper et al., "Infusion into the brain of an antisense oligonucleotide to the immediate-early gnee c-fos suppresses production of fos and produces a behavioral effect," Neuroscience (1994) vol. 63, No. 4 pp. 917-924.

Hsiao et al., "Correlative memory deficits, Aβ elevation, and amyloid plaques in transgenic mice," Science (Oct. 4, 1996) vol. 274 pp. 99-102.

Isacson et al., "Lack of efficacy of 'naked' small interfering RNA applied directly to rat brain," Acta Phsyiol. Scand. (2003) vol. 179, pp. 173-177.

Izant et al., "Constitutive and conditional suppression of exogenous and endogenous genes by anti-sense rna," Science (1985) 299-345.

Kashani-Sabet et al., "Reversal of the malignant phenotype by an anti-ras ribozyme," Antisense Research and Development 2:3-15 (1992).

Kawarabayashi et al., "Age-dependent changes in brain, csf, and plasma amyloid β protein in the Tg2576 transgenic mouse model of alzheimer's disease," The Journal of Neuroscience (Jan. 15, 2001), 21(2): 372-381.

King et al., "Behavioral characterization of the Tg2576 transgenic model of alzheimer's disease through 19 months," Physiology & Behavior 75 (2002) 627-642.

Kitabwalla et al., "RNA interference—a new weapon against HIV and beyond," The New England Journal of Medicine (Oct. 24, 2002) vol. 347, No. 17.

Klement et al., "Ataxin-1 nuclear localization and aggregation: role in polyglutamine-induced disease in SCA1 Transgenic Mice," Cell (Oct. 2, 1998) vol. 95 p. 41-53.

L'Huillier et al., "Cytoplasmic delivery of ribozymes leads to efficient reduction in α-lactalbumin mRNA levels in C271 mouse cells,") The EMBO Journal (1992), vol. 11, No. 12 pp. 4411-4418.

Lisziewicz et al., "Inhibition of human immunodeficiency virus type 1 replication by regulated expression of a polymeric tat activation response RNA decoy as a strategy for gene therapy in AIDS," Proc. Natl. Acad. Sci (Sep. 1993) Vo. 90, pp. 8000-8004.

Liu et al., "Specific inhibition of huntington's disease gene expression by siRNAs in cultured cells," Proc. Japan Acad. 79, Ser. B (2003).

Matilla et al., "Mice lacking ataxin-1 display learning deficits and decreased hippocampal paired-pulse facilitation," The Journal of Neuroscience (Jul. 15, 1998) vol. 18, No. 14, pp. 5508-5516.

McGarry et al., "Inhibition of heat shock protein synthesis by heat-inducible antisense RNA," Proc. Natl., Acad. Sci. (Jan. 1986) Vo. 83 pp. 399-403.

McManus et al., "Gene silencing in mammals by interfering RNAs," Nature Reviews (Oct. 2002) Vol. 3, pp. 737-747.

Miller et al., "Allele-specific silencing of dominant disease genes," PNAS (Jun. 10, 2003) vol. 100, No. 12 pp. 7195-7200.

Morel et al., "Multiarchitectonic and stereotactic atlas of human thalamus," The Journal of Comparative Neurology 387:588-630 (1997).

Naldini et al., "Efficient transfer, integration, and sustained long-term expression of the transgene in adult rat brains injected with a lentiviral vector,"Proc. Natl. Acad. Sci. (Oct. 1996) vol. 93, pp. 11382-11388.

Noonberg et al., "In vivo generation of highly abundant sequence-specific oligonucleotides for antisense and triplex gene regulation," Nucleic Acids Research (1994) vol. 22, No. 14 pp. 2830-2836.

Ohkawa et al., "Activities of HIV-RNA targeted ribozymes transcribed from a 'shot-gun' type ribozyme-trimming plasmid," Proc. Natl. Acad. Sci 89 (1992).

Ojwang et al., "Inhibition of human immunodeficiency virus type 1 expression by a hairpin ribozyme," Proc. Natl. Acad. Sci. (Nov. 1992) vol. 89 pp. 10802-10806.

Paxinos et al., "The Mouse Brain in Sterotaxic Coordinates," Acad. Press 2nd Edition (2001).

Salehi et al., "Diminished neuronal metabolic activity in alzheimer's disease," J. Neural Transm (1999) 106: 955-986.

Sapru et al., "Small interfering RNA (sirna)-mediated silencing OFα-synuclein gene expression," Annual Meetign Soc. Neurosci. Abstract 297.9 (2003).

Sarver et al., "Ribozymes as potential anti-HIV-1 therapeutic agents," Science (Mar. 1990) vol. 247 pp. 1222-1225.

Scanlon et al., "Ribozyme-mediated cleavage of c-fos mRNA reduces gene expression of DNA synthesis enzymes and metal-lothionein," Proc. Natl. Acad. Sci. (Dec. 1991) vol. 88, pp. 10591-10595.

Serra et al., "The brain bench: virtual tools for stereotactic frame neurosurgery," Medical Image Analysis (Jul. 1996) vol. 1, No. 4 pp. 317-329.

Stackman et al., "Prevention of age-related spatial memory deficits in a transgenic mouse model of alzheimer's disease by chronic ginkgo biloba treatment," Experimental Neurology 184 (2003) 510-520.

Sullenger et al., "Tethering ribozymes to a retroviral packaging signal for destruction of viral RNA," Science (Dec. 3, 1993) vol. 262 pp. 15661569.

Taira et al., "Construction of a novel RNA-transcript-trimming plasmid which can be used both in vitro in place of run-off and (g)-free transcriptions and in vivo as multi-sequences transcription vectors," Nucleic Acids Research (1991) vol. 19, No. 19 pp. 5125-5130.

Thompson et al., "Improved accumulation and activity of ribozymes expressed from a tRNA-based RNA polymerase III promoter," Nucleic Acids Research (1995) vol. 23, No. 12 pp. 2259-2268.

Ventura et al., "Activitation of HIV-specific ribozyme activity by self-cleavage," Nucleic Acids Research (1993) vo. 21, No. 14 pp. 3249-3255.

Vickers et al., "Efficient reduction of target RNAs by small interfering RNA and RNase H-dependent antisense agents," The Journal of Biological Chemistry (Feb. 28, 2003) vol. 278, No. 9 pp. 7108-7118.

Weerasinghe et al., "Resistance to human immunodeficiency virus type 1 (HIV-1) infection in human CD4+ lymphocyte-derived cell lines conferred by using retroviral vectors expressing an HIV-1 RNA-specific ribozyme," Journal of Virology (Oct. 1991) vol. 65, No. 10, pp. 5531-5534.

Whitesell et al., "Stability, clearance, and disposition of intraventricularly administered oligodeoxynucleotides therapeutic application within the central nervous system," Proc. Natl. Acad. Sci. (May 1993) vol. 90, pp. 4665-4669.

Xia et al., "siRNA-mediated gene silencing in vitro and in vivo," Nature Biotechnology (Oct. 2002) vol. 20 pp. 1006-1010.

Yamamoto et al., "Reversal of neuropathology and motor dysfunction in a conditional model of huntington's disease," Cell (Mar. 31, 2000) vol. 101 pp. 57-66.

Yu et al., "A hairpin ribozyme inhibits expression of diverse strains of human immunodeficiency virus type 1," Proc. Natl. Acad. Sci. (Jul. 1993) vol. 90 pp. 6340-6344.

Yu et al., "RNA intereference by expression of short-interfering RNAs and hairpin RNAs in mammalian cells," PNAS (Apr. 30, 2002) vol. 99, No. 9 pp. 6047-6052.

Zhang et al., "Uptake and distribution of fluorescein-labeled D2, dopamine receptor antisense oligodeoxynucleotide in mouse brain," Journal of Molecular Neuroscience (1996) vol. 7 pp. 13-28.

Mucke et al., High-Level Neuronal Expression of $A\beta 1$-42 in Wild-Type Human Amyloid Protein Precursor Transgenic Mice: Synaptotoxicity without Plaque Formation, The Journal of Neuroscience, Jun. 1, 2000, 20(11), pp. 4050-4058.

* cited by examiner

SEQUENCE LISTING

<160> NUMBER OF SEQ ID NOS: 85

<210> SEQ ID NO 1
<211> LENGTH: 21
<212> TYPE: DNA
<213> ORGANISM: Homo sapiens

<400> SEQUENCE: 1
aaccaagagc ggagcaacga a            21

<210> SEQ ID NO 2
<211> LENGTH: 21
<212> TYPE: DNA
<213> ORGANISM: Homo sapiens

<400> SEQUENCE: 2
aattcgttgc tccgctcttg g            21

<210> SEQ ID NO 3
<211> LENGTH: 21
<212> TYPE: DNA
<213> ORGANISM: Homo sapiens

<400> SEQUENCE: 3
aaccaagagc ggagcaacga a            21

<210> SEQ ID NO 4
<211> LENGTH: 21
<212> TYPE: DNA
<213> ORGANISM: Homo sapiens

<400> SEQUENCE: 4
aattcgttgc tccgctcttg g            21

<210> SEQ ID NO 5
<211> LENGTH: 21
<212> TYPE: DNA
<213> ORGANISM: Homo sapiens

<400> SEQUENCE: 5
aaccagtacg tccacatttc c            21

<210> SEQ ID NO 6
<211> LENGTH: 21
<212> TYPE: DNA
<213> ORGANISM: Homo sapiens

<400> SEQUENCE: 6
aaggaaatgt ggacgtactg g            21

<210> SEQ ID NO 7
<211> LENGTH: 145606
<212> TYPE: DNA
<213> ORGANISM: Homo sapiens
<220> FEATURE:
<221> NAME/KEY: misc_feature
<222> LOCATION: (1)..(145606)
<223> OTHER INFORMATION: LOCUS     AF163864              145606 bp
      DNA       linear   PRI 24-JAN-2001
      DEFINITION Homo sapiens SNCA isoform (SNCA) gene, . . .
      ACCESSION  AF163864
<300> PUBLICATION INFORMATION:
<308> DATABASE ACCESSION NUMBER: AF163864
<309> DATABASE ENTRY DATE: 2001-01-24
<313> RELEVANT RESIDUES IN SEQ ID NO: (1)..(145606)

<400> SEQUENCE: 7

```
aattttcctt gaaaaacata gatgtccagt tctatctctc atattttttc ttttcataga      60
gatatggcac tttaggatta atttaagctg caaacagcag aaaaatgcaa ataacagtg     120 gcttaaatga aatagaaata ttttatctct tgaaaaagtt ctgataaaga cagtcaaatg    180
ctagaagggc aactgtgttc cagaaggttc tcaaggagcc aggctacctc taacccactg    240
ctctgccatc tctaattcat gtcgtatgtc ctcagggtcc acaatggcag taagaacgct    300
cctcatcata tctgtgtttc aaatagtaga atggagagaa agagaagaaa aggaggcatt    360
aaggaaggtt ccagaagctg ccatttgaca cttctgttaa catttaattg gccaaaattt    420
aatctcatat cgcataagct gtaagagatg ctggaaaact tatttgtctc cactctacat    480
ggacattatc agagtatttc tcaacagaga ggtctatgta ataatagtaa aaagtaagag    540
tggacacaaa cctagtcctt tacctttcag tagaagtaaa aatgctatat taatatttac    600
tctctctctc tctctctctc tctctctctc tcattttttgg ttttgacaat caaattcagc   660
taaatatgat tgaaactaaa atcaaggaaa atgcattata ctctgttgtt atggtaactg    720
gaatggtgaa atgtgtggat tattttcaca ccttcaataa tatgtttcta accatatatt    780
ttttaaaaat tgctgcaggg tttgcttaat gaccagagta taaaggcaca ttttttttctc   840 agttggcaaa aacacagttt tgacaaattt gacaagtttt tgtagatctg taatttattt    900
gatttaatta aatttttcatc ttgttttcac aatgagttat tgaaaataaa atctaaagct   960
ttaaacagga aaattttaaa tttgaatttt cttggttgaa ctacttatac ttttcacttt   1020
caattcacta acagaataaa tacatcattc cactgaatat gagccatcca tacaaagagt   1080
ccatgaccaa atgcaatgtc actaggtatt taaagtaacc tataaattat gttctgtctc   1140
attgtccaca aaatattaca acctgcatat ttggaaaaac attttgttca tgatatgtac   1200
atatatgagg catgcatatg gataaataca tataaagttg tgaaaattag gcaaattta    1260 tattttcgtc cactcttgaa actttcattt ttcaaaaaca aaatttaaaa tgctaacttt   1320
taaaataaat gtgccatagt agcacaatat gttaatattg gggaaaactg catggaaaat   1380
atacagaaat gcttcatact ttacaattct tttgtacatc ccatattatt tcaaaagtta   1440
aaagttttaa atatgttcag tcttgaaatg tatcagaaat gtttatctaa agttttgttg   1500
gtgttaagat taatatatta gtaatattac acacagaaag acagaaggta aaagtaaagt   1560
tagtttgaat atgactgtca ttttaagtca ttaacattta actttaccaa cttcatctca   1620
agttggccca tatcactgcc caacttaaac acatggctac atgcagcagg taagtacat    1680 ggcaggacta ttgagatatc aaggagtcac tgtgtgtcag gaaatgataa agttccccag   1740
cgtctcctca cctgtgtcag gccgacttag ggaaaccaca ttctacgttc ataaagagtg   1800
atctgcgggc ttgaaaggca agtaagcaga aagaagtgtt tatcccagca attcatgaaa   1860
```

```
atgttgaaaa aaaagaaaaa ctaagtcagc tttccttaga acccaagttt cggcctgcct    1920
tttaaaattt tctctatcaa agctgccacc ttttttccag atgctcaaga taaaacactc    1980
aacacagaaa tgcatgattt tgttgctgag ataccggttt gttgtttaca ctctgccctc    2040
ctatccattg caccttccag ttccgcttgc tctcagtctc cacctctgat tgctacttac    2100
acaatttatc ccatgaaaca ccatcagatt attccagcac accagtatct ctctgggcct    2160
tccctggtgc actgcactct tcctttcca cagagcctgt ggaaagagtg gcacagtagc    2220
tggaggggca cagggtac agagcacctt tccccaccca actcttgcgg tgctgtagac    2280
ctgaggtggt accatgaagg aaacatggac agttgagacc acatgcaaga gcccagacac    2340
acggctcaag ctcccagggt cagtgatagt gtatagctag ctgggaaccc tgcactggcc    2400
ctgtgttcaa catgagtggg tcaccctaaa agacatttca gcgtggttct gcctaccaaa    2460
tcttgcaaag aaatacctct ccactcagtg agaagtgatc cactagccag gctgccctcc    2520
tagacctgaa ttaaccatag agtcccagaa ttattctata ggcttgagcc ccagcattct    2580
gtggggcatc tggttgaccc cacaggcagc agggctagga agtctgagag tagcatctca    2640
aaagggtgaa gaggctggcc cacagggtgc ctgttcaggc tgagagtgca gctcctgaaa    2700
agcactgcaa accctgaagt tcccagcgtg ggagggaggg cgatttggag aattgtgagg    2760
aaggcattcc aaagtgctac ggtgcccaag tgaagactta cgtcgagaag aaatagaaaa    2820
atgacagctt ttccccaagt ggtaacaaga attagctaaa ccaagcctaa ttgtatattc    2880 ttcccaatt taacccatt attaaatcac tgaagctctc ctgagcagaa taaggggtag    2940
ggaaagaatt cagaataatt cagggaaaat gcctcctcat gaaaactcta aaatttggaa    3000
aacggttggt tcctagtaat cgagatagct atattttcct tcacttacca aaatgaaact    3060
taggaagttc attctctttt actcctaatc tgcaaatacc ttagtccagt gaacaaatgt    3120
gaaccgaaag agccaatctt tcaaaataca acctgagtgg ctaaatgggg ctatgtttta    3180
aatagaggca agtggccatt tgctgactaa agatcacaca tgtatactct gagttccctg    3240
aaaacctaca gctctgctca actttgggac ttcagagct cacctgatct accaatcagg    3300
cctggactgc ttcaaccaat cagggctcag ctgtatcaaa caatgggaac tgagcatttg    3360
cataaacaaa cctgactgga aacttgggtg ggaacttttg ccataataac tgaaccctct    3420
cttggttctc tggatcacac cttcatttta caccaaaagc tttgaatcac ggtttgcaaa    3480
ctgttcactg gaataaagtc tctttcttcc aaattccttt tcagagaact tttgttcaca    3540
gtccctatta tccgagataa atctgtaagc aatatgtatg tgatggaaaa tgtttcttcc    3600
ttcctcccca actttcaatc cttgttcttt tctaatcatc ttatagataa tgtctaagaa    3660
attggcttat ttaagttaaa agttttgact tccttactac tcatttgaaa gtacaaaata    3720
cctcagttgc acatgcctac ctactacgtc aacagtgtgc tgctgcatat taaaagagat    3780
ccaatttcaa atcacctaga aaaggctaaa tcttactttt tcttgcttta gatgacctct    3840
ctctatatat aaggctgata tcagccacaa acctcccctt ccttgtgaga ggagggcagc    3900
cttcaaactg aagttcagag cattgttgta caatattcct gaggtatatt gctccccata    3960
ggattgggat ctgtgccata gaacctataa atgggattta caagtttc tgttattgtc    4020 cagggaataa attttggacc acaaaagtga aatatataat tcccaatgcc ttttaaatgt    4080
ataaatatgg acagcagctc agtgcacttt tcactggatt aacagcatgc tgctatattg    4140
cgatactgcc aaaaaagacc ttatatttca agcagaata cattagtcct agaaaaggag    4200
aagagcagct ctagggtatg tccatgatcc ctctgtgaat ctattgtctg cttcattgcc    4260
```

```
tgaggcagaa caaaagagca cgtggccaag aatgaggctc tggatcagcc cagcttgggt    4320
cctcggcctc aaactatggc ctcagcgaca gtttcctgat ttgcggagta aatactactg    4380
tgagtatcca acacaattca gaggattgaa tgaggttaat taacttaatt aacaagtatt    4440
aattaattaa ttaaaaacac taggtcacag cctgggccat aataagctat caataaacac    4500
ttactattgg tgttagcaat cttTacttTt atttaagtga tgtaattact ccaatgtact    4560
ttatttgagt gatggaatta tagatatata tttataactt atataagtgt aagtagttac    4620
actTttggaa tatacttata caagtactta tataggttat attaaagtat atatttataa    4680
catatttata ggattaatgt aagaatattt tttataaaat gatctaacat gctaaaatat    4740
agaaattaat tagtaaaatt ataatttact ttagcttgtg tttatttgac accaactacc    4800
tggacattta gtccatttac tgcagtactt ctccaggtat gattcttggg ccagcaccat    4860
cagcattacc tgggaaatga gttagaaatg cacattctca ggccccacca caggcccata    4920
taaaaaccat ggattagtg tatctagaag gacaaaaatc aaaacactta gcttcattca    4980 ggaaaaaat aattctgata ttgatagata cctctcttca cttttaaaag tttcttctta    5040
tagaaaccag atctgattgt attgttaaaa ttaaacttgt aaatttttc acaacgaatt    5100 tcctgtatgg tggtctatgt ttggggaaat actcatcccg gaactcaact gtacagggtt    5160
gggcatgttt tacatacaag tgtatgtctc tcttcttgtc ttccttctcc cttgaaccct    5220
agtctccctc cctgccttTt cagaagtttc ccctggagt tctcagccta ttctctttta    5280
tctttccatc caaacgtagt caccaatata gtcctctttt ctctctcaat ctacacagca    5340
gaagcctcca ctgctgcttt agaatccaga gatatttcca atcccattat ccccaaagat    5400
gaagtctctc ttaaaaatcg agattctcta ttttagtagt ggtggctctg tgttcatgct    5460
gttccctctg cctagaacag catttcttca tattttcaca tattttTaca gcacatggca    5520
cataaaaagc acacaataaa caccaacatt ctgagttaaa aatgtgaaat gtcttttcct    5580
gcaaaaataa tatatgcctg tgtttgtcc cagttcaata cacatttatt gactgcctaa    5640
tactttgcag gcattgaaca aagcatgggg tagaaataat aacagtatt tctccccaca    5700 ctgaagtagt gtgcactcta caaatagga agatatatat atcttcctta tattatatat    5760
atttatatat ataaatatat atttatatta tttatatata tataaacata tatatataaa    5820
tagattactt tcacataatg tcacaggtgt agcaatagga gagtacacac agtggcttgt    5880
gaatactgag gccaacttga gagatcagaa aaggttttta ggagaaggtg atgaagggct    5940
gaatatattt taaaactgtt aaatgtgttt tcaaagggca ataaacaccc atatgttcca    6000
taaatattat aaacagcatg cttattcaag ttagttcaga ttatgttttc aaaagcaaaa    6060
tagatttaag tcacacttat tctttccttt aaataaaatg ttcttcaagt taaaagtatt    6120
atgaagtatg tctgggaacc attttcttgt tggaggccct taacatcttc acatattccc    6180
aaatcagaaa ttagcaaacc attttgacat ctccctcttc ctcaattctc tcatacaagc    6240
atccctaagt catatccatt gcatttccaa tgttttcaa attatttttt cctttaacat    6300
ttgtattgtc agtgccttat ttttgcatct cctaatttct ttctagataa catcctaatt    6360
ttttccccca atctagtttt tcatcccctc caaatatctg caagatatca cagtgctctt    6420
taagcaaaac aaatcggatc acattttTct cttatttaaa tcttttatta ttatgctcct    6480
ctaactagga tgaatatgca tcccagtttg tccaaatgta gatattccag ttTtatactt    6540
gctgactagc ataattgtca ggagtgtctc ctttcactct cagaagtgcc tgttctgaat    6600
tcaaaattat atagttagcc ttctcattgc cttcattatt ttgtttTaat tcaataatct    6660
```

```
tacattaaaa tcttcattta taatgtgagt cctgccatta agagatgcaa gattgctctt    6720
acacccggct ttacccttt  acaatttgag ttcatcaaaa tcatggatta tgtcttaaaa    6780
acaactagta tttaacacca tgcctgccat tgaataggca tgtaatgatg tttattaaat    6840
tttaaatagc tacattaaaa attgaaggtt ttgttattaa tcatattcta tgtgaaacat    6900
ccttagatta ttgaaagcat ccatatgctt ttcgacattc ttttatatat atattttat     6960 tatactttaa gttctaatgt acatgtgcac aatgtgcagg tttgttacat atgtatacat    7020
gtgccatgtt ggtgtgctgc acccactaac tcgtcattta cattaggtag atctcctaat    7080
gctatccctg ccccatcccc ccaccccaca acaggcccct gcatgtgata ttccccttcc    7140
tgtgtccaag tgttctcatt gctcaatttc cacctatgag tgagaacatg tggtgtttgg    7200
tattttgtcc ttgcgatagt ttgctgagaa tgatggtttc cagcttcatc catgtctcta    7260
caaaggacac gaactcatca tttgttatgg ctgcatagta ttccatggtg tatatgtgcc    7320
acattttctt aatccagtct atcattgttg aacatttggg ttggttccaa gtctttgcta    7380
ttgtgaatag tgccgcaata aacatacatg tgcatgtgtc tttatagcaa catgatttat    7440
attcctttgg gtatataccc agtaatggga tggctggatc aaatggcatt tctagctcta    7500
gatccctgag gaattgccac actgtcttcc acaatggttg aactagttta cagtcccatc    7560
agcagcataa gagtgttcct atttctccac atcctctcca gcacctgttg tttcctgaat    7620
ttttaagatc accattctaa ttggtgtgag ataatatctc gttgtggttt tgatttgcat    7680
ttctctgatg ggcagtgatg atgaccctt  tttcatgtgt ctgttggctg cataaatgtc    7740
ttcttttgag aagtgtctgt tcatatcctt tgcccacttt ttgatggggt tgtttgtttt    7800
tttcttgtaa atttgtttga gttctttgta gattctggat attagcccct tgtcagatga    7860
gtagattgca aaaattttct cccattctgt aggttacctg ttcactctga tggtagtttc    7920
ttttgctgtg cagaagctct ttagtttaat tagatcctat ttgtcaattt tggctttcgt    7980
tgccattgct tttggtgttt tagacatgaa gtccttgacc atgcctatgt cctgaatggt    8040
gttgcctagg ttttctccta gggtttttat ggttttagat ctaacattga agtctttaat    8100
ccatcttgaa ttaattttc  tataaggtgt aaggaaggga tccagtttca gctttctaca    8160
tatggctagc cagttttccc agcaccattt gttaaatagg gactcctttc ccaatttctt    8220
gtttttgtca ggtttgtcag agatcagatc attgtagatg tgtggtatta tctgagggct    8280
ctgttctgtt ccattggtct atctctctgt tttggtacca gtaccgtgcc attttggtta    8340
ctgtagcctt gtagttttgg tgtggatgtc ctttctgttt gttagttatc cttttgacag    8400
tcaggatcct cagctgcagg tctgttggag tttgctggag gtccactcca gaatctgttt    8460
gcctgggtac cagcagagcc tgcagaacag cgaaaattgc tgaacagcaa atgttgctgt    8520
ctgatcgctc ttctggaggt ttcatctcag aggggtacct ggctgtgcga ggtgtcagtc    8580
tgcccctact tggggtgcc  tcccagatag gctactcggg ggtgaaggac caacttgagg    8640
aggcagtctt tccattctca gatcccaaac tccatgctgg gagaaccact actctcttca    8700
aagctcttcg acagggacat ttaagtctgc agaggtttct gctgcctttt gtttggctat    8760
gccctgcccc cagaggtgga gtctacagag gcaggcaggc ctccttgaac tgcggtgggc    8820 tcccccagt  ttgggcttcc tggccacttt gtttacctac tcaagcctca gcaatggcga    8880
gcgcccttcc cccagcctcg ctgccacctt acagttcaat ctcagactgc tgtgctagca    8940
atgagcaagg ctccgtgggc atgggaccct ctgagccagg cgcaggatat aatttcctgg    9000
tgtgccgctt gctaagacca ttggaaaagc gcagtatttg ggtgggagtg acccgatttt    9060
```

```
tcaggtgccg tctgtcacag ctttgcttgg ctatgaaagg gaattccctc accccttgca   9120
cttcctgggt gaggcaatgg ctccctgttc ttcgggtcat gctcgatgtg ctgcacccac   9180
tgtcctgcac ccactgtcca ataagccaca gtgagataaa cccagtacct cagttggaaa   9240
tgcagaaatc accagtattc tgcgttgctc acactgcaag ctgtagactg gagctgttcc   9300
tattcggcca tcttggaact gccctcactg actcaacatt attttttaaca tgtttattta   9360 cacatttata aaatgatcac tgagtactta atacataatc tagttgagca atgtcctggt   9420
gatgcttgga tatgagaaaa tgaaaaaaca aacatctaat tacagatgct cctcaattta   9480
cagtgatgtt atttctcgat taacctatca taaattaaaa atattgcaaa tcaaaaatac   9540
acttaaacac ctaacttatc aaacactata gcttaagctt ttcctaactt aaaatgctca   9600
gaacactcac attaacctac aaatttggac tcctacattt gggtaggcta atgtaagtat   9660
tctgagccct ttaaggcagg ctaggctaag ctatgtttgt gcatgacaca aagcccattt   9720
tacaataaag tgttgaatat ctcaggtaat agtattatat cacatatcaa tagcccagga   9780
aaagatcaaa atttaaaatt ttaagtacaa tttctactaa atgggcatca ctttgacacc   9840
attgtaaagt caaaaaatca taagtttggg atcatctgta aatgagggca caattcccac   9900
aagaagattt cagaatcaga ttcaagatat tgtgaggaca caaagagga agttatcaac     9960 tctcagggag tggaggggaa aaaacggctt tatgaaagaa atgacttttg ggcagtcttg  10020
gaagataagc aattgtaaat aatcagtaga actgcagtag gacataagac gagccatgga  10080
ttagcctaga caggttacat agaggtcaga gctcagagga gattattggc cagtccttgt  10140
aaacaacgat gagtgtctaa agagtgtcat gtaagagaaa gagagaaaca gtataaaaat  10200
tcataaaagt cagcctggta gcagtgtgac aagcgtactt aaagaaaaag acacttgccc  10260
taagtcaaca aagtttattt cagaataaga attatattaa tatataggca tctgaattca  10320
atagtatttt tgccaaaatc aaggcataat gtgtaaaaat gtattcattt atatcccacg  10380
ttgattgaag tcatttcttc taattttcag gttttagctc tgcctatgca cgtggatgag  10440
acctaggtct caatcaaggt ctggcagttc agaaggtcaa gtcagaccat caaccatggt  10500
agctacttca ttgaccagcc tcacctagaa tgagtataac tgtgaagctt ttcaattttc  10560
tttattattt tagccatact gctatcatta ggatatttga cctctccaaa cttcacgttg  10620
aaatttgatc cccaatgttg aacatggggc ttcatggaag gtgtttgggt aatgggggca  10680
gatccctcat gaatagatta atcccctcct taggcatggt gatggtaagc gaattctcac  10740
tctattagtt accaagagag ctggttgtta aaaagggctg ggcctggtac ctctctcccc  10800
tctccctctt gcttcctttc tcaccatgca atctctgcac attccagctc cccttcacct  10860
tctgccatga gtggaagcag cctgagacac tcaccagatg cagatggcca attttaaact  10920 ttttctcgaaa tcagaattgt gagccaaata aatattttt ctttataaat tatcagtgtt  10980
ctttactagc aacacaagtg aactaagaca catactgtgt ttgctttctc tttcccatcc  11040
cttaatctga gtagaaatta aactttgac aaattcaatc attaaattta ctccaaaagg  11100
tggtaaacta attcaaaact ttctcctccc tcacattagg ccagaattgt atgatatctc  11160
tggcaacatc ttctccttc cactccttt agagtaaaca gagatgaatt tatgcattgg  11220
ttgcctgtac gtggtatgag aacatccttg gcctcagttt acttcgttca gatttcatca  11280
gttgctagta gcttttgctg atatgtgaat gttctgtgct tattaagaaa ggttattatt  11340
gtggtaacaa aatctaccctt taaatctagc gttataaatt caattatttt actgttgatc  11400
cctttaaatt caccatattc catgaataga aagtgtctag gacttggtcc tgtgggaatt  11460
```

```
tcttatttta agtaaacact gagtgctaat gcatgtcagc tctcctcttg ccattttgag   11520
attttcaaga tcttgctagc tttgaaagtt gaattgggtg aaataaaaat gctgcaatat   11580
taaaaaaatt taaatctcaa agacctcaag acatagttca agacttttaa aagttcaagg   11640
gtttgtcaat aaataataaa gaatcatttg ttgctttaac aaagaacagc aaaggatgtg   11700
taacataact ggaacattca ataatggctc tatcaaattc ctaaaataag cttaaagaaa   11760
cataagatct acatattaat atttatgact gtttctgaaa aggatatgag ttaaaatctt   11820
tcccaacagt tgatattaaa caaaatgttt gtccaaacaa aaaaacagaa atttaattgt   11880 attttttaatt aaaatgatgt aactcatatt atatgccaat taaaaaataa agggaaccac   11940
tgggggattg gtcatttaaa aaactgatat aggggctggg cgaggtggct catgcctgta   12000
atcccagcac tttgggaggc cgaagtgggc ggatcacctg aaggcaggag tttgagacca   12060
gcctgaccaa catggagaaa ccctgtcttc tactataaat acaaaattag ctgggcgtgg   12120
tggtgcatgc ctataatccc agctactcag gaagactaag gcaggagaat cgcttgaacc   12180
tgggaggcag aggttgtggt gagccgagat tgcaccattg cactccagct tgggcaagaa   12240
gagtgaaatt ctgcctcaaa acaaaacaaa aaactaatat aggtgatgaa aattgtggct   12300
gttgttataa attgttactg gtcaatgagt ttactacaga aacgtgtaca cacacgtata   12360
caataaatgc tatatattac atgaatttga aaaataatat gcattatggg acagcaactt   12420
caacttttca cagattttaa atgcaaacat ttgaaaaatg aaggaagaag agaatataga   12480
agtggagaag gagctgggga aaaggaaag gaaggaaatg agaaatacac cttggataaa   12540
caaactgata agttggtgca ttttgaaaag agagttggat agagaactga accatattgg   12600
taactggaga tatgactcat tatttcatgt aatgatggta ttaagcacca actgggctaa   12660
gaatgcatta aaggaaaaaa cataggcatt ggaaacagga gagctgcgtt caaatcctgg   12720
acctatagtt aaagctccct aaggactcac tttccttatg tttcaagtaa gagggagaga   12780
ggtactcatt attcttacct taaaggttaa tgtgggggt taaatgctaa gaggcaagaa   12840
acatattgct tgctacaatt agtgctaaaa aatattaccc cttttcttac tcaatttgag   12900
aggtgctagg ttcttaacat ttgtgcattt tcttgtttgt tttacatata ggcagaggaa   12960
aggcaagata ccatctttag tcatttaaat ctatgatttg gagaaaagat gttttcaaag   13020
tatccttgct cattgacttt gctatactag acagtatgag tattagcttg cagactttat   13080
gagtgtaata ataaaacaga attctatgca tctagaagta taagcagaat ttttactgag   13140
taattttaaa acttttttg ctattgttca gatcagctta gtccaaattt tttaattagt   13200
tattgaggta gagactaaaa tgtactttct cttacattac atactgaaaa tattattgca   13260
tgtttgatta gttaatatgc atattattaa ttattgtagg tagtaagaaa actgatctaa   13320
aatctttgtt tactcaacct gtttatcatg gtcttaagga acttttgta aactgcttta   13380 taattttact gtcatatatt cagaatagtc ttattcaaat acatccaaaa cactgagtat   13440
atcaataaag tctttcaaaa accaggaaaa aatagtgggt ttttccaaag atagaactta   13500
atataagaat ttctgtaact gtactgaagg actgccaaag gacataatgg agtaacagaa   13560
agattaataa attcagaaag cagggatctc ccataaaaga agagcaatga aagatagagg   13620
ttggggttat taaaaccaaa aagcttaaag ccatacctct gtagagttgg cacttatact   13680
tctgaggtga ggtgctggca cctcaggggg catgaggtga agccttgagg gcttcagtc   13740 agatgcatga ggaaggggca ctgcatggat ggctggtgct ggttactcag atgctcaggg   13800
gaggagtccc acattgttgg gcctcagaga tctgaggaga ggatgctgca ttcgaggtcc   13860
```

```
cggaatccct gaggggagct tatatggttt ggctctgtgt ccccacccaa atctcatctt     13920
gtagctccca tagttcccac gtgttgtggg agggacctgg tgggagatag ttgaatcatg     13980
gggtcgggtc tttcttgtgc tgctctcatg atagagagta agtctcatga tatctgattg     14040
ttttaaaaat gggagtttcc ctgcaaaagc tctctcccct tgcctgctgc catccacata     14100
agacgtgact tgctcctcct tgccttctgc catgattgtg aggcctcccc agccatgtgg     14160
aactgtaaat ccattaaacc tctttctttt gtaaattgcc cagtctcagg tatgtcttta     14220
tcagcagcat gaaaatggac taatacagta tattggtacc aggagagtga ggcactgttg     14280
aaaagatacc ccaaaatgtg gaaatgactt tggaactggg taacaggcca gggttgtaac     14340
actttggagg gctcagaaga agacaggaaa atgtggaaaa gtttgaattt agtagagatt     14400
tgttgaatgg ctttgcccaa aatcctgata gtaatgtgga caataaagtg caggctgagg     14460
tggtctcaga tgaaaatgag gaacttgctg ggaactgaag caaaggtaac tcttgttata     14520
ttttatcaaa gagactggtg gcattttgcc ccgccctcga gatctgtgga actgggaact     14580
tgagagagat aattcagggt atctggcaga agaagctcct aagcagcaag gcattcaaga     14640
tgtgacttgg gtgctgttaa aagctttgaa ttttaaaagg gaagcagatc ataaaagttc     14700
agaaaatttg cagcctgaca atgtgataga aaacaaaatc ccattttctg agaaattcaa     14760
gctggctgca gaaagttgca taagtaacaa gaaaccgaat gttaatgccc aagacaatgg     14820
ggaaagtgtc tccaggacat gtcagaggtc ttcacaacag tcccttccat cataggtctg     14880
gaagcctagg agggaaaaat ggttttgtcg gccaggccca gagtccctgt gctgttgtag     14940
gctagggaca tagtgcccta catcccagct gctccagcca tggctgaaag aggccaatgt     15000
agagcttggg tcatggcttc agagggtgca agccccaagc cttggcagct tccacatggt     15060
gttgagattg caagtgcaca gaagtcagga agattgaggt ttaggaacct ctgccaagat     15120
ttcagaggat gtaaggaaag gcctggatgc ccaggcagaa gttttctgca ggggtggggc     15180
cctcatggag aacctctgct agggcagtgc agaagagaaa tgtggggtgg gagccccata     15240
cagagtccct actggggcac ctcctagtgg aactgtgaga agaggaccac tgtcctccag     15300
aacccagaat ggtaggtcca ccgacggctt gcaccatgtg cctggaaaag ctgcagacac     15360
tcagtgccag cccatgaaag cagccaggaa ggaggctgta ccctgcaaag ccacagggc      15420 gaagctgccc aagactgtgg gaacctacct tgtgtgtcag agttacctag atgtgagaca     15480
tggagtcaaa ggagatcatt ttggagcttt aagatttgac tgccccactg gatttcagac     15540
ttgcatgggg cctgtagctc ctttgttttg gccaatttgt cccatttgga atggctatat     15600
ttactcaatg cctgtacctc cattgtatct aggaagtaac taacttgctt tgatttat       15660 cataggtggt atcataggtg gaagggactt gccttatttc agatgatact ttagactgtg     15720 gactttgaa ttaatgctga aatgagttaa gactttgggg gactgagaaa acatggttgg      15780
ttttgaaatg tgaagacatg agatttggga ggggccaggg gtagaatgat atggtttgtc     15840
gctgtgtccc cacccaaatt ttatcttgta tctcccataa ttcccacgtg ttgtgggagg     15900
gacctgatgg gagataattc aatcatggga gtgggtcttt cctgtgctgt ctctcatgat     15960
attgaataag tttcatgaga tctgatggtt ttaaaaatgg gagtttccct gcacaagctc     16020
tctcttcttg cctgttgcca tccatgacat gctcctcctt gccttccacc atgattgtgt     16080
ggcctcccca gccatgtgga actgtaagtc cattaaactt cttgcttttg taaattgccc     16140
tatctcagct atgtctttat cagcagcatt agaaaagatt aacacaagag caataagaat     16200
gtttctggac atgtagaaag aagttaaagg ctggaaccaa ttgctgtcac tggaacaaag     16260
```

```
gaagatggct ggagtgcggg tgccactaac agtaacaatt atcaaataag aaggatcaaa    16320
cgccttttct cccgcctttt actgtcttct aaagtcatta attggcagaa tatcatagaa    16380
agccagatgg tacaggaaca taatttgtag accttagccc cagtgccaga gagaaagggg    16440
aaaaaaatag acttaaagag caatggcttt gtaactagca tactgacatt ttgtaagttt    16500
agaaaactct tattttatca gttttgttct gcaaattcac ttatttagtt attaacatgt    16560 gttgttttg tgataatcca tcaaaaagaa ctgagtatct ggtgtttatg gaaagcaaac    16620
taatatctga gtataatttt catttcaatg ttaaatgtct ttatttaaat acagagaaca    16680
gtcgactatc atcatcattt caactgatta tccaactatg acatctagtt gtaaaacaga    16740
aattaattct cagaagttat tactttctat caaaccttaa atattcatca ataagataca    16800
tcttttctag gaccctataa aatgattaat aaatttatta ttattattta ctgtacaaat    16860
attctgctgt tatttattaa aacagaagta ttccatatcc tgaatcagta caatgttaat    16920
ctcctctgtt tactatgtcc atggaaaaat gtgccagtga tttgattagg accataaata    16980 tttgttttg tattcagagt cccttcatgt tgtcaaaatc cttactgcct gtataatcat    17040
gtttattcct tgtgattttg ttcgttttt tttgttttg agacagaacc ttgcgctgtc    17100
acccaagctc ctggagtgca gcggcatgat cactactcac tgcagcctcg acctcacatg    17160
ttcaagtgat cttccccct cagacccca agtagctggt actacaggtg catgccacca    17220
agcccagcta atttttaaat ttttttgtaga tacaggatct ccctttgttg cccagacagg    17280
tctcaaattc ctaggcccaa gaattcctcc cacctcagcc ttccaaagtg ctgagattac    17340
aggcatgaga caacatgccc agccctggca ttcaatttca gcatctataa aactgtattt    17400
attttaaggt tcctcttgaa tcacaattta tccactgagt atacatatca ggacacaaaa    17460
cacactctat cacaactgga aggacaggaa atttggagaa tatagtataa aactaatgta    17520
gtaacaagag tagcctaatt tttcccaaag ggtccatgaa ttcacaccct actggacagc    17580
tgctctcaag ttttcatttt tttcacagag tgttcaataa ttctgtcatt gaaaagtgtt    17640
tctgccagga ttgatggtgt gaaataaaat ttatgggagc cattgctttg gactgagatc    17700
ttgcactagg cccaagggac cagacaaaaa tagtgactca tgttacagtc ccacattatc    17760
aagccaaaac taagttgttt gtctgacctt cctagaaatc aagagagtaa gagacaatag    17820
ccaaatccct agaggagcca gttttagcta gcatgataag gaagtcccct ctgctttaac    17880
ttttataagg aaagaacctt tgaaataaga aatctacttt ttgctctctg tttctgcttt    17940
ccttggcctt ttactgtata taaaaccaaa ctcctctgct cagcttatca aaaaactcat    18000
tatattatat agaatgaagt gtagcctgat tctagaatta cagataaaag ccaattaaga    18060
cctttaaata agttgtaatt ttgtcttttg gcaacagttt ctgaactgag tctgggaaat    18120
aaataatcca acaaccaggt aaaaggaata gagaaagatg agtgaattcc ttaaagctgt    18180
cttttctcat tctggtaagt tccttcactc tactaaaata aataattcta ccacctggat    18240
aaatttggtt ccttaatgga aaaataatat catcagtaaa agtggaaact ctgggtaaga    18300
aaacggaaat aattaaaatg cctaaaccaa ctttattgtc attaaaatat caaacagatg    18360
aactagaatg attcaataag atttcaaatc aactgttagc agtcttttca tgtagaaaga    18420
agtctgcatt taggaagccg ttgaaagaaa ttgctaagct ctaaggacag gtcctgtcca    18480
gaccaaagca ggcccctagc cctaacaggg atcccttggg taaggagacc atttgctgca    18540
ataagaaaaa atgacatcaa aggagaggct gagtgctatg atctgaagat cagcaggtga    18600
ggaatctctt gggaatctcc tggatgcttg ctctggacac aaggcaggca ctggagatgt    18660
```

```
aaagaaatgt gtggccctca attgttcaac aaatagccat cagttcaaac tgaatatgta    18720
ataacgcatc ggtctgcaat cagaatttca agcccagag  aaatacattt aaagatcaa     18780 tcctttagaa tatagcaata ttcttattg  tctatgccct gtttagcaat caaccttcca    18840
cattttctac tgagttttct agacagctta gaatgaaagt cctacagggt aagaagttca    18900
agagttaatg gatgcttttg ttcttccagt tggttctaat aagagtggta aaatacaaca    18960
gcatattctt tataatttga ttttaatcca attttgtaca ttctcagacc taaacattgt    19020
ttaccacact aattattttt gaagttaacc tcccctcaat acccttttta aagagtgagt    19080
gctgaaatta aacagccat  atgatattga tgaggctgct tttagagcct caaattcaac    19140
tccagaaatt tattttagt  tgtgcatatt tattgtaaaa tatttgtagt gccagcttat    19200
gttttctatg tccagatttt gttctccacc ttctgaagcc cacagagtgt gaaacaagca    19260
tttacaatgg agatgatggt gctaatttta tgtattttat tccctggcat atttgattgc    19320
aatagagtag acaaaaggat ggattagtag ctatgatctc tctctctctc tctctctctt    19380
tctctctctc tctctctctc tatatatata tatatacaca cacacacaca cacacgga     19440 aggcatcaga tatctcatgt gtgtatacac atacatatat ataggatata atgatttatg    19500
tgatatatat gtgaggtaag tcttcatgtc ttccataggt atagtaccag ttggttaatc    19560
ttgggccagt catgtagctt ctacaaactt taggctttct ggacaaagca gtatataatg    19620
ttcattatgt agctatgcca aaacaaaggt caaaataaag aaagattcta cctagagcaa    19680
aagagaattt atatatataa attttatatg caaattatat acagctttat atacaaatat    19740
aaatatcacc ctgatgtagt agtttgctag gattgccata acaaaatgct acagactgtg    19800
tggttaaaca acagaaattt attttctacc aattctgaaa gctagaagtc tgagatcaat    19860
gtatcagcgg ggttggtttc ttctaaggcc tctctccttg gcttgcagat ggctgtcttc    19920
ttccagtgtc tttatattgt cttctgtgtg tgtgtgtcag tgttctaatc tgctcttctt    19980
ataaaaatat cagtcagatt agggttcact ccaaggtaag aactgaagag catgctcttt    20040
tctttgatgg ggacaagtga ctctatctag acataagtct ttggagagca gtctctcaga    20100
tgctgaccct ctctacaatg gagagagcgc atggcatggc ctgctaagct acttctctgc    20160
cattctgcta ggcaggtttc aggccctgac aatataagac gtgagcctct actcatcttt    20220
ggataagtct ctctgcatta ttgcaaatac aagaagcatt ttgtagctgt gtagtaaaga    20280
gaggagaaca cttgcaatat tctcagtcaa gattctcaac tccctgaaga aaaacagtgt    20340
attttacata aattcatgct gttataatta cattatataa aaagattatt aaccaaatat    20400
tgtacatatg aaaacagagt tgaaagctct tcaactatt  caactgatga ctcccaagat    20460
ggacctgact gtactgatat aatctgatgg atttttattt gaagctattc taacagaact    20520 atatttatg  gtatggaaac gaagagaatt gttttaggga agagcatgtt taatgttttc    20580
aaatattttt gtctctgact taaattttgg cttttctagt ttgtttcaaa ttttcacact    20640
tgggtcaatt ctcttttgct ctaggtagtt ttttttttta tcttgacttt gttttggtgt    20700
atttctgcct gactggaaaa gttttgtaa  ccccactttc ttttcatccg attagtagct    20760
cttctgtgtc catagataaa tatatccttt acttctgtga gcattatttt ggtatatgta    20820
tttttgttcc agttaggaaa agagcagcaa aatgattttc tttcttgttt tcttcctaaa    20880
acttgattta gaagctaagt gggagcagcc ctttcacaca ccatcatggt agttatttac    20940
gtgcattagc gcgattcatt ttcacaaatt tatgagatgg ttaaagttaa cttcattc     21000 ttaaagagag agaacaagtg gagaaaaagt tcaactgcag aggcttgaga ttgtattgtg    21060
```

```
tgttgcttaa gaagaaatat ggagtcaaag tgcctcatca tttaccagtt gtgtgacata    21120
tcacaaaaag agggagtgta accagccaaa aatttaactt ggacaattgg attggtaaaa    21180 acttttatg ggatatgcag gaatacagtt cttaaaattt tataagatgg cataaaattt     21240
atttctttga taaatgatat tttcttaaga tatctttcta gaaatggaat tgctgagtca    21300
agatgcatat tgagggattt tgatacatat ttttaaatta cctttagaa aaggtaattt     21360 ttagtaggaa agtagaagtt tatctcctat tgctaggcat actgatttt ttcttttct     21420 tatctgcatt taatcacttt tctttaatga gcatatacta cttgtataac agaaaataaa   21480
ggatgattat atttgggaag tgtcatgtca gattgtcctg tccagtttga aatccacttt    21540 gactttaat ctaccttgag atgttatttt agctccctac aggttaaggg cataatccaa     21600
gatgattaag gagattgaat tctcatttaa ttgattgttg ccacagacac ttacacagag    21660
ataaagtcat taaacacatg tctctttac atttgaaaag acatggcaaa taatttact     21720 gctttcttta gtacataaa tgtcataata ttgtgagtgt gcatgtgtat accattctgt     21780
ctatatctta atgatctaga atgtatatgc tactttctta catgcaaatg agctgtacat    21840
atttgagtaa tattggtgac ttttttata aaatcaattt ttcctttga tgattacatt     21900 atacgaagat gtttgaatgc tgtttttct ttgttatgtg tatgcttata tctgtgaaac    21960
atctagctag atgtcctgca ggaatcagtt ttacatatgt aaacaggcat atttctgcac    22020
tctaaatttt gataattaaa ataattcgta actttattat tcaactctca agtgtttaat    22080
agccattact aacaaaaatt tctctttgtg gctaatctga ttacttggaa tctttttat    22140 tgtgaccaaa aaaagcaacc ctgcacatac aactttaact tcaatatttt aatgacgaaa    22200
tttaaggata atttaaatag aaatggactc agaaaagaat cagtaagact tagtgaagga    22260
tcattgtcta ttatagagaa gttgatttaa gattaactta ttagtaatat ttaacatata    22320 taagaatta ttagactggg tatatagaca agcgttttat tcttggaaga caaaagaag     22380 aaaaattgaa ttcaaccgat gtatacgaaa ataaaaagta acagtaaatt aaaaatagat    22440
aattaaataa atatatgata cagtataacg ttttatagcc aagatgatgt tacaaatcca    22500
tatttattga catggatatg ttttatact aaagtgttta tcaaatagcc attaagagat    22560
aacttctttg aataatttgc tttctaaatt tcttaactac ataaatttcc agctttatat     22620
ggaacaccaa gttttcaaac cattagtgat gtgcttttta tatggtgtta aaagtttct    22680 ttctttcttt tttctttttc ccccaagatg gagtcttgct ctgtcgccca ggctggagcg    22740
cagtagtgcg atctcggctc agtgcaacaa ccacctcctg ggtacaagca attctcctgc    22800
ctcagccccc caagtagctg ggattacagg cacctgccac cacgtccagc tgattttgt    22860 atttttagta gagacggggt tttaccatct tggccaggct ggtctctaac tcctgacctc    22920
aggtaatctg cccacctcag cctcccaaag tgctgagatt acaggcgtga gccaccatgc    22980
ccgacctaaa aagtttctta aacgtcactt tatactctca aattatctag aaaggaaaac    23040
gtattagatt cctggatatt ttggatattg taaggaacat acttatttgc tgtatatact    23100
ctgtttgtaa cagtattgta acttcagttc aaaacaatac acaaaacatt acaagttccc    23160
gtgatatttt aaaaattcat ttattttctt cctttctgaa tacaaatgct gttcagtctg    23220
ttgattcttc actaatctga aatattaggg actgattcct gaattggata ttcattctga    23280
agcctttcag agccactggc acaaagggtc tgtcaaactt ggaacaccat tgttgtatc    23340 attttatttc tttctcttgg caaatccaca taattcatac aggactatgc cagtgtcttt    23400
tgaaagaaac aaggtttaag aaagtaaaaa tgttaataaa gatagtgaat gttaattctg    23460
```

```
tcattgttac tgtatttctt caagctgtgg ctgcaaactg ctttgagtga tgttattgta   23520
actcgcacat tagggagaga aagagatgtt tggtagattt ttaattaatg atccctatca   23580
atgctccttg agcttcccca ctctatctct ccacaacttc catccctggt tggaaatttt   23640
ttgcttaccc atactaagtg agagttattg atgggaaggc atcagatatc tcacgtgtgt   23700
tgctggtggg atgggagact gtggaggatg ggaacaggtg gaaatctact gcaatggaaa   23760
aaaaaaaaag catgtcctag gacacccaaa acatggaggc tagataataa caatagctac   23820
ttgtactgag agcttccact ctgcctggct ctttgctatg agccacatta ttcattcctt   23880
acaacaatca aacaagacaa gtaaaatatc atgcccattt tttaatgaga aaactagaga   23940
ttagagaggt tatagatact tgctctgagt cactagtaat gagtagtaga gctttaataa   24000
gtccctgaat ttaggttgta tctagtacat ttactcttag aagtctatca tgctcaccag   24060
agttgcagag ttgcgtgtat ttcttgggct cattaatgtg ttttttttctt tctaaaacta   24120 aagtcatttg aacttgttag attttgaaat atttaaatat cttttctatc tggctttaac   24180
atctttaatc ttggaatctt gcatgccttc atattcttag gaccacgaaa ccacaggaat   24240
atttaaaatg atatctagtg gaaacaatat gaagttggcc atgggtcaa attagagaat   24300 ctgaatacta tgcttctcct tgattgctct tcccatttct tcagagtaac cctattcccc   24360
catctcatgc tcaccccctt tccaaaatca tacataatga tctcccaaca ggatgcatta   24420
ggctttctct actctaccca ctatgaaatt acacaagaag cctatcgcaa tctcactacc   24480
tcgtctctct cacaggttta cagaaggtga gaggaaggtg cagatagaga ataagaagca   24540
ggtggctcca gcatcaacat tacatcaccc cttgtgttca caacaaatat ggaatattat   24600
ccaaagataa taaacgttgt atttttcttaa cttaaacaca ttaaatcagt cctctcttta   24660
atcacttgtt aatgggcagc atctttattt tcatgccatt ctactctgct gtctttgcta   24720
tagcacaagt ttaccacata ccatacctaa aaattcagtt gttctatggg ggtaaacaaa   24780
gtctaggtta agcatatatt tcatagaatg ttaatctata gcaaaattaa tgaattaaat   24840
ccagataaaa gaatcctatt atggtctggt aaaatattta tatttcactt agcaaagaga   24900
aaacaaaaca tgaatattgt agttatgaac agaatatgca tgttagtaat gcttccaaat   24960
atgttattac ttcataactt catatttctt atgaggtaca agccattcaa ttagtttaac   25020
gttatattca gagaggctaa agatttactg aagaccatgc tgtccatcaa taatgaaaag   25080
aaaaattaaa aaaactttat tttaacttct agttccccttc tttgtacttg agcagctttc   25140
cctccttaag aatacagacc tagaacatat gcaatatcac tatcaatatt atgtgtaatt   25200
aaaagttcat tggatgttta ctgtgttcaa ggcattttaa ggagtgacaa gagttaaaca   25260
tatagttgta attcaaaatg acaacgaaat tagtttacag ttttcttttt ttgtaggtag   25320
taagaaatca tctcccccta ttgaggaata ccaatataga aaaggcaaaa ctttaaatat   25380
gaatgaactg tttcataata acataagttc ttcttgattt ccattgtcac atccaaattt   25440
gaaggctatt tctaacacag ctgggttcta ccttttttcct tctcactctt taccacaccc   25500
aatctgtgag gcttcagaca caaactgcta attcaggaga caattgtgcc ttctgtaaca   25560
gtttctgcta aattgtctca gctctgccac ttaaaatagc taggtgatct cagcatatca   25620
ccaaaactct tggagctcag tttctctgtc tataaaagtt acataaaatg taattgatct   25680
gcttgttatg actaaataac atagtacatt agtcctttgc caaaggacta acaaattacc   25740
aaataaaagt ttggaatcat gttaaacgtt tataagaagt acaactgtcc agaaataatt   25800
ctctcacatt ggtctgttgt aatgagacct aaaatatctc attttatta cctctttgac   25860
```

```
ttaaagcact aggtctcaag gaggtcatgg ttatactata aatatgtcat gtgaaataat    25920
atattaaata attgttgtaa tactctattg agatactagt tgtaaagagg cacaatggaa    25980
aacttatact attaacagta gtaaaaagaa acaacaaaaa gcaataaaaa acaaaacacc    26040
cattcatgca acgacatgaa cgaacctcac aaatattata ctgagtaaaa gaagtcagac    26100
aaatataaaa caaagtttat actacgtgat tagatctttta tgacattcta gaatatgcac    26160
atgaaggtac aagtaactg tctggaatga tgaaaatgtc ctgtgtcttc aaaatagtgt      26220
gggttacact aatgcatggc tttttcaaaa ctgatttaaa gggacacaac atctgagcat    26280
ttccctaggt gtaaattaca ctgcaatttt aaagaatcat ctaatgatat tgtggttatt    26340
tttaaacagt ccttaaattt tgtggatgca tactgaatgt ttacagcgga aaagatatat    26400
ataaagcttg aatttggtaa aaaaaaaaaa aagagggagg attggtagtg ataaagtgag    26460
tggacttatg gatgagacat gatcagccat gcattgaaaa aatgtaaaag ttggatgatc    26520
ttcacatgag agtcctttat tctgtctact tttgcatatg tttgaatatt tcccataaca    26580
aaaagttgaa aatagagtga tcacatgagt taatctccta atttacaaaa aagaaaactg    26640
gaaacagaag gagaacaaaa cttgttcaag gtctcaaagc cagacagcaa actagctccc    26700
aagtccaacc ttcttgctcc ggtcctaagc aaacaaaaaa tattaatatg agctactgca    26760
ttaaggaaag tctgcttttc caaagggcag accaatagtt caaggaagag tttaaataat    26820
aaatatttgt gatcttactt tcatgctttt ctatttccca ctgaacacat atgcattatc    26880
ttctatatgt cttttatgta taatcatttg cttcctgttc cttgtggttt taaagttgtt    26940
ttgtatgttt aaatttgatt ttactcaaat ttcagaaccc aaattagcgc aagaatcaga    27000
caaagcataa ctttctataa atataaaaac aattaaaaaa aaaacataca gcaaaaacga    27060
gttgttgttt ccccctcct cttccagtgc ttaactaatc ttccgaatcc aggcacagaa     27120
agcaaaggct ttctgctagt gggaggagct tgcttctcca ttctggtgtg atccaggaac    27180
agctgtcttc cagctctgaa agaggtgaaa atgtgttaag cgatgcaaaa attgtcttga    27240
agttcgcgtg tgtatgtctg tgtgcatgtg cgtgtggtgg gtgggggag agaaaagggg      27300 gtgtcaattc tgagggcaac gagaatcaga agtcagaaag gtgagtggtg tgtagcatct    27360 cccttcaga aggggctgaa gaagaaattg gatatgatgg tccggtaggc taaatcacgc     27420
tggatttgtc tcccagataa agggaggtct gcaaagtaag tcccatttct agagcgaaaa    27480
gccttaggac cgcttgtttt agacggctgg ggaatattta ttccttgttc cactgatggg    27540
aaaatcagcg tctggcagga gctgattggt ggaaaggaaa atggtgatag tggcgtggaa    27600
agaggatttg ctgagccttc tcctgcctcc tcaacctgtg actcttcctt agtagtctcc    27660
ctttcaccct caggacccctt tccggctctt cctagattaa gagcaaacga aaaccttgaa    27720
gatatttgaa ctaaagcgac ccctaacgtt gtaacctgtg accgtgatta aatttcagcg    27780
atgcgagggc aaagcgctct cggcggtgcg gtgtgagcca cctcccggcg ctgcctgtct    27840
cctccagcag ctccccaagg gataggctct gcccttggtg gtcgaccctc aggccctcgg    27900
ctctcccagg gcgactctga cgaggggtag ggggtggtcc ccgggaggac ccagaggaaa    27960
ggcggggaca agaagggagg ggaagggaa agaggaagag gcatcatccc tagcccaacc      28020
gctcccgatc tccacaagag tgctcgtgac cctaaactta acgtgaggcg caaaagcgcc    28080
cccactttcc cgccttgcgc ggccaggcag gcggctggag ttgatggctc acccgcgcc     28140 ccctgcccca tccccatccg agataggac gaggagcacg ctgcagggaa agcagcgagc     28200
gccgggagag gggcgggcag aagcgctgac aaatcagcgg tggggcgga gagccgagga     28260
```

```
gaaggagaag gaggaggact aggaggagga ggacggcgac gaccagaagg ggcccaagag    28320 aggggggcgag cgaccgagcg ccgcgacgcg gaagtgaggt gcgtgcgggc tgcagcgcag    28380
accccggccc ggcccctccg agagcgtcct gggcgctccc tcacgccttg ccttcaagcc    28440
ttctgccttt ccaccctcgt gagcggagaa ctgggagtgg ccattcgacg acaggttagc    28500
gggtttgcct cccactcccc cagcctcgcg tcgccggctc acagcggcct cctctgggga    28560
cagtcccccc cgggtgccgc ctccgccctt cctgtgcgct ccttttcctt cttctttcct    28620
attaaatatt atttgggaat tgtttaaatt tttttttttt aaaagagag aggcggggag    28680 gagtcggagt tgtggagaag cagagggact caggtaagta cctgtggatc taaacgggcg    28740
tctttggaaa tcctggagaa caccgggtgg gagacgaatg gtcgtgggca ccggggaggggg    28800 gtggtgctgc catgaggacc cgctgggcca ggtctctggg aggtgagtac ttgtcccttt    28860
ggggagccta atgaaagaga cttgacctgg ctttcgtcct gcttctgata ttcccttctc    28920
cacaagggct gagagattag gctgcttctc cgggatccgc ttttccccgg gaaacgcgag    28980
gatgctccat ggagcgtgag catccaactt ttctctcaca taaaatctgt ctgcccgctc    29040
tcttggtttt tctctgtaaa gtaagcaagc tgcgtttggc aaataatgaa atggaagtgc    29100
agggaggcca agtcaacagg tggtaacggg ttaacaagtg ctggcgcggg gtccgctagg    29160
gtggaggctg agaacgcccc ctcggtggc tggcgcgggg ttggagacgg cccgcgagtg    29220
tgagcggcgc ctgctcaggg tagatagctg agggcggggg tggatgttgg atggattaga    29280
accatcacac ttgggcccgc tgtttgcctg aggttgaacc acaccccgag tgagcagtta    29340
gttctgttgc ctacgccttt ccaccatcaa cctgttagcc ttcttctggg attcatgtta    29400 aggataccccc tgaccctaag cctccagctt ccatgcttct aactcatact gttaccccttt    29460 agaccccggg aatttaaaaa aggggttaat cttttcatgc aactccactt ctgaaatgca    29520
gtaataacaa ctcagaggat tcatcctaat ccgtggttag gtggctagac ttttactagc    29580
caagatggat gggagatgct aaattttta tgccagagct aaaaatgtct gctttgtcca    29640
atggttaaat gagtgtacac ttaaaagagt ctcacacttt ggagggtttc tcatgatttt    29700
tcagtgtttt ttgtttattt ttccccgaaa gttctcattc aaagtgtatt ttatgttttc    29760
cagtgtggtg taaggaatt cattagccat ggatgtattc atgaaaggac tttcaaaggc    29820
caaggaggga gttgtggctg ctgctgagaa aaccaaacag ggtgtggcag aagcagcagg    29880
aaagacaaaa gagggtgttc tctatgtagg taggtaaacc ccaaatgtca gtttggtgct    29940
tgttcatgag tgatgggtta ggataatcaa tactctaaat gctggtagtt ctctctcttg    30000
attcattttt gcatcattgc ttgtcaaaaa ggtggactga gtcagaggta tgtgtaggta    30060
ggtgaatgtg aacgtgtgta tttgagctaa tagtaaaaaa tgcgactgtt tgcttttcca    30120
gatttttaat tttgccctaa tatttatgac ttttttaaaaa tgaatgtttc tgtacctaca    30180
taattgtatt tcagagaaca gttttaaaaa ctcatagtct tttaaaaaat aatcaagaat    30240
attcttaaga atcaaaatca ttgatggatc tgtgattttct tttaccatca tgaaaaatgt    30300
ttgtcaattt taatccattc tgattttta aatatgactt tgatatgccc ctgtgatgtg    30360
tataaagaga cctatttgtg gccctaaaat ggaaagaaca gattagtctt tgataaagtt    30420
acttcatgtg atcatttggt ctctgtgaac actgaggaca gagaaaagtg cttgagggct    30480
gctactaatc tctcagaaac atttgtatag ttcatccatc aaatgacaca catactaaaa    30540
gaataaagaa attgatgctt attacctact tgttcctaaa gttccacctt ggggtataca    30600
cccaaactct gactctcttt tctgtaactt gaactgtatt caattgagtg ttattttaca    30660
```

```
aaccactctg aattccttgg aaaagaatag acacacactc tcatccacag gcatagacac    30720
acacactcaa cacagacaca ttgcccattc ttcctctctt ctttctcctc tgagcttttt    30780
cacattctct ggtggcaact atagcagtaa gagtcacagg atgaacagtc aggtggagga    30840
tgaccacatt gagttgccta gctgaaacat gtgctctgtc tatgtctgca aagtgaaaga    30900
aagctacact atctcttcaa catagatcag tgggggaaat tttatacttg ggatgattta    30960
tatgaatgca tctcatcaaa gttcacaaca catttttttt ttcagttttt tattttcagt    31020
ttttagagtc agggccttgc tctgtcgccc aggctggact gcagtgatgc tatcatagct    31080
cactgcatcc ttgaattcct gggctcaagt catgccccca cctcagcctc ctgagtagcc    31140
aggattatag gcatgtgcca ctgcctcatt atttagactt ttcttatgtt gacttaatct    31200
tcccacaaat cttcaattaa attacttttt ttctacctta aaacatattt tcagaaagtc    31260
attgaaatag ggtgttacaa gaggaaaaaa ttgatgagtt aattttaaat attttatgaa    31320
gtgtgaatta tacctttta gatggaattt ggaatactga atcagtgaca tgcagtttat    31380
cagtatcttt ccgtttgtcc tcagatttcc aagttctgca agcacaagtt gctttgactt    31440
agttaccttg taactgttca ttgaaatcat tttcaatgtc tctcatggca tttaacacat    31500
agcacattct ataaattatt tattggttac attctgagtt ctaattgaga gttgaactta    31560
cacacagaat ttaagataaa aaatgaccat gtgaagacac aatagtatag tccagggatt    31620
ggcaaaattt tgggtaagga atcagatagc acgtatttta agccatgaga tctatgtctt    31680
ggccaggtgc cgtggctcag gtctttaatc ccagcacttt gagagcccga ggctggtgga    31740
tcacttgagc ccagggggttt gagaccagcc tgggccacag ggtgaaaccc tgtgtctaca    31800
aacaacgcaa aaattagccg ggtatggtag catgcacgtg tattgccagc tacccaggag    31860
gctgaggtag gaggatggct tgagcctac agctcactgc agaggttgca gtgagccgag    31920
atcgagccac tgcactccag cctgggtggc agagtgatac cctgtctaaa aaaaaaaaa    31980 aaaaaaaat ctatgtctca attctgctgt tgaagtgtga aggtagtcat aaacaataac    32040
tagtgtggct gtgttccaat aaaacttcat ttatcaaaac aggtggtggg ctggaattgt    32100
cttgtatgtt gtagcttgct gactactgat agagtggaaa gaacatgcac taatcacaca    32160
aaccaaagtt ttagttgaga ctacatcact tatcacctttt agggtcttgg ggaagcgtac    32220
ttaacatctc tgagcatcac ttccctgatt agtaaaaaat atgatttaga aaacttcaac    32280
taccttgcag tttttgtgag aatgtcataa taagacagga catatgaata attgagcaca    32340
cttttatata taggaaccat ggttattatt atcaaataaa ctctccaacg gaataattac    32400
tttgccaaca cgttttccat ttattctttt atccttcatt acataactag tttgaaaggt    32460
tggaggcgac caaagaccat tttataattt cacttatggc cgaagatgtt tggtagaagc    32520
ctcataagaa aagtaatctc attcctttat aagaatatac ttttaacaac tacttttttaa    32580 ctcattgaat aactacctta atgatcagtg ttatttttat gggttttgtt ccctccattt    32640
ttgttatctg catacaccaa ttttcaatca acatacttca atttaataga caaaaatttc    32700
ttcaaatgac tcagaaatta attagatcta aatccaaaag cagaaagatt taattatctt    32760
tatataatgc tcagtaatat aaatgcaata aatacaagaa aatgatgatc tttgagtgtc    32820
ttccaatgcc actctgctca ataagcagca gtggccatca gtgaaattga tagcaaattc    32880
tcaagtcaaa atgtgcttca cctcactaag ctgacaaagt caacataaca tgcacaacag    32940
ggataactga gttctcaaaa ctctcaggta ttacttctga ccttcttctc cactctgtgc    33000
tcttttgagg ttgggaagac aagataggt gtgtgtggga cacctccgct cagggaagcc    33060
```

```
atcagctctg gtgtccctac agcatttata ccttgctagt cacataacca cttggcacct    33120
attttgtagg tgtatgttat caattacaga ttactcataa attaaaggct aaccatcaat    33180
tacagattat tagtaaataa ttatgacctc aaagaacaac tgattggttt gatacatggt    33240
aaccttatga ggactctcat ttatctcgtt tttttaagtt atatacctat ctctttgggg    33300
ttgcactaca aaatatataaa atatgttgca taagatattt ataaaaaata attaattata    33360
agttctagtg gtgtggttta gtggcattct tttttttttc tttttttctg agatagggtc    33420
tcaatctgtc acttcactcc aggctgaagt gcagtggtgt gatctcggct cactgcaacc    33480
tccgcctcct gggttcaagt tattcctcctg actcagcctc ctgagtagct gaaattacag    33540
gcacgcacca ccatgcccgg ctaattttttg tattttttagt agagatgggg tttcaccatg    33600
ttagccagga tggtctcgaa ctcctgatct catcatcctc cgacctcggc ctcccaaaat    33660
gctgggatta caggcgtgag ccattgcacc cggcctagtg gcattctttt ttaaaaataa    33720
atttaattgt gtatatttag ggtatgcaac atgatgctat cagatacatt agacactaaa    33780
aaattactat attgaagcaa attaatatat tcataatctc tcatagttac cttttttgtt    33840
gttttttgtgg caagggcagc taaaatccac ttatttatca tgaatctcaa atatagtaca    33900
attttatcac ctacagtcct catacattag atctgtacac ttgttcatct tacacatctg    33960
ctacttgctt ggatcctatg gcctatatgt ccctattttc tacctacttt tccacccccta    34020
ttaaccctgt attttacgta gtctctgtat atttgaattt tgtttcaagc ttccacatat    34080
atgtgagata atgtaaatatt tttctttctg tgtttggctt atttcactta gcataatttt    34140
gtctgggttc atccatgttg taaatggtag atcttgtttt ttttagggct gactgatatt    34200
ccattgtatc tatgtaccac aatctttta tctacctatc tatcagtaga cactttagtt    34260
gtggctatta tgttttttctt ttttttctttt ttggagacag ggtcttgctg tcacccaggc    34320
tgcaatggag tggtgttatc atagctcact gtaacctcaa acttctgggc tcaagagatc    34380
ctcctgcctt ggcctcccaa gtagctggga ctacaggcat acattaccat gcctggctaa    34440
ttttttaatat tttttgtaga tatagcatct cactctgttg cccagactgg tctcaaactc    34500
ctaattcaaa tttagaatag agtatgacaa ttctgtaaaa tataaaaaac atgtccactc    34560
cgtataggaa gttatacaat gagaagaaga caaacactat ttacattact cttgataagt    34620
tttttacaaa gaaataaaac actttaattt ctaatgtttt aaattctggt ttgctaaata    34680
aataaatatt agttttagtg ttttttaaaat tccttatata gttataagtg atcttcctgc    34740
ctcagcctcc caaagcactg ggattccaag caagagccac tgtgttgggg cccttggaaa    34800
cagatatgct gaaatctttt cttgtggatc tacacccaga agagggattg ctgggtcata    34860
tgctactcta ttttttaattt ttcttttatt tttagtgaat atgtaataat tgtatataat    34920
tgtgggatcc agaattatat ttccatacat gtatacagtg tgtgataatc aaattagggt    34980
aattaacata tccattacct gaaacattta tcattccttt gtggtgggaa cagtaaaaat    35040
taaaaattct ctcttctaga ttttttgaaca tatgcaataa actattgtta agtatatcac    35100
cctacagtac tacagaatgc tagaactcat tcctcatatt tggctccaat ttcatattct    35160
ttaaccaacc tctccatatc ctcccctccc tcttaccctt gtcagcctct aataatcata    35220
attctactct ctacttctat ctcattgtct ttgatttaga atatgtttca taatttaacc    35280
aaaggtcaaa ttcttaggta ctgctaaggc aaagaacaaa gatcgcattc cagctgttag    35340
acatttctta ctactagtca tttttaagac aacatggggt gcaggtggtg aggatgagag    35400
atagagattg aaacatattc tcttaaatat cagctgttct cactctgcat agttccagca    35460
```

```
caaacaaatt ccaggtacta tggttagtta aataacacca gccctaaca acacaattca    35520 aatttctgtt accacagtat accgaaagtc attgcataaa gtacaaactt tgctgctaac    35580
tcttcagcct tcaaatcatt acataaataa cagaaaccca ttataatcag tgacaaaacc    35640
acagcacttc tttcaaagct ttttggagat tggttgcttc acatctgtta tgcagttcat    35700
acagacagca atgcccggac ttgtgtggcc acattgtctc ccagtggtga gcccatgtga    35760
tgtttcacaa aaatgcgcaa tcaaaagagg aaactggcca gcaaagatga aagagtagca    35820
aacaaaggaa gtgaaacatt ctggaagtaa aatttgaatc aaacataagt tgatgtatac    35880
aggaagtagc caccctgagg atgttgtcac tgctgcaatt caggagactc taaatatgca    35940
gtcagaggaa cgtagtgagg tgaaggtatc cgtataatgg ggaagaggt tgtgataaag     36000 agtgaaggtg tcccagagga agcgatgctg aaaaatacac cttatgttaa atacactgtc    36060
agtatatcat gacattaaag tgcaaatgat aacattttgt aaactgatcc aaacttaaaa    36120
aggagtatga taattctgta aaacataaaa atcatgccga ttccataaat tatacagtgt    36180
gaattacact gaaaaatcca acattagaga ggatatgaat acaattttt acaagcataa     36240 ttttaataat acacataata attatttgta ttcaagttta gtaatggtca aggtttggaa    36300
gaaattctga tcctgtgtag agaccctagt ttgaatgtgc ttatagccta ttattacatg    36360
tgtaatgtta cataaattac ttaactcaga ttttaatt catcagctat ttaaaatggg      36420
cataatataa ctatattaag tggatgttat gaagattaaa taagatgata tgtaaaatgt    36480 gtttttgtt tgtttgtttg tttgtctgtt tgttttttg agacagagtc ttgctctgtt      36540
acccaggctg gagtgcagtg gcacaatctc ggctcactgc aagttctgcc tcccgagttc    36600
atgccattct cctgcctcag cccctcccaa gtagctggga ctacaggcac ccgccaccac    36660
gcctggctaa ttttttgtat ttttggtaga gatggggttt caccatatta gccaggatgg    36720
tctcgatctc ctgacctcgt gatctgccca cctcggcctc ccaaattgct gggattacag    36780
gcatgagcca ctgcgcccag cctaaaattt ttttacata atgggtgttc agcacatgtt     36840
aaagccttct ctccatcctt cttccctttt gtttcatggg ttgactgatc tgtctctagt    36900
gctgtacttt taaagcttct acagctctga attcaaaatt atcttctcac tgggccccgg    36960
tgttatctca ttcttttttc tcctctgtaa gttgacatgt gatgtgggaa caaaggggat    37020
aaagtcatta ttttgtgcta aaatcgtaat tggagaggac ctcctgttag ctgggctttc    37080
ttctatttat tgtggtggtt actggagttc cttcttctag ttttaggata tatatatata    37140 ttttttttt ttctttccct gaagatataa taatatatat acttctgaag attgagattt     37200
ttaaattagt tgtattgaaa actagctaat cagcaattta aggctagctt gagacttatg    37260
tcttgaattt gttttgtag gctccaaaac caaggaggga gtggtgcatg gtgtggcaac    37320
aggtaagctc cattgtgctt atatccaaag atgatattta aagtatctag tgattagtgt    37380
ggcccagtat tcaagattcc tatgaaattg taaaacaatc actgagcatt ctaagaacat    37440
atcagtctta ttgaaactga attctttata agtattttt aaaaaggtaa atattgatta     37500
taaataaaaa atatacttgc caagaataat gagggctttg aattgataag ctatgtttaa    37560
tttatagtaa gtgggcattt aaatattctg accaaaaatg tattgacaaa ctgctgacaa    37620
aaataaaatg tgaatattgc cataatttta aaaaagagt aaaatttctg ttgattacag     37680
taaaatattt tgaccttaaa ttatgttgat tacaatattc ctttgataat tcagagtgca    37740
tttcaggaaa caccccttgga cagtcagtaa attgtttatt gtatttatct ttgtattgtt   37800
atggtatagc tatttgtaca aatattattg tgcaattatt acatttctga ttatattatt    37860
```

```
catttggcct aaatttacca agaatttgaa caagtcaatt aggtttacaa tcaagaaata   37920
tcaaaaatga tgaaaaggat gataatcatc atcagatgtt gaggaagatg acgatgagag   37980
tgccagaaat agagaaatca aaggagaacc aaaatttaac aaattaaaag cccacagact   38040
tgctgtaatt aagttttctg ttgtaagtac tccacgtttc ctggcagatg tggtgaagca   38100
aaagatataa tcagaaatat aatttatatg atcggaaagc attaaacaca atagtgccta   38160
tacaaataaa atgttcctat cactgacttc taaaatggaa atgaggacaa tgatatggga   38220
atcttaatac agtgttgtgg ataggactaa aaacacagga gtcagatctt cttggttcaa   38280
cttcctgctt actccttacc agctgtgtgt tttttgcaag gttcttcacc tctatgtgat   38340
ttagcttcct catctataaa ataattcagt gaattaatgt acacaaaaca tctggaaaac   38400
aaaagcaaac aatatgtatt ttataagtgt tacttatagt tttatagtga actttcttgt   38460
gcaacatttt tacaactagt ggagaaaaat atttctttaa atgaatactt ttgatttaaa   38520
aatcagagtg taaaaataaa acagactcct ttgaaactag ttctgttaga agttaattgt   38580
gcacctttaa tgggctctgt tgcaatccaa cagagaagta gttaagtaag tggactatga   38640
tggcttctag ggacctccta taaatatgat attgtgaagc atgattataa taagaactag   38700
ataacagaca ggtggagact ccactatctg aagagggtca acctagatga atggtgttcc   38760
atttagtagt tgaggaagaa cccatgaggt ttagaaagca gacaagcatg tggcaagttc   38820
tggagtcagt ggtaaaaatt aaagaaccca actattactg tcacctaatg atctaatgga   38880
gactgtggag atgggctgca ttttttaat cttctccaga atgccaaaat gtaaacacat   38940
atctgtgtgt gtgtgtgtgt gtgtgtgtgt gtgtgagaga gagagagaga gagagagaga   39000
ctgaagtttg tacaattaga cattttataa aatgttttct gaaggacagt ggctcacaat   39060
cttaagtttc taacattgta caatgttggg agactttgta tactttattt tctctttagc   39120
atattaagga atctgagatg tcctacagta aagaaatttg cattacatag ttaaaatcag   39180
ggttattcaa acttttgat tattgaaacc tttcttcatt agttactagg gttgaatgaa   39240
actagtgttc cacagaaaac tatgggaaat gttgctaggc agtaaggaca tggtgatttc   39300
agcatgtgca atatttacag cgattgcacc catggaccac cctggcagta gtgaaataac   39360
caaaaatgct gtcataacta gtatggctat gagaaacaca ttgggataaa tcagctgcta   39420
tcataatcat tcctcttcca catcagataa atgaattaac ttttgaata gggttattta   39480 atataaagtg cttaagtcta attatgagaa gaaataagat aattacactt caatggttaa   39540
agagagggag aataatttgc atattatgcc tgatgtaaaa tgtttattat gggtacatat   39600
taagtgctaa ctaatcgtta attgttcttg ctacaagtct taatgcaggg aaacaagaaa   39660
ttattacata gtacctaata ttatcttcta atattaaaga aacaatttcc cctaaattca   39720
tcccattagc ttttttttt cggtggggca ggggagaaat acagacttca gtaaacttgg   39780
gccgggaact ttctacctac aaagttcaaa taaaataaat tatcctagtt agataatatc   39840
aatgaaaaat ccaccaactt aaatcctggc tgtttgatct caggaaatta tttcagttat   39900
caacttaatg catcatatta tagaaatata tgaaaatgtg tttaattaaa cttactgaat   39960
gatatgtttt ttaaggtact ttaaaaataa acctatgata taaagttact tatttttcat   40020
gcaagtatag tataaagaaa tttctaacac tggagatttt ctgaaggttt tgattcttat   40080
aaatttatta catcataatg aacaaaacta attttcaaca tattatgatt taaatttcct   40140
tagtaaattg tttttaaattt attttctta aatccatatt tacatatgta tatttaaata   40200
tacatattta cttgtataac aattcaaaac catatattaa ttttataatt ttgtttaatg   40260
```

```
tcaaaggtta gatttggcta tatctattct aaaagttgct atcacatttc cttttggaa   40320 ttttatttt aaagtagcta aagtcaaata taaacctatt atttatatta atgcagacat    40380
tagaggtaga cactaaattc gttttagtat attctaaatt atttattatc tactatgaaa   40440
taatataaag aaaaataaag cagaatccct gatttcaaag aactcagttg ccgaaaaaca   40500
gttaccattt attagaccca aaatgtacta atatgagtgt gtctcttttc cttttgtttt   40560
gtcacccgtc atttggaatg tcagtgagta gagagatagt gtgaaaggcc ctcaagggga   40620
aaaatagagg ttaaaggtca gcagagaccc tactagagaa atcagttcta cagaaatgtt   40680
tttaaatgtg tcgattattg ctacatgtac actctgtcat tttgtaatgt agccatttta   40740
tttatgatta taataataaa acaacaaaat tataataatg tgtagagtac attttactgt   40800
gcagtgtatt gcattaaaac tagattaaaa tttatacata tataaaggt tatctagata    40860 ttataaaatt tatggctgga tctgtaaaaa attcaaaacc tatttttaat cttgctttga   40920
gattttataa caagaaaatg ttcgtttcaa gcaaaatttt caattcacgt ccttgaaaag   40980
gaaaaaaatg acaacttgaa acacataatt gactattttt aaaggatcaa catttcagaa   41040 atgtttaaa acataagatt ttcagtacag cttttcgctg gcatttaaat cgaactttga    41100
attgtaaata gctcttactc ttaaggagac atcagccata tccttagaag tggcacggag   41160
ttggtaggta gttgtacaaa attctagcct aaaagacaaa tagggagcaa cactactgtg   41220 gacccttttct ggtcttgggc tgtgtggcta tgtcaggctt gcccacattg cctgaactaa  41280
ggagaaagcc tcttgtcctt acagacccc ttagcttaca tagtctattt gaaaacgaat    41340
tgctttgtcc acaccattta aatattggct tcaggccggg cacggtggct cacgcctgtt   41400
atcccagcac tttgggaggc tgaggcgggc agatcacgag gtcaggagat cgagaccatc   41460
ctggctaaca cggtgaaacc ctgtctctac taaaaatata aaaaaattag ccgggcgtgg   41520
tggcgcgcgc ctgtagtccc agctgctggg gaggctgagg caggagaatg gcctgaaccc   41580
gggagtcgga gtttgcagtg agccgacatc gtgccactgc actccatcca gcctgggtga   41640
cagagcaaga ctccgtctca aaataaataa ataaataaat aaataaataa ataagtaaat   41700
attggcttct tcaactggtg agatgaaaac tatacaataag tcatgtgaat agcactaaac   41760
agctgacatg gtgtaactcc tctcagactg aggcttatct ggggagtaca aagcatgtca   41820
agaaaatgtg ccttcatttc cttagatgag tgtccccatc ctccactctc ctccactgtt   41880
ctcctctctg cttctatgat atcaactttt ttttttttct ttagattcca catgagtgag   41940
atcatgtggt tgtttgcctt tctgtttctg gcttatttaa ctgaacaaga aagttttga   42000 catgaaatta aacttctgct tgtaaactca attcaaacta tttacactgt cttctcaaaa   42060
atgttaactt attttaataa atctactgaa tgaccgtatc tcatttttgtt ttatgaaaag   42120 aaattgtaag ggtgctcaat agcctcttca ttttcatact gtctagctcc tgtgctccta   42180
ttaaaattac tgcaaattta gcttttaag aacccttttgt ttcactacct gaagttctat    42240
aaaaagatcc aagttccttc acaaccgttt cttatgctgt tattcgtaca tatgtgataa   42300
taccacgtct gaacacgtag ataataagta ggggctgggt gcggtggatc atgcctataa   42360
tcccagcact ttgggaggct aaggcaggtg gatcacctga ggttaggagt tcaagaccgg   42420
cctggccaac atgatgaaac cctgtttcta ctaaaaatac aaaaaataat aataataata   42480
attagccagg tgtggttgtg ggcacctgta atcccagcta ctcgggagac tgaagcagga   42540
gaatagcttg aactcaggag gcggaggttg ctgtgagctg agattgtgcc attgcattcc   42600
agcctgaaca acaagaatga aactccatct caaataaata aataaataga agtatgtatt   42660
```

```
gtgttgctta gaaggtgtgg tggaaattaa cttgctgagt gagatcaaag gattggcact    42720
gaattgaaat aaagaaatat tcatgctgag tctggttcaa atataactgc acctgtaaga    42780
attgctttct gtaaactttc catagtataa accaaatcca aatcactcat ggctttacat    42840
tcctgatcgt taaacttgaa gcactttta atactgcatg actttagcca aaatatctta    42900
gccaagattc aatgtttggt tgaaccacac tcacttggac atcttggtgg cttttgtttc    42960
ttctgaccac tcagttatct atggcatgtg tagatacagg tgtatggaag ccgatggcta    43020
gtggaagtgg aatgatttta agtcactgtt attctaccac cctttaatct gttgttgctc    43080
tttatttgta ccagtggctg agaagaccaa agagcaagtg acaaatgttg gaggagcagt    43140
ggtgacgggt gtgacagcag tagcccagaa gacagtggag ggagcaggga gcattgcagc    43200
agccactggc tttgtcaaaa aggaccagtt gggcaaggta tggctgtgta cgttttgtgt    43260
tacatttata agctggtgag attacggttc atttcatgt gaggcctgga ggcaggagca    43320
agatacttac tgtggggaac ggctacctga ccctccccct gtgaaaaagt gctacctta    43380 tattggtctt gcttgtttca ggcattaacc cagataaatg ccatgcaaat tttataatta    43440
ttatgattgt ttcaatttct ggaagaaagt taatgaaaca aaaaatgtag taaaatgcca    43500
aaggaacagt gacatttcag aaagaatgag ggctttcatg ttaattgtaa gtcttggaat    43560
ttctcttcct tggagtaaca aatccctttg tgcctaattt cctaatttcc aaaataaagt    43620
tcttttactt atttctttat agtgacatca tctcttatta aatggcatat ctgcatatta    43680
cataacagtt cattgccaaa tacatatttg tgggaaatga gagacttaaa atacatacca    43740
accagagata tagttttgag gtagatttta aaattctgag aagaattttg actgaatttt    43800
tttgacaaac atgggacacg aataagatta taccaaagat attataactt tcatttaaa    43860 tatgaaacta atacagtatg aggtgtcaac aacgttgaag tttcacaaac atcaccacaa    43920
cagcaaaata atttttgctt tttccctgcc acaatgacct ccttgctatt tcttgaataa    43980
atcaagcata cccttgccct gacacgttct tggggaggcc tgccctaatc tatataaaat    44040
tggagccatt cttctcacct ctggtattcc cagtctccct acttttttc cttcttctt    44100 tcttttcttt tttcttttctt tctttccttc tttctctctt ttctttctttt ctttacttc    44160 tttcctttct ttctttttccc ttccttcctt ccttcttccc ttccttcctt tctcccttc    44220 tttctttctc tttttttcttt cttgcttcct tccttccttc tttcctttc tttctttcc    44280 cttccttcct ccctctctcc ctcccttcct tcctcccttt cttctttct cttttttctt    44340 tcttgcttcc ttccttcctt cttttcctttt ctttcttttt cctttctttg ccaaagtgtt    44400
attcaccttt aaatataata cataatgtgc ttactttaat gtatgatttt tattttattt    44460
ctcccttcta gaatgtaggc accatgagag tgaaatatat ttattttgtt cattgatatt    44520
tcacaagtgt ctgggagagt ttccaactta cagtagacaa ttaacaaaca tttattaaat    44580
taaggaggga aggaagtgag taagcacaac aactttcatt tctgggtctt ttataatcat    44640
atgcttagta taagaacagt gctattcagc tatccaaaag ttacaatcaa aatgattttg    44700
gatgaatatc ttgaaaattg tgagaaagaa gttttatttg ctggcaaact attctgggtt    44760
gtttccactt catgtaatcc taagtagcag ccttaccttg atagcccatt aaaactctga    44820
taataaaaag gcagaacaaa aatatctgtg atatatttag atttactaca tgtacttaca    44880
tgtctagtgt ctggtgcaat ggatgctaat gatggcaaat ccttactggg cttcagtga    44940 agttcttcag ctaatgcttg aatgcatggt tggtcatggt ggtaccccctt tgtacaaaat    45000 atgcttttca ataatctta ttagggataa taattatatt aattcctggt ttccatctaa    45060
```

```
aattttaatt ctatttatag cttcgtaaga tttcacaagt taagagggac ctcagattaa   45120
attagtacac aggcaattaa tcagttttgt gtctccgacc cttttcacgg gctaatagaa   45180
gctatagacc ctcttagctt cagaaaaatg tgcactcaca tacgcacatc aaagagctta   45240
atgggaagtc cattgacaga ccctctgttc agatcaatct tctgattgta gagatgagga   45300
aacagaaatc tacagaggaa gtgggtagtc caagattgca cagtcatttg gaatagactg   45360
gacaccagta gtacttttcc agccactata tcacttcccc aagcacttcc tcaaaactta   45420
ccttcctttg ggtctttata cattcagtta tggacaacta gatttaacta gaggatttta   45480
ttgcttcaga atattaagca acagggaaac atgtaccgtc ttttattcac ctgcatttaa   45540
ggcatacaat ataaattgca aatggagcat gaaagtgctt aatctttttac aaaactgggt   45600 ttgctttcca cccatctaaa aatacttcta tttatttaa tatttaaagc agaaatctaa    45660
gtgatgtgac aaaattaatc atttggagat attttcccta taggtagtat agtttcttac   45720
tgatttctaa tatgaaaatg aagccataga acctagaaat tgcagcatag ttgtggaaat   45780
aaacattgga ctgagagtga aaatggctag tcttcctctc tgctcataca ccacctgact   45840
ggataacctt ttgcagatct cctaaaagtc tttctcataa aatgaggaag ctctactaga   45900
aaattgttga agtctaattt agcaataaag ttctgagttt ctataataat tcaaagaata   45960
ctctaataaa tgtctgcaat tgtggtcaca tctatgggat gctaaaaaat ctggatggtt   46020
tcaatgaaag tatttaattt gttcattatg aactttgaaa taatttattt cattttttaa   46080
actttgatca aaatgaccct ggtaaataga aataagcaaa ctcttttgc ttgaaatgct    46140 tattaatgac tgcattgaga cactcattca tcattcaaga aagaatgttt gctcacactg   46200
tgccagaaac ttggaggaag agggatgtga caagtagggg tactggatgt ctagcttgta   46260
gaagtggatt aatggctctg cttttaagat caggaacact gaaagggagt aatggcaccg   46320
gttttcacct ttcatgccct ttgagggtat ctggtccatc accctctagt tgatgaggga   46380
gggaaagttc cctctcccttt cacaaatagg tggaaattaa atgacataat tctgaacaac   46440
caataaatcg agagtaaatc aaagcagata cctgttttgt taatttgatc atatgaatgt   46500 agctgcccttt agtaataatt tctaagtata agactagtta aaggacaaat gagttatctt   46560
gaattataag attttgttttt acagaacaat attaactctt gtgtttagta cattagaata   46620
atagatattt tgatccatat ttttactcat gtgcacataa gaagttatca gtcatacaat   46680
tcatttcttg aagttcatac ctttcattgg cagagtagaa acaggttaaa agtgcactgg   46740
cagaaatttt aagtgcaaag caacagtgat gttatataga gaaaatttat atttcctact   46800
tctattgaag aagaaagatc tgcttgttct aagaatattg tacaaagaaa gtgacttgaa   46860
tcagcgttat tctgtaatgc tactatgcgt gcagtgtgga gtagccacta gaacacttgg   46920
tctatcccag ctcctcaaca gtgtcttgct tgtggctggt gctcaaataa atccttgctg   46980
aactaatgag catctctttc atgccacatg gaatgctcta aaagagttgg atcctgaagt   47040
ttttatattt ttgtaattttt ctggagtgtt agagagcaaa agtcctgaat aaaactgtgaa  47100 gccactgcct gacaaataat acagcagtca gcttcgttat catatcccat tgagacacga   47160
cttatctaca tgatgattaa tagttttcac gcaagaaata agcttgaaat gtctgttgcc   47220
ttgggtactt aaaacatcca ggttcagcga tgttatttat tgttgttcaa aatcagaatg   47280
aagttcctaa gcaatgccat tttgaaaaaa ttcatcaat atattatgaa caactttttt    47340
taaatcttga tttcaaatgg attgacacgt gtatattctg taataatcct gacttaattc   47400
ataaaaggat agctagccag ttgtgtgcta gatgaataaa aaaaaagcag gttttaaaat   47460
```

```
gtcaggtttg acatcgtgaa tataatatct aagtatcctt ttactcattt cctttgactt    47520
actatggctg tcatgttggg cttcatgaaa atttatttt aaacacttga gtgttatgga    47580
ccctctgatt aaatgattaa tcagatgatg tatgttgcca tcagctgaat catttaatgt    47640
tgatttcaca aacaagcaca ggtcacaggc aacatttcag atttctttga agaagcacac    47700
acaggtcaca ggcataatct taaaataatt ttataacaag gtagtaataa gagatgtcag    47760
gactggagaa atattttaat ttatagtaag ctttcccctt aagtgtctaa taattgttaa    47820
tataatacat tgcctcaaat aattaaaagt ttggttcttg tccttgtgct tgacttcaga    47880
agataaccag atgactatta ggtatattta gacctaaatt aaaagctttg agacacaatg    47940
aattgcctga tttgtatttg tgtttcgagt ggcatatact attactggca ctataatctt    48000
agattaaagc atactgtgat tattaaagaa aaatttaaga ttgatttgtt tctaaaggta    48060
tgtaacagtg acattttgca atgtggtatg taaaagttgg tatttctcac tcatatgaga    48120
gcccactaat ggtacataaa ctgtccccac ttagaaacac aattattatg gcctttcttt    48180
gtatctgaca aaatttcact gggttcaaga tggatgaata gtgaattcta atgaccctta    48240
atcctgtaag gttctaggtg ggaaagtact ctgtaattat gtataaaatt ataaggaaaa    48300
taggcttact gctatgtttt cattaaaaat cattaactga gtacttaata tgtgccagac    48360
actcagctgg gcaccatgag aaatacaaaa ctgagtaaca tatgggtggc tcctgccttc    48420
aagaaatggg cagttcaggc cgggagactg acatatttac cctgggaaaa agggagcagc    48480
tgtggtctct gagaacaata tggttttgtta caagtatata tccatcatgg aaaaaaagag    48540
atttatctta gaaatgagag aggctgatgc tctcaataaa tatcatacat taaattgtgt    48600
ttttgtcagt agactgaaat tacctcacat acacgcacag atagtagcca tgatatttta    48660
gctgcttaga tatagagaca aatacttcca cccaaatctt aggatcagtg gttaatagtc    48720
tgtaagcatt acaatcccac aacatatgca tgactataca tccaatttta atattcaaag    48780
aactgattgc gatgatagtt tgtttgtca agaaatgta ttataggatg agtgggatag    48840
aactgcatca cgttcaccaa acaaataggt ttaaatcata tttgtgcact tcccttgttc    48900
cttcataaat gtttaacata gcttaaaatt ctgtggactg caacgtgaga gcaatgacca    48960
cacttctgtg aacccatttt tactgtgcat gtgctaacgt ctattgttag tattccttca    49020
cttgcaaaga tggcatgata attttgctgg tttcattaat gagatactgt taaatgtagg    49080
atgacttcaa acttagttgt attgtaaaat tatttttaat tgtatacatt taagttgtac    49140
agcatgatgt tttgagatac ttatctttat ttatatatat atataatata cacacgtata    49200
taaaagtgat tcctacattg aagcaaatta acatacccat catcatatgg ttatctttgc    49260 tttttttacta tcagtgccta aaatctactt tcttgaaaaa ttaccagtat gcactacaat    49320
attattaaca ataatcttca tgttgtacat tagatcttta gacttactca tcttacatga    49380
cttaggtttg tttttacctc tactaccatc tgagccatat ttccactttg taatttgata    49440
ataaacttgg aaaaatagca cttatatgtt taggtgacgg gcataaatag gataagatgt    49500
gtttatatat tattccatat atcttgtctc caactacaat gataaacaac ctgtttgtcc    49560
ctaaaaagta agaaataact tgactttct gccccttcaa gcataggctg ttagctttta    49620
agttttaggg agacattgat gatgctattt gctttatcaa gaggaaattg tcaaaagagg    49680
tcttttggtt ctcaaactat tcaaagtatt taaaaatcag gacaaaatat gtttacgtga    49740
tattcaaggt tacagaaatg aggtaaatga gatgccaatt gtatttgtca tgcaaatata    49800
taattatgtg tatgagagtt agatgataca tctcatcaat ttaattgttc ttctacaagg    49860
```

```
agaaaatgaa caatttgtca actcgtatat gaagtaattt ttataagaaa ttttattaaa   49920
acttttaaca acatttggat ttttaagttg caatttaaat atcccttct accaggtgat   49980 tctggaatca ctaagcagtt acctgtgaaa attccaaagt agcatttaat tcttattaat   50040
gtcatagtga acactaatgc aaagaatact gagccagaaa ttatgcttgt tgaataaata   50100
gattatttat tgaacaagta agtgaaaaaa tggaataaaa gaacagatat atattttatc   50160
ttcctgctta gatgtgggac tgtcctactt ttctctggtg ttcacaacaa caatatgata   50220
aatctaattg gaattcagtt cataggaatg aattcagtta cattatggat tgtgatgaat   50280
aatgtacact tttaatttaa tgaaatcaaa tagattttaa ctatctatgc ttacaatggg   50340
gtgacataag tctgacaatc cttaatatca agtcatctcc aattcacatg tatacacact   50400
ttttttctat ttggctattg ggaatcctca caaaaatcga aaattgccct ttcagtgtac   50460
gttacggtat ttcatgccac acagattttc tgaggttgta catacagctt tgccttgagg   50520
ttccaatttt tgctcagtgg attgagtata tattatttgc tatatatcag aagaggcatg   50580
tgcttcctac ttatgtcacg taactttggg attaatgtaa ttgtcctaca aagcatagat   50640
agatagaaat acttcatcct taatttctaa tattatgaca tatctaaagt aggcaccttt   50700
aaaagataat ctccactaaa tacgaatgac tgcttatagt ggcaattcat ctttcatggt   50760
agtcctccta caaaggtata ctaacattta tgagtttgaa acaaaggcaa ttcacaagtg   50820
ttctgctaga gatggtctat atctgctgtt tgatccagca tgatggccag ctggccctcc   50880
tgtgcatgac ggctcgtggt ttaactgcac cattttgttt ggtcatatac agggaaaaca   50940
tggcatggtg tggagggcat gggcttgaat tcagggaaca gagagttggt cttctctctc   51000
tcactctact ggatgatgtc atctcccctc tctaagcatg agttttctta tctgtgaaat   51060
aaaaatgttg aattaaatga gttcaaaatg ctttcagtct gtgtttaata gcttgaatct   51120
taagacaatg tattcaatta tgcgttgcca gatccctggc aactcatgta accttctaa   51180 accatagcta ctcatctgta actggccagc caactgccca gggttggagt gtgaatgaaa   51240
taagataatg cagacaaaag attttttaaaa attgtagtgc attatacagt tgtaatattt   51300
tgccaagaac ttcatttttc tctaagaagt gtgtcgatac atgatcacag aaaatctttt   51360
ccatattcct ttgtagtttg atgatattaa gtaagtaaat tgtataacac aaagagggaa   51420
aagcatcact gaacatgccg ttttatttag ctaaataaaa tgtaatcact attagttttc   51480
ctctgatttc cccaaagtca tgtgattcca ttgagtatta tgcacatggt ataattagaa   51540
tggattctct gctcaaataa ttttgggaaa catttaaatt aacaaagttt aaaagtatct   51600
ctgttaagct gaagcaaatc tcaaaggcct taatattgta tgtaagagga atagttacca   51660
tctttcctaa tgcctctttg acgccaaacc catggagaat agttctaggt gttcagtaaa   51720
acacagattt gggatgccac aggttaattg gaactgtccc ctgcaatctt tttctcttt   51780 tcttaataat ggctgattgc aggtcctaga tgaaagacat ttagagagat tatcaggact   51840
cagcatccca tatcagaatc cattcttta tagtcatttt ctgttacatt tcttgggaca   51900
acaccaaaga aatgaccatc ttcattcaca taggctttgt accaaatgct gacaaagatc   51960
cttggtgacc tagatggggg caggtctaag tagattgcag ctgtaaaatt ggctgatgaa   52020
tgatctcagc ccctttact cacactcaaa ggcaggacag tccattaagg ggaaggaggg   52080
cagagttttt ccttaggcca attccctatg ccagaacttt ttagaatgga agcatttcca   52140
gaggagaaac aaccccaagc acagttcaaa gcccctcct cccaagttca tttgaaagtg   52200
ggatggttta tctgcaaagg gggaaaagat gagggatagg gacgggaata tccctaccct   52260
```

```
tcagagagtc tggtttcatc ctgcacttttt actgcacagc cacaaatgcc ttggggtgaa   52320
tctacaatat gatacatcat atggtctaaa cgtgcctggc tgatcctctc taatacttca   52380
ggggtctaaa agggataaca tgctctcctg ttactcaccg actctgtccg ccatatttca   52440
cccagccagc cactgccttc acttccgtcc gaggcctaat ctgagcccat gggaaaccta   52500
agaaccccta ccacaactgc ctcaactctt gggaatcagg gtgtatgggg gtgacaggaa   52560
gtgagcatac attctccaac ttgatatgtc agccccacg tctgtatgaa tgtttgctca   52620
cactgtgact gccggccttg ctcctcaggc tgcatcctac cagggagtaa gacccaagtc   52680
cttcctgctt tcagacaaca ccaagcctca tgagtcccca ctcagaggaa ggaccagaga   52740
caaactctaa tgttccacta atacttccct tcttattact ttccttgaaa atcccttctc   52800
cctctttctt tttatacttc gctaatgaaa ggtaatgaaa gggtctggca cttggaatt   52860 agaattgata catggttttt aacccgcgga cgtattccac aataacccctt gcatcttcta   52920 ctaagatgtg ggctaggaag ggaccagcca gttcccaggg tcacagtgcc tcagctgatg   52980 tttcatatt tcagcaactt tatgttagag atgtccatca atcagaacaa tatggttaga   53040
gaataaacta ataaaagtca cttttgagga catgttggaa gtctatcaaa agcattgaaa   53100
ttatgcatgc tctgaccagt cgcatgtcta agaatttaaa tatgatcata agtttaaata   53160
tgaagatgtt tatcacagaa ttgattataa aacaaaattg aaaaaaatag tgctagaagt   53220
ttgatcatag ggacctcatt aaatgcatta tggttgatcc atgcagtggt ttgctgaaca   53280
gccattaaaa tgttgtagaa taattattaa tggtgtggaa ggatgctatt gttgcagtat   53340
gtgaaaagaa caaattacaa agcagtttgt gcagcataat attttttattt tttaaaaacc   53400 tgtatgtggc ttatgtacat ataaagacgt ggaataaatg cacaaggtac tcagttttt   53460 tcagtgaagc ccatttttgca ttttgggctg ggtaattctt cgctgtggag aactctcatt   53520
cattgtagga tgtttacaag ccctgggcct tacctcttta acgccagtag gcaccccag   53580 catggcaaca agcacaaaat ggtctctctc atattgccct tgaggaaatt ttgcaactaa   53640
gtaactatta ctgggtccta gattacagtc tggattattg cgttcctttc ttattttat   53700 tttctccaat tcccttttaat aagcatgtac tggattcata aaaaaacaac ataaatggta   53760
attacaatat tccgcactgg ttaaaactta tgtaaataag cattctgctg ctttagccac   53820
aattgcaatt tatgctcctt ctcttttctta agttcccagt tcccacgtac attcattcga   53880
ctgattcaaa agtcattta gcttgataga ctcttaaaag ttagagttat catttctgct   53940
atttattctt tcaattatcc atttgtccac ccatccatct gatccatttt gttgatgcat   54000
gctgtgtata aaatactaca ccagcctggt gcggtggctc acgcctgtaa ttccaggact   54060
ttgggaggcc aaggcgggtg gatcacctga agtcaggtgt ttgagaccag cctggccaac   54120
gtggaaaaac cctgtctcta ctaaaaatac aaaaattagc caggcatggt ggcagacgac   54180
tctaatccca gctacttagg aggctgaacc aggagaatcg ctcgaaccca ggagatggag   54240
tttgcagtga gctgagatca tgccaataca ctccagcctg ggtgacagag caagactccg   54300
tctcaaaaac aaacaaaaaa aatacaatgc caagcatcat aaaaaatata gtgatatata   54360 agacctatt gttgtgctct aggcattgac atctagctgt caaccattaa tatgtgtagg   54420
agtctatcta tcaatattat ggactgtgct tgaagacttc ttccccaatc ttttctctt   54480 cccattaagt ttgaagtgag gttttctgag tgaagtatca tagtacatac agtctcatta   54540
tttttcaaaa atctctggtt atagtacatt tctttccttt atccccttg ttcccaacta   54600 tcaaaccatt ttggatatcc agtattggta tccagtatta ttaaaaagca aaacagagaa   54660
```

```
ctattaacaa aaaaatttgt aggagtaatt ggttgtatgg tatccagtac tattagatag    54720
taaatcagaa aattattaac aaaaatttta gacgaataat ggattgtctt gcccaagtga    54780
attgagtgat ttagttgttc tttcattttt agcaagtaca gctgatcatt tgaggcctta    54840
ctcattgttt gattttgcaa attcttacta ttataaatgt tttgggctct gagaaagctg    54900
ttgtcttaat ctgtttgtgc tgttataaca aaatacatga gactgggtaa tttacaaaca    54960
acagaaattt atttctcata gctctggagg ctgggaactc caagatcaag gcatttgtct    55020
tcaggttcag tatctggcga gggccggttc tctactccca agatggtgtc ttgtcactgt    55080
atcctccaga gggccaaatg ctgtgttctc acatggtaga gagatagaaa gggccaactc    55140
actccctcaa ggcctttcat aatgttacca attccacttg tcagggctct gcccccgtga    55200
ctttattacc tctgcaaggc cccaccactt aatactatca cgttggttat tacgatttat    55260
cacatgaatt tcgaccatac tagttgccat cctttcattt tcatatatcc ttaaaacttt    55320
gcctttctca ttttaatgta ctttatccac agtatgccaa cttttcgata cttttgttaa    55380
cctgtctgac gatatatagg aaactgtaaa agtgcagttt ttgatacact ctttagctgc    55440
ccgtttactt ctactgtcgt tagagaaccc catccatagt gcatgtgttt attttgtgta    55500
tgaacaaaga ctttatatat agtttgggtc atttttattc attagtgctt cccttataat    55560
ctctgaatac cattttatta gtacatactg ctattcttaa tagtaactag catgcctgat    55620
catcccaaat gtctaggttc acattttaaa ataagttata tctttgggct taacagttta    55680
ttgaaaggta acaaggattg agtcatagtt gtatgttttt ggaagtagaa ttcaactgta    55740
aatagaaatt ggttgtttag atctcactat atatgaaaaa atgaaggctt taggagaaaa    55800
tctccccaaa gtacccattt ttcatgtgat aaatatcatg aaatgatttg agaaaaaaat    55860
gtatatttgt tacagctaac aaatatttgt gttttttatt cttcatggag agaatgaaat    55920
ttcttctctt ctttacacat ttcttttttct tattagaaac taattggtgc ctttataaaa    55980
attaactgca gagcactaac gtgtatatat aagtattatg tagggtgtag ggtatgttca    56040
gggtatggtg tgtgtgtgtg tgtgtgtgtg tgtgtgtgtg tgtagctgtg tgtgtatata    56100
atgaaatata tggtagtgtt gtttcagaaa tctgcttggt cttcccagag ttcattcatc    56160
ttataaattc atctacattg atctctattt ttggaatcca tgaaatgttt tttggcagta    56220
cttcctttaa tatagtgtgc tggaaatctg gaaattccta gccagattag ttacaaaaaa    56280
ttagccagtg gttttgcact ctctatagaa tcaaggccca aggcctactc ttgttactca    56340
gggccttgtt ttatctggcc tctttctttt cagccatata gctctcaaat actcaacaaa    56400
attcttcatt ctaggtagac aagtatcttc aaaatacttc ccaattatct aataactgtc    56460
ttaccactaa gaaggctttt atgtctcctg tctgaatttt atccatgcaa aaagtccag    56520 cccaagcctc cagaactcca aaaagttatc cctaactgct gaaacacagt aatttcacta    56580
tgtgaaattt cactttggtc tcctagcatt tgcagatata ccatacatat ccttgatcct    56640
tttcctttca taccttttat atctaaccct taagctaata attttaccta cactgtaatt    56700
caaaatgtat ccccagtctt accatgtctc ccttctctac tgttaccacc ctaggctagg    56760
ccttcatcat ttctcacctg gactccttcc ctaacctctg aactgatctg cctgcttcca    56820
cttagacacc caacctagtc cattcttgag cagtcggaat aattcttta agaaagaaac    56880 cagatcacat cccctctgc tcccaaccat ccagtgacct cttatcatac atagaatgaa    56940
atgcaaatct ttactgtgtt ttaaaggccc tacattatct ggccctcagt aacttcttac    57000
ttcctatccc ttttctcctt gtatgccacc ctccaactac actctaacta cactgtcttt    57060
```

```
ttccctgttc ttcagacctg ccaaccatat tttcactgct caattaatat gtagaaaatg   57120
aattgttcgt taaatgtaga ctgtttcctt cttaaagcaa agataaatga cattgtcttc   57180
aaaaacaact aactgcccag aattcctgat tttaattta aaaagacaaa ctgcaagaat    57240
gtgttaaaca gtaaggaaac aattcactac ttcagaattc tatatgattt cactgcacgt   57300
tagtaatttt gtatattata gaatatgagg gtattctaat aaacttaact ctatgctgta   57360
tacttatcat gatagctcat tttcttatat gtttataaca gcactactta ttgtacatgg   57420
atacgtggga aataaattaa ttttctcctt aagaacaaag caaccatttc actcatgaga   57480
taaatcttga agatttaaaa actacttata attaattata cattattcat ataatgttaa   57540
gtattttctt agtaaaccac ataatttaga atggcaattg gacagatggg cagaaccaca   57600
tgcatccact attaggcagt tggtgagcat aagatgccag aaagaagatt aggaatatca   57660
aggcagggag cttccgatcg ctcttgaaaa cattgaccct tcactcctca ctctccacga   57720
tgcatttcct ttgaaaagta atgccttcca aaacaaagtt ctctgtttta tatctaaact   57780
tactcaatag tttctcatgg ttattgatat ataaaaaata aagtaaaatg tttaggcaga   57840
ccaaaagaag aatttccccc tccctctgcc ttttatgcca aggtgacagc tatgaaatgt   57900
acagtacgtt tcctctgcaa ggaatgtagc agtgttccat tgcaagaaga tgagagggag   57960 agaaggttg cacgctgagg aatatagtgt catttgtcac tgcctagact catcagctgt    58020
gtggaactct gagaggcacc aggcttcttt atttatttct tcagaaactt cagcaaaaaa   58080
gatttcatta ggagcagaga aaaatgtgaa aaacgaatta gcttttgtga tggggagtag   58140
tcatctctga atattgatca agattaagag ggttgtcttc gtaacttctt ttatccatag   58200
tctatactga tttaactaga aaactaattt caggtggtat ttcgggtgtg gcagatcttt   58260
atagtaaatg aagaatctag tcaaatctac tgaaaaactc tgcttacttt aatgtttgat   58320
ctggttgaaa ccatttttagc ttaacaatcc ttcctctgaa acagggaatc aattgatatc   58380
ctacagcaaa attatgtgga agggccatta gcttcacatc caatgcaaat tttgcctgtg   58440
tttactcttc cccaatccaa aatatatcag atcctagatg ccagtgaaat cgtttgagct   58500
agatggcttg agggtcatag cttttttcat ttcctgttct cagacctctt ataattgata   58560
gaataaaatc agaagagccc tagagctgtc ccacctattc tgcctcacaa agtagaagt    58620 aatggcaacc actatcatag ggatcatgct caccttttc ttaccagaca aatttggata    58680
ttagcttgaa attaatacct tccttaaaat gttggaattt ggttatatgc gaaattttgc   58740
tctatttatt cattatattt tgtatggaat tatttttgcc ctatatttc acttaagtgt    58800 tctctaccca agattttaat tgaacccaaa tcagccagac acacagacat ggattttgct   58860
gccaccaagg ttaattcttc tttaaagtt aactttaaa atttggtaaa atatagcttt     58920 gaaatttgc attcgtctag tgtttgttat gtatttcccc cttttgtttg attatatgtc    58980
tatatttttc ttgtagaaat tgattttaa cctgcttttt atgttagctt ttatgagctt    59040
ctgtctgaat tctgaatatg tctttcttaa tgtcttctaa atgtttcttt ctggattatt   59100
aaaagattta ttaggctttt aataattata tttgttacct tagggaatgt gtttgaaaat   59160 atttaaatg gaattgccag ttaacacagc attgaacttt ttcttgttag agatacattg    59220
ttttctaggc atttattgg gagagaagtt agtatgatat aatgtctttg gctgatatta    59280
actcttctaa gatgcattgt ttctgagaac accattgtct gatttcattc agggaaattt   59340
cacacaagcc agtagagtca atactttttt caagacctgt taattgatat atataaaaac   59400
ttgccattgt ttacatgccc atttcagatc ctttatgtga cctaagctag aaatgcattt   59460
```

```
taacagcatt tgttttccaa aaatatttta tttatttatt tattatagag acagcgtctc    59520
tctatgttgc ccaggctggc ctcgaactcc tgggctcaag caattctcct gcctcggcct    59580
cccaacagtg ctgggataca ggtgtgagcc attgtgccag gcccttgttt ttattttttt    59640
taaacattgt attttgaaag gggtttgaag gtgatcccta gatagcaacc agtaatgatt    59700
cgagcagcaa aacaatctaa aaagtaattt tataagaaaa tgcagaacat aaatgagccc    59760
ataaaaaatt atattaggtt ctatttacat tactaccttc tttcacatgt aatatttcac    59820
taacatttaa tgaatttctg tgcagtgcca tataccatta tgaattctag gatagaagaa    59880
tgagtgagaa atgttcttag gccttaggaa gaaggaacaa gcatctctgt gtaatagtta    59940
tttcaactct tcttttacac ctcattccca tattaaatct cagaaaagct aaagtaatag    60000
ctatcccaga tctattttag actccagaca cttacttcaa tgtcttgttc tccttatcag    60060
actggaatca ttccaaacct cttaacttct gggcaaccat gataatgcga cagaaaggac    60120
actaaatctg tcgcaaattt atcttgatat tctatccagt cttacttggt actgaaggtc    60180
acaagtaaaa taaggtggtt gttttttgtt tgttttttt ttttttttga cagaagagaa    60240
aagaacactg tgagcacaga gtgaatgtct aacattgatt cttgagtagc aggaattctc    60300
tatgcgagag gatctctatg caaaaagatc tcatattcta gcacaattta aggatctcta    60360
tgcaaagata tcccatattt tagcattatc aataagctat ggggtaatat attgtatgtg    60420
gtgtggcttg aattctagaa atttgatttc tagaaatggt ccctgtagtt aaggatatat    60480
aatgtggccg tctccagttt tctatgagga ataggaaaat actatcatta ttagctgtgt    60540
gaccatggac aacttgcttc gttcttcagt tgcatcatct gtataaaata agaataagaa    60600
aatttacatc tgcaaggtgt gatggagatc acatgggata attgtggtcc cagagcctgg    60660
cacaaaaggg cttaatattt ataatcctcc ccatttctcc gtatactcta aaggaagttt    60720
attgcttatc aaattgtgcc gtggttagtt gtacagcttc cctgccaaat tgtaaactcc    60780
aacactaatg tgacgttaca ttttatatag tgctatgatt ttcaaattgt ttgcataatt    60840
tcaaatacac agtaaattgc ttttttattag tataattatt gctattgtca atattattat    60900
tacaacagct tcacagtaag atgggcagaa aaaaatttaa tttccatttt acaaatgcac    60960
ttttgaggct cacagaagtc aaatagacca aagtcacagg gctagtgagg gacccagaag    61020
aaacaaattg taattcactg attccaagtt cagtggttgc cttactgcat cataaaggct    61080
attacacaat ccaggtgtat catatgattc ttgtctatat attcatacat atcagaaaaa    61140
gtgttctact caaaattgct agcaatcaac agatactgat agtcattagt acttaaatct    61200
ttatcaaatg aaatattaat acccatgaaa gagaggacaa tgaaaggttt gtatcatttg    61260
tatgtcacaa gtcaactttt ttcaatcact cattattagt ttaactgtaa aaaattattt    61320
acatttagcg tgaaactttc ctgtattctc aacatatttc cttcggtaga aaagcaaacc    61380
tccagttctc tgttctttgc ttggatactt gccagtttgt aactcagcta tcaaacagta    61440
aagctcacaa aacacttatt aaaatgacta aaatccaaaa caccaagagc acagcatgct    61500
ggtgagatgt ggagcaacaa gaactttcat tcattcacta atgctggcaa tacaaaatgg    61560
tacagtaact ttggaagata ggttgacaat ttccttacgaa gctaaactat acttaacata    61620
tatatttgtc cattttcaca gtgctaaaaa gaagttcccg agactgggaa atttataaag    61680
gaaagaggtt tatttaattg actcacagct cagcatggct gaggaggcct cagaaagctt    61740
ataatcatgt tggaaggaga aggggaagca aggcacctac ttcacaaggt gacaggaagg    61800
agaatgaatg caggaggaac taccaaacac ataaaaccat tagctctcgt gagaactcac    61860
```

```
tcgttatcat gagaacagca tgggggaaac agctctcatg atctagttac ctccacctgg   61920
tctctccctt gacatgtggg gattatgggg attataattc aagatgagat ttgggtgggg   61980
acacaaagcc taaccatatc accatatgat ccaaaatcat gctacatgat attcacccaa   62040
aggaaatgta aactgtgtcc acaccaaaac ctgcacatgc acgtttatag cagctttatt   62100
cataattgcc aaaacttgga agcaaccaag atgttcctca ataggtgaat gaacaaaaag   62160
actggcacat gtactcaatg gaatattatt cagtgataaa aagaaatgag ctatcaagcc   62220
acaaaaacac atggagaaaa cttaggtacg taagccagtt tgaaaggttg cattctatat   62280
gattccaata tatgacattc tgaaagagac aaaattctgg agacagtaaa aagatcagtg   62340
attgcctggg gctctgagaa agtgcagagg gatgaatggg tgaagcacat ggcatgttta   62400
ggacagtgaa actattctct atgatactgt catggtggat acatgacctt ataccttttgt   62460 taaaactcag aattttacaa tacagagtga attctaatat aaactatgga ctttagttgt   62520
aataaggtat caatgttatt tcataagttt taataatgta ccacactaat gcaaaattat   62580
aataataggg gaattggggg aagggtaatg gagtatatgg gaatgcactg taatctcagt   62640
acaattattc cacaaaccta aaacttcttt caaaaataca agctattggt caggtgtgat   62700
ggcttatacc agtaatctca gcactttggg aagtcaagac cctcagatca cttgaggcca   62760
ggagttcgag accagcctgg ccaacatggt gaaatcctgt ctctactaaa aatacaaaaa   62820
aaaaaaaaga aagaaagaaa agaaagaaag aacagaagaa atgaaagaaa ggaaagaaag   62880
aaagaagaaa agaaagaaag agaaagagag aagaaagaa ggaaagaaag aaacagaaag   62940
agagaaagaa agaagaaaaa agaaagaaag aaagaaagaa agaaaagaaa gatgcggttg   63000
ctcatgcttg taatcacaac tactcgggag actgaggcat gagaatcgcc tgaactcaga   63060
aggtggaggt tgcagtaggg tgagattacg ccactgcact ccagcctggg tgacagagca   63120
aggctctgtc tcaaaaaaaa aaaaaaaaag ctattaaaaa tatgtaaagc tcagtctaga   63180
tacagtacca gaatagtagg aactttattt cacctgtcct acaaattatg gttgtgtgcc   63240
acttgggtaa aactcagaat ccaaatatgt gaatgtaaga tttatgggga aattatttgt   63300
atttcaaaat aatccttaat gaatgcactc cttctaaagt agccattaat aaagcagtta   63360
atgtttcatt taattataga ttaatgtaca taagatatgc caggaatgca attaggaact   63420 gggaagggg tgttattcta ataacttcca catagcattg tgagacattt tctgctttct   63480
tcaaatttca tttaattaca ttttaaacaa atattttgt gagcctatta tatagtcctt   63540
cgctagcact gaggagacat gctttgtgac cttggtgatt tcacattcaa atttcccttt   63600
cacctacact cttccttgtt ttttcatgcc tgtgtagatt gtaaattctt cctcagatta   63660
agacatttta ttcacctttg taacatccac agtatctagc acaatcagtg ccttcaaaaa   63720
caattggcct caagaattga ttgactcaat gagtgactga aagactaaat taataagtac   63780
acatctattt gtacttccct gcttacttat aaggtatgac aatgaaatac tgagacagtt   63840
atacattact tacggactca atctcatttc tttacaatct ctattcttct tttttgagta   63900
taatgttatt ttacaattcc actaacttgt cactctttat tataaattca tatctccatt   63960
tcacctgaga ataataaagg caaggaagta ttttaaatga tcttgttttt tataactagc   64020
attcattgag caaatcaaag tatgaaaata atataggtgt cagtgattat tataaagttg   64080
tatgcacaaa acattccaat gattgggggcc aatacagaga aaacatctca atatttggaa   64140
ttttgctttt ctgtaaatac tttgatatgt acttacatca tatcaattat aactcctgct   64200
gaaaacaaac agtgcacaca aatttggtag ttggaggaga ctttataaag ggactaatta   64260
```

```
cgaaggttta gaccgggtta ggaaaaacac atggaatagt gcaatacttt aggatggcaa    64320
cagcgagcac cgttataacc actaggccaa aatgaactaa atgaacaggg agattaccat    64380
ttatcagaaa agagggaga aaggaaggag agatgaccaa gcaagtccta tgtgaagacg    64440
gctgcctgac ttgagctgtg tgatctttgg actgatacca cctgcctgca ctggcctagc    64500
agggcgagaa tagtcaatat ctggaaaatg gatcacctga ccttactttc ctccctccct    64560
gtttcctctt tgtggtgttt ccactggcca aactcacagc gtagacaaaa ggagtgcatt    64620
gatgtagcag tggttctaat ccagggccaa ttgtgctccc agggaacatt agtggttatc    64680
acagctcagg ggaggaaggg agaggagtgg agtgctacta tgattcactg agggattttt    64740
ttaaacatct acaatgcaca ggacatcctt ccacaacaaa gtatccagtt aaaaaatgtc    64800
attactgcca aggttgaaaa accgtggtgt agtcagtaca attcatcttc tccaggcaca    64860
gtgcaggagt ggggtggagt gtctgaaggg gaagaaggaa gaaaccagca caccccacaa    64920
aagtaaccaa tgcaaatacc aaataggaaa agacagcact taaaatacaa aagtctcagg    64980
aatatatctg atagtgtttt atggaattta ttaaaattta gcctggagtg agtaatattt    65040
agcaagccag gtttgtcttt agagaaatcc ttgtggggtt tatacaacga tttattaaca    65100
aagggcacac acaatactca tattacagtc agtctggtta tgtaaaacat gggcaagaat    65160
gtaacaggac aatgtgatgt attcacaaag gatttttagga ctacacagat aatcctctaa    65220
tgctttcact tacgtactat gaaaggctat agtttgcata gtgatatagc cacgtaagat    65280
agtaaacttg acattcatgc agctatacat gtttgcacac accaggatgc atgcccttc     65340 tacctggttg attttttatt cttttattaa tctctaattt attccccaga acactctcca    65400
taaaaacttt ctcacaactt aaatctttaa tctattgtgt ggatttctga ctcattctcc    65460
aagcttttcc tcttccctcc gcaatgcctt atagtcttat gactatttat ccctttgcct    65520
acatttctag ccagatctct tgcctgatac acactctcat atttctcttt gcacgctaca    65580 cattttatt tagatatcac actactactt tgatttcaac aggtctcagt ttaacttaat    65640
ttttccttca agcaaggagt cccttcatat cagttatcac cattggcacc agaattttc    65700 ttatgacttc ccatgaccta caatataaac catataaatc actgatgcct ccatagttcc    65760
ctccctctca aatttagcca taagatgatt ttaggatcct tgtttttcc aatctctctt    65820 tcattctctc ccccatctct tccattatga aggtttggat aggacacaac tcatgcctag    65880
attagtgcaa tagatgctga gcctgtgcag cggtagttta gctttctctc ctggttaact    65940
ttaactgcca catatatcac ttcacacgtc attttcatt caaacgtatt taactggctc    66000
ttcattcata agaagctgga atttgtcgtt tgactgatat tttaaagatt ttatatttt    66060 tctccatcct cgttctaatg ttgtatcttg tgtcatttgt tcattcataa acttaagact    66120
tagctaacca ctgagcatcc aggaaattca gtatctatca tgtgaattct ctaatactgg    66180
ttgatccatt gtcaccagag catagcaggc ttctcctgcc tttatgtatg tttgtcatat    66240
agttcatgcc taaaattctt tcttaaatct taaattccta agatacacac ttttgcccaa    66300
gatcacagta atctctgcca taatctctgc tggaatctgt tcactgtgtt gctcctgctg    66360
aacttcttac agatgacttt tttcttttt ggtttccctg gtatctagta taatttctta    66420
tataggtact caataaatgt ttcctgttga tctctacacc tactctgtac aataccatag    66480
tgactagaca catgttgcta tcaagcattt caaaagtagc tagcctgagt tgagatatag    66540
gggtaaaata cacaacagat ttcaagacat attatgaaaa aaacccataa aatttctcag    66600
taattttttt atagattaca tgtagaaact ataacatttt gaataagttg tatcaaataa    66660
```

```
aatataaaat tcacccggtt cttttttaatt tgttaaatgt ggtggctaga aaatttaaaa   66720
ttacataatt ggctcacaga ataattataa tggatggtat tgctttagat caagtttgtc   66780
taacccgtgg cccatgggcc acaagcggcc caggatggtt ttgaatgaga tccaacacaa   66840
atgtgtgaac ttccttaaaa cattatgaat tttttgtttg ttttgttttt gttttttttct  66900
catcagctat catgagtgtt agtgtatttt atgcatggct caagacaatt aattcttctt   66960
caaatatggc ccagggaagc caaaagactg gacaaccctg ctttagatag taaagcatat   67020
gagtagttaa tgtgtactat aagcagtgtg atctgataga ctatttaatg ttgtttgatg   67080
gtacattatt caagtcgatt attatgtcta cctatgcagt ttaacgacgg taatgagaga   67140
gggcagcttg attacaggtc ttatcttttg actaacttgc taggccacct gagaaggacc   67200
caaattatct gaatgcttaa ctcaactaat ttgtattcac ttgaagaatt tcaaggatgt   67260
ttatatgcca tcaacttgct ttaaattttt tctctcagtg aaaatttttc ttaaaatgag   67320
tatgtggtat tcaaatttat ccttgttttc tatgattatc ttttcatagc actgtggttt   67380
ccaggaacct ttttttttt gagatgcatt ctacatgtaa ctattgcaca gtttgcatgt   67440
agtaaggttc attattcttc tacttttcca acacctggc atgtttactt gaggttggta    67500
caccttgtat cccagatttt gctgttttta acctaaatat tgaatatttt gattaaacat   67560
tatgaaagt ttaaatgggt caagaaaaat agcttttctt cccatgaaga acaatacggc    67620
ataggagtta agagcataga tttaaagtca gaaaacctgt gctgcctact tgtgcaaagt   67680
cacttacatg ctgtacttct gtttcttcat ctgtaagttc tacccctagg tatttactta   67740
agattaatgg aagcatatgt tcatacaatg acttgtacag aattattcac gatagcatta   67800
ctcttaatag ctctaactgg taacaacaca ataatcaatc aacaattgtg ctgtattcat   67860
acagcagaat actacttagc aacaaaaatg gaatggacta ctgataacct caacaacatg   67920
gatgaatctc aaaactatca tgctgtgtga tgccaggcac aaatcagtac atactataat   67980
tccagaaaag acaaatgtca tccatagtaa caacaagatc catgcttgct ggaggtagag   68040
gcatcagttc agtcattcag gaagctgatt ccaagatggt gttagaatta caaccatcca   68100
caagagattt attgcaggca atagctatga aaggtagaaa gagaacagga gaaaaaccag   68160
gcaaggaaaa accacaatgt agttgtgata tcacttcaaa gggaggcaga aggaaggaga   68220
attgggtagg aatagccaca gattacagtg cagttacaag aaagtcttgg cttccaacaa   68280
aggttacttg ttgaggagtc atgcattagg cagacatgtc tgggctgtag tttccttgct   68340
gctcccagtc attggctgga ggccagtctg ggttcctgtg ctgtggtgga tcccattgct   68400
gctgcagcag gaggccaata gcactcctgg cagctaattg gagagaaaag atccaagagg   68460
tgtaccttca tggctacccc catggggctg gggtggaggt ggaggagaag gagaaggaat   68520
taactagaaa aaggcacaaa ggaaaattgg ggaaaataat gaagatatat gatttctcaa   68580
ttgtggtggt cgttacatgg gtttattaat gcatcaaaac tcaagaaatg tacatttaaa   68640
atgagtgcat atgattgtaa gtgaattata cctcaatata gttaattttt taaaaatcat   68700
agatttcttt atatttaatg catgaacata aacctaagac actcctccac tccaaaactt   68760
aattccttg tgatcagcag agcagaaggt actttgtgat atataggtag agaagatgaa    68820
gtcttgtgac atttaacaag ggacaggaaa atggaccttg tcctaagtta ccaaactgca   68880
aaaatatcac ctacaaaggc tattcataac atacattttc aagggggtta caatatttgc   68940
ctactataaa attttggatc tgtaaagggg ttaaattatt tgtgcagggg aataaacatc   69000
aaagaaacat taagaggtcc agagaagtaa aataggaagg gtcttttggc tagaggagat   69060
```

```
atttaactttt cagaacatgt ggaattaagt tgtattgatt atgatctgat cttcttcccc    69120
ctaaatttga tcctcttcct gtaatctatt gtttccatca tcttcaactc ttcccttttcc    69180 ctctcccttg tccctcagtt ctagtcaatc acaaagtcct acagtttcac tttctgtata    69240
ccttatttct ggaattcatc tctagacttc aaaatatata tatatatatt ttttttttgag    69300 atggagtctc gctctgttgc ccaggctgga gtgccgtggt gcaatctcag ctcacagcag    69360
cctctgccac ccaggttcaa gcgattctcc tagttcagcc tcctgagtag ctgggattac    69420
aggcatctgc caccacgcct ggttaatttt tgtattttca gtagagatgg ggtttcgcca    69480
tgttggccag gctgatctcg aactcctgac ctcaggtgat ccacccgcgt cagcctccca    69540
aagtgctgga attacaggtg tgagccactg cttccagccc aaaatatctt aagtagataa    69600
ttgcacgact aatctctgct tttctctccc agcagcctc caaattcatg tctcacagct    69660
gacagagttg ttcctgcctt cagattcatg acctggctct gtgttccagc tcaggctttc    69720
tctctcatat cacctcttgc ctctctgttg cccccatatt ttcccctctg ttggttggt    69780 gctcctttgg aaccctctgc atatcttttc aagaatatta tgacttatta tgcctataaa    69840 cttttgtttaa ttatttattt ctaaaatttg acagggaact ttccgaaggc aggtattgtg    69900
tctttctcat ttaaaagcaa attctcgcct ggcatggtgg ctcatgcctg taatcccaca    69960
ctttgggagg ctaaggtgga cagatcactt gagcctagga gttcatgacc agcctgggca    70020
acacagttag accaaaaaaa aaatatatac gaaaattagc ctggcatggt ggcacacccc    70080
cgtagtctca gctagtctgg tagctgaggt gagaggatca cttgagcctg gatggttgag    70140
gttgcagtga gctgtgattg tatcactgca ctccagcctg gcaaaaaag taagatcctg    70200 tctcaaaaaa aaaaaaaaaa aaattagtg aatcctcagt gttttaaaag tccataaaca    70260
tactaaacat agaagacctc caaatgaaat taatcaatta ttatttagtg ggttgcttct    70320
cttttgtttt aatatagttt taacaaagag taaaagttat gatcttttta tatgtaaaat    70380
aaataatgcc gggtttgaca taaattttag gaaaactaga gacgctactt cctaaaaatt    70440
ttctttctat aatcttccta aatattttc cataaagtac aaaataatag aaaaaaatta    70500
agagattgag tatcctttca ggaagtgata tgacaaatag ggttcgagaa ctatttgaat    70560
tctcaccact tttcataagg gcagatctca agttaaattt ttctattcga atttaaatga    70620 cttttcactgg aataccatta cagaaaagct tctgtgttta gatggcaata tggagttct    70680 tttcttggaa tattaattga aggagaagtc ttaattttt aagtctatat ctccgtatat    70740
atttgaacct attttatatg ttagtccttc tctttagtaa ccttcatcca cagtgaacaa    70800
gatttaccct tacctttaag cagtagcggc tactttatgt gaagtgaaca gctgcttttt    70860
ttatctgcat ctagacatca agtagtccag agtcctttct aacaccctag caatagaagt    70920
aagaatattt tgaccattcc atgacttgat gatacttcta gtaataatac tgtattatta    70980
aaaacaaaca aacctttgtg cagtggtaat tgaagcagtt ccttgggaac atgtattaag    71040
tactttttag cagttaagtc cactctctgt aggttaagga atatttaaat aaaataatgt    71100
ggcaaatgag ttcaagatga taaatgcgat gagaactaaa acagctttaa ttttatgtgg    71160
gaaataaata gaggaaaagt acattacagg gctcctggac ttatttcttt ttcaaagtg    71220 tttctcctag cgaatattat tactattttt tctcttaagt aaaaaataca caagtatga    71280 atctacacag gataataata ttgaagttaa ggatgatgtc tcctccttca ctctccaaaa    71340
tactatttac ttggcttcat ggaaatctct ctcactccaa ttccaccgtg tcaactgagg    71400
tcttctgttc tttctctccc tatagcatat tcctgttaca taaatcctaa actgtgtcgt    71460
```

-continued

```
gttagtcaca cactgtaacc tctagataag cgcctgtcca gaggttctca atcagagcct    71520
tgcaaatatg tattaaatca atgggtcatc ttcagtgtct cagtgggccc ttggatatgt    71580
tttgcagact gctgtgagta tgtagggatg tccagtatcg agggaagtgt ggatggcttt    71640
cattggttct tatagggctg aagaacacat agagcagtaa gcacttctac tgtagggaga    71700
gatcgagctt ctcccatccc cactgctggc accaccacca ccctacaccc cattttgagt    71760
tctgaaagtg aatccttgag aaagaacaca caaaacaacc atcataatag tgggcacagc    71820
tgtgggtggt agaataacat tcccaagctt cttttcctac acatgattaa tattaattca    71880
gcaaacattt attcagctcc tacttttaaa caggcactat tctaggtact aaagacatag    71940
aggcaaagca tacaagactc tgcctttgtg aaacaattaa gaaataagta aaagaaaag     72000
aaacagaaaa ggcaatttgg atagtgtcag gtgctataaa gaaacaaaa tgccattta      72060
ataaataata ataatacaat gttttcatac tatgtgctag acactatgct agtaggtatt    72120
tatagacata acctcaatta atcctcaaaa tggcatgttg atatcaatac ccaagtttta   72180
catatgagac ttaagatgtc tgagtatatt ccccaggta acaattaata tgcacaataa    72240
aacttttgc tcattcattt attaacctat gttgattgag tacctatttt gtgtcaggca     72300
tcattttaag gcacctggat atagttatga acaaacaaat aaaaatctct gccctcaaat    72360
aattaatatc tcacagaggt taggcaaaat ataatcagaa ataagtata acgtatagga    72420
tgccagatca tgaaagaagc tatgaatggc atcaagaagc tggaaaaggc aaggagacag    72480
attttctcct agagtctcca aaacagaaca cagtcctgcc gacaccttaa ctttaggcta    72540
gtgagacccc tattggactt cagacttaca atcccacaat gtaataaatt tgtggtaatt    72600
cagtagggga acaatagaaa actaatacga tatcaaaaca aattatatca tagaacaaga    72660
aaatgtaatt gtgacaaata atacctacaa aaatgttgta aatgctaggc aaataatgtg    72720
tttaaagcac ttaggccaat gttcaacgta aagtaattca tgctataata tcatcatcat    72780
cattaccaat atttaggggc tctaacaaat gatgtacgtg taagcagatg taagaaaatt    72840
tccttgctga agaggaggta ttaatagagt atataacaat agataacaaa ttccaaataa    72900
aggcaaacta aatgttttat tggattaaat ttaattttaa aaactacaag aggccgggcg    72960
cggtggctca cgcctgtaat cccagcactt tggaaggctg aggtgggtgg atcacgaggt    73020
caggagatcg agaccatcct ggccaacatg gtgaaacgct gtctctacta aaaatacaaa    73080
aattagctgg gcctggtggc gcgtgcctgt aatctcagct atttgggagg ctgaggcaag    73140
agaatcactt gaacaaccaa ggagtcgag gttgcagtga gccaagattg tgccactgca    73200
ctccagcctg gcaacagagt gagatcccgt ctcaacaaca acaacaacaa caacaacaac    73260
aacaacaaaa ctgtgagatc catggtgggc ttttaagagg aaaatgcaag ctaaggttg    73320
tttagactct gagtactgca tgtgtaaaaa taaaggcatg atgaaaagat caagagatta    73380
gagtgatact ttttatctac tagtgtcaga gtcatgacca ggggattggc tatgagaata    73440
cataagctgt gccaggagta atccaaggag attgtttcaa tttggaagag tgtccacaga    73500
atgattctca tactagacgt tgggctattg taaagaaagt tggtaggtac tccatcgcta    73560
ggatcatatc agggagaaat tgaacaggat ggccctaatg accctgttgt accccctagct    73620
tatggattag gcaagtcact tctactcgta taccctgttt ccccatttgt aaataagagg   73680
atgtgttact ctaaggatct ctaagattct ttgcagttgt taaattgcat agctctccac    73740
tgattccatg gtggaaattt gctattctat tacaaatatt ctaaatgtat gagatatcag    73800
acatactcat ttaaaaaaca aaatacaaaa aataagtatt ctacaaataa acacagataa    73860
```

```
tgtttaaatt ctatatgtct ttgtttctct tcagaagcat ccaaaataca aaccatctaa    73920
gaggcaagaa aatgtcgtga tgttcctagt gcaagttaaa aagatttgct ttcctcaagt    73980
cggaaagccc ttctcatttt tgaggttttt ttcttctttt ttttttcaag tgaaagcatt    74040
ttggaggagt caatatccat ctttaaaggt agccaggtca catgtataca tatgtaacta    74100
acctgcacaa tgtgcacatg taccctaaaa cttaaagtat aatttaaaaa aaaaagaatt    74160
taaataaaaa aagaaaatca gagagaaaaa aaaaaaagat gcatgtgcac cctgatacta    74220
ccatccatag tgatacggtt tggctttgtg tccccaccca aatctcatct tgaattgtaa    74280
cccccatgtg ttgagggagg gaccttatgg gaggtgattg gatcatgggg gtagtttctc    74340
catgctgttc tcatgatagt gaatgagttc tcataagatc taatggttta aaatcatggc    74400
acttcctttt gctctctctt tctcctgcca tgtgaggtgt gccttgcttc cccttcccct    74460
tctgctatga ttgtaagttt cctgaggcct cctcagctat gcagaactgt gagtcaatta    74520
aacttctttc tttataaaaa aaaaaaaaaa aaaaaaagg tagccaggta aaaattactt    74580
gtttccagga cattttcacc tgaaagaagc attgtcatat aacatagaag caagaaatcc    74640
agtagtgggg gttatttaaa aatagctgga aaatttcaat cagcatgagt ttgaagcaac    74700
aatttatcat caccttttat ggtgggtggg gttaagaaca tttcagcggg caaagtggtg    74760
gtgatgggga agagacacca ggggaggtga ttcccattgc attgctttgt aaacagaggc    74820
acaggttctt cattttgtc acacaaaatc acagctatgc agaatttatt aatttattct    74880
tctgagacaa gaaaaagcc accaaggaa accaacagct tgctcctctc acactggggg    74940
aaccgtatga gagacttatc tatccctgac tttaattttg acctgaggag agctcctctt    75000
aaggaaaaca aattaattca atgactatac tacttaatca ttgaccttta tttaataaga    75060 gattttcca taggatatgc tgagctgtct cacttacatc agttgtgtct cctgaggtgg    75120
gtgacaggag accacaaata ttgcatagca cacaaatcgt taatagcagc tgtataccaa    75180
accattacct aaatatgtag agtacaattc attctcacta atgtcagaga gcatgctata    75240
aaatggtgaa tccggacagc tgaagatact gaataataac ctctattttg aacaagttta    75300
cagtgttcca atcagtaatt aaattgatac ctgatgaata tatgtgtgtg tatgtattca    75360
tagcagagat ggttttcctg agataaggat tttgttattc ggataggctg ctgctggaat    75420
tgtccttcta cccttgtttc tttgtcctta gtcatcactc atacctcttt ccactcttct    75480
gccatcactt ttgtcaccaa agtcatggtc ctttccccgc cgattgctgc tgcaggtcta    75540
gggcaccaag acttaggcag cactcaccat gtgccaagaa ctggaccaca ggtaccatcc    75600
agcattgctc atggagactc tgtcccttc tgtaggacac cctcctttta gctagcaacc    75660
cctccaccac ctagagcctc tggacctctc attttaatat taagaactag gaaaacttac    75720
cgctgagaat aactagtaca actagaactg gtagagaaat ctgggtctct tgggaatgga    75780
tttttaggct ttattgatta gaggtgtatt aataatgcag tgttatagtt tcatgacata    75840
acgaataaaa aagttcattt tggacttgcc tttcagctcc ctaggagcta aaagacgtat    75900
ttaatgtaac ttgtgtggtg gaaataagtt ctttttcag gcaaaagatg tgcaaaccca    75960
tctggggaag aaacattaaa aactaaggag acagtgtcct agataactat gttcttttcc    76020
tgttttagtc taaaataatg attagttttc ttatatatct tcatttgtct tggttccttt    76080
tagcccaatt taataatatt attgcagata ttgatgaaaa cctttacctt cctcttaatt    76140
catcaaagta cttgataaaa tttatacata gtacattaat tgggaggttt ttatgagatt    76200
aattaatata atgaactgat gttgaaatta tttaaaacct gaattattat tgtattaagt    76260
```

```
aggacactta atacagttaa tcagttctgt ctttattcat ttgtgagaat ttttggcaag    76320
ctattgtgaa tattcaggga agggaatgta tttttagcag gaatcttata cctcctacat    76380
agaaatgaag catttactga aacatccatg aaacaaaatg tttctgaatg tgtactatac    76440
acttgttata agccccttt cttctgtagc tatattttgg agaaaaatct ttgctttgac     76500
aaaaaaaatt atgttgactt acacatatat tttataacta agcagtgttt ggtttgtgat    76560
aaaggataca aaaatataaa aatgttcagc acacgtaagt aaggccttgt tgacaatgtg    76620
agttatgcta ctggatactc aaaaggaaca ttcagtgttc tcaggtggtc tctagactgt    76680
ctcaagccta ggaagatatt ttataagcaa aggaataaga gaaggaagat tcagatttaa    76740
tccaagtgaa gaattcagtt ttgtgtgcct tatcctgtta ttttgagagg cagccaaaag    76800
atgctggtca gcaaggagaa ttgtaagttg ggcagccaac tctgatttct caacctctta    76860
gctgttttct taaactcaga attttaatg aatttaaatg tccatatcag gtagactttg     76920
gggatgcttt taccagtgat tttcagaatg ttactttctg gcatttcttt tcacgtagca    76980
ttatattaaa aatgaattca ttcatccacc ttcccttgtc cttactaatt ttccctccta    77040
ctcccttccc ccttgttctt gccatgggga catgcaaaca ctggtggttg atgtctgagc    77100
aaggctgctg acaggggag gaaggagatg tcaagcagag gtcaatggca gtgtgcccag     77160
cagcctagga agtaggaggg aaaagagaga gagacagaga tggtggatga aagagaaagc    77220
caggatgatt atggtggtta tgatacttgt catgctgaac acccaattga gcacccaata    77280
agcacataat aatttaatca tcctctggct tggatggcag tgttctatca gtgttgactt    77340
cctggttgtg acagttttac agtgttagtg tagaagagaa tccttgcttt agagaggtac    77400
ttactgaagt acttagggtt aatgcaccat tgtgctggaa aaagatacgc acacacgc      77460 acacacacac acacacacac tcacacacac gcacaaatac atccatgtgt taggcagagg    77520
gagcaaatga ggtaaaatgt taataattag gaattctggg tgaagtggat agagggactc    77580
tttgactgtt cttgaaactt ctctatacat ttgatctgtt tcaaattctt cagaaaatca    77640
aactacaaaa acttaattca tttagtgaac atctactgaa catctgtata ttaaatagtg    77700
ttaaatgaat gtcaattaaa atgctcaaac acagtagagg ttgattctca ttcacataag    77760
tccatggtag gtgtttttgg caggtgggtg agtttctccc ttagggagat tgaggaaccc    77820
agactcctcc caagttgcag ccccaccgtc ttctgagggg atgcatccat acccacttcg    77880
aagtagcata cattatttcc tttctcattc ctttggatac cagccacaat ttattcaagg    77940
tagacagaaa attgtagtat atagccatat gccctgacaa agaagggaga acagattttg    78000
gtggacaact agcaaactct gatacaatct gttattaagc actgtgtgtg gatagatgct    78060
aactagaagg agattatctt cccttcagca aatataaact gaatgccgtt tatttggttg    78120
aaactaagct agatcatggg agtatagaaa ttttataaga agacatagtc acttctgtca    78180
gtgagctcaa gaagaattag tatgcggaat gtaatcatac ctacaggggg cttgtgccac    78240
ttaagtaaaa tgaaacatta ttttgagtac aatttagcaa taaatgtact acgagatcat    78300
taaaaatcat gtttgaatgt tattgtgtca aggatgggaa aaagactttt gggttgtaga    78360
cttgataatt atagttaaaa acagttttta ttcttgttta gtcttatttt ttatgtttaa    78420
acatatttat acttgctaac atttatactt gctaagtaaa gactgttttt acaaccatga    78480
caagaacaaa acatattagt aatgcaaatg ccacatttcc tacaatcaac taatcacact    78540
aacatatttg catggaagaa tcactgggat tgatctggcc acgtgtgtag tcatgcccaa    78600
aatgtgaagt ccatctgttt tgcaattttt tttaaccact gttatccaaa tgctccttgg    78660
```

```
attttttttta ttagtggata tattttggag gtcagacacc ctcttggcta gatcatcacc    78720
tttataacaa atatatatac tattctcatg gaaatatatt tagacgttgc cctactggga    78780
atttttttca agtaattaat gtacagcttg tgcaacagct tgatcttggc ttcatggaaa    78840
taattcactc ttagcagcat ctaatgccac aaagcattta tggatgtcag ctcagaactt    78900
acttttattt atctctgagt tactttttt ttttttttt ttttgagaca gagtctcact    78960
ctgtctttgg cttgtcccta acctcttaac agacttaata ttaagctcca tttcactcag    79020
tcgttctgtt gtcatataaa tgagacattc tacaagcata gttttagtt tctgccagag    79080 catcatacaa cattgtgagc tatgatgaag ataaagacct agagaagata tttaatatga    79140
agttcattat ctaatatttg gtatgtgtgg caaaatagca atctactgct tggttctgct    79200
gtaatctatt tacccaccca tcccatcttt ctttcaattt aaaaggataa tgattttagt    79260
cacgattata cataaaccca ttaccatagg caataaacaa tggggcaaac cattggtccc    79320
atagttggag tgtggtctga agtgtgtttt ggtggagaga gatctatgtc tggagatagc    79380
taacatggat ttggatccca gatctgctcc tacctgttgc tgtgcctgtg accaaatcat    79440
gtgatctctc tggtttcagt ttacttgtga ataaagtaaa taccttcatc aacacctgtt    79500
tttgaataca atgtttttct gtaattttg cttcttataa tgttataatg atcatcctta    79560
catctaaatc ttggtttaca ttttcatcaa ttcttttgga aagattggag aagtaaattt    79620
tggagatgta tgtcggctat taaaaatgtt taattttta attaaaaatt aaaacgttga    79680
aaaatcctga tgcaaaataa atgcattatg cttagtgaac tcttctcatt tcgaagttta    79740
ttcaccttct tgttttgca agtttcctga aaaatgcata taaagtcact aagttagcag    79800
aactttataa aattatataa ctatatataa tcttttgata tcagtgaagc cagctgatcc    79860
tatagaaata atgtaggaat tataatcact agcacataat ttaagagtcc tgtggtctta    79920
ttcatgttat ttaccctctc tgaatcttac atatagtaag agggttatta tacataaat    79980 gtgtacatgt atacaggtaa gtaagtatat atgcttatgt gtaaaagcag agttattgtg    80040
agagtcaaat ggaaatgtga agtactttg tagtttttta ttactattat taatttttaa    80100
taaaatggta acattcattt aataatcatt agttttaact tcagattgta ctggatttcc    80160
tctagtattt cttaagatta gtgaataaag tatttctcct aataaatata ttgactactg    80220
tctttcgatc aaacatatta ggtatatttt tacagtagca tcaggcagtg aaaatttgaa    80280 gctcttata gaggactgat ttatgatgaa aaggaataac atgaacaaat ggaattatat    80340
gaagcttccc cagaaatatc taagagggggc caatttaag aaatatctga cttcttttttc    80400 atggacattt caaaataaac ctaactcata tggtacagtt tttaagaggg aaaagaaaaa    80460
accatctgag aatctctgga attctgccga agtatcact tggcatttta ttctaccttc    80520
tggatgcagt tgattgacag tagtgttatg atgccagggg tatagtgact agaaaaagaa    80580
aaccagggaa ttcagtgttc ttgctcatga agaacagctt ggttctttaa aaacaatgag    80640
attttgccac cccatctcac aaacctatga tttgtgagaa caatcccttt tgtgttgcaa    80700
gacttttaca tttctcttcc cacactatat tagaagaata aacattgctt cataagtacc    80760
gattgatagt ctcatttcat atttttaaaa tagagttact ttaaggttaa atttttcatg    80820
tagattaaaa tgactaagta accattcaca tatttcaaat aaaatatatt tttactacaa    80880
aaggaaaata actagattct taagtgttat agtcaagtgt aattgagtaa tatgaattct    80940
aaatgaattt ctaagatctg ctcagctttc actactttag gaaggaacaa cttaagaaaa    81000
attttaataa agatatctct tcacacacat ggcagtgttg tacttagaga acatgaccca    81060
```

```
aaattttta tgactgcata ttgaattcct gatactcttg ggaagctcca aaagcaccag    81120
tggagtttcc agatgtaact gtggctgcag acccgccagt cccggtgttg gaagggatca    81180
ttataggctc ttgtgtgcag actcatcttc agacccagag gaattaaata acttgcccaa    81240
agtcgcacaa ctttctcatg gtaggttggg cactagaata aatattgctt tttcttaaga    81300
gttttagcct ccgtattatg aaatcttcta tgttctgctg atgatatctc ccttcttcat    81360
ctgttttcta tttttaagca atggaaatac aaacttgcaa ctccccattt ccaacacaac    81420
ttagaaaaaa caatatttaa agaaaaaatt acaggcatct catctccttt acctgacaga    81480
tgcttgatag taatggcctc tagataggga tgacatctaa tataaatgtg tcctttcaag    81540
tcaagctttc tctgttcatt agtagaaata ttgtatatca agtgtgcaaa aattttcttc    81600
aacagggagc tttgtttccc tcctttatt ataacaatct gagctttgtg gtcccagggt    81660
ctcctagtgc ctgtctttag gtctgtttat tcacatgaag aaagcatgtc atatagtatt    81720
atctaagact caggctgctt atgcatgatg acagaagggt tcccaggcac aaacattcat    81780
ccatgcattc atccatccac ctattcatcc attgatttgg ctgataatta ttgactactg    81840
ttgagttgcc ctcagattta gtttctgtcc ttctgccatg gggaaatatg gggttaagcc    81900
acaacatact cttctcttct ttttctgcac cttcttagta tatttagttc cattttgtct    81960
agccctgcct ctgacttctt tgttgtactt caggttttt atcattgaaa gttatttctg    82020
gatcatagat cattctcttg gtcactttgc ttgttcactt ataaaattaa ttcagaaaaa    82080
atgacccaca gtaattactg taaatcacag accataaact ataatactgt atattgtatt    82140
atagtacaga aatatttata ctttaaaatg ttttaaatat agatattata aaagatatg     82200 tctcatataa gtaatataaa tacttttta ttacctcttc tctccctatt ctccaggcca    82260
gtgttttaaa aatccatctt tatatgtcca tcctggaaaa aactcatgat cataaatgag    82320
tttctcaata gagtttataa gcccacagtt gaaacacaat tgtcttagca tccatttagt    82380
tgtcatactt ttaagattta atggcaaata ttatgttttg tttcttcaaa agaaatattt    82440
taaaatttta gtaaaggcag ttagagaagg tagagataat ggactgttta atcctacttt    82500
tcatcccaca agtgaacaaa aaaatgataa aacattttc ccaaaatgta gctttaacta    82560
tacttaaatt tggactaaaa tgggagatat cttttctact attgaaaagc cgtgtctgta    82620
gattaatgct aaaatcgggt gtaaaagcaa aatttgtttg gcttgattgc caatggccca    82680
ttcatttggc tacagaaaca atagcacata gcaacagata atgatgtgag atcacctagc    82740
tcaagtaaga gtgtctgatc cgtcaaaaat atatacatca agattcaaaa gaaatgtgtg    82800
ttttctcaag tcatctctgt aaaaatacat taaatagagg aatagaagtt tgactttgaa    82860
aatacattgc agacccaatc cgtctttcct attttctggt gaaaagtatc aaatatgtgg    82920
aacctggaac tgctattctc cttcttaaaa atctttctta atattctatt gataactggt    82980
gcaagcctaa ctttttgtct tacccgattc ttctcacacc aaagtgatag gaccttcagg    83040
tagcctttgg atagaagata aataataatt taactattga tggaagttag tattagaatt    83100
agacttggaa gtctatggaa taaaatgatt ctacaacaat ttgtacttca gacattagta    83160
taacaaaaca tgtttgcccg tgcatgcgga acaaccaat ttcatgtgga tgcttatatt    83220
cacaaaggag taaccacctg gggtttccca ctgttgctcc agagaaaact agcagcagga    83280
gaacttctct gaaggtatca agacatcttt aaaaaacact tgttaagtgt tggttcagct    83340
aaagcaggga gttttcagtt agtaatggct tttaaaaatt aaaacaagtt tagcatgtag    83400
gtcattaacc ttgaatcact gtcatgatta ttattaacca tctgttctca aatcgaaaga    83460
```

```
tatttttctt ttctagatca catttattct cacattgctc aatttcacta tatatcaaga   83520
catgaaaact gtaaaaatca caccttctac attattattt ttattgaaaa attcctaatg   83580
aaacagtgcg ctctgggata gagaaaggaa ctaactgaca ttttgcttct taacttgttt   83640
ttatgcaagt tctaagtggt ttctggccat gtacataaaa gacaaatatc tggaaaaaaa   83700
actagcagaa gtcagttatt tggctctatc tactttgaga attatgttat ataaatgtta   83760
ggaaattttt tgtaatattc ttatttagaa atgaaatata aaaagtttta aaatatctca   83820
aggacagtat acagtcctaa agtaaagctg ttaggtaaat gctacacaat cctcttatta   83880
cagagtcact tacctgagaa tataagaaga gggcctcttg tttaagagta aatgtgagct   83940
gcaatcagga ttctgcactc atttggacac ttagttttgt ttttccatga ctggtgttgc   84000
ctgttactga gacacctacc tgtcatgtga ccacagctta tgttacaatg tgtcagtca    84060 gacttagaga tgtgtgaaag agcagtacct agacgggaaa ctatgggtct ataaaggttt   84120
tgccttcttg ggcggagttc aaactaggaa gccacaaaac ttccagttgc attttcacag   84180
attaatgaaa tatattttac acttttcctg aaagatattt tatttgtgca aaccttgtta   84240
caaagtacag ccagttgatt aatcgatgaa gtgatttgta gtggattctt atattttgtg   84300
taagggtata tgtgaggccc tatatatgag gctttctata taatgaagta taattcagtt   84360
cagcatttca attcagcaat cacttattgg gcctctactc agttgccttc agggctttat   84420
aatttaattg ataaagggag gttaattaat taattataac aacagatcgc ttaatagtgt   84480
aactactaat ttaattaatg acaaataaca atacattaaa agaaatgcat taataaaaat   84540
aatatattgg tgttatagac aataattttc tgattaactt tattattatt atttcaatag   84600
cttttgggga gcaggtggtt tttgttata tggagaagtt gtttaggtat gatttctgag    84660
attttggtac actcataacc tgagcagcat acactgcacc caatgtgtag tctttcattc   84720
ctcaccttcc tcccaccctt cccctcaagt ctccagagtc cattatatca ttcttatgcc   84780
tttgcatcct ttagtttagg tggcagttat aaatgagaac atgtaatgtt tggttttcca   84840
ctcctgagtt acttcactta gaataatggt ctccaactct atctacgtag ctacaaatgc   84900
cattattttg ttccttttta tggctgagta gtattccata gcatccacac acaccccct    84960 atgctttata tatatatgta aatatatcac attttcttta tccactcatt ggttgatggg   85020
tatttaggct ggttccatat ttttgcaatt gtgaattgtg cagctataaa catgcatgtg   85080
caagtgtctt tttcatataa tgacttcttt tcctctgggt agatacctag gagtgggatc   85140
gctggaacaa atgattgttc tactttttagt tctttaagga atctccataa cttttccatg   85200
gtggttgtac tagtttacat tcctaccagc agtgtaaaaa aatgttccct ttttaccact   85260
tccatgccaa cgtttatttt tttattttt aattatggca attcttgcag gagtaaggtg    85320
gtatcacatt gtggttttga tttgcatttc cctggtcatt aaagatgttg agcatttttt   85380
catatgtttg ttggctgttt gtctatcttc ttttgagaat tgtctattca tgtccttagc   85440 ccacttttg ataggattat ttgttttttc ttactgattg tttgagttc cttgtagatt     85500 ctggatatta gtccttttgtc agatggatag tttgcagata tttctcccat tctgtgggtt   85560
gtctgtttac tctgatgatt atttcttttg ctgtgcagaa gctttatagt tttaggtccc   85620
atctatttat cttttttgtt gttgttgcat tgcttttgg tttcttggtc atgaactctt    85680
tgcttaagcc agtgtctaga agagtttac caatgttatc ttctataatt tttaaggttt    85740
tgggtcttag atttaagtct ttgatccatc ttgagtggat ttttgtataa gttgagagat   85800
gaggatccag cttcattctt ctacatgtgg cttgccaatt atcccaacac catttgttga   85860
```

```
ataggatgtc ctttccccac cttatgtttt tgtttgcttt gttgaagatc agttggctgt    85920
aagtatttag cttatttct ggattttcta ttctgctcca ttgatctaca tgtctatttt    85980
tatagtagta ccatgctgtt ttcctaacta tagtcttgta gtatagtttg aagttgggta    86040
atctagtgcc tccagatttg ttattttttg cttagtcttg ctttggctgt atgggctgtt    86100
gttttgttcc atgtgaattt taagattttt tttcttgttc tttgaagaat gatggtggca    86160
ttttgatggg agtcgcattg aatttataga ttgttttggg cagtgtgctc attttcacaa    86220
tattgattct gccaatccat gaataaggga tgtgttttca ttagtttctg ttgtctgtga    86280
tttctttcag caatattttg tagttttcct gtagagatct tccacctctt tggttaggta    86340
tattcctaag catttttttt ttttgcagct gttgtaaaaa ggctcaggtt cttaatttga    86400
ttctcagttt tgttgctgtt ggtgtatagc actggtactg atttgtgtac attgattttg    86460
tatctggaaa ctttactgaa ttaacttatc agatctagga gcttttgga tgagtcttta    86520 ggttttctag gtatacaaac atatcatcgg caaagagcaa cagttgact tcctcttag    86580 cagtttggat gctcttatt tctttctctt gtctgattgc tctggctagg atttccagta    86640
ctatgttgaa tagaagtggt gaaagcaggc attcttgtct tattccagtt ctcggggaa    86700 atgctttcaa attttccccc gttcaatata atgttggctg tgggtttgtc ataagtggct    86760
tttattacct taaggtgtgt atcttatatg ccagttttgc tgagggtttt aatcataaag    86820
caatactgaa ttttgtcaaa tgcttttct gcatctattg agtttatcat atgattttg    86880 tttttactcc tgcttatatg gtgtatcaca tttattgact tgcatatgtt aaagcaaccc    86940
tgcatccccg gtatgaaacc cacctgatca tggtggatta tcttttgat atgctgctgg    87000 attcatttag ctagtatttt attgaggatt tttacatctc tgttcatcag ggatattggt    87060
ctgtagtttt ctttttttgt tatgtccttt tctggttttg atattagggt aatactggct    87120
tcatagaatg atttagggag gattccctct gtctctatct tttggaacag ttcaataga    87180 atttgtacca attttctt gaattctga tagcattcac ctgtgaatcc atctggtcct    87240
agactttttt tgtttcctga cattttttct attattgttt cactctcact atgcattatt    87300
ggtctgttaa taatttctat ttcttcctgt tttaatctag gaggtttgta tatatgcagg    87360
aatttgtcca tctcttcttg gttttctagt ttgtgtacgt aaatgtgttc acagtagtct    87420
tgaataatct ttttattc tgtggtatca gttgtagtat ctcccatttc atttctaatt    87480
gagcttgttt agatctttt tcttgttttc ttggttaatc ttgccaatgg tctattgatt    87540
ttgtttatct tttcaaagaa gcaggtttt gtttcattta tcttttgtat tgtatttgt    87600 gtttcaattt tatttattta ttatttatt tttatttta tttttgaga tggagtctca    87660 ctcttgttac ccaggctgga atgcaacagt atgatcttgg ctcactgcaa catctgcctt    87720
ccaggttcaa gtgattctct tgcctcagct gcccgagtag ctgggactac aggtgcctgc    87780
caccacacct ggctaatttt tgtattttta gtagagacgg ggtttcacca tgttggccag    87840
gcaggtctca aactcctgac ttatggtgat ccgcctgcct tggcctccca aagtgctgcg    87900
attacaggtg tgagccacca cactaagact caattttatt tatttctatt ctgatctttg    87960
ttatttcttt tcttctgctg ggtttgggtt tgctttgtct tgtttttcca gttcctagag    88020
gtgtaagctc agattgtcta tttgtgctct ttcagacttt ttgatgtaga tatttaatgc    88080
tatgaacttt gctcttaaca tggcttttgc tgtatcccag aggttgtgat aggttttgtc    88140
attattattg ttgaattcaa atattttaa aattttcatc tttcttgatt tcattgttga    88200
cccaaagatc attcaggagc agattattcg atttccatgt atttgtatag ttttgagggt    88260
```

```
ttctttgga gttaatttttt aattttattc cactgtggtc tgagagaata cttgatataa    88320
ttttgatttt cttaaattta ttgagacttg ttcatatggt ctgtcttgga gaatattcca    88380
tgtgttgatg aaaaggatgt agttgttggg taggattttt tgtaaatatc tgttaagtcc    88440
atttgttcta gggtatagtt taagtccatg tttctttgtt gactttctgt cttgatgacc    88500
tgtctagtgc tgtcagtgga gtactgaagt cccccactat tattgtgttg ctgtctatct    88560
catgtcttag gtctagtagt gattgcttta taaatttggg agcccaagtg ttagatgcat    88620
atacacttaa gattgtaaat ttttcctgtt gaactaatta ttttatcatt atataatgtc    88680
tctctttgtc ttttttaatt gttgttgctt taaaatcttt tttgtctgat ataagaattg    88740
ctattctttc tcactttgag tttccatttg catggaatat cttttttccac ccctttacct    88800 taagtttatg tgagtcctta cgtgttaggt gagtctcttg aagacagcag atacttggtt    88860
gatggatttt tatccattct gccattctgt atctttttaag tggagcattt aggccattta    88920
cattcaacat tagtattgag gtatgaggta ctgttctatt catcatgata gttgttgcct    88980
caataccttc ttgttgttgc tgttgttaat tgtgttatta ttttatgggt cctgttaaat    89040
ttatgcttta aggaggttct attttgatgt attcaagtta ctgtttcaag atttagagct    89100
ccttttagca tttctcagtg ctggcttggt agtggcaaat tcagcatttg tttgtctgaa    89160
aaagacttta tctctctttc atttatgaag cttagtttca ctggatacaa aattcttggc    89220
tgataattat tttgtttaag aggctaaata tagggcccaa tctcttctgg ctagcagggt    89280
ttatgctgag aaatctgcta ttaatctgct atgttttctt ttataggata cctgatgctt    89340
ttgcctcaca gctcttaaga ttcttttcctt catcttgact ttagacaacc tgatggctgt    89400
gtgcccaggt ggtaatcttt ttgcattgaa tttcccaggt gttctttgtg cttcttatat    89460
ttggatatct agatctctag caagactagg aagttttttct tgattattcc ctcaaataag    89520
tccttaatga ccccactata taacatgaaa tatctgttat tggtactgag gtgctggcca    89580
caaacaattc tgtgtgtcct gaaaactctt cagaatattc gtcatcttta gcacttgtta    89640
tcttagtgtt tgggcttggc ttagagtgat acatctcata acagggcaac agaaagaacc    89700
aggaaccaag atttatataa cataagtcag taaaactaga ggcaccagag gtttacattt    89760
acattaggtt acattttcta acaggtagca aagcacatga atgaagttca gtggaaggcc    89820
ttcctcagga atccagtaaa aaccaaacat acacacacac acgggacat ccgtgaggca    89880 ggaagggatg tccactatag tacagacaag catcctggaa ggccatcaag gagtaggtgg    89940
gtttcagttg cctcaggaat gtggcatgga cccaaactaa gtgagtacag atacttgtca    90000
ttgaggagaa gattcaaaat agcatcctag gtgtaaaaac tgaggcacct ggggcagggg    90060
aactaggtct ctggaatgtt ggcttaaaag caccctctc aggaaaggcc tcatatgcca    90120 tgcaggggt tatatatgtg ttgtgggaca cagatggcaa ggagataatt ctatgcacca    90180
ggctccacta ctaacaggta aacagaccaa cattaacaga gacttaggta aaaaggtagg    90240
tgcccagtgg tcagttctca ggcacttcca agatgcacct aacagaaatg taacttggtg    90300
tctattgtgt cctaggtcta acaactgaag agaagtgaat tagtacctct tgtggacaga    90360
gaaacagggg cagagaccca ttacaaagct gtctcgata ggcatttgaa gctgttttaag    90420 tatgtagagg cttaagtcag gctggttctg aaatgtgaga gagggttaag cttcatggga    90480
aatcagcagg gtagttttgct attttttatt ataaccaatc tcacaatagt ttgggacatc    90540
aaatatcaaa ttgttgggaa tatttatcca tattagtctt tttgccacta atatttaaaa    90600
atagtttaca atatacaaca aaaagttgta aaatttccat ctccacttaa tcgatcttat    90660
```

```
gtaacccata caatacatca aatgtccttt ccccacttta tgtttttatt tgctttgtca    90720
aagatcactt ggctgttagc atttgggttt atttctaggt tctctattct gtttattgg    90780 tctgtgtgcc tattttata ccagtgccat gctgttttgg tgactatggc cttatagtat    90840
agtttgaaag caggtaatgt gatgcctcca gattttctt tttgcttaat cttgctttgg    90900
ctatgtgggc tctttttgg ttccatatga atttaggat tgttttttct agttctgtga    90960
agaatgatgg tggtattttg atgggaattg catttaattg tagatttctc ttggcagtat    91020
tacccaggct tttcttattt tggcaccctg tgctgctgtc tccttttcct tctttctgct    91080
tctcttaacc aactgttacc tacacttcaa tactttctga gggcaattca tcctccagta    91140
agtctccctg aatcttctct tccttccctg gcttattata tatccttcct cttggttccc    91200
atagcaccta tgcacacttc tgtcattgca cttgccaatt tgttttataa tgatctgctc    91260
atctgtctcc tcacttagac tatgagctca ctgagagcaa tggctgttgc attcaccta    91320 tatcctcaac accattctga aggcaagaga aagaataccc agaggtggag ctgggaagct    91380
ggttgtccaa gtagtgaatg actctagttt gaattgaact ctatagccag tgggcaatgt    91440
ggatgtgttg acagttttt aacaggggac tagtgaaaac acattttggg tttagaaaaa    91500
attgcaagtc tgatgacata cataggagaa gagattagag ataggaattt cacttcagaa    91560
atttaaccac aagagcaagt gacagatcac ggaagtctga accagactat aaatgtgaga    91620
atagagaaaa aagttaacaa tttgggtgtg aaagggcgag ggagagaggt gtgaagaatg    91680
actaagtgtg gatctgtttt taaggattga atggaaattt gagcatttta gctaatcagg    91740
cctaatattg agcaaagcaa aactcttgca aattgttatt tcaagtgtgg gctgagaaaa    91800
tgaaaaaata taaattctca cgttataacc tcttccgtgt gtctgatttg atagaatcca    91860
gccccattgc ctccaaattc cattgcatct tagaccagca aacacaagtg aattctactt    91920
aaccccagaa ttctgtatga aaatcttact gccttttttt ttctaatcat gtgtcaaagt    91980
gtgggaagaa cttttatta tgttttaata aattgtcagt ataaccattt ttacttgaaa    92040
atattataat ttttcaagta aacaaattgt ttctctaagt tgaaaattt atgatggaat    92100 aaaagtattt ttcctcaaaa cacatagaaa ttttacaaca atattttaga gttaactaaa    92160
tgtttcttta gtagtttagt cacttaaaaa gtgatatgat tatgaaaata cttaaacttt    92220
gtcttttaac tatttctaat aatgctattg gtataaatttc atatttttat actgatcttt    92280
tctccaaact ttagtaaaac atacttctgt aaaccctgc ccacaaaact gaagtccaca    92340
tttacttctg aatgactgat aagtttgtaa agtatgcat gaatttcgtt attaaattaa    92400
agtttttatt atatttttatg cacaatggta taaattatta aattaatttt caagcttata    92460
gaacattgat aaagattgtc attagaaaac cctgagttga ttgttataca ttacataacc    92520
tttcattggt ggattagtga atatgttata gggtgaccat gaatccaaag aatcaaagct    92580
ggctacagca aacagagggt caaaaggata tggaactatg catgatccag caaaacactc    92640
aatatctgtt ttcctggaat gttaaaagac aaagaagaaa acttggggaa cactagatgc    92700
atatagttct ggttctttaa gaataaaaat atgggccggg cccggtggct catgcctgta    92760
atcccagcac tttgtgggag gccaaggcgg gtggatcaca aggttaggag ttcaagacca    92820
gccaggccaa catagtgaaa ccctgtctct actaaaaata caaaaaaaaa ttacaaaaaa    92880
aatacaaaaa aaaaaatagc caggtgtggt gacaggcacc tgtattccca gctacttggg    92940
aggctgaggc aggagaatca cttgaacccg ggaggcagag gttgcagtga ccaagatag    93000 tgccactgtg ctccagcctg ggtgacatag tgagactctg tctcaaaaaa aaaaaaaga    93060
```

```
ataaaaacaa gaatggtcag agtcctagta ccttgtccag tgtagtgctg ccttgagatt    93120
gcattgcaat ctgtctgaga gatagtaaaa gaaagtgata ccttccttag ccctgtttct    93180
ctttagacta tgcttTccCC tctccaagtt aatatctctc agtctaaagc ctgggaaaag    93240
gtgccaattt tgttttTctt tcttcctcac acctcctaga agttacactg ggacactatt    93300
acttttTTcc aggctttggc catgtgtatt gttttggaga gtcaacttcc ttttTtcttt    93360
cattctgcaa atagttttga gctgtcactc tgtactaggt gctataaaac ttacaggtgc    93420
atTTtacatg cctatTTcct ataggccacg atTTaacaaa atgttcataa atgagaatta    93480
ggagtgcatg tattgaatca ccacacatta actgaacagc tTTcattggc cagagactat    93540
attgacagtg gagattcaaa gataaactag agaaatctca tgcttaaata actttctata    93600
ataaattata taagagaagt aggttcaggg atcttgggag ctcagaagca ggatgagtta    93660
aacaaaagtt ggatTTTgcc tTTagcttgg tttcattatc ctgaaggaag agcctgaaat    93720
atagtgtagg gtgcaagtag tatatgtggg tggcaatctc gggaaacagg agcatgtgat    93780
gaataaggag aaaaagccaa tataaaggta ctgcattgag ggcaatgagg gctctaattc    93840
tctgcacctt ctcaagcatt gtgcagattg gtttTctgga ttatcagcct gaaggacaaa    93900
acgaagaaac agccattagc tcctgtctcc cattgtctga gagctgccac taggatatta    93960
acttcctgaa attctgcaga aatctcctct tactttggca ctggagatgc ccatacgcag    94020
aaagcaaaaa ggcacagcat atttaaggaa gctcataaga aacagtgcat ccagaagtgg    94080
cgagaattgg aggaatggac atgagactct aagaaccagc gcctttgatg ttccttttga    94140
tctgttatgt agctcttctt gtacacaggt gagcaaaggc atgctggaca aatggattca    94200
catgtgctaa agcatggggc aaaaaccaca tattaattca ggaaaagaca agatgcgtgg    94260
ccctctctgt ctctgtctaa gggtgaatta agagggggat atatgtacag agtggcaggg    94320
caggacttga gataagaagg ctaggtgggt gctctcatgc tagtagcatt atagtacagg    94380
tgatgagaag ctcctgaaga atcatcttaa catttgtatt ttagagcaac agtattgagt    94440
tctgacttag agacagcaaa actaaagaca gaaagactat tttgattatt aatgatgtag    94500
atataagaat atcgtcaatg tgaactaaag catgaagcta cttatgatat atcattaaaa    94560
ggatttaact gattggagac aaacgagagg gatggggaaa agaattcatt tgttttTagt    94620
tgctcttTTT ttcctactta ttcctTtgtt ccgagtgtga ataaactttg taactTTTa    94680 tactaaaaca ttctgctcat tcatacttat ttctttgatg aaacaaggaa acccttgtat    94740
agttataaac gtgtgaatca atTTaatat taggaaattt ttTaaataa agctagtttt    94800 ctgaagggga aaaacttggt tcaatttTTT gctggcaatc tgctttgtga ttTTTgaaca    94860
tgatatctac atctagactc atgtTTtgct agctggaatt tTTTTtcaaa ttaacgctac    94920
cattattata tgcttTacta TTTagcttTT gcagccttgg aaatctatga ttaatacaaa    94980
taattctcta tggcaatTTT aaaaatacat gtaaaagcct tcaatctaca ttgctactgt    95040
gtcgtagcac aaaaaaagaa aatgtgatca attttTaata aaatctacaa tttattccct    95100
tctaaataca gtcctagctc aggagaaagg aagctatttg tatTTTTcag aatcaaatTT    95160
ccctaaatga atatagagaa agaattataa ctgaaatatt gttgaaacag tggtcatctc    95220
aaatctgaag gtcattccaa aaaagtTTct gagtTTTcat tgcctcaatc taaaagttgg    95280
ccttTTTggt aatagatgaa agtaaaataa ttgaaagggt ctgttgcagt tttggaatat    95340
cttgaaaata tagtagagtg aagccttctt cccttaaata aagacaagt tgctgattgt    95400 tttctTTcta gccagataag aataatgcct tcttTctctt gttagtctta acacctcact    95460
```

```
tgttactatg tgtcagaaag gcgagacacc ataaatggag atactactga tggaggtcat   95520
ctgacatggg gctggtaggc agtgggaaga ctggtatgga cacaggtggc ttaggggttg   95580
gggaatgata tggaactaag gaaatgataa ttagcagaac ccagtgtgca tgtgtgtgca   95640
ttcgtgtgtc cgtgtatgtg tgtactgtag cacaatgcaa gaaagaaaaa acaaggcaga   95700
cttttcataa tttcagggat aaataaatcc tttatcactt catgtagaat attggctact   95760
tggaggtata tctaaacgta aatatataac tatataacta catgctaatt aaaaacatac   95820
aaagaagaag tgcctaaaga attacaacag aaagtggcat agtgattatt agagttaata   95880
taatataaat aaggccaggc atggtggctc atgcctataa tcccagcact tttggaggtc   95940
aagttgcagg gatcacttga ggacagggga tagagacaag cctagccaac atggtgaaac   96000
ccatctctac taaaaataca gaaattagct gggtgtggtg atgggcgctg gtaatcccag   96060
ctactcaaga aactgaagca ggagaattgc ttgaacccgg aagctgtggc tgcagtgagc   96120
caagatcgcg cactgcactc cagactgggg gacagagaaa gacccggtct caaaaaatta   96180
aaaaatagta taaataatat ttcaaaacac aagtctgtta agataaaagg tacagaggaa   96240
tggtgagatg acttttttat ttgtgtgata agggactgtt ttctgtgatt gtgagaagga   96300
ccaggagtta agaaaaagtg gccatcaata aatcagccac ttatggggaa gaaccataaa   96360
ccactctcag atgaaataca aatgcagtca ttatttaata ttattggaat atttgtatta   96420 gttttttggta tgtgctgcta gtgctggtac attttagtag tcaattaata ttttgttaat   96480
cttaatttct aactaaattc cagagtgaaa tggaaataat aatgaaaaaa ttttatttac   96540
aaaacagatt ttgttttttt ctgttaagaa tgatacacag ttgtccttca gtagccatag   96600
gggattggtt tcaggacctc ccttgggtac taaaatctgc agatgcctaa gcccctgtta   96660
taaaatggct tagtatttgt atataaccta tgcacatcct ctcatatact ttcaatcagg   96720
ggtccccaac cccagggcca tgaccagtac tggtccatag cctgttaggc tgttcgatac   96780
caggctgcac agcaagagct gagctcctcc tcctgtcagc tcagtggtgg cattagattg   96840
ccataggagc acgaacccta ttgtgaactg cacatgtgag ggatctaggt tgtgcgctcc   96900
ttatgagaat ctaatgataa atgtaatgtg cttgaatcat cccaaaacca ttccccttcc   96960
cctcaccatc cctgtccgtg gaaacatttc ttccagaaaa ccagtccctg gtgccagaaa   97020
ggttggggac tgctgcttta aataatctct agattactga taatgcccaa tacaatgtaa   97080
attctatgta aatagttttt atactatatt gtttagagaa taatgaaaag aaaaagtcta   97140
catgttcagt ttaagtgttg ataagtgtgt agagaaaagg gaacccttgt acattgttgg   97200
tggaaatata gattggtgca gtcattatgg acaatagtac ggaggttcct aaagaaatta   97260
aaattagaat tacctaagac ccagcaatcc ctcctctgga tgtacccaaa ggaaataaaa   97320
tcatcacctc ataaagatat ctgcactgct atattcattg cagcattatt tacagtagcc   97380
aagatatgga aaccacctag gtatgtgttg gtgcatgaat ggataaaaga aactgtggta   97440
tatgtatata caatggaata ttattcagcc ttaaaaaagg agaagaccct gtcatttgcc   97500
acaacatgca tggacctgga ggatattaag ctgtgggaaa taagtccaac acacatccac   97560
acacaaaatt gcataatctc acttatatgt ggaatctaaa aagaaaaagt tcaaatataa   97620
agttagaata aaacagtggt taccggccgg atgtggtagc tcacgcctgt aatcctagcc   97680
ctttgggaag ccgaggtggg tgaatcacct gaggtcagga gttcaagacc agcctgacca   97740
acatggtgaa atcctgtttc tactaaaagt acaaaaatta gccgggcata gtggcaggtg   97800
cctgtaatcc cagctactca ggcagttgag aaaggagaat cacttgaact caggaggcat   97860
```

```
aggttgcagt gagccgagat ggcgccactt cactccagcc tgggcaaaag agcaaaactc   97920
tgtctcaaaa taaaaaaaca aaaaacacag tccacacact ggttaccatg agtgaggtgg   97980
cagggaggag attgggagat gtagatctaa ggatacaaag tagcagatat gtaggaggaa   98040
ctaaaaagct gacatgcagg atgacaacta tagttagtaa tagtgtattg tattcaggat   98100
ttttgctaat tgagtagatt atagctgctc ttgccacagg ggaaaaagtg ggtaactacg   98160
tgagatagac aatggatgtg ttaatttttg tcactataat aacctttca ccatatacat   98220 tcatcttata acagcatgtt gtttactgta aatatataca ataaaattta ttttttaaata  98280 tctgagtatg atttgatgat ttgtgaaaat agagtgaatt ataataattt taaatgtaag   98340
ttaatgttat tagaaaagaa acagaaagaa cataccacac agaaagtctg tctgaaggat   98400
ctttgttttc tccaccaata caagtgttca ttgattcaga ggtggattat gagatatgac   98460
cataaaacaa aaatttcaag ggaaatatat tttattcaat gaaaaattct caacacaact   98520
gttatatgcc agtaaacact atatctttta aataacaggt catatctatt atatttaaaa   98580
ttcaaggaga gactacatta gagatgctat tagatcaact tctaatttca aagatttcta   98640
agatatggaa cagttactcc ttatacaaat taaaaaagca aatgctgaag aaattcagct   98700
acatggatac accatgaggt ggaaagatgc tccataactc ttagttaaac tgcactaatt   98760
acacataaaa ggaaaatgtt tcatttcact gtaatttgga aaccaaagaa agaaaagact   98820
gaatttttac atactgttaa agagattgcg tatctgttct aagtttaaga cagaggcaaa   98880
atgtatttta ttcatttgtc ctgcaccgtt tagaaataaa attcaacttc cttttaattt   98940
tttttaagaa taaaaaactc agtctaagga aagtcttaaa gttttcattt taagtgatcc   99000
actgttctag aagtttaata tttttgtttaa aatgtttatg ttctgtattc caccaagtct   99060
agttttaaaa caaacaaac aacaacaaaa tacttctcta acttggagtt taaggtgaaa    99120
gaaaccaatt acgtggtttg gaaatgtcac acttttcatc tctttttaa aaaaattttt    99180 aattcaggac agaaattgta tggatttagt gtaagtcttg ggatctcaca agtgtcagta   99240
tttcactctc ctccatatct tgatagcaat aacttgaaat aggatctcag tagctcaagc   99300
aatactgggc tctgagagtt ggttaaaaat tatttggctg agcgcctgtt gctgagggaa   99360
gaactaatct cgagcatatt tttggagcca ataccaaat tgtttgtgct tagcaacaca    99420
gcaccaggct tgcccttcag aatgattcta gaccaaatgc cagaaatgct ctggttctga   99480
ctacagagtt ctattcacaa atgacaggag gcaagaggtc ctcctcactt tcagaagaaa   99540
ggtcctttgc tttcttagtc aatggtagga aaaccattgt ggttttcatt gcattacata   99600
atttttaagg tgattacttc aataagaagt gctctgtgta tatgtgtgtt tatagacgca   99660 tttttaaac actggagaat ttctgaaagt agtacaaacc ttgtaatgtc aagtagatgt    99720
gggaaaaagg gagtttacaa cattctctcc tgacattgct ctcctttggc atctgcattt   99780
ttaaaatgtt aaaaatgttt aaaaacgtgt gcttaacact taatttggtg atagttgctg   99840
ttaccaaggc aactctgtaa ctccacccag ataaaaataa atcttgaaga tgagtttctg   99900
tgtctctgag caaatatttt tgtgaatagt agaagcagag aaagttaaag atacctgagc   99960
ttttgatctt tactagtttt atagatatgt ttatagttat acatttttat tcatacattt   100020
tagataaata actttgtaaa gcaattgatt cttcttgtaa aaatcaagta tattcttaat   100080
agactgataa acttttcttt tttgagacag agtcttgctc tattgcccag gctggaatac   100140
agtgccatga tcttggctca ctgcaaccta cctctgcctc ctgggttcaa gcaattctcc   100200
tgcctcagcc tcttgagtag ctgagattac aggtgcatgg taccacaccc cactaatttt   100260
```

```
tgtattctta gtagagatgg ggttttgcca ttttggccag gctctgagaa acttttaag  100320
gtctcttttg cagccagcta tttgtctacc ttatttcatt cttaatctca ctagccaata  100380
ttttttctgt ttaagtgctt tcagcaaata ttaaatgctt gtgccttcag tcttatcctg  100440
tggaaacact ggtaatgaca aaacacata tttcaaccta atatacaata gaaacagaat  100500
gccagttatt catggaggag aagaatagac ttctgtattt aaaataacat tttgctctgt  100560
gttttaaaat cattcttcct tcatcaattg taagcatctt gactataatt tatacaccta  100620
aagataaata attcagtagc aatgataact gaaaacagga cacatacaat gaactagcta  100680
aattaccata cattctcatc catttcaaaa atagctctgt acttttttca gattttgtta  100740
gaagaatatt caatacaaat ttttattcaa tgaacacttc agatgtcaag attgttaccc  100800
acatggacaa cagtaaccta ggtaaagatt ctgcagccag gcgtggtggc tcacacctgt  100860
aatcccagca ctttgggagg ctgaggcggg cagatcatga ggtcaggaga tcgagactat  100920
cctggctaac atggtgaaac cccatctcta ctaaaaatac aaaaaattag ccaggtgtgg  100980
tgtcatgtgc ttgtagtccc agctgctcgg gaggctaagg caggagaatc gcttgaaccc  101040
gggaggtgga ggttgcggtg agccgagatt gcaccactgc actccagcct gggtgacaga  101100
gcgagactct gtctcaaaaa aaaaaaaaaa aaatttata cctgggctct gtgctcacca  101160
gcagaagggg taacatggct tcttaggaca accttacttg accatttact tctttgacac  101220
tagggqtatt cttagatcag caggtccttc cctccactta tgcacatgag gctcacagag  101280
agtctgggag gcagggaatt tatgattgga aacagtatac tttttatcta agaaattatt  101340
aatgtcactg cattcaagtg attaacacca tcaatatctt caagactaag gggattacat  101400
gatgtgtaaa attagaaaac tgtcatctac tagtggctag gcactttaat tatattaagc  101460
atgcaacaag agaactcttc aaatgaatcc atctctcctc tgtattattt ccaacccttg  101520
gatccccatc tgtttctgca gacaacagct atgctgctga atgtcttaat ggtttgctgc  101580
cccaactagc ttcaagatac tgcaggtcaa gcatagcatc ttactcttcc ctgcatctcc  101640
agcacctctc agaatgttgg tcacatagaa gatgtttgct gaggagttga ataagaatat  101700
gtacaaggga cacaattagc attgtttaaa aaagatgtaa caagataggg taaggaaag  101760
cttggagga taaatctttaa gaacaatcaa taatatcttc tcctctgttg gttagttgcc  101820
cttcaatctc agccactgaa tcaaatacaa cataattact attctgatat gttcttgaat  101880
cgaatatcca ataataagat attcggatgc atagccatgt ctaatatcaa agcccatgct  101940
tttcgctatt attgtactcc atacattagc ttccaaattt atttgcaatc caatattaa  102000
aagcaagtca taagcttagt atcgccaatg tgatactaag tatccactta ctaaactta  102060
ttttcaaaat gtggttttat ctcagtttaa tgaacacggc atgttttaat ttacactttc  102120
atattatata gtaagggcgt ggttacagat atgttaattt cctgtgctgc ttcacaatga  102180
tggaacataa tagcaaatga aactgttaat ttgcagatac ccataggcct ttggtgtctg  102240
aatagaaata aacacaccta caactgagag aggaagcatg tgaagcattc cagtgaacag  102300
aggccattta ttcagtcaca gacacaggag aaaaacaaca attaaaaaaa atctctgat  102360
gaaaagttca taaaaagttc actcagttta agcatatgtc ctataactac ttaaaataga  102420
gttcttctta aatatcattc tttgctgttt ttagatttct tctgcctgta tcaaattaat  102480
agaacacagc atacttttaa tttgctctgg tttcttagtg gggcattat taaacacatt  102540
aaaacaaatag tctcagggtt ttactgctga tgttaaagtt ctgctttcct acttaccaac  102600
tgtgtcatct taaggcacat actttgcctc tctctcaaat ctcccaaatg gagaatgata  102660
```

```
agaatacgta cctcaattaa agaagctata acaagtagaa tgtttggaaa agtgccgggt   102720
acaccataag cccactatga gtattggatt gtattacctc tgaaagctgc agaatggaat   102780
tctcaaagtt atatgtccct aaaatcctct taagtgacag aaatggagaa attagcagtc   102840
tgtctaagag agcttttcta gagtctgggc atatgttttt aggacaagac agttcagctt   102900
cagcttaaaa tgagagagca cgtctgtgtc cttactcctg ggtgccaggt ttcttgtccc   102960
catcttaaga caaataattt tggtggagaa gaggcagtct ctttgatttc gctctaaaaa   103020 cctttctgg aggaggtaga cactctccac ccccgttttg agactcatgc agctgaggat   103080
gactggctga gtacaagcaa ttgttccttc taagcagttt caattcttat aacttgtgga   103140
gatattctta agtccagggg attttgtgta tggtggattt ttattacaaa gtcctgtact   103200
tcataggaac aaaataattc aaagtcagga accagatcaa agccacaact cagatatggc   103260
accttgagaa gttcatttgt atttcacttg cataaaaacc ctcaccactg ctatctgatt   103320
ttcacaaatc attcaacagc tatccatgaa gcacccactg tgtgtctggt ctctgtgtca   103380
gtccctggct tcatgtgtct ttccttctgt accctgactc cccaactcat gaacacatga   103440
agtaaaaaaa tgaaaatctt tttctgacct ctcttcaaaa tcacttttt caaaacaaac   103500 acctctcacc tgctcatcct ccagccagta aatcacaggg gcctagaaat gtcacttaca   103560 aatatttct gattctgtcc ctcccttcaa gcttgccaac attatcacag tttagggcct   103620
gctcatcttt cccccaatct ccaattagat ctctccacaa tgcaattctg cacattccct   103680
gttacaaccc ttcaattatt tcccagccca tccaaaataa atctaagcc tcttactaac   103740 acattcagga actctgtggc ctacggtttt ctacagacta atttccagc agttgacttc   103800 cagtgcaagt gaaaacctag tgtcatgcct gcatgataga taaatttgaa gctgaagagc   103860
ccaaatgtat agaccatgcc atgaaaggtt tatagtcatg acacagtggc cctatagtac   103920
agtgcttgaa gctggctctc tactgtcaga cagaccactt gccagccatg agacctgggg   103980
caaaatgcct taattttat gtgcctcaag ttctcatgtg agatgagaat aaaaattacc   104040
cctatttcat aagatttgat aaagtgttta gcataatacc tcataacaat tgcaattcag   104100
tggtggttat tattataaag aaaagatgat taactttatc ttaatgttta acttgttctg   104160
atagttattg atctatagct ttgatatgga ggtttgagaa tgacctggaa agaattggcc   104220
acaatgattg aagatagtga tacaagaata aaagatgact gcaaaatgta aacctgcaat   104280
aacagaaaga atgaagtcac tggtctcatg ggaactgata tgggagaaaa aaacagatca   104340
aaaggctatt catgttttgg gcctctttgt caaaatggaa atgagaaact ggggaataaa   104400
aattaaagca attctagcat ctggttttaa cataattctt atccctaaaa agaatctata   104460
agaaactccc aaaatgacag gcagccgtgg gtagcattgc atttcaagta atcttttaat   104520
tgttaaaatt taagtttcca acatgaacat aaaattttca acctaaaaga aatgagttcc   104580
aaatctgaga caagtgaaaa aggataaagc ctactagggg gtaaattcca tctcttagga   104640
gatctagtac ccaatttagc aatgtccaat caagcctta actactacat ttgaacacct   104700
catcatttca aaatgttact taatgatgcc aattaactgt acaatgtctc tgcatagcac   104760
atagccctaa aatgatttgt gcaatgttac tgtcagtaaa actgaactac agggaatgct   104820
catattctat gtcattatat acagaaatgc aatatcaata aagtgatatc tgttggtatt   104880
agaaaaaagt gaaaatttc atatctttct attttctttt ttcctcaatg ggatgctctt   104940
gttaaagata gctctgcata gtaaggtttg tataaacatt atttagctaa agttaaaagg   105000
ggtaacatac tggttctagc acagatatta aaacaaatta gtttgtaggt agggcagcaa   105060
```

```
tcaattatat tactaaccat agctttggtc cttttatcct ttcccatttg attttacaca  105120
gtgggatgtt aaaggttgaa tgtctttggt atctataaac ttaattgaaa gctgttattt  105180
gtttgtttaa gtctgttgat ttttataatc ataattttac tcctatagat ttcttgtagg  105240
agtactatat gaatttatgt tgcactgaat tttgttatgt tatacaaatt aataggcttt  105300
tatttatgga aagctactat tgatctgtca tttcttaaaa aattactaaa aagtgttaaa  105360
actttaaatg ttggagagtt tatattttaa aagttacatg ctagaaaaac atgatgtctg  105420
agtatattag aagttataga taattcatct gtcaactata aaactctcca acactgcctt  105480
tctttaatga ataatatgaa atttagcagt gaaaatgtga caatgtacaa tcctaaataa  105540
atcaacaaat ttagagatgt acctctaaaa ccattgtaaa ttcaacagtg taattttcca  105600
ttggactttc acttattcat tcattaaaca aatgtttgtg agtgcctgca atgtatgaga  105660
cattgtactg aagctaggca gtgtgagtta tcatatggga ttatccttta aatacttctg  105720
agggcaaaaa aaaaaaaaaa aagaagagaa aaggtgtgag gaaagataaa gggttaattc  105780
attaaaaaat aacacttgag gactgttttc tttgcaaggc ataaagttat caccctttca  105840
aacagtagat atttcacatt taggatgcga gactccagtt ccaacaaagc tcattgcaca  105900
gctgctaccc tgattaaact gctacatgaa ctctgagcaa tgtagcatgg tagccgcatg  105960
cttctgcttg catgatggtt aattccttcc attctcatta gtgattttct gagctttgaa  106020
attctgatgg tacctaggat ataaagcata tttatctaac tgaaaaacag ataattagat  106080
gtaacataaa atatgaatgg ctttgtcact ttattgtagc agagaatgaa tgtgggataa  106140
attaaagctg atgctagaac atatgcctat tttttagctg gaaaatttca agatttatgt  106200
actttgggct tgagaaagaa atggagttta tttttttatgc actgacatct cttttttttt  106260 tttttttggaa gagctctctt aggaatgaat ggtatgtaaa tacagtagga atgtaattat  106320
agattttcct gacccagttc ctaaataata gatatcattt cagaagtgcc ccaatacctg  106380 acctttttgct ccaagccata tcaaagcaca catctagtct acttttcact ctcattccta  106440
gccactatga caatactatt cagataaaac ttctagtcct ctacttatgt gactcatacc  106500
aacttgacct tacgatagtg actggggggtg catatctagg ttcatgctgt ttgtccatta  106560
ttatggtttt gtgagaaaag gcaaaatttc taggtaaagt gttatgagga cgaataatcc  106620
accaggcaac caactgaccc tttcatttgc catcttgtca cttcaaacag ctctccagaa  106680
cctgcagcca gcacagacca aagtcaggtt tgtctcctct tctgttgatg aacaaaggtt  106740
gattccatat cgtggctatt gtgaatagtg gcagtaaaca tggcagtatt gtatgaaaat  106800
atcacagata gcccttaaat atgtgcaact atgatgatct atcaaaatta aaaattaaaa  106860
tttattttta aaagttcagt tagaaagctt gtagttcctg gcaaactact accttttctcg  106920 gcaaaagaat ttgatatctc ttaaatatttt tctgcctaat gctgatagat tgtatttaca  106980
tattccatta atgcaataaa taaaattaca ccaaaacatc agcattattt atttccaggg  107040
gcatctctca aaataaattc ctccaaaatt cacaaaacca aaaccaatgt gaaattgtac  107100
tcagggatgc aaatgtagcc cagtgaagca tttgcccact tgtttggtat tattgaagca  107160
caattagaaa aatgtgcaat gtatgcccaa aaattctata ataagggcca ggcgcggtgg  107220
ctcacacctg taatctcagc attttgggag gccaaggtgg gcaaatcatg aggtcaggag  107280
atcgagacca tcctagctaa caccatgaaa cccagtcttt actaaaaata caaaaaattg  107340
gcccagacgt ggtggcggga tcctgtagtc ccagctactc gggaggctga ggcaggaaa  107400 tggcatgaac ccaggaggca gagtttgcac tgagcctact ctccagcctg aacgacagag  107460
```

```
cgagacccca tctcaaaaaa aaaaaccata ataagaactt tttaatatac tatattataa   107520
tgtaaaaaga ctagatgtca aacaaattag gtgatgggaa ggaattgagg gagaatttta   107580
gactaagcaa ttgagcagca cctgtttttc accacaaatc tgttacatgt attgctcaat   107640
tgtgctgaat ccatattggg tcctggtggc tatgtaatag tctctttctt ggataaatgt   107700
ttgtcctctc ttatggttta ctaatggtgt acagaacagc attgaatagt ggttatttcc   107760
tatgacttcc tagatatctc tctcataatc ctgaatgttt taaagatcat tcttagatag   107820
agtacagcta gacacgaacc atagtggaaa tcaggtagac aaaatttaaa aggagtctta   107880
attgaaggtc attttattgt cctcagtatt aatcttactt aaaacaaacc tgtcactgag   107940
cagaactcaa acaccagag cccttgcca aatgtgattt tttacaacag gagcgctggc   108000
agttgagagg agtattctgt cacacttgag agaattcgag tccctgaaga tttatatgaa   108060
tgcttagcta ttatcgaacc atctcttcac agatgactta gtaaatgtct gcctttgcat   108120
cagataatgg cttacaagtt aatctcctct tgctccctgt tacacacata tacaccttct   108180
tcctaaacag ctcataaggt gaaagaaaga ctcagatttc tgactatgta attgataata   108240
tcacacggac tgcctgctca tcatctgcta gtcacattgg cagagttgac agttttggag   108300
acactgaaga cagtgcatat attaggaaat aagcagtttc ctgatataaa ttttcttgta   108360
gtttataaat tacatagcat ttattattcc ctcatatttt ataacattta ataatagaac   108420
tgacacatat attcatttta aactcaattg tgtataataa ctatcatagc aacccttcag   108480
tgcctaaata tcaaatcttc cattcctccc atgaacatct tgaatatata ggtactgtgg   108540
ttagctccaa caagcttttg gttagaattc attgcactga tacatagaca ttgttttaaa   108600
ggcaatttca aatcaaagct gtcagctgtg aatcaagcac accttaaaaa gtgacacatt   108660
tgtcactaga ttccagcctc tcaaattact gacacgcatc cttttatgt aaagatgaca   108720 ttgttctttc ctgatatatt gcattcctca tgaatttctt atagtcatag aattttata   108780 aaccatttca gaatcgctga aataaacatc aatattttta acttttcat tctgtcaaaa   108840 atattgtatg cagagatatt gctgtaagtg tgtatacctg tgcttaagag actagggctg   108900
aagagaagta atcaaccgaa ccactggtgt aaatgtgcgt cacatttta gtgactagaa   108960 attgaaataa ttccaacaaa tttatgtgct ttgggcttga gaattcagac tgccttaggc   109020
taagataaaa atcttttcct ggtactatat accttctttt attgaatgac tacctggctc   109080
tttctattat atatgcagat tttgtacctc tggtcatctt tgtaaatggt gcctaaaaga   109140
tatttgaaga ataagtgacc agcaataaga acaaatgtct atacaaaagc acccttagt   109200 tggatgtaat tcactacttt gagttgttaa taacctctaa ggatgacagt agctattagt   109260
tgaataaacc attatgtcta ttattagaac actagatagt ttataagtcc aaacaatgca   109320
taaaatacct atctcatgtt accattgttt aggttaccag ataattgttc tgtccaatta   109380
ttccacttaa ttttttgctt gcccattagc taaatggcaa gataaaattt gtcaaacggg   109440
ggggaatgta ttgaaaatgc tagacaacta cacttaaaat gaaaacaggc caggcgcggt   109500
ggctcaggcc tgtaatccca gcactttggg aggccaaggc gggtggatca cctgaggtcg   109560
ggagttcaag accagcttga ccaacatgga gaaactccat ctctactaaa aatacaaaat   109620
tagccgggca tggtggcaca tacctgtaat cccaactact ggggaggctg aggcagaaga   109680
atcgtttgaa cccaggaggc ggtggttgca gtgagccgag attgtgccac tgtattctag   109740
cctaggcaac atgagcgaaa ctccatctca aaaaaaaaa aaaaagaaa gaaaagaaaa   109800 caaatgcata attttgcaaat attattttta tattgtatgt tatctagggc ttctaaatgc   109860
```

```
attcttctta taagcctagg tttgcaataa cattcattta gaattgagta attttaaata   109920
taatatttta taaaataaaa tataataatt tctcttaatt ctttgaaaat attaaattaa   109980 aaggggggttg caaactctgc attccacatt tccatcccaa catttaattt tagcaatttt   110040
gtagtctgcc taaaatgcaa tccatcattt actgtttaga aaatagggaa tgtacacaaa   110100
ggcctttcag cttteectga actccataaa aatcttttg cttctttact gcccccettt   110160 gtcaggagtt ctgaggaact gttttttatc ttaagtctca caaagcattt aggagaatat   110220
ttaaacttaa attcttttaa aacttatgtt caggacaaag taacattgta tgcattggtg   110280
tcatatgtat ttaaattttg aaattttaa tactggcaaa atgaggtttc aattttaata   110340
taaattattt aacaatctta aatcattaaa tatattactt aatatattta atatatctaa   110400
acagtcacaa ttttcccata ctaataatca taaaaaatct tacccaatgg tcatatagat   110460
atacttaatg gagttttggg ggggtatttt tgtatattaa aaaattcata tatttgcctt   110520
acttagaaga actgattaaa tgaaagtata atattaacaa acatattgtt attttatatt   110580
tgcatttgtg ataattatat ttgaaacgtt caagattttc caatgaattt cttttgcatt   110640
tgcgtatttg tgccttttta ttataaaaat aggtggcttt ttagttccac tgcataagtt   110700
tcaacatagg tctacaaata gtgcatcttt ttgaagttaa tcattataat cacaaattga   110760
agttgcctga gctccaattg gagtctaaat ggatgactga atcttattat tcgaaaccca   110820
ctgttgctac acaatatggc cacacaagag agtacacaag acccgtctga ttcagcctca   110880
gtgccataaa tattttaatg gtttcgttgg aatctggaaa tggagctcac cacaggagat   110940
gcttcttcct ttgactctca ttattatttc ctttacaaat taattaataa aaacttagat   111000
gctaaattag cacttgatga aaacttatat agccttgaca ttttgattct gtgagtgaat   111060
aaaaatactt ggagaaataa aaatcctaat catgttcagg aatacccaca aggtaacaag   111120 tacatttta aactttaaaa acatttatta ttcatgataa aacatgttgt gtgatttaaa   111180
tataaatttt tattatttgc tttaacttat ttccggatta aaaagtaaat gtttacctag   111240
ctgttctaaa tggtaatcct catgattaaa acagcaattt gtcatatttc agttacaaat   111300
gatcttttat tattagttat agaacataag tttcttcatt gactgaggcg atgtttcaag   111360
tagataaatc tgttaaaaaa attgtggtca tattctgtta aattctcata ccaggcaatt   111420
tgtttgatat tcaggaaaaa cctagccact gaccaaaaac tctacctgcc ttctcagttg   111480
tatcctcttg gacttaaagg ggactgggaa agttataaga tggttcatga tagtccatca   111540
acatcccaag aacaaaaaca gatgttgtac tgacagcatc atatgatcat atgcatgtaa   111600
gagcacattc atattgccaa atcagttgga attttttcacg gttgaaagtt aaatgaaatg   111660
cttagatgta tgagtcatcg gagttaaaga caattacagc cagatttatg gctgtgctaa   111720
aataaagcta gttagaaaac agaccaaatt ccatgacgat accaagtctg actaatgatt   111780
caccttaaat ttcggagcaa catttatcct cacttgtttg tttatttgac aatgtgccct   111840
tatccattaa gtaactagga ggaagggaaa agcactacgt gggtgagtga caagacactg   111900
acactgattt gtgactttgg ataattcctg gatgctgtta tctgtttgg catagagatg   111960 gatctgtaac tgctaataat tgccgactgt gaccatccca gaggccattt acttaaccca   112020
ggtatttcag acctgacagc ccgaggataa acacgatttc cctccatcac taacttcatc   112080
tgcagggcct aagcctcctt cacagtctct ccagtgattt attggcatct ccaagggtat   112140
ctcacatgtg ctgaagaaca aatctgctca ctttcatctg cttggttttc ccttttgaaa   112200
tctgctgctt taaaattact aagggaggaa tcatgcctgc tgctacccctt gccagtgacc   112260
```

```
ttgcagtttg tgccctgatt gttccaatta ccacaatcaa aacagaagcg tttgcagtta    112320
ctgcagtgct ctctctgtgg atgtcaggtc tgactcagag agccaggctg gggaacagcc    112380
atttccactc ttgtacctct gcaaaaggac ttccatgttc cgtaaacaga ctcccacctc    112440
tcattttccc cccaagcaaa gcatcataaa ttagagagca tgtaacggga agaaaatcc    112500 attagccatt tgggttcagt cagacaagcc agctcatgga aagtttatac aggaaggtca    112560
catttcaatt gagatcagga gggtgaaagg gtccagctgt gtgatgagag agagaatgtt    112620
cgggaatgtg aacagaggt atccaaggca gaacaaactc gtatatgaag gctttaaggg    112680
tgtgcaaatc tagcatattt tatgacataa aagagtcctg attagctaga atatgatgaa    112740
tgtgagaaga ggtgaaggct ggagatagga aaaattattc cagatcttat aagctatagt    112800
aagaaatttg catattatat atagacttgt gggaagccat tggattttgt aagaaggaga    112860
ttaacattat cttatttatg ttatttgtga tttataaccc caaatgtgcc agatacaaac    112920
aaaccaaaaa taataataat aataataaga agaagaacaa caacagcaat ggaactgtgg    112980
tgatggtttt ggtcacaaaa tgcatatata tctattttc acaatgcaaa aatatttcat    113040
tatttcaaat tttaacataa atgtgggtat gcatgagctt acaaatcttg aagtttattg    113100
gggaatattg gtgagcatgg tttttattgc atggtcacaa cttactaatg ggaaacatct    113160
gaatacctat tgagttaatg catgcacatt tttatttcc tggaatactg agaaaaaggt    113220
tgctacataa tgtcttgata gcttctaagt catggctcaa aagtgaatgt ggaatctgct    113280
aatcggaatg gactcagatt cagccaagtt ctcaaaaaca tttgctttca tagatgtctt    113340
caagaaacaa ggagtcttga atttaaattg tgaagtgtct atcttagaat agagagattt    113400
aaaatctgac tgtattttgt ttaaaaaagc ctatataact gtattatata aaattattta    113460
tactacagtt aaaaaaagaa tcccatccta tttgtgccta aataagtgcc tgcttgtagc    113520
atgaaaacta tttgttgagg gtccttagat cctcagagca tgctgtgaaa gtaggtacaa    113580
ttgttctttc tatataagcc tcttaagata acagataatt gccagaaata cagcacacag    113640
tacaaaatta ccttgtttta cttttgccac aaaaaacaat ttcttttggc tttgagcaat    113700
aaagtccaat gatttttttc cttttcaaaat atcttcctcc ctctccataa gttttatatt    113760
tattcacgaa ggaatattcc aatatcggat gttttgtct gtgtctcttc ctggaacaaa    113820
tgttaattaa tctcttgg tttgtatgtc aagtggaggg gtggggattg gggacaggtg    113880
atagttgtct agggagttaa cttcatctct ataggagagt ggatagacgc tgtatacgaa    113940
aagctcttga aaagggaaat acagcagcca cttcctcagg gcttccatgg tggtcagact    114000
ccttgattgc tttagattaa ctctggcttt tgtccttcgg aggccaccag attgggtgga    114060
tagacattgt ccttgctgtt cttttgacct acctacttgt actttagggg aaaaaaatgc    114120
ctgtaatagg ttaaatgctt tctcaaagat caccaaagta tataacacat ggcaaataga    114180
cagagaaatg agacagtata atcagtataa tttataaaag taccttacag caggatccca    114240
tgggatatgg gttttttttta aaaaaaatct acctaatctt ttcattgaac tcctattcag    114300
gattcattat attgaatatg gctcagagac ctggaaaatt gttccacct ttttaattta    114360 ttcaccatca tttatggaag ttttcaagga cgtttactta cctacctcag ttaacagatt    114420
gtactacttg ggaagtctat aaatatgagc ttaaagcatt ttctgagttt taaaataatt    114480
tagattgtgt agaatgttaa aactaaaaga ggaaaaaatt attcagttcc tcagttgaac    114540
ctagcaattt atcttttcac agtgtgctca agtatagttt ttgaaaagta aagaagatgg    114600
tttttataca aacataaaca catttcaaag attttattca actaattaat tagtagtgga    114660
```

-continued

```
gccaataagc tggtaagact ggtttaaagg aatatctgag gaataaagat ttatagaaac   114720
agtcaaagaa attctaaaga gaattgacta atagatataa atctagtaaa tatttgatta   114780
ataatagcag taacctatgg aattatgttt tctactgagc ataaatgagc atgaatctct   114840
ttgggtttgt atgtcaagtg aagggtggg gattggggac aagtgatagt tgtcaaggga    114900
gttaacttca tctctatagg agagtggata gatgctgtat aagaaaagct cttgaaaagg   114960
gaaataaagc agccactgca catctgcaca tataacctgt agatctgggg gctctaataa   115020
aaaagttaat ggcaatgtca aaatctggtg ttttatctta gataacttca tagtcattga   115080
ttgagcccct taaaaataac atttaaagga catgtagtca ttctgtttct ttattgccaa   115140
gttttcagca atttttctca tgagaatgag tgctaagaaa cttttggtgg agcgtggtgg   115200
ctcaagcctg cagtcttgca ctttgggacg ccaaggctgg ccaattactt gagatcagta   115260
gtttgagacc accctggcca acatggtgaa accttgtctc tactaaaaat acaaaaaaaa   115320
aaaaaagtgg gatgtggtgc atgcgcctgt aatcctggct actctggagg ctgaggcacg   115380
agagtcactt gaacccggga ggcagaggtt gcagtgagcc gagatcctgc cactgcactc   115440
cagcctgggc tacagaggga gactccatct caaacaaaca aacaaacaaa aagaaactt    115500
ttaaaatata acaatagaga cattacatag gcccacaaaa ccacctccaa aaaagcattc   115560
tatcacctgc aagaaagcat atatatatat ctgcttttgt gtatatatat atatatatat   115620
atatctgctt ttgtgtatat atatatacac acacacacac acatatgtgt gatatcagca   115680
tgtgtattta cacatatatt ttgtgcatgt atattttaa ctaaaaatgt gctaggagtt    115740
agatatgaac tgattttgga ggaggtgata tgctgtagag agagagaatg ggagaatagc   115800
agtattataa tctctctcca ttgtattcag ttttttttctt tgtctgaatt tttaatagaa   115860
gtcagccaga agatgttagt ttctgggaaa tgtgttgaga tttacagtca aatccagaga   115920
gaactagagg cttatgagta aataagtaaa ggttatgcag agaaagtatt cttttttcctg  115980
tgtaaacttg aatattggcc aggcgcggtg gacacctgta atccagcact tgggaggcc    116040
aaggcgggtg gatcgactga ggtcaggagt tcatgaccag cctgtccaac atggtgaaac   116100
ccattctcta ccaaaaatac aaaaattagt gggtgtggtg gcaggatcct gtaatcccag   116160
ctactacgga ggctgaggca ggagaattgc tttaacctag gaggcggagg ttgcagtgag   116220
ctgagacagc gccattgcac tatagctacg gcgataagag tgagacttca tctaaaaaaa   116280
aaaaagaaaa gaaaaccttg aatatttctt gtacttgtgt tcaaatcata cagttatgaa   116340
agtttacccc tagctgttac acttaaaatg tacttctgaa atatacagag agatgataca   116400
gactattaat gagttccact aaacttttaa tggtttagaa aatacaaata ttttcttatt   116460
tttctggaat tccagccatt aatgtaaaac attggtttca acataaataa cacactggca   116520
tgcacatatg cctaagcatg ggcccccaca catacagaca ttctgaaaga ccactttta    116580
aaaatattca gtaccgtata ttgtgcattc cttctttatc cacatactta agctgctgca   116640
agcatcccat tgataacacc agtaataaaa gatgggacca tcagtaatga gatttgaaag   116700
cccctttgc aagaaagtaa ggactagaag gtggaaatca ctctgtctta gagtcatatg    116760
gattggggct ttgctagaag tgtgtgctct caggggaaagc tgcctttta tttttctccag   116820
agaaaagcct ttttgtcagt aaaagaagat gtatcatcca atgcatatgt aaaattctaa   116880
acagcagata aaacaacatt cactattaat ctctgcaaaa gaagatatat tgaaaaatc    116940
ctcaagtgtc cctctttggg tttctttgtt atatattaaa gcagttatct ttagatgcat   117000
gagaatcacc tgaagacctt atttttaaaa ttcagattcc tgtcagttca ctcccaaaga   117060
```

```
ttccgattca gtagttaaga gacaaagcct aggaatgtga atttacaatc aacacctcag 117120
gtgatagcca tgcatgttct taatgctcta ctactatcta tgcataaaag gaagataaag 117180
ttttaaaaac ttgaaatgtg gtataacagt ttagtattga ataatataca tttttactta 117240
ttgtaacaaa ttatgatatc tacttggggc aacagtatct tttatttggg atctgaatcc 117300
taattttggc taggtatcac tgagggattc ttagtctaaa acaattaaat ggagttagtg 117360 gttttttta gtaactcttg attttctgtt tttttccatt ggcatcttac aaaatttatt 117420
cattcatttt tcccttttc acttggcatt atttgttaga cagtggacaa agaactata 117480 gaaagtagag aagcatgtga tgttgtcctg ctcttagatt ctcgcaactc aggagaggac 117540
attcgcttac accaatcatc tcaaaacatg gcagtttatg ctgaactcag tccaatggga 117600
gagcatttga ctgagcacat agggagagaa gttagctctg ttgaaggata atcaacgaag 117660
aattcttagg aaaggtacag tcattcattg aatatttgct cggcacttac taggtgcata 117720
tgtgcactaa gatctaagga tgggctgatg aagaacccag gtcccttttc ttctagtgga 117780
catgcagact ggcctaaaaa aaaaaaggta actggaaaat ggataaggaa actgagtcac 117840
tcggtttatt tattatcact cggtttattt gcttttgttt gtattttcat tttgacacag 117900
cacagtgtca tcttaacgca tcctccaaag tgaaggatgg ggtggataac actttagttg 117960
gcatttctgt agccaggagc caggatcttt ctcccataat tgcattaacc tgggaaggca 118020
ccctctaggt agatttgtat agcaccctgg ttaatcaatt atcagtttac ttcttgtctc 118080
actaagcttt aacaccttac atttatgaag cagtgtaaat ataactttag catcttgatc 118140
acagcaagca cctgatttgt atttttttat tagctcaagt gaaatcagat cagagaagta 118200
cattacaggt cataaaatat gtgcaaattt cataatgacc tccttttaaa atgtgcaaaa 118260
ataagattgt taaggcacat tccagagcct tggggggtgt gtgtgtgtgt gtgtgtgtgt 118320
gtgtgtgcgt gtgtgtgtgt gcttgtcttt tgagaatatc tgtatatcag aaaatttggc 118380
tgagaagcaa tcttcttctt agtggttctt tttctctttt gaaaataaag tactaaaaat 118440
acttaaagat gcagaacagc aacctgttcc cagtgagact ctcgtttaat taatgtggtg 118500
atctatatag agaaaaggga caattgcaaa agtccctcaa taattatcta accacagtct 118560
ttaggtaatt acagcagaaa gattttcaag acacaaaaca ccctggaaaa tttgacctct 118620
tattttgatt caggcctttc atttcttaaa tattttcttt aatgttgatg tttatgcttg 118680
acaaggtcag cctaatgcca gatgaatccc tggaactcaa acattgctg aattcacagt 118740 tgaaggattt taatataata taccagcttt taaaaatcct acagtgagaa taacaggact 118800
gaataaaaaa attaagaaat gctcaggtag aaataaatag agaaatttag aaaaaaaata 118860
aaacgtattc aaaataagta ttaagcattg gcaaagaaaa aatagtagca gacaattaca 118920
tgttccattt gtaaagatga ttattaatta gtggtcttgc aaaacattgg agaaaatttg 118980
ctgaaccatc acattcataa atattaaaac cacccattag tgaaaatctt tttactaaac 119040
ttcacaactg atagtcaaat aatgttcagt ttttctccat tgcaataaaa aataaaggct 119100
tttgccttca gatcagtctc tgggccttat taattcagtc agccagaagc cacatggaaa 119160
tattttgttt tgttaaaagc cagcttgccc tcatgatctt ttaaaatctt ttaaaaatct 119220
tccatcagcc ctctccctga cttgaattat ggcagtgctt tctaaactgg taaactcaat 119280
ctccttggtg tgcctcaaga tagagtacat aaaccctcct tagaaattga gctctcaatt 119340
ctaaattgca ctctccatga gagcaagcaa gaatgctttg ctttgtatta agtggtcaca 119400
atattaaata taaccataga cagcactgta ttttctaaac accttatttt cttttaatga 119460
```

```
ctgacataaa ttagatcata agtatacaaa tgcatatctg ttgtattttt cagcaccatg   119520 tgttttttt tctttttct gagttatttt cctgctttcg gcagccttt ctctcaggt   119580 ccttgtgatc cacagtggtg tgtgttcaca ctaaccaaag caatagtctt acctgccaga   119640
aatagctgtg acatttaaag agaggtccag gggaaggcac agtgcttaac atccaagtct   119700
gaagagctaa tagtgaaatt ggggcatcag ctacagagag atttagggga agtaacaggc   119760
aggttaaata ttttatggaa atgatttctg ttctgtatat gattgcaatt aacacatgtc   119820
aatctgtttc attaatttgt taactcatct attatgctat gccatgaaga aaataaaatt   119880
ggagttcttt atttttttga gatggagtct cactctcttg cccaggctgg agtgcagtgg   119940
caggatctca gctcactgca atctccacca cccaggttca agcgattctt ctgcctcagc   120000
cacctgagta actgggacta caggtgcgtg caaccatgcc tggctaattt ttgtattttt   120060
agtagagatg gggtttcacc atgtgggcca ggctggtccc aaactcctga cctcaagtga   120120
tccgcctgtc ttggcctccc aaggtgctgg gattacaggc gtgagccacc gcgcccgcc   120180 acaaaactga agttctaagc ttcagtttag atgctcacta aatgcttgtt ttgcaatacc   120240
tgactgtaac tggcaggaat atgttttgaa agtcctcatt ttccaggtat gcagatgaaa   120300
tataggggca ttatctacta tgtcaaatta taatgattta tcagtggcac atgaaagtcg   120360
cctcacattt cttaatcagt gatataccat tatgtcatgc cacctttaa tgtaatatgt   120420 ttacatcttt ctttagatgt aagcattcat ttagttcatc acggtggctt tcacacttac   120480
tccaagaacg ctatgagttc ctttgatgtg ctcaagtctc ctgccccagg gagaaaggga   120540
gtggtgagca ggaatcgctt taatctattt acacagatat tttcttttcc atttatttta   120600
aaggaatttt ttttaactta atgagtatgc agtgacggtg gtgatgatga tgatactaag   120660
gtttaaatga ttagatagtc aaatctgggc tggaattgta atactgtttt gacttttaat   120720
cttagagaag ctccagtctg cttattttct gggcataaac acatgagaac aataacacag   120780
ttctgttatc tgaatgttgt tatattttgt ttgaaacatt cagtgacttt caaatattgt   120840
atttgcctaa gaaaattcaa cagagtcaga cattctcttc caggttaaat ttggtgagtc   120900
tgctaggaaa ataaattttg tgcactggtc attctgatct agtggacgtt ctaataaaag   120960
cacctttgtg ctgcctacgt cttcacttta aagataagat acctgggtac tcgacaccaa   121020
attatagttt gagatctcaa aaatgggata gggaaaccac agctcaaaaa caaaaatact   121080
agcactggaa aagatagaac tagtgaagat gaatcattct ctagacttta aattcagaga   121140
tatcaaaatt aagaaaaagt aggaggaata aaaaagagg gtaagcaaaa caatataagt   121200
ttgtatagca agagggtata aagcaaatac aatatttttc agaaaaatta aataaaaata   121260
gatttacata acattgtttt taatctcaaa gatcaaattt caattttcat ctcattttaa   121320
aacccatatg cacagtctcc tttatataca tcagttgggt gtcaaagtga cttttttctt   121380
gtttccaaat acagttattt ttaaaattta attgtatgat ttaggaattt gaaagcaagc   121440
cagtttgcac acacatatgt tattatatgt gtgctttaga cttggttttt agttaatgta   121500
acatgacagg gccacctgag ttatttgttt acaaactagc tggaaagcca ccctggagga   121560
gaaacctggc aacaaaatgg tctgcagctt tgttattgtt atctatagga ttggatgcca   121620
ttattgctgt aaaatagttc acaagaactc agtctatggg aaagactcaa aaattctttg   121680
cctgttaaag aaaaatcagg atattggact ggttagttta actaaaaagt gatgatactc   121740
agattctgct tggattcact gcttctcagc agttgttttg tttctttcta attgatattt   121800 tattttcag agaacccatt ataaaactct tcttcttccc ttaaaatcac aaccacacaa   121860
```

```
cagcaattaa aacatgcttt gacgtaagac tgatatggtt ttaaacccag cttgactatc    121920 gaattttta cttaaggcaa aacacctctg acatttatgt cttatcgtca gtaaaaaggg    121980
gtgattaaca gttttacaag attattcaat aaataaatat aaattcctcc ttttccttcc    122040
tttcctttct tcatcttcag catctgcatg ccataagctc attttagttc tctggactca    122100
tgttaacatg tcccaccttt cccaaattaa acatcatctc tgttattggc tccattcttt    122160
tcctctcatt tgagacaatt ctttatcaac caacaccctc tctgctctgt attgtgaaac    122220
tctgctccta ctacattaac agtctcttgg tttctttaaa agaagacaa aacaattaaa    122280 gaacagaagc aaaaaatcta ctcaaatccc caattgttac cctcaaaatt aattgtccca    122340
cccctagctt tctcattgca caactctttg tcaaaatgtt ttctaccatc acagccttca    122400
atgatctttc tggttccttt atctcctgaa gtctgacttc tacctccatc tttttctgga    122460
ctattcaaca cactttgaga aaaacatac ttttgttaaa caggtatgca tccctgaagc    122520
ataaaataca tagtactgaa agtgcacatg tgtggttctt cccatttttt ttacagcact    122580
tgaaactgac aagtagtagt accaattact tagtaaaaga ccttttttcat ttcatttctg    122640 aaatattgtt attttccttt ttcatcttcc atctctgact acacctccaa ttttacctct    122700
ttgctgcctt ccttcctaag aaagttcttc atgcaatgcc atcttgtttt tcttcacttg    122760
cctctttttc tcactttaat tttatgaact ctgatgactt acctctgtag tgtaactact    122820
caaaatatgt atttctgaag tctcaactcc aatctcatat tttcaactta tatttatgga    122880
ggcatctcag actcaaccta cctaaaaaat ggcttatctg ccctaaaatc tactttgttc    122940
tttttttctc tactgctaat aattatcttc ctagttggtc aagctcaaaa cctaatcatt    123000
tttactcctt gtccctgtgt cagctgtcca cattcaagca gcgtatcatt tctgcacatt    123060
tttcaagcaa gtcagtaact gccttttgtt tgggactgtc ttttcatata gtgaacagcc    123120
ttggaagata gaaatcattt ctccttctaa aacaaaaggc aggtgtgctt gcagccttgg    123180
atagaggtag tgcctctttc taaagcaaag ggacatcttt actggccatt ataaaatatc    123240 catgttttcct gagctctgcg ttcctctttt ctaatgcaac ccactgagca tgtaggtgtc    123300
acctgagctt ttctgtggga attgcggctt gaggaatcag tgcaagaaaa tcatgatact    123360
cttgctaatg ctattaatgt gagtagtaaa gttaattgtc tctgacccag cactattgtg    123420
tctttgccca gcactcaaaa gactggcagg cttgcaagta ggacaaaatg ttagattttt    123480
cacagttctt ctgcttataa gtacttgtta aaaccaatta aaacacaact tgtagtttgc    123540
acctataatt ttgtagcatt tgcttcttat ctatgtcact aggatgtgct tagtgacaga    123600
cccatctatc atctattact caagtttttg gctgtattcc taggcaacag agagaagggg    123660
aacaaacaag aggacctgtg cacagtttga gaaaggcaaa acaccgagct taattgcaga    123720
cttgaatgta gctagcaaac gaagtaaggc aaaaggttcc ttttttttt ttttagatgg    123780 agtctcactc tgtcgccagt ctggagtgca gtggtgctgt ctcggctcac tgcaacctcc    123840
gcctcctggg ttcagcgat tcttctgcct cagcctcccg agtagctggg actacaggca    123900
tgtgccacca tgcccagcta acttttgtat ttttagtaga cggagtttt caccacgttg    123960 gccaggatgg tctcaatctc ttgaccttgt gatccgccca ttcggcctcc caaagtgctg    124020
agattatagg tgtgagcctc cgttcccggc caaaagtttc cattttttaa atagttgggt    124080
ttttagtttc gattctttcc aaaaaaaggt tttcttaaaa aaataaaatt agcaataaga    124140
tgaaatataa caacaatata atcttattaa gacaatatat gatatacatt tatcaaaata    124200
cttatatttt caaaagtgct taaaataatc tagcacatag tagatgctca gtaaatattt    124260
```

```
gatattatga ctgtgcatgg gtcattatag gctactttat gtatatcatt tcatttagta    124320
caacatcact ctgaaaaatg ttttattgtt accgttttc agttgaaaca tttacgttgc     124380
tcaagatctc actggtacca tctactatta ggtcagtctg ccaccaaatc tcatgctctt    124440 aaatgcccctt tttctcctga gcttccaaca aatagtgtac tgtatataat tgttgaaggg   124500
aggggactgt gagacaaaat atttagagtg aatgtgtagc cacaatttca gttcctcaac    124560
aaagtgataa aattaggaat catcctcaat atatattctt ccaacacaca cacacacata    124620
cacacacaca cacacacaaa taccacaagc ccacttgaat gcaccccacc tacacattgc    124680
aaccatagag acaattgcag cattaaatac agaatattct gtgtgttgtt tgtttgttct    124740
ccctttgcta caaaaatcag aatttctact caataaacag caagggagaa tacaaatgaa    124800
ccaaattaaa gaaggaaaaa atgttgaaaa aattatatac agaactatgt attgattat     124860 tgagagttca gtaatgtaat ccagaaataa tggatgcctt aaaagtaatt aaaagaatgc    124920 aaatcaaacat ttagtgccaa ttaaagaaaa agaaatacaa cattagacaa aataaaagat   124980
attcatttga tgcaatgagg aaataatctt ttattcctct ttaaattctc tgtggaataa    125040
ggcatggtta taaataaata aacatctgcc ccatggactt aatggatcgt tatattttat    125100
tgcgataatc ataatgaaat tgttgggagg gattagtatc tctagtgtaa tgctaagaaa    125160
gataaagcct gtgcccaggc aaaagctttc ttggttggtc aaaaggtttg aagcatttc     125220 aaactattct aaaacaaaca aacaagcaaa caaacaaaaa acatacaatg tctttgccac    125280
atatttagga aacaaaatga acaatttatt tctgacaacc tcatagtctt tgttctgtca    125340
gaacaataat ggaaaggtct aaaccagaaa atgctatgca ttgaatttat aataaactat    125400
tttttcctgt aacaaaaaat tgataaactt gatatttgca gatttaatga ttatgtgttt   125460
aaaaaaaatc tggttttgc ccttgcaaaa aatcatatat atacacatag atatgtatgt     125520
gtgtgtgtgc atagtatata tatatgtata tacatatata tacacacatt tatatatata    125580
aacatttcct ttaacctcct attttattcc aataaaaata ttggtattag agatagttct    125640
gatatttcat catgaatagt taacattgca tttggaaagg attaattttt ttgaaacgta    125700 attttaccctt aataagtagc ccagcgtaat attttagtaa ttacacagat ttttttttca   125760
agacatttga caactaatat tgcataatag ttaagagtgt gggctttgga gccagacttc    125820
ctatctctgt tcattcactg ataaaatgga gacagtagta acttcctcaa agagttgttt    125880
tttaagatca aataatgcat ataaaactct tgaaatggta ccaaatacag agtaagcacc    125940 aaaataaacat taactgttat tgttattcca tgtccgaata acacagaaaa gtaagaattt    126000
taatatttca tttgaatgac ctttttaagga tacacctagc ccattatctt tcttgataat    126060
cttgtaagat gattccttt ttatctccga tctgttgagg catggataga ggttttcaga     126120
gaaaacattt tctaggtaac tgaaagaaag tagcaacaac aaactgtgac aaaacttaac    126180
aatgagagaa tttacaagat agaataattg caactccttt tgaaatcaac cactatggtc    126240
ctctggctgg gatagctaag caaagatatt ccagcctgaa ggttgagatc tacttgaaga    126300
gttttctatc cagattgtga gggcccctca aacttcactt agtatctgtt tctattagta    126360
tggaaacttc tggaaccttg tggtatcaca ttcacttgac tactttattc ctgctctagc    126420
tatcttaaag cctttcttaa tcttttatct tttagagaag atacttctag gttttaaatc    126480
caccgatctt gaagctattg ccttcactct ctgcttcaga gcccatcctt ttgtatatga    126540
gtagtttgtt ttgcctaaag tactttctcc cagtcagatt ttaagtccag tttctcatct    126600 gttttttgaga gcaaactcct gggccttggc tcactaacat cttgacagca tatttcttct    126660
```

```
ttcctatggg cttttcagca ttccctgggt ttttctaaaa tatgaaagca gactctttat  126720
ctcttacttt gtcaaagcct accctcccca ctgatttctc acccagttgc tagttttaag  126780
acctgcctct ggccgggcgc agtggctcac gcctgtaatc ccagcacttt gggaggccaa  126840
ggtaggtgga tcacgaggtc aggagatcga accatcctg gctaacacag tgaaaccctg   126900
tctctactaa aattacaaaa aaattagcca ggcgtggtgg tgagcgcctg tagtcccagc  126960
tactcgggag gctgaagcag gagaatggcg tgatcccgtg aggcagagct tgcagtgagc  127020
tgagatcgcg ccactgcact ccagcctggg cgacagagcg agactctgtc tcaaaaaaaa  127080
aaaaaaaaa aaaaaaaaa aaagacctgc ctccaaatat cattgtattt gcaaacatga   127140
aatgacttat tgattctgag ctcagcacaa gagcaaacct ttctcagctt gacccatctt  127200
cacatcgtta atgtcttatt cagtcactac ccaagggct gaccttcaag attctaatcc   127260
atgaaagctt aaaatagtaa acaaatttga atatagttta acatacataa taaattttat  127320
ttctagaaga ggaggatcag cccttagaca tgaaaagtaa aaatagttta ttcccagatt  127380
tccctttgtg cattagtata ttcaaccgag tctatccaag taacaggaca aaaaagctg   127440
gcagttgttg ctgcgctgtg aagtcttatt aggtgagtca gctaattata tggcactacc  127500
ataaatacag caggcactgc cctgcttgtt aggcttgcca aggaaaataa ggatttaaag  127560
cagcatacta cctctttgct atataatgac attttcttct taaaaatgat tttgcaccaa  127620
ttcctgattt atccaccaat tattttttaa tttatggttg aatgtattta aacctgaatt  127680
cagagataaa actagtaaat agctccccaa aataacccca aatatattta atatattagc  127740
tttactctct cctccactgc caaaccttta aaaactgaaa taaattgttt ttatttcatc  127800
ttttctcttt ttctctctct ctaaggtgat tgccaagact aaagaaacag ctagaagggc  127860
aaaagacaag aaaatcagta agatagtaac agattatcca agtagagca cggctcaggt   127920
gcagtggctc atgcctgtaa tcccagcact tcggaggct gacgcaggag gatcacttga   127980
gtccaggagt ttgagaccag cctgggcaac ataatgaaac ttcatctcta taaaaaaaa   128040
aaatttaaat agccgagcat ggtggtgtaa gcctatagtc ccagctattt gggaggctga  128100
ggctggagga tcacttgggc ccaggagttg agactacag tgagctatga ttgtatcact   128160
gcattacagc ctgggcaata gggcaagacc ctgcctctaa acaaaagata aacaaagtag  128220
agcataaatg gcttctaaat atatgttatt tatgtgtaag actgggttct ctaaaggtat  128280
catttaatta aaatagattt gcattctcaa tctgtaggta tggattatgt ataatgtatt  128340
taagatatga cttacagcgt tcaccaatgt gactattccc aagtgatcca gatggctgat  128400
gacatagtaa tttgtacatt tgctgagacc tgatctgagt aggtatgtaa cataactgag  128460
ggagagcaag tccatttgcc gaagaaagc ctagcatatg acccaggagc cacatcttca   128520
ctcagccttg ttgctaggtt tggcttagca tatataatag catagcatgt ataatttatg  128580
acaaaaatt atactttgca cttttttaatt agaacattca aaatgatctc aggaagtggc  128640
accagagatc atcagtggtc tactgtactt cgtgtgtatg tgtctgtgag tatgtatgtg  128700
tttgtgtgtg ttcccacatt ctaaggcatg tcttttacag gttagtagaa aatgttgata  128760
gaaaattata gatttcaaca tctaaaaacac agtaggtcac tacattgtta aaacttggaa  128820
ttttttatct tgttgtaaag tcaggccaac caaacctaaa atactgctac attgaaatag  128880
tgcaaaatat tcaaaatact atagttatag atttggtagt aggactgtac cagacctgtc  128940
actctataca agacttatgc cttgcccttt cacttacctg ttccctttta catctatctt  129000
actagatgta atgctataaa ttatattct aatatattat aatttatcat gtattataat   129060
```

```
gtatcaaata ttacaaatta tgttgcaact ccccttacct ttcgtctgca tattgcctca   129120
gaaagaacag atggatccaa cagacttcaa ccacaggccc ttagtgacaa atagctctta   129180
atgctgggct tgccactttg atgcatttct aaagttatag aatgttaaat gcaccaagtc   129240 cttggtcat tttatttcta ccttagatct aagccataac tatactttcc caaaaattaa    129300
agtttgaatt ttaacttaac catatataat tggaaaagga ggttgggttc gttaagtgta   129360
attttatcat gctttattat cctttgggca ttggatacag cagaacatgc caatttctat   129420
ggcttctcat gtgacagaat atacttacta ggatgcaatt aaatactcct cagagtatgt   129480
aaacaataaa tgtaatcatt acattatttt tatattgttc tttcttatgc ataatagtaa   129540
gactgaaaat atagtgttat ttctgaaata tgcatattgt tttgcttttg atgattaaat   129600
aacattgtcc aaagttttag gttttttgaa atcttatatt tttaacaaa atatctagcc     129660 tttccaaaac aagacctcaa taattcgttt aagacccaga gttgttcctc tccacataga   129720
tctcttaaaa aggcagagga tttatgacct caagagaaat cagagtatcc aaagtttgct   129780
ttaattcaat gttttaaaaa taaaattcct tagatttat caaaaattga gattagtttg     129840
attttgaatc agatgccctt tgctccccac cccaaaatgg cattatgagc agactaggaa   129900
ttgataatag aaaattgaac atatgaaata tatctttacc ttgctttta acaaggtatt     129960 catgtctatc gccttcattt ttaagtgcat caataaaata catggtaatt ctcttagtga   130020
aatatactat ctacactatg tacacactcc cctgtctgag gtagagaagt agagaatatt   130080 cacattttg aaacgtctat gctattttta tttaaatacg agttctgggc ttgatttcat     130140
tttggaacac gggtgtgtgc ttaagttgaa cctttttttc ctcttaagtc aaagttcttt   130200
tttagtttct tctttatct ttttggctac tatctctctc cttcatcctc ctggtgtgag     130260
ttgttgagtg aaggtattaa ttccattatt tgaggctaag tgacattgtt caataatgca   130320 gcaaacaat ggttctaccc aaaatatctt caagtgtaaa agcagtgggc aaaagagaaa    130380
gtgcgcttct gctgctttga atgtttaagg ctgtgaaagt tgatcacaca aattgggtca   130440
ttcttgttat acccaactaa aacaatcaag aagcctggga ggaaaagcat tcaagaaaca   130500
tcacattgct ccaaaagtgt aattttctac aagtccgcat gctgaggctg cctgttgtaa   130560
cctgggacca attttttctg taactgctga aaaaacttgc tgcagctcta ggactaattt   130620
tgcccaccac tgtcactcac caattgaagc ttactagctc cccagaacct ttctagtgcc   130680
aatgaacttt ctcaaagagc agcgtgtatc atttctcttt ttcagaacac ctccaacctc   130740
ctctttgttc tttgggtata ccaaagacca accagccttg aatttcaatt tttcttccca   130800
cataaaagtt ttaatttaga aatgtatctc tacatttcta actttgacaa agcatagata   130860
ccagataatt gatgaaacct tgctatttta acgatcacca tggattactt cccagtgtct   130920
tcagataacc ctcaacattt gccaacattt gatggacttc aaaatgagca tatcttttt     130980 aaaaaaaatt attcacactg acagcaagta cattggtata ctctatatta aattatacca   131040
cagggtttac aaacaattgg tgatgtcggg cagtggtttc caaggaacat acttaacaag   131100
acactcacaa ggccctacaa acctgcattt ttaacaaggg ccctagatga ttctagaaga   131160
gtgtggtttg gaaagcaatt tttgccttta ttatgtgtca tttaaatat atttaaaatt     131220 aaagttataa gtcatagaat tgaataaaga taatttcctt acagaaagta ttactaggta   131280
tctaaataca atatggttca aaacaggaaa tttaaaaaga ttatgtaaat tctgtagttg   131340
tattcctaaa gacagtagct gaatttttt cctacttctc cttgtatcac ttcccttttc     131400
cttcactttc acttccctgg aattgtactt cccaataagc tattagcagt gaaggaagct   131460
```

```
tcgtctcatg atctgtttta tagagcactt cagctgggac gagtacgaaa tgataatcag    131520
ttatatcagc tattcaaccc tacaggttta tttaaaaaga acttgaataa gcttttagg    131580 gagaaagagg tcagtctcag ccatttctgt ttcctaatat agcttttaag tctttcctta    131640
ttagcaatga gggtcattcc attgtaattt tttgataacc atttttcttt ctgtgtgtca    131700
aatgcagata taagatactg aactgagtct atttcactgt tcgtaaaaca atcccatttg    131760
aaaaaaaaaa gtctacagct attccaggga tagggcctag tagagagaga ataaaaggta    131820
ttttcttact atgtctctat atcctaccct gtaggttctc ttattaagca tacaggcata    131880
taccaaaatc cagacgtttt tctcatttat tttattgccc taacatattc tgggttaata    131940
taatatcata atgaaaattt gagaaaaaat tgattttttc aaaagtgttt aacatttgtt    132000
atattggtag ttttttttct tgtttgtggt aaaaataaat agaaggtgca cttcacacct    132060
tcaagtatga ttatattttg aaaacaagtc atgaatactc ataaaatgca aattttaatg    132120 ttctttttt gttacagcca aactatatta ggcacagttg taaattggag ttgaaattta    132180
atatttcttt atagataaca atgttttag aaataggttt atgaaacagt aaatatacag    132240
gtatagggat aaaattgtgt ctgatggtca tatgaagtgt ttgttgttat attctccttg    132300
gaatagctgc caaatatttt agtatgctta aaatctacga atgtgataga gtcaacaaat    132360
ttagatcaca tattcagaaa aacatagtta gagaactaac tattgaaatg agcatacagc    132420
agtcttcctt tatctacagg gatacattct gaaaccccca ctaggacacc tgaaattgcg    132480
gatagtagca aaccctacat atactgtttt ttccaatgct tatgtaccta tgaaaaagtt    132540
taatttataa actaggcaca gtaagagatt aacaacaata actaataaca aaagagaaca    132600
attataataa tatactgtaa taaaagttat gtgggtatgg tctcgctttc tctttccctc    132660
tctctctgtc tctaaatatc ttagtatttt ggggttgcaa ttggtggtgg gcaactgaaa    132720
ccatggaaaa caaaccacg gataaaagga gactactgta tatactttt aaaactgatg     132780 aaatattaaa ctcatgtttc ttctatatcc cacccatttc ccccacccaa acctagatag    132840
atatcttatt tgatctgtaa acatttaatt aatttgtaaa agttaagaac tttttgaagt    132900
aaaactgcaa tatatcatca cacctaaaga aataaacaat aattcttaaa tatcaagtca    132960
gtgttcaaat ttccccaact acctcatatg tgttttccat ttgcttatgt agggttccca    133020
atgagaatga aataaagttc ttaggttgca attggctaat gctctctcac ttctacttta    133080
agcggcaggt tcccactaac ttctttttag ttgcaattta cttattgaaa ttagacgtat    133140
tctttgtctt gtgtagtttc tcacagtgca aaatttgctg attgtagcca ctgttgtaag    133200
caatgaacat gttttcacc accttatatt tgctgtaagt tgtcagtgat agttaaatgt    133260
taatcaaatt caaattcgga tcacgtaggg ctttctttt tttgttttct ttttctattt    133320
atatatttat ttatttattt tgagacggag tctcactccg tcaccaggct ggagtgcaat    133380
ggtgtgatct gggctcactg caatctccac ctcccgggtt caagtgattc ccctggctca    133440
gtctcccgag tagctgggac tataggagaa ccaccacgcc cggctaactt tttgtatttt    133500
agtagagatg gggtttcacc atgttggcca ggatgctata gatctcctga cctcaccgat    133560
catgtaggac ttcaattgtc gaacaaacga acctttaata gcagttacac cattaggatg    133620
acctgatcca acatcgaggt cgtaaaccct attgtcgatt tggactctag aataggattg    133680
tgctgtcatc cctagtgtag cttgttccca cttgatgaag ttattggatc agtgaacaat    133740
agcccactta aactagtaca gtcttagttt aagatggtga tgtgtatgta cttccatcag    133800
agggcacata atacagtaaa tcctcactta acttcatcaa tagtttctgg aaactgtgac    133860
```

```
ttgaagcaaa acaacatata acaaaaccag ttttaccatt ggctaattga tataagcaag    133920
aattaagtcc tatggcaaat ttctggacac aaaaacacca tcaaactcct aaataaagat    133980
aaatcacttc tgacattaaa cattgaaatt aatgtgagct atatatacgt ttaagaaaga    134040
ttaatacaaa caagtcaaat aacttaccta attatttcgg tggaggccgc aggtggttgg    134100
agcctatcct ggcagctcag ggagcaatat gggaacccac cccggacagg acgctgttcc    134160
attactgcag ggtgctcttg tacacaccca ctcacccagg ctggaaccat gcagacacac    134220
acactcacct aacctacaca tctgtgtaca tccttcaaag ttcagccaaa taacatataa    134280
acaaatccag taatatccat cagtcttagt tccgtcataa caactccttt ttgatcatca    134340
aacaacaaac agggtaggtc tgccatattt acttgtctgg tccatatcaa aattttctaa    134400
caaattatat tagaaaatca aatctctgtc agtttcaaaa tcatggaaaa aaatttgcct    134460
tatttccctt atacttggat atcctaacag taatctaaat attaatgaga aagttaatga    134520
tgtcgtttcc ttctccctgt tgtaaagaag gttttgctgt cccgtttgat cactaagact    134580
aattgacact cagaaaaagc ataggaaact tctcagcatc acaaaagctc tgtcatctag    134640
agaagctagg acttgagctc aagtcctgtg acatggaagg ccttgtgcct agccatcctg    134700
cagcagaggc gtatctacca agaagtgaaa cactacgaaa acagtatgtt tactccacat    134760
tttaaagtga ggtagtttgg ggtggttcat atttttattta atttatatat tatttggatt    134820
ttttttagtt tataaaaagg gcattggcaa gggcagaatg atctgtaagc ttctctgccc    134880
acctaccata agcatgatct ttagtgtgac cttttcttac tgttagccat tttcttatac    134940
ttctgcgtcc ctgtcagtca cttccatgtg aagacatggg gaagcttttt tacatcagac    135000
atgttgttga aaatcagccg cgttggctga gggattattt gatctctttc tccaagtccc    135060
tttaggctca cattgcctct ctgttctttg aattttcact tacctttatc ttcttataat    135120
tactttgctg aaataaatgc aaagcaacaa aaggtattta gtgaagaata ccaacaaagc    135180
catgaccatt tcaggctgag ttttgtagta ttctttgtct aggaagagat acctagaaaa    135240
attttctgac catgtatttg attattttcc ttcaatatgt atagtctcag tcttcaaatt    135300
tcagaaaaga atttgtttct tcattgtcat ttaaaattaa tgtgttaaat atgtatgctt    135360
ttacattata agtggttata aaagttaaac acttagaaaa aaagtcaaaa taacatacat    135420
actatccaac aaaataactt tcatatttta ttgtgttttc ttccaaactt tttacctttg    135480
cgtctgaatt ctgtgtaggt tgtatctata atatagacaa cactttatag cctgctaaat    135540
attataccat aaatagggtag ttgttacata attctcaggt aatagtaata caggtctta    135600 tcataatcta ctgagtagtt gaatgataat ttttttttaag acaaggtctc cctctgtcac    135660
ccaggctaga atgcagtggc atgcacatgg ctcactgtag cctctacctc ccaggctcaa    135720
gtgatcctcc tgcctcagcc tcccaagtgg ctgggactgt aggcatgtgc caccatgccc    135780
agctatttat ttgtattttt agtagagatg gggtttcatt gtaacagccc aggctggtct    135840
tgaactcctg gactcaaatg atccacctgc ctcagcctcc caaagtgctg aaatcacagg    135900
agtgaaccac tgcacccagc aataattttt taactcttca ttattcattg aacatttagt    135960
taacaattct aaaaattttg tttcctgctg tcattgatct tgtgaaaaat atctttggac    136020
tatagctgtg gattatttcc taaatagtaa attacttgag caaaaagttt acatactttg    136080
agggttgata acccatgttg ccgcaatgtt tccccggagg cattgtggag tttagaatgc    136140
cagtagtaat attaaggtgt gccatttttca agatccgtgg ccaacatccc tatatgtaag    136200
atttttccaa aacatggttc tgattttttaa aagtgaaaaa tgctacttca tcatgttctt    136260
```

```
tttgtgcttc ttactttaaa tattagaatg aagaaggagc cccacaggaa ggaattctgg   136320
aagatatgcc tgtggatcct gacaatgagg cttatgaaat gccttctgag gtaggagtcc   136380
aagctgaatc tttctaacaa gacagtacca aaaacctgtc attgtcacat ttctctttca   136440
ttagtgctta gtgagaatca tttgctctct acatgctcat tacgtggaca acttgcaagt   136500
taagaatagt ttttacattt ttaaagggtc cttaaaaaaa aagaggagga ggaagatgaa   136560
gaagaggaag aaaggatgta aaagaaatca tatgtagtcc acatagctta atatacttac   136620
tacttgaccc tttacaggaa aagtttacta acccctgcat tagagaatat attttagaa   136680 actttacatt ctaaaataaa tttctaaatg gaaagttagg gaaatcaatg gaatgccaaa   136740
ggaaggttat tattttttgc catacatgtc caatgggatg acgcatagta aaataaaagt   136800
tacccacaca agttatagaa taaaagata atgcatgat ttgcgacaat tgatatattc     136860
cagtataatg ttttaaacaa cacaatatga ttgttaattt tattttgatt gaaaatgaaa   136920
gtatctttaa tagaaaatgt atcaaaaggg aaattagaaa atactgttag atgaataaaa   136980
ctggcccaag aagaaacagt aaatctgaat agatttgtaa cacagcgaat agattaaatt   137040
agtaataaaa aaaaaaacct acctgcaaag aaaatcccag gccgagatgg catcactggt   137100
aaattctacc aaacatttaa agaggaatta atactaatta gttaacacca attaatatct   137160
cttacaaaac agaagaggag acatttccca actaattttg tgagaccaat attaccctga   137220
taatcaaaac caaacgaaga tatcacaaga aaagaaacta tataatggct ccattaaaaa   137280
ttgagttcaa gtatgttgta gtttggttat gtattattcc tcacggcatt attaaaaggc   137340
atgtcgagga tgggcacagc agttcacacc tgtaatcccg cactttgtga gccaaagtgg   137400
ccaggttact tgaggccagg agttggagac cagtctggcc aacatggtga accccatct    137460 ctactaaaaa tacaaaaatt agccgggcat ggtggtacac gcctatggtt ccagctactt   137520
gggaggctga ggcatgagag tcacttgaac ccaggaggca gaggttgcag tgagctgaga   137580 tggcaccct gcactccaat cttggtaaca gagcaagact gtctcacaca gacacacgaa     137640
aggcatattg ataataattc aacttataga aattgagatt aaattgtttg tttgcctaat   137700
aagaatttcc aatattttgg ggtctttat gcaagacaca gtactaaaca caatggaaaa     137760
ctatagagta attgacatta ccaggacata aggagtttac agtctggtag gtttgatgaa   137820
aaaaaataga aattcattca ttcatttctt cattatgatt cctttaacaa acataattga   137880
ttgtcttcga tgtaccaggc atcacaggag caaaaatata taagacatac taaaaagtaa   137940
aacattttaa agatctgttt caatcaatca ggagaagttt tattgaggag gtaatgttga   138000
tctgggtggg aaaaggtaag agatatagta ggtcaaaaca aacagaggac attctggcac   138060
aagggaatat cagaagcaaa ggcatgtatg tctgagcatg caaatggata tgtctgagaa   138120
cagtgaataa ttatgactca agcttaggaa caaggaaaat ggtgatagat tgaatttgca   138180
gctatgggtc aaagacaagt tatagagtat taggataatc ttgtcatttc agcttgtatt   138240
ctattcagaa aacaacttga gttattgaag ttatgcttat ttgtttgttt ttaagcagaa   138300
tcctgatatt attagagttg ctctttagga ggaataatct gatccctta attaaatcca    138360 ttaatatttg tgttgtggat gctatccaga tactgtatgg agagcttgag gtttgaaata   138420
caagtaataa ttgaagccat agatgaagac gaaattttca actgggagag tgaaagtagg   138480
gaaaatgtat cttgccttca aacatcttaa tttccttctg agaattagag catcttagtc   138540
tggaaaaggc tttatagaca gcttgatttt gttctcacat tttacaggtg aagaaactga   138600
gaaccagaca gtccaactta tttgtcctac caaactaggt atatgatcat taaatggtgc   138660
```

```
atccggatca gaacctagat attttaactc tgactactac tgtaattcac ttttatatca 138720
gacaagaaag acacaactat taaaaataag ataatatttg ctgcagaata tttgcaaaaa 138780
cattgattgt aaattttagt gtaagtgggg agccatttcc tatctcattg gctgtcagtg 138840
ctgatgcgta attgaaactt atactaacag tgtgtgctgt cttttttgatt tttctaatat 138900 taggaagggt atcaagacta cgaacctgaa gcctaagaaa tatctttgct cccagtttct 138960
tgagatctgc tgacagatgt tccatcctgt acaagtgctc agttccaatg tgcccagtca 139020
tgacatttct caaagttttt acagtgtatc tcgaagtctt ccatcagcag tgattgaagt 139080
atctgtacct gcccccactc agcatttcgg tgcttccctt tcactgaagt gaatacatgg 139140
tagcagggtc tttgtgtgct gtggattttg tggcttcaat ctacgatgtt aaaacaaatt 139200
aaaaacacct aagtgactac cacttatttc taaatcctca ctattttttt gttgctgttg 139260
ttcagaagtt gttagtgatt tgctatcata tattataaga ttttaggtg tcttttaatg 139320 atactgtcta agaataatga cgtattgtga aatttgttaa tatatataat acttaaaaat 139380
atgtgagcat gaaactatgc acctataaat actaaatatg aaattttacc attttgcgat 139440
gtgttttatt cacttgtgtt tgtatataaa tggtgagaat taaaataaaa cgttatctca 139500
ttgcaaaaat attttatttt tatcccatct cactttaata ataaaaatca tgcttataag 139560
caacatgaat taagaactga cacaaaggac aaaaatataa agttattaat agccatttga 139620
agaaggagga atttagaag aggtagagaa atggaacat taaccctaca ctcggaattc 139680
cctgaagcaa cactgccaga agtgtgtttt ggtatgcact ggttccttaa gtggctgtga 139740
ttaattattg aaagtggggt gttgaagacc ccaactacta ttgtagagtg gtctatttct 139800
cccttcaatc ctgtcaatgt ttgctttacg tattttgggg aactgttgtt tgatgtgtat 139860
gtgtttataa ttgttataca ttttttaattg agccttttat taacatatat tgttattttt 139920
gtctcgaaat aattttttag ttaaaatcta ttttgtctga tattggtgtg aatgctgtac 139980 cttttctgaca ataaataata ttcgaccatg aataaaaaaa aaaaaaaagt gggttcccgg 140040
gaactaagca gtgtagaaga tgattttgac tacaccctcc ttagagagcc ataagacaca 140100
ttagcacata ttagcacatt caaggctctg agagaatgtg gttaactttg tttaactcag 140160
cattcctcac tttttttttt taatcatcag aaattctctc tctctctctc tcttttttctc 140220 tcgctctctt tttttttttt ttttttttta caggaaatgc ctttaaacat cgttggaact 140280
accagagtca ccttaaagga gatcaattct ctagactgat aaaaatttca tggcctcctt 140340
taaatgttgc caaatatatg aattctagga ttttttcctta ggaaaggttt ttctcttttca 140400 gggaagatct attaactccc catgggtgct gaaaataaac ttgatggtga aaaactctgt 140460
ataaattaat ttaaaaatta tttggtttct cttttttaatt attctggggc atagtcattt 140520
ctaaaagtca ctagtagaaa gtataatttc aagacagaat attctagaca tgctagcagt 140580
ttatatgtat tcatgagtaa tgtgatatat attgggcgct ggtgaggaag gaaggaggaa 140640
tgagtgacta aaggatggt taccatagaa acttcctttt ttacctaatt gaagagagac 140700
tactacagag tgctaagctg catgtgtcat cttacactag agagaaatgg taagtttctt 140760 gttttatttta agttatgttt aagcaaggaa aggatttgtt attgaacagt atatttcagg 140820
aaggttagaa agtggcggtt aggatatatt ttaaatctac ctaaagcagc atattttaaa 140880
aatttaaaag tattggtatt aaattaagaa atagaggaca gaactagact gatagcagtg 140940
acctagaaca atttgagatt aggaaagttg tgaccatgaa tttaaggatt tatgtggata 141000
caaattctcc tttaaagtgt ttcttccctt aatatttatc tgacggtaat ttttgagcag 141060
```

```
tgaattactt tatatatctt aatagtttat ttgggaccaa acacttaaac aaaaagttct 141120
ttaagtcata taagccttt  caggaagctt gtctcatatt cactcccgag acattcacct 141180
gccaagtggc ctgaggatca atccagtcct aggtttattt tgcagactta cattctccca 141240
agttattcag cctcatatga ctccacggtc ggctttacca aaacagttca gagtgcactt 141300
tggcacacaa ttgggaacag aacaatctaa tgtgtggttt ggtattccaa gtggggtctt 141360
tttcagaatc tctgcactag tgtgagatgc aaacatgttt cctcatcttt ctggcttatc 141420
cagtatgtag ctatttgtga cataataaat atatacatat atgaaaatat gtatttggtt 141480
tctgcctcca gttcttacaa agagctccta aaacccttgt aatttcctga gtagtagggg 141540
tgctagggtc atctttttgtt ctaatatttg gtctttgact ctgctttctg acagagctcc 141600
ttagtccctg ggtgagagta gcatcttctc ttctaatgaa gtgactcttg ctgggttcct 141660
ggatgggggc tggtcaccag aaaggtcaag ccatgataag aagcttgaag cttttggccc 141720
cattcacatc ttctggggac gggagagaag aggagctgga gattgagtta ataagcaaca 141780
atgcttccat gatgaagact ccataaaaat ccctaaaaga caggattcag agtgctttga 141840
aataggtgaa catgcagagg tgctgggaat tgtggtgtgt ccagagaagg catgcaagct 141900
ccccacgcct cccccatacc tttccctgtg catctcttcc atctggctgt tcctgagttg 141960
tatcctttta taacaaactg gtaatctagt aagcaaactg ttttcctgaa gtctgtgaat 142020
cacactagca aattatcaaa cctgaggaga gggccgtgga gaccttggat ttgtagacaa 142080
gtcaaacaga agctatgagt aacatgagga ctcattgctt gtgattgtca tcttcagtgg 142140
gaagggaaa  aatcttgtaa aactgagtcc ttaacctgtg ggtcaatgct aactccaggt 142200
agatagtgtc cgatttgaat tacgggacac ccagttggta gccacaaaga atgggagaat 142260
tgcttggtgt agaaaacaca ccccacacac acatgtggtg tcagaaatga accggaaata 142320
ttgtgttccg gaaatattga gtgttgtgag tgagtgtata gaaagaaaaa cagcgttttcc 142380
ttttcactac tagattaaaa caaacacact catgcattca cacatctcaa agacaactat 142440
taattctcaa agacagtgct gtctaaatcc atactgagga agaaaacaca tttctttttc 142500
aaatctgtaa acctgacaga ctgcctctgt ccacacacta atggaactct gtgtttcatc 142560
tgaaatgtgt tcatcccact ttgttctttc tgtcttgggc agggcaagag tgcaacaggg 142620
ctgacatttt catatgagct ctgtcccctgt tattggctat actttagaca aattattatg 142680
tgtcaaatat agatgtaagt gatttatcaa tattaagtca tttaattctc aaaacaacct 142740
taataggttc cattatgatt ctaatttac  acataagcca aaggaggcac ccacaggcta 142800
gataactttc ccacggccac acagctagta agcggcagag ccaagaggcc caacattaca 142860
gcaccacagt ctgtgctctc agccccttgg ccacatagtg tcagagtgag gacacacagc 142920
tatttaagaa aacttccaga agtctaggaa atggggtgat agccccactt ttctaggtat 142980
aataattaga tatttgtttt tcttcaggta cctaaagaaa atttactaga gtttgagcct 143040
ttagtaagtt ttgctagtac atctgttttt cttcaggtgc ctgaagacaa acatatacac 143100
acacacacac acacaaacac acacaaaatg tgtatctata tatgtgtta  cacatatctc 143160
tcatctctat atatatgtct ctgtatatct atatatctat aaacatatct atatctatag 143220
atacatatag agagatttct tttttttttt ttttgagatg gagtcttgct cttgccacct 143280
aggctggagt gcaatggcac aatctcagtt cactgcaacc tccgcctccc aggttcaagc 143340
gattctcctg cctcagcctc tcgagtaggt gggattacag gaacacacca ccttagcccg 143400
actaattttt gtattttag  tagagacagg gttcaccacg ttggccaggc tggtctcaaa 143460
```

```
ctcctgacct caggtaatcc acctacctcg gcctcccaaa gtgctgggat tacaggtgtg  143520
agccaccatg cctggccaag atttctaatt ctaagagaaa ttagcacctg ataggtattt  143580
ccttgtaaat aaaccgggca tatcctgatt atagaactaa gttaattatt ttccgtggaa  143640
gatacgaatg ttgatgcaat aagagcagca gtctacagta aggtgggctt tgtaattttc  143700
tgtgttgaat catggcatgg gtacttggct tatgtcaaat agacaaaaaa atataaatta  143760
aggtataact gggattgtca attatacata tttagtaatg gaatgaatga atttataaat  143820
agatagtaaa gggcatgaat taagaatcta taggtataaa taatattagc aacttaatat  143880
tgtataataa agtttgattt tctaggtgta gttgattgat gcagtaatgt tcgttttatc  143940
ctttgagtaa gcctagaatt gaagaaccca aaatgcaata gaatagatat aacattgaaa  144000
ctattcctaa atatgatttt agttccaatg ttctttgtgt aattacctaa gcttttcttt  144060
aatgtttttg ctgctactac agtatcctta attatttgaa atcttatatt ggaagcagtt  144120
aaaccacatt ccttcaaaga gcccttagtt tgagcctcta gtaagttttg ctagtataat  144180
ttggttttaa aattggctag aattgcatag ggaatttcca taacgtatag ttgatctgca  144240
actataggtt aacatactag gatggcttct cttatgaacc ttatgaaaat acatcctcag  144300
attccctgga aggtcagtga ccagaaatcc tcgttgtttc tatggcaaca cagcaagata  144360
tggtgccttg gaaatgtgct gcattttaat taggttcctc tagggcttcc taactgcctt  144420
ttgcaggtaa actaaatatc agattgcctt ttatcttgca acaaaatgaa acctaaccca  144480
tgtctgtaaa tgtcaaagct aagctgtgtt ccagtaaagc tgaatccaaa caaatatagt  144540
agcaagtcat gttttatct tagaaaagaa tacaatactc tttacctaga atagtcaagg  144600
atgctgctta atgaggtagg ttagagtaat agagactatc ctgaactcca aaactattaa  144660
tagactatgg aacttcgact cccatttatg tctcttacta cttaatatta gtgtctctgt  144720
ttccttatat gtaaatatgc aaatgataaa aatagtgcct catagcattg ttgcatgcat  144780
taagtgagtt aatgtaagtg gaatacttag gactgcctgg ctgatagtaa gtgatctatg  144840
agtcaatgat gctatttatt agtagtagta ctagtacagc acactgtatt tttaaaggta  144900
aataagaaat aacaatttt ttaaatgttc atatacattc acatgtcttc ttttaatata  144960
aaatagcaat caagatcagg ataatggtag agatattttg gagacacaag gcagaagcta  145020
tttactaata gctaggggag catttttacta gttactaac caatattact atacttatgt  145080
gtacttagca gaatatcacc tagcaccaaa aagaaattaa gaaagtgtaa cttactgaga  145140
agtgaatatg caccaactcc ataaacacta tgtttatgga acacatctaa ctttagactt  145200
agctatactc atcgactcac atatcttctc atccaagtgg gatgtgttta atatttacca  145260
tatattcata agttcactga gtattgttct ggtaactaga aaaaaaaaag gacaagcata  145320
tataagtaaa actcactgat ttaaaacaga gtattatcaa ctacaaaaga aaaaaaaaac  145380
cacttgaacc tccactgatt tctcaaatct catttatttc ccattatctt ccctcatacc  145440
tcttgcattt attggttaa atttcttttt gatccaaaag gaagcaatgt ttacctgaca  145500
atttctactt tatgccagaa caacaaatgt accagcaatt acaatatttc caagaaaagt  145560
attgtttgtt ttctcttcat gtctttggtg agtctctcgg aattag              145606

<210> SEQ ID NO 8
<211> LENGTH: 4349
<212> TYPE: DNA
<213> ORGANISM: Homo sapiens
```

```
<220> FEATURE:
<221> NAME/KEY: misc_feature
<222> LOCATION: (1)..(4349)
<223> OTHER INFORMATION: LOCUS      DRPLA                   4349 bp
      mRNA    linear   PRI 13-MAY-2002
      DEFINITION  Homo sapiens dentatorubral-pallidoluysian atrophy
      (atrophin-1)
      (DRPLA), mRNA.
      ACCESSION   XM_032588
<300> PUBLICATION INFORMATION:
<308> DATABASE ACCESSION NUMBER: XM_032588
<309> DATABASE ENTRY DATE: 2002-05-13
<313> RELEVANT RESIDUES IN SEQ ID NO: (1)..(4349)

<400> SEQUENCE: 8
acgccatact ggacgccaag tgggaggaac ttcaaggctg tccctgcgg gcctcccgct       60
ctgcttctgc gaaggtttca ttgaaaacag atcctgcaaa agttccaggt gcccacactg     120
gaaacttgga gatcctgctt cccagaccac agctgtgggg aacttggggt ggagcagaga    180
agtttctgta ttcagctgcc caggcagagg agaatgggt ctccacagcc tgaagaatga     240
agacacgaca gaataaagac tcgatgtcaa tgaggagtgg acggaagaaa gaggcccctg    300
ggccccggga agaactgaga tcgaggggcc gggcctcccc tggagggggtc agcacgtcca   360
gcagtgatgg caaagctgag aagtccaggc agacagccaa gaaggcccga gtagaggaag    420
cctccacccc aaaggtcaac aagcagggtc ggagtgagga gatctcagag agtgaaagtg    480
aggagaccaa tgcaccaaaa aagaccaaaa ctgagcagga actccctcgg ccacagtctc    540
cctccgatct ggatagcttg acgggcgga gccttaatga tgatggcagc agcgacccta    600
gggatatcga ccaggacaac cgaagcacgt ccccccagtat ctacagccct ggaagtgtgg    660
agaatgactc tgactcatct tctggcctgt cccagggccc agcccgcccc taccacccac    720
ctccactctt tcctccttcc cctcaaccgc cagacagcac ccctcgacag ccagaggcta    780
gctttgaacc ccatccttct gtgacaccca ctggatatca tgctcccatg gagccccca    840
catctcgaat gttccaggct cctcctggg cccctccccc tcacccacag ctctatcctg    900
ggggcactgg tggagttttg tctggacccc caatgggtcc caaggggga ggggctgcct    960
catcagtggg gggccctaat ggggggtaagc agcaccccc acccactact ccatttcag   1020
tatcaagctc tggggctagt ggtgctcccc caacaaagcc gcctaccact ccagtgggtg   1080
gtgggaacct accttctgct ccaccaccag ccaacttccc ccatgtgaca ccgaacctgc   1140
ctccccacc tgccctgaga cccctcaaca tgcatcagc ctctcccct ggcctggggg      1200
cccaaccact acctggtcat ctgccctctc cccacgccat gggacaggt atgggtggac   1260
ttcctcctgg cccagagaag ggcccaactc tggctccttc accccactct ctgcctcctg   1320
cttcctcttc tgctccagcg cccccatga ggtttcctta ttcatcctct agtagtagct   1380
ctgcagcagc ctcctcttcc agttcttcct cctcttcctc tgcctcccc ttcccagctt   1440
cccaggcatt gcccagctac ccccactctt tccctccccc aacaagcctc tctgtctcca   1500
atcagccccc caagtatact cagccttctc tcccatccca ggctgtgtgg agccagggtc   1560
cccaccacc tcctccctat ggccgcctct tagccaacag caatgcccat ccaggcccct   1620
tccctccctc tactgggccc cagtccaccg cccacccacc agtctcaaca catcaccatc   1680
accaccagca acagcaacag cagcagcagc agcagcagca cagcagcagc cagcagcagc   1740
agcatcacgg aaactctggg cccccctcctc ctggagcatt tccccacca ctggagggcg   1800
gtagctccca ccacgcacac ccttacgcca tgtctccctc cctggggtct ctgaggccct   1860
acccaccagg gccagcacac ctgccccac ctcacagcca ggtgtcctac agccaagcag   1920
```

```
gccccaatgg ccctccagtc tcttcctctt ccaactcttc ctcttccact tctcaagggt    1980
cctacccatg ttcacacccc tcccctttccc agggccctca aggggcgccc taccctttcc   2040
caccggtgcc tacggtcacc acctcttcgg ctaccctttc cacggtcatt gccaccgtgg    2100
cttcctcgcc agcaggctac aaaacggcct ccccacctgg gccccaccg tacgaaaga      2160 gagcccgtc cccggggcc tacaagacag ccaccccacc cggatacaaa cccgggtcgc      2220
ctccctcctt ccgaacgggg accccaccgg gctatcgagg aacctcgcca cctgcaggcc    2280
cagggacctt caagccgggc tcgcccaccg tgggacctgg gccctgcca cctgcggggc     2340 cctcaggcct gccatcgctg ccaccaccac ctgcggcccc tgcctcaggg ccgcccctga    2400
gcgccacgca gatcaaacag gagccggctg aggagtatga accccgag agcccggtgc     2460 ccccagcccg cagcccctcg cccctccca aggtggtaga tgtacccagc catgccagtc    2520
agtctgccag gttcaacaaa cacctggatc gcggcttcaa ctcgtgcgcg cgcagcgacc    2580
tgtacttcgt gccactggag ggctccaagc tggccaagaa gcgggccgac ctggtggaga    2640
aggtgcggcg cgaggccgag cagcgcgcgc gcgaagaaaa ggagcgcgag cgcgagcggg    2700
aacgcgagaa agagcgcgag cgcgagaagg agcgcgagct tgaacgcagc gtgaagttgg    2760
ctcaggaggg ccgtgctccg gtggaatgcc catctctggg cccagtgccc catcgccctc    2820
catttgaacc gggcagtgcg gtggctacag tgcccccta cctgggtcct gacactccag    2880
ccttgcgcac tctcagtgaa tatgcccggc ctcatgtcat gtctcctggc aatcgcaacc    2940
atccattcta cgtgccctg ggggcagtgg accgggct cctggggttac aatgtcccgg      3000 ccctgtacag cagtgatcca gctgcccggg agagggaacg ggaagcccgt gaacgagacc    3060
tccgtgaccg cctcaagcct ggctttgagg tgaagcctag tgagctggaa ccctacatg     3120 gggtccctgg gccgggcttg gatccctttc ccgacatgg gggcctggct ctgcagcctg     3180
gcccacctgg cctgcaccct ttcccctttc atccgagcct ggggcccctg gagcgagaac    3240
gtctagcgct ggcagctggg ccagccctgc ggcctgacat gtcctatgct gagcggctgg    3300
cagctgagag gcagcacgca gaaagggtgg cggccctggg caatgaccca ctggcccggc    3360
tgcagatgct caatgtgact ccccatcacc accagcactc ccacatccac tcgcacctgc    3420
acctgcacca gcaagatgct atccatgcag cctctgcctc ggtgcaccct ctcattgacc    3480
ccctggcctc agggtctcac cttacccgga tcccctaccc agctggaact ctccctaacc    3540
ccctgcttcc tcaccctctg cacgagaacg aagttcttcg tcaccagctc tttgctgccc    3600
cttaccggga cctgccggcc tccctttctg ccccgatgtc agcagctcat cagctgcagg    3660
ccatgcacgc acagtcagct gagctgcagc gcttggcgct ggaacagcag cagtggctgc    3720
atgcccatca cccgctgcac agtgtgccgc tgcctgccca ggaggactac tacagtcacc    3780
tgaagaagga aagcgacaag ccactgtaga acctgcgatc aagagagcac catggctcct    3840
acattggacc ttggagcacc cccaccctcc ccccaccgtg cccttggcct gccacccaga    3900
gccaagaggg tgctgctcag ttgcagggcc tccgcagctg acagagagt gggggaggga    3960 gggacagaca gaaggccaag gcccgatgtg gtgtgcagag gtggggaggt ggcgaggatg    4020
gggacagaaa gcgcacagaa tcttggacca ggtctctctt ccttgtcccc cctgcttttc    4080
tcctccccca tgcccaaccc ctgtggccgc cgcccctccc ctgccccgtt ggtgtgatta    4140
tttcatctgt tagatgtggc tgttttgcgt agcatcgtgt gccaccccctg cccctccccg   4200 atccctgtgt gcgcgccccc tctgcaatgt atgcccttg cccctttcccc acactaataa    4260
```

```
tttatatata taaatatcta tatgacgctc ttaaaaaaac atcccaacca aaaccaacca      4320
aacaaaaaca tcctcacaac tccccagga                                        4349

<210> SEQ ID NO 9
<211> LENGTH: 13994
<212> TYPE: DNA
<213> ORGANISM: Homo sapiens
<220> FEATURE:
<221> NAME/KEY: misc_feature
<222> LOCATION: (1)..(13994)
<223> OTHER INFORMATION: LOCUS      SEG_HUMHD           13994 bp
      DNA     linear    PRI 12-FEB-2001
      DEFINITION  Homo sapiens huntingtin (HD) gene.
      ACCESSION   AH003045 REGION: 316..14309
      VERSION     AH003045.1  GI:663286
<300> PUBLICATION INFORMATION:
<308> DATABASE ACCESSION NUMBER: L27350
<309> DATABASE ENTRY DATE: 2001-02-12
<313> RELEVANT RESIDUES IN SEQ ID NO: (1)..(614)

<400> SEQUENCE: 9
atggcgaccc tggaaaagct gatgaaggcc ttcgagtccc tcaagtcctt ccagcagcag       60
cagcagcagc agcagcagca gcagcagcag cagcagcagc agcagcagca gcagcaacag      120
ccgccaccgc cgccgccgcc gccgccgcct cctcagcttc ctcagccgcc gccgcaggca      180
cagccgctgc tgcctcagcc gcagccgccc cgccgccgc cccgccgcc acccggcccg        240 gctgtggctg aggagccgct gcaccgaccg tgagtttggg cccgctgcag ctccctgtct      300
attaatttcc ttctttttt tattttaga aagaaagaac tttcagctac caagaaagac        360
cgtgtgaatc attgtctgac aatatgtgaa acatagtgg cacagtctgt caggtaattg       420
cactttgaac tgtctagaga aaacttgaca gtttctcttc ttttttttgct tagaaattct     480 ccagaatttc agaaacttct gggcatcgct atggaacttt ttctgctgtg cagtgatgac      540
gcagagtcag atgtcaggat ggtggctgac gaatgcctca acaaagttat caaagtaaga      600
accgtgtgga tgatgttctc ctcacttcca taaatctctt gtgatttgtt gtaggctttg      660
atggattcta atcttccaag gttacagctc gagctctata aggaaattaa aaaggtgggc      720
cttgcttttc tttttttaaaa atgtcttaat gcaaccctca ttgcaccccc tcagaatggt    780 gccctcgga gtttgcgtgc tgccctgtgg aggtttgctg agctggctca cctggttcgg      840
cctcagaaat gcaggtaagt tgtacactct ggatgttggt ttttagaatg acttgcgttc     900
ttttgcatac acaggcctta cctggtgaac cttctgccgt gcctgactcg aacaagcaag    960
agacccgaag aatcagtcca ggagaccttg gctgcagctg ttcccaaaat tatggcttct   1020
tttggcaatt ttgcaaatga caatgaaatt aaggtatgat tgttgcctca ggtcacaaac   1080
atgttttatc tacttggact tttgcttccg taggttttgt taaaggcctt catagcgaac  1140
ctgaagtcaa gctcccccac cattcggcgg acagcggctg gatcagcagt gagcatctgc   1200
cagcactcaa gaaggacaca atatttctat agttggctac taaatgtgct cttaggtaag   1260
gtggaggcat atgagtggaa gagtctgtta agatgtcttg cttccacccc cacaggctta   1320
ctcgttcctg tcgaggatga acactccact ctgctgattc ttggcgtgct gctcaccctg    1380
aggtatttgg tgcccttgct gcagcagcag gtcaaggaca caagcctgaa aggcagcttc    1440
ggagtgacaa ggaaagaaat ggaagtctct ccttctgcag agcagcttgt ccaggtagga    1500
gcacagggtt tactctagga actgaccaga acacctgtgt ttctctgttt ctaggtttat    1560
gaactgacgt tacatcatac acagcaccaa gaccacaatg ttgtgaccgg agccctggag    1620
ctgttgcagc agctcttcag aacgcctcca cccgagcttc tgcaaaccct gaccgcagtc    1680
```

```
gggggcattg ggcagctcac cgctgctaag gaggagtctg gtggccgaag ccgtagtggg    1740
agtattgtgg aacttatagg caagttatta gcaaggtcta cacttacaaa ctttatctgt    1800
cactttctgt gatttgcagc tggagggggt tcctcatgca gccctgtcct ttcaagaaaa    1860 caaaaggtg attatttcag aaatcagagt cttgtgttaa aaggaatgtt ggtacattat     1920
ttactaggca aagtgctctt aggagaagaa gaagccttgg aggatgactc tgaatcgaga    1980
tcggatgtca gcagctctgc cttaacaggt agttctcact agttagccgc tggtgtggtt    2040
tgacaaatga gtgtttctct gtcttcagcc tcagtgaagg atgagatcag tggagagctg    2100
gctgcttctt caggggtttc cactccaggg tcagcaggtc atgacatcat cacagaacag    2160
ccacggtcac agcacacact gcaggcggac tcagtggatc tggccagctg tgacttgaca    2220
agctctgcca ctgatgggga tgaggaggat atcttgagcc acagctccag ccaggtcagc    2280
gccgtcccat ctgaccctgc catggacctg aatgatggga cccaggcctc gtcgcccatc    2340
agcgacagct cccagaccac caccgaaggg cctgattcag ctgttacccc ttcagacagt    2400
tctgaaattg taagtgggca gaggggcctg acatctttta attctcacag ccccccttga    2460
accgtttagg tgttagacgg taccgacaac cagtatttgg gcctgcagat tggacagccc    2520
caggatgaag atgaggaagc cacaggtatt cttcctgatg aagcctcgga ggccttcagg    2580
aactcttcca tgggtatgtg gactacaggt gatgcgctac aaacacttaa tcttgatttc    2640
tctgttttta aagcccttca acaggcacat ttattgaaaa acatgagtca ctgcaggcag    2700
ccttctgaca gcagtgttga taaatttgtg ttgagagatg aagctactga accgggtgat    2760
caagaaaaca aggtgaggga cataggcttg agacgacttg gtgacaaaca agtgtcattg    2820
tctcctttct agccttgccg catcaaaggt gacattggac agtccactga tgatgactct    2880
gcacctcttg tccattgtgt ccgccttta tctgcttcgt ttttgctaac aggggaaaa     2940 aatggtgagt acaaaagggg atgtgcacag ttgactgaag gtggcttggg tgatttcttg    3000
gcagtgctgg ttccggacag ggatgtgagg gtcagcgtga aggccctggc cctcagctgt    3060
gtgggagcag ctgtgccct ccaccccgaa tctttcttca gcaaactcta taaagttcct     3120
cttgacacca cggaataccc tggtatgtta aaagttcaca tctgatgtgc tcgttccatg    3180
gctgagcaat ttatctccac agaggaacag tatgtctcag acatcttgaa ctacatcgat    3240
catggagacc cacaggttcg aggagccact gccattctct gtgggaccct catctgctcc    3300
atcctcagca ggtcccgctt ccacgtggga gattggatgg gcaccattag aaccctcaca    3360
ggtaacggcc agtttttcag ctgtgttttt tatgatgttt gttgcttgtt cttctggtta    3420
ggaaatacat tttctttggc ggattgcatt cctttgctgc ggaaaacact gaaggatgag    3480
tcttctgtta cttgcaagtt agcttgtaca gctgtgaggg tgagcataat cttctgtgga    3540
accatttctt gtcctcttgc cttggacctt tgttccagaa ctgtgtcat gagtctctgc     3600 agcagcagct acagtgagtt aggactgcag ctgatcatcg atgtgctgac tctgaggaac    3660
agttcctatt ggctggtgag gacagagctt ctggaaaccc ttgcagagat tgacttcagg    3720
taagtgagtc acatccatta gatttcatga tttcattgtt aaatgtgctc ttttgttagg    3780
ctggtgagct ttttggaggc aaaagcagaa aacttacaca gagggctca tcattataca     3840 ggggtaagca gtttattttt gtgagatgct gttttgtttat ttttattatc cttctctcta   3900
aagcttttaa aactgcaaga acgagtgctc aataatgttg tcatccattt gcttggagat    3960
gaagacccca gggtgcgaca tgttgccgca gcatcactaa ttaggtattt accaatatt     4020 tatctctttt cctttaagc aaattaacct tactttgtg ttaggcttgt cccaaagctg      4080
```

```
ttttataaat gtgaccaagg acaagctgat ccagtagtgg ccgtggcaag agatcaaagc    4140
agtgtttacc tgaaacttct catgcatgag acgcagcctc catctcattt ctccgtcagc    4200
acaataacca ggtatgctga cccagtggca tcttcacatt gtattttaag tctctatatt    4260
tttgttatta gaatatatag aggctataac ctactaccaa gcataacaga cgtcactatg    4320
gaaaataacc tttcaagagt tattgcagca gtttctcatg aactaatcac atcaaccacc    4380
agagcactca cagtaagtct cttcttgat gcctcttact gaggtgtgat tttattgttt    4440
ctttcttctg agtttggatg ctgtgaagct ttgtgtcttc tttccactgc cttcccagtt    4500
tgcatttgga gttaggttg gcactgtggg tatgtatttt cctcagtata tattaatagt    4560
aatttgactt tgcaaatgtc tgcttccaga ggtgcctcca ctgagtgcct cagatgagtc    4620
taggaagagc tgtaccgttg ggatggccac aatgattctg accctgctct cgtcagcttg    4680
gttcccattg gatctctcag cccatcaaga tgctttgatt ttggccggaa acttgcttgc    4740
aggtactggt actgagttga aacagggact ccggagaggt nntgtctgtg cccatatcac    4800
agccagtgct cccaaatctc tgagaagttc atgggcctct gaagaagaag ccaacccagc    4860
agccaccaag caagaggagg tctggccagc cctgggggac cgggccctgg tgcccatggt    4920
ggagcagctc ttctctcacc tgctgaaggt gattaacatt tgtgcccacg tcctggatga    4980
cgtggctcct ggacccgcaa taaaggtaat gtcccacttg ggtgctggat tcatattgtt    5040
ttttgttttt gtttttctat tttaggcagc cttgccttct ctaacaaacc cccttctct    5100 aagtcccatc cgacgaaagg ggaaggagaa agaaccagga gaacaagcat ctgtaccgtt    5160
gagtcccaag aaaggcagtg aggccagtgc aggtaggaaa cagcgtgggg aagggaggga    5220
caagtttatc ttttgtgtgc atattttaa agcttctaga caatctgata cctcaggtcc    5280
tgttacaaca agtaaatcct catcactggg gagtttctat catcttcctt catacctcaa    5340
actgcatgat gtcctgaaag ctacacacgc taactacaag gtatgggcct ctgcatcttt    5400
taaaaatata accgtgtgtt ctctccttca ccttcccaag gtcacgctgg atcttcagaa    5460
cagcacggaa aagtttggag ggtttctccg ctcagccttg gatgttcttt ctcagatact    5520
agagctggcc acactgcagg acattgggaa ggttgtgtc ttgttttttc tccttgggtt    5580
gtcgcttaat gtctgacttg tcttttctaca gtgtgttgaa gagatcctag gatacctgaa    5640
atcctgcttt agtcgagaac caatgatggc aactgtttgt gttcaacaag taagagcttc    5700 attctttcc tcttctgtta ttgttgatgc ctcattttt tcactgtagt tgttgaagac    5760
tctctttggc acaaacttgg cctcccagtt tgatggctta tcttccaacc ccagcaagtc    5820
acaaggccga gcacagcgcc ttggctcctc cagtgtgagg ccaggcttgt accactactg    5880
cttcatggcc ccgtacaccc acttcaccca ggccctcgct gacgccagcc tgaggaacat    5940
ggtgcaggcg gagcaggaga acgacacctc ggggtaacag ttgtggcaag aatgctgtcg    6000
ttgctctgct tccctttat tcccatttgg cagatggttt gatgtcctcc agaaagtgtc    6060
tacccagttg aagacaaacc tcacgagtgt cacaaagaac cgtgcagata aggtaaatgg    6120
tgttgtttgt ggatgtgaac tcattctttc tttctttttt tcttttttat agaatgctat    6180
tcataatcac attcgtttgt ttgaacctct tgttataaaa gctttaaaac agtcacgac    6240 tacaacatgt gtgcagttac agaagcaggt tttagatttg ctggcgcagc tggttcagtt    6300
acgggttaat tactgtcttc tggattcaga tcaggtttgt cacttttatc tttcatccat    6360
catattgatg taaattttat tttccttcct gtaggtgttt attggctttg tattgaaaca    6420
gtttgaatac attgaagtgg gccagttcag gtaatagcat tttattattt tagatttttt    6480
```

```
aaggatctaa atggatgttt ttgtttctag ggaatcagag gcaatcattc caaacatctt    6540
tttcttcttg gtattactat cttatgaacg ctatcattca aaacagatca ttggaattcc    6600
taaaatcatt cagctctgtg atggcatcat ggccagtgga aggaaggctg tgacacatgg    6660
taacnggaca cacctttcac tgtcgtcttc ctgataaggg taccctttg tccccacagc     6720 cataccggct ctgcagccca tagtccacga cctctttgta ttaagaggaa caaataaagc    6780
tgatgcagga aaagagcttg aaacccaaaa agaggtggtg gtgtcaatgt tactgagact    6840
catccagtac catcaggtaa gaggaatgta tgttggaact gtcgtgcaga ctttctaatt    6900
gtgcacgctc ttataggtgt tggagatgtt cattcttgtc ctgcagcagt gccacaagga    6960
gaatgaagac aagtggaagc gactgtctcg acagatagct gacatcatcc tcccaatgtt    7020
agccaaacag caggtttgtc cccgcagcct tggcttgttg ttgtagaaat gtttgtggtg    7080
tctaattcca cagatgcaca ttgactctca tgaagccctt ggagtgttaa atacattatt    7140
tgagattttg gccccttcct ccctccgtcc ggtagacatg cttttacgga gtatgttcgt    7200
cactccaaac acaatggtga gtctctcgcc tggctcagca gatgaagctg tgacttatgt    7260
attatgttta ttttaggcgt ccgtgagcac tgttcaactg tggatatcgg gaattctggc    7320
cattttgagg gttctgattt cccagtcaac tgaagatatt gttctttctc gtattcagga    7380
gctctccttc tctccgtatt taatctcctg tacagtaatt aataggttaa gagatgggga    7440
cagtacttca acgctagaag aacacagtga agggaaacaa ataaagaatt tgccagaaga    7500
aacattttca aggtatgctt tctatctgag cctataacta acttcactgt catcttttt     7560 cttt cttgga aggtttctat tacaactggt tggtattctt ttagaagaca ttgttacaaa    7620
acagctgaag gtggaaatga gtgagcagca acatactttc tattgccagg aactaggcac    7680
actgctaatg tgtctgatcc acatcttcaa gtctggtagg tgaatcacat tagtcttcct    7740
ggagtaaaga catttctcct taactttgtt tctaggaatg ttccggagaa tcacagcagc    7800
tgccactagg ctgttccgca gtgatggctg tggcggcagt ttctacaccc tggacagctt    7860
gaacttgcgg gctcgttcca tgatcaccac ccacccggcc ctggtgctgc tctggtgtca    7920
gatactgctg cttgtcaacc acaccgacta ccgctggtgg gcagaagtgc agcagacccc    7980
gaagtaggtt cataatgccc cacagcccag ggccattgtc aatgcatctg ttgctccttc    8040
tagaagacac agtctgtcca gcacaaagtt acttagtccc cagatgtctg agaagaggga    8100
ggattctgac ttggcagcca aacttggaat gtgcaataga gaaatagtac gaagaggggc    8160
tctcattctc ttctgtgatt atgtcgtaag tttgaaatgc ctgtaaacgg ggttgaaatg    8220
aatctctcat catatttttc cttagtgtca gaacctccat gactccgagc acttaacgtg    8280
gctcattgta aatcacattc aagatctgat cagccttttcc cacgagcctc cagtacagga    8340
cttcatcagt gccgttcatc ggaactctgc tgccagcggc ctgttcatcc aggcaattca    8400
gtctcgttgt gaaaaccttt caactgtacg tcttcatcct gccgactatt gccagatctt    8460
ttcttctttt ccttcttgct gttagccaac catgctgaag aaaactcttc agtgcttgga    8520
ggggatccat ctcagccagt cgggagctgt gctcacgctg tatgtggaca ggcttctgtg    8580
cacccctttc cgtgtgctgg ctcgcatggt cgacatcctt gcttgtcgcc gggtagaaat    8640
gcttctggct gcaaatttac aggtattggg aagagaaacc ctgatattga ttcaaacaca    8700
ctaatgtgtt tttgtctatt agagcagcat ggcccagttg ccaatggaag aactcaacag    8760
aatccaggaa taccttcaga gcagcgggct cgctcagagg taatgctgga aacacaggtc    8820
gtccttgtga ctgtaatttc attttttattt gtatttaga caccaaaggc tctattccct    8880
```

```
gctggacagg tttcgtctct ccaccatgca agactcactt agtccctctc ctccagtctc    8940
ttcccacccg ctggacgggg atgggcacgt gtcactggaa acagtgagtc cggacaaagt    9000
aagtgtccag cgtgtctgca tgggaggctg ttccccttat ccattttttt cttcccagga    9060
ctggtacgtt catcttgtca aatcccagtg ttggaccagg tcagattctg cactgctgga    9120
aggtgcagag ctggtgaatc ggattcctgc tgaagatatg aatgccttca tgatgaactc    9180
ggtacggggg gagcagtgga ggcaaggaat cgtttgttaa cctttaatgc tctgatttca    9240
ggagttcaac ctaagcctgc tagctccatg cttaagccta gggatgagtg aaatttctgg    9300
tggccagaag agtgcccttt ttgaagcagc ccgtgaggtg actctggccc gtgtgagcgg    9360
caccgtgcag cagctccctg ctgtccatca tgtcttccag cccgagctgc ctgcagagcc    9420
ggcggcctac tggagcaagt tgaatgatct gtttggtaat taaaattaaa atttatctta    9480
ttttagcacc cacccacgag gtccttctgt ttcagdggat gctgcactgt atcagtccct    9540
gcccactctg gcccgggccc tggcacagta cctggtggtg gtctccaaac tgcccagtca    9600
tttgcacctt cctcctgaga aagagaagga cattgtgaaa ttcgtggtgg caaccccttga   9660
ggtaagaggc agctcgggag ctcagtgttg cggcattctg tgactcggta cttccctta    9720
ggccctgtcc tggcatttga tccatgagca gatcccgctg agtctggatc tccaggcagg    9780
gctggactgc tgctgcctgg ccctgcagct gcctggcctc tggagcgtgg tctcctccac    9840
agagtttgtg acccacgcct gctccctcat ctactgtgtg cacttcatcc tggaggccgg    9900
tgagtccccg tccatgaacg gtgggttcca ttcttctctt tgttctgttg taatttagt    9960
tgcagtgcag cctggagagc agcttcttag tccagaaaga aggacaaata ccccaaaagc   10020
catcagcgag gaggaggagg aagtagatcc aaacacacag agtaagtctc aggacccatt   10080
tttttcttac aaaagtcctc tcttaaccgt tgcttgttta gatcctaagt atatcactgc   10140
agcctgtgag atggtggcag aaatggtgga gtctctgcag tcggtgttgg ccttgggtca   10200
taaaaggaat agcggcgtgc cggcgtttct cacgccattg ctcaggaaca tcatcatcag   10260
cctggcccgc ctgcccccttg tcaacagcta cacacgtgtg cccccactgg tgagtctgct   10320
cgttccttgc agaagaccag atgatgtcac ttccttttca tcttctcagg tgtggaagct   10380
tggatggtca cccaaaccgg gaggggattt tggcacagca ttccctgaga tccccgtgga   10440
gttcctccag gaaaaggaag tctttaagga gttcatctac cgcatcaaca cactaggtac   10500
tcttggggcc tctccttcag gtcacccact ctctcatgta agatttatat ttgtaggctg   10560
gaccagtcgt actcagtttg aagaaacttg gccaccctc cttggtgtcc tggtgacgca   10620
gcccctcgtg atggagcagg aggagagccc accagaagta aggccacacc ctgtgctggt   10680
tggcacagct cttgttacat gtgggctctc cttccaggaa gacacagaga ggacccagat   10740
caacgtcctg gccgtgcagg ccatcacctc actggtgctc agtgcaatga ctgtgcctgt   10800
ggccggcaac ccagctgtaa gctgcttgga gcagcagccc cggaacaagc ctctgaaagc   10860
tctcgacacc aggtttgctt gagttccac gtgtctctgg gaaacactct ttacctttt   10920
tctaaaatgt aggtttggga ggaagctgag cattatcaga gggattgtgg agcaagagat   10980
tcaagcaatg gtttcaaaga gagagaatat tgccacccat catttatatc aggcatggga   11040
tcctgtccct tctctgtctc cggctactac aggtacctga gggaaaggga gcgggggagc   11100
gggatcaaga ctcagggtgc tggtgttcac aggtgccctc atcagccacg agaagctgct   11160
gctacagatc aaccccgagc gggagctggg gagcatgagc tacaaactcg gccaggtcag   11220
tctcgcgnnc ccgccgcctg gcctcacact gagcagtgcc ccgtttctgt ggcaggtgtc   11280
```

```
catacactcc gtgtggctgg ggaacagcat cacacccctg agggaggagg aatgggacga   11340
ggaagaggag gaggaggccg acgcccctgc accttcgtca ccacccacgt ctccagtcaa   11400
ctccaggttt gcagatggcc tttttatttt taacagtgga aaatacccat ctcgcatatt   11460
ccacaggaaa caccgggctg gagttgacat ccactcctgt tcgcagtttt tgcttgagtt   11520
gtacagccgc tggatcctgc cgtccagctc agccaggagg accccggcca tcctgatcag   11580
tgaggtggtc agatccgtaa gtgagccttc ccattcccct cacaccctt gccctcctgg    11640
ttttccacat ctccagcttc tagtggtctc agacttgttc accgagcgca accagtttga   11700
gctgatgtat gtgacgctga cagaactgcg aagggtgcac ccttcagaag acgagatcct   11760
cgctcagtac ctggtgcctg ccacctgcaa ggcagctgcc gtccttggga tggtaagtga   11820
caggtggcac agaggtttct gtatgcagca gcttttgtct gtgtgtgcct aggacaaggc   11880
cgtggcggag cctgtcagcc gcctgctgga gagcacgctc aggagcagcc acctgcccag   11940
cagggttgga gccctgcacg gcgtcctcta tgtgctggag tgcgacctgc tggacgacac   12000
tgccaagcag ctcatcccgg tcatcagcga ctatctcctc tccaacctga aagggatcgc   12060
ccagtgagtg ggagcctggc tggggctggg gcgctgagcc tggatgctgt ctcccgtttt   12120
gagctgcgtg aacattcaca gccagcagca cgtactggtc atgtgtgcca ctgcgtttta   12180
cctcattgag aactatcctc tggacgtagg gccggaattt tcagcatcaa taatacaggt   12240
gagtgggccc tggctgtctt cctctgcatt tgacacagag gcctttgtcc ctgtgcagat   12300
gtgtggggtg atgctgtctg gaagtgagga gtccacccc tccatcattt accactgtgc    12360
cctcagaggc ctggagcgcc tcctgctctc tgagcagctc tcccgcctgg atgcagaatc   12420
gctggtcaag ctgagtgtgg acagagtgaa cgtgcacagc ccgcaccggg ccatggcggc   12480
tctgggcctg atgctcacct gcatgtacac aggtgagcat gtacacggtg cccataaggc   12540
cataaccttc gtactgaaca cttttgttac aggaaaggag aaagtcagtc cgggtagaac   12600
ttcagaccct aatcctgcag cccccgacag cgagtcagtg attgttgcta tggagcgggt   12660
atctgttctt tttgataggt aagaagcgaa ncccatccct cagcccgttc agtctctgac   12720
ctgcgtccct cctcccagga tcaggaaagg ctttccttgt gaagccagag tggtggccag   12780
gatcctgccc cagtttctag acgacttctt cccaccccag gacatcatga acaaagtcat   12840
cggagagttt ctgtccaacc agcagccata cccccagttc atggccaccg tggtgtataa   12900
ggtgaggttg catgtgggat ggggatggag ttgacactca ggcgcctgct tgctcttgca   12960
ggtgtttcag actctgcaca gcaccgggca gtcgtccatg gtccgggact gggtcatgct   13020
gtccctctcc aacttcacgc agagggcccc ggtcgccatg ccacgtgga gcctctcctg    13080
cttctttgtc agcgcgtcca ccagcccgtg ggtcgcggcg atgtatcctc tctggntccc   13140
tggtnctggc ccgccggcct ttttccttaa ctcctgcacc agcctcccac atgtcatcag   13200
caggatgggc aagctggagc aggtggacgt gaacctttc tgcctggtcg ccacagactt    13260
ctacagacac cagatagagg aggagctcga ccgcagggcc ttccagtctg tgcttgaggt   13320
ggttgcagcc ccaggaagcc catatcaccg gctgctgact tgtttacgaa atgtccacaa   13380
ggtcaccacc tgctgagcgc catggtggga gagactgtga ggcggcagct ggggccggag   13440
cctttggaag tctgtgccct tgtgccctgc ctccaccgag ccagcttggt ccctatgggc   13500
ttccgcacat gccgcgggcg gccaggcaac gtgcgtgtct ctgccatgtg gcagaagtgc   13560
tctttgtggc agtggccagg cagggagtgt ctgcagtcct ggtggggctg agcctgaggc   13620
cttccagaaa gcaggagcag ctgtgctgca ccccatgtgg gtgaccaggt cctttctcct   13680
```

```
gatagtcacc tgctggttgt tgccaggttg cagctgctct tgcatctggg ccagaagtcc    13740
tccctcctgc aggctggctg ttggcccctc tgctgtcctg cagtagaagg tgccgtgagc    13800
aggctttggg aacactggcc tgggtctccc tggtggggtg tgcatgccac gccccgtgtc    13860
tggatgcaca gatgccatgg cctgtgctgg gccagtggct gggggtgcta gacacccggc    13920
accattctcc cttctctctt ttcttctcag gatttaaaat ttaattatat cagtaaagag    13980
attaatttta acgt                                                      13994

<210> SEQ ID NO 10
<211> LENGTH: 118777
<212> TYPE: DNA
<213> ORGANISM: Mus musculus
<220> FEATURE:
<221> NAME/KEY: misc_feature
<222> LOCATION: (1)..(118777)
<223> OTHER INFORMATION: LOCUS      AF163865              118777 bp
      DNA     linear   ROD 24-JAN-2001
      DEFINITION  Mus musculus alpha-synuclein (Snca) gene, complete
      cds.
      ACCESSION   AF163865
<300> PUBLICATION INFORMATION:
<308> DATABASE ACCESSION NUMBER: AF163865
<309> DATABASE ENTRY DATE: 2001-01-24
<313> RELEVANT RESIDUES IN SEQ ID NO: (1)..(118777)

<400> SEQUENCE: 10
gaacctcaga cagctgacag aaagtcctcc aattctgagc tacaggagtg aatctgctac      60
tgaaaacaca ggcagagcag acacgctgct gtagacacag aggaagatga cagggacagg     120
aagatgtaga cactgatagc aattagctaa ggagattcat ttcttttttc cctaaccagg     180
caaggaccct gactagaaga cattttgttg ttgaaacatg ttgttgaaga tacagttttg     240
gggatgtatg tgagaaaatg aagagtaaac ctgaatttaa caagccatgg ctttgggtct     300
ggtaccatga cgaagcataa gttacagaat actttctcgt tgccgttttt tggtttgtaa     360
attcagtcct tcaaatatcc atacatactg ggctcttgag aacccatgaa gaaggatgg      420 aatacttggt gtttatgcaa acttatttaa tacctactgc aaagttcaag tcaaggctta     480
atgccttgac tactttcaca atcagccact acttattgga ttgggtggtg aaaacatggc     540
tgagacatct tgtagtcata attttttttt aaagaaaagt acctgatcct tcttagaagg     600
gggaacaaaa tacccatgtg gggagataca gagacaaagt ggaacagaga tgaaggaaa      660 gaccatctag agactaccct acctggggat tcatcctata tagagacaac aaatccagac     720
actatagtgg ataccaacaa gtacttgctg acaggagcct gttgcagttg tctcctgaga     780
ggctttgcca gtgtctgaca aatacagagg tggatgcttt cagccaacca ttggactgag     840
cacagaggcc ctaatggagg ggctagagaa aggacccaag aagacgatga ggtttgcaat     900
cccataagag gagcaacaat atgaaccaac cagtaacccc agagttccta gggactaaac     960
caccaaccaa agagtataca cggagggact catggctcca gttgcatatg tagcagagga    1020
tggccttgtt aatcatcaat ggaaggagag gcctttggtc ctgtgaatgc ttgatggccc    1080
cagtgtagtg ggatgccagg accaggaagc aggagtgagt gggttggtga gctgtggggg    1140
atcaggaaaa gggataacat ttgaaatgta aataaagaaa atatctatta aaagaaatta    1200
cccttcatgc tgtcaaacac cttttagttc ctgtaatcag gcttcctggt tcttctttct    1260
tccccttttg acacagactc tatgtccaca aggctagcct gactgttgca gtaattctct    1320
gaccaaatct ctcaagtgct gaaatcatag gcactaacta ctaggcctgg ctctaacact    1380 ggattttta  gatcctataa atcctggaca ctttaaactt ctattttact cagaattttg    1440
```

```
ttggagaacg tactgtgtgg gacacaaatc actgctatag tgtttccaga aatttgaaga   1500
atactgagtc ctgttatgtg gtgactgaat ggagctgtga cctcctacaa agtagagctc   1560
aaggttctac attctctgtg gggtctccag taattccatc attgcaatgg actcctgcca   1620
ggaccatagt ttcagaatgg agtgtagaaa ataaatagta caacatctgg gtaagaaatt   1680
tggagaaaca tgatggagcg cttcaaagct gtctacacac acacacacac acacacacac   1740
acacacacac acacacgtga tcatgatgca ttgagagtaa gaataacaac attgctaaag   1800
agagtttgtg ggtacagaag agaaagagaa aaatgcttaa attaaacatg caaataaaac   1860
ttcatttaag aagtttgcag aatgaatctc caagctctaa agacaaatat tatccaaaac   1920
tactatgctg gaatgccagt caacacaggg gccactgggc aagttttctc taatttaaac   1980
aaaaccaaaa accaaaccaa accaactaat taaccaaacc aaaatcccaa ccaaccaact   2040
aaccaaacaa gcaaacaaaa atcctggaac aacatgagag cccaaggact gtgaatagaa   2100
tctcaatatt caaggtgtat ttgggaagct ccagcaagtg agctaagacc acaaggcaga   2160
ccagggaggg ataaagagac agtctctcta gatcaatctc taaacagtca tagatacaaa   2220
ctacacaggg gcttactagg ccacagttta aatttcacac aaaaaacaaa attcattgaa   2280
aagctgatcc cttagagtat gtaaaaattc cttgtttctg ctctagttgg cagtgtcatg   2340
agccttatca actggatggt gcagggactc catgttacac aatgtttttc ttcttctatt   2400
tgtttctaaa atcagtggtg agatcaggca cattttaaa aacatgacca tactcttgtt   2460 cattccttc tcaagtaaaa aaaaaaaaa acctatgatt tggcgggttc tgattatgga   2520
gggctgaaat agtaatatca gtcatgaaca gctgagagca ctggtttctg agcctctgat   2580
tgaagcttta gaatcctgtg tttggatgta taatattaaa gaaacaatag tcataagcct   2640
cagcctgtac tcaagatagt tttaaatgtg tggttatttg ctggtatgta tgtccgtgca   2700
gcatttctgt gcctgatacc tgtggaggtc agaaaagtgt gttggatttc ctgggattgg   2760
agttacagac aattttgagc tgccatgttg gtactgggac tcaaatccca gtcctctgca   2820
agagcagcct gtgcccttat ctgctgagcc acctctctag ccccattata acaagaattt   2880
ataaagctga tgacctattc catgtatccc ctagttcatt gcattgtgag agtgaataat   2940
ggtatttgta gataggttga aattataaat gtatttccta ttggttcatc atgagccaga   3000
catacagctt ttccaagatt taggttccct ggataaagcc ctcagtcata ttatcagcta   3060
tcaatgtaat gttatgttgt aaatataaat attagcccta gtacactaag gtagccacga   3120
gaagacttgc tgtgtcttaa acaagagaaa tttgttttct cacagttctg gaggttagaa   3180
gtctaatatc agatgtcagc agggttgatt tattctagtg ctgctgtcct tggctcacag   3240
gccactgcct tcagtgtgca gcctctatgt ctacttctaa tgtattctag cctactcttc   3300
ttgtaaatac atcaatcatg gtagatttgg gcactcttca atgacacatt ttaacctta   3360 tgtcctcata ctgagggtaa gaacttcaac acacagttgt aaaaatttat ttgtaagtca   3420
tttacttaaa aagttttttaa taacaaaatt tttcgtgtga atataacgca ttcagattac   3480
tctcatcttc cactgtcttt tatttaccct ttactcttat caaatctcac tgtcatcccc   3540
ccccaaaaaa aactcttttc cacatttatg tcttttgtt ttgtgaccca ttgagtttaa   3600
atatgtccat ttatgtgaca atgaatatgt gaccattgga tcctggtgag cttactagtg   3660
ggtacacagc taaagacaat gactttatgt cttcaccat ctatcaatag caaacaatta   3720
atcatgagaa ggtaggggca catacaccct tctactggtg gtacataatt aacaggcaca   3780
gtcttgaata gatccagtgc caagaacttc agctgctgta agctcatgat taaaatggct   3840
```

```
gtattatggc ctgaagatta tgttttgtac tctttctcca taacatttag catattatat   3900
tcttcccctc ttcagctttc attccataaa ctttagatgt actggttcaa atgtcctgtt   3960
tagggatgaa atatggagac aaagtgtgga gcagaaactg taggaaaggc catccagaga   4020
ctatctcacc tgaggatcca tcttgtatat agacaccaaa cccagatact attgctgatg   4080
cccagaagtg cttgctgaaa ggtgcctgat atagctgtct actgagaggc tctgacagag   4140
cctgacaaat acaaatgtag acgctcacag acaaccgttg ggctgagcac gtaggtccct   4200
gataaaggag ttagagaaag tagggttagc aaccccatag gaagaacaac aatatcaacc   4260
aaccagaccc cccagagctt ccagggacta agccacctac caaggagtac acatagaggg   4320
acacatagct caggctgcat atatatgttt ttcaggcatc aatgggagga gaggccctcg   4380
gtcctatgaa ggctggctgg atgccccggt gtagggaat tggagggcag ggaagcagaa   4440
gggtgtggat gggttgggga gctccctcat agaagcagag gaggggatg ggatagggg    4500 tttcaggtgg ggatcaggaa agcagataac atttgaaatg taaataaaga acatattccc   4560
cccaaaaaga caaatatcac atcacacaca cacacatgtg cacacacaca cacacacaca   4620
cacacacaca cactcagaga gattgagaga gagagagaga gagagggaga gagagagaga   4680
gagagagagg tgcagagagt ggaagaggca gtttaaccag gacagttgaa cagagacagg   4740
ttgcacaaag agaacaagct agacacagaa gacagaataa accaagggat gagaaagagg   4800
cagagtagaa catattgcca aagttagtat caggtcaagc agagcaattt agaagaggcc   4860
gagagagaga agccagaatg aatcaatcag tgtggagagg atttttgagcc ataacagctg   4920 agttgaacca tgtagagtta aaaagaaca agagagggtg agcttattca tcattaagtc   4980
ttagaggctg aaaatattct agacctagat aatactgtat ggagggtaga agcttccagg   5040
actaggccta tgttagcaga gagaggcagt aagcctctga tatgacaatt acattaggtg   5100
aaaaatagtt acaattacat ttaggtagca tgtttcatt attcatcagc tgacagacat   5160
ttagaccgtt tctatttcat ggctattatg aatagagaag aaattaacat ggatgagcaa   5220
gcctctctga agtggaatat agagttcttt gggaatatgc ccaggagtta tacagcgtga   5280
tgatatggaa gacctacttc ttctcttttg tagaaactct acattgattt tcatagtgaa   5340
tgcttcccct tttctccaac catcattaaa ttaatgtttg cctttcccaa gtctgtacta   5400
gaatttgtta tttgtccatt tgtcttagac atcctgagtg gggtaagact ggggcctcca   5460
gtctcttgag ggttaggtgc atcatctctg tatgaacaca gccttggcag tcctctactg   5520
taagtgtttt gggggcctca tatcagctga tatatgctct cggttggtg gtccagtttt   5580 tgagagatct tgggggtcca gattaattga gactgctggt cctcctacag aatcaccccc   5640
tttctcagct tctttcagtc ttccctaact cggaaacagg ggtcagctgt ttctgtccat   5700
tggttggttg caagtatctg catctgacac tttcagctgc ttgttgggtc ttctggtctg   5760
tggtcatgat aggttggtcc ctttgtgtga gcgctccata gtctcagtaa tagtgtcaag   5820
ccttgggacc tcccttgag ctggaatcca ttttggacct gtcaagggat cttcttcagg   5880
ctcctctcta tcttttctca aatgtatagc taataaatat tttgaaaatt ccctcagtt   5940 ttcagaatgt ctcttcacac aaaggatggt gttcttttaa gcttcacagc cctatttgtg   6000
agttattctt aatatctgtt caactgtgtc ctgttccaca acctataagt tgaggtatat   6060
tttctttctc ctctgaggaa tcatgttatc agatttgtgt tgaggtgctt ggagttggat   6120
tttgtacaag gtgaagtaga agaatctagt ttcacttttc tacacattgc tattcagttt   6180
gaggaacata attgaactat tctgaactga gattctctaa actgaacaga actgaattga   6240
```

```
actgaattga aatctctatc cttccctgat gtttaagtag cctcttttc ctgtctgttc    6300 ttgtgagagt taggcatatc ttatttgtgt ctcattctgt aaaatctttg tctgtacctc    6360
aattagatat cactgtttgg gattaaaggt atgtacaaaa gatatgtcta aatcccagcc    6420
agggaaatta aatgtatgtc tactctgcat tccagtagaa ttatatcttt gtatgtgatt    6480
ccttgcccaa gcacccatgt tgcttgatta aaacctctac aacatttatt ccaagatatt    6540 ttatttttc tgtggttatt gtcaccactt aatttgatga cataattatt aaaataatta    6600 ctctcccct gaggaagact gagctacacc atctctatgc tagctcaaga catacttcct    6660
actggcatga ggattctaat tgactcccta tcttctgaat tcagagtgag ttatatatga    6720
cacacgatat tcattaacac aattaaagga taagtatgaa tatttggtag tttttaatgt    6780
ggtcaacagc atccaacaat gacaggagag tttgaaaaaa tttcatagga aaattgtcac    6840 tggttttaa ttaacactta aaaggtgtaa catttttttt atgctattaa gctctattcc    6900
aaaaagtgtt aagttcattt tgtctatttg ggaaaaagaa gaggtagaaa atatcttgag    6960
aagaaggaat attgtgatca caaggctaca gtgaaatggg ccatgtccac tagagtagta    7020
gaggaaaagt aatagaggaa attatcatgt attgtaaaaa tgcactttta ttatcagcaa    7080
ggtggagcag tagaatgttt gtatgctgcc tagataggaa tgaaagagca tgcttctttc    7140
tttgatggga acaaatgact ttgtacagaa acatttttcct ggagataggt ctctgagatg    7200
tggaaccttc cctagtgaaa aggaccatgt ttcctgctgt gctgccatga atattttag    7260 tcttgctcat ctttggctaa gcctcagtgt ttgtggatac cagatgcatt gtgcaggtgt    7320
gatgtggaaa caggaaatct gactacttgc catattctca aacatatttc ttatctccct    7380
gaagcaaaag tagaacataa aacatttctg ctatccaccta ttctaattaa atgcatatat    7440
aggattattt attaaaaata gtatttatga aaaaggctga aagctctgtg attttttcagt    7500 taactccttt atgcacatgg ctatactgct gatatctgat gaatatgtgt ctgatgctat    7560
ttgtgttcat cacttttctg ttgccgtgac aatataccac aaccaaagca tcttatagaa    7620
ggaagagttt atttggctta tggttttctta tgaagatcct gaaagtaaag gaagccctga    7680
aaaaccattg tgtgaggctt tgaaaatgaa gcctgggtta cagtagatcc caaaggctttt   7740 agagattcca aagccttaca cagtggtctc tcagggcttc ttttccttc agtatcttca    7800 ttcaggatga acttgccaca tatagcatgg cctcagaaac tctctcaaac aatggagaaa    7860
actccatgag cccttaactc ttaaaaaaca aacttccaca atattcatgg aaattatgat    7920
attcttggac attaatctat ctctgaagat gcatcttcca ttagagtcta taaaaggta    7980 aacaagagaa aacaaggcag agaaaaaaaa tagataaagg taagtggcca aaggtttgta    8040
aacaacactg agccaaaaat tcctggcctg gaaatgagta gagtaaccag atcataagga    8100
tggtcagaat ctcagatgtt taagtgaaac tgtattctcc tacataacaa aatcattccg    8160
tgtcagcgcc aacatggctc caaagagtca gatctggtca acagccaaat ccttaagaaa    8220
tctagctcca agttcatttc caactgacta gaggtaaatg ttatgctttc ttctgagtaa    8280
ttttctctaa atgatttaaa gaaagggtga agataattta gaactcaaat taaaggttac    8340
taaacaaaat tcaaacttca ttttccagtt cttttttcagt ttgttttta aaaatataat    8400 tatatcattt ccactttttct tttttctttc tccaaactct cccatatagc caatttgctc    8460
gcaaattaat tgcttcctct ttataaaact gttattacaa ttttgcatat tatcattttt    8520
aatactttat agtatctgca ataacaataa ttaaatataaa cataatacta atatataata    8580 tatatttttcc tatacataaa accaccacct ccttggactg tataatgtta ctgtgtgtac    8640
```

```
atgttttgag ggttggtcat ttggtattgg aaagatcttc cttggggagc attatttcta    8700
ccattctcat cactccttag gaacctacaa ttctttgtgt aggqtttgag gcctcttcag    8760
cccccattca cattagcatg cgtattggtg tgttccttgg ttgggtcatg tttaggcacc    8820
catgaggatg agactttggg tatagtttct tacatttctg ggagacacag ttttacagca    8880
cactctgtgc tcctctggct cttatagtgt ttctgctccc tttccagaag ggccttcaag    8940
cctaaaggaa ggacctgtgt tgtagttaca tcagttgggg tgtggctcta caactctgaa    9000
ttttaattgg ttctggtttt ctgctatagt ctctgtctgt tgcaaagtga agtttcctca    9060
atgagggagg aatgagaatt atacttatct ataaatataa tgacatacat ttcaaatgta    9120
gttagagatt ataattgttt gtaggctctc caatgttcat gactttgcaa gtcctgggta    9180
gttggctagg tttcaatgac cagacatgtt ttctcccttg ctgtgcaggt cataaattca    9240
atgagagcta ttggttgtca cgaaggtatg catgccactt atacacccca agggttatca    9300
ctccatgctg gtcacttgtg tttcacaggc atatatctgg gtagaacaag gggttgcttc    9360
tcacctttgc tagtgtacat ggcaccttct ggtactgaaa gctactcctt agggaggagg    9420
cttttaggtc agttccagct tagggcctct gtgctccgtg tttgaagtac atattgtcat    9480
cagcaataac aatttacctt ctacttctga aggacaacca aaagaaataa tatcagtaac    9540
gtataatgta ttctgtgtct cttctataat cctgaccaat aactcaaaag aggatttctc    9600
actcatcaac ccctgtaagt atcgttgttg ttttgttttg atataattgc aatatttcac    9660
ctctcttttc ctctcttcaa gttttccagt atacctctcc caggtctcct tcacattgaa    9720
tgttctcttt ttcttaact gttattgcat aatatatgta tatacatatt tattcttcag    9780
tataacctac tcagcctgag agtgaataat gctacttgaa tgtatgtttt cagggctgac    9840
cacttggcac tggacaagca atttgtatgc tcttctctac agagatcata tctcctgcac    9900
ccagcttttc tcagttacct attgtccttc atgtagcatt gaggtctcat ggacttttcc    9960
ctgtccactt tgacatttcc ccttgtgcta accttgttca gttcaggttt gagtagtcat   10020
gaatgtgaga cttcatgggt atagcttctg acattattag cagacataat ctcatgcaaa   10080
cttctcttgat cctctggctc ttacaatctt tctgtttcct cattcataaa tgtttctatt   10140
gggactgggc tctaaaactt tgtattttga ctggttgtag cttttctgta gtggtctcta   10200
tttgtttcaa agaaaagatc ccttataagg agcaaagtct atacttatct gtgggtataa   10260
caacaaatgt ttgtagattg tagttaggga ttattctggt ttagtaaatt agtggttgta   10320
gtttctcctc caacatccat gacttcacta gcactgacta gttcactagg ttttcaggta   10380
ccaggcatgg tttctctctt gctgaatgac tcatacccac aattagaggg ctgttggtta   10440
atactcacaa gtatgcatgt gactcctgca tgcttttggt tatcatggac cctgatgcca   10500
ctgaaacaca ctaacatcac ctttttttat tttatcgctt tcaagaaaca gaaaataggg   10560
tctctttagg gagcttgaaa ccttggtttg tggagtattg tttgaggaca cccttccctt   10620
catttcaatg caaagtagac ctgtccttaa tggtgtaaaa cttttaaata attacagcct   10680
tccttctgtt gctttggcag taacataaac atactgttgg tcttttttctc tctaaactat   10740
acattttgta tttctgcccc agttgctctt tctttcatta tagatctgca taagtgttat   10800
agtacaacca ttccacagat tcatcattat gttgtcttac aatcacttcc actaaagaaa   10860
ttcatccttt acttttcaat tgagtctcag gcaagtattc tgctcaggac atgagcagaa   10920
ggtggccaca aaccatgatg aaaaaatgaa tagcctccaa cacacttgct gttaacgtcc   10980
ttcattcctt ctgaaacctc ttggtccagg cttctacagt atttatccct ctcagccctg   11040
```

```
ctgtcttcca atcttctacg agaaggacct tttcatctct gctcatagca ttcatctgcc   11100
tttcgctttc aatgtttaca ttcctccaaa ccccaaaatg attgggttct tcacagaaat   11160
agccaacttt tttggtacca acttctgttc tcatttcttt tctattgctg tgaaagacac   11220
cacagccaga aagcaacttt ggaggcgaac ctttatttca gcttgaaggt tatagtttat   11280
catcaaagga agtcttggca gaaactgagc cagaggccat ggaggagtgc tacttgctgg   11340
cttacttcca gaatcacatt cagctacctt tctttcttac atgtcccaac ttcattgttc   11400
acagtagact aaactctttt acatcaatca tgaagcaaga aaaccactac atatacaccc   11460
acaggccaat ctcacaggta tcagttaagg ttctcccctt ctcagacata tctcaattca   11520
taacacgttg taagcacaac cagcacacta ttcaaacaga tttgcttagt gatggggaa    11580 gcaaaaggaa ctgtcttaga ctgatatgct tgcaatgttt tcaaatagct tcatctctgg   11640
actaaatttt gggtttttttt tttgtttgtt tatttcaaat gtttatattt ctttaatttt   11700
gtaatgtaaa tatgctgaga atagtatat agtatttgtt gaagagcttt aattcaatct    11760
ccttgaactt catatccaga tatcaatcac tttttataaa attatatttt cttttgccct    11820
aaatacgtga cctaggaatc agtataaata taataaaatg taagtataaa tgcaagcatt   11880
tatgtgtcaa tagtctttgg cctcttagtc aattcttct ttctttcttt tttgtttgtt    11940
ttcttcaaga cagggtttct cagtatagcc ctggctgtcc tggaactcac tctgtagacc   12000
aggctggcct tgaactcaga tatctgcctg cctctgcctc ccaagtgctg ggattaaagg   12060
catgtgccac caaagcccac tttcttagtt agttcttgtg gctgcttaaa catggtttca   12120
tcgctagttg gaaataactt acttgccaga gtaagattaa tggagagttt gtataatttt   12180
tcttcttttt cgccaattag tatcactctg gaaacatatg cagatctgct tattaactgg   12240
gcaaatttca attgggcaga catattttat tatatatatt ggtttcacct aagaaaagca   12300
cagcaatgtg aatactctct tttttctttt gtttgtttgt ttcctgatat atattgcata   12360
agctaagtgg gtcacccatc atcacaacac ttgtttgtat gctttaggtt gctatatgct   12420
ttaaaaaact ctgggaccag aatggttggt catgtcctaa tggatgaaac accttttcac   12480
ataaagagtg ggtgacttag atagatacct gagcaaaaat tttacatgga caattgcttt   12540
ggcaaaaaaa ttatggaaag tgcaggatca ttatcaacag tttataaaat ggtaaaacat   12600
gtttcttgga catatgtcaa cattctgagg atgtatattt tataatcatc aaggaaagat   12660
tgtcttttaa tataaaattt tagtcaaatt taaaaatttg tttgtgagga agactgatac   12720
catattgagt ttaattttc tatcatcatt gatctaattt ttttcaacta acagtaaaaa   12780
tgaaccattc tatatgtatt gtatgaagtc tgttcatttg tcacagaaac tcatgttgat   12840
ttcccatctg tctttagtgt tattttaact acttaaataa tctctataca taagaccaca   12900
gcacaagata attaaggagc tagaatgctc attcacttaa ttattgccca acacacttac   12960
agagctccat tttacatttg aaaaatttgt caaattgttt tactctctct ctctctcttt   13020
atatatatat atatatataa aaggtgtgtg taatagtatg tgtgtagtat atgtatgtgt   13080
gcaaatgtgt tttaatatgt atagtctatc actctctatt ttcagtatca ttaaaaattt   13140
tatgctattt ctttgcttga gaagaaactg cacatttgag taaataagt tggattttt     13200 ctttggataa ttcattgtg tgaagatgtt taaataagtg ttttttttcat atgcacatat    13260 taaagatcat ctgtgaaaca tctatatttg ttatgaatta aaaagacaaa tatttagaaa   13320
gccatatttc tatagtctag gctttgacaa gtaaagtgag aatccatagc tctgttcttt   13380
ccatcttgag catgacacac acacagtctc tttgtaaatt actcaggctt tcttattctg   13440
```

```
atataaatac aaacacaaaa taacttgtat tttgatgaga aaactgaagt ggaacttaaa    13500
tataaatgga cttgaagatg ctatatttag aagctaaagt attactttgc ccctaatttc    13560
attttctaat ttgtttaatc acttgttcca tatttgatat ggaataacaa gctttcacaa    13620
tactgatgat gcattttata taatgttgta ggcaatcgtt tcaatgctac tccatacttt    13680
caaattgtct aaacaggtaa aaagtattag aatctctgag cgcctgctgg acatgctcct    13740
tttattgact ttctgttatt tatttccttg aaaggcataa taaccaaatc aatactgtca    13800
gaaaaatata aatcctcttg gtatgctatt ttatccactt attttccct  ctgaaaataa    13860 atattactga aaaatatatc tgtcttatta atctgcccag ttttgctcac aaagatatt    13920 ataagttgga tttcataact tttctatctg gttggaaata ttttacatcc tatagtaaga    13980
taaagctatt gatggcagtc acagacatct caggtatctt gtgaatgaac taagaaatga    14040
ttcaaggctg caaataagac ctgaccaaat taaagaaat  gcttcctagt tcaccctaaa    14100
catcagttta cataaaaatc tccactcatc gtactaaaga gacagtttag taattaagag    14160
ctcaaattgc tcttgagatc tgagttcagt tttgagcacc tacatcagga ggctcaaaca    14220
tcctgtatct cctgcttcag gtgaccttat acctctaggc tccttgagca ctggattcat    14280
atttatacac actaaagtaa acattaaaaa catgcagtca tttttaagaa tgcactcagt    14340
tgaattattt ctaagaacac tcttatttct gtcattacac aatacacata aaatacctgc    14400 cctatttttac agagattaga gaggtgaggt gctagctcta actcactgct agttcatagc    14460
agcacacagg tccatctagc ctctgagttg tatgtggaca ccctgtctca gatttatgtc    14520
ctgctttctg gagttgagtg catttctggg gttcatcagt atgatctttt tcctcatttt    14580
gaaataaata aatttcttat attccaaaat atcaaatgta ttttctattt ggttttatag    14640
tctttaagtc ttgaaatcat ggacatcttc attttcatag gactacagca atggttgtga    14700
tgtttagaaa gacatccaac tgaattattc acatatgcca tgctattttc ctgtggccaa    14760
agttaacacc tgttcttcat tgttgttcat taccctctga gcgtgtggaa taatagaata    14820
aactgcacaa gaggtcaaat taaagatttt cttcagacac tacattccct cttcattgat    14880
tcttttttct ttttaaattt agtgtcccat tattgttctg tctcaagttt aaatctttga    14940
aaatgaaata tgattatcat cttaaagcca tatattggca gcttctctgc tgcatatccc    15000
atataagatt gtaagataca tatatgcaga tttcagcagc acatgtctca tgtaattaca    15060
gaagatgaag gagggacagg cagatactaa gaagcacata atactaagca tattatgtct    15120
gtactcagtt aagcccatta aatcaacgct ttccacccctt ttaatcactt tgcgaccatc    15180
agcttccttc tcaccatgac atttcactct gctttctttg taatagtgta ctgttaaact    15240
caggacaaac ctcaaaactc acttgtctca tgggaaatca aagagagtgc aggtcaagta    15300
tatatttgcc tagaacatta atctacagca taattacgtg attaagctca gttaaatcaa    15360
tgctattagc atggcaaaat attagatttc actcgtggga gagcacctgc acacatcact    15420
cacatgtccc attaagttgc tctgccttac actacaggct ttgagtttaa actttaagtt    15480
ttaaagtgat tttcagaaca aggctttgat actaatggag gtgcgggaca gaaaggagaa    15540
aacaacagga atgtccagtt cctctctttc ttacagaggg ctgcagctcc attataaatg    15600
cagagacaag aacccacagg ttgatcttag aaaccgtcag catagtttga aaagctgctt    15660
actgtgctca gagtgctttg aagtgtgtat agaataaagc agaaatataa taataaatca    15720
aaatggtgaa aattattttta caattttatt gtagtctttt tgtaatctgt gcatgtgtgt    15780
gcgtgcatgt gtgtgttcat gcatatgtgc aagcatgaat gtgtgtgtgt gtgtgtgtgt    15840
```

```
gtgcatagaa agaatttccc aacaccaaag aacgctgata cagatactcc aaatataact   15900
gatatgtgtc ttcatgtgta cctcagctcc cgatttttcca tgttcatatt cacatttgag   15960
ggcgatttgt aacacagctg ggtcctacct tgttactttc catccctgct ctgggagact   16020
tcacagactg gtttacagtg atagaggatt gtgccttctg gaaaagccta ctggattatc   16080
tcatatctga ctctgatgtg atctgagtcc aatgcactct cagagctcca gtttccctgt   16140
ctagaaaagt gacacaaaac taaacttatc cccttgtgat gattaaacgg ttcagcacct   16200
ctgttctttg ccagacataa agcacagtgc acagatgtgg agttatggag ccattgtagg   16260
aagcacaact atcccagtga gtccttcgtt gctcggcagt tgggccttaa agtatctgac   16320
attttatttc tcttttaact gaaatcccaa ggcttaagag gagatccctg tgaatttata   16380
aatatgtcat atcgggaaat atattaggta gttgtcactg cagtctatcc aactaactga   16440
attttatggg tcactgtgaa aatgcattat tggcagtaat aaaagaagaa aagaaactaa   16500
taaactagtg atttatgcaa cagcataggt gaactaacac atcatgctga ctggtataaa   16560
caaaggccat atactccatg gatatgtaca gaatcaaata gaattataaa catagttcaa   16620
agggatgaaa catttccttt tatcttttga gatttcactc aggtcagata actggccaga   16680
ctgtgtgact gaagataata gaaaccagac agtgctgatg ttaggagcaa caccctgacc   16740
agtaccgctt agttttgcat gcaatgagtg ttctagatat tgaaatagtc tctctttaaa   16800
atggtatgct atcacttgga cttttttcaaa atctgcagac acaaaatcag agcagttcac   16860
tctataaact ataattcaat gtagaatatc atttgatgcc atcctgggta tttcagtcat   16920
tctcacattt attaatgtgt gctagaatgt tcccagatgg aaaaacatga aaagcttaaa   16980
tctctagaag gagagaagtc gatagtgaca gagtagccat gctgaaggca cagaatgatg   17040
cttgtggaag ctggtgatat ttatgtagga atcttagtct cacaactgta aatatgttta   17100
aatgttttac attctaaaat tttagaggag aggtgtcatc tcaattcact ttctcttcta   17160
taatagaaaa aaaaaaaacc tggctaaata gaacataact tggtaaagtt ctgagaggca   17220
gaaaaccaac gcccagacgc aaccaaaaca ggcctggcaa acattatcc cgaggaaacg   17280 tttgtgtcct ctcatctggc tttagactat tgacaaatag accccaagaa attggaagtc   17340
ctccaggaat ttgctgaggg aaggaaaagg ctgaagcctt gtgtcaatta cagggtgagc   17400
atgtctccca ggaagaaata tcagatatca gatacttagt cagacctcct tgcagaagag   17460
actggagcgg agacagagac agtagctgga agcacacttt gacctactgc ttagtcatac   17520
atacatcctg acctctatct aaacaagatg aacttggggc actaaacctc tgttcctctt   17580
cttaacgtgg ccacattgaa ttactcccat ttctagtatt tcactattta tatgtcactt   17640
tacctggctg gttgaggaca ggtgtcctaa cttggcagga tggggatgct agagcccagg   17700
atctaaccct atctactgca gaggtgccac cttttccttt aatttcaagt aaacatggta   17760
tgtgccacta gtgtgtagga aggttgattt ttaaagggaa taagaattga aggcgttgct   17820
taaacagtta atttctgtca cattacttgt actctgcatt tgtggtttta tctgcctcct   17880
tcctttatag catgccaaac aagctgcttg tcccttgttt caaatgcttt tttagacttc   17940 aatttatttat tttatttatt tatttatttat tttattttttc aggattcaga agtcaactga   18000
cttcaaggat cagagaaagc attccctcct acgaccccc cccccttttta atacagtaaa   18060 cgcttgattt agcttccagt gcccaacaca agttcagaat acaagaaagg aaaagcaagg   18120
cactctgctg ggggagggagc ttggcactca aatccactct gctataaaac agtggtattc   18180
tgctcatctc agagagaagt gggaacgtgt taagtaacac agaaattgtc tcaaagcctg   18240
```

```
tgcatctatc tgcgcgtgtg cttggattgg aagaagagtc tgttcgctgg agctccacgc   18300
agccagaagt cggaaaggta agaggtgtgc aaaatctgcc attaagtagg gactaaggaa   18360
gaaactgcct gtgatggtcc cagagggtga atcccacagc cgctaccttc ctatcctgta   18420
actctatagt aagccacttt ctcaagtgca aaaaagcctt gaggcagctg gttttcgacg   18480 gttggggggat atttattcct tgctccacag atggggaaaa aaaaatcagc gtctggcagc   18540
cgctgattgg tggaaaagaa aatggtgata gtggagtggg aatgaggatt tgctgagcct   18600 cccctgctt cttcgacctg taactcttcc ttagtcggct cccctttgca cccagaaccc   18660
ttttagactc ctccggggta aaacaaatg gaaatcttaa gctgtgtgaa caaaagcaac    18720
cccaagggtg tgtgctccct ctccattgcc tggctccgca cacagaccat ttcaggcggt   18780
ccagctctct ggtgtggcat ctgggctcgt cctggaggag ggggtcgcct agaggaactg   18840
ggaacagact gaggcaggga aggaggggggg tggggcagga gaggcgccag ctcaagttca   18900
gccacgataa aactgagggc cctctgaact cgagggggagg ctcaggccgt cctctcttcc   18960
ttccatccgg gggaatgtgc tccagatacc cacagccctc acgcaccgca cctccaacca   19020
acccgtcccc tccctaggaa gaggagcgaa ggcacgaggc aggcgagggg cggggagagg   19080
cgctgacaaa tcagctgcgg gggcgacgtg aaggagccag ggagccagag cgcccggcag   19140
caggcagcag acggcaggag accagcaggt gttccccctg cccctgcctg cccttgcctc   19200
tttcattgaa attagattgg ggaaaacagg aagaatcgga gttcttcaga agcctaggga   19260
gccggtaagt acctgtagat gggggcagctc tggggatctt agctagccgg agcaaagagc   19320
cgggacgcct agagaagacc aactacagct gctttggcgg tggggactgg gccagtgcgt   19380
ggaaagtaca tcactcggct ttccttttcgc tggagacatg cccttccatc ctgtcaaagc   19440
ccgagggaaa ggccaggttg cctgtggcat ctgcttttttc aagcggaaac gctagggtgt   19500
ttcatgttga gtgctggatg gtggaagctt agtgctgggc attgggtgga attttgagcat   19560 ccaactttca tgctccaacc ccaggcattt cagcttcttt ctgtagagga agaagggtgc   19620 cttttggccca tgattaatag aagtgcagag gacagtaggc aacaggtgat aaagggttaa   19680
tgagcatggg gtgcagggtc ttctagagga ttccagctga ggacagagct tcttggttgg   19740
gtggtgctca agtgagactg ctcaagtgta tggacagcgc ctgctctggg cagatagcag   19800
gcaaagagct agtggtgggc agaaggtctt gcaagattag aaaggctggg cttcaagcag   19860
ttccctactt ctagattaaa cagttcccct cccttccttc tccaaagact gactcctctc   19920
tgggtctttt atcctcttgc ccccactcca tctctgtacg cccacctccc atgttccttt   19980
tctagatagt cttttttactt tgaatgtaac ctttgggccc tgggaacttg atggggtaga   20040
ggatgcccac ctccccttct gcaactcttc ttctgaaata tgtatgtaag agcagtcgaa   20100
tgatcaaact agatccatcc catccttaag tgacatgact ttttcctagt attgagtgac   20160
ataactcaac aatcaatcaa cactgtgccc agcacccccca catccccccca cccaagaaat   20220 cacacttaca ccaggacttg ggggaaggca tactgatttt tcccccctcaa tttccttctt   20280 ttctctagct gttttaaacc ttattattat tattttttta cccaaatttt ctaattcaaa   20340
atgtattctg tattctctag tgtggagcaa aaatacatct ttagccatgg atgtgttcat   20400
gaaaggactt tcaaaggcca aggagggagt tgtggctgct gctgagaaaa ccaagcaggg   20460
tgtggcagag gcagctggaa agacaaaaga gggagtcctc tatgtaggta ggtagtgaca   20520
ctgtgactaa tgaattgggg tggctggtgt gtggtgtctg attcgtgtgc atcacagctt   20580
ctcagaagag tgacagctgt gtggaggtga gagaatatga acctgcatat tagctctcag   20640
```

```
aaacaaacag ggacaatgtt ttctgtcctt agattcatta atcttgttat ttatgtaggt   20700
tttttatttg gttttctgtt tctgtgtatg aatacactga attttaaaaa ttggcaaccc   20760
atgaaaaata accaagaata tgcttatgaa tcaaagacat gtatggcagt aagcctggtg   20820
gcatttggga agtggaggcc caaggaccag gagttgatgg tcatcttcag ctacacagag   20880
aatttgatgc cagcctgaac tatgtgagaa cacacacaca cacacacaca cacacacaca   20940
cacactcaca ctctctctct ctctctctct ctctctctct ctctctctct cacacacaca   21000
cacactcaca cacacacaca atacacacac acacactctc tcttacacac acacatacac   21060
acatacacac atacacacac acacatacac acacacacac actcacacac acacacaaag   21120
aaataaagaa ataaaggaag gaaggaagga aggaagaaag aaagaaagaa agagaaagaa   21180
agaaagaaag aaagaaagaa agaaagaaag aaagaaagaa agaaagtgag ccacaagtac   21240
tcatgggact ttgatttctt tcatcatcac tataggtaat acctgctaag tttaataaat   21300
tataaagctt taacaatag ttttgcataa ttttatttta caactgtgaa aatacaactc   21360 ctttgacccct caaatagaag aaagaaagca agtcttcttt ggtggatctc cttttaggga   21420
tcacttggtc agtgggaaca gcgggactta aggaacttca gaaatgtttg tttagttcac   21480
ctgtcagaga tcatacatgc tgaacagtaa gaggttgata tttagtgcca ttttctgcct   21540
gactgtacac attgaaagga aggccaacac tcccttctc tgtctttccc tgtgttaaat   21600
tggctgtaac tttacaaatc ccttctagta cttcatgga aggaatagac acccatgcac   21660
acatgcttat ccccagcaga gacacaggtg cacatgggag cacagttgca gggttcatct   21720
acctctcttt cctcctgtga acactgtttc caccttctta ggagggcatc tctcttggtg   21780
gaagactcag ggtaaacatt caggctgaaa aggagcagaa caggtggcaa aagtgatgca   21840
gatgctaccc agagtaccaa tcggggggaag ccatgctgac cctccaaacg atcagtgagg   21900
aattgatact tgtaaacatt ttcatgaatg tgtcttttca ttgaagtttc tagcagatca   21960
cctttcctaa ttcttcacag aataatttta cattgaatta attctctttt tctacttaaa   22020
acatcctttc agaaagtctt gtaatgagta ttgtaagaga agggtgtcaa tgagctaatt   22080
ttagagtgtt ttttttttaa tgaattgtga agtataatgt tttagataga attcagaata   22140
taaaagcagt aatttgtaga tttggggaaa aactcaattc ttccacaact acaggcttgt   22200
gactgatttt ttttttttt acttcagttg cttaagaaac atatctgtag atcactaatt   22260
taaagcaaat ttagaagttg ttgaatatta atttagtata ttactctttc tggataataa   22320
atggattttg tcaagcagaa cacttctttg tttttattgt taattttgag tttgggcaaa   22380
taaagtgatt atattttca aagattaatt ttgttggtct ctgtgaggcc attatattga   22440
aagtgtaatt ttaatatgtc taatattatt aaaattatca atgtctgtta ttatatttaa   22500
aacatgttta attaatcaat tgcttattat gttctggaat ctaattaaaa gctgaacaca   22560
tgcatagagt ttgggatgaa gagtaatgtg tgaagataag aatgatagct cagatatttg   22620
tcaacttctg ttaatgttcc aacacatatt agaaaatctg tcatagataa tcagctgtac   22680
tgttggctat actgattatt gcttagataa tcaactgtgc tgttaaagta tgaaaacaac   22740
cataggcaaa aaacagtgtg actctgcctc tgtctttatt gactcagaga ctatagaaa   22800 atgaaaggaa tgtagactct ggacttgact tgatacagac agaaatttaa ttcaagccac   22860
atgatttctg cctttagcat ctgcaggagg taacttgata tctttgagtc tcctcccctt   22920
tttcacatac acatagttca taaaaatgca actgctttgt aaagttacta aagttatgta   22980
gttaaggtag taactgagtg cactttcata tttaggaaac ttgaatcttg tcagagaagt   23040
```

```
tgttcaatct atctgttact cagtcaacct aatttcttac ttttatcca agatatgaaa   23100 ctattattaa tacctaacct gaaggattag aaataatctg gactttggac atagctcccg   23160
tggcacagtg cttgtctgcc agcatgcagc cctgggttct attcccgtac cagaaaaaca   23220
aaagattaaa aataaaaggt tagaagtaat caaagaaaaa caatgtaaac ttcagcactt   23280
atggctgaaa aggcttggca gaagtctcat ctcatctcta ataacaaatg ccttggacaa   23340
ctgcctttca atgaattgaa gacctgccat actaatcagt gtgctgattg tctctgtgat   23400
atttgcacaa aaaattcaat taacatattt tagcttcata atcaacagtc tcaatggcgt   23460
gatgtataat tataaattga atttaaagtc aaaaagtttt cttcacttca tgttagtttt   23520
attaatacta taaagaaaat caccttcaag ttctgtttca ctgcctggtg aagagctgtg   23580
gtcacacatc taactcctaa gtctcacatg tgagacttaa ctacatgttg ctaagtagtc   23640
agcatataaa ccaatgatat gactcatttc tcacattcct cttaggtccg tatccttgta   23700
atattccaaa taaacaagac agggtgtggt ggaaggcagg gtacatttct aggctcagag   23760
aagccattat tatattgttc cccagcttcc atatcttact tcttatttgc tacttgatga   23820 ctaattttt tttgctatat cttatcagtt agatctcacc tgtaaactga agataaacta   23880
tcatttataa cttagctgat aattaggata acaaggtgaa gaggtatggt ttgagataca   23940
gggccttcaa gactcatttg tctttcatta aagaggcatt ccatgatttt accaaacgtc   24000
aaattctctg ttactgctga ggcaaagaag acagacaaga gaccagccag tgagcattag   24060
ttttccttgg tcatgctttt tttttaattg ggtatttat gtatttacat tttaaacgtt   24120 atccctatt ctattctaaa ccccttccct ggcttctatg agaatgctcc cctgccaccc   24180
atatactttc acctcacggc cctggcattc ccctacacta gcgaatccag ccttcacagg   24240
tccaagggct cttcttctat tgatgccaga caatgccatc tctactaca tatgcagctg   24300 gagctatggg ttcctctatg tgtactttt ggttggtggt ttatgggagc tctgagggt   24360 cttgttgatt gatattccta tggggtttca aaatggttgg cttccagcat ccgaatctgt   24420
attgatcagg ctctagccga gcctctcagg agacagctgt atcaggctcc tttcagcaag   24480
cagttcttgg tattagcagt agtgtctggg tttggtgtct gcaaataaaa tgaagccttt   24540
ccttcagtct ctgctccact ctttgtccct gtgtctcctc tagacaggag ctcttaaagc   24600
ttgttgtagt gaagatgata cagaagagtt gagttctctc acgcaagctg ttctactact   24660
tgtgcagggt gccctgccca ccaccatttc cagttgtgat gtgaatagca cctgtctcat   24720
aaagcacaac ttaaacacct gtgattgcag tgcataaatt aatagtaatt attcgaggta   24780
caaactttac tgctagcact tcaccctaaa aattatcgca aaaataatga agcccaatg   24840 taattggtga ctacattaaa ctacttcttt cagaatttgt ccatgagctg ccactttcca   24900
tctgttacaa gatttgcaca aaaagcagca cctgtgggtg tgctgtcttt tgtaacctgc   24960
taataaatcc gtgtgatatt tttacagaca cacatctcag aaagggaaa ctgaccagct   25020 gaggtgaagt cacatcaagg caataaagtg caaaatcctg ggagcaattt gtttatagaa   25080
aaataacagc tgaatattca gattgcagaa atgtaaattg aatatttaat aattttggaa   25140
atagcaattg gttcataccc gggttagtgt atatcaactt gaaagaaagt agagctagca   25200
tatgtggtct ctagtgtagt cctagatagt atgtacacac ttcagggtca ggaggtaaat   25260
gtacaagctt acactgagga ttgtgacata tcagaagcca ttgtctcaga ggaagtaatg   25320
ccttcttaac cccatgctaa aagaactatc agagtcagat cgcggcatga agagttgtgg   25380
tggtttgaat aggaatgcca cccagagtct catgaacctg gtaccagcca gtggtactgt   25440
```

```
ttgggaagga atatgcagtg tagccttggt agccgaggta tgtcacaggg agaggcagtg    25500
aaggtttaat agccacccat cattcccagt gtactcttgg tcccctgctt ttggatcaat    25560
atgcaagctc tccattgttc ctgctgccct tcccttccta ctccactgtg gattctaaca    25620
cacccaatgt tttaggacat gaaaaagata cccacaccgt aaaggcatat gcaatgagaa    25680
gaaggcaagc tttgttgaaa ctacttaata agcacattgt ttttgcaaaa attaaaaatt    25740
ctaaactaca aaatataaaa taaatattag ctttaacatt ttatcatttc caacatact     25800 tgtgtttaat aatttgactc atagccccct caccatccac tgcttataca gtttcccat     25860 tcattgttag gttctgtaca ctgatcagct cagcttgtcc tcacagctct acagtccctt    25920
gcaaaatgag cagtgcctat gaaatgcatg cagacagcac ccatgcagaa cacatatccg    25980
ttcctgctaa caagtgtgcc tttctctctg cgctgcttct agtgcggtga tctttcctgt    26040
gctttcagct tcagcttctc cttcagaggc atttgtatgg gtaagaacaa gagtttgcac    26100
catgtctgta tcatgcattc aacagtactg agggctttac ttcaacgatt tccttttatt    26160
cttttgccaa gatcatgatg cagatttcgt taacctttag tgaagtgaag agttaaatct    26220
ggactctgta tcggggtggg ggtgggtggt tctttatttt caaaataaaa gttcctacat    26280 atgcttttt aattaatgag ggtttaattg actcctttct aaaatattat tttaaataaa    26340
atagacaaaa attctcttaa ggctatatgt atatatcttc aaaactattt actaaataat    26400
ttaacatact tttgtacatg tacttaggtt atcttattga tcatattatt cagcttgtag    26460
aaatgcacat ctgaattta agcaatttg gaattagaaa ttacctcata gttagtgttt    26520
gtcaacttga caggaagtag agatatgtgg gaagaggaca taacatttga ggaaatgtct    26580
acctctgatt tacccatagt aatgtttgtg aggatatttt cctgattgac aactgatgga    26640
ggagcaccca gcccactgtg ggtggcacca cccctaggca ggtattttg agtgttataa    26700 gaaagcaggc tgagcaagat atggagagca aaccagtgag cagcattttc ccgaggtctc    26760
cacatcagag cctgcctcca ggttcctgcc atgcttggag tttctacttt tggttccctc    26820
gataatgaac ttccaaactg gaagctgaga atctcctttt tccacacttt gtgtttggtc    26880
acagtgttca tcaccaaaca gaagactttg attggcaagt tagttatgta cagggaatgt    26940
ttactctaaa tgttggtatc tgtactttat gactgagcag ttggcttcta ggaagctatg    27000
tatatgatat agttttgta ctagtttttt ttcctcttct tgttttctgt ccatgtagca    27060
agacattttt tttcttctca aatagtgcat ttttaaaatc cactatttta agtttaaa     27120 attccccccc ccccacatgc tggcctaagt cttttcagc ttatatgtcc tcatgtcctt    27180
tttatccttt gcattcttct gtgtctagat aagattattt tagttaatgt tcctctctcc    27240
atctctttag tcctttcttc cttggtttct tggtaatatt ggggatcaaa tttaggtcct    27300
taaacatcag aaaacagtgc tgcactaaga actatgtctt tatccctata ggatagcttt    27360
cacttaaaaa tgtgtatttt tatatgtatg tatatataat atgcatgtat attgtatata    27420
tatacagata tataaaaatt ttatgcatgc agataaaatt atcagtattg attgtacaaa    27480
gtgagaggcc tcattatgat gtgtgggtct cccccttcctt ggaggtaatt ggcaactggc    27540
ctaataggct gaggggagca gaggcggttc aggcttcaga ctaccataag tatgatggat    27600
tgacttctgg gatcagcttt agtgagacat aacaacttag acagtgctag ggatttctgg    27660
gtgggtgtag attattggct aggttcgagg tgctgaggat gtgtcattta aagaaagagg    27720
aattccagga attattggga gagaggttgt tgaatctgta atctggccat tgacaacatg    27780
attgtcttta taggtgaggg acatagaggc ctgatgccac agcaagtaga ctaagaatag    27840
```

```
ggagagagtg atcctaactc ctgcctgtct aaggatgaga tttgtcagca tcttgatccc   27900
gtctcactct tgctccaggc tagctctgct ggctgcacat tctcacaatg atcttcccac   27960
agatgcattt aatatacaag gttatagcca cccttctatt actagttttt tattattatt   28020
tgtagagata atgcttttta tatttttatt tgctttgtta ttcctgcgct ttcatttttg   28080
ttgtgtatac tcattgttca tggttccatt ccataaggac attttttatat aagtatatag  28140 aacacgattt ttcacaattc atgaatgtat tttgatcata actcctctcc tttattcttt   28200
ctcccccttg ctcttcctct ccacttcttt agtaaagccc agctgctttt gcgtactttt   28260
tatcactcta tgcatatctg ggagaaaaaa tgatgctatg ttttctctg tgagctgggt    28320 catttcattg aacatgatga tctgactttt tccctacaca tatcataatt tccttctttt   28380
ttatttccga ctacaagtca attatgaaac ccagtgtgtg gagaattctt aaaaagtaag   28440
aaataaaatt tccagccatg ccacttctgt gcaaccacca gagccaccat acaagaatga   28500
tgtactgcat accatgcata tttgactatt caaccataga gtgttatgga agcaacccag   28560
atactcacca gtggatgact ggaagaagag actctggtat aaatcaaaac cagagttttt   28620
caaatgaacc ttaaatctcc aaactattta atcaaatggt ggtcattata ctgaaatttt   28680
aagcattaga aagattattt ttaaaatgat taacaaactt acttttaata atatgtgcaa   28740
tagctatttc tttgtttagt aatggctcaa ggcataggtg aaattcttat cttacataca   28800
gtcctagttt gaaagtaaca tgctgttact taataattat gcaaatcact taattatgat   28860
ttttagtttc cttatgtatg aaatgggtat tgaatggctg catcagagat gatgtgaggt   28920
caatctgtac caggggttgg gcagacgctg atatcttctt cctctcccct ttttgttgt    28980 ggattgtgca gtctctgctc tgttgtgctt ttacagcatt tcaggtctg cacagagaat    29040 cttactatgc ctgtgttatc ttcccttttcc ttctctctgt aaattgatga agaaagcatc  29100 aagcaaggt tatgtaaaga gtcgttatgt tttgtgcatt gtgttttatg ttttatctga    29160
taaataaagg cacaaaactt ttaccagtgt tgcctctggt gcagttccca tccatgttca   29220
cattgtgtgg tcaagctaca catatctgtt gcctctaaca tatgtcagat ctttatgata   29280
ttaaccactg aagcttgtag ccttttgaga tccacagtgc ccagttgctg tctattatct   29340
cccaggtgga acagcacagg agcttcatac tgctgactaa ctcaactggc tacccactaa   29400
accctctcca ggcttccctc ctgaactcaa cctggatagg ctggtggtag cttttcctctg  29460 gggtggtggc cagatccccc ccactttagt gatttctgag tgtgattggt ggttgttagt   29520
cttctgaagt tatctttgta cattcccttc tgaatattga gaattttaa ttggctgctg    29580 taaattgaag gacagtttaa tatttatgcg ttcaatttct ttgttcttta ggttccaaaa   29640
ctaaggaagg agtggttcat ggagtgacaa caggtaagct ctgttgtctt ttatccaggg   29700
gtgatatgcc gaatgccttc taggctaaat taacttgatg cttatacttc aagatataag   29760
tgtaagagcc attgtctaca gaggaacatg ggtcaattta ttttttatg tatctaattt     29820 ttaattttgg tatggtgaga tggagtttag ctacacaagc cagaacagct tctgcttcaa   29880
tcttctaaga actgggagta caggtatcac caatggacct tgcatattgg ctttgtttaa   29940
agtttaatgt ttatgcaatg aaatatttt aagtagacaa atatggatta aaaatgtata    30000
gcccaatatt ctaatggcta agaatgacgg atttagattt gtcaatggta tttaattcta   30060
ataatttggt atttgggtag taggctaaat aaataaaata taatgatgct attattaatt   30120
taaatatttg atgtaaacat ttcttttagta tttagtattt ataccatcag ttatactgat   30180
tagatatttc ctctgtgatt aacaatcctt tttagaaaat atacttagta gtgtgttatt   30240
```

```
tttaaaaagc tgtatatttt tattttattt gtatccactt gtcatatctt caaaaagatt    30300
ttcaataaga ctaaaataat aaatattgaa ctaatatgac taaaattata atgatcaaaa    30360
atgacaaaga caatgaattt actgtgggag gaaaagcaac aggagaacaa taagaaggga    30420
aaaaccaaag agaaaatgat aaacataacc aagctgccaa agcttggtgg tagctaaagt    30480
tccttatgtc catttgccat gcatcagact accttaagtg ggaaaagacc tgtcaggaat    30540
gaacttgata tgatcaggaa ccttggccat gacaccacac aacaaagcaa atgcactgca    30600
taagatagca tcacacagtg gcaacctgtg tcttccagtg gctctttccc aagaatcatt    30660
tgctggccat ggaggaaaag aactcattct ttttagcaca ctgataaaga ataatgatgc    30720
taaagcaaca ctgaagccca ggaacaagac ccttttggaa gttcacaatg gtgaggactt    30780
ctttcagttg ctgtcccaca aaagtgcag atagcaagag agtaagcaga ctgattggtt     30840
cctggaagct gaaacttagg cttgactctc ataagacaga taagacaggt acagagtgct    30900
ggaggcccac atccagagcc acgatgttcc agcttccata gttgagggag aaggaactgg    30960
tgagattcag agtctattgt ggatgcattg ttctctattg acaactttgg aaatttttaa    31020
tattccctga atgacaagga tataaagcat gagttttttat actgtgtgga aaagagagtg    31080
ggggctggag gagcaagaga ggtcagaggg gtgtggaaag tttctgcagt aggcaacatt    31140 ttagaaaatat ttctagaaa ataattgtca gcaagcttgc atttccatag ttttataatg    31200
ttgacaattt acatgccttt tatatatcct tttagtctat taaggaactt gaaatgctcc    31260
acagtaggta aagacacatt atataatata acccaggatt cttgaatatt tactactgaa    31320
agttcccttc catatttaac tgtatcaaat ctagtgttaa caaaacacta aagagacac     31380 gttttgtt gtttgttttt tgttttgttt ttgttttgc ttttgggac agggtttctc       31440 tgtatagccc tggctgtcct ggaactcact ttgtagacca ggttggcctc aagctcagaa    31500
atctgtcttt gcctcccaag tgttgggatt aaaggcatgc acctcccggc tataagagac    31560
actgttaagc agcaaggaca cagtggtgtg gttgtggcac cttgtaccac cattctacca    31620
gtttagaaac ctgacagtaa tatataatat caaatatact gtcacaatta gtcagactat    31680
gaagaaatgc attgtcaaga aaggccacag taagtgctat ctctccccat cacatataaa    31740
taaattgcgt aatttattga gtagtatttg tgctgctcaa aagttaagaa tttaggaaca    31800
ttttgaattc tggactttca aagaagtgcc actacatatg tttgaaatgt tacttagaag    31860
ggataataga agtgactttg ggaagtgagg tcacagagct agctggcttt gatactgaaa    31920
ttgtatagca atgctcagac ttgacactgc acctggctgc aatgttttgt gtccactcac    31980
ctcaatgcaa accaaatcca attcacttgt tgctatgtgt tataattaaa ctcccaatat    32040
tttctaattt ctgcactaaa ttcatattca gtgtttggct gaaacatgtc tcttctacct    32100
tgctgtcttg tttcttcaga ctcctgttac ctatgatata tgtgtctata aagttgaca    32160 gctgctagaa gtggaattat taaagtctct gtcacaccat catcttttac tctgttgtca    32220
ctcttgattt tcttaagtgg ctgagaagac caaagagcaa gtgacaaatg ttggaggagc    32280
agtggtgact ggtgtgacag cagtcgctca gaagacagtg gagggagctg ggaatatagc    32340
tgctgccact ggctttgtca agaaggacca gatgggcaag gtatggctgc ctgttttatg    32400
ctcagtaata acctggaca ccatgtcctt gcatgcatca tagagcatgc acatgatgca    32460
cactgtgggg aacactgcct ttaaagggct cttattttga tgcactgatg tccttgggaa    32520
atgtcatgca cacaataacc ctgattgttt tagtttctgg aagaaagata tagaactaaa    32580
aaaacgtagt aaacactaag agaccagtga catttcagaa agaataaccg ctttcatgta    32640
```

```
aatggtaggt ctggaattcc tctttatagc aatagcaagc attttcatga gtaattttta    32700
cactgaactt agccaaaagg ttgagaagca atcatgagta atttctaaat tttcagaaag    32760
aagatctttc atttgattta tttggaatga catcatctct tattaaatga catatttgca    32820
tatcatgtaa caactcattt ccaaatatga ttttgccaac tgggagactt aaagttcata    32880
ccaaacacag atcatggttt catatggtga ttcttacatt ttcagaattt taaatttgct    32940
tctggataaa tatgaggctg cagtgacata ttctaggtat aattttccta tcaaatgtta    33000
aaggaacaga aaatgaggac ccctggaaga tgacgtttca caaacctcat gatcttacag    33060
taggatgagt tttgcatttt tatgtcacat gtacttttat acttttttg agagattcca    33120 gcttcccccc aaaaaagccc atctcagttt ctcttgctct gggtctttgt aaatgacat    33180 cttccttgca atgcctaatt tatttaaagt tggaaccatt ctcacccatg aaaccataa    33240 cctttctatt ctaatttctt cttgtttgat aaagtgtcat tgcatttaaa ataaattaaa    33300
taatctactt gttttgagta tgttattttt ctttgtctat gtaggcacta tcataatgta    33360
aatatttatt ttgcttgttg atacttcatg tgtctaggca agttcctaac tacaaattca    33420
gtaatgaata agagcttatt aaggatcgaa agaatggata aatgacaatt ttctaaggat    33480
taataatcat atacatggtg taaaaccttt ggctattgac tgatccaaaa gttgtaatca    33540
aatgggttct gaagtagaca tcctgaaaca caaagaaag atactttcac ctgtgggcag    33600
actactatgg gtcttctcta tttcactcat cctaggtggc agaacaaacc atggatagtg    33660
gattgggaaa ctgaggatgt acatttcata gacagttcta ttgttaggga aattaaatgt    33720
aacccaagat aatctaggaa gtgttcagag aagtgctcag ctgatgtcaa catggactga    33780
tcaattcagc tctgctctga gtgcaatatg ctttttgtggt aacgtcattt ttgtggtaat    33840
aactatatca atgcctattt tccatttgac attgtaatca tatgttttatc tttatcatac    33900 ttaaaatttt aagagacttc agattagtat caaggagtct agaattacag gttctttgac    33960
aatctagtga aaacaaggga acctcttgtc agaaaaacac atgatcacac atatacaaca    34020
aagcaccaaa ggaaggccat caacagaccc tcaatttaaa accaactcct gatgaggaat    34080
gtggaatttg tagaggggaa gtgagtgtca agttcctgca gtgactggag ttacccgatg    34140
accctcacac acatctatct gagttggcaa gatgtgaagt gttttaataa accgtttgtg    34200
acttataatg catgttttaa gtgcagacaa agtgacatca cttgcccagc tgtgtcacca    34260
atacataccT tcctttgtct actgattgaa ttgtgcaata ctagagttag tggaaaacct    34320
tagtgctttg gaatgtataa aggctgggaa gcatgtctca ttccatttcc cactttgtct    34380
gcacctaaaa catgcattat aagtcacaaa cggtttatta aaacacttca catcttgcca    34440
actcagactt attttctacc ttttataata acaatccata ttttagtatt ctaaagcgga    34500
aatctaccag tgttacaaaa tgaaacattt gcagatattt ctcctagagg aattaactct    34560
gggctcctaa aatttctaa tataaaaatg aaaccataaa cagaaattgc agtaaaaaaa    34620
attgggataa aaccctgttg gtttggggtt agatggttga tcttcatagt atactggtca    34680
tttggtagct atgaaagctt gtgctaagcg cccaagacct atccttatgt aatggggagc    34740
tctgagtttt gctaccttac caaaaagctg gtaaagccca atttagaaat gaattctgaa    34800
tatctacaat aactcaagga atacacaaat aaatgccagt aattgtggcc atattacttg    34860
attcaaaaca tatccacagt ttaaataaaa ttggatttat ttctaaagaa atttgaaata    34920
ttttatttca tctttcagat tctaattaaa attatcttgg tgaaagaaa caagcatata    34980 tttgttaaat tttttaattg attgttagtg accccaattg gcccatttgt aacaaataat    35040
```

```
gattgtgtct cgtgtgtgag aaacttggaa gaacagggat ttgaccaata gctctcatat   35100
actaataaaa ggctaataga agggattagt cacactatct tggtggttgg gtctcaagga   35160
ctagcttttt ttttttttgt aaagttttat tcatttattt tatgtatatg agtacagcat   35220
tgctttcttc agacacacca gaagagggcg tcagacccca ttatagatgg ttgtgagcca   35280
ccatgtggtt gctcagaatt gaacgcagga tctctggaag agcagtcagt gcccttaact   35340
gctgagccat ctctccagtc ctgttccag  ctttaataag acaattaatt atatttatgt   35400
tatttatctt tatctatttt tctgaataac taactatgtc tgcctagcac tgagaaggag   35460
ttcaatgatg attaattata tctatctttt attatttatt ttaatttaaa ataacaataa   35520
aatttaaaat gattactcta caaaaaagta gaatatgtca taacacatgt taacagtaga   35580
atgttatatt aagtatacat acaaccacaa actgttatag caatcaaggt aattaacata   35640
atcaatgact tcaatgactg tggtggcagt caggtattat taactgcaag aactgtgtca   35700
catgttaagt ttcaagggca ttccctccct cccagttcct taccccctgat aacttatgag   35760 caacatcttg ccatttcttc caccttctag cccctggtag ccacaaatct aacctgtttc   35820
tatggacttg atgttttctt agaatatatt ctacatagat gagagatacc aaagtatata   35880
gctttgttcc tctggtttac tttgcattgt ataatgtcct caaggcttat ccatgctgtg   35940
gcaaatgtaa ggatttccct gtctgtatag accttttgaa ggcttaataa tattgcattt   36000
gtacacatat gcacacatct ttacccattt agctgctaat tactctttgg catgtttgca   36060
catcttaact attctgcggg tttctttctt tatatctacc aattcgagtt tcagactata   36120
tggtagctgt gattttagtg tttgaggact tgcactcagt cttagtagtg actcagttat   36180 attttagca gaggtgctaa agcttccctg tcctctacac cctcaattct tgccgtgggt   36240
tgtccttttg atgaccagtc taatggcgat aggtgataat agatcattgt ggctttgaat   36300 tgttttact tacgggttag tgaagaattg ttttcataca gcccttggct atttgtatgt   36360
cttctgtgat aagtgtcttt ccagccaatt agttcagtgt gtgtgcatgt gtgtgtgtgt   36420 tgttttggt gtgtttatat gtgatatgtg tctgttgtgt gtctgtggta tgtagagtat   36480
atgtgtatgt gcatttatg  tgtagtttgc atgtgtatat gtatgtaaca tgtgcatgtg   36540
agtttgtgtg tgttatgcaa attcacttgt ctgaacaggc atgtatagag tccatagatt   36600
gacattggga tattttttca gtcatttgtt tcaggatcca tttcctagtg ttgaatttac   36660
aggtgtgcac tgtcacgtgg cttttcacgt ggatcttggg gatccaaatc aaggacatgt   36720
gtttacacag caagcatgtt actcagagag ccaactctaa agcttctttc gtcgattttt   36780
ttctcttaac caaaatagat ttttttatac agaatattct gaatatagtt tccctcctcc   36840
aactcctccc agtctccccc catctcccct ctcatttgta tccataccct ttctgtgtct   36900
cttagaaaac aaacaggtat ctaagggata ataataaaat tagataaaac gaaaacaaac   36960
agaagaaaag cagtgaaaga aaagcacaa  agaacacaaa tgaatgcaga gacatacgtt   37020
tacacacaca ggaatcccat attaaccaca agaatggaag cggtgataca tgcataaaga   37080
cctgtaagtt aaatacagtg ctctgacaaa atattagaag agaagaacc  tccaaagatg   37140 ccactgacgt aattttctct ttggcatcta ctgctgggca tgcagcccat ggcttgttac   37200
tccagtgagt cttgcttgga gaaaccaagt ttttatttgc aagtggttat ggattggagc   37260
aagcttctag tgagggctga aggcatgtgt ccacttctcc tttcatctct aggactccat   37320
ctggtgcagc tgtgcaggct ctgtgcatgc tgcctcaggc tgtgtgagtt cctctgtggc   37380
catgtttaga ggccttgttt ccctggtgtc ttccattccc tttggctctg atactatttt   37440
```

```
tcacttactt tcttttttgtt gagcactgaa caaatacata gtttgcaaat tgtttctcct    37500
ctttacaggt tactcctgta tcttgatagt agtctaattt acagtggaga agctgtcagt    37560
ctgatgcagc ttctatgtat tcccactcta gccagtagat tttgagtttt accaccaccc    37620
ccaaatattg ttcagaccaa tgttgataca ttttcctttg cactttatta taatagtttt    37680
caagtgttga atgttgtgtt tgagcttttg gctgttcagt tttcccagca atgtctattg    37740
atgatgtcct agagctgctt tccccattgt gtgattttga cacttttgac atagcttgcc    37800
tgctgttgag tctgtgggtc tacagttctc tgttccagtg cacacattat gccagtacaa    37860
tgctgttttg gttactcaag tcttgttacg gatttttaaa tctggcattc tgatgcctcc    37920
aggttgaatc tgaaattttg atattattgc ttgtttctta aggtggcttg gatatttaaa    37980
gtcctctgat ttgactcttg tgggtttagg gtttttgact atgtctgtaa aatgtttcat    38040
tttagtttgg ggaagaggca catcccatct ctaagtcatt ttggcgacgt tggtaattct    38100
tcagatccat gaatacaggt tttcttttcca tttacctctg tctcacttttt taaaaaatca    38160 atgttttata attttttagtt atttaggctt taaaacctac gttcgattta tttctatgta    38220 cttttttattg acactcttaa tgctcttgac actatttaag tggaattact ggtttctttc    38280
ttagttagat atctgtgtaa aactgattct taattttgcc tattgacttc atatcttgaa    38340
actactttat ttattaattc tatttggtgt aatatttaga ttcttttacat gtacatatca    38400 attttaccat ataaaacata tgtatatatt attactgtac tataaacaat caggcataaa    38460
cacttaatga tataaaacat ggaagatttt agaagtgact cagtacttgg tagatctgat    38520
ctacaatgtg ctatgtgtaa aagcttatca gttgttacaa actcattcag ttgattgtta    38580
cagtggaaac tgactaatat gagttgacag aaatataagc tagtagtggt tttatgtaca    38640
gcatataaaa ctagtccccca ttttcacaga gagaacgatc tgcttgtacc aagaatgttg    38700
aacttaggaa gttactggcc tccatgctgt tgagtaatgg cacagtgttt acaatgcaaa    38760
gctagtcact gagcatctgt ctgggacatc tggcctgtct gtctgcttaa tggtgttctg    38820
tttgggccta ctatttaaac caaccattgc taaataaatg gacatctttt tagttccatc    38880
tagagtgctc tgaaaagttg tagctaaata tttaaaaaat gttttgaaaa tgagtgaagg    38940
actgagtcaa ttgtggagtg tgctgccttg catatatgac attgctctgc ctcttatcct    39000
gtgcttttag gtatcaatct attcacatga taactcatag ttttcacaca ggtaagcttg    39060
aagcaccaaa gatcaggagt gttaattatt tttctccaga gtcagaagaa agtgctgaag    39120
cattgataat cgtgaaacat tcatcattag attataaata atttttttaaa tttatctgtc    39180 tggtcaactt tattttttttt tggattgcat tttattttat ttagttatttt ttttacactc    39240 cagattttat tccccccacc ctgtccaccc tccgactgtt ccatatccca tacctctact    39300
ttacccactt gtcttcacaa ggatgtcccc cgccctcacc caaccagacc tctaaattcc    39360
ctgaataaaa ataatgtttg aaaaccttaa tttcaagaca gaataaaaca catgcagtct    39420
ataatcattt cttgattgat aagaagagag ctaaccaaat gcagaaagaa cagtgtcatg    39480
tttggcatgg tctttaatga tcatgacatt cttctccctg cttcctgttg gcacgattga    39540
tgagcgcagt gttgtgcaca ttaagtccta aacactgaaa ctgactttga tcagatgata    39600
tatgctgcct ctaggtgagt gatttgatca caatctcaca aagaatccac aggtcatagg    39660
caacattttg catttctcta aggaaataca tatattacag gtggaatcaa aggtgaggat    39720
tagtgaaaca ttttcccttta ttttaagatg ttttccttca gtgtttaata atgaccaatg    39780
caataagttg tgtgaaagca ttagaactcc aagttctgtc tgttcagtcg aagatagtca    39840
```

```
ggacagtatt caaacctaaa tgaaagcttt gtgatacagt gagtgatctg ctctgttgtg    39900
gtagtggagt ctgtgagcag cattggaatc ttaaagtatg ataatacccc tcaaaggaat    39960
aaacacaatg ggcttacttg atctgtttca aaatcagtga tgttccatat catcagtagc    40020 attttttgcaa tgtgatccat ctaagatagt attttttcact aaaaggagaa catgctaatt    40080
gtgtacatta tccttgctta gaaacaacag gggaatgcca gggccaagaa gtgggagtag    40140
gtgggtgggg gagcatgtgg gggactttg ggatagcatt ggaaatgtaa atgaaataaa    40200
tacccaatta aaaaaaaga aacacacatg ttgagtggtt gtattgtaca taaatgtttc    40260
actgctctta tatgtatgga gaggaattgt gaatcttagt gatttctaat cagggaaatt    40320
tctaaaagga aaagaattct gtaattgtaa ggaaaaatag ccttactgga cttttgtttg    40380
ttgtaattcc aaagcactga gtcatttgct aatatgtgat tggtatccag atggatcagc    40440
aagaaatgca tgaatcatga atgcatgttc cctgtgttat gtatgtagac cactgagggc    40500
aacagacatt atccctagtg aaaaacagtg agtatagtat gtatattccc taagcttata    40560
tctattatag aaagagttaa gtggcttttg ttagaaatga aagagaattt gtattattcg    40620
aaataaatac taactctgat gagtgttaac ctgggttttt gtgaatagca aatgaagtag    40680
cttcagacaa ataataacca taatatttca cctgcttgac acaagaacac aaactttttc    40740
cactcaagtt ctatgttcag tggtttataa tctgtcagca tgaaaccttc agcaacatag    40800
acatgaataa aaatgtttaa aggccagact atggatgatg ctctttacaa aagaaattgt    40860
aaggccagca tggtagtatg actttaagca taccagtgga caaatacaag ctatactatg    40920
caaatctgtt tattttctca caagtgctgg cagaggttaa tattctaaca agtgctaata    40980
cagtttcatg aattgatttt taaattttt attggttatt ttatttattt acatttcaca    41040
tgttatcccc cttcctggtt tccctgcata aaacctctac tccatttcct ttccccatta    41100
cttatatgag ggtgtccccc ccccactccc accttactcc actatcattc tcctacactg    41160
gggcattgat ccttctcagg accaagggcc tcccctacca ttgatgccag acatggccat    41220
cctctgctac atatgaagct ggagccaagg gtccctccat gtgtactctt ggattggttg    41280
tttaatcctt ggaaactctg ggggatctgg ttggtggatt tgttgttcta attggtctta    41340
gttgtataca tgtgaacatt tattgctact gtcctttcac ataaaaccat tgtataatat    41400
tttatagggt ttcatttgag ctgctactat tatgtttaag atgatttcaa acttacatga    41460
ttttatggaa tttatttatt aaagggatta aaatgatac atatgcgcgc gcgcacacac    41520
acacacacac ataccacatt tctacaatcg aacaagttaa catgcctgct atctcacaga    41580
gtacttctct tgtttttta gtaacagaag ctaaagtta ctcttttgga aaattgcttg    41640
catacactct atattaggta ttgtctttac attcctgagc tcgccagact tgctcacaca    41700
gttgactgta ttcttttta tatctttgca catctaactt gtattttac tttgtaatga    41760 aatggcaaac tcttcatatg gaggcagaat ctgattataa tgtgcttatg tgacagtcac    41820
tagtcttatc ccaaattcaa agagtaagaa ataatttgat tagttccttt tttggatgta    41880
ggctttgact agaaacatag cttgtattgc tacttatcaa aataaaatga cagaaaatgt    41940
cctatagttt tccaaatatt cacaatacac aacaattcag gacataagtc aattactgat    42000
atttccctcg acaatttcag gaataggaat aaataagacc agttgtgttt gcattgggaa    42060
tatatgatta tgaaagtggg aattagatgc tatcatgaat ctgattattc tattaggtga    42120
aaatgaatta tcaattccta tataaggtaa ttgctcccata agaaactta ttaaaatttc    42180 taattacact ttaattttta ggtatacttt aagaatccac cctactccct ggtgtagtgg    42240
```

```
aattattaaa catatttgta atattttcat ggtagtattt aatttccttt agagctataa    42300
tacatagtaa aacaaacagt gtagtctgaa atgagtgaat agataatgat gaaataagtg    42360
aaaaatgcga aaaattatgt acatttcaat ttccttttta aaaaatttt attaggtatt     42420 ttcctcattt acatttccaa tgttatccca aaagtccccc atacccaccc ccctactccc    42480
ctacccaccc actccccctt tttggccctg gcatttccct gtactgaggc atataaagtt    42540
tgcaagacca atgggcctct cttccaatg atggctgact aggccatctt ctgatacata     42600
tgcagctaga gacaagagct ctggggtact gattagttca taatgttgtt ccacctatag    42660
ggttgcagtt ccctttagct ccttggttac tttctctagc tcctccttcc tttctgcctc    42720
atctttcatt cgtattttct tattcaaaca ataggactaa tttgtttgga actcagttca    42780
acaaatgaat acagttgcag gtctgtgtat gcaaggagta aaatgaaatt tacattttaa    42840
ctacacttgt gaggggatgt gtttgaaaat tcacatctct atttgattat gggtgtcca    42900 cacacacaaa tgagaaacaa tttaaatatg ttatatgatt tcctgtcatg caaccttatg    42960
gagtgcgtac tcagcttagc ttggacactt taagctttgt tcagtaattg tatgttatct    43020
gataagtctc tgggggtagg catgtgcttc ctacttatgc tacctagctt ggaattaatc    43080
tatctgttat acaaagtcta aaatttacta gaatatttca tctttaatct aattttataa    43140
caaatgtaag gcagatacct ttcaaaatat ctctgctcaa actaacagaa ttgcttatag    43200
tagcaatcat ctgtccatgg aggacagcca ctgtaagatt gacagagagg tagttcttac    43260
atgttctgtt agagctactt catacctgct actcaatcca ctttgatagc ctgatctta    43320 tccccagggt ctggtttata tgccctattt gctcaagcat atagaaagtg tggctgggta    43380
agagggcagc tctgtacttc atggagtgtg gcattatctc tttccacatg ctgtatgagg    43440
tcaccacact gctttgagca ctgacatttt tatccatgaa atagaattgc tgaatgaaat    43500
gagctcaaaa tgttttgtat ctcgattcag tggcttgaaa tttaggacag ttgttttca    43560 attatgcact gccagacccc tggcaactca tttaaccttt ctgaagaagc gtttatcctc    43620
tgtaattggc cagccaactg cagagttgga atgagaagga aatgtagcag caaaggcaaa    43680
caatcaaatg gactgtggca taattgtgat attttctat aaagaatctg atgtttctat     43740
ttatatcttt ggtttagaca tgtgattatt gagatgactt ttttttttt tggtgtggtt     43800 tggctttatt aagtggttta acaccaaaag gaatacactt gagagagggg atctctttat    43860
tgggcttaat aaattgagtc acattctttg tcttagtttt ttttttcca tgttgatctg     43920 attaaaatcc tctgacttaa gcaacttgaa gtagaacagt tttctttcac acacagatca    43980
tggatacagt acatcatggc agggaagcag aggcagcaga acatgaagc gtcaagtcac     44040 ttacaaaaaa aaaaaccta gtcaagtaca gagagtgacg attgctagca attcagtcat    44100
ggcctttttt atatataatt caagatccta gtctaggaca tggtgttact cacagtggac    44160
tggttttccc aattcagtta tctaatcaac ataacctctc acaggcattc ccagaggcta    44220
atctcctagg tgatcctaga ttccatcaaa tttacaattg aagttagcaa taacacctct    44280
gttacattga attaaatttc tcaaaaccaa ttttattaaa ggtttatta aatgttatct     44340 tcatgtttta attagaaagc atcctgttca aaggattttg agaacactgg tataaacaaa    44400
gttttaaaat ttatctttta aattgaaaat gccaagtact tagcattata ttgcaagggc    44460
ataattatct ttcttagtgt ctcttcacac cagatgcata gagaataatt ctaagtactc    44520
atggagcaca tatacaagat ggcctgagta atgaccgttc tcactctgtt ttccttgtct    44580
tagtaatagt cttttagat cccagataaa aggacactca gaacaagtga atgatctctc     44640
```

```
agcatttcat atcacaatct attttttgga gacactttt aaaacattct tgaaagaagg    44700
acaaagacat aattcctgtg ttccatgtaa ggttttccat caaatcatgg aaaagattct    44760
gatagcctag atgatgagag tccagctaga ccagctatga aattctcctt gctctcttct    44820
ctctttgtgg tgagccagcc tacacttcct ttcaacacct aatttggacc cagataacct    44880
aggaatctgc cattgcagtg ttgaatctca tgaactgagg ttagtgtggg aagggcacaa    44940
tgctctctgc tgatgctcac atgttgagca tgtctgtgtc acaggttaaa aatgcagtga    45000
tagaagcatc cctgagtaca cacggtacac tggcggaaaa gcactgcaag tatgcctctc    45060
cactcagtgt attttgtgtc taagagttta acagctctag atttacatat aaggttattt    45120
atcaaagcat tggtaatgat acatttctta aatgctggaa acttggcaat agccactagg    45180
ctaaatacat gatggcttat cccctgtaat aattatttca acagaaaggt acagaagagc    45240
aatgggtgac ataataggtt gttcttgctg cattaagtga aaatatgagg ttatagaaca    45300
tattaaagtt tgtaaacact tttgttatta aaaacaaaca tgtcatgtga tgtctgtgtg    45360
tatttctaag cagtcttttc atttaattac aattagaaat taaggtaca acattttatt     45420
ttacttgttt gtccaaatcc caactttaat tgatttataa ataaatttta cctatgtagg    45480
acattaatgc agttattaat atgactgtga ccattgctgt ttattcattt acttagccac    45540
acatatatgt gttggcctac ctaattcata ctatgtgttc tactttgcac caagtattat    45600
aactgtaggg atgtagaagg ttgatttcca ggacccagtt cattgacatc aatcatcttg    45660
tctcctccta gtatgaaata agacttgttt tgttttcttt gttttgtttt gttttgtttt    45720
ttcgaagcag ggtttctctg tgtagccctg gctgtcctgg aactcactct gtagaccagg    45780
ctggcctcaa actcagcaat ccacctgcct ctgccttcca agtgttggga ttaaagatgt    45840
gtgccaccac tgcctggcga aatcagattt cttttgtgaa gttctgaagc ttttaatcat    45900
taaaaattcc aacctggaat agttctttta tatattatta ttattgataa taattatcaa    45960
atcaatatga aataccattt cagcaattct ctttcttgtt ggcttatgat aattgcatgg    46020
cttatccaaa taccgaaaca cacttgaaca aaaaatttct aagagcaaag aattgtatta    46080
cctgagtggt taatttaatg gctcatgtat atttgacaag aatttctgat cttctgagcc    46140
ctgataatta actggctttg ctgattctta tctttggact ctgagagaga gctatcctca    46200
tagtcagtat atgctagggt aacaaaacac atgcaattga gtaattcttg aaaacagaa    46260
tttacttatc acattgtaaa gctgggaact cagagatcta gacgagtttt gtgtcctgga    46320
gaatctcatc tttgttctga gatgacatct tgttactgtg tcctggagga gagcatttc    46380
aaggtgaata gaactgaagg ggtaaaactg tccccttgta cagcacaaac cccacatggt    46440
accattacct gtaaagagcc ctacctcaca attgggacat tagtgacgac atttcaagta    46500
atgggttttg gggatattca ggtcataata gctattatct ttattttcat gtaccattag    46560
aatgttagct tcttcttttt attaatatca ttcacagtag ggagaaatcc ctgtattaaa    46620
taccattccc tgtgtgcttg ttatccactt tggtaagaca cagaaagcca caaagcaca    46680
ctctggaact ttgctttcgt catttcactc ccagtagtta gacacatcca tagtgtatgg    46740
gtttatttta caactgaaca ggaatctcac atgtcatgtg ggagtttttt taactataca    46800
tgcttgtatt tgaaagcaac atttaactgt gcattttcct ttggaaataa caccttccaa    46860
aacaattttc cccagctcaa atcgaaacat acacaatgtt tcctgtagta attagaatat    46920
aagcaagaaa atgaaactct gaggtaggca cagaaaggt ttcatgttcc ttctgccttt     46980
attgccttta actagtcata caggatgcca gtaaaaaaaa aaaagtaaat tccttgaaaa    47040
```

-continued

```
ggaatacttt agtttactta atgacaagga tgagagagac agagacagaa agagaacaca    47100
tatacacaca actctctagc tctctctctc tctctctccc tctctctctc tctctctctc    47160
tctcacacac acacacacac acacacacac acacacacac acacactcag aggatgtgta    47220
ttaaggacta caaatgagat tgtgctgctg tgatgaatgg gacagtgtga ttttatcact    47280
ggactctgca gttcagtgga accctgtagg tcctgctgaa accctaggct gcttaaattc    47340
ttcagcaatg atactttcat tgtacaaaga gacatgtcaa aacacatttg cttttgtgat    47400
tctgagtatt cacttctgaa attaatcaat gttccacaag gaaaactgtg atttccttta    47460
tttatagctt gtaataatct agctagatat ttctcatttg gaggcatatc ttcaattta    47520
acaaatcatt gtattacaaa agcatattca aaattcccaa gaaatttacc ctactgcact    47580
gtttgttctg gttgaaaaca ctgtaggtag gtgtcttagt cagtgttcta ttactgtgaa    47640
gagtcattat gaccatggca agtgttataa tgaaactctt aaaactgggg cttacttaca    47700
gattcagagg cttagtccag tgtcgttatg gcagggtcca tggcagcatg cagatagcca    47760
tggtgatgga aaatagctga gagttctgta tccaggtctg cagccagtag gaagagagaa    47820
agccactgga cctcgcttgg gttactaaaa cttcaaagct ctctactagt aacacttcct    47880
ccaataatgc cacacctcct aattctgtta agtagtgtca cttcctgatg agtaaatatt    47940
caaatataaa tatctataga gctattctta ttcaaaacat agttagcaat ttctctttgg    48000
tgggagagaa tcaactgata cgctatagca caaccatgtt caatgctgtt acctgtatgt    48060
ccaaggcata ttttgtgtgc acttattcct tcattcaaaa cacacctgtg gtatctggag    48120
gccagtgaga attatgtgag caagatgttt gagagacaca gtctttcacg tctgtacttg    48180
cttgaccctc atctaagtga cgttgttaga gaagtccaaa gctggcgttg tagcattctg    48240
ctgccacagg tcatcatcca caccttatcc tactctattg ggataattac ttggaattaa    48300
aaccaatcta atttgtaggg gaattggtta tgcaaataat cagcttagat ttttctggat    48360
ttattcacag tatttaatgt gtaattattt ctgccctcac ttttacatgt tctttaccca    48420
gcattttaac caaacctaag acaggctgca tgtgcacatg ggcaggtttt ttttgtgttt    48480
tgttttttgt ttttgttttt ttttctgca atcagaacca ttttttcttg gaaaattaat    48540
ttcaaaatac attcagtcag aaaaaaaagt gcttataatg tttgtctggt gtttcacaag    48600
agctgccctc atgtcctact gcttacatat ctatagtttc catataaagt ttcattttct    48660
acgggctttt catgttagtt cctctaagtt ttctctcaat ttgaaatttg ttttcctcaa    48720
tttctttcct atgtgtttct ttttggataa ttgaaagaag atgcacaatt tcttaattct    48780
tatatttgaa ataattgaaa tgtgttttaa aagtcatcac tgttactata acacagtttt    48840
ccacaagagt tctatctttg gttttgtgc atttcagtgt gcctggctga tgttcagtgt    48900
cctaggatgc gctgaaatgc tatggcatca tttcatccag ttatatttca catgagctgg    48960
tagagataat cctttagtcg ggacctattg atgcctagat ttttaacagt gtcatacttt    49020
acctgtctta gcatgttgtc ctaagataca agaatgatta agatgtattc ttagatccag    49080
gataatgagc atagcatctc catggaatac ctctttctct tattttctgt tgaattccca    49140
tactaaattc aaaaattaac cgaaaggtag agtttcctca gtctgtctta acacacgaca    49200
ttctgtgcag tgctggtttc tcctgtccac agtggaatca tctcaaactt cttaactctt    49260
gggcagccat gaagatgaag gctaagacac taaatcttcc acaaatttat cttgctcttc    49320
tgtctactct cactttttact ggcagtggca aatagaattg aggttgttaa gagtctgttg    49380
ttacttattt aatagaagga aaaagtaaaa cagtattatt gctacagagc cttgatcaaa    49440
```

```
accaagactc aaggaagtac aaatccttgt acttccagta agagcatctg gcaaagagac    49500
ccaagatttt ggcaccatcc atatgctatg tgataatgta tgcatatggt gtggttttaa    49560
gaaattagaa ttctaaaata gtttgtatag tcaggctatg taatgtcgct ttctctagtg    49620
tcctgcagaa agtgagagtg ctctcattag gtacctggtc aggaacaaat tgcttcattc    49680
ttcagttatt taataatgga aacttaaaaa aacaaaaacc caaaacatg ttttagaggt     49740 gtggtgataa atgtcctagt gcctgccata taagagctta gagattatag acttggtatt    49800
ctttcgaggg ctagatattt taatgctta tcctgacatt tatcaaattg cacttcggtt     49860
ggtgagtgtc acattaccct gacaaattat taacattata agaaaggac tgtcaccaat     49920 gagtcaatat aatttttata gtgttttata aatttcatat tttgtataac ttaaggtgca    49980
tgggatattt attaatttct atttgttgtc aacactaatg ctacataaaa tgtaatgtaa    50040 tttattttg caaatacatt ttaaagtctg taaaaggac ccaaatatac tccaaatctc      50100
ataaatggta agtgaccctg aaagacaacc tactgagatt tagtgacttg aaagtccatg    50160
tttgcatgac tcatcagaag tactgtacct caaagaattt catcttaagt catagaagtc    50220
tcatgaatat agtcatatgt atcgcaacat gcggcctttt actcaaaaat cctaacagtt    50280
aacaaatcta tatcctatga aatatttaaa ccagtagaaa atgggtagtg aaagatttat    50340
atcttgtcta cgtagaagtc aaattttaaa agtcacccat taaaaatctt agtttagcct    50400
ggcgtggctg tgcacacctc taatcccatag cactcgggag gcagaggcag gtggatttct    50460
gagttcgagg ccagcctggt cttcagagtg agttccagga cagccagggc tatacagaga    50520
aaccttgtct caaacaaac aaacaaacca aaaaaaaaaa aaagaaaac aaaacaaaaa      50580 tcttagttta actactttga tattccctgt atttaacatt ttgcctatca gtagtatcta    50640
ttcatttctt tagtgcttga ttggaacagc aaagaaagtc tatatgacag ctagccacct    50700
gaaaagctca ctatataact gctggatgac caaatctata tcagagaggg gtggttagga    50760
agagaaaccc aagcattgca tctgtataca cagagcatgt tttgtcattt tggaatacag    50820
tttggatgtt tcttttcgtg tttgtttgtt tgtttgtttt tacaaagcta actctgtata    50880
tgatccaaga gtcaaaatca ttggtatttg cttgcttgag ttgaatacct atgtttacat    50940
gtgaacctgc aaataattgg taccagcttt atctgcagtc caccaaacat ggaagaagtc    51000
aagaactttt ttaataagga aacacaatgc atccattttg tggaatttta ttcagtgatg    51060
attaaaattt gagccatgat agcacaaagg cacatggagg aaattaaaat atatatgcca    51120
aatgaaataa gacactcttt agactatgaa ccaaggatgt gatgatatat aaaaatgtga    51180
tcgttttgga atgccaaaat tctgaggaca gtaagaaagc aaagcaatag ttgcagggc     51240 ctctggagag gtggaagact gtgtggtcaa acaacaggat gggagtgggg tacaactagg    51300
cagggaagtt attatgacag catggttttc tatggtaggc atttgctgac tcatataaaa    51360
caaggaggtg ccaactgtga tcttcagtga tgttatctca attctcatta acaataggaa    51420
ctttcaagtt cgtaactcag taaggcaaga taataacgtg ggattgtaac atctggaaat    51480
cctctttatt gctgtgtgat tattctgccc aaagtgtcta taaaacaat gtatcagaag     51540 ggtgtaaaca catgaaactc aagaagaaca agaccaaag tgtggacact tgcccctta     51600 aaattgggaa caaaacaacc atggaaggag ttacagagac aaagtttgga gctgaggcaa    51660
aaggatggac catctagaga ctgccatacc cggggatcca tcccataatc agcctccaaa    51720
cactgtcgcc attacataca ctagcaagat tttgctgaaa ggaccctgat atagctgtct    51780
cttgtgagac tatgccgggg cctagcaaac acagaagtga atgctcacag tcagctattg    51840
```

```
gatggatcac agggccccca atggaggagc tagagaaagt acccaaggag ctaaagggtc    51900 tgcaaccota taggtggaac agcaatatga actaaccagt accccacaga gttcatgtct    51960
ctagctgcat atgtatcaga agatctagtc ggccatcatt ggaaagagag gcccattggt    52020
cttgcaaact ttatatgcct cagtacaggg gaacaccagg gccaagaagt gggagtggct    52080 gggtagggg gtggaggtga gggtatgggg gacttttggg atagcattgg aaatgtaaat    52140
gaggaaaaca cctaataaaa taaaagggtg taaactcttg agtatcgaaa tttccagagt    52200
gctcagagcc tcatttgtac cctttaccat cctatctcat gctgttggat tcattgtggt    52260
aagagtataa atgtaaatat gtaggtttaa aatgtatggg aaaatatttg tatatcaaaa    52320
ataatctcat tactacacag gctggacgta ggcctcctgc acatatgtag cagaaatgca    52380
gtttaatctt catatgggtc cctaactatt agagtcaggg ctaccccaaa agctgatgcc    52440
tgtaagtgga atatgttctt ctagctgggc tgtcttgtct ggcttcagtg ggagaggaag    52500
cacctagcca tgaaaagact tgagtgccag ggtgaggagg acatccaacc actcagagga    52560
gaaggggtgg gggaggcttg gacaagtgtt gtgggagggg attgcagtga gcaggataca    52620
aaagtgaaca agtaaataaa taaatacaac tgtaattttg ttactacagc gttcctcaaa    52680
taaagaggag cagaacatgt caaatgagta ccttaaccac ggaagactgg tgggcatcag    52740
ctacatctgt agctggagcc tgagagaagt gtttactctg atagctccac acaaaactga    52800
agcactggga agagattttt gtcttctccc ttcagacttc atgtaacctg gatgcattca    52860
ataagtattt gttgtggcat tgttgagtag tcccttata ggcactgtaa aggtttctta    52920
gtgacactga tggtttaata tcaggtttta atgtccagtc cctatatagt cttaattgct    52980
tgtcttgctt tggaggataa cacatcttcc tcaggctcag actgcatctt acttgcactt    53040
gcacttctac agtattgatc tcatttcaca ggcacctata atgcgtggac tcatgaaatg    53100
atcccataac taaaggagta gccagacata tatttctcct tgcttgtttg tttataacat    53160
tagacaggtg aatgctacag aaggtatttg ctgcccatgg cctcagggca tggcctcagg    53220
tcatgacctc agggtcgact gccttagggc acctctgggt gcccttgtag cagtgctgtt    53280
ttgcaaagcc catgatgagc cactccttat tataaacacg tatttcacat gagaatgata    53340
aggtgagttt ttaataatct ttctaattaa acaaataaag gtatgaaagg aactgaaatg    53400
tttagtgcat gattactaca aggctgtatg cactaacatc ccagtgtcta gggccaagat    53460
ggagagaact tagtaactat ctacaatttt tctttctct aaatattgcg atatatactt    53520
tctctgtatt tattataatc cccgtaagaa cagatggcct gcacagatta gacaacttca    53580
ttaagtgaca aattgtggag gttggtaata aaagaacctt acagcaacca gttaatcagg    53640
agaggtcatc ataaagagaa ggaagagagc tagggagagg gatggatttg gagaagggag    53700
gacaacagag aggtcatgag agcaggggaa gcaaatagca agccctgtgt gaaaatggcc    53760
ttctgactgg gcttgccatc tgtgaaatgc ctgcttaccc tgggcctggc aggtagtagc    53820
ctaggactgt ctggaaacag attgcctcac ctcatatgac cttccccatg ccctctttat    53880
ggtgcttcat ttggccaatg tcttataatt gtgtagacat gaagcagcat ttagacatag    53940
agtactttat gtaggacagg tttctccaaa gggactcttc gagtgcacct caatccatga    54000
gagagatgta tttcccaaca ttctctgcat agaagctaag gattctctgt ccaacctcta    54060
gtggtcagaa tacatcctat gattcagtca actgtttaga tgttaatagt gtaagtctca    54120
acaagcccca gtgcagtcca tatggttctt ctctgggcat ggcaggagta ggtggttgcc    54180
agtgtctgaa acataaaaca ggtgaaaaca gacctgcgga gagacagcag gaaaaataga    54240
```

```
agacagctcg caagtacatc tggtggtgtt tatgagattt attaaaattc aacaaggagt    54300
gcttaacatt tagcaaatga agtttgtctt taggaaaatc cttgtgggat ttatacaagg    54360
atctgttaat aaagggcaca tacaacactc ataatacagt cagacatgtt atgtaaaaca    54420
ggacaagaaa gtaataggat aacagagtgt ttgcacaagg gattttgtga tataacacat    54480
gattcttcag ccttcgctct gcactttttag aggctgggat ttgcatagtg atgcagccac    54540
acgagacagt aaccttgaca tttttgcagc tgtacatatt tgcacacacc aagacacata    54600
gtcttcctgt ctagttacta tttgattctt ttgttcatct cttatttatt accaaaagta    54660
gtgttcacaa aactgtttct cacaatttaa gcttttaaat catggtgtga attacagaca    54720
ttttatccaa gtttaccttt ttcagcagaa atgccatatg ttctcaaaac catttatcac    54780
tttatttaca attctagcta ggttgtttgc ttaatatttc ttagcataca ccacatatgt    54840
ttactttgat actccatttc tgcctcaaat ggtcaaaaag ttcaacttaa tcttttttcct    54900 caaataagca tttctacctt atccatcaat aacgttgcaa acagtatttt actgtgatcc    54960
ataacacaaa tcacagatgt atttgaggtt tgtaattctg cttctctctc caatataatg    55020
aacctaggtt ctgtctttac aactctgtct tccatcattt tcattcagaa ggtttggatg    55080
agactttgca tggagagtgt aggagaccat caacttgtct acctgcttgg cctttccttc    55140 cagtaactc ttagctgcct ttgtccctag ccacatcatt tcctgtgaac acagactttc    55200
ccaggtcctc atgataaggc agagtttctc ttaagcttct gcttttctcc atcttcattg    55260
tgtgcattgt gtgaccttct gtcatttgtt tattcacgca tttgaatgag ctaattattg    55320
aagatccaag atagtaccct ttctaacaca gtggctaata agtacttctt gttgatctct    55380
atagttttct gcctaaggca tttgtaattg ggttgatatt gctttctaac ctttagaact    55440
gagatgcagt tgtagcacac acttaactga tagataggtc aaataggttt ctacacacaa    55500
tctcaattgc gacataggtt aaataggctt ctggccacca cattacaaac tacaaagaaa    55560
cctacttaat ctatctacca atggttgtat gtggaatctg tgtaagagta tcaagaaatt    55620
ttatgttatt taaagacat gttttctatgt cttagacatc cagtcacactc tttatacccca    55680 caccctcacaa tttaacattt gacacatttg gagtctatca atgtatcaac tttatatgat    55740
gctgcaagat agtgtaacca tcttcttatg cctattgtca gcactgcaag gtaccctctc    55800
taaatccttt cattattaat cttcttcatt aatactttgg tatatgatga ttatgaaacc    55860
tttgcttggc tattcaaaaa aattaattaa gcaagtagga taaagttttc agaagcagaa    55920
gtctaaaaag aacaacagca attgaggact ggaagaggac tcttgttata caaatgtgag    55980
gaatttaact ctgaatcaca cgagctaatg tggactcagg tatagcactg tgtgtctgta    56040
ttcctaggtc tctctcatat gatggacata ccatctttgt tgtggctaga gaaatggctc    56100
agtcttcagc tccttgggta ctttctctag ctccttcttt gggggccct gtgatccatc    56160 caatagctga ctgtgagcat ccacttctgt gtttgccagg cactggaata acctcacaag    56220
agagagctat ttcagggccc tgtcagcaaa atcttgctgg catatgcaat agattctggg    56280
tttggtggtt gtatatggga tgtatccctg gatggggcag tctctggatg gttttttcctt    56340 ctgtcttagc tccaaacttt gtctctgtac ctcctttcgt gggtattttg ttccccatta    56400
taagaaggac caaaatatca acactttggt ctttcttctt cttgagtttc atgtgttttg    56460
caaattgtat cttgggtatt ttaagttttcc aggctaattt ccacttatca gtgagtgcat    56520
accatgtgtg ttcttttgtg actgggttac ctcactcagg atgatatcct ccagatacat    56580
ccatttgcct aagaatttca taaattcatt gttttttaatt gctgagtagt actccattgt    56640
```

```
gtaaatgtac cacatttttt gtatccattc ctctgttgag ggacatctgg gttctttcca   56700
gcttcaggct tttataaata aggctgctat gaacatagta gagcatgtgt ccttattata   56760
agttggaaca tctttgaaat gtaatgaaga aaatatctaa taaaaaagtt ttggcaggta   56820
aaagaaaaag gcttaattaa taattcaata atataccatg gtcttaaaac aaaacaaaac   56880
aaaacaaaac caacaaaaaa agaaacttag aaagatttcc tttcctaaag ttgggatata   56940
tcttttccct tttatccttt caagtcacag gagttgtagg agtcactcca agtatttgaa   57000
gacagagcaa aattacttgt ccagaggaca tcttcatctg tagattctgt ggccatatag   57060
cacagaaaaa agaaattcag tgatgggtat gtttataaag actgaggtga aagcaatctt   57120
gagaggatag tgtgttgcca ccttgtcaca tgtttgatac taagagcatg tcactgatcc   57180
aagtggtgac attctaaatc acagtggtgt ttattattaa ttctttctgt gaggaaacaa   57240
aaaagctacc agtggacatc aagttgccct cttcatattc agaggatggt gtgacttcct   57300
atcaatcaga gaccactgtt agaggaatca tgtccaccta atggccaggc tacttgatct   57360
ctatctcagc ttcattagca ggttttttc tctctctttt tgacatgtgg aactgtcata   57420
tgaaacagga atgaagtggt cacagcatta gaaggtatac agaccttgag taagagctgt   57480
gtgcttgagc attaaagtag tcctgactcc tgtcagaaga cattctagaa agtactggat   57540
tcaggcaggc tacagacatt gcctagcaac tatttttttgg ccagcttgta cttctgttaa   57600
caaatgatta tttcctgagg ccagaatttc gtcccttcga tagactatct ctgaactttt   57660 tgttttctt tgtttcatag ttcttgagta tcactctgtc ctctgaagtc acttcttccc   57720
tagcagcagg ccatcagcat tgagttcctc tccctgttca ttgccactaa gtaaagttat   57780
gatgaagaac ccgtgtatac tacccatcag gtgtacatgc acactgcttc actttctaaa   57840
agccagctcc cctctgcagt gacacctcct ttacaccatc actaagttct tcccccatac   57900
agggcctcag agcttcttgt aatatgaatt aggaaggctt aatactgca aggatattaa   57960 gttcaactag aggtggtaga gaaatgaggg tcttgagagt ggattttggg aatcatgagg   58020
ggcaaggaca cagcattaag tcttataata aatttaaaag gattatttg ggcttttctt   58080 gggaattaaa cacacccta ataaaaattc tcaggtgaaa aaagaaattt ttttcagatt   58140
aaagacttgg taagtacata ttagggagaa gcacatttct aacttaaaat tcatgctttc   58200
gtcatgttac attaggaaac acgattggtt tgtatatcct tatatctgtg ctttcagttg   58260
aaactaacag cattattgag ggaaacaaag aatttttttt cctttactgc tagcctatca   58320
aacctctcaa tgaaattta tgcatagtac agtaatcaag agattttgt caatatttaa   58380 tacaatggat agatgcagaa attattgaaa atccaaatta ttattttgtg aaccatggta   58440
ccgatgttca ggcctgcctt catgcatttg tgagaaattt tgacaagctg ttgtgagtgt   58500
tcaccaaagg gaacacactt ttggcaggac ccttgcattt cctacatgga cagaaagtgt   58560
ttactgtgaa acaactgttt ctcgatgtgt actgtcctct cctaatttaa gcataaacct   58620
cttttcttcc tgaatgtaga gttcagagaa aggatttgtg atgacccaaa gtcttgactt   58680
aaagagatat tttataaagc agtgctgtgg ctcataataa aaagctgtaa gatgctaaat   58740
gccaagcata cagaaataag acattgccag ccatctgact tttgcaactg gatgatttaa   58800
aagaacattt gttgatctca agttgtcctt agaccatcct agttctaaca agatccaaag   58860
tgaaatgtga atgtctgcgt ttggtttctg atagggatgt ttttttaaaa aatattttta   58920
ttaggtattt tcctcattta catttccaat gctatcccaa aagtccccca tactctcccc   58980
ccaactcccc tacccaccca ctcccacttt ttggccctgg tgaaaaactg attttcaaat   59040
```

```
cattctggca tgactttgaa agcatacctg ttcaacactt tttccttgtt cttctacctg   59100
cccttttgata tttctaacca cccccatatt ggtatgggga tatgaaaaca ttagtgcctg   59160
gtatctgaac aggcctgctg aacaggaaaa aatgaaatta agtcatgtaa aggtgagtgt   59220
ccagaagcca cagaagtagg aaaggaaaga aagaggtgtc tgaacagtgc tgaaagaagg   59280
tatggcttca gactgtctgt cacaccaaaa attaatggaa caaataataa gtagaataat   59340
tttaacattg tctggctttc atagtggtgt tgtggttggt attggctttc tgactgatga   59400
gaaattttat gttgtttgca tagactagtc ttctttccag gggatacatg ttgaaagggt   59460
tacgtcccat catctacctt gctacacaca caacacacac acacacagat agagagagac   59520
agagacagag agagacagag agaaacagag agacagagag agacagagag agagacagag   59580
agagagacag agagaaagag agagaggaag aggaggagag aggaagaagg agagagatgg   59640
agtgagggag gaagggcaag agagagaagg agagagaggg gaaagggaga gagtgtgtca   59700
atgaatagat aaatgaggta acatgtttat gattagagat tctgagcaat gtgggtataa   59760
tgctccttaa aaatattatt gaaactttc tgtgggtttg aattttgaat taagtaaaac   59820
ttaaattaca aaataagtat gattcactga atctcctata aaaaagatt aattataata   59880
aagacaaagt gggtgttttg gaaagtggga actttctaag caaagaaatt taggcagcca   59940
atttctctcc tgctactggg tactgcccta tccaagagtg tgtccatcat tctgtcctgt   60000
gcttgtagta gcgcatatca tttgtttttc cataccatga gctctgattc ataatctaag   60060
gaggctggaa aaatgtcctg ttgtgtacat gtcagacaga gaaggagaa cagatttttg   60120
gcagatcact agaaagccac aataagcccc ctatgaagca caatatgggg tctgatacca   60180
gaaccttcc tcaagaggag agctgatcat ctttcttttg tttgaaactg ggctaggaat   60240
ttaacaagaa gataccgttc tgtcagtgag atcacaaaag gtgaatgtgt gaaaaataat   60300
aatgcctatt caaaactagt acaatttaaa taaaatggaa cattctaaag tacaatttag   60360
caataaattg ctgtaggcag gctgaaactc atcattaaat acatcatgtc aaggagaaaa   60420
agatgagttg cagaaatagt aattgctaaa acagttaccc cccttttttg tttaaagata   60480
tttatacttg tcaacattca agattgtaat tttaaaacca cagtaagaaa acatgttatt   60540
aatgaaagtg ttgcatttt tcacaggcag caatctgatc accttggttg ctctgtacag   60600
aactgacctg gccatgtatc tagccatgac cagaatacaa ggatgcccat ttgtgctgca   60660
gatttccacc cactcacatc caattcctcc tcacatagtt ttactagtgg catattctga   60720
ggccagactt cctcttggct agaacataac cctttaaaca aatctatatg ctattctaat   60780
ggaaatatct tcaggcattg ccctactggg catagattca agtcagcttg tgggccagct   60840
tgaacttggc ttcttgtatg tggtttgcct ctagaagcat ctactgccag caggacactg   60900
gcagcctttg tgaatgtaag ctcagaactt tcttccaata tacgttatct tttatttgaa   60960
atagttttg gacttatgaa ggaaatcaaa attattatgt gggtaagtaa attatatgaa   61020
gaagactcag ttaagtgtct atggtgactt atcccttact tttcaataaa cttttttagat   61080
tccttttcac ccaggccttt tgtcgctacg tcgtgagcca agtgttcata gactagtttt   61140
taatagacta tcaaacacaa ctgtgacatt atgtagaagt aaaggcagga ggacttgggt   61200
tttaggtaaa ctggaatata cagtaagttt aaggccaaca aagactacat ggtgaggtcc   61260
tggaggtcct gtctccagag aacaaaaagc aaaaacaata gcaaaaaaaa aaatcccaaa   61320
aacaacaaaa aatacaagga aagagattta acattatcat atcatctaac ttttggcatg   61380
gtagcaacat aatagtagta gctctactat agtctgttac ccatcactgc ttgtgatttt   61440
```

```
acaagatcca caagtatata caagatgaag ttcacagatg caactgcacc aaccacaagc    61500
actttgggta gaatatggca gtatcctagc agggagaatt tatgctcagg cagctaacaa    61560
gtgattaaat ccaagtctgc ttttgctctc ctgcaatgca gtgaggaaat cagatagccc    61620
ctttgccctc tgtttatttt gaattaaact ttatccactc aattttttaaa aatttactag    61680 attaattaat gttttatata ttataaatac agttttgttg gacatctttc ctaatatctt    61740
aactggtcct tgggaaaatt tatagtaaat aatagaagta caaaattgcc actcaaagta    61800
ttgtaaattc ccaatggata aattcatgtt tagtaaacat ttcacattta atatttgttc    61860 acttttttcat tttcacgata ttttttttcta aataagtgcc tgtcaggtca tgaaaatgcc    61920
agtaaaatct catgaaatca tttatccata aacaatcttt tgatgttagt gggctagttg    61980
attctatcaa aggaatttag agattatcag tagcacacag ttttagaatt ctagggtctg    62040
attgtgttac acctcctgtt agagtctagt tatagcagaa tagttgctgt caatatcttg    62100
ttgctgccaa tatcttgtaa ggcagtgtgt ttactggttg gaaacatgta aatctaacca    62160
ctttataagc agtaatagtt tttatagttt gaccgttatt aattttttat taataaaata    62220
tataacactt tcaatttcag ttatatatat atatattcag tcctctttaa tacatcataa    62280
cacttgtcaa tagctatgat ttatttatta tattgtgtgt atgcgagtac cagtatgttc    62340
attacatgtg tgtatgatcc ctgcagaggc cagaagaggg tgtcagatcc cagggaacta    62400
gagttgcaga aggttgtgga ccacagtgta ggttttggga acagaactca gattcttgcc    62460
aggagcatca agtgatttca taactgctta gccatctgtg tagccttgtt ttttctattt    62520
tttggagtat gatgtgtttc aaaatacagt atctaaatct gtagtccagg atagcttgag    62580
attcactata caggcttccc cctagactca agcaaatagt attggtttta actaagctac    62640 attttaaaaaa tccatttgcc agtgtgtttt agttgaacat atagacttac ttgaagcagt    62700
ccctagacac agatcagttc atggctcaat tccaagatgg gtctcatatg gtgtatgata    62760
aaaggaaagc agtacaagaa atccatctga tctttggagg cttgtagaaa ggttaacttg    62820
acatcttatc ccaccttctg gtgcaggtag gtaactgaca cagtgatatg atgactgggc    62880
atgatggacc cagaaagaga aagctagata atagcatgat gtcccttcag aagagcagct    62940
tgtttcatac aaaacaatga aaaaattatc acctgttgat ggagaaatgg ctcatcattt    63000
acgatgactt gctcttcctg caatgaacct ggcctcagtt cccagcaccc acatggtgat    63060
tcacaactgt ttgtaactac agttctaggg atactacatc ctcttctgat ctctatggtc    63120
attaggcatg tgcatcacac agagacacac aatcagggca aaacatatac atacataaaa    63180
ggaaaataaa cttttttttca cattgaaaaa atatttacct catccccact tgtacaagaa    63240
atatgtgtcc aataccattt gtattgtaga atttttatact gtttccctat actgtcttat    63300
acaagtaaaa cctaaactag ataatctgat aatcttattt tatatatttg aaattctttt    63360
tagattgaat ctctgttttc agattaaaat gagtaactac acatatattc caaacaaaat    63420
aatttgtaaa agaagcatga ttattttttaa gttttataat tgagtaaata gcattgactc    63480
tgaatgagtt attaaagttt ttcttaattc tcatttattg ggaaggaacc atcaaagaaa    63540
cgttttactt tacactcatg gcagtttttt gattagaaaa taatttctta ttacatatca    63600
aattcctaat attttgtgca agcttcaaaa gatgccaatg aaatttccag aacaagagtt    63660
cagaaacaac tgtctacatt caggtaggat gcacactgtt ctttatgttc agtttttatct    63720 ctagatccag atgaactgaa ttacagtcag tcaactagac agggaaaatg agcatctgca    63780
cagctctagc tttggctgat ggagccaact tactacatag cttcctgtgt tgtggtatca    63840
```

```
tcaaatattt aacttctgtg atatttcttt gcctgttgcg taagtttaac caacaaaaac   63900
acatttccca ttgcccatcc caacatgtaa tagcagcaat tatttaaaaa tcatagtcat   63960
ttgctcttta tgtctacaag acaatacttg ttagtacatt caatataaat gttttctttc   64020
acaccaaggc agtttcctga ttcattagag ggaattttgt atctgagcag aggaactctc   64080
atgttccccg ctttcccttg ttataacatt ctgagctcca tgaccatgta ttattccagc   64140
tccatgtttg gacacgggtg aaggaagcat atcacatgtt cttcctaaga gacttagact   64200
aagtatgcaa aagacccaaa attttcgaag gtccaagtcc ctatctgttc ataagctcat   64260
ccctagtcat tcattgcttc agctgctgtt tttggaccag tattgagtca acttcacatg   64320
cagtttctcc ctttctacca tgaccatttg tacatcctct ttgtttcatg gtttaatcct   64380
gcaaaagtat atatttactt ttgtttggcc taatcttgac cataacctag attgtacttt   64440
agacttctta ctctttaaaa ttttaaaatg tgcagcataa ataattttct cctactttga   64500
ttaatccaaa aactatttcc aaggtcatta taaaaggtcc caaattatga gttccaatat   64560
tatggtcagt agacctattt gtgctctata acagtgttat ataatatttt aataggaata   64620
ttagaacgga aatgggcctc atgtgaacaa tgtgttttat attactccct tccccattta   64680
tcatgcctgg tatatgtgag tatgtatgta tgtatgtatg tatgtatgta tgtatgtgtg   64740
tattttttat gtattgttat gtatatacaa gtgatatata tatatataat atatatgtgt   64800
gtgtatatat accttatgt atgtatatac acacacacac acatatatat atacatacac   64860
acatatatat atatgtatat atatatgtgt atgtatatat atatactgtg tgtgcattca   64920
ggtgcatttg tgtgtggagg catctatgtc tttggcaatg attctcatag aattttttga   64980
aacattgtct ctcactgaat ttggaattac tgtttcagct agactggctg gcccttgaac   65040
ttcttcaaag ccccctgcac tgggtttata aacacatcta tgccagcttt tggttgtatg   65100
gtaggtatac aagttcattt cctccttctc ttcagcaaac actttaccca ttcttcataa   65160
ttcctatgct ctaagccaag atatttttt cttaatgtgt ccaccatggc aaaggctcag   65220
aattataaat gtgtttctcc aaaaccctca gttaagaata tggctgccta attatgcatt   65280
taactaatag gcttctgaaa ttaataacca atataatatc gtggttcact aagacaaata   65340
tttgtagatt ttaataaagg caggtaatga agctaaagtt aaagaaaacc ttcaatacta   65400
tttatcactg tttgtgaaca aaatatgatg aaaatatttt gcccataaca taacactgcc   65460
ttaactatat ccatcttgac tcaaagagat agaaatccgt tctgtcactc acagtatatg   65520
tttgcagatg aatgctagaa ctgatcacag atgggaaact aggtgtgcat tgcaggggct   65580
caggtatagg tcacaactct atcagtctct gaacatcatg acacaggtag gaagaccagg   65640
aagaaatgtg ttttgtttca ggcctctata atgaaaagtg aatgtgaaaa ctcaaaactt   65700
caccttgaaa agcctctgta tatcttatat gttttttccca tttcctggtg aataggtaga   65760
atacagggaa caaaaccac tgctctcatc ccagtatcag cccagactct tttcccagta   65820
cctcatctca cagatattcc tccattcctt cctccccttc tcctctgaga ataggagcc   65880 ccacttctcc ctataacctt acccccaacc cctggcacat caaatcacag caggtccatg   65940
taaatcccat cccactgagg ccagataagg cagctcagct aggggagcag gatccacagg   66000
caggcaacag agtcaggggc agccctgtt ccaaaccatt ctcattccta gtaatgctgt   66060
cctagcacta tgctgatgac tggaccaaac atacaatttt tgttcttact tgactcttac   66120
aacttcaaaa attaacagtg taaatttcca gttagctttt gattttaaga caagctaatt   66180
agtgaagaat taggcacaga aatctacata ataaaataat tacagaaaaa gaaagtatct   66240
```

```
aaggtcagca ttagtatggc atcttatttt ctgtctgtca tggggaaaca agcaattcca   66300
tatggatcgt agaggtcaga aagaggcact gctgatccca cactgctgtt ctatctagca   66360
caagcagcaa gagactctcc aaagcccagt aagcaaaagc gccctgctta tgttggctcc   66420
actaatgcag ggaatttcaa atgatggatg aattaaaaaa tttgaaagag gttccgcctg   66480
acagccactc atctgtgata tatcctttgc tgtcacgatg attagccatc tgttcctttt   66540
ctagatctta cccatccact atcattacca tccaccatca ctatctacta ctaaaaccat   66600
taaagcacat ttaaagatgt gaggtctagg aatggtatct ttaaggtagc atatatgtcc   66660
agtgtggtag cacgtgctca ggataggtcc tgagttctat cctccagcac catcaaacca   66720
caaaagataa aaaatgaaga tgtatgaact atatacttta ttagcttcta tctattacta   66780
gcaatacaat gtcacactcc atggcagtgg aaggaaggag ataccaggca tgccacttga   66840
caagttttta gacttgtgac tggtttcagg ttatgttcat aaaagacaca tggaaaggaa   66900
aagtagttaa atttgtgtgt ttggatggat ttactttgag gactgtggtt atgaagcact   66960
tgtttctaga ttatttcctt ttatccaaag tagaagggac ttaaaattgt ctacgttagt   67020
agttctcaac ctgtacctgt ggattgcaac cccttgtgg tcacatatca gatatctaca    67080
ttatgattca taacagtagc aacattacag taatgaagta gcaacaaaag aatcttatgg   67140 ttggggtca tcacagcatg aggaactgta ttaaagagtt gcagcatgag gaaggttgag    67200
aaccagtggt ttaaggtcag tgtacagtcc caatttgaag cagcacagat gcaagtgctc   67260
ttgggtaact tctacatggt tgtttttactg tagttactga tctaactgtg aaaagtggtc  67320
agcctgttgc agactgaatc tgaatagaaa tcacaatttt gcatactctt ggtttcataa   67380
ttcctttatg cacatccttc tgagaccctg gttgtactac actactacca cttgggccta   67440
gagcccctct cactgtgaaa gaatgattgt atccttgggg agctataaag attatgactt   67500
tgtgaattaa tctcaaatca gggagccaca ggacttccaa ctttattttc aaatatgtgt   67560
gaactcccct gtgagatggt ttatcgaagc ctttgggagg tgcagccatc tgattgacca   67620
gttatcttat ttgcaattga ctctttttatt ttatatgaag ctctgtttgc taagaaggac  67680
aattcaatca gcagtcactc atagaactac tcagttgatg taatgaataa agagacatta   67740
gggtcagtga aatgactcag tgggtaaaga aacattctgc caagtctgct gacccaggtt   67800
tgatacccta ggatcgacat agttgaagga aggaacacta ttccaccagt tgtactttga   67860
cctccccatt ctcactttag cacatatgca tgcccatact aaataaatgc aaagtttaag   67920
agaaacacca agacttattc aacaaattta ataacttatt agaatactca agtacacagt   67980
caaagaaaga agttatatta tggattaata gcaaaacaca tactgagtgt taaaaattat   68040
atactggagg agaatgggga agggtagatt gagagctaga catatacaac agagtgaact   68100
ttcatctggc ccttcaaaat tcttagtatg aaaaggaata gggacttgca actgaaaaga   68160
actctaatgg caattcataa aaactttagg gtagaattta gaagagggaa ttaaaatttt   68220
aagtctacaa tcaattcata caacaatctc tttatataac agtgttttt gtacactgaa    68280 tactgtgcaa atattttgta aaggtatca agaactattc tgttaacagt ggcttgcata    68340
taatcagaca agatggcata catactctac ataacgcaca tttgtataaa acataaataa   68400
attgtaaaaa caatagccta cacactatat ttttaaagta gcattttctt attttttgtaa  68460 taaataagat ttttgagatt tagcttattt agccaactaa tcattgacct ttttataagc   68520
agatgtagta attcttaaag ttcccaatta aaataaaatg caaagttttt gctattggtt   68580
ttgatacact gactccaaac catatggtag tataaagata tttcttgaaa actctgaaat   68640
```

```
cttttcattg tcttctctta gaattgtttt atgactgttc ttctttaaca gtgtagatga   68700
atgaatgaac atccaaaatg aatagaccaa gcagcccgtg ttagaaaatt cattagtttt   68760
actggattcc actgaggact ggacaataag tggcaaaaca tatgaatgca gttctgtgga   68820
agcttcctca ggatttaaat aaattcaagc aacacacaca cacacacaca cacacacaca   68880
cacacacaca cacacacttg tgtacaggga ggagagccat tgtattagaa aatgcaacct   68940
ggatggccat cagggtgtga atgtcagcta ccacaaaata tatcagactc aaagctgaac   69000
aggcaccagt acttttttatg gagaagaacc aggatggcct caaactcacg attacccgtc   69060
tcatcctccg gaacactggg attataagta tacgccacca catttggtga aagaaaggac   69120
ttgttttgaa tttctgtatg aatgaagttt caaaagaatg caattaagta cgagatcaaa   69180
tttagaagaa agatttgatc taaaaaatac aactaaatga gaaaaggtgg ataggaaaaa   69240
gcacagtatg cattctttat tgtgttgctt tcacgatgtc aaaaacaaat taaataggct   69300
agtaaaatgg aaaggccatg aacaaatgtt ccttgtagta tagaatatac tagactatct   69360
cttctatata aattgattta aaattaatga caaacttggt ttcaattcaa ccagctcatt   69420
ctaaaaagtt gaaatataca tatgtgtgtt tgtgtgtgta caaatgaata tataatgtat   69480
ataatgtaca atgtgcatat acattgtata catatatatg ttagaatgat gggtgtaatc   69540
atgtatttat atttttgaat aaattctaaa cataaccaaa ttccagaaca acttagcagt   69600
actaagaatt actgattaca ttaaagttta tttataatca atacacaaag atattaatgc   69660
atgtaattct atcagtattt atgtttctga tgttataatg ccaatgttta tttcacatac   69720
gtttgaatat tgtttaatat tatacatatt ctaaatatag taccaaatga tatttttatt   69780
tacattaatg agaaaatgta agtcctggtg aaattctgtg aaaaaagtta tgtatcagtg   69840
aaaaatggta tggaacaact ttcttttcagc tccaaaaatg gcaatacttt tcccttttatt   69900 caataaagag tatttttaag tagaaaagtt aaaaaaaaaa aacgggattc tagtcagaca   69960
actcgaaata tatgggtcag agtaacagta tctctggaat gcaggcttaa aacctgacta   70020
agatcagaga cttgagtacc atacaggggtt ttatgtgtgt attgtctgat aatggcaaaa   70080
gaagatggtt ttaaaaatga ctgattcata agcaagtcaa cattaagtga aacttgaatg   70140
gaaatttagt tttctagtaa taagcattta gataataagg agtgccttat tattattaga   70200
tattaagctg gtaccccctg tgccttggct atgactctga aatgaataga atgaagttac   70260
agttaacaga gatgcagagg cagacacttc cctgtgctac ctaaacaggt acttagtgta   70320 cttttgaacct tatttctgac aggtctgaga tgtaaaagga gggaaccag tgagcccagt   70380 gattctagcg ttgccgtgaa ctgctcagag gtagtttgtc attgcacaga gctgttctca   70440
taatagttat gatcccaagc cttaaattgt tgggaactat gttactgttt atttgttgtt   70500 gtttttttttt ttttcctcta ccctctggtt aaaatataat tttgatgcat cagcatagtt   70560
atgaagggga cttactagca agtgcttttt aacactgata tttgggtctc ctggattcta   70620
tgaaagtcat gtctccttaa ctactttatc tcctgcactg cgccctcccc cccatatcca   70680
cagagcatct gaatggtcac tcgtggccat gctccagagg tgagtgatgt acacacgggt   70740
ggagaatcca atttaaaata gcatgagaat gtagaagaga caaaggagca ctgcaggagc   70800
atgtgcagat ataagtgctg gaagtcccca gactgctttc tccagacttt ctcagctcct   70860
ggtgttgctg cccactctgc tgccctggtc cttaccttaa ccagctccct tatatgcttc   70920
catgttttat ccttcactaa gtctcttttct ctctggttct ggatgcttag atgttcttcc   70980
atttggttcc atgtcatatg gtcatttctg tttctgcagc agctaaactg ttggataatg   71040
```

```
gtttgcaggt ctgactccca agtaccactg tgagctcatt aacaatggct gccatctcct   71100
tgtatcctct gcactatacc agcagatgaa gttggaccat gggctgtatt ccatggtgaa   71160
tgagtgctct gtgctggttg gaaccctata gcaatagaca atgtgaatac attgacagtg   71220
ttttgttgtt gttgctgctg ttgctgttgt tgttgttgtt gttgttgttt ttggcaagat   71280
actcacttca gggttttaag aacatgaccc aacctgttaa aaatcaataa attcagacag   71340
aggattttt agttaagagt taaggtacaa atgagagatc actgaaggtt ttaagcagac   71400
tgtaaggtaa gaagggaaga aagttcccaa agtatatgct aggagctagg gctccagtgt   71460
aaaggatggc taaacgtggg tctgttttaa ggggtgtaca aacatatttg ggctaagaag   71520
gcccaatatt tactttcgaa tgagggaaaa tgcttgtgac ttaacaggtt gcctgttcaa   71580
tgaactaaaa aaatgtaaac tcttactcca taatctcttt aatatctcac ttttgccaaa   71640
ggaatctaac cttattgcca ccaaatccca ctgaactcct agacgagcaa aaaaaaaaa   71700
aaaaaaaaaa aaaggggggg gggagttcta ccaatcccca tgacattctg caatttttcta  71760
attatagatt gaaaagagg gttgaattca tttcatggga cattcactgt gtgtccctac   71820
aggatgctga gccataattg acccacacat gtggtgtgtg atatttgatc agggatccta   71880
ggctggaaag acagctcagt aggtaccttg caaacacaag gatttggatc cacagaactc   71940
aattttaaaa agctggtcat gataacacac atgagtgatc cccgctctaa aagacaagga   72000
tagtaagatg tctgggtttc ttggctaacc agcacaacct acttggcaga ttccaaacct   72060
gctagagata ttgttggaaa gaaagttctc aacagaatct gaggaacaac accagaaaca   72120
gtctacatgt ctacacacac ctatcatccc cccacatcca catatacaca tgtacatgta   72180
tacctataga taaacattac cctcccccac acttgaaaat acacatatac acaacattca   72240
ttttaaagac acaggctaca gttttcactg tcttgggcat tgctcattct ttttttgttaa  72300
gaaactgcca atgccattcc ccttgctaat aaatgttata aactgtggtc acattatgct   72360
gcagtagaaa tgccagagac tcttccttc tactagtatt ctgatgtgtt tattcagctt   72420
cctcccacct cctctatccc tgtttaccct tcatagtgtc tcatgacagc tttctactct   72480
ctatatcttt gaaataaaga ctttaccaac atttttaataa ttttttttcat ttgccgtttt  72540
tattttatc ttttttaaaat tattattagt tattttcctc gtttacattt tcaatgctat   72600
cccaaaggtc ccccatacc ccccccccaa tccccctaccc acccactccc cctttttggc   72660
cctggtgttc ccctgtagtg gggcatataa agtttgcaag tccaatgggc ctctctttgc   72720
agtgatggcc gactaggcca tcttttgata catatgcagc taaagacaag agctcccggg   72780
tactggttag ttcatattgt tgttccacct atagggttgc agttccctt agctccttgg   72840
gtaaattctc tagctcctcc attggggcc gtgtgaccca tccaatagct gactgtgatc   72900
atccgcttct gtgtttgcta ggccccggca tagtctcaca agagagagct atatctgggt   72960
cctttcagca aaatcttgct agtgtatgca atggtgtcag catttggaag ctgattatgg   73020
gatggatccc tgcatatggc aatcactaga tggtccatcc tttcgtcaca gctccaaatt   73080
ttgtctctgt aactccttcc atgggtgttt tgttcccatt tctaggaagg ggtaaagtgt   73140
ccacactttg gtcttccttc ttcttgaatt tcatgcgttt ggcaagttgt atcttaagtc   73200
ttgggtatcc taagtttctg ggctaatatc cacttatcag tgagtacata ttgtgcgagt   73260
tccgttgtga ttgggttact tcactcagga tgatacccctc caggtccatc catttgccta   73320
ggaatttcat aaattcattc ttttaatag ctgagtagta ttccattgtg taaatgtacc    73380
acattttctg tatccattcc tctgttgagg agcatctggg ctcttcccag cttctggcta   73440
```

```
ttataaacaa ggctgctatg aacatagtag agcatgtgtt cttattacct gttgggatat    73500
cttctggata tatgcccagg agaggtattg tgggatcctc cggtagtact atgtccaatt    73560
ttctgaggaa ccgccagact gatttccaga gtggttgtac aagcttgcaa tcccaccaac    73620
aatggaggag tgttcccctt tctccacatc ctggccagca tctgctgtca cttgagtttt    73680
tgatcttagc cattctgact ggagtgaagt ggaatctcag tgttgctttg atttgcattt    73740
tcctgatgat taagggtggt gtgactctaa ctaaggaagt gaaagatctg tatgataaga    73800
acttcaagtc tctaaagaaa gaaattaaag aagatctcag aagatggaaa gatcacccat    73860
gctcatggat tggcaggatc aacattgtaa aaacggctat cttgccgaaa gcaatctata    73920
gattcaatgc aatccccatc aaaattccaa ctcaattctt caacgaatta gaaagggcaa    73980
ttggcagatt catctggaat aacaaaaaac agaggatagc aaaaagtctt ctcaatgata    74040
aaagaacctc tggtggaatc accatgccag acctaaaact gtactacaga gcaattgtga    74100
tcaaaactgc atggtactgg tatagtgaca gacaagtaga ccaatggaac agaattgaag    74160
acccagagat gaatccacac acctatggtc acttgatctt tgacaaggga gctaaaacca    74220
tgcagtggaa aaaagacagc attttcaaca attggtgctg gcacaactgg cggttatcat    74280
gtagaagaat gcgaattgat ccatttctat ctccttgtac taaggtcaaa tctaagtgga    74340
ttaaggaact ccacataaaa ccagagacac tgaaactcat agaggagaaa gtagggaaaa    74400
acctcgaaga tatgggtata ggggaaaaat tcctgaatag aacagcaatg gcttgtgctg    74460
taagatcaag aattgataaa tgggacctca taaaattgca aagcttctgc aaagcaaaag    74520
acaccgtcaa taggacaaaa agaccaccaa cagattggga agggatcttt aaaactgtac    74580
tacagagcaa ttgtgatcaa aactgcatgg tactggtata gtgacagaca agtagaccaa    74640
tggaacagaa ttgaagaccc agagatgaat ccacacacct atggtcactt gatctttgac    74700
aagggagcta aaaccatgca gtggaaaaaa gacagcattt tcaacaaatg gtgatggcac    74760
aactggcggt tatcatgtag aagaatgtga attgatccat ttctgtctcc ttgtactaag    74820
gtcaaatcta gtggattaa tgaactccac ataaaccag agacactgaa actcatagag    74880
gagaaagtag gtaaaaacct cgaagatatg ggtacagggg aaaaattcct gaatagaaca    74940
gcaatggctt gtgctgtaag atcaagaatt gataaatggg acatcataaa attgcaaagt    75000
ttctgcaaag caaagacac cgtcaatagg acaaaagac caccaacaga ttgggaaggg    75060
atctttacct atcccaaatt ggataggga ctaatatcca atatatataa agaactcaag    75120
aaggtggact ccgaaaaatc aaataatccc attaaaatg gggctcagag ctgaacaaag    75180
aattctcacc tgaggaatac cgaatggcag agaagcacct gaaaaatgt tcaacatttt    75240 aataatttta atacagtcat ttattgtaac aaccatttca aaaacacttg tttccttaga    75300
atgaaaattt taactagata aatgtggtta tccatgaaaa tattaaagaa tatacaatat    75360
acattatatt attgtatata taatatggta tagcacatga tataacacac acacacacac    75420
acacacacac actttacaaa aatgttaaaa aataatacca cacagaatgt tgtgagaaaa    75480
tagcattagt gtctgactca tcttctcata cttttagaaa taaaattaaa gttcttcaca    75540
ctttgtgtaa agcccaaaag gttcagccct aaggaaaact tgaaatttgg gtgttaaata    75600
agccaccagt ctaaaagttg gacatttctg aattaaggct catgcctcat ttccaccaag    75660
tgctgcttca aaacaaaaca gtgataatgg ccacaaaaaa cctctggcaa ctctaattta    75720
aggtgacgta tactgatgaa tgattttattt atccttagaag tgccaatatt tcactctttt    75780
ccatgtcttt aaagcaactg aaatagtttc atgagcacag gcataactgg attcttggat    75840
```

```
ttggggagaa atgatttggc tatgtgcctg ttgctgagga agaaactgc caacactgag    75900 gatgttctta aagccaagtg ccaaattgtt tgtgcttagc atcatgtatc aggctggccc    75960
tgcaagatga ttccattcca aaggtcagaa atactctgcc ctgtttccag aattttattc    76020
agaaattgga aatagagaca gcttcaaaat agtacacatc ccatcttctt ctcagaatga    76080
gggctttgat ccaagccttg ctatgtaaaa tgcatgggag gaagaggaac ctaatacaaa    76140
ctttgtttat tctatccgcc attgctgttt tcatcttcag aagaattctg cttttttggtt   76200 tagtggtaat aacttgtacc aagtcgatgg caactccacc cagataatga tgagtttgtg    76260
agaacatatt tttcacatgt ttgaagaata gagctacata gggttgaatc tgccttgcaa    76320
tttgatcttt atcagtttta tggaggcata tctccatgat taccctgtg tatgtttact     76380 ttaattagat aaataaccag aaaccaattg ctccctcact tatgattatg tgtattctcc    76440
atggagtgag agacaatagc tagtagccat ttgtttacct tcttactttc ttactctcac    76500
tacccagtat ttcctaatta aagctatcag cagccaccat atgcctgtga catgagtctt    76560
actctgtgga aacaccatga tcaaacaaac aaacaaacaa acaaacaaac aaacaaacaa    76620
caggttgcat tctcagcagt tgcagaaaaa ctcactttct tttgcatttt caacttgttt    76680
ttacattaat cacaaacatt aacagtctaa caacataatg tgttcactta aagataaaca    76740
acacagcagt tgttaactga aactcagatg tcaacactgg gttaagagaa ttatggtggg    76800
tttaccgaaa agttgaaaga gagaattgtc tcagtgaggt gtggccttca actggaagca    76860
ctgaagccag acaattagag ggaagattca aaggaggtgc tctccaggatt taagtcacca    76920 tgtctcagtc ttcagaagaa tgtgcagctg accaaggcca gacctgtgaa gagacccaga    76980
aactacaggt tgcagcagcc tccatcgatg ttgaggagcc atgttcctca cctcatctta    77040
tggctactag tctgaaggac cagaccagtg aggagaccca agtctccaag gatgtggagg    77100
aaccatgttc ctcttctcaa cttcttatgg ctagcgacca ggatgattct gaagatgaga    77160
cagccagtac ttccagtgat cttcagcatc cctatgactc ttcaagcgag tctactgagg    77220
atcttgatga ccaagaagtg cagggtagcc cagtcattcc accagatcag tcagatagca    77280
cagatttacc tgtgatgact gtagatggga agttgatttt cttggtgaat tacatgctgt    77340
acaagtatca ggtgaaagag gtgatgagta tgaatgatat aatgacactc attgtcagag    77400
aggatgaaga tcgttttcat gaaatcctca tgagagcttc tgagcgcatg gagatggtct    77460
ttgggctgga tgtgaaggaa gtagatccta tcaaccattg ctatgctctc tttatcaaat    77520
taggtctcac ctatgatggg atgcgcaatg atgagtacag cttttcctaaa actggtctcc    77580 tgatactcat cctgggtgta gtctttatga agggcaaccg tgccactgaa gaggagattt    77640
gggaagtatt gaatccaatg ggaatctatg ctggatgac tcatttcatg tttggtgacc     77700
ctagagagct gataactgat gagtttgtga gggagcaata cctggaatac cagccaatag    77760
ccaatagtga tcccatacag tatgaatatg tgtgggggct acgggctaaa gctgaaacta    77820
gtaagatgag agtgttagag tttgtggcca aggttcatgg gtcagaccct actgtgttcc    77880
tttctcagta tgaagaggca ctgattgaag aagaagagag aacccttacc atgctattag    77940
agcatgctga ttcaagttct acttctggtg aaagttctag tgacacaagc agcaacttct    78000
ctcaggtcta gtacagtcag agatcagttc cttctgtata atttacagag aattttaaa     78060 cttgcgggga aagatgtacg acctagattg tataggagag aggagcgtc ttagctgcat     78120 agttctaatt tgtataagca ccatgccatg tttttcattg tttgcccttt atatatgaaa    78180
atacttacac ttaaaagcat tgttgtttag tttcaaaatc tcaacttaat accattcaca    78240
```

```
aatttaataa gagcgttgtc ataacataaa actaattggg aaataatccc atctatctgt    78300
acagttatct ggaatagtta aacatgcgtt ttctaagctt ctacctttta aacagctttc    78360
ttctaattac tcccttttgta cctttccatt tctcagtaaa attacatgct ctatgtggag   78420
ttgtttactt tatagttgcc aataaaattc aagaaagttt aaaaaaaaaa agagagaatt    78480
atggtaattc ctctcaaaaa aaaaagtgtc tcaccattat tttctcacat cttattagaa    78540
gggtatctaa caagatccgt aggtatgtag agccagcaag catctggctt ctcatctctg    78600
tggtggaagt aattaaagta ggaagtgccc attttgactc tgctgtcagc agaagagaac    78660
acactagact tgttagtgca gccttagcca ggccatctac ttccatgaca tgggataggt    78720
ataaattagc atggccatcc tttcttgtct ttgtagttca tacagaatcc aggaagcaac    78780
acatttagga gtaggagttg taccattttt gcataggaaa tgtacagttt cagtgtcaat    78840
gcagggaatt actatattta taaaaatcac agagtccctc tggctggtgc tttttagtca    78900
aatatgaaat gagtagtatt ggaattacaa gctggcatca cttccgtcat tggagacctg    78960
tttctgcagt cacagctgct aaaacagctt catgattcct ttactacgag ctttgtggtc    79020
ctgcagatga aggatatcat agtacatttc ctgcatctct catgacactc gtgatcagca    79080
tataagactt ttcttttgtc gagaattaaa taagaatatg gccaaggaac agaattagta    79140
ttgtgaagaa ggtgtaatga gataagataa agaatgattc agagctgcca atcatgtatc    79200
cctcttgctg ggttcattgt ctctctatct caggcattga atgaaacata ctcttgttcc    79260
tgactataaa atcagtaata taaacaacc aatttaatag catttagaag agactcaata    79320
gaccggcagg gagaagactg tatccactga tttaaaatat gtattatgat accataaatt    79380
ttaaaaagaa aggaaggata gtcttataaa ttcctaagtt tgatagcaca taagggctga    79440
atggtgatca cttgggtccc ctttaccttc attggttctt tgcatcttca cctcgagcaa    79500
ttgattgtgt ttcgcttgtt tgggttctct gcctttctcc acactccatg attttttttca    79560 aaactgtctt ctgttcccct tcttgcccac attgtaaaca tgtgaagtag aaaagtgaaa    79620
gtgattttgg tgtctttttct tcagaatcat tatgttttcc agcaagaact aacactgaaa    79680
gctacctgaa acacaaataa attaatagaa ttgagccata cagtcatctg tatataaagg    79740
tgtaacgtaa aagggccact atataggaag gcagagtcag cataaggctt gatttaaaaa    79800
aatggcagaa caattatccc tttgatgaga tagacttaca tcttacaagt gtagtcatgc    79860
tacatcataa gttgacctca ttttctaaat tagtcagagg agcataactt tttttttctgt    79920 cttttcatttt tttttgctttg tttttgtttt tctagacagg gttctctgt gtatcactgg    79980 ctgtcctgga actcactctg tagaccagac tggcctcaaa ctcagaaatc tgcctgcctc    80040
tgccttccaa gtgctgggat taaaggcatg ggccaccacc attgcccggg tcgtctgtct    80100
tttctaagta tgcttcctcc agtacatgta atgtttctcc ttttttccca tattttcctg    80160
ttctgggcag ctgttaggat ttacagattg cttgcttgcc tttggttatt tcctgttgcg    80220
ctgtaataaa actgccctct tttaataaac ataggctttg cttgacttca gaacctgttt    80280
tagatgtgtg tttccaaaaa ggttcccatc tgtattctta dacccttat gtcttgcatg    80340 agcacattct tccccagttt gtatactaaa gatacttggt tgaacccatg tttgtttgga    80400
acatatttat ttcatttgga ttctgagttg ttcctttgct ttacctagtg gagcagagct    80460
tatgggaccc cagagtcttt tctggataag ctttcttcca tgaagcaagg cttctgggat    80520
tttataagat gttctaagga aaattcagtt taaaatgaga cgttatgttg atgtgataaa    80580
ggtacaaatt tatgacaact actttattgt tgccagttaa gaaccacatt gtaaacatac    80640
```

```
cccctagaat acatttaatt ccatagcact taactatatg tccctacaag taaggtatga    80700
cactcttctg tatataaagg catcctcata atctttatca tcagtgtttg gtaaacattt    80760
acctgttcaa attctgcttc atggtgagaa ttttttattca gaaatataac aaactaatta   80820
aatccttttt tgacaattt ctgtattatt taaatacatc atactaaaga ttttagtata     80880
ttaactaaat aaagattata atattattta aagtaagccc atcaatgaat aagatatata    80940
cgcacatagg gacccttag tcacagtcta gtagactcag gcttctcatt gtttcctttt     81000
ccatcctttc cttttctagt tgatacctat gagtttgcag gtttgttgtt gaaggaagtt    81060
gctcctgaaa gactctgtcc aggccaacag tggccacaag agcagggcca gatgcaagtc    81120
tctcttccag ctctacagtg atagttaaga tggctgccat cttaccctcc acagctactg    81180
tcaaccatct gaactagcag ttccacatac atctcccta agcttgctta cattaagatc     81240
agcatctcct tttccctggt ctctagttag atctttccat attatatttc caactacaac    81300
ttttaaatgc tttctcaaaa ccttcaaaac attgtaaagc atattattaa caaacccagt    81360
ttgtcattgg tctaacttca ttttcttctg ctgctacttt tccagcaact agcttccact    81420
gcaagtaaaa tttactatc accaacacat gagaggtaaa catgaagcca gaggagtctg     81480
tatgtgtatt ttgtgcaata agttggttca tggccattac accaaatgcc tggttgtact    81540
ggttgacaac tgtctttcta ccagatagac tgtttgccca ctgtgcgatc ttggacaaca    81600
tttaaatttt tgtgtttctt agctttttta catgtgacat gaggataaaa attactccta    81660
cttcatcaga tttaaataaa gtgttttaac ataatacccta ccctataaca attcagttca   81720
atgatggtat catgaagaga aaacacatga cttaattga attttagagt tctgatgtgt     81780
gtgtgtgtgt gtgtgtgtgt gtgtgtgtgt gtgtgtgtgt gcatgtagat ataaaatatg    81840
aaccagagga ttacctggaa ataactggaa acagaatgac agaatgtatg atagattcgg    81900
aatgaccata gaattaatat ttgcaaataa atagtagaat gattccactg atcttttgga    81960
aactaaaaga gagaagaata tttcaaacag cttttcagtgt ggctttctgt gatgctctct   82020
gtctgctgct tctgctgctg caaaataaag cttccctcct cccccttatg agcagtgaga    82080
gtgacacttc cctgtgggtg ttgggataac tatttagaat gcagcgagga attacattgc    82140
ttagaaacgt ggcaatagaa cttctcttct agggtccatt aagtcaccag acacaggtag    82200
tgggctgatc ttacagtaac caagcatgaa tctccccata tttagcaggc catgagccaa    82260
ctaggagacc agtatagaaa tctatagcca gcaagaaggc agagaacaat tgactcttgc    82320
ttgcttgtcc ccatcaattc atttacaaac agcccatata ccaaaggtgc tggagacact    82380
gtggaagagg gggtagaaag acaatgagac cagaggactc agtggtttgt tagcatatgg    82440
ggtcttccta ataaaatgca aaaggggtat ggagagggga gtgtgagtga atatgtgcat    82500
atgaccagat acagtgtatg aaattctcga agaattaaat tctcaatata actcccaact    82560
gcaggctaga gagttattct tagacccaca gataagtgta gcccttacca ttcatcatag    82620
aaagccacag ttaaaagcca tctaaattgc ttttccctc tatcatgttc cagaagctca     82680
gtgacatcat tattcccccc catttacaaa tataaattct atagtatttc cattttttaa    82740
aatttcctgt tttcggtgtt tattgttgt ttgcttgtat gggattcttg ttgttgttga     82800
ggcagaatct ctctacgtag ttctacctgt cttataacta cttgtgtaaa ccaggctgac    82860
ttcaaacaca cagagatctt cctggcctct gcctcctgaa tactgagatt atagatgtgc    82920
agtgccattt ccagctactt attttcaaaa ggctgttcat atttggtgc ctgtttctgt     82980
caaactccaa gtgagaagat ttggattaag aattatagcc cctttccatc tggtttgcac    83040
```

```
ctaattctga tcctaaaaca aagtaagctt cttttcaaat tatcttttat ttatcaaaac   83100
catggtttaa atttccagca tgaatataca atttgccatt taaaagtaat gtttgaaagt   83160
tgtgacagct gaccagagac aaggcctact gaaggtgagt tccagtgctg tggagggaga   83220
ggtcatgaat ggtcttgatg aagcttattg catgcaagat catcacaact tcagaaaaga   83280
ccttaagatg ccaactaact atgttattgc tggggttcag agagcctaaa atgtggtgtg   83340
gattgtattg gcaatgtaac taaagagcaa gaatgttcat attttatgtg attttaaagg   83400
tattaagtat caatgaacta attctttcaa gagcagagat aaatgaaaca ttttatcttt   83460
ctgttttcct tcttactctc taggaggctc atgttgaaga caagtctgaa taggaatgct   83520
tgtagaagca ctcattaact aggattaaaa tagctagcat ggattcacca cagaccttac   83580
agtaattggt ctgcaagcca ttcaatcctg ccaccataac attagtcctt tttaaatttt   83640
ttaaatttta tttatcaatt tcaatctgat tttacatagt gaggttttca aatttcaatg   83700
tctttggtcc ctgcaagctt tattgaaaga tatattcatc tatccagggc taatggtatt   83760
tataagcata actgtactca catggatttc ttaagaggaa caatacataa aatttacatt   83820
acaacaaatt ttgtgaagac tttatataag tgtgcctcag cttatagaaa gtatagatag   83880
aaagtttaat ggctatcaac atcatagact ttatgtttgt aaagttaaca agaaagtcta   83940
cactataaag cgataataga taattataca taaagtatgt aactaatacc aacttccttt   84000
aataaattgt agggaatttg gcagtaaaat tacagcaatg tgctaaccta gtaactcaat   84060
cactgtgtat cacctctaaa attcatttta aattcaacag tataatttct cataagcaat   84120
ggcttactca ctcattgaac aaatgttgag catttgtgga gacatagtac ttattctagc   84180
caggtatgtt gttatgtggg ctcattttgt atatacagaa tataagaaat tatctgagaa   84240
aagacagagt taaagaattc aacagtaatg cttgagagtg gttattgttt ggcaaggcac   84300
ccagctgtcc tttctagaga gtaacaactt cagcattggg atgagaaatt ctcacttctt   84360
tgtacctcac tgaccagggg tgagcagagc tgctcagaag ctctcttggt gcctaatacc   84420
ctccattctt gttagtgatc tgaaactctg gaatctccca cagttcccca ttcatagagc   84480
ctgtttatct aagtgaaaaa ataagaataa aaaagggtgc tgtaacaaat acacaagaaa   84540
tatgaacggc gttctcaccg tgttcttgta gaaatgtaat agaaatttaa gctgatgtta   84600
ggtgacaatt aaaatctggg aggtgttttg tacactatca cctctttggg atgagatctt   84660
atgaatgagt gatgtctagt agaaaagacc tgtaatcata ggttttgttg accctttttcc   84720 tagataatag acgctgtctt agaagcgcca ctaacctctg atattttcct ccaagacctc   84780
tgcaaacctg tattctgctt attgtacatt gccatggcaa tactgtctag tctgcccatc   84840
caggtcccta ttcatatgac tcacttggct gctccacagg agaggagtta gcttcaccta   84900
accagcacca ctgtagcttc caggaaggga catgggaaag aatagcctgc caactagcca   84960
gcaggcctgc tcgtcccctc tttacttcta atagcaactg cagggctata gccagcacag   85020
atcactgtta atattaaaag cttgtgaatc atggcaaatc atcgtctttt atggtcagaa   85080
agaatgatgc ctcttataag tcttttctgc ttaattatgg tagaaggttt ctacatgttc   85140
ctctaattat agcaaatata atcagactaa agcttggtag ctaatgctat acttatagga   85200
agtgtacaga acagtgaata atgtagatgt tgataatata cacatgctaa agtatcctct   85260
aagaaaagaa ggcagtgtcg caaatgaaag taatttaagt gaaagtgttc ctatgaagaa   85320
tcattgtcgt cacaagcctg gcaacatatg aatgtataat ccctgtggtt ccttctgtga   85380
taatatgaac tcgatcttct tacttccata aaggaatgac aagccaagct ataggaacaa   85440
```

-continued

```
gaaagcaagc aaggcacaca agtattgcct acttttctt ttcttttctt ttttttgtg      85500 attacactgt cagaactcag caaatgccta tatccctgg tagcctttaa caggaacatt     85560
ttcattgtct ctgtcataaa acgactgtat gtcacatgga ttgagtgaaa ggaaggcact    85620
gagtaagaac tgtggattct gaatatcagg atatcctgtt tttacgccaa ggctctttgt    85680
taaccatctt gatcaatgat gccaaactag tctagattta ggctgtgaga taaacatttg    85740
ttcttgtata cagttccccg atcatggcca aaggacagca tgaacagagg tgaaggctct    85800
ggtttcccag acagtggtct cattatctct tttgcatgtt ttaagggtca ttcttaacta    85860
cagcccaaga ctcttgataa cagggctcac gtagaataat tgcaggacag gtttagtata    85920
gtatcatttt tcatcctcca atgctaatca gattgaaaat aaacctgtca ctgagcagaa    85980
gaaacaaggc caaggccatt tgctgcatgt gatcttttca cactggcttg ctgagtttca    86040
gatgattttt ctgtcacact ccaaagaaca tgagtccctg aagacttttg tgaaggctta    86100
gctattatca agccattgcc tcatggatga cttcataaat gtttgctttt gcatcaggta    86160
atggcataca acataaattg ttcctgactc cccactatac acacatatat ctcctttgac    86220
attagctaat aaaatgacag agagacgttg atttctgact gataatatca caagagctcc    86280
ccacacactg tctcctacaa atagagtgga atttacagtt ttataatgtc cttaacattt    86340
ttctttcaaa tgattatatt taaacatcta acatttatgc atacatttat agcaaagcat    86400
ttaatttcag caaccttcct gctcctaatt aagcagtcat ttactctata gaataagga    86460 gtatatcaat ctcaaaggcc atctttcaac atgctcacac ttgacactct tgtttcattt    86520
acccatgttt tctgtcacag gttctgatgg attaatttct gatttctctc aaagcctacc    86580 aaaaatttt ttatcataaa atcatttaga gtggttattt ttaggaataa ttaatattgt     86640
atgcttgtga aaaatataga tatttaaaat aaaatattag agttaataaa ataaaataaa    86700
ataatcatat aatgtgtttg tttgataaaa ttaagcttaa acaatatttt atttattaaa    86760
tttacatatt ttcttatata tatttaatat atctgttcac agtgttctta taataatcat    86820 caaataccccc tctcagtggt catataaagc aaatttata aatttctcat ttctgttatt    86880
tatccaccaa taatgtatat gtcattgtcc ttctatataa cactcctgcc tagtggttat    86940
ataaagtatg ctttgtaaca ttttctctct tttaaaattt acacatcaat aattcatata    87000
ccgttgttcc tccatatttg taagtgaagg ctccagaccc tcttcagatg ccaatgattg    87060
aggtagcatc gtcatcactc tatatctata ggacatagtt ttagaacccc cttccaatgc    87120
ccatgagtca aatgttatca tccatttgta cctataagaa atggctccaa caccccctt    87180 gagaggccag attgaaattg cttgaattca ttaaactgta taataaatac tttcaacttg    87240
tatcttccta caaacttaca ttatagtacc taatacaagg taaatgtcat gtaagtagtt    87300
gttataatgt attttttatgg acttttggtc tagcattgat atcaatctat ggcttcacaa    87360
atgaataaga ttcttttgctt tgattaatta cagttgcatc ttttccttct gtgggtgtgt    87420 ttgctgttttt tggagggtac taggttgtag aacagtttgg taatattttt gtctgttaga    87480
ctggtatctc aagcaccagg ttctatatcc aatctgccct tgtgtactct ctatggcaag    87540
tctttatcca acagcaaacc actctgatat taaagaaagt ggtggctaaa tccacatact    87600
tgttaggtgc ttattagttt gaggagtcaa gtgacttcag aagtactgtt taattagtag    87660
ggttatgatt ggaaagggaa aagagagttc agaaatgatg ggaaacgagt gacacgtatt    87720
agattattag ataggaatta gaggaggagg atatgtgtgt gggaataatt gatgcaaagg    87780
ggagaaatgc catgtatgtg tggaggttag agctaggaga ctaaaaggag taggtaaaaa    87840
```

```
tacgtactca gatatcataa accaggtcag ccgctgatct ttgggagatg tggcaataag    87900
tgggaaaggt acagaaagaa ggaaaacacg gaaaagaaag tcggaaaagg aaagacgatg    87960
agggagataa ggaagacaag caggaggaga agaaaaggaa gagagggaga gaaagaatgc    88020
caatcagtaa caggtggaga gtgaagggcc ctgggttgaa ggctacttca tctactagac    88080
tgtaaagaca ggaaatagct gtgcagagag aagagctaag cagaaatagg aaatctctgc    88140
cagatatgtt actggtggag agatatggac aatataagga aatgaggcaa ctggcttgag    88200
tgctgttttt tttttttttt tttttttttt ttatcatcct agtggatctg gggcttaggc    88260
ttccttggtc ctggtctttg ctttatctct gttgagttta actggtccag ccgtcttttg    88320
tactcacatt tctccttgca tttggagttt cttgactatc ttttgtgaac tgtggatagt    88380
gtggatgcaa actcttccaa actgagttgc tgtgattttt tgtctttttt tttaattagg    88440
tattttcctc gtttacattt tcaatgctat cccaaaggtc ccccataccc accccccca    88500 atcccctacc cacccactcc cccttttttgg ccctggcgtt ccctgtact ggggcatata    88560 aagtttgcaa gtccaatggg cctctctttg cagtgatgtc cgactaggcc attttttatg    88620
atcaacagag gagtctggct ttgtggtgcc caaatgactg ttttgagctt gccttcctc    88680 acgggttgc tgatgatggc ctgagcagca gtcacagcaa acttccttt taatatctgt    88740 acaagcacag ctttttgtaga ttctttgata ggaacctgca gtccactttt ctggagtgtg    88800
atagaaaagg caactgagtt ggaagctgtg ttgaatttag attcagctgg aaatccaggg    88860
taatggcaaa gaaggtgtgt gcatccaaca attgactttt gttagtatgt tgatcaagtc    88920
aatacagagg ctagagaagc tgagcatcat taaatacttc tatttacttg ttttcctaa    88980 gtaaggatat gttttagcat ggcttctaat caccattctg tcccagttta atatatttaa    89040 atatatac ttacttggat ctcattaata tatttaaata tatatactta cttggatctc    89100
attgaattga aaaccacagt tctatatgat aactaattgt ttataattta accagataga    89160
tgaaatgaaa atatattatt aacatgtgta tataatactc agcttaaaat gagggggga    89220 tgtctccatc aatgtcctcc cctcagatct tagggaaccc tgtggaataa aaagcagaaa    89280
gaaccagagg agctggagga caccaggaga acatgcattc tgaataaaaa aaccaggctc    89340
atgtgagatt gaataaccaa gcacagggcc aacatgggcc aacactaggt ccccggcata    89400
catatcacag cttccagttt agtgctttta tggttcttca agtgtgagaa tgagtgggtc    89460
ttgtgccttc tcctgggttc ttttcattct attggtttat attgtgcaac attgatatga    89520 tcattttgt tttatgttat tatattttat ttgctatatt ttattattat ctcttagaag    89580
cctgttcttt tctaatgaaa gacaaaaggt ggctctagat aggaggagta gaggatgggg    89640
aaaatgtaat caggatagat tgtgtgagga aagaatctat tttcaacctt aaaaaagtgt    89700
gtcctgatat tttgtattta tatcataata atcatgtctg aaacaagcag tcaagttcta    89760
attagtttct tgtgctattg tatattttttg cttttgggac ccacatagac ttgtaaacag    89820
cgttactatt tttgaaattc accataactg caaactgaag ccgtcttcac tgccctggga    89880
gcctgactgg atgtctgagc cttatctttc caaaccctct actgctgtac aatatggtca    89940
cataggtgca tacacaagcc tgttggactc agtctccaag ccataaatag tctgttgaat    90000
ggcttaattg gagtctagaa atggagctgt tcacatatca tgcctctttc tttgaatccc    90060
attaccttcc ttatgagttg atgaacaaaa actgttaaca gttgaagtct tcaagatctt    90120
tgtatttaga ttcagtcagt gaataaaagt tcccagaaat taaaaaatgc cacccatgat    90180
tggcaactat cttttatttt gtcttaatcg tgtctataat tatctttaac aaatgactga    90240
```

```
ctgcatgtgg gcatttgttc ctgtagagga tatcaaacat ggttttgaaa catacaaaga    90300
tttggtgttt attgtgaaac atattaaaca cactttaaaa tcaaactgat tgcttaaatt    90360
taattttaga ttaaaaaatg acaattcttg agatcaaaaa aagcaattca ataactcgat    90420
taaatataaa ctttattcct aacagctatt cagctttata taaacttatc actgactgat    90480
gatgttatag caaatatgtt tttaaaatga atagttatgc tgtgttcatt ttctttttttt    90540 tttgatgtgc actctgagct tagtgctttg tcttttacta gtttattaat ttatataaat    90600
attaatgcaa aataaatcat aataagatca tgtagtaata catttttttca agttattcta    90660 gattttttagt ttttttttaa attaggtatt ttcctcgttt acattttcaa tgctatccca    90720
aaggtccccc atacccaccc cctcaacccc ctacccaccc actgcccctt tttggccctg    90780
gcgttcccct gtactggggc atataaagtt tgcaagtcca atgggcctct ctttgcagtg    90840
atgaccgact aggccatctt ttgatacata tgcagctaaa gacaagagct cccgggtact    90900
ggttagttca tattgttgtt ccacctatag ggttgcagtt cccttttagct ccttgggtat    90960 tttctctagc tccttcatta ggggccgtgt gacccatcca atagctgact gtgatcatcc    91020
acttctgtgt ttgctaggcc ccggcatagt ctcacaagag agagctatat ctgggtccta    91080
tcagcaaaat cttgctagtg tatgcaatgg tgtcagcatt tggaagctga ttatgggatg    91140
gatccctgca tatggcaatc actagatggt ccatcctttc atcacagctc caaattttgt    91200
ctctgtaact ccttctatgg gtgttttgtt cccatttcta agaaagggta aaatgtccac    91260
actttggtct tcattcttct tgaatttcat gcgtttggca agttgtatct tatatcatgg    91320
gtatcctaag tttctgggct aatatccact tatcagtgag tacatattgt gtgagttcct    91380
ttgtgattgg gttacttcac tcaggatgat accctccagg tccatctatt tgcctaagaa    91440
tttcataaat tcattctttt taatagctga gtagtattcc attgtgtaaa tgtaccacat    91500
tttctgtatc cattcctctg ttgagggggca tctgggttct ttccagcttc tggctattat    91560
aaataaggct gctatgaaca tagtagagca tgtgttcttc ttaccggttg ggacatcttc    91620
tggatatatg cccaggagag gtattgcggg atcccataac cccattaaaa aatgggggctc    91680 agagctgaac aaagaattct cacctgagga ataccgaatg gcagagaagc acttgaaaaa    91740
atgttcaaca tccttaatca tcagggaaat gcaaatcaaa acaacactga gattccactt    91800
cactccagtc agaatggcta agatcaaaaa ctcaggtggc agcagatgct ggcgaggatg    91860
tggagaaaga ggaacactcc tccattgttg gtgggattgc aagcttgtac aaccactctg    91920
gaaatcagtc tgtgttcatt ttctaaaagc ataattaatt tgacattaaa ggaaacatct    91980
agtgaccgaa tatatactcg gccatagcca ctgcctctca aagatttcct attttactta    92040
gagtaggtca atgaagatat aaaatggttc aagttaactg acattgcaag aaaaactatg    92100
accctagaat cctgtgcatt gaaaggatca tgcaatacag agatgagtgc caattcctac    92160
tgtcacatca gttgcaggtt tccattgttg aaagttaaat ggatgcttac atgtactcca    92220
tcatggagtt aaagacaatg acaatggcat gtctgtacta aaagaaagct ggttaggaac    92280
agatgaaatc ccgactgata gagtttcact agttattcag cttatgtgtg tcttcccttg    92340
tctgttcaac agctgaccta tagctgttta gtagtgagta ggggagggct gagcaatgag    92400
tgtgtacctg acaaggcact gaagtaggtt tgtggctttt cataatctta gacactatgt    92460
tggtatagag atggatctgt aactgctaat cattgactct ttccatccca cagctcattt    92520
ccttaccccg aacatcttca aacctagtag cttgagacta aacatgtttt tttttttttg    92580 ttttttttcat tgtaaatgct atctttgggc aacaagcctg cttcccagac cactagcgat    92640
```

```
ttattagcat ctatcagctt atctcataca cttgagaatg aataagtttg ctttgacctg    92700
cttggctgtc cttttgaaa ccagctacct atgagttact cagagaggaa tcatgcaagt    92760
ctgttcccct tgctaatgac ctagtttctt gtgtctggag tattccagct ggagagtcct    92820
ctgtggatag cagtgcaatc cttcatgcca ggctggaaat aagcactgct tccttaatct    92880
ctcccatagt tacttacatc tattgtgatt ttgtgaatgc aggcacatac atatttttca    92940
aattattata aaataacagc atatgagata tgaatgtaat acagcccatt ttatatatag    93000
gttatacaga aagcctgcat ttcaatgtgg aacatacaga caaagaatca aaccatatca    93060
caatagcaga ctgtcaggga tggtcccatt agattgtagg attgacatat tcaaagcaga    93120
aaaattcctg tatgaagttc gaaagatttt gagaatcttg tgtcttaact tcatgaaact    93180
gcagtctgag ggtagatgga ttaggtcagt tatagcaaga ataaaatttt aattttgtat    93240
atacacttgt taatatttta tgaaaagaat tattattgtc tagcttaaga catattttac    93300
ttataaccag ttctaatcca gaaacaaact tggacaccaa tactgggatg gtagtggcca    93360
gcagggtccc aaaatgcatg tatatgcttt atacagatgt aaagctcttt tactactttc    93420
cttacgaatt tatacatgca tatgtttgtg aatgctaaat tttattggtg atggttgcta    93480
aaatgatttc cacttactaa taagaaacat atcactcttg agctaatgca tgcacttctt    93540
tttttaacct tcttagaata ctggaagaag aaattacttc aaagtgtaca taagggcttt    93600
caagtaattt tgtgactaga gagggtataa atggttggtt tatggcttca aaaccatcac    93660
tgaaagcaga tgtatagtat ggattcccct acctccatcc attctctaga tgatgagtat    93720
ctgggcttgt tccattgcct atgcttgaga agggagatga agggaggaag agagatactg    93780
agagaacaat ggagaaagaa atcaaatagc tcacgttttc tctcatatac agaatctaga    93840
tttaaatata tattgctcta agtatgacag gaaaatacaa gtgaagcatt ggggaagaag    93900
agaggtgtcc gtatgaagga gagaagggtt aaaagaggac aatggggaga atatgatcaa    93960
gtacagtgat gtaaacctag ggaaatactg taaggaaatc aatcacttca catgctcact    94020
taaatattta atttaaaagt gaacttggaa tttaccaatt gaaatagact cagaattccc    94080
acattctcaa agcatttgct ttcatgggtt gcttcaagta gcaagacatc ttttaaagt    94140 gttgaggaca aggctgtaga ttttgctgta taaaagatg ctgaaagaaa gaaagaaaga    94200
aagaaagaaa gaaagaaaga aagaaagaaa gaagaaaaga aggaaggaag gaaggaatta    94260
agaaaaaaga agctccgttt acaccagtat tacatgactt tatttacaaa tggatactat    94320
tctgtctttc tgctggcagc tttactgtct gcttgctcaa tcttctactg atctccttgc    94380
tagactttag acactttatc catttgatgt aatcttctca gaagaccaag gctgcagtta    94440
cagtccacat tcaatatctt attcttttcc tttattttga acataagtaa cacttgtctc    94500
taagtaacaa ggtcaaggtt tttgctttat ttctgcctcc ctcaaaacat ttctcttcct    94560
ctctacaagt ttcaaactta ttcacaaagg aatattgcaa tacggatgct attgtccgcg    94620
tttcttcctg gaacaagtgt taattgatct ctttgggtct atgtgtagag aggagttggg    94680
acctaggaaa ggtattatct ggggagttcc cttgtccttg gaacagaaca aagagatgct    94740
gcctacaaag gctttacctc cccagggctt ctctgtggct agactcaatt acagctggag    94800
aagctgtggc ctatgtgctc ccaaggccat ttgacaagat agtcagctgt ttattcttgt    94860
ttcttccctt gtacctgtac tcctcagaaa acattcttc gaataagtga cacatttaat    94920
ctgcaatctt caagggcat agtgtgttca aacacaaaaa taaatgagac aatgcaattt    94980
ctgaaatcga cttacagcga tatcccatgg gagtgtactc caaaccatcc acccaggctc    95040
```

```
attgctcttc taggcaagag ccattacaga gagcacagct ggaaacctgg aaaacagctt    95100
tccctagcat ttgtggttgt agagcttttc ttacctactt aggtgacatt atagtactta    95160
cagagtctat aaatagacta agatatttt tgaggttaaa acagtttaaa ttgtacagat     95220
tattagaact aaaaaaggaa aatgattcca ttacacttga ccttagttta cgggttgctc    95280
tccttagact agatgaagca ttttcaaaa gctaaaaggc tgtggcgatt gcacagaagc     95340
aaaaacaaca catatcatag acgttatctg attatttaat ggacaggtgg gaagattgaa    95400
acactgcttc ataagacctg aagtgggtta gccagtggga agactgataa gcattatcta    95460
gggttgaacc tgtgctttct actgcagaat actacaagtt acttataaaa ctgtgaggtg    95520
gtagggctct aatcagtcaa atagttatca gggcaatgcc tgagtcagtg aagttcttgc    95580
cattcacaag acaaatacct ggctcctgta cagccagcct atgctagtca gagtcccagg    95640
ctaaacagac accttgtttc aaaaaacaaa ttgtacatat cctgaaaaaa tgacactcaa    95700
ggttgccctg tggcctgcac ccccaccacc cccagacata catgtgcaca catataaata    95760
aaagagaaaa aaatagtaaa attgagggca tgctttggtt ccctagttct aatgtccatt    95820
ttctcatgaa actgaatgct gacaaaactt gacaaaagcc aagaatcaca cagggtctca    95880
gaacaacctc tcaaaaagca tgcctaactc aagtgtgacc taaataggct tcttaagtac    95940
ctgcatctta cctatatcta acatacaaag ttgcccgttg ataaccactg tggaagaagt    96000
gccagtcttt agagatgcaa tctgagagtg acagtataat gatccattgt gttatctgtt    96060
tttgttcttc taaatattta atagaagttt gtaagaagat gtattagttt ctgagcaatg    96120
tgaccaaatt taaagccaaa tctagaggac actttcgatt tcagaataag atgtcaaatt    96180
aaaaaaaaat ttcatatgta aagcaatatt tgtgtgtgtg tgtgtctgta tacaatcaat    96240
tataaagttc ccacatgtct gtaatagctt tactgtagta ttagaaagtg tgtaatgcac    96300
actgaatgaa ttcaatggta ctttctatta ttttgaaagt aaaagtattt ccccatcttc    96360
ttgaaatttc agaccataag gtgaagactg gtaagtggtt tctgccatac tggcttgctg    96420 tccctaagc atgaagccac acatgaatgt gctctgagag gccctggggt ctggtagctc     96480
agaatgaagc cttgcttcct aatcatcctc tgtaatggag agctctgggt taatcatctt    96540
cagagtaagt gtaatccttg atgacaccta ctgagactga gctaaagttc tgtaaaggga    96600
acttaaaaaa aaaggggcca ttccacgcta gtgccggcta ctctctgacc ccggcagtct    96660
cgctacctcc atggctagcc ccatgtagca accttacatc tcgtggttct cttttttgcag   96720 attgtaaccc gataaaataa aaactctaga ggcttgtgat ttattaatca gatttatatt    96780
agtaaattct caacccacaa aatgcctgca caatgaactc aaaactcaat taatataaac    96840
acaagctaca cccctagatg aggcacatga accctactta ttatttaatc acctatgtaa    96900
gaaatcccca atacttaccg ctcccaggac tgtttgcttc tggctcctct tcctctccta    96960
ctggttccat cttatctctt cctctccccc cccttttt ttctcttggt ctctctgtcc      97020
tcatctctaa aatcctcagc ccactttcct tgtctactgc ccagtcacag gctctcacct    97080
tatcttgtaa ctgtcctcac ctgcatatag acagcagcct tcaaagttct cagtgtgttt    97140
ctgacaagga ctaaatcttc agaaatgtgt caatgtaagt cctctgccct acagccccct    97200
ttattgtcaa gattctgtag atttaaacct tgcccacata actcatcttc tggcaatttc    97260
tgagaaactg tgccttctgg taatgtcaga agctacaccc ataaagtctc atcaatatga    97320
ctgcctaaac atgaactgaa caatgacaat gaaatgctaa actggaagga aaagagccca    97380
tgggatctca actctacaca aagaactata ggcagctaaa gaaatctgat aatgagagaa    97440
```

```
atagtcttcc ccagggaaga gcacaacaac tggctatcca ataccagaca gctctgaaaa    97500
tgcacacata agtaacatta taaagactga agaatattat atttagaaat atgtatagta    97560
tatatataca tgtacatatg tgtatgtaac aacaatgaat gaaaaggtg ccattagttt     97620 gaaaaggagc aagaggggt atatgggagg ggttagaggg aagaaaggga agtgataaat     97680
gatgtaatta tattaaaatc tcaaaacaga aaagaacaac tcaatatcaa caatgcgcat    97740 gttttttccta tgatataaga aaatcatata tgcttaggac agtagttcct tttaaaattc   97800
agccacaaat cactgagagt ttccagttta aaaacagtta aattgtctca catatttatg    97860 cttttccattt tcaattttca gtttaaaatt gagaaaaact tataaaagtt gcagataatg   97920
gtatgtgatt tccttatttt taagatcttc atcaccatat tggaataaag gcttttatgt   97980
actccagaac tgtccatcat ggcactctat gtggaagggt acttgcatta gcacataggg    98040
aagaaataat tccattagaa ccaaggttga ctctcatctg tagaatctaa gaatagggaa    98100
caccattggg ttactcttct catatccctt ttcttcttgg ggcatatctc ccagccttag    98160
cacaaaggac ttaggagagt aggtgaggga agggagtcca agtttatcag tcaagtaaca    98220
cattactata acataggcag cctctgaatg tctctgggaa atatgcttta atgctcatct    98280
taccatcaca ttgttatccc aagagaagcc cttgggctag atgtgggcca gtctccagtt    98340
gatcacttca gttctcagct cactcctcat cttgctgtgc tttctcacct gacagtggtg    98400
atacagtgtg aagacaattt tagccacttg atgacagcca gcacctggtt cacatgtcta    98460
tgctagttca aatgaatcag ccagaaagta tattagaatt catcaaagat gtgtgaattt    98520
caaaatgacc tatttcttta aaatgtgtaa aagtacaatt gtgaaggctc attctagaag    98580
attctttcct ttgcttctcc cttttttcctt aaatctctga gtgagaaaat gtagctgaga   98640
agcaggcttt ttatcttaat atctccccaa ctctgttaag aaataaaaga ctaaaaataa    98700
attactttaa gattcagagc agcaacctgt ccccagtgaa gctctcttaa ttaatgtggt    98760
gacctgtgta gagaaaaggg acaactgcag agtctctcag taattatcca accaaagctt    98820
cagataatta cagtagggag gttttttgaga cacaggacat cctgaaaact tgaacttcct    98880
tgttgactta ggccttctat tcattcatgt tggggtttgt aattgacaaa gtcagagcat    98940
atcagaaact cacacattac taaagtctct gtgtttgtac ttgacaaaga cagcacatat    99000
cagaaattca aacactacta aagtctctgt gcgagttctc aacagaaaat aaagtgcctc    99060
ataaaatggt ggaaattagg ggattagcta aaggtaaaat tgagaagtgc tcgtgcagta    99120
ctgagtaatg tgggccagat aaaagatata ttttatatag actataagat atattagaca    99180
gcaaattgag aactgttgtc aaagattgat accagacaac aatatgttgt attcataaag    99240
agtattcttc agcactccaa taatgggcag tgttggaaaa tctttccaag gtgctgtatt    99300
tatgaatgtt caaactactc attagctaaa tttccttttg atttaaactc ataattggta    99360
atcaaaataa atttcaattt cccccctttgc ggctttaaaa aagtggaatc tcagtggcct   99420
tcaggtgact cactggactc gtacattcag tcaatctgaa accacataaa tggatttggt    99480
ttcattaaaa ccatttcgcc ccagtggctt tctaagccta taaaaaaacc tgctctcagt    99540
gacccagtct aacttaaatc acagcagtgc tttctcaaaa caataaatgt tatcttttcc    99600
atgggagtca agatgagaag ctaaaatcac cttagagacc aagctatctc atagatgtcc    99660
tgtccttcaa taaagaaaga atatttgctt tgcactgagt ggccacagtg ttcattttag    99720
ccacagacca tgcatgttct ttttggcaca gctatgtagt aggctacaag atggaaggct    99780
tatattgact gttctcagta ctctcctcat gtctcctggg ttgctctcct gctttggtag    99840
```

```
cctttctca caggtgcctt tgctgcacag tactgtgtgt tcattaagca agagagtcat   99900
tgtttcttcc agaaagagaa ggcctttaaa agaaagggtc tgtggcaaca atggcctgta   99960
acatgcaaag cagatgaaat gataagttaa agagtggttt gggagcaatc cgtagcagct  100020
ccatttcaaa tacagtcaca aatggttgca tgtaatgaac aataacgctc ctcaactagt  100080
tgcagcagat tgctgactca tccggtacat attttgatgg tatatgaaga aaataaaggg  100140
aaattctaaa ttttctaggt gtgctgttga tatgcagcat attgggtact cagtcaaatt  100200
gtaatttatc agtgcaatgg acgtggcctc attcattaat cagtagcagt ggattgtatt  100260
atgtatgtct tttggtagaa atatgactta gtttactgct gtggttttca cacttgttcc  100320
agtgaatcgt atagatacat tttatgtgtc taagtcatat aatccagcag aggcaggtgg  100380
atatctgagt tcaaggccag ccttgtttac agagtgaatt ctaggatagc cagggttaag  100440
cagagaaacc ctgtcttaaa taatcaacca accaacaaac aagatatttc tcccccaact  100500
ctatatatcc tcccaaggag tctttgatgg gggcagcagc tagcacaaga ggtggtatgc  100560
actgcccctc cacactgctg ggctttcaca cccatcacat ttgtgctacc tacatcatga  100620
tcaatctgca cagattgaat gttcaagtac tagacacaaa attatgattt aaggaatgaa  100680
taataagcaa gaagagccac agtttcaggg gaaaatgcca gcattcaaca aatgtcacta  100740
ggaaatagct cagaattgag agttatcaaa agcaagtgat agaaccaata tgcattctat  100800
ctatttgtga aaatctcaag gagtaaaaat gaaatttaat taaaaaatta agtagcaag   100860 aatgtatcaa attcggtaag tcgaatagta agtttctcta gagagataat acaaaaaaaa  100920
accaatattt gctcagaaca aataaataaa aacagatcca tttgtgtttc atttcaaaaa  100980
gcaactctca atttttaaag ttcattgtgt aaaatcactt ttgtgtaagt caatttttatg  101040 ttcaaatgat atttttcttt ttagatcttt gttggtttc ttttacatcc aatatttaa   101100 tacaggaatt taattcatga atttgatagg attatatttt gcatatgtgt tacacatgtg  101160
tttaacttgt catttagtag ctgtgacatt gtagggcacc tgactccttt atgtcccacc  101220
tagctgaaca tgctccttgg agaattgttg ctgttacttt ggacagtatt ttttcattat  101280
aaatacaaac agtctgtatg ttatttttgtt cttaaaagat taataatttt tactgtcttt  101340
aatttttaga gaaaaatgaa gacatcaggc tgactgacta acccctaaat ggcaaggccc  101400
aggttctatt tgttatgctc cacttcttcc tcaacaatgc ccaggtccca ttagttacac  101460
attgcctctc tcagcagttg gctaatttcc ttctaattta ttttttcagac tccattatag  101520 aacttttcca attacagcta catctcagca cttaagaccc atgctttggt ttaacatttg  101580
cacggctgca gactgagctt gaaggccatc actgtcactc cagagataga gatgtactct  101640
caagttttac tactctaaat aagataggtt gaattcctgc ttcacagggt tacttggtga  101700
ataaatgaat ccccctttct cttttgcttt cttattctgg atcttatcag tttcaatgag  101760
aaaagaaagg gtgtgtcatc tttggactct cccatcaggg tagaggacta ttgcttatac  101820
attagccaga gatttatgtt tgttggctca gctgcagact tatttctctg aactttaacc  101880
acctgtgacc ctggaactta cttcctattg taaccatcaa tttccagctc caatgaatgc  101940
tctttgcatg caggcagctc ctgccagtga taacagccct ctgtaggaca ccaagactag  102000
gacccatagc taccatggct agtgttgtag ccttctgaaa cagttcttcg ttactattct  102060
cctcatctct aaagcactgt gtcatagttc caggattgtt tgggttgtca gctgttgaca  102120
gcatccagga tacaaggtct aagtcatctt catgcctggg ggcttcctgg aacttgcagt  102180
ggaggtaggt gtgcagctta ttgtatctag ctccttacag ccttcatggt cttcatgacc  102240
```

```
tctgctcccc gtcatctctt ctcagctgtt ctctggagct tttcagcctc tctcttcact 102300
gctgtgcagc tgttctcctt tcttttgttg ccatatcagc tactctactg atggctaatt 102360
gactgacagt cggtcactca gacagggtac cagagaaatt ctagcagctg tcagttagcg 102420
aggtacactc cacaccaacc cattccatag tttatttaaa agaaaagcat gcgtcaaaat 102480
agtgttcagg ataaaggctt atcataaata ttactgatgt tttaatggta tttagcaatt 102540
tctaaatctg cccagtgcct cagttacagt ggcctccttc tcttatttgt ctttaaaaca 102600
cacttatagg ggctggggac aaaaaaaccc acacacttat atatctgata tctttaatgc 102660
atcatttatg gtaggtttga agaagcatct ccgacaatgt ataccagaca ggatttatgt 102720
gccctgaaat gtcttttttt ctatagctag taacagtccc tgtcttgatg atcaatcaaa 102780
cacaaattcc aataactggt caatgaaaac atacatataa gtaacattat atggagtcaa 102840
caggctatgt tagaaatgta tatctatata caaatacatg tgtatgtgtg acataatgat 102900
gaaaatatga cctcaaattt gaagtagaac agagggtggt atatggaagg atttagagga 102960
agaaagggag aaatataatt aaattataat ctcaaaaaat attaaaaaat gctaaaaaac 103020
caatcagttc atcccctttc tttctaacac ttatccagat tcacacagtc ttggaatcca 103080
cagatctcac atttctgcat attttaaaca aggcaccaat tgctttcgct tgggtctgcc 103140
ttcatgagga tattagcaca atgatcagcc ttgaaaggta gaagtagttt ctcctcctga 103200
gtcaaagaca gatgtgagtg tgtagccttta gtcagatgct cggtttatag tcattcctta 103260
taatttaaaa aaaatctgga ttggtgagat ggctcagtgg ttaagaacac tggctgttct 103320
tccagaggac cctgttcagt tcgcagcatt cacatggcag ctgacaactg tctgtaactc 103380
catcccagag ggtttggctc cctcacatag acatttgagc aggcaaaaca tcaatgcaca 103440
tgaaaataaa tcttaaaaga tgctatttcc ttaagttcca aagttctctt ctatcatgaa 103500
cccagtgact gggagttttg gtgtctttaa actttcctgt gagaattggg acgttccctg 103560
tggctttggg atttccatgt gagatctgtg ctctggctcc tgctattttc ataaacagtc 103620
atgtaacttg tctcaaaatt ttgtattttg tttcaacttc tatagtattg atcttgacaa 103680
atgtgataat ttacaagtag tacaaaacca aactgtggac aacttttaag taatcattgc 103740
caattcaaat gaagtaaatt atagctactc catcttcatt tttaatatgc aacctgtcca 103800
acataaggtt tcgctgtcat gtgcacctga tcctcatgtc ctgcagccat tctgcaggtc 103860
actgccagac tgatttacct gaaaccaatt ttcaccttat agctgtcagt caaagcatgg 103920
tggttattaa atgtgcaagc cctgttggca agtgttcccg gtactcatct acctccaatt 103980
cccattagcc cagggacagt atcactttc ttctgccata ttttgtccat gatatatccc 104040
gtgtttagtt ttcccagcta gcctcaaaat attgagattc aatactgatg tttctgggag 104100
taatcgctcc tcattttgaa tgtgttattt ttacgtctca gtgccctaga ccaaggttat 104160
atagtcttct gttttttcag atctcacatt ttatttaatt ttctagaatt gatagtttga 104220
ggtgaaactt atgtttcact atatactttg caattattga cctcattcac agtatataca 104280
aatgtttata ctgctaattc ctccttcttt tgaagaacca atatgctgat attagtagga 104340
acactgtaga tttgttggca ttaagcatag atctcatcaa ggagttagaa tgtagagaaa 104400
caacattttc tattcaattt catgaaagtt ttttagtttt tctgctacat aaaaatacaa 104460
tgttcttatg acttgatcaa ttcttcatat aaaataactt aaagtctaca ttttcagaag 104520
tcttataacc tcttaaccca caaaatatat catggttttc aaatctggct actatgcggc 104580
gagttgctgt cataagcatt aatactgtgt gataattaat tgtcagcttt aagacagtaa 104640
```

```
ccttactttc tgtgctgtgc ttatgtcaca gttgtgtctg tccaatataa gcaacataca    104700
gtttcgtaga gagtacatta ggtcttctgg gagtttgaag acagagactc aaagaaaaag    104760
tcatgctttt cagagagttc ttaacctgct ttacttaaag agaaccagtg actgaaatat    104820
taagagctgt tttcttggca gcatcataag aatcaataaa agactactca ttctccagaa    104880
ccaaggctgg aaagttgtcc caccaagtgc tttgttgtca cctcagctct ggctgctgtg    104940
ggtaagcctg caagtgaagg atcctggcag ctgcactttta gtttctgctc tgtgcctttg    105000
tctcacacca ggtgcttcct acccatggct agggcttcag cacctgttcc tacagtctac    105060
acctaaattc ctgggcagct gagaggtggg gatatggaat atgtgtccca ctttgacaaa    105120
gacaaacatt gaggttttgt agagtctcaa atgaaactaa ttggtgaaag cagacaaaaa    105180
gtttctatta taaaaagata aaaaatgaag cctattctga agaaaaactt agctacaact    105240
tgataatata aaaataataa gtactcatta attaaataat atgtgtttat taaaatacgt    105300
aaacaaatta gatgctatcc gagtacatag ggtctcagta aatattctgt tatataacta    105360
tgtactggtg attactggct actctatgtc accgtgttta atatctctaa tgtcacaggt    105420
accatttgcc acatggcaag tcagttacca aatattttgt ttagagcagg gaggggtata    105480
ctttatccag agtttccaat caacccgtca tatgtgcagt tttgaggaag ggactctgac    105540
acaaggtgct tggagtggtt ttgtaaggaa gcttttatttt gttccataaa gtgataaagc    105600
tggccatttt ttacagatgt acttctctgt cacatacgca tgcactctca ccacagaaga    105660
gtgcctgcag ctactgctca cattcataaa gatgctcaca ttgtcttatt acagatactc    105720
tgtctgtggg aaactgagaa ttcctgttga acattcataa gtagatctaa aggaaccatg    105780
ctgaaggaag atccattgag aatgttgagc agagctgtgg attgacttat tgagagtttt    105840
ataatgtgtg taatccagaa ataatggatg ctttagaagt aattaaaaga ctataaataa    105900
acacttagtg ccttaatata aagaggagaa agacaacatt gagctcatca gctgtgatga    105960
cgaagtaatc tttctcttta aacgctatgt gaataagtaa gcaaactaca cttgatgact    106020
agatacagca tctgcctcat ggacttaatg gatcatgatg ccttattata ataatcaaag    106080
tggacataaa tgcaggggct taagagggat taccaccttc agtgctcagc aaagctttgc    106140
tccttgtcag caggggagaa gaaagcactc aagtgatgat aattcaaact attctagttt    106200
gaagttccta gtggcagaac ctccaataaa atggcttact acaaattcag aagataacat    106260
tgtctgagca gctctcttca ttagaagcaa tgtgttcatt gccccctaaa taaaaggtc    106320 catttttgta cttggcaaaa catcaggcac acacacacac acacacacac acacacacac    106380
acacacacac acactcaact cccttagctg tctgagatta ctcctcttga tgcaaatagt    106440
aacaagcttt aattaatacc agaggtagtt gaggtactca gacattaatt atacctcatt    106500
catggaatct ggcttaatgt tttattatga aaggtttatt tacaagaagt gtcacaaaat    106560
acaacataat aattaggagg gcagactttg gaaccaggtg tagtctgttc tgcagtgggt    106620
aaaatgggaa tcataatggc agccttctct aaggactagt ttgagttcag gtaaagttta    106680
taccgtcttt ggaatgtgtc cagaccccaa taaagcacca aggagagtct ggtttgttgt    106740
tattattgtt gttttttaaac tgtggtttat ttataagtaa gatgggcaag aaatcatttg    106800
gtagcatttg cttttaatta ccttaatttt ttttaaaatt taacttagtg tattaattta    106860
cttagtttta aaatcaagcc tcactctata tttcatcctg acttgaaact tactaggtaa    106920
aaatgggtgg cctcaagtcc ttggcattcc tgcttgagtc tccaagggca gtattacagg    106980
catgaagcac catgacaggt tttgccttgc atatcaggtt tctttataat ctagtttaga    107040
```

```
gttcccctttt atcactaatt tgtccaaaca gatttgaagt tcccagaaat actctaagtt 107100
tagaaaagtg accactggca cgatgtgaca atatttaact gtgacagtat tttcaaatcc 107160
ttctgaagtg tattgctgtg atctgcgtgg ccctacttcc tcagtgctga tgatcccatg 107220
gagacactga tagcacagtc actttaatag gctggggccc agtgaggaac ttttccttct 107280
agatggtaga cctggtagac ttcacttggc ctcagctcac attcttgctt cagctttctt 107340
aaagcctttt aatcactcag ataagaaaga catagcctcc ttgtgtacta taagaacat 107400
atctaataaa aaaaagagt tcttggtttc atatctattg atttctaagc cttcagtcta 107460
tgtcagaacc tcacaactct tgtcattttt ttggatacaa gcatcttgtt ttgcctgaag 107520
cattttcat cagtcttata gtaagataga ctatccacca tttctttctt tgtttaaagc 107580
aagcacccgt gccatggttt gctaaagtgt gaatgttccc tcttttttc cttcaaattc 107640
ttcaccattc cgtaaggtct tctaaaatga aagcatcaat cctgttttat agatggccaa 107700
agtctacctt ttttattcag ttactgattt taggacttcc tttcaaagac cattgcatta 107760
atgaacagga tgcagccttt aaaagtccaa tctatacatg tttaaagtaa tagtaaaaag 107820
aacctcatgt atacatgcaa tcatacaaaa atcatacatt ccctcaacag tcctaaagca 107880
ctggaaatgc aggttattct caggtttcca ttgtgtgtga gtatttccac cagaacatat 107940
tcaaataaca ggaataaaag ctggcagtgg ttgcctcgct gtgtaggctc attagatgag 108000
tcagctaatg acagggttgt gcattcaaaa gggcaggcac tctgccactt accaaagaga 108060
atgaggatta agatagcatg ttacctcctg aaaactagag ttaaaatgc ttttgcctag 108120
atacctactt agtgtgccaa gtgttttata caactggggtt tttgataatt gattaaaacc 108180
ctcttaaaag attcttcaag tatatttaat atattatctt gctttttcct tgtctcccaa 108240
aacttttaaa agaatgaggt aaaggagtgt ttatctattc tctgtactgt tctgtccctc 108300
taagagacta aatcactgtg ccagagggga ggagaacctg agcaatcaga ctttcaaagc 108360
agaacacagg cacatgttca atgagaagag gagtacacgt catttccatg taggactaga 108420
ttctccatga atgccactga actgtataaa aatttataca cataaaaatt tattgtattc 108480
acaatctgaa aagtgacccg agaagagtgt gttttcggca ttgcttatca gtgttcccta 108540
actttgctat tccagtgtga cacatgcaat tgatggcata gcaatttcct gttcactgag 108600
gaaatcttgc tagatgtaat gaagctggat gtgccataat aaatgagggc agataagtca 108660
ctctgatcag caagtagcct ttcagatgag ctaggaaact cctatcttca gtcagcttgt 108720
ggctagtcat tttgttgtgg ttgtggttgt taaaatcagg ctgtagttat ggttttgttt 108780
tatggttta aaaactcaac tactgaaccc tttagtttta atatatatat taatatatat 108840
atactctgta tcaccatgta tatgtatatg aatataggt gcctggtata gggtttgcct 108900
gttagtagat atatataggt taaagataat ctggaagtag ttttttccag gttccacaca 108960
ggcagagtca tttggagaca tggaactgag agtagattag cttgtctaat cagcaagctc 109020
caaggatcta cttgtcctta atgcccatca ttaacctgcc gcccactctc cgctgccaca 109080
tatatacaca tatcctatcc agagaataca agcacacgct actctacttg gttgctcatg 109140
catagaaagg ggcatttttc atttttcaag ggctctctcc ccgcctaatg ttttcatata 109200
gaacaaagcc cctccaagtt gtaaattgtt tatgatggtg aatatctagg ccagggcaaa 109260
aattggcaac agaaaaggct gaatacatgg taaatatctt gtttgtttgt ttgatttttg 109320
agacagggtt tctctgtata gccctggctg ttctggaact cactttgtag accaggctgg 109380
actcgaactc agaaatccgc ctgcctctgc ctcccgagtg ctgggattaa aggcatgcac 109440
```

```
caccatgccc ggcatatggt aaatatctta cacttatgtt ctaacaagtg tttttttttt    109500
atttctgcca agttcacttt tttaatgtgt ccatataata catggctatt tctcttagta    109560
aaatgtgctt tgtaatatat atatatgcac ttccctacgt gggaaatgaa gtatatggtg    109620
tgtacacttt ttctattaaa tttacctaac cgttttacac acacaaacac acacacacac    109680
acacacacac acacacacac acacacacat cttctaatta ctctctccct aacaccatta    109740
tttttctttc atccctatta agaccttact cccaccattg ctactagtcc cttcccaga    109800
ttcatggatt ttggttttgt gactcatttg gtttagtcag acctttttct gtgaactttc    109860
gattgagact gcacatcagt acatgatgtg atcttcagtg ggtataaaac tgaaggcaat    109920
gatttaccct tgccccaaat catcagtagt aagtagtata gcagtgacag ggtcatctga    109980
gtccttctat ctatttctga catttgacag gctcatattt gtgtatatac aaaatattta    110040
tgcatatatt tgcatatatt aggcatatat ttatgcatat acagagcaag cacctgtagc    110100
ttctataagt tcatgattga aattcctatg atttgccatg gaacactatt tcttcctttt    110160
ggcccttaca atctttctgc tgcccttct tcactaccta ctggtcctta gaagagacag     110220
gataagtgta gtgtttatac ctgagcacta ataclctgcc ttttgtaacc tggaaccacg    110280
tgtctctaca tttaccattg ttcactgaaa ggagaggttt atcttattaa ggctgaaagt    110340
agcttttgtt ccatgctact gtgacagaca acaaagagga atggcaagaa cctgtactgg    110400
ttgagggggt tacttgtgtc tttgtgatga acagtcctgg aatttgggtt ttggtataat    110460
aaaatgactt ccaggacaaa ttttgttcag cctgtacttt tttttttaaa tagatctatg    110520
ttatttttta tttaaaatgg aattctggga tgtattttat attagagata cttaacacag    110580
taagatgtat gcttaaataa accttgccct atcatgtcaa agttctttta aatgtctgcc    110640
tttttcttta tggctgttgt tttctccatc tttatgatct attgagcaaa tgtgttactg    110700
tatttattaa tgggttgatt aatattacct gacattataa caaaatactg gtctcatcca    110760
aaacatatgt ttagcataag agcagtggga tcagatcttg acctgctgct ttcagtgttg    110820
taagtgtaga tatcaggtac ttgttttagcc cttacatttg aaaaaatacc atatactctt   110880
ccagctgtct ttcagaaacc cagttttcct ttagctcctt gtaaatttg aagcagagat     110940
caccttttat tttcctgtat ttatattggt agatagaaca ttgttatttt cttatattaa    111000
atgtcactgt ggaggtgaca aatgattgct gacagtggat agtaattacc agggtcaatt    111060
gtaaattttg gtcagttctg atcttaaatt ctgtttacgt gaataatctt tgttttctgt    111120
attgcaacat tgccaccaag aattatcctt tacaaaatac tttgttgtaa acatcagtga    111180
agattatgat gcaagctatg catggggagg taagatgtat actatacatg ggagccaagt    111240
agcatgcaag ttagggtaca gtctatgcat taggggccag gaagtttcaa gacatttatg    111300
agggttgggt aggatggaaa ctgtacatga aaagaccagg tagcatgaaa gctatatttt    111360
aggaactaga aacatgcaag atatatgtgg aggtggcagg taggatataa actatgcatt    111420
tggagtccag gcagaatgga aacatgttag aaggattcaa gctatgcatt aagaaccaga    111480
cagaattcaa gtgataagga gggggtatgg agggggggggt agtgggatac aagctgtgca    111540
ttaaatgcaa tgtgacctgc tggctatgca ttaggggcta ggtaggatgc aggatataca    111600
gtaaggacca agtagcatgc attaaagtcc aggtagtata cgagtataca agctacacaa    111660
aagaagctag gtggtattgc agcacagatc tctctgaaaa agaggagata catatttgat    111720
atccttgata cagaatttg acgatcttct ctgcaggaaa aatggtggat gcgagcctgt     111780
cttttgtatg gccactaaat ctgtaccaac accttgacct gtactagatc ctctatcttt    111840
```

-continued

```
gcccttttgac aggttttgcc cacatgcagg ttaccagtta gtgttttttt gtttgtttgt    111900
ttgtttggtt ggttttttt tgtttcgttt tataggtcaa gacacttgct tttttattta     111960
gacagcatct ctcttctttt gagtatgtat ttatatttta aatgatacag ttctctgttc    112020
acagataaac ttatggacac atccgtggtt tcacttttat tatagaaatt atggatcctt    112080
tatgatttta tggaacccct gcctacaaat taagctgtga attttttaaaa aaatctttga   112140
taaatttgta gctggagctg tgagtccctc catgtgtact ctttggatgg tggtttagtc    112200
cctgggagct ctggggggtac tggttgcttc atatcgttgt tcctcctata gggctgcaaa   112260
tcctgtctgc tccttgggtc ctttctctag ctcctccatt gggaccctg tgctcagtcc     112320
aatggttgac tgagagcatc cacctctgta tttgtcaggc actggcagag cttctcagga   112380
gacagctata tcaggctcct gtcagcaagc acttgttggc atccacaata gtgtctggct   112440
ttggtgactg tatgtgggat ggatctccag gtggagcagt ctctggatgg ccttcccttc    112500
tggtcatcaa taggaggaga ggccgttggt cctgtgaggg ctcaatgccc cattgtaggg    112560
gaatgccagg accaggaatt gggagtggat gggttgatga gcaggggga gggagagagg    112620
atatgggggtt ttcagcaggg aaaccaagaa agggtagata cttgaaatgt aaataaagaa   112680
aatatctaat aaaatatta agcacacata caaaaaaaac tttgataaag ataactcctc    112740
aagatttgtg gaacacggtg tttcctaaat gaatgccagg agagtacaat ctttagcaca   112800
ggaaaatgta gtactaagaa acacaaacac gtatactatg tttttaaaaa gaaaccaaca   112860
attattgatt tacaacttgg atgatttat gattaaaatt gacatgaagg gatttttaatt    112920
gattgtattt catggtaaac ccaggaagga atttctaagc aacattcagc attatctgga   112980
tgaactctga agggcaaaca cagttatccc cttatacaca tggacaccca cagcctgtga   113040
catcctcttc tactaatgta ggaatatcag agttaggagc ccccaggggtt ggcctttcat  113100
attgtcttat ccagtttata acataaatct cacaagttac attggaaaat gcactgaaga   113160
ggtggtttac tatatttcct tcctatgagc tgtataaaaa tcacgtaaac atcagtgaga   113220
ggggtccatt gtgtcacttg ctcctcccag ttatatacaa atgaaaagat ctctttgctg   113280
tcttttctca acacagttag ttgatgctca ggagtggtgg taacatgccc agagtcacaa    113340
aagataactt aggctggaat tgtaatgtgc atcctatgat caagttctgg ggctgaacta    113400
ccacacaacc aaaacctgga ttcttatact accatgtaaa atactgttac tctacatttt   113460
gaagtgaggt gatttgggga cagtttaaga cttatttaac ttataaacaa attggcctct   113520
ctgggtttgt aaccagagat tgttgatatc tatacagcat gataggatga tctgtaaggt    113580
gccctgccaa gctaccgaaa gcatgacctt cagagtctga ccttgcctta gtgtcaactc   113640
ttatttcttc cctctgccca cctgtccatt atgcctatga taaaagcaga gggagatagc    113700
atttacagtg agtatattgc ccacagaagc tgagcatcct ttgatctcat tgaaatagac    113760
catttagcct ctagttgctc tttgagtatt tgctgaactc tgtcattcaa taattacttt   113820
ggtggaacaa atggaaaaga acaaaagatc tttgatgaag gatacaaaaa agctccatca   113880
tgtcaagctg aatgctaggg tgtctgcatt gtggagagat aatctgaaat tttgtccaat   113940
catatctttg ttttggtttt ggttttggtt ttacttcaag tacatataat ttcaaacttc    114000
agctttccaa agagaactat ttctttggca gcatttaaga atgaattatt ggggctcaaa   114060
atatagctca ctgtttaaga acatatgtat ttttcttcca gaggactcta gtttataatc   114120
tagcacctat atgagaatc acaaggatct atagctccgg ttccagggaa tgtgatgccc    114180
tcattattca ccacacatgc acatagtcca cacacatact cacaaataaa agaaaagaaa   114240
```

```
acaatgaatt ataaaacaca tgtactttac cttttaaaat ttaggaaaaa taaataataa    114300
tgataatttg tcaatatttg ttttactttt ttggaacatt tttactttt cattgaaatg    114360 ctatgtgggt tctgtctaca aatgacatcc tgttaaacat tacaccaaaa ataagctatc    114420
cttattagag aattggcaaa tgatttcaga aaagttttga atacattact gttatttgat    114480
tcatcattac ccattgacta caaaccattg ttactatagc attgcgctta tggagagaac    114540
ttatggactt tagcttttggc aacttccagt gtagttaatt acctgtgcaa aatatttgta    114600
ctctttagat tggtaaccca tgcatgcaca atgttttttc cagtggtttg gtacacttag    114660
aatccatcaa taatacagaa gaatgcactt ctgataacac ttcgtgcagc accttgaaga    114720
taaggtgtct ttttcaagct ggttttcaga agttaaaaca ctctcttatt gtgctttctc    114780
ttccctctct gtagggtgag gaggggtacc cacaggaagg aatcctggaa gacatgcctg    114840
tggatcctgg cagtgaggct tatgaaatgc cttcagaggt aaatgcctgt ataaagaaaa    114900
ctaagcaaaa cactttaggt gtttaatttg gaacacatac catcaaaacc ctgccactat    114960
cagatctctc tcacattatg gttggcatag ttcaatcaag aaaatatttt agagcaaatg    115020
attttaatct ttgtgggaga gggtaaggga tatagtaggt caaaattaaa acattctaga    115080
acaagagact ggtagtaaca aaggcatatg gaaatgtctg agtaacaacg ggcagttatg    115140
aatcatggtt agaaaacaga aaaatgacag attaaggctg aagacataac taaggtttta    115200
gacaaactgt agagccccaa gttaccatca tttaagttta tttttacatt tggaaaaaga    115260
agagtttgat gataggttta gtttaacagc acaatcctaa ttagagttaa ttttgaggaa    115320
ggctatcaaa ttcagttaca ttgggtcatt actgtcatga atgttatctg gattttgtcc    115380
aggaggcttg ggcttttcatg tgaaagatcc ttcatggaag caattcatga aggtggagtg    115440
ttctaatggg ggagagaaag gcgaaagatg agctctggag gaggcttcat gcagcttacc    115500
taggtgtgca cagctcacac tgcagagcaa aggagagaat ccagagaccc tgccaattca    115560
cactgcagga ggagagcaca gatcaaatga tatacctaga attgggccta ataatctaac    115620
ggtgatgtcc tctataactt acagttgata cgtatgaaaa agccaataaa tgtcaatgac    115680
agataagttc caaacactgc tctgaggatc aattttatct gattgaaatg atgagccctc    115740
ccccactgtg aagcagacag ttgatatctg tcacttcact gacaaggcat gctgttatta    115800 ttttctttc ctgatattag gaaggctacc aagactatga gcctgaagcc taagaatgtc    115860
attgcaccca atctcctaag atctgccggc tgctcttcca tggcgtacaa gtgctcagtt    115920
ccaatgtgcc cagtcatgac cttttctcaa agctgtacag tgtgtttcaa agtcttccat    115980
cagcagtgat cggcgtcctg tacctgcccc tcagcatccc ggtgctcccc tctcactaca    116040
gtgaaaacct ggtagcaggg tcttgtgtgc tgtggatatt gttgtggctt cacacttaaa    116100
ttgttagaag aaacttaaaa cacctaagtg actaccactt atttctaaat cttcatcgtt    116160 ttcttttttgt tgctgttctt aagaagttgt gatttgctcc aagagtttta ggtgtcctga    116220
atgactcttt ctgtctaaga atgatgtgtt gtgaaatttg ttaatatata ttttaaaatt    116280
atgtgagcat gagactatgc acctataaat attaatttat gaattttaca gttttgtgat    116340
gtgttttatt aacttgtgtt tgtatataaa tggtggaaaa taaataaaa tattatccat    116400 tgcaaaatct ttcctggttc cttttacttt agtaacaaaa tcatgcatat cgggaacatg    116460
aacatttaat gacaactgac acagtgaact ggaatgaaaa gttgcaacat gtcttaagga    116520
accgagggga tttagagatg gaacagcagg aaggattctc cagtgagatt gaacacagcc    116580
agctttatct acagttctgc tcagagctgt ggctgcactt gaggaaacac ttcattggaa    116640
```

```
ctaaaacgtg tgagggatag tgaactttta catattcata agacacatta gcatatcaga    116700
ggcaggccat tgaagaacct taatttggaa tttatggcat gtatatgtgt gtgtgtgtgt    116760
gtgtgtgtgt gtgtgtattt gtgtgtgtgt gtgtgtgtgt gtgtgtgtgt gtgtgtgtgt    116820
ataaagaac ccaggaaata ccttaaaact cctcagggac cccaggcagt gggctatgta     116880
tatgatacct tagcaggtac gcaaaggtaa aagcaaaatg gaacaaaagg caatgtcaat    116940
ttgtgaataa cagggatttg ggaatatctt ttaggaaaag gtttctttag ataggcttaa    117000
ttacccatga atgaagacaa aaacttgact gactgagaaa ttactcagtt catcttccta    117060
attattcaga agaaaaccag caaagccaca gtgaaaacca cttgcagaga gtacactttt    117120
tgtaacgaat attgttgctc ctgtacggtc atgagtaatt gatgtgtgtt ggacagtgac    117180
aggaacagaa gaggagtggg agaccatgaa gatagcacca ctggaacttc cttctgccca    117240
gttgagaaaa tactatggag tgttcagttg catgtgtgct ttgaccctgg aaataggtga    117300
taactcctta tctaatttat gtttccttga agctgatgaa ggattcatta ttaaggtagc    117360
ccagatggtg tttagggtac attatatatt taccgaaagt accctcttct taaaaaggaa    117420
agatacaaac agaacacaat caaattgatg acaatgacaa tgagcagtgt aggactggag    117480
gcagactgtg cttgaccttg agaactgcta ttgatgggta tggtattgta aagctcttct    117540
tctcttaagc agtgccacgc tgtcaatgtg cgaacagtta atgagttttt gctgtttagc    117600
tttcttttat cttaagagtg tttcactcac cacctaaagg aagctcctta gttcacacaa    117660
gccctggtag gagtccagcc cttgagaagt gcagtctgag gatgcctctt gactagagct    117720
ttagcttttcc agatttaaat cccaagtcag agctgtttga tttgtaatga gtccacgaag    117780
gactttaaag aaagccgtcc acagcaggct tgggccccac aattggcagc actacacaat    117840
caaatgtaca ctttggaatt tcaactttg ccttcttttc aaaagtctct tctccagatt     117900
gtaagatgca agtatacttc ataatttgta tagctatttg tggcataatg gaatttatac    117960
atagggtgtc atacaactag tacacttata atctattcag agccaggagg cttatggttt    118020
gagacactgt ctcaggaaac atattcagaa tgtttctgcc tctaattcct ggaggagtaa    118080
tttaaaagca ttgtgatttt atgtgccata tgattgctaa gtgtgtctct tattctaata    118140
actgatctat cgatatctat ctatctatct atcatctatc tatctatcta tctatctatc    118200
tatctatcaa tcatctatct atctatctat ctatctatct atctatctat atcatctatc    118260
atctatcgat ctatctctca tccgtggttt gcacatagct cccagtgcta agaatttctt    118320
aactcttgtt ctgatgaaat gcacacaatt tggcttctga agctggctga tgtataagag    118380
agaaaggact atatttacct caatcagcac aaggatggca gtagatatct ctgtaagaaa    118440
gaagagcaaa atgaagagct aacttagcta accaaagttt ggcatgatag atgaggagtt    118500
aggcattaag ggctaaaaat agtagaaaac tatatttta tgtttgaatt ttgtagaaga    118560
ataaacagtt ttatagaact atggttaact tcaaatgtca tatcacctaa tggaaatata    118620
ctgagagggc tgacaaatcc agtttgtatt tttcttgctt ctgttagtat tctttccttc    118680
ggagatgggt gagtattact tgagggtctt cagagatgga aaggtcagag agaaggagga    118740
aggtaggggg gagagagaga gagagaaaga gagagag                             118777
```

```
<210> SEQ ID NO 11
<211> LENGTH: 4047
<212> TYPE: DNA
<213> ORGANISM: Mus musculus
```

```
<220> FEATURE:
<221> NAME/KEY: misc_feature
<222> LOCATION: (1)..(4047)
<223> OTHER INFORMATION: LOCUS      Drpla                  4047 bp
      mRNA    linear   ROD 16-MAY-2002
      DEFINITION  Mus musculus dentatorubral pallidoluysian atrophy
      (Drpla), mRNA.
      ACCESSION   XM_132846
<300> PUBLICATION INFORMATION:
<308> DATABASE ACCESSION NUMBER: XM_132846
<309> DATABASE ENTRY DATE: 2002-05-16
<313> RELEVANT RESIDUES IN SEQ ID NO: (1)..(4047)

<400> SEQUENCE: 11
cacgacagaa taaagactcg atgtcaatga ggagtggacg aagaaagag gccccggc         60 cccgggaaga gctgagatca aggggccggg cctcccctgg aggggtcagc acatccagca    120
gtgatggcaa agctgagaag tccaggcaga cagccaagaa ggcccggata gaggagccct    180
ctgccccaaa ggccagcaag cagggccgga gcgaggagat ctcagagagt gagagcgagg    240
agaccagtgc gcccaaaaag accaaaaccg agcaggagcc cctcgcccg cagtctccct     300 cggatctgga cagcttggat gggcgcagca ttaacgatga cggcagcagc gaccctagag    360
atatagacca ggacaaccga agcacatccc ccagcatcta cagcccgggc agcgtggaaa    420
atgactcgga ctcatcctct ggcctgtccc agggccccgc ccgcccctac cacccacctc    480
cactcttccc tccttcccct ccaccaccag acagcactcc ccgacagcca gagtctggct    540
ttgaacctca tccttctgtg ccgcctactg gatatcatgc tccgatggag cccccacat    600 cgagattatt ccagggccca ccacctggag ctcctcccac acaccacag ctctaccctg     660 ggaatgctag tggaggtgtt ttatctggac ccccatgggt tcccaaaggg ggagccgctg    720
cctcctcagt gggtgcccct agcggaggca agcaacaccc cccacccact accccaattc    780
caatatcaag ttctggggcc agtggtgctc ctccagcaaa gccacccagt gctccagtgg    840
gtggtgggag cttaccttct gcaccaccac cagcttcttt ccccccatgtg acaccaaaacc   900 tgcctcctcc acctgccctg agaccctca acaatgcctc agcctctct cctggcatgg      960 gggctcagcc aatccctggg catctgccct ctccccatgc catggggcag ggcatgagtg   1020
gacttcctcc tggcccagag aagggtccaa ccctggcccc ttctcccac cctttgcccc    1080 cagcttcttc ctctgccct gggcctcaa tgcgatatcc atattcatcc tccagtagct     1140
ctgccgcagc ctcttctagt tcctcctcct cctctgcctc ccagtaccct gcttcccagg   1200
cccctgccca gttatcctcat tccttccccc caccaactag tatgtctgtc tctaatcagc   1260
cacccaagta cacccagcct tctctcccat cccaagctgt gtggagccag gtccacctc    1320 ctcctcctcc ctatgccgc ctcttggcca acaacaacac ccatccaggc cctttcctc     1380 ctactgggg tcaatctaca gcccaccag cagcccctac acatcaccat caccagcagc    1440
agccacagca acaacatcat catgaaact ctgggccccc tccaccgga gcgtatcctc     1500 accctctaga gagcagtaac tcccatcatg cacaccctta caacatgtca ccctccctgg   1560
ggtctttaag gccctaccc ccagggccaa cacctgcc tccacctcat ggccaggtgt      1620
cctataacca agcaggtccc aatggtcccc cagtttcttc ttccaactct tccgggtctt   1680
cctctcaagc ctcctattca tgttcacacc ctcttcatc ccagggcccc caaggagcat   1740
cctaccccct tccccagtc cctccagtca ccacctcctc agctacccct tccactgtca   1800
tcgccaccgt ggcttcctcg ccagcaggct acaaaacagc ttcgccacct gggccccctc   1860
agtacagcaa gagagcccca tccccagggt cctacaagac agccacccg cctggataca    1920 aaccgggggtc accaccctcc ttcagaacag ggaccccacc cggctatcga ggcacctctc   1980
```

```
cgccagcagg cccagggacc ttcaaaccag gttcaccgac cgtggggccg gggcccctgc    2040
cacccgcggg gccttcaagt ttgtcatctc tgcctccgcc acctgcggcc ccgactacag    2100
ggccgcccct gaccgccacg cagatcaaac aggagccggc ggaagagtat gaacctcccg    2160
agagtccggt gcctccggcc cgcagcccct cgcccccctcc caaggtggtg gacgtgccca    2220
gccatgccag ccagtcagcc aggttcaata agcacttgga ccgcggcttc aactcgtgcg    2280
cgcgcagcga cctgtacttc gtgccgctgg agggctccaa gctggccaag aagcgcgcgg    2340
acctggtgga gaaagtgcgg cgcgaggccg agcagcgcgc gcgcgaggag aaagagcgcg    2400
agcgcgagcg ggaacgcgaa aaggagcgcg agcgcgagaa agagcgcgag ctggagcgca    2460
gtgtgaaact ggcccaggag ggccgtgctc cagtggagtg cccatctctg ggtccagtgc    2520
cccatcggcc tccctttgag cctggcagcg ctgtggctac agtgccccct tacctgggtc    2580
ctgatactcc ggccttgcgc actctcagtg aatacgcccg acctcatgtc atgtctcctg    2640
gcaatcgcaa ccaccccattc tatgtgccct tgggggcagt ggaccccgggg cttctgggtt    2700 acaatgtccc agccctgtac agcagcgacc cagctgcccg agaacgggag cgggaagccc    2760
gtgaacgtga cctccgtgac cggctcaagc ctggctttga ggtgaaacct agtgagctgg    2820
aaccctcaca tggggttccc gggccaggcc tggatccctt ccccgacac ggggggcctgg    2880 ctctacagcc cgggccacct ggcctgcatc ctttccctttt tcatccgagc ctggggcccc    2940
tggaacgaga acggctagcg ctggcagctg ggccagcctt gcgtcctgac atgtcttatg    3000
ctgagcggtt ggcagctgaa aggcagcatg cagaaagggt ggcagccctg gcaatgatc    3060 cactagcccg gctgcagatg ctcaacgtga ctccccatca ccaccagcac tcccacatcc    3120
actctcacct tcacctgcac cagcaggatg ctatccacgc agcctctgcc tcggtgcacc    3180
ctctcattga cccctggcc tcagggtctc accttacccg gatccctac ccagctggga    3240 ccctccccaa ccccccttctt cctcacccctc tgcacgagaa cgaagttctt cgtcaccagc    3300 ttttgctgc cccttaccgg gacctgccgg cctccctttc tgctccaatg tcagcggctc    3360
atcagctgca ggccatgcac gcgcagtcag ctgagctgca gcgcttggcg ctggaacagc    3420
agcagtggct acatgctcat cacccattgc acagcgtgcc actacctgcc caggaagact    3480
actacagtca cctgaagaag gagagtgaca agccgctgta gagctgcgat ccagacagca    3540
cccactgctc cttcatccag accttggagg accaccccaa ccttttgacc ccaccccacc    3600
cccagccgag gagagggtgc tgcccgcttg cagagctcct gcagctgggt agagggaggg    3660
agggaagaag ggacagacaa ggtcagggcc cggggttgtg tgcagaggtg ggaagtggca    3720
agggtggggg cagaaagtgc acagtatctt ggaccaggtc cctcctccta tccctgctt    3780 ttcttctcct ctatgccgaa tccttggtgg ccactgcccc tccctaacc cattggtgtg    3840 atttttttca tctgttagat gtggctgttt tgcgtagcat tgtgtgctgc cccgcccat    3900 ccctgtgtgt gcaccccctc cctcggcgat atgtgccctt acccgtccca cattaataat    3960
ttatatatat aaatatctat atgatgctct ttaaaaaaca tcctgaccaa aaccaaccaa    4020
acaaaaacat cctcacagtt ccccagg                                        4047
```

<210> SEQ ID NO 12
<211> LENGTH: 10033
<212> TYPE: DNA
<213> ORGANISM: Mus musculus

```
<220> FEATURE:
<221> NAME/KEY: misc_feature
<222> LOCATION: (1)..(10033)
<223> OTHER INFORMATION: LOCUS      MMU24233            10033 bp
      mRNA    linear   ROD 18-JUL-1995
      DEFINITION  Mus musculus huntingtin (Hd) mRNA, complete cds.
      ACCESSION   U24233
<300> PUBLICATION INFORMATION:
<308> DATABASE ACCESSION NUMBER: U24233
<309> DATABASE ENTRY DATE: 1995-07-18
<313> RELEVANT RESIDUES IN SEQ ID NO: (1)..(10033)

<400> SEQUENCE: 12
```

| | | | | | |
|---|---|---|---|---|---|
| ggctgagcgc | cttggttccg | cttctgcctg | ccgcgcagag | ccccattcat | tgccttgctg | 60 |
| ctaagtggcg | ccgcgtagtg | ccagtaggct | ccaagtcttc | agggtctgtc | ccatcgggca | 120 |
| ggaagccgtc | atggcaaccc | tggaaaagct | gatgaaggct | ttcgagtcgc | tcaagtcgtt | 180 |
| tcagcagcaa | cagcagcagc | agccaccgcc | gcaggcgccg | ccgccaccgc | cgccgcctcc | 240 |
| gcctcaaccc | cctcagccgc | cgcctcaggg | gcagccgccg | ccgccaccac | cgccgctgcc | 300 |
| aggtccggca | gaggaaccgc | tgcaccgacc | aaagaaggaa | ctctcagcca | ccaagaaaga | 360 |
| ccgtgtgaat | cattgtctaa | caatatgtga | aaacattgtg | gcacagtctc | tcagaaattc | 420 |
| tccagaattt | cagaaactct | tgggcatcgc | tatggaactg | tttctgctgt | gcagtaacga | 480 |
| tgcggagtca | gatgtcagaa | tggtggctga | tgagtgcctc | aacaaagtca | tcaaagcttt | 540 |
| gatggattct | aatcttccaa | ggctacagtt | agaactctat | aaggaaatta | aaaagaatgg | 600 |
| tgctcctcga | gtttgcgtg | ctgccctgtg | gaggtttgct | gagctggctc | acctggttcg | 660 |
| acctcagaag | tgcaggcctt | acctggtgaa | tcttcttcca | tgcctgaccc | gaacaagcaa | 720 |
| aagaccggag | gaatccgttc | aggagacctt | ggctgcagct | gttcctaaaa | ttatggcttc | 780 |
| ttttggcaat | ttcgcaaatg | acaatgaaat | taaggttctg | ttgaaagctt | tcatagcaaa | 840 |
| tctgaagtca | agctctccca | ctgtgcggcg | gacagcagcc | ggctcagccg | tgagcatctg | 900 |
| ccaacattct | aggaggacac | agtacttcta | caactggctc | cttaatgtcc | tcctaggtct | 960 |
| gctggttccc | atggaagaag | agcactccac | tcctcctgatc | ctcggtgtgt | tgctcacatt | 1020 |
| gaggtgtcta | gtgcccttgc | tccagcagca | ggtcaaggac | acaagtctaa | aaggcagctt | 1080 |
| tgggggtgaca | cggaaagaaa | tggaagtctc | tccttctaca | gagcagcttg | tccaggttta | 1140 |
| tgaactgact | ttgcatcata | ctcagcacca | agaccacaat | gtggtgacag | ggcactgga | 1200 |
| gctcctgcag | cagctcttcc | gtaccctcc | acctgaactc | ctgcaagcac | tgaccacacc | 1260 |
| aggagggctt | gggcagctca | ctctggttca | agaagaggcc | cggggccgag | gccgcagcgg | 1320 |
| gagcatcgtg | gagcttttag | ctggaggggg | ttcctcgtgc | agccctgtcc | tctcaagaaa | 1380 |
| gcagaaaggc | aaagtgctct | aggagagga | agaagccttg | gaagatgact | cggagtccag | 1440 |
| gtcagatgtc | agcagctcag | cctttgcagc | ctctgtgaag | agtgagattg | gtggagagct | 1500 |
| cgctgcttct | tcaggtgttt | ccactcctgg | ttctgttggt | cacgacatca | tcactgagca | 1560 |
| gcctagatcc | cagcacacac | ttcaagcaga | ctctgtggat | ttgtccggct | gtgacctgac | 1620 |
| cagtgctgct | actgatgggg | atgaggagga | catcttgagc | cacagctcca | gccagttcag | 1680 |
| tgctgtccca | tccgaccctg | ccatggacct | gaatgatggg | acccaggcct | cctcacccat | 1740 |
| cagtgacagt | tctcagacca | ccactgaagg | acctgattca | gctgtgactc | cttcggacag | 1800 |
| ttctgaaatt | gtgttagatg | gtgccgatag | ccagtattta | ggcatgcaga | taggacagcc | 1860 |
| acaggaggac | gatgaggagg | gagctgcagg | tgttctttct | ggtgaagtct | cagatgttttt | 1920 |
| cagaaactct | tctctggccc | ttcaacaggc | acacttgttg | gaaagaatgg | gccatagcag | 1980 |

```
gcagccttcc gacagcagta tagataagta tgtaacaaga gatgaggttg ctgaagccag    2040
tgatccagaa agcaagcctt gccgaatcaa aggtgacata ggacagccta atgatgatga    2100
ttctgctcct ctggtacatt gtgtccgtct tttatctgct cctttttgt taactggtga     2160 aaagaaagca ctggttccag acagagacgt gagagtcagt gtgaaggccc tggccctcag    2220
ctgcattggt gcggctgtgg cccttcatcc agagtcgttc ttcagcagac tgtacaaagt    2280
acctcttaat accacggaaa gtactgagga acagtatgtt tctgacatct tgaactacat    2340
cgatcatgga gacccacagg tccgaggagc tactgccatt ctctgtggga cccttgtcta    2400
ctccatcctc agtaggtccc gtctccgtgt tggtgactgg ctgggcaaca tcagaaccct    2460
gacaggaaat acattttctc tggtggactg cattcctta ctgcagaaaa cgttgaagga     2520
tgaatcttct gttacttgca gttggcttg tacagctgtg aggcactgtg tcctgagtct     2580
ttgcagcagc agctacagtg acttgggatt acaactgctt attgatatgc tgcctctgaa    2640
gaacagctcc tactggctgg tgaggaccga actgctggac actctggcag agattgactt    2700
caggctcgtg agttttttgg aggcaaaagc agaaagttta caccgagggg ctcatcatta    2760
tacagggttt ctaaaactac aagaacgagt actcaataat gtggtcattt atttgcttgg    2820
agatgaagac cccagggttc gacatgttgc tgcaacatca ttaacaaggc ttgtcccaaa    2880
gctgttttac aagtgtgacc aaggacaagc tgatccagtt gtggctgtag cgagggatca    2940
gagcagtgtc tacctgaagc tcctcatgca tgagacccag ccaccatcac acttttctgt    3000
cagcaccatc accagaatct atagaggcta tagcttactg ccaagtataa cagatgtcac    3060
catggaaaac aatctctcaa gagttgttgc cgcagtttct catgaactca ttacgtcaac    3120
aacacgggca ctcacatttg gatgctgtga agccttgtgt cttctctcag cagccttttcc   3180 agtttgcact tggagtttag gatggcactg tggagtgccc ccactgagtg cctctgatga    3240
gtccaggaag agctgcactg ttgggatggc ctccatgatt ctcaccttgc tttcatcagc    3300
ttggttccca ctggatctct cagcccatca ggatgccttg attttggctg gaaacttgct    3360
agcagcgagt gcccccaagt ctctgagaag ttcatggacc tctgaagaag aagccaactc    3420
agcagccacc agacaggagg aaatctggcc tgctctgggg gatcggactc tagtgccctt    3480
ggtggagcag cttttctccc acctgctgaa ggtgatcaat atctgtgctc atgtcttgga    3540
cgatgtgact cctggaccag caatcaaggc agccttgcct tctctaacaa accccccttc    3600
tctaagtcct attcgacgga aagggaagga gaaagaacct ggagaacaag cttctactcc    3660
aatgagtccc aagaaagttg gtgaggccag tgcagcctct cgacaatcag acacctcagg    3720
acctgtcaca gcaagtaaat catcctcact ggggagtttc taccatctcc cctcctacct    3780
caaactgcat gatgtcctga agccactca cgccaactat aaggtcacct tagatcttca     3840
gaacagcact gaaaagtttg gggggttcct gcgctctgcc ttggacgtcc tttctcagat    3900
tctagagctg gcgacactgc aggacattgg aaagtgtgtt gaagaggtcc ttggatacct    3960
gaaatcctgc tttagtcgag aaccaatgat ggcaactgtc tgtgtgcagc agctattgaa    4020
gactctcttt gggacaaact tagcctcaca gtttgatggc ttatcttcca accccagcaa    4080
gtctcagtgc cgagctcagc gccttggctc ttcaagtgtg aggcccggct tatatcacta    4140
ctgcttcatg gcaccataca cgcacttcac acaggccttg gctgacgcaa gcctgaggaa    4200
catggtgcag gcggagcagg agcgtgatgc ctcggggtgg tttgatgtac tccagaaagt    4260
gtctgcccaa ttgaagacga acctaacaag cgtcacaaag aaccgtgcag ataagaatgc    4320
tattcataat cacattaggt tatttgagcc tcttgttata aaagcattga agcagtacac    4380
```

```
cacgacaaca tctgtacaat tgcagaagca ggttttggat tgctggcac  agctggttca   4440 gctacgggtc aattactgtc tactggattc agaccaggtg ttcatcgggt tgtgctgaa   4500 gcagtttgag tacattgaag tgggccagtt cagggaatca gaggcaatta ttccaaatat   4560 attttcttc  ctggtattac tgtcttatga gcgctaccat tcaaaacaga tcattggaat   4620
tcctaaaatc atccagctgt gtgatggcat catggccagt ggaaggaagg ccgttacaca   4680
tgctatacct gctctgcagc ccattgtcca tgacctcttt tgttacgag  gaacaaataa   4740 agctgatgca gggaaagagc ttgagacaca aaggaggtg  gtggtctcca tgctgttacg   4800
actcatccag taccatcagg tgctggagat gttcatcctt gtcctacagc agtgccacaa   4860
ggagaatgag gacaagtgga acggctctc  tcggcaggtc gcagacatca tcctgcccat   4920
gttggccaag cagcagatgc atattgactc tcatgaagcc cttggagtgt aaatacctt   4980 gtttgagatt ttggctcctt cctccctacg tcctgtggac atgcttttgc ggagtatgtt   5040
catcactcca agcacaatgg catctgtaag cactgtgcag ctgtggatat ctggaatcct   5100
cgccattctg agggttctca tttcccagtc aaccgaggac attgttcttt gtcgtattca   5160
ggagctctcc ttctctccac acttgctctc ctgtccagtg attaacaggt taaggggtgg   5220
aggcggtaat gtaacactag gagaatgcag cgaagggaaa caaagagtt  tgccagaaga   5280 tacattctca aggtttcttt tacagctggt tggtattctt ctagaagaca tcgttacaaa   5340
acagctcaaa gtggacatga gtgaacagca gcatacgttc tactgccaag agctaggcac   5400
actgctcatg tgtctgatcc acatattcaa atctggaatg ttccggagaa tcacagcagc   5460
tgccactaga ctcttcacca gtgatggctg tgaaggcagc ttctatactc tagagagcct   5520
gaatgcacgg gtccgatcca tggtgccac  gcacccagcc ctggtactgc tctggtgtca   5580
gatcctactt ctcatcaacc acactgacca ccggtggtgg gcagaggtgc agcagacacc   5640
caagagacac agtctgtcct gcacgaagtc acttaacccc cagaagtctg gcgaagagga   5700
ggattctggc tcggcagctc agctgggaat gtgcaataga gaaatagtgc gaagaggggc   5760
ccttattctc ttctgtgatt atgtctgtca gaatctccat gactcagaac acttaacatg   5820
gctcattgtg aatcacattc aagatctgat cagcttgtct catgagcctc cagtacaaga   5880
ctttattagt gccattcatc gtaattctgc agctagtggt cttttatcc  aggcaattca   5940 gtctcgctgt gaaaatcttt caacgccaac cactctgaag aaaacacttc agtgcttgga   6000
aggcatccat ctcagccagt ctggtgctgt gctcacacta tatgtggaca ggctcctggg   6060
cacccccttc cgtgcgctgg ctcgcatggt cgacaccctg gcctgtcgcc gggtagaaat   6120
gcttttggct gcaaatttac agagcagcat ggcccagttg ccagaggagg aactaaacag   6180
aatccaagaa cacctccaga acagtgggct tgcacaaaga caccaaaggc tctattcact   6240
gctggacaga ttccgactct ctactgtgca ggactcactt agccccttgc ccccagtcac   6300
ttcccaccca ctggatgggg atgggcacac atctctggaa acagtgagtc cagacaaaga   6360
ctggtacctc cagcttgtca gatcccagtg ttggaccaga tcagattctg cactgctgga   6420
aggtgcagag ctggtcaacc gtatccctgc tgaagatatg aatgacttca tgatgagctc   6480
ggagttcaac ctaagccttt tggctccctg tttaagcctt ggcatgagcg agattgctaa   6540
tgccaaaaag agtcccctct ttgaagcagc ccgtggggtg attctgaacc gggtgaccag   6600
tgttgttcag cagcttcctg ctgtccatca agtcttccag cccttcctgc ctatagagcc   6660
cacgccctac tggaacaagt tgaatgatct gcttggtgat accacatcat accagtctct   6720
gaccatactt gcccgtgccc tggcacagta cctggtggtg ctctccaaag tgcctgctca   6780
```

-continued

```
tttgcacctt cctcctgaga aggaggggga cacggtgaag tttgtggtaa tgacagttga    6840
ggccctgtca tggcatttga tccatgagca gatcccactg agtctggacc tccaagccgg    6900
gctagactgc tgctgcctgg cactacaggt gcctggcctc tgggggggtgc tgtcctcccc   6960 agagtacgtg actcatgcct gctccctcat ccattgtgtg cgattcatcc tggaagccat    7020
tgcagtacaa cctggagacc agcttctcgg tcctgaaagc aggtcacata ctccaagagc    7080
tgtcagaaag gaggaagtag actcagatat acaaaacctc agtcatgtca cttcggcctg    7140
cgagatggtg gcagacatgg tggaatccct gcagtcagtg ctggccttgg gccacaagag    7200
gaacagcacc ctgccttcat ttctcacagc tgtgctgaag aacattgtta tcagtctggc    7260
ccgactcccc ctagttaaca gctatactcg tgtgcctcct ctggtatgga aactcgggtg    7320
gtcacccaag cctggagggg attttggcac agtgtttcct gagatccctg tagagttcct    7380
ccaggagaag gagatcctca aggagttcat ctaccgcatc aaccctag ggtggaccaa      7440 tcgtacccag ttcgaagaaa cttgggccac cctccttggt gtcctggtga ctcagccct     7500 ggtgatggaa caggaagaga gcccaccaga ggaagacaca gaaagaaccc agatccatgt    7560
cctggctgtg caggccatca cctctctagt gctcagtgca atgaccgtgc ctgtggctgg    7620
caatccagct gtaagctgct tggagcaaca gccccggaac aagccactga aggctctcga    7680
taccagattt ggaagaaagc tgagcatgat cagagggatt gtagaacaag aaatccaaga    7740
gatggtttcc cagagagaga atactgccac tcaccattct caccaggcgt gggatcctgt    7800
cccttctctg ttaccagcta ctacaggtgc tcttatcagc catgacaagc tgctgctgca    7860
gatcaaccca gagcgggagc caggcaacat gagctacaag ctgggccagg tgtccataca    7920
ctccgtgtgg ctgggaaata acatcacacc cctgagagag gaggaatggg atgaggaaga    7980
agaggaagaa agtgatgtcc ctgcaccaac gtcaccacct gtgtctccag tcaattccag    8040
aaaacaccgt gccggggttg atattcactc ctgttcgcag tttctgcttg aattgtacag    8100
ccgatggatc ctgccatcca gtgcagccag aaggaccccc gtcatcctga tcagtgaagt    8160
ggttcgatct cttcttgtag tgtcagactt attcaccgaa cgtacccagt ttgaaatgat    8220
gtatctgacg ctgacagaac tacgagagt gcacccttca gaagatgaga tcctcattca    8280
gtacctggtg cctgccacct gtaaggcagc tgctgtcctt ggaatggaca aaactgtggc    8340
agagccagtc agccgcctac tggagagcac actgaggagc agccacctgc ccagccagat    8400
cggagccctg cacggcatcc tctatgtgtt ggagtgtgac ctcttggatg acactgcaaa    8460
gcagctcatt ccagttgtta gtgactatct gctgtccaac ctcaaaggaa tagcccactg    8520
cgtgaacatt cacagccagc agcatgtgct ggtaatgtgt gccactgctt tctacctgat    8580
ggaaaactac cctctggatg tgggaccaga attttcagca tctgtgatac agatgtgtgg    8640
agtaatgctg tctggaagtg aggagtccac cccctccatc atttaccact gtgccctccg    8700
gggtctggag cggctcctgc tgtctgagca gctatctcgg ctagacacag agtccttggt    8760
caagctaagt gtggacagag tgaatgtaca aagcccacac agggccatgg cagccctagg    8820
cctgatgctc acctgcatgt acacaggaaa ggaaaaagcc agtccaggca gagcttctga    8880
ccccagccct gctacacctg acagcgagtc tgtgattgta gctatggagc gagtgtctgt    8940
tctctttgat aggatccgca agggatttcc ctgtgaagcc agggttgtgg caaggatcct    9000
gcctcagttc ctagatgact tctttccacc tcaagatgtc atgaacaaag tcattggaga    9060
gttcctgtcc aatcagcagc catacccaca gttcatggcc actgtagttt acaaggtttt    9120
tcagactctg cacagtgctg ggcagtcatc catggtccgg gactgggtca tgctgtccct    9180
```

```
gtccaacttc acacaaagaa cttcagttgc catggccatg tggagcctct cctgcttcct    9240
tgttagcgca tctaccagcc catgggtttc tgcgatcctt ccacatgtca tcagcaggat    9300
gggcaaactg aacaggtgg atgtgaacct tttctgcctg gttgccacag acttctacag     9360
acaccagata gaggaggaat tcgaccgcag ggctttccag tctgtgtttg aggtggtggc    9420
ggcaccagga agtccatacc acaggctgct tgcttgtttg caaaatgttc acaaggtcac    9480
cacctgctga gtagtgcctg tgggacaaaa ggctgaaaga aggcagctgc tggggcctga    9540
gcctccagga gcctgctcca agcttctgct ggggctgcct tggccgtgca ggcttccact    9600
tgtgtcaagt ggacagccag gcaatggcag gagtgctttg caatgagggc tatgcaggga    9660
acatgcacta tgttggggtt gagcctgagt cctgggtcct ggcctcgctg cagctggtga    9720
cagtgctagg ttgaccaggt gtttgtcttt ttcctagtgt tccccctggcc atagtcgcca   9780 ggttgcagct gccctggtat gtggatcaga agtcctagct cttgccagat ggttctgagc    9840
ccgcctgctc cactgggctg gagagctccc tcccacattt acccagtagg catacctgcc    9900
acaccagtgt ctggacacaa aatgaatggt gtgtggggct gggaactggg gctgccaggt    9960
gtccagcacc atttttcctt ctgtgttttc ttctcaggag ttaaaattta attatatcag   10020
taaagagatt aat                                                      10033

<210> SEQ ID NO 13
<211> LENGTH: 3616
<212> TYPE: DNA
<213> ORGANISM: Mus musculus
<220> FEATURE:
<221> NAME/KEY: misc_feature
<222> LOCATION: (1)..(3616)
<223> OTHER INFORMATION: LOCUS       Sca1             3616 bp
      mRNA     linear   ROD 07-JAN-2002
      DEFINITION  Mus musculus spinocerebellar ataxia 1 homolog (human)
      (Sca1), mRNA.
      ACCESSION   NM_009124
<300> PUBLICATION INFORMATION:
<308> DATABASE ACCESSION NUMBER: NM_009124
<309> DATABASE ENTRY DATE: 2002-01-07
<313> RELEVANT RESIDUES IN SEQ ID NO: (1)..(3616)

<400> SEQUENCE: 13
ctcttcctcc actccctcca caggaagggc gtcacctgtc agattgcggc atcctggaac      60
agaatgaaag gatctgtgtt gaaacagcta cagtagggtt acagtagacc ctgagaaaac     120
agagtggact tcagcctgca cggatgagct tgaagcagga atggtttggg ttcaggcctc     180
ttacactgaa tttctctact gccacccttt ctactcaagc aacatcttac ggaaaagatc     240
tcccgggaag gaagtggctg cttgtggctt tgcactgtga tgaaggcaaa tggtacagtt     300
ttccaaagaa aatagaccaa aactttcttc ttgagaagaa acaaacctgc tgttggcaga     360
gggtatttct aacctctctg cgaaagaaag aaagacacca ccagaacctg gcatcccag     420 ctgctgaggg aagtttccat ggtgaagtct caggaggct tcctgggagc agagcatagt      480
gaatgctaat ccggagctgc cactgccagc ctaaagaacc cacggagat gattcccat       540 gaagggcctg gatcccctac agaaatccaa tgtgactctc tgtttatcag actaaaacca     600
gagccggcca gccagtgaaa cagccaccgt ggagggggga cggcgaaaaa tgaaatccaa     660
ccaagagcgg acgaacgaat gcctgcctcc aagaaacgt gagatccccg ccaccagccg      720
gcccctcgag gagaaggcca ctgctctgcc cagcgacaac cactgcgtgg agggtgtggc     780
ctggctcccc agcacccctg gcatccgcgg ccatggggg gggcggcacg ggtcagcagg      840
gacttccggg gagcatggtt tacaaggaat gggtttactt aaagcactgt ccgcagggct     900
```

-continued

```
ggattactcc ccacccagtg cccccaggtc agtccccaca gccaacacgc tgcccaccgt    960
gtaccctcct cctcagtcag ggaccccggt gtctcctgtg cagtacgccc acctttcgca   1020
taccttccag ttcattgggt cctcccaata cagtgggcct tacgcgggct ttatcccttc   1080
ccagctgatc tccccatcag gcaacccggt caccagtgca gtagcctcag ctgcaggggc   1140
caccactcca tcacagcgct cccagctgga ggcttattcc accctgctgg ccaacatggg   1200
cagtctgagc caggcaccag gacataaggt tgagccccct ccgcagcagc acctcagcag   1260
ggctgcagga ttagtcaacc cggggtcccc tcctccaccc acccagcaga accagtacat   1320
ccatatttcc agctctccac agagctccgg gcgggcgaca tctcccccac ccatcccggt   1380
ccacctccat ccccatcaga cgatgatccc gcacacactc accctggggc cttcatccca   1440
ggtggttgtg caatatagtg atgccggagg ccactttgtt cctcgagagt ccaccaaaaa   1500
agccgagagc agcaggttgc agcaggctat gcaagccaag gaagtcctga atggggagat   1560
ggagaaaagc cggaggtatg gggcatcatc ttctgtggag ctgagcctag caaggcaag   1620
cagtaagtca gtgcctcatc cctatgagtc caggcatgtg gtggtccacc caagcccagc   1680
agactacagc agtcgtgata cctccggggt ccgtggatct gtgatggttc tgcctaatag   1740
cagcacaccc tcagccgacc tggaggccca gcagaccacg catcgagagg cctccccatc   1800
caccctcaat gacaagagcg gcctggcacc taggaagccg ggccacaggt cttatgcgct   1860
gtcccccccac acggtcattc agaccacaca cagtgcatca gagcctctcc cggtgggcct   1920
accagccacg gccttctacg ctggcactca acctcctgtc atcggctacc tgagcggcca   1980
gcagcaagca atcacctatg ctggtggtct gccgcagcac ctggtgatcc caggtaacca   2040
gcccctgctc atcccggtgg gcagcccctga catggacatg cctggggcag cctcggccat   2100
cgtgacgtca tcacccccagt ttgctgcagt acctcacacg tttgtcacca ccgccctgcc   2160
caagagcgag aacttcaacc cagaggctct ggtcacccag gcgtcctacc cagccatggt   2220
gcaggcccag atccacctgc cggtggtgca gtccgtggcg tccccccacca cggcgtctcc   2280
cacgctgccg ccatatttca tgaaaggctc catcatccag ctggccaacg gggagctgaa   2340
gaaggtggag gacctgaaga cggaggattt catccagagt gcagagatta gcaatgacct   2400
caagatccac tccagtactg tggagagaat cgaggagagc cacagccccg gggtggccgt   2460
gatacagttt gctgttggtg aacaccgagc ccaggtcagt gtcgaagtct ggtagagta   2520
tccttttttt gtatttggac agggctggtc atcctgctgt cctgagcgga ccagccagct   2580
ctttgatctg ccgtgttcca aactctctgt tggggacgtc tgcatctcgc tcaccctcaa   2640
gaacctgaag aatggctctg ttaaaaaggg ccagcctgtg gaccctgcca gcgtcctgct   2700
gaagcaggta aagaccgaca gcctggctgg cagcagacac agatacgcgg agcaggaaaa   2760
cggaatcaac cagggaagcg cccaggtgct ctctgagaat ggcgaactga gtttccaga   2820
aaaaatagga ttgcctgcag cacccttcct cagcaaaata gaaccgagca aacccacagc   2880
cacgaggaag aggaggaggt ggtcggcgcc ggagacccgt aaactggaga gtcggagga   2940
cgagccacct ttgactcttc ccaagccttc gctcattcct caggaggtta agatctgcat   3000
cgaaggccga tctaacgtgg gcaagtagag accttgcgag cagcggaggc ccggggctct   3060
tttactgtct gtatccagat tactgtactg taggctaagt aacacagtat ttacatgtta   3120
catcctcttt aggtttgtat tctaaccttg tcattagagt caaacaggtg tgtcgcagga   3180
gactggtgcg tttgcattgt ctgcaagggt ctgttgagga gctggtgggt tggaggatgg   3240
tcagaaccat gtccatggag ctcccgggca tccttagtgg ccctgaatgt ggcttcatca   3300
```

```
gcccctgcct tctccggcag tgtgcagagt cgaggggcat cagttcccac tggtttcaag     3360
aacaaacaca gtgggaagta tcctgcaagg gagtgtctgg gtgcgtgtcc cttgtgaagg     3420
agtgcgagtg agggtgtctc tttctctgcc tctgtctccc tcacttgctc cctctcagtg     3480
tggggttggg ggacctgggt ttcccacctg caaagtcatc agggaaccca gcttccaggc     3540
attgtaggga gacatcagac aggcggatgg gaaactagtt tcaaagaacg tggttctctc     3600
caacatattt tacaat                                                      3616
```

<210> SEQ ID NO 14
<211> LENGTH: 1543
<212> TYPE: RNA
<213> ORGANISM: Homo sapiens
<220> FEATURE:
<221> NAME/KEY: misc_feature
<222> LOCATION: (1)..(1543)
<223> OTHER INFORMATION: LOCUS      SNCA                    1543 bp
      mRNA    linear   PRI 05-NOV-2002
      DEFINITION Homo sapiens synuclein, alpha (non A4 component of
      amyloid precursor) (SNCA), transcript variant NACP140, mRNA.
      ACCESSION  NM_000345: VERSION    NM_000345.2  GI:6806896
<300> PUBLICATION INFORMATION:
<308> DATABASE ACCESSION NUMBER: NM_000345
<309> DATABASE ENTRY DATE: 2002-11-05
<313> RELEVANT RESIDUES IN SEQ ID NO: (1)..(1543)

<400> SEQUENCE: 14

```
ggaguggcca uucgacgaca guguggugua aaggaauuca uuagccaugg auguauucau       60
gaaaggacuu ucaaaggcca aggagggagu uguggcugcu gcugagaaaa ccaaacaggg      120
uguggcagaa gcagcaggaa agacaaaaga gggugиucuc uauguaggcu ccaaaaccaa      180
ggagggagug gugcauggug uggcaacagu ggcugagaag accaaagagc aagugacaaa      240
uguuggagga gcagugguga cgggugugac agcaguagcc cagaagacag uggagggagc      300
agggagcauu gcagcagcca cuggcuuugu caaaaaggac caguugggca agaaugaaga      360
aggagcccca caggaaggaa uucuggaaga uaugccugug gauccugaca augaggcuua      420
ugaaaugccu ucgaggaag gguaucaaga cuacgaaccu gaagccuaag aaauaucuuu      480 gcucccagu u ucuugagauc ugcugacaga uguuccaucc uguacaagug ucaguucca      540 augugcccag ucaugacauu ucucaaaguu uuacagugu aucucgaagu cuuccaucag      600
cagugauuga aguaucugua ccugccccca cucagcauuu cggugcuucc cuuucacuga      660
agugaauaca ugguagcagg gucuuugugu gcugugggauu ugugggcuuc aaucuacgau      720
guuaaaacaa auuaaaaaca ccuaaagac uaccacuuau uucuaaaucc ucacuauuuu      780 uuguugcug uguucagaa guuguagug auuugcuauc auauauuaua agauuuuuag        840
gugucuuuua augauacugu cuaagaauaa ugacguauug ugaaauuugu aauauauau       900 aauacuuaaa aauaugugag caugaaacua ugcaccuaua aauacuaaau augaaauuuu      960
accauuuugc gaugugиuии auucacuugu guuuguaau aaauggugag aauuaaaaua     1020
aaacguuauc ucauugcaaa auauuииuau ииииаucccа ucucacuииа auaauaaaaa     1080 ucaugcuuau aagcaacaug aauuaagaac ugacacaaag gacaaaaaua uaaaguuauu     1140
aauagccauu ugaagaagga ggaauuuuag aagagguaga gaaaauggaa cauuaacccu     1200
acacucggaa uucccugaag caacacugcc agaaguguguu uugguaugc acugguuccu     1260 uaaguggcug ugauuaauua uugaaagugg gguguuaaag accccaacua cuauugaaga     1320 guggucuaии ucuccccuucа auccugucaa uguuugcuии auguauииuig gggaacuguu     1380 guuugaugиg uauguguииa uaauugииaи acauииииаа uugagccuии uauииaacaиа     1440
```

```
uauuguuauu uuugucucga aauaauuuuu uaguuaaaau cuauuuuguc ugauauuggu    1500
gugaaugcug uaccuuucug acaauaaaua auauucgacc aug                     1543
```

<210> SEQ ID NO 15
<211> LENGTH: 10660
<212> TYPE: DNA
<213> ORGANISM: Homo sapiens
<220> FEATURE:
<221> NAME/KEY: misc_feature
<222> LOCATION: (1)..(10660)
<223> OTHER INFORMATION: LOCUS      SCA1              10660 bp
      mRNA    linear    PRI 31-OCT-2000
      DEFINITION  Homo sapiens spinocerebellar ataxia 1 (olivopontocere
      bellar ataxia 1, autosomal dominant, ataxin 1) (SCA1), mRNA.
      ACCESSION   NM_000332
<300> PUBLICATION INFORMATION:
<308> DATABASE ACCESSION NUMBER: NM_000332
<309> DATABASE ENTRY DATE: 2000-10-31
<313> RELEVANT RESIDUES IN SEQ ID NO: (1)..(10660)

<400> SEQUENCE: 15

```
ctactacagt ggcggacgta caggacctgt tcactgcag gggatccaa acaagcccc      60 gtggagcaac agccagagca acagcagctg caagacattg tttctctccc tctgcccccc   120
cttccccacg caaccccaga tccatttaca ctttacagtt ttacctcaca aaaactacta   180
caagcaccaa gctccctgat ggaaaggagc atcgtgcatc aagtcaccag ggtggtccat   240
tcaagctgca gatttgtttg tcatccttgt acagcaatct cctcctccac tgccactaca   300
gggaagtgca tcacatgtca gcatactgga gcatagtgaa agagtctatt ttgaagcttc   360
aaacttagtg ctgctgcaga ccaggaacaa gagagaaaga gtggatttca gcctgcacgg   420
atggtcttga acacaaatg gttttggtc taggcgtttt acactgagat tctccactgc    480
caccctttct actcaagcaa aatcttcgtg aaaagatctg ctgcaaggaa ctgatagctt   540
atggttctcc attgtgatga agcacatgg tacagttttc caaagaaatt agaccatttt    600
cttcgtgaga agaaatcga cgtgctgttt tcatagggta tttctcactt ctctgtgaaa   660
ggaagaaaga acacgcctga gcccaagagc cctcaggagc cctccagagc ctgtgggaag   720
tctccatggt gaagtatagg ctgaggctac ctgtgaacag tacgcagtga atgttcatcc   780
agagctgctg ttggcggatt gtacccacgg ggagatgatt cctcatgaag agcctggatc   840
ccctacagaa atcaaatgtg actttccgtt tatcagacta aaatcagagc catccagaca   900
gtgaaacagt caccgtggag gggggacggc gaaaaatgaa atccaaccaa gagcggagca   960
acgaatgcct gcctcccaag aagcgcgaga tccccgccac cagccggtcc tcgaggaga   1020 aggcccctac cctgcccagc gacaaccacc gggtggaggg cacagcatgg ctcccgggca   1080
accctggtgg ccggggccac gggggcggga ggcatgggcc ggcagggacc tcggtggagc   1140
ttggtttaca acagggaata ggtttacaca aagcattgtc cacagggctg gactactccc   1200
cgcccagcgc tcccaggtct gtcccgtgg ccaccacgct gcctgccgcg tacgccaccc    1260
cgcagccagg gaccccggtg tccccgtgc agtacgctca cctgccgcac accttccagt   1320
tcattgggtc ctcccaatac agtggaacct atgccagctt catcccatca cagctgatcc   1380
ccccaaccgc caacccgtc accagtgcag tggcctcggc cgcaggggcc accactccat   1440
cccagcgctc ccagctggag gcctattcca ctctgctggc caacatgggc agtctgagcc   1500
agacgccggg acacaaggct gagcagcagc agcagcagca gcagcagcag cagcagcagc   1560
atcagcatca gcagcagcag cagcagcagc agcagcagca gcagcagcag cagcacctca   1620
gcagggctcc gggggctcatc accccgggt cccccccacc agcccagcag aaccagtacg   1680
```

```
tccacatttc cagttctccg cagaacaccg ccgcaccgc ctctcctccg ccatccccg    1740 tccacctcca cccccaccag acgatgatcc cacacacgct caccctgggg cccccctccc   1800
aggtcgtcat gcaatacgcc gactccggca gccactttgt ccctcgggag gccaccaaga   1860
aagctgagag cagccggctg cagcaggcca tccaggccaa ggaggtcctg aacggtgaga   1920
tggagaagag ccggcggtac ggggccccgt cctcagccga cctgggcctg gcaaggcag    1980 gcggcaagtc ggttcctcac ccgtacgagt ccaggcacgt ggtggtccac ccgagcccct   2040
cagactacag cagtcgtgat ccttcggggg tccgggcctc tgtgatggtc ctgcccaaca   2100
gcaacacgcc cgcagctgac ctggaggtgc aacaggccac tcatcgtgaa gcctcccctt   2160
ctaccctcaa cgacaaaagt ggcctgcatt tagggaagcc tggccaccgg tcctacgcgc   2220
tctcacccca cacggtcatt cagaccacac acagtgcttc agagccactc ccggtgggac   2280
tgccagccac ggccttctac gcagggactc aaccccctgt catcggctac ctgagcggcc   2340
agcagcaagc aatcacctac gccggcagcc tgccccagca cctggtgatc cccggcacac   2400
agcccctgct catcccggtc ggcagcactg acatggaagc gtcgggggca gccccggcca   2460
tagtcacgtc atccccccag tttgctgcag tgcctcacac gttcgtcacc accgcccttc   2520
ccaagagcga gaacttcaac cctgaggccc tggtcaccca ggccgcctac ccagccatgg   2580
tgcaggccca gatccacctg cctgtggtgc agtccgtggc ctccccggcg gcggctcccc   2640
ctacgctgcc tccctacttc atgaaaggct ccatcatcca gttggccaac ggggagctaa   2700
agaaggtgga agacttaaaa acagaagatt tcatccagag tgcagagata agcaacgacc   2760
tgaagatcga ctccagcacc gtagagagga ttgaagacag ccatagcccg ggcgtggccg   2820
tgatacagtt cgccgtcggg gagcaccgag cccaggtcag cgttgaagtt ttggtagagt   2880 atccttttt tgtgtttgga cagggctggt catcctgctg tccggagaga accagccagc   2940
tctttgattt gccgtgttcc aaactctcag ttggggatgt ctgcatctcg cttaccctca   3000
agaacctgaa gaacggctct gttaaaaagg ccagcccgt ggatcccgcc agcgtcctgc    3060
tgaagcactc aaaggccgac ggcctggcg gcagcagaca caggtatgcc gagcaggaaa    3120
acggaatcaa ccaggggagt gcccagatgc tctctgaaa tggcgaactg aagtttccag    3180
agaaaatggg attgcctgca gcgcccttcc tcaccaaaat agaacccagc aagcccgcgg   3240
caacgaggaa gaggaggtgg tcggcgccag agagccgcaa actggagaag tcagaagacg   3300 aaccacctttt gactcttcct aagccttctc taattcctca ggaggttaag atttgcattg   3360
aaggccggtc taatgtaggc aagtagaggc agcgtggggg aaaggaaacg tggctctccc   3420
ttatcatttg tatccagatt actgtactgt aggctaaaat aacacagtat ttacatgtta   3480
tcttcttaat tttaggtttc tgttctaacc ttgtcattag agttacagca ggtgtgtcgc   3540
aggagactgg tgcatatgct ttttccacga gtgtctgtca gtgagcgggc gggaggaagg   3600
gcacagcagg agcggtcagg gctccaggca tccccgggga agaaaggaac ggggcttcac   3660
agtgcctgcc ttctctagcg gcacagaagc agccgggggc gctgactccc gctagtgtca   3720
ggagaaaagt cccgtgggaa gagtcctgca ggggtgcagg gttgcacgca tgtggggtg    3780 cacaggcgct gtggcggcga gtgagggtct cttttctct gcctccctct gcctcactct    3840
cttgctatcg gcatgggccg gggggttca gagcagtgtc ctcctggggt tcccacgtgc    3900
aaaatcaaca tcaggaaccc agcttcaggg catcgcggag acgcgtcaga tggcagattt   3960
ggaaagttaa ccatttaaaa gaacattttt ctctccaaca tatttacaa taaaagcaac    4020 ttttaattgt atagatatat atttccccct atggggcctg actgcactga tatatatttt    4080
```

```
ttttaaagag caactgccac atgcgggatt tcatttctgc tttttactag tgcagcgatg   4140
tcaccagggt gttgtggtgg acagggaagc ccctgctgtc atggcccac atggggtaag    4200 gggggttggg ggtgggggag agggagagag cgaacaccca cgctggtttc tgtgcagtgt   4260
taggaaaacc aatcaggtta ttgcattgac ttcactccca agaggtagat gcaaactgcc   4320
cttcagtgag agcaacagaa gctcttcacg ttgagtttgc gaaatctttt tgtctttgaa   4380
ctctagtact gtttatagtt catgactatg gacaactcgg gtgccacttt ttttttttc    4440 agattccagt gtgacatgag gaattagatt ttgaagatga gcatatatta ctatctttaa   4500
gcatttaaaa atactgttca cactttatta ccaagcatct tggtctctca ttcaacaagt    4560
actgtatctc actttaaact ctttggggaa aaacaaaaa caaaaaaaac taagttgctt    4620 tcttttttc aacactgtaa ctacatttca gctctgcaga attgctgaag agcaagatat    4680
tgaaagtttc aatgtggttt aagggatga atgtgaatta tgaactagta tgtgacaata    4740
aatgaccacc aagtactacc tgacgggagg cacttttcac tttgatgtct gagaatcagt   4800
tcaaggcata tgcagagttg gcagagaaac tgagagaaaa gggatggaga agagaatact   4860 cattttgtc cagtgttttt cttttaaga tgaactttta aagaaccttg cgatttgcac     4920
atattgagtt tataacttgt gtgatattcc tgcagttttt atccaataac attgtgggaa   4980
aggtttgggg gactgaacga gcataaataa atgtagcaaa atttctttct aacctgccta   5040
aactctaggc cattttataa ggttatgttc ctttgaaaat tcattttggt cttttacca    5100 catctgtcac aaaaagccag gtcttagcgg gctcttagaa actctgagaa ttttcttcag   5160
attcattgag agagttttcc ataaagacat ttatatatgt gagcaagatt tttttaaac    5220 aattacttta ttattgttgt tattaatgtt attttcagaa tggctttttt tttctattca   5280
aaatcaaatc gagatttaat gtttggtaca aacccagaaa gggtatttca tagttttaa    5340 acctttcatt cccagagatc cgaaatatca tttgtgggtt ttgaatgcat ctttaaagtg   5400
ctttaaaaaa aagttttata agtagggaga aattttttaaa tattcttact tggatggctg   5460
caactaaact gaacaaatac ctgacttttc ttttacccca ttgaaaatag tactttcttc    5520
gtttcacaaa ttaaaaaaaa aatctggtat caacccacat tttggctgtc tagtattcat    5580
ttacatttag ggttcaccag gactaatgat ttttataaac cgttttctgg ggtgtaccaa    5640
aaacatttga ataggtttag aatagctaga atagttcctt gacttcctc gaatttcatt     5700 accctctcag catgcttgca gagagctggg tgggctcatt cttgcagtca tactgcttat     5760
ttagtgctgt attttttaaa cgtttctgtt cagagaactt gcttaatctt ccatatattc    5820
tgctcagggc acttgcaatt attaggtttt gttttctttt tgtttttta gcctttgatg    5880 gtaagaggaa tacgggctgc cacatagact ttgttctcat taatatcact atttacaact    5940
catgtggact cagaaaaaca cacaccacct tttggcttac ttcgagtatt gaattgactg    6000
gatccactaa accaacacta agatgggaaa acacacatgg tttggagcaa taggaacatc    6060
atcataattt ttgtggttct atttcaggta taggaattat aaaataattg gttctttcta   6120
aacacttgtc ccatttcatt ctcttgcttt tttagcatgt gcaatacttt ctgtgccaat    6180
agagtctgac cagtgtgcta tatagttaaa gctcattccc ttttggcttt ttccttgttt    6240
ggttgatctt ccccattctg gccagagcag ggctggaggg aaggagccag gagggagaga    6300
gcctcccacc tttcccctgc tgcggatgct gagtgctggg gcggggagcc ttcaggagcc    6360
ccgtgcgtct gccgccacgt tgcagaaaga gccagccaag gagacccggg ggaggaaccg    6420
cagtgtcccc tgtcaccaca cggaatagtg aatgtggagt gtggagagga aggaggcaga    6480
```

```
ttcatttcta agacgcactc tggagccatg tagcctggag tcaacccatt ttccacggtc    6540 tttctgcaa gtgggcaggc ccctcctcgg ggtctgtgtc cttgagactt ggagccctgc    6600
ctctgagcct ggacgggaag tgtggcctgt tgtgtgtgtg cgttctgagc gtgttggcca    6660
gtggctgtgg aggggaccac ctgccaccca cggtcaccac tcccttgtgg cagctttctc    6720
ttcaaatagg aagaacgcac agagggcagg agcctcctgt ttgcagacgt tggcgggccc    6780
cgaggctccc agagcagcct ctgtcaccgc ttctgtgtag caaacattaa cgatgacagg    6840
ggtagaaatt cttcggtgcc gttcagctta caaggatcag ccatgtgcct ctgtactatg    6900
tccactttgc aatatttacc gacagccgtc ttttgttctt tctttcctgt tttccatttt    6960
taaactagta acagcaggcc ttttgcgttt acaatggaac acaatcacca agaaattagt    7020
cagggcgaaa agaaaaaaat aatactatta ataagaaacc aacaaacaag aacctctctt    7080
tctagggatt tctaaatata taaaatgact gttccttaga atgtttaact taagaattat    7140
ttcagtttgt ctgggccaca ctggggcaga ggggggaggg agggatacag agatggatgc    7200
cacttacctc agatctttta aagtggaaat ccaaattgaa ttttcatttg gactttcagg    7260
ataattttct atgttggtca acttttcgtt ttccctaact cacccagttt agtttgggat    7320
gatttgattt ctgttgttgt tgatcccatt tctaacttgg aattgtgagc ctctatgttt    7380
tctgttaggt gagtgtgttg ggttttttcc ccccaccagg aagtggcagc atccctcctt    7440
ctcccctaaa gggactctgc ggaacctttc acacctcttt ctcagggacg gggcaggtgt    7500
gtgtgtggta cactgacgtg tccagaagca gcactttgac tgctctggag tagggttgta    7560
caatttcaag gaatgtttgg atttcctgca tcttgtggat tactccttag ataccgcata    7620
gattgcaata taatgctgca tgttcaagat gaacagtagc tcctagtaat cataaaatcc    7680
actctttgca cagtttgatc tttactgaaa tatgttgcca aaatttattt ttgttgttgt    7740
agctctggat tttgttttgt tttgtttttt aaggaaacga ttgacaatac cctttaacat    7800
ctgtgactac taaggaaacc tatttctttc atagagagaa aaatctccaa tgcttttgaa    7860
gacactaata ccgtgctatt tcagatatgg gtgaggaagc agagctctcg gtaccgaagg    7920
ccgggcttct tgagctgtgt tggttgtcat ggctactgtt tcatgaacca caagcagctc    7980
aacagactgg tctgttgcct tctgaaaccc tttgcacttc aatttgcacc aggtgaaaac    8040
agggccagca gactccatgg cccaattcgg tttcttcggt ggtgatgtga aaggagagaa    8100
ttacactttt tttttttttta agtggcgtgg aggcctttgc ttccacattt gtttttaacc    8160
cagaatttct gaaatagaga atttaagaac acatcaagta aaatatatac agagaatata    8220
cttttttata aagcacatgc atctgctatt gtgttgggtt ggtttcctct cttttccacg    8280
gacagtgttg tgtttctggc ataggaaac tccaaacaac ttgcacacct ctactccgga    8340
gctgagattt cttttacata gatgacctcg cttcaaatac gttaccttac tgatgatagg    8400 atctttctt gtagcactat accttgtggg aattttttt taaatgtaca cctgatttga    8460
gaagctgaag aaaacaaaat tttgaagcac tcactttgag gagtacaggt aatgttttaa    8520
aaaattgcac aaaagaaaaa tgaatgtcga aatgattcat tcagtgtttg aaagatatgg    8580
ctctgttgaa acaatgagtt tcatactttg tttgtaaaaa aaaaaagcag agaagggttg    8640
aaagttacat gtttttttgt atatagaaat ttgtcatgtc taaatgatca gatttgtatg    8700
gttatggcct ggaagaatta ctacgtaaaa ggctcttaaa ctataccttat gcttattgtt    8760 attttgtta catatagccc tcgtctgagg gaggggaact cggtattctg cgatttgaga    8820
atactgttca ttcctatgct gaaagtactt ctctgagctc ccttcttagt ctaaactctt    8880
```

-continued

```
aagccattgc aacttctttt tcttcagaga tgatgtttga cattttcagc acttcctgtt    8940
cctataaacc caaagaatat aatcttgaac acgaagtgtt tgtaacaagg gatccaggct    9000
accaatcaaa caggactcat tatggggaca aaaaaaaaaa aaattatttc accttctttc    9060
cccccacacc tcatttaaat gggggagta aaaacatgat ttcaatgtaa atgcctcatt    9120
ttattttagt ttatttga tttttattta atataaagag gccagaataa atacggagca    9180
tcttctcaga atagtattcc tgtccaaaaa tcaagccgga cagtggaaac tggacagctg    9240
tggggatatt aagcacccc acttacaatt cttaaattca gaatctcgtc cctccttc    9300
tcgttgaagg caactgttct ggtagctaac tttctcctgt gtaatggcgg gagggaacac    9360
cggcttcagt ttttcatgtc cccatgactt gcatacaaat ggttcaactg tattaaaatt    9420
aagtgcattt ggccaatagg tagtatctat acaataacaa caatctctaa gaatttccat    9480
aacttttctt atctgaaagg actcaagtct tccactgcag atacattgga ggcttcaccc    9540
acgttttctt tcccttagt ttgtttgctg tctggatggc caatgagcct gtctcctttt    9600
ctgtggccaa tctgaaggcc ttcgttggaa gtgttgttca cagtaatcct taccaagata    9660
acatactgtc ctccagaata ccaagtatta ggtgacacta gctcaagctg ttgtcttcag    9720
agcagttacc aagaagctcg gtgcacaggt tttctctggt tcttacagga accacctact    9780
cttctcagttt tctggcccag gagtggggta aatcctttag ttagtgcatt tgaacttggt    9840
acctgtgcat tcagttctgt gaatactgcc cttttggcg gggtttcctc atctccccag    9900
cctgaactgc tcaactctaa acccaaatta gtgtcagccg aaaggaggtt tcaagatagt    9960
cctgtcagta tttgtggtga ccttcagatt agacagtctt catttccagc cagtggagtc    10020
ctggctccag agccatctct gagactccgt actactggat gttttaatat cagatcatta    10080
cccaccatat gcctcccaca ggccaaggga aaacagacac cagaacttgg gttgagggca    10140
ctaccagact gacatggcca gtacagagga gaactaggga aggaatgatg ttttgcacct    10200
tattgaaaag aaaattttaa gtgcatacat aatagttaag agctttttatt gtgacaggag    10260
aacttttttc catatgcgtg catactctct gtaattccag tgtaaaatat tgtacttgca    10320
ctagctttt taaacaaata ttaaaaaatg gaagaattca tattctattt tctaatcgtg    10380
gtgtgtctat ttgtaggata cactcgagtc tgtttattga attttatggt cccttctttt    10440
gatggtgctt gcaggtttttc taggtagaaa ttatttcatt attataataa acaatgttt    10500
gattcaaaat ttgaacaaaa ttgttttaaa taaattgtct gtataccagt acaagtttat    10560
tgtttcagta tactcgtact aataaaataa cagtgccaat tgcaaaaaaa aaaaaaaaaa    10620
aaaaaaaaaa aaaaaaaaaa aaaaaaaaaa aaaaaaaaa                         10660
```

<210> SEQ ID NO 16
<211> LENGTH: 1900
<212> TYPE: DNA
<213> ORGANISM: Homo sapiens
<220> FEATURE:
<221> NAME/KEY: misc_feature
<222> LOCATION: (1)..(1900)
<223> OTHER INFORMATION: LOCUS           MJD                      1900 bp
      mRNA     linear    PRI 31-JUL-2002
      DEFINITION  Homo sapiens Machado-Joseph disease (spinocerebellar
      ataxia 3, olivopontocerebellar ataxia 3, . . .
      ACCESSION   NM_004993
<300> PUBLICATION INFORMATION:
<308> DATABASE ACCESSION NUMBER: NM_004993
<309> DATABASE ENTRY DATE: 2002-07-31
<313> RELEVANT RESIDUES IN SEQ ID NO: (1)..(1900)

<400> SEQUENCE: 16

```
ggggcggagc tggaggggggt ggttcggcgt gggggccgtt ggctccagac aaataaacat    60
ggagtccatc ttccacgaga aacaagaagg ctcactttgt gctcaacatt gcctgaataa   120
cttattgcaa ggagaatatt ttagccctgt ggaattatcc tcaattgcac atcagctgga   180
tgaggaggag aggatgagaa tggcagaagg aggagttact agtgaagatt atcgcacgtt   240
tttacagcag ccttctggaa atatggatga cagtggtttt ttctctattc aggttataag   300
caatgccttg aaagtttggg gtttagaact aatcctgttc aacagtccag agtatcagag   360
gctcaggatc gatcctataa atgaaagatc atttatatgc aattataagg aacactggtt   420
tacagttaga aaattaggaa aacagtggtt taacttgaat tctctcttga cgggtccaga   480
attaatatca gatacatatc ttgcactttt cttggctcaa ttacaacagg aaggttattc   540
tatatttgtc gttaagggtg atctgccaga ttgcgaagct gaccaactcc tgcagatgat   600
tagggtccaa cagatgcatc gaccaaaact tattggagaa gaattagcac aactaaaaga   660
gcaaagagtc cataaaacag acctggaacg agtgttagaa gcaaatgatg gctcaggaat   720
gttagacgaa gatgaggagg attttgcgag ggctctggca ctaagtcgcc aagaaattga   780
catggaagat gaggaagcag atctccgcag ggctattcag ctaagtatgc aaggtagttc   840
cagaaacata tctcaagata tgacacagac atcaggtaca aatcttactt cagaagagct   900
tcggaagaga cgagaagcct actttgaaaa acagcagcaa aagcagcaac agcagcagca   960
gcagcagcag caggggggacc tatcaggaca gagttcacat ccatgtgaaa ggccagccac  1020
cagttcagga gcacttggga gtgatctagg tgatgctatg agtgaagaag acatgcttca  1080
ggcagctgtg accatgtctt tagaaactgt cagaaatgat ttgaaaacag aaggaaaaaa  1140
ataataccctt taaaaaataa tttagatatt catactttcc aacattatcc tgtgtgatta  1200
cagcataggg tccactttgg taatgtgtca aagagatgag gaaataagac ttttagcggt  1260
ttgcaaacaa aatgatggga aagtggaaca atgcgtcggt tgtaggacta aataatgatc  1320
ttccaaatat tagccaaaga ggcattcagc aattaaagac attttaaaata gttttctaaa  1380
tgtttctttt tctttttttga gtgtgcaata tgtaacatgt ctaaagttag ggcattttttc  1440
ttggatcttt ttgcagacta gctaattagc tctcgcctca ggcttttttcc atatagtttg  1500
ttttctttttt ctgtcttgta ggtaagttgg ctcacatcat gtaatagtgg ctttcatttc  1560
ttattaacca aattaacctt tcaggaaagt atctctactt tcctgatgtt gataatagta  1620
atggttctag aaggatgaac agttctccct tcaactgtat accgtgtgct ccagtgtttt  1680
cttgtgttgt tttctctgat cacaacttttt ctgctacctg gttttcatta ttttcccaca  1740
attcttttga aagatggtaa tctttttctga ggtttagcgt tttaagcct acgatgggat  1800
cattatttca tgactggtgc gttcctaaac tctgaaatca gccttgcaca agtacttgag  1860
aataaatgag cattttttaa aaaaaaaaaa aaaaaaaaa                          1900
```

```
<210> SEQ ID NO 17
<211> LENGTH: 1735
<212> TYPE: DNA
<213> ORGANISM: Homo sapiens
<220> FEATURE:
<221> NAME/KEY: misc_feature
<222> LOCATION: (1)..(1735)
<223> OTHER INFORMATION: LOCUS       MJD                      1735 bp
      mRNA    linear    PRI 31-JUL-2002
      DEFINITION  Homo sapiens Machado-Joseph disease (spinocerebellar
      ataxia 3, olivopontocerebellar ataxia 3, autosomal dominant,
      ataxin 3) (MJD) . . .
      ACCESSION   NM_030660
```

<300> PUBLICATION INFORMATION:
<308> DATABASE ACCESSION NUMBER: NM_030660
<309> DATABASE ENTRY DATE: 2002-07-31
<313> RELEVANT RESIDUES IN SEQ ID NO: (1)..(1735)

<400> SEQUENCE: 17

```
ggggcggagc tggaggggggt ggttcggcgt gggggccgtt ggctccagac aaataaacat    60
ggagtccatc ttccacgaga aacagccttc tggaaatatg gatgacagtg gttttttctc   120
tattcaggtt ataagcaatg ccttgaaagt ttggggttta gaactaatcc tgttcaacag   180
tccagagtat cagaggctca ggatcgatcc tataaatgaa agatcattta tatgcaatta   240
taaggaacac tggtttacag ttagaaaatt aggaaaacag tggtttaact tgaattctct   300
cttgacgggt ccagaattaa tatcagatac atatcttgca cttttcttgg ctcaattaca   360
acaggaaggt tattctatat ttgtcgttaa gggtgatctg ccagattgcg aagctgacca   420
actcctgcag atgattaggg tccaacagat gcatcgacca aaacttattg gagaagaatt   480
agcacaacta aaagagcaaa gagtccataa aacagacctg gaacgagtgt tagaagcaaa   540
tgatggctca ggaatgttag acgaagatga ggaggatttg cagagggctc tggcactaag   600
tcgccaagaa attgacatgg aagatgagga agcagatctc cgcagggcta ttcagctaag   660
tatgcaaggt agttccagaa acatatctca agatatgaca cagacatcag gtacaaatct   720
tacttcagaa gagcttcgga agagacgaga agcctacttt gaaaaacagc agcaaaagca   780
gcaacagcag cagcagcagc agcagcaggg ggacctatca ggacagagtt cacatccatg   840
tgaaaggcca gccaccagtt caggagcact tgggagtgat ctaggtgatg ctatgagtga   900
agaagacatg cttcaggcag ctgtgaccat gtctttagaa actgtcagaa atgatttgaa   960
aacagaagga aaaaaataat acctttaaaa aataatttag atattcatac tttccaacat  1020
tatcctgtgt gattacagca tagggtccac tttggtaatg tgtcaaagag atgaggaaat  1080
aagactttta gcggtttgca aacaaaatga tgggaaagtg gaacaatgcg tcggttgtag  1140
gactaaataa tgatcttcca aatattagcc aaagaggcat tcagcaatta aagacattta  1200
aaatagtttt ctaaatgttt cttttcttt tttgagtgtg caatatgtaa catgtctaaa  1260
gttagggcat ttttcttgga tcttttttgca gactagctaa ttagctctcg cctcaggctt  1320
tttccatata gtttgttttc ttttctgtc ttgtaggtaa gttggctcac atcatgtaat  1380
agtggctttc atttcttatt aaccaaatta accttttcagg aaagtatctc tactttcctg  1440
atgttgataa tagtaatggt tctagaagga tgaacagttc tcccttcaac tgtataccgt  1500
gtgctccagt gttttcttgt gttgtttct ctgatcacaa cttttctgct acctggtttt  1560
cattattttc ccacaattct tttgaaagat ggtaatcttt tctgagggtt agcgtttttaa  1620
gccctacgat gggatcatta tttcatgact ggtgcgttcc taaactctga aatcagcctt  1680
gcacaagtac ttgagaataa atgagcattt tttaaaaaaa aaaaaaaaaa aaaaa         1735
```

<210> SEQ ID NO 18
<211> LENGTH: 5832
<212> TYPE: RNA
<213> ORGANISM: Homo sapiens
<220> FEATURE:
<221> NAME/KEY: misc_feature
<222> LOCATION: (1)..(5832)
<223> OTHER INFORMATION: ACCESSION   NM_012104
    VERSION     NM_012104.2  GI:21040369

```
<220> FEATURE:
<221> NAME/KEY: misc_feature
<222> LOCATION: (1)..(5832)
<223> OTHER INFORMATION: LOCUS        BACE       5832 bp     mRNA     linear
      PRI 05-NOV-2002
      DEFINITION  Homo sapiens beta-site APP-cleaving enzyme (BACE),
      transcript variant a, mRNA.
<300> PUBLICATION INFORMATION:
<308> DATABASE ACCESSION NUMBER: NM_012104
<309> DATABASE ENTRY DATE: 2002-11-05
<313> RELEVANT RESIDUES IN SEQ ID NO: (1)..(5832)

<400> SEQUENCE: 18
```

| | | | | | |
|---|---|---|---|---|---|
| ucccagccc | gcccgggagc | ugcgagccgc | gagcuggauu | auggugccu | gagcagccaa | 60 |
| cgcagccgca | ggagcccgga | gcccuugccc | cugcccgcgc | cgccgcccgc | cgggggacc | 120 |
| agggaagccg | ccaccggccc | gccaugcccc | cccucccag | cccgccggg | agcccgcgcc | 180 |
| cgcugcccag | gcuggccgcc | gccgugccga | guagcgggc | uccggauccc | agccucuccc | 240 |
| cugcucccgu | gcucugcgga | ucuccccuga | ccgcucucca | cagcccggac | ccggggcug | 300 |
| gcccagggcc | cugcaggccc | uggcguccug | augccccaa | gcucccucuc | cugagaagcc | 360 |
| accagcacca | cccagacuug | ggggcaggcg | ccagggacgg | acgugggcca | gugcgagccc | 420 |
| agagggcccg | aaggccgggg | cccaccaugg | cccaagcccu | gcccuggcuc | cugcugugga | 480 |
| uggcgcggg | agugcugccu | gccacggca | cccagcacgg | cauccggcug | ccccugcgca | 540 |
| gcggccuggg | gggcgccccc | cugggcugc | ggcugccccg | ggagaccgac | gaagagcccg | 600 |
| aggagcccgg | ccggagggc | agcuuugug | agauggugga | caaccugagg | ggcaagucgg | 660 |
| ggcagggcua | cuacguggag | augaccgugg | gcagccccc | gcagacgcuc | aacauccugg | 720 |
| uggauacagg | cagcaguaac | uuugcagugg | gugcugcccc | ccacccuuc | cugcaucgcu | 780 |
| acuaccagag | gcagcugucc | agcacauacc | gggaccuccg | gaagggugug | uaugugcccu | 840 |
| acacccaggg | caaguggga | ggggagcugg | gcaccgaccu | gguaagcauc | ccccauggcc | 900 |
| ccaacgucac | ugugcgugcc | aacauugcug | ccaucacuga | aucagacaag | uucuucauca | 960 |
| acggcuccaa | cugggaaggc | auccgggggc | uggccuaugc | ugagauugcc | aggccugacg | 1020 |
| acuccccugga | gccuuucuuu | gacucucugg | uaaagcagac | ccacguuccc | aaccucuucu | 1080 |
| cccugcagcu | uugugugcu | ggcuuccccc | ucaaccaguc | ugaagugcug | gccucgucg | 1140 |
| gagggagcau | gaucauugga | gguaucgacc | acucgcugua | cacaggcagu | ucucgguaua | 1200 |
| cacccauccg | gcgggagugg | uauuaugagg | ucaucauugu | gcggguggag | aucaauggac | 1260 |
| aggaucugaa | aauggacugc | aaggaguaca | acuaugacaa | gagcauugug | gacagugca | 1320 |
| ccaccaaccu | ucguuugccc | aagaaagugu | uugaagcugc | agucaaaucc | aucaaggcag | 1380 |
| ccuccuccac | ggagaaguuc | ccugaugguu | ucuggcuagg | agagcagcug | gugugcuggc | 1440 |
| aagcaggcac | cacccuugg | aacauuuucc | cagucaucuc | acucuaccua | auggugagg | 1500 |
| uuaccaacca | guccuuccgc | aucaccaucc | uuccgcagca | uaccugcgg | ccagugaag | 1560 |
| augugccac | gucccaagac | gacuguuaca | aguuugccau | cucacaguca | uccacgggca | 1620 |
| cuguuauggg | agcuguuauc | auggagggcu | ucuacguugu | cuuugaucgg | gccgaaaac | 1680 |
| gaauuggcuu | ugcugucagc | gcuugccaug | ugcacgauga | guucaggacg | gcagcgguuc | 1740 |
| aaggcccuuu | ugucaccuug | gacauggaag | acuggcua | caacauucca | cagacagaug | 1800 |
| agucaacccu | caugaccaua | gccuaugca | uggcugccau | cugcgccuc | uucaugcugc | 1860 |
| cacucugccu | cauggugugu | cagcgcgcu | gccccgcug | ccugcgccag | cagcaugaug | 1920 |
| acuuugcuga | ugacaucucc | cugcugaagu | gaggaggccc | augggcagaa | gauagagauu | 1980 |

```
ccccuggacc acaccuccgu gguucacuuu ggucacaagu aggagacaca gauggcaccu    2040
guggccagag caccucagga cccuccccac ccaccaaaug ccucugccuu gauggagaag    2100
gaaaaggcug gcaaggugggg uuccagggac uguaccugua ggaaacagaa aagagaagaa    2160
agaagcacuc ugcuggcggg aauacucuug gucaccucaa auuuaagucg ggaaauucug    2220
cugcuugaaa cuucagcccu gaaccuuugu ccaccauucc uuuaaauucu ccaacccaaa    2280
guauucuucu uuucuuaguu ucagaaguac uggcaucaca cgcagguuac cuuggcgugu    2340
gucccugugg uacccuggca gagaagagac caagcuuguu cccugcugg ccaaagucag    2400 uaggagagga ugcacaguuu gcauuuugcu uuagagacag ggacuguaua aacaagccua    2460
acauuggugc aaagauugcc ucuugaauua aaaaaaaaaa cuagauugac uauuuauaca    2520 aauggggcg gcuggaaaga ggagaaggag agggaguaca aagacaggga auagugggau    2580
caaagcuagg aaaggcagaa acacaaccac ucaccagucc uaguuuuaga ccucaucucc    2640
aagauagcau cccaucucag aagugggug uguuuucaa uguuucuuu ucuggguug    2700 cagccugacc aaaagugaga ugggaagggc uuaucuagcc aaagagcucu uuuuagcuc    2760 ucuuaaauga agugcccacu aagaaguucc acuuaacaca ugaauuucug ccauauuaau    2820
uucauugucu cuaucugaac cacccuuuau ucuacauaug auaggcagca cugaaauauc    2880 cuaaccccu aagcuccagg ugcccugugg gagagcaacu ggacuauagc agggcuggc    2940 ucugucuucc uggucauagg cucacucuuu ccccaaaauc uuccucugga gcuuugcagc    3000
caaggugcua aaaggaauag guaggagacc ucuucuaucu aauccuuaaa agcauaaugu    3060
ugaacauuca uucaacagcu gaugcccuau aaccccugcc uggauuucuu ccauuaggc    3120 uauaagaagu agcaagaucu uuacauaauu cagaguggu ucacugccuu ccacccucu    3180 cuaauggccc cuccauuuau uugacuaaag caucacacag uggcacuagc auuauaccaa    3240
gaguaugaga aauacagugc uuuauggcuc uaacauuacu gccuucagua ucaaggcugc    3300
cuggagaaag gauggcagcc ucagggcuuc cuuaugccu ccaccacaag agcuccuuga    3360
ugaaggucau cuuuuucccc uaccuguuc ucccccucc cgcuccuaau gguacguggg    3420
uacccaggcu gguucuuggg cuaggagug gggaccaagu ucauuaccuc ccaucaguu    3480 cuagcauagu aaacuacggu accagguua gugggaagag cugggguuuuc cuaguauacc    3540 cacugcaucu uaccuaccc uggucaaccc gcugcuucca gguaugggac cugcuaagug    3600
uggaauuacc ugauaaggga gagggaaaua caaggagggc cucuggguguu ccuggcccua    3660 gccagcugcc cacaagccau aaaccaauaa aacaagaaua cugagucagu uuuuaucgu    3720 gguucucuuc auuccacaacug cacuggugc ugcuuggcu gacugggaac accccauaac    3780
uacagagucu gacaggaaga cuggagacug uccacuucua gcucggaacu uacuguguaa    3840
auaaacuuuc agaacugcua ccaugaagug aaaaugccac auuuugcuuu auaauuucua    3900
cccauguugg gaaaaacugg cuuuuuccca gcccuuucca gggcauaaaa cucaaccccu    3960
ucgauagcaa gucccaucag ccuauuauuu uuuuaaagaa aacugcacu uguuuuucuu    4020 uuuacaguua cuuccuuccu gccccaaaau uauaaacucu aaguguaaaa aaaagucuua    4080
acaacagcuu cuugcuugua aaauaugua uuauacaucu guauuuuuaa auucugcucc    4140 ugaaaauga cugucccauu cuccacucac ugcauuuggg gccuuuccca uuggucugca    4200
ugucuuuuau cauugcaggc caguggacag agggagaagg gagaacaggg gucgccaaca    4260
cuuguguugc uuucugacug auccugaaca agaaagagua acacugaggc gcucgcuccc    4320
augcacaacu cuccaaaaca cuuauccucc ugcaagagug ggcuuuccag ggucuuuacu    4380
```

```
gggaagcagu uaagccccu ccucaccccu uccuuuuuc uuucuuuacu ccuuuggcuu    4440
caaaggauuu uggaaaagaa acaauaugcu uuacacucau uuucaauuuc uaaauuugca    4500
ggggauacug aaaaauacgg cagguggccu aaggcugcug uaaguugag gggagaggaa    4560 aucuuaagau uacaagauaa aaacgaauc cccuaaacaa aaagaacaau agaacugguc    4620
uuccauuuug ccaccuuucc uguucaugac agcuacuaac cuggagacag uaacauuuca    4680
uuaaccaaag aaaguggguc accugaccuc ugaagagcug aguacucagg ccacuccaau    4740
cacccuacaa gaugccaagg aggucccagg aaguccagcu ccuuaaacug acgcuaguca    4800
auaaaccugg gcaagugagg caagagaaau gaggaagaau ccaucuguga ggugacaggc    4860
aaggaugaaa gacaaagaag gaaagagua ucaaaggcag aaaggagauc auuuaguugg    4920
gucugaaagg aaaagucuuu gcuauccgac auguacugcu aguaccugua agcauuuag    4980 gucccagaau ggaaaaaaaa aucagcuauu gguaauauaa uaaugucccu ucccuggagu    5040
caguuuuuuu aaaaguuaa cucuuaguuu uuacuuguuu aauucaaaaa gagaagggag    5100
cugaggccau ucccuguagg aguaaagaua aaaggauagg aaaagauuca aagcucuaau    5160
agagucacag cuuucccagg uauaaaaccu aaaauuaaga aguacaauaa gcagagguugg    5220 aaaaugaucu aguccugau agcuacccac agagcaagug auuuauaaau uugaaaucca    5280
aacuacuuuc uuaauaucac uuuggucucc auuuuuccca ggacaggaaa uaugucccc    5340 ccuaacuuuc uugcuucaaa aauuaaaauc cagcauccca gaucauucu acaaguaauu    5400 uugcacagac aucuccucac cccagugccu gucuggagcu cacccaaggu caccaaacaa    5460
cuugguugug aaccaacugc cuuaaccuuc uggggaggg ggauuagcua gacuaggaga    5520
ccagaaguga augggaaagg gugaggacuu cacaauguug gccugucaga gcuugauuag    5580
aagccaagac aguggcagca aaggaagacu uggcccagga aaaaccugug gguugugcua    5640
auuucugucc agaaaauagg guggacagaa gcuuggggg uacauggagg aauugggacc    5700 uguuauguu guuauucucg gacugugaau uuuggugaug uaaaacagaa uauucuguaa    5760 accuaaguc uguauaaaua augagcguua acacaguaaa auauucaaua agaagucaaa    5820
cuacuagggu ua                                                       5832

<210> SEQ ID NO 19
<211> LENGTH: 5757
<212> TYPE: RNA
<213> ORGANISM: Homo sapiens
<220> FEATURE:
<221> NAME/KEY: misc_feature
<222> LOCATION: (1)..(5757)
<223> OTHER INFORMATION: LOCUS      BACE              5757 bp
      mRNA      linear    PRI  05-NOV-2002
      DEFINITION  Homo sapiens beta-site APP-cleaving enzyme (BACE),
      transcript variant b, mRNA.
      ACCESSION    NM_138972; VERSION    NM_138972.1  GI:21040365
<300> PUBLICATION INFORMATION:
<308> DATABASE ACCESSION NUMBER: NM_138972
<309> DATABASE ENTRY DATE: 2002-11-05
<313> RELEVANT RESIDUES IN SEQ ID NO: (1)..(5757)

<400> SEQUENCE: 19
uccccagccc gccgggagc ugcgagccgc gagcuggauu augguggccu gagcagccaa      60
cgcagccgca ggagcccgga gcccuugccc cugcccgcgc gccgccccgc cgggggggacc     120 agggaagccg ccaccggccc gccaugcccc cccucccag ccccgccggg agcccgcgcc     180
cgcugcccag gcuggccgcc gccgugccga uguagcgggg uccggauccc agccucuccc     240 cugcuccccgu gcucugcgga ucuccccuga ccgcucucca cagcccggac ccgggggcug     300
```

-continued

```
gcccagggcc cugcaggccc uggcguccug augcccccaa gcucccucuc cugagaagcc      360
accagcacca cccagacuug ggggcaggcg ccagggacgg acgugggcca gugcgagccc      420
agagggcccg aaggccgggg cccaccaugg cccaagcccu gcccuggcuc cugcugugga      480
ugggcgcggg agugcugccu gcccacggca cccagcacgg cauccggcug ccccugcgca      540
gcggccuggg gggcgccccc cuggggcugc ggcugccccg ggagaccgac gaagagcccg      600
aggagcccgg ccggaggggc agcuuugugg agauggugga caaccugagg ggcaagucgg      660
ggcagggcua cuacguggag augaccgugg gcagcccccc gcagacgcuc aacauccugg      720
uggauacagg cagcaguaac uuugcagugg gugcugcccc ccacccuuc cugcaucgcu       780 acuaccagag gcagcugucc agcacauacc gggaccuccg gaagggugug uaugugcccu      840
acacccaggg caagugggaa ggggagcugg gcaccgaccu gguaagcauc ccccauggcc      900
ccaacgucac ugugcgugcc aacauugcug ccaucacuga aucagacaag uucuucauca      960
acggcuccaa cugggaaggc auccggggc uggccuaugc ugagauugcc aggcuuugug      1020
gugcuggcuu ccccucaac cagucugaag ugcuggccuc ugucggaggg agcaugauca      1080
uuggagguau cgaccacucg cuguacacag gcagucucug guauacaccc auccggcggg      1140
agugguauua ugaggucauc auugugcggg uggagaucaa uggacaggau cugaaaaugg      1200
acugcaagga guacaacuau gacaagagca uuguggacag uggcaccacc aaccuucguu      1260
ugcccaagaa aguguuugaa gcugcaguca aaccaucaa ggcagccucc uccacggaga      1320
aguucccuga ugguuucugg cuaggagagc agcggugug cuggcaagca ggcaccaccc      1380
cuuggaacau uucccaguc aucucacucu accuaauggg ugagguuacc aaccaguccu      1440
uccgcaucac cauccuuccg cagcaauacc ugcggccagu ggaagaugug gccacgugcc      1500
aagacgacug uuacaaguuu gccaucucac agucauccac gggcacuguu augggagcug      1560
uuaucaugga gggcuucuac guugucuuug aucgggcccg aaaacgaauu ggcuuugcug      1620
ucagcgcuug ccaugugcac gaugaguuca ggacggcagc gguggaaggc ccuuuuguca      1680
ccuuggacau ggaagacugu ggcuacaaca uccacagac agaugaguca cccucauga      1740 ccauagccua ugcauggcu ccaucugcg cccucuucau gcugccacuc ugccucaugg      1800
ugugucagug gcgcugccuc cgcgcugcugc gccagcagca ugaugacuuu gcugaugaca      1860
ucucccugcu gaaugagga ggcccauggg cagaagauag agauucccu ggaccacacc      1920 uccgugguuc acuuuggucaa caaguaggag acacagaugg caccugluggc cagagcaccu      1980 caggacccuc cccacccacc aaaugccucu gccuugaugg agaaggaaaa ggcuggcaag      2040
guggguucca gggacuguac cuguaggaaa cagaaaagag aagaaagaag cacucugcug      2100 gcggaauac ucuuggucac cucaaauuua agucggaaa uucugcugcu ugaaacuuca      2160
gcccugaacc uuugucccacc auuccuuuaa auucuccaac ccaaaguauu cuucuuuucu      2220
uaguuucaga aguacuggca ucacacgcag guuaccuugg cguguguccc ugugguacc      2280 uggcagagaa gagaccaagc uuguuucccu gcugccaaa gucaguagga gaggaugcac      2340
aguuugcuau uugcuuuaga acagggacu guauaaacaa gccuaacauu ggugcaaaga      2400 uugcucucuug aauuaaaaaa aaaaacuaga uugacuauuu auacaaaugg gggcggcugg      2460
aaagaggaga aggagaggga guacaaagac agggaauagu gggaucaaag cuaggaaagg      2520
cagaaacaca accacucacc aguccuaguu uagacccuca ucaagau agcaucccau      2580 cucagaagau ggguguugu ucaaugauuu ucuuucugu gguugcagcc ugaccaaaag      2640
ugagauggga agggcuuauc uagccaaaga gcucuuuuuu agcucucuua aaugaagugc      2700
```

-continued

```
ccacuaagaa guuccacuua acacaugaau uucugccaua uuaauuucau ugucucuauc    2760
ugaaccaccc uuuauucuac auaugauagg cagcacugaa auauccuaac ccccuaagcu    2820
ccaggugccc uguggagag caacuggacu auagcagggc ugggcucugu cuuccgguc      2880
auaggcucac ucuuuccccc aaaucuuccu cuggagcuuu gcagccaagg ugcuaaaagg    2940
aauagguagg agaccucuuc uaucuaaucc uuaaaagcau aauguugaac auucauucaa    3000
cagcugaugc ccuauaaccc cugccuggau uucuuccuau uaggcuauaa gaaguagcaa    3060
gaucuuuaca uaauucagag ugguuucacu gccuuccuac ccucucuaau ggccccucca    3120
uuuauuugac uaaagcauca cacaguggca cuagcauuau accaagagua ugagaaauac    3180
agugcuuuau ggcucuaaca uuacugccuu caguaucaag gcugccugga aaaggaugg     3240
cagccucagg gcuuccuuau guccuccacc acaagagcuc cuugaugaag gucaucuuuu    3300
uccccuaucc uguucuuccc cuccccgcuc cuaauggua gugggua ccc aggcugguuc    3360
uugggcuagg uagugggga c caaguucauu accccccuau caguucuagc auaguaaacu    3420
acgguaccag uguuaguggg aagagcuggg uuuccuagu auccacug cauccuacuc       3480
cuaccgguc aacccgcugc uuccaggua g gaccug cu aagugg gaa uuacugaua       3540
agggagaggg aaauacaagg agggccucug uguuccugg cccagccag cugcccacaa      3600
gccauaaacc aauaaaacaa gaauacgag ucaguuuuuu aucgggu uc cuucauucc      3660
cacugcacuu ggugcugcuu uggcugacug ggaacacccc auaacuacag agucugacag    3720
gaagacugga gacuguccac uucuagcucg gaacuuacug uguaaauaaa cuuucagaac    3780
ugcuaccaug aagugaaaau gccacauuuu gcuuuauaau uucuacccau guugggaaaa    3840
acuggcuuuu uccagcccu uuccagggca uaaaacucaa ccccuucgau agcaagcccc    3900
aucagccuau uauuuuuuua agaaaaacuu gcacuuguu ucuuuuuac aguuacuucc     3960
uuccugcccc aaaauuauaa acucuaagug uaaaaaaag ucuuaacaac agcuucuugc    4020
uuguaaaaau auguauuaua caucuguauu uuuaaauucu gcuccugaaa aaugacuguc   4080
ccauucucca cucacugcau uuggggccuu ucccauuggu cugcaugucu uuuaucauug   4140
caggccagug acagaggga aagggagaa cagggcgc caaacauugu guugcuuuc        4200
gacugauccu gaacaagaaa gaguaacacu gaggcgcucg cucccaugca caacucucca   4260
aaacacuuau ccuccugcaa gagugggcuu ccaggucu uuacgggaa gcaguuaagc      4320
ccccuccuca ccccuuccuu uuucuuucu uuacuccuuu ggcuucaaag gauuuggaa     4380
aagaaacaau augcuuuaca cucauuuuca auuucuaaau uugcagggga uacgaaaaa    4440
uacggcaggu ggccuaaggc ugcuguaaag uugaggggag aggaaaucuu aagauuacaa   4500
gauaaaaaac gaauccccua acaaaaaga acaauagaac uggucuucca uuuugccacc   4560
uuccuguuc augacagcua cuaaccugga gacaguaaca uuucauuaac caaagaaagu   4620
gggucaccug accucugaag agcugaguac ucaggcacu ccaaucaccc uacaagaugc   4680
caaggagguc ccaggaaguc cagcuccuua aacgacgcu agcaauaaa ccugggcaag    4740
ugaggcaaga gaaaugagga agaauccauc ugugagguga caggcaagga ugaaagacaa  4800
agaaggaaaa gaguaucaaa ggcagaaagg agaucauuua guugggucug aaaggaaaag  4860
ucuuugcuau ccgacaugua cugcuaguac cuguaagcau uuuaggcccc agaauggaaa  4920
aaaaaaucag cuauugguaa uauaauaaug uccuuucccu ggagucaguu uuuuaaaaa   4980
guuaacucuu aguuuuacu uguuuaauuc uaaaagagaa gggagcugag gccauucccu   5040
guaggaguaa agauaaaagg auaggaaaag auucaaagcu cuaauagagu cacagcuuuc  5100
```

| | |
|---|---|
| ccagguauaa aaccuaaaau uaagaaguac aauaagcaga ggugaaaaau gaucuaguuc | 5160 |
| cugauagcua cccacagagc aagugauuua uaaauuugaa auccaaacua cuuucuuaau | 5220 |
| aucacuuugg ucuccauuuu ucccaggaca ggaaauaugu cccccccuaa cuuucuugcu | 5280 |
| ucaaaaauua aaauccagca ucccaagauc auucuacaag uaauuuugca cagacaucuc | 5340 |
| cucaccccag ugccugucug gagcucaccc aaggucacca acaacuugg uugugaacca | 5400 |
| acugccuuaa ccuucggggg aggggggauu agcuagacua ggagaccaga agugaauggg | 5460 |
| aaagggugag gacuucacaa uguuggccug ucagagcuug auuagaagcc aagacagugg | 5520 |
| cagcaaagga agacuuggcc caggaaaaac cugugggüug gcuaauuuc uguccagaaa | 5580 |
| auagggugga cagaagcuug uggggguacau ggaggaauug ggaccugguu auguuguuau | 5640 |
| ucucggacug ugaauuuugg ugauguaaaa cagaauauuc uguaaaccua augucuguau | 5700 |
| aaauaaugag cguuaacaca guaaaauauu caauaagaag ucaaacuacu agggüua | 5757 |

<210> SEQ ID NO 20
<211> LENGTH: 5700
<212> TYPE: RNA
<213> ORGANISM: Homo sapiens
<220> FEATURE:
<221> NAME/KEY: misc_feature
<222> LOCATION: (1)..(5700)
<223> OTHER INFORMATION: LOCUS       BACE                5700 bp
      mRNA     linear    PRI 21-MAY-2002
      DEFINITION  Homo sapiens beta-site APP-cleaving enzyme (BACE),
      transcript variant c, mRNA.
      ACCESSION   NM_138971; VERSION    NM_138971.1 GI:21040363
<300> PUBLICATION INFORMATION:
<308> DATABASE ACCESSION NUMBER: NM_138971.1
<309> DATABASE ENTRY DATE: 2002-05-21
<313> RELEVANT RESIDUES IN SEQ ID NO: (1)..(5700)

<400> SEQUENCE: 20

| | |
|---|---|
| uccccagccc gcccgggagc ugcgagccgc gagcuggauu auggüggccu gagcagccaa | 60 |
| cgcagccgca ggagcccgga gcccuugccc cugcccgcgc cgccgcccgc cggggggacc | 120 |
| agggaagccg ccaccggccc gccauugccc cccucccag ccccgccggg agcccgcgcc | 180 |
| cgcugcccag gcuggccgcc gccgugccga uguagcgggc uccggauccc agccucuccc | 240 |
| cugcucccgu gcucugcgga ucuccccuga ccgcucucca cagcccggac ccgggggcug | 300 |
| gcccagggcc cugcaggccc uggcguccug augcccccaa gcucccucuc cugagaagcc | 360 |
| accagcacca cccagacuug ggggcaggcg ccagggacgg acgugggcca gugcgagccc | 420 |
| agagggcccg aaggccgggg cccaccaugg cccaagcccu gcccuggcuc ugcugugga | 480 |
| ugggcgcggg agugcugccu gcccacggca cccagcacgg cauccggcug ccccugcgca | 540 |
| gcggccuggg gggcgccccc cuggggcugc ggcugccccg ggagaccgac gaagagcccg | 600 |
| aggagcccgg ccggaggggc agcuuugugg agauggugga caaccugagg ggcaagucgg | 660 |
| ggcagggcua cuacguggag augaccgugg gcagccccc gcagacgcuc aacauccugg | 720 |
| uggauacagg cagcagüaac uuugcagugg gugcugcccc caccccuuc cugcaucgcu | 780 |
| acuaccagag gcagcugucc agcacauacc gggaccuccg gaaggugug uaugugcccu | 840 |
| acacccaggg caaguggggaa gggagcuggg gcaccgaccu gccugacgac ucccuggagc | 900 |
| cuuucuuuga cucucuggua agcagaccc acguucccaa ccucuuccc cugcagcuuu | 960 |
| guggugcugg cuuccccuuc aaccagcucu aagucuggc ucucucggga gggagcauga | 1020 |
| ucauggagg uaucgaccac ucgcuguaca caggcagucu cugguauaca cccauccggc | 1080 |
| gggaguggua uuaugaggüc aucauuguigc ggguggagau caauggacag gaucugaaaa | 1140 |

```
uggacugcaa ggaguacaac uaugacaaga gcauugugga cagugcacc accaaccuuc    1200 guuugcccaa gaaaguguuu gaagcugcag ucaaauccau caaggcagcc uccuccacgg    1260
agaaguuccc ugauggauuuc uggcuaggag agcagcuggu gugcuggcaa gcaggcacca   1320
cccuuuggaa cauuuccca gucaucucac ucuaccuaau ggugagguu accaaccagu     1380 ccuuccgcau caccauccuu ccgcagcaau accugcggcc aguggaagau guggccacgu    1440
cccaagacga cuguuacaag uuugccaucu cacagucauc cacgggcacu guuaugggag    1500
cuguuaucau ggagggcuuc uacguugucu uugaucgggc ccgaaaacga auuggcuuug    1560
cugucagcgc uugccaugug cacgaugagu caggacggc agcgguggaa ggcccuuuug     1620
ucaccuugga cauggaagac uguggcuaca acauuccaca gacagaugag ucaacccuca    1680
ugaccauagc cuaugucaug gcugccaucu gcgcccucuu caugcugcca cucugccuca    1740
ugguguguca guggcgcugc cuccgcugcc ugcgccagca gcaugaugac uuugcugaug    1800
acaucucccu gcugaaguga ggaggcccau gggcagaaga uagagauucc ccuggaccac    1860
accuccgugg uucacuuugg ucacaaguag gagacacaga uggcaccugu ggccagagca    1920
ccucaggacc ucccccaccc accaaaaugcc ucugccuuga uggagaagga aaaggcuggc    1980 aaggugggu ccagggacug uaccuguagg aaacagaaaa gagaagaaag aagcacucug    2040
cuggcgggaa uacucuuggu caccucaaau uuaagucggg aaauucugcu gcuugaaacu    2100
ucagcccuga accuuugucc accauuccuu uaaauucucc aacccaaagu auucuucuuu    2160
ucuuaguuuc agaaguacug gcaucacacg cagguuaccu uggcgugugu cccugugguo    2220 cccuggcaga gaagagacca agcuuguuuc ccugcuggcc aaagucagua ggagaggaug    2280
cacaguuugc uauuugcuuu agagacaggg acuguauaaa caagccuaac auuggugcaa    2340
agauugccuc uugaauuaaa aaaaaaaacu agauugacua uuuauacaaa uggggcgcggc    2400 uggaaagagg agaaggagag ggaguacaaa gacaggaauagug ggauca aagcuaggaa     2460 aggcagaaac acaaccacuc accaguccua guuuuagacc ucauuccaa gauagcaucc    2520 caucucagaa gaugggugu guuuucaaug uuuucuuuuc ugugguuugca gccugaccaa    2580 aagugagaug ggaagggcuu aucuagccaa agagcucuuu uuuagcucuc uuaaaugaag    2640
ugcccacuaa gaaguuccac uuaacacaug aauuucugcc auauuaauuu cauugucucu    2700
aucugaacca cccuuuauuc uacauaugau aggcagcacu gaaauauccu aaccccuaa     2760 gcuccaggug cccugugga gagcaacugg acuauagcag ggcugggcuc ugucuuccug    2820
gucauaggcu cacucuuucc cccaaaucuu ccucuggagc uuugcagcca aggugcuaaa    2880
aggaauaggu aggagaccuc uucuaucuaa uccuuaaaag cauaauguug aacauucauu    2940
caacagcuga ugcccauauaa ccccugccug gauuucuucc uauuaggcua uaagaaguag    3000
caagaucuuu acauaauuca gaguggauuuc acugccuucc uacccucucu aauggcccu    3060 ccauuuauuu gacuaaagca ucacacagug gcacuagcau uauaccaaga guaugagaaa    3120
uacagugcuu uauggcucua acauuacugc cuucagauac aaggcugccu ggagaaagga    3180
uggcagccuc agggcuuccu uaugucccuc ccacaagag cuccuugaug aaggucaucu    3240
uuuuccccua uccuguucuu cccucccccg cuccaauggg uacgugggua ccaggcuggg    3300
uucuugggcu agguaguggg gaccaaguuc auuaccuccc uaucaguucu agcauaguaa    3360
acuacgguac caguguuagu gggagagcu ggguuuuccu aguauacccca cugcauccaa    3420 cuccuaccug gucaacccgc ugcuuccagg uaugggaccu gcuaaguguig gaauuaccug    3480 auaagggaga gggaaauaca aggaggggcu cugguguucc uggccucagc cagcugccca    3540
```

```
caagccauaa accaauaaaa caagaauacu gagucaguuu uuuaucuggg uucucuucau    3600
ucccacugca cuuggugcug cuuuggcuga cugggaacac cccauaacua cagagucuga    3660
caggaagacu ggagacuguc cacuucuagc ucggaacuua cuguguaaau aaacuuucag    3720
aacugcuacc augaagugaa aaugccacau uuugcuuuau aauuucuacc cauguuggga    3780
aaaacuggcu uuucccagcc ccuuuccagg gcauaaaacu caaccccuuc gauagcaagu    3840
cccaucagcc uauuauuuuu uuaaagaaaa cuugcacuug uuuucuuuu uacaguuacu     3900 uccuuccugc cccaaaauua uaaacucuaa guguaaaaaa aagucuuaac aacagcuucu    3960
ugcuuguaaa aauauguauu auacaucugu auuuuuaaau ucugcuccug aaaaaugacu    4020
gucccauucu ccacucacug cauuggggc cuucccauu ggucugcaug ucuuuuauca      4080
uugcaggcca guggacagag ggagaaggga gaacaggggu cgccaacacu uguuugcuu    4140 ucugacugau ccugaacaag aaagaguaac acugaggcgc ucgcucccau gcacaacucu    4200
ccaaaacacu uauccuccug caagagugg cuuuccaggg ucuuuacugg gaagcaguua    4260 agccccucc ucacccuuc cuuuuucuu ucuuuacucc uuuggcuuca aaggauuuug       4320
gaaaagaaac aauaugcuuu acacucauuu ucaauuucua aauuugcagg ggauacugaa   4380
aaauacggca ggugccuaa ggcugcugua aguugaggg gagaggaaau cuuaagauua     4440
caagauaaaa aacgaaucccc cuaaacaaaa agaacaauag aacuggucuu ccauuugcc   4500 accuuccuug uucaugacag cuacuaaccu ggagacagua acauucauu aaccaaagaa    4560 aguggucac cugaccucug aagagcugag uacucaggcc acccaauca cccuacaaga     4620 ugccaaggag gucccaggaa guccagcucc uuaaacugac gcuagucaau aaaccugggc   4680
aagugaggca agagaaauga ggaagaaucc aucugugagg ugacaggcaa ggaugaaaga   4740
caaagaagga aaagaguauc aaaggcagaa aggagaucau uuaguugggu cugaaaggaa   4800
aagucuuugc uauccgacau guacugcuag uaccuguaag cauuuaaggu cccgaauug    4860 aaaaaaaaau cagcuauugg uaauauaaua augccuuuc ccuggaguca guuuuuuaa     4920 aaaguuaacu cuuaguuuuu acuguuuuaa uucuaaaaga gaaggagcu gaggccauuc    4980 ccuguaggag uaaagauaaa aggauaggaa aagauucaaa gcucuaauag agucacagcu   5040
uucccaggua uaaaccuaa aauuaagaag uacaauaagc agagguggaa aaugaucuag    5100
uuccugauag cuaccacag agcaagugau uuauaaauuu gaauccaaa cuacuuucuu     5160 aauaucacuu uggucuccau uuuucccagg acaggaaaua uguccccccc uaacuuucuu   5220
gcuucaaaaa uuaaauucca gcaucccaag aucauucuac aaguaauuuu gcacagacau   5280
cuccucaccc caguguccu cuggagcuca cccaaggucac ccaaacaacu gguugugaa    5340 ccaacugccu uaaccuucug gggagggggg auuagcuaga cuaggagacc agaagugaau   5400
gggaaagggu gaggacuuca caauguuggc cugucagagc uugauuagaa gccaagacag   5460
uggcagcaaa ggaagacuug gcccaggaaa aacuguggg uugugcuaau uucuguccag    5520
aaaauagggu ggacagaagc uugugggua caugaggaa ugggaccug guuauguugu      5580 uauucucgga cugugaauuu uggugaugua aaacagaaua uucuguaaac cuaaugcugu   5640
uauaaauaau gagcguuaac acaguaaaau auucaauaag aagucaaacu acuagggyua   5700
```

<210> SEQ ID NO 21
<211> LENGTH: 5625
<212> TYPE: RNA
<213> ORGANISM: Homo sapiens

```
<220> FEATURE:
<221> NAME/KEY: misc_feature
<222> LOCATION: (1)..(5625)
<223> OTHER INFORMATION: LOCUS       BACE                    5625 bp
      mRNA      linear    PRI 05-NOV-2002
      DEFINITION  Homo sapiens beta-site APP-cleaving enzyme (BACE),
      transcript variant d, mRNA.
      ACCESSION   NM_138973; VERSION   NM_138973.1  GI:21040367
<300> PUBLICATION INFORMATION:
<308> DATABASE ACCESSION NUMBER: NM_138973
<309> DATABASE ENTRY DATE: 2002-11-05
<313> RELEVANT RESIDUES IN SEQ ID NO: (1)..(5625)

<400> SEQUENCE: 21
```

| | | | | | |
|---|---|---|---|---|---|
| ucccagccc | gcccgggagc | ugcgagccgc | gagcuggauu | augguggccu | gagcagccaa | 60 |
| cgcagccgca | ggagcccgga | gcccuugccc | cugcccgcgc | cgccgcccgc | cgggggacc | 120 |
| agggaagccg | ccaccggccc | gccaugcccg | ccccucccag | ccccgccggg | agcccgcgcc | 180 |
| cgcugcccag | gcuggccgcc | gccgugccga | guagcgggc | uccggauccc | agccucuccc | 240 |
| cugcucccgu | gcucugcgga | ucccccuga | ccgcucucca | cagccggac | ccggggcug | 300 |
| gcccagggcc | cugcaggccc | uggcguccug | augcccccaa | gcucccucuc | cugagaagcc | 360 |
| accagcacca | cccagacuug | ggggcaggcg | ccagggacgg | acgugggcca | gugcgagccc | 420 |
| agagggcccg | aaggccgggg | cccaccaugg | cccaagcccu | gcccuggcuc | cugcugugga | 480 |
| ugggcgcggg | agugcugccu | gccacgcca | cccagcacgg | cauccggcug | cccugcgca | 540 |
| gcggccuggg | gggcgccccc | cuggggcugc | ggcugccccg | ggagaccgac | gaagagcccg | 600 |
| aggagcccgg | ccggaggggc | agcuuugugg | agauggugga | caaccugagg | ggcaagucgg | 660 |
| ggcagggcua | cuacguggag | augaccgugg | gcagccccccc | gcagacgcuc | aacauccugg | 720 |
| uggauacagg | cagcaguaac | uuugcagugg | gugcugcccc | ccaccccuuc | cugcaucgcu | 780 |
| acuaccagag | gcagcugucc | agcacauacc | gggaccuccg | gaagggugug | uaugugcccu | 840 |
| acacccaggg | caaguggga | ggggagcugg | gcaccgaccu | gcuuugugu | gcuggcuucc | 900 |
| cccucaacca | gucugaagug | cuggccucug | ucggagggag | caugaucauu | ggagguaucg | 960 |
| accacucgcu | guacacaggc | agucucuggu | auacacccau | ccggcgggag | ugguauuaug | 1020 |
| aggucaucau | ugugcgggug | gagaucaaug | acaggaucu | gaaaauggac | ugcaaggagu | 1080 |
| acaacuauga | caagagcauu | ggacaguguc | caccaccaa | ccuucguuug | cccaagaaag | 1140 |
| uguuugaagc | ugcagucaaa | uccaucaagg | cagccuccuc | cacggagaag | uucccugaug | 1200 |
| guuucuggcu | aggagagcag | cuggugugcu | ggcaagcagg | caccacccccu | uggaacauuu | 1260 |
| ucccagucau | cucacucuac | cuaaugggug | agguaccaa | ccaguccuuc | cgcaucacca | 1320 |
| uccuuccgca | gcaauaccug | cggccagugg | aagaugggc | cacguccaa | gacgacuguu | 1380 |
| acaaguuugc | caucucacag | ucauccacgg | gcacuguau | gggagcuguu | aucauggagg | 1440 |
| gcuucuacgu | ugucuuugau | cgggcccgaa | acgaauugg | cuuugcuguc | agcgcuugcc | 1500 |
| augugcacga | ugaguucagg | acggcagcgg | uggaaggccc | uuugucacc | uuggacaugg | 1560 |
| aagacuguggg | cuacaacauu | ccacagacag | augagcaac | ccucaugacc | auagccuaug | 1620 |
| ucauggcugc | caucucgcc | cucuucaugc | ugccacucug | ccucauggug | gucaguggc | 1680 |
| gcugccuccg | cugccugcgc | cagcagcaug | augacuuugc | ugaugacauc | ucccugcuga | 1740 |
| agugaggagg | cccaugggca | gaagauagag | auucccuugg | accaccuc | cgugguucac | 1800 |
| uuuggucaca | aguaggagac | acagauggca | ccuguggcca | gagccaccuca | ggaccccuc | 1860 |
| caccccaa | augccucugc | cuugauggag | aaggaaaagg | cuggcaaggu | ggguuccagg | 1920 |
| gacuguaccu | guaggaaaca | gaaaagagaa | gaaagaagca | cucugcuggc | gggaauacuc | 1980 |

| | |
|---|---:|
| uuggucaccu caaauuuaag ucgggaaauu cugcugcuug aaacuucagc ccugaaccuu | 2040 |
| uguccaccau uccuuuaaau ucuccaaccc aaaguauucu ucuuucuua guuucagaag | 2100 |
| uacuggcauc acacgcaggu uaccuuggcg ugugcccug uggacccug gcagagaaga | 2160 |
| gaccaagcuu guuccccugc uggccaaagu caguaggaga ggaugcacag uuugcuauuu | 2220 |
| gcuuuagaga cagggacugu auaaacaagc cuaacauugg ugcaaagauu gccucuugaa | 2280 |
| uuaaaaaaaa aaacuagauu gacuauuuau acaaaugggg gcggcuggaa agaggagaag | 2340 |
| gagagggagu acaaagacag ggaauagugg gaucaaagcu aggaaaggca gaaacacaac | 2400 |
| cacucaccag uccuaguuuu agaccucauc uccaagauag caucccaucu cagaagaugg | 2460 |
| guguuguuuu caauguuuuc uuuucugugg uugcagccug accaaaagug agaugggaag | 2520 |
| ggcuuaucua gccaaagagc ucuuuuuag cucucuuaaa ugaagugccc acuaagaagu | 2580 |
| uccacuuaac acaugaauuu cugccauauu aauuucauug ucucuaucug aaccacccuu | 2640 |
| uauucuacau augauaggca gcacugaaau auccuaaccc ccuaagcucc aggugcccug | 2700 |
| ugggagagca acuggacuau agcagggcug ggcucugucu uccuggucau aggcucacuc | 2760 |
| uuuccccaa aucuuccucu ggagcuuugc agccaaggug cuaaaaggaa uagguaggag | 2820 |
| accucuucua ucuaauccuu aaaagcauaa uguugaacau cauucaaca gcugaugccc | 2880 |
| uauaaccccu gccuggauuu cuuccuauua ggcuauaaga aguagcaaga ucuuuacaua | 2940 |
| auucagagug guuucacugc cuuccuaccc ucucuaaugg ccccuccauu uauuugacua | 3000 |
| aagcaucaca caguggcacu agcauuauac caagaguaug agaaauacag ugcuuuaugg | 3060 |
| cucuaacauu acugccuuca guacaaggc ugccuggaga aaggauggca gccucagggc | 3120 |
| uuccuuaugu ccuccaccac aagagcuccu ugaugaaggu caucuuuuc cccuauccug | 3180 |
| uucuuccccu ccccgcuccu aauggacgu ggguacccag gcugguucuu gggcuaggua | 3240 |
| gugggaccca aguucauuac cucccaauca guucuagcau aguaaacuac gguaccagug | 3300 |
| uuagugggaa gagcuggguu uuccaguau acccacugca uccacuccu accuggucaa | 3360 |
| cccgcugcuu ccagguaugg gaccugcuaa guguggaauu accugauaag ggagagggaa | 3420 |
| auacaaggag ggccucuggu guuccuggcc ucagccagcu gcccacaagc cauaaaccaa | 3480 |
| uaaaacaaga auacgaguc aguuuuuau cugggucuc uucauuccca cugcacuugg | 3540 |
| ugcugcuuug gcugacuggg aacaccccau aacuacagag cugacagga agacuggaga | 3600 |
| cuguccacuu cuagcucgga acuuacugug uaaauaaacu ucagaacug cuaccaugaa | 3660 |
| gugaaaaugc cacauuuugc uuuauaauuu cucccaugu ugggaaaaac uggcuuuuc | 3720 |
| ccagcccuuu ccagggcaua aaacucaacc ccuucgauag caaguccau cagccuauua | 3780 |
| uuuuuuaaa gaaaacuugc acuuguuuu cuuuuuacag uuacuccuu ccugccccaa | 3840 |
| aauuauaaac ucuaagugua aaaaaaguc uuaacaacag cuucuugcuu guaaaaauau | 3900 |
| guauauaca ucuguauuuu uaaauucugc uccugaaaaa ugacugccc auucuccacu | 3960 |
| cacugcauuu ggggccuuuc ccauuggucu gcaugucuuu uaucauugca ggccagugga | 4020 |
| cagagggaga agggagaaca ggggucgcca acacuugugu ugcuuucuga cugauccuga | 4080 |
| acaagaaaga guaacacuga ggcgcucgcu cccaugcaca acucuccaaa acacuuaucc | 4140 |
| uccugcaaga gugggcuuuc cagggcuuuu acugggaagc aguuaagccc ccuccucacc | 4200 |
| ccuuccuuuu uucuuucuuu acuccuuugg cuucaaagga uuuugaaaaa gaaacaauau | 4260 |
| gcuuuacacu cauuuucaau uucuaaauuu gcagggaua cugaaaaaua cggcaggugg | 4320 |
| ccuaaggcug cuguaaaguu gaggggagag gaaaucuuaa gauuacaaga uaaaaaacga | 4380 |

| | |
|---|---|
| auccccuaaa caaaaagaac aauagaacug gucuuccauu uugccaccuu uccguucau | 4440 |
| gacagcuacu aaccuggaga caguaacauu ucauuaacca aagaaagugg gucaccugac | 4500 |
| cucugaagag cugaguacuc aggccacucc aaucacccua caagaugcca aggaggsccc | 4560 |
| aggaagucca gcuccuuaaa cugacgcuag ucaauaaacc ugggcaagug aggcaagaga | 4620 |
| aaugaggaag aauccaucug ugaggugaca ggcaaggaug aaagacaaag aaggaaaaga | 4680 |
| guaucaaagg cagaaaggag aucauuuagu ugggucugaa aggaaaaguc uuugcuaucc | 4740 |
| gacauguacu gcuaguaccu guaagcauuu uaggucccag aauggaaaaa aaaaucagcu | 4800 |
| auugguaaua uaauaaugau cuuucccugg agucaguuuu uuuaaaaagu uaacucuuag | 4860 |
| uuuuuacuug uuuaauucua aagagaagg gagcugaggc cauucccugu aggaguaaag | 4920 |
| auaaaaggau aggaaaagau ucaaagcucu aauagaguca cagcuuuccc agguauaaaa | 4980 |
| ccuaaaauua agaaguacaa uaagcagagg uggaaaauga ucuaguuccu gauagcuacc | 5040 |
| cacagagcaa gugauuuaua aauuugaaau ccaaacuacu uucuuaauau cacuuugguc | 5100 |
| uccauuuuuc ccaggacagg aaauaugucc cccccuaacu uucuugcuuc aaaaauuaaa | 5160 |
| auccagcauc ccaagaucau ucuacaagua auuuugcaca gacaucuccu caccccagug | 5220 |
| ccugucugga gcucacccaa ggucaccaaa caacuugguu gugaaccaac ugccuuaacc | 5280 |
| uucgggggga gggggauuag cuagacuagg agaccagaag ugaaugggaa agggugagga | 5340 |
| cuucacaaug uuggccuguc agagcuugau uagaagccaa gacaguggca gcaaaggaag | 5400 |
| acuuggccca ggaaaaaccu guggguugug cuaauuucug uccagaaaau agggguggaca | 5460 |
| gaagcuugug gggguacaugg aggaauuggg accugguuau uuguuauuc ucggacugug | 5520 |
| aauuuuggug auguaaaaca gaauauucug uaaaccuaau gucuguauaa auaaugagcg | 5580 |
| uuaacacagu aaaauauuca auaagaaguc aaacuacuag gguua | 5625 |

<210> SEQ ID NO 22
<211> LENGTH: 3880
<212> TYPE: RNA
<213> ORGANISM: Mus musculus
<220> FEATURE:
<221> NAME/KEY: misc_feature
<222> LOCATION: (1)..(3880)
<223> OTHER INFORMATION: LOCUS       Bace                  3880 bp
      mRNA     linear  ROD 07-JAN-2002
      DEFINITION  Mus musculus beta-site APP cleaving enzyme (Bace),
      mRNA.
      ACCESSION  NM_011792; VERSION     NM_011792.2  GI:6857758
<300> PUBLICATION INFORMATION:
<308> DATABASE ACCESSION NUMBER: NM_011792
<309> DATABASE ENTRY DATE: 2002-01-07
<313> RELEVANT RESIDUES IN SEQ ID NO: (1)..(3880)

<400> SEQUENCE: 22

| | |
|---|---|
| ccccagccug ccuaggugcu gggagccggg agcuggauua ugguggccug agcagccgac | 60 |
| gcagccgcag gagcugggag ucccucacgc ugcaaagucc gccuggaaga cccgaaagc | 120 |
| ugcaggcucc gauagccaug cccgccccuc ccagccccac aaggggcccg auccccccgc | 180 |
| ugaggcuggc ggucgccguc cagauuuagc ugggucccc ggaucgccau cguccucuuc | 240 |
| ucucgugcgc uacagauuuc uccugccac ucuccaccgc cggagcagg aacugaucga | 300 |
| aggggccugc agacucugca guccugaugc ccccgaggcc gcucccuga gagaagccac | 360 |
| caccacccag acuuaggggc aggcaagagg acagucacc aaccggacca caaggcccgg | 420 |
| gcucacuaug gccccagcgc ugcacuggcu ccugcuaugg gugggucgg gaaugcugcc | 480 |
| ugcccaggga acccaucucg gcauccggcu gccccuucgc agcggccugg cagggccacc | 540 |

```
ccugggccug aggcugcccc gggagaccga cgaggaaucg gaggagccug gccggagagg    600
cagcuuugug gagauggugg acaaccugag gggaaaaguccc ggccagggcu acuaugugga  660
gaugaccgua ggcagccccc cacagacgcu caacauccug guggacacgg gcaguaguaa   720
cuuugcagug ggggcugccc cacacccuuu ccugcaucgc uacuaccaga ggcagcuguc   780
cagcacauau cgagaccucc gaaagggugu guaugugccc uacacccagg gcaaguggga   840
gggggaacug ggcaccgacc ugguagcau cccucauggc cccaacguca cugugcgugc   900
caacauugcu gccaucacug aaucggacaa guucuucauc aauggcuucca acuggagggg  960 cauccuaggg cuggccuaug cugagauugc caggcccgac gacucuuugg agcccuucuu  1020
ugacucccug gugaagcaga cccacauucc caacaucuuu cccugcagc ucuguggcgc   1080 uggcuucccc cucaaccaga ccgaggcacu ggcucucggug ggaggagca ugaucauugg    1140 ugguaucgac cacucgcuau acacgggcag ucucuggguac acacccaucc ggcgggagug  1200
guauuaugaa gugaucauug uacgugugga aaucaauggu caagaucuca agauggacug   1260
caaggaguac aacuacgaca agagcauugu ggacagugggg accaccaacc uucgcuugcc  1320
caagaaagua uuugaagcug ccgucaaguc caucaaggca gccuccucga cggagaaguu  1380
cccggauggc uuuuggcuag gggagcagcu ggugugcugg caagcaggca cgaccccuug   1440
gaacauuuuc ccagucauuu cacuuuaccu caugggugaa ucaccaaucc aguccuuccg    1500
caucaccauc cuuccucagc aauaccuacg gccgguggag gacgugggcca cgucccaaga  1560 cgacuguuac aaguucgcug ucucacaguc auccacgggc acuguuauugg gagccgucau  1620 cauggaaggu uucuaugucg ucuucgaucg agcccgaaag cgaauuggcu uugcugcag   1680 cgcuugccau gugcacgaug aguucaggac ggcggcagug gaagguccgu uuguuacggc   1740
agacauggaa gacuguggcu acaacauucc ccagacagau gagucaacac uuaugaccau  1800
agccuauguc auggcggcca ucugcgcccu cuucauguug ccacucugcc ucauggauug  1860 ucagugggcgc ugccugcguu gccugcgcca ccagcacgau gacuuugcug augcaucuc   1920 ccugcucaag uaaggaggcc cgugggcaga ugauggagac gccccuggac cacaucaggg   1980
ugguucccuu uggucacaug aguuggagcu augaugguua ccuguggcca gagcaccuca   2040 ggaccccucac caaccugcca augcuucugg cgugacagaa cagagaaauc aggcaagcug  2100
gauuacaggg cuugcaccug uaggacacag gagagggaag gaagcagcgu ucuggugcua  2160
ggaauauccu uagacaccac aaacuugagu uggaaauuuu gcugcuugaa gcuucagccc   2220
ugacccucug cccagcaucc uuuagagucu ccaaccucga guaucuuuc ugccuuccua   2280 gaaguacugg ugucauacuc aggcuacccg gcaugugucc cugugguacc cuggcagaga   2340
aagggccaau cuucauuucc ccugcuggcc aaagucagca aagaaagug aaguuugccc   2400 guugcuuuag ugauagggac uugcagacuc aagccuacac ugguacaaag acugcgucuu  2460
gagauaaaca agaaccuaug cgaugcgaau guuuauacuc cuggggggcag ucaagaugag   2520 gagacaggau aggauagaga caggaaggag augguagcaa aacugggaaa ggcagaacuc   2580
ugaucacuuu cuaguuccaa guuuagacuc auccaaaga cagaagccca ucuggacuaa   2640
gagguaucau uccccaaugu gccguggguu uagucugaa cugaaaugaa augggggaaa    2700
aagggcuuau uagccaaaga gcucuuuuuuu acacucuuag aggaacagug cucaugagaa  2760
aagucccacu ggacagauga auuccuaucu uguuaauucu gucucucucu gcuucuucaa   2820
caugcuaagu ggcaccaaaa ugacccaacc ccaaggcucu aggugcccua ugggacaaca   2880
guuagaauau uguagggcua gggauggucu ucccagcaua gguucacucc aaccaaggug   2940
```

-continued

| | |
|---|---|
| cuaaaaggaa cagacaggag aaguccuccu cucugaucca caaaggcaga gcccucaaga | 3000 |
| uucauccagc caggguuagg gcugaugcau uugccucugc cuggauuuug uuuuuauuuu | 3060 |
| cuuucuuuuu gcccaagugg guacaaaacg auaagcucuu uauggaauac ugaguggguu | 3120 |
| cauuccucuc uugcccucuc caauggcccc ucuauuuauc uggcuaagga aacaccacgc | 3180 |
| auuggcuagu auuaaacagc aacuguaaga uagagggcuu ucuguucuau gucauugccu | 3240 |
| ucaguaucaa ggcugccugg agaaaggaug gcagccucag ggcuuccuua cuuucuucuc | 3300 |
| cuuuccugac agagcagccu uucuguccug cucucugcug ccccucccaa uauaauccau | 3360 |
| ggguacccag gcugguucuu gggcuagguu ugggggccca cacucaccuc uucccugcca | 3420 |
| guucuaacac gacagacaug aagccagugu uaguggaag agcuggguuu ucccaggaug | 3480 |
| accacugcau ccucuccugg uacgcucuac acugcuuuca ggcuggggac cugccaagug | 3540 |
| ugggacaguu gaugaggaag agacauuagc agggccucug gaguugcugg cccagccagc | 3600 |
| ugcccacaag ccauaaacca auaaaauaag aauccgcgu cacaguuucc agcuggguuc | 3660 |
| ucuuccuugc ccucgcacug gugcugcucu ggcugaguag gaauacaccc acagacugcc | 3720 |
| aggaagaugg agacuguccg cuuccggcuc agaacuacag uguaauuaag cuuccaggau | 3780 |
| cacuaccaug aaaacgccgc auucugcuuu aucauuucua cccauguugg gaaaaacugg | 3840 |
| cuuuuucccc auuucuuuac agggcaaaaa aaaaaaaaa | 3880 |

<210> SEQ ID NO 23
<211> LENGTH: 1096
<212> TYPE: RNA
<213> ORGANISM: Homo sapiens
<220> FEATURE:
<221> NAME/KEY: misc_feature
<222> LOCATION: (1)..(1096)
<223> OTHER INFORMATION: LOCUS       SNCA                    1096 bp
      mRNA     linear     PRI 05-NOV-2002
      DEFINITION Homo sapiens synuclein, alpha (non A4 component of
      amyloid precursor) (SNCA), transcript variant NACP112, mRNA.
      ACCESSION   NM_007308: VERSION    NM_007308.1  GI:6806897
<300> PUBLICATION INFORMATION:
<308> DATABASE ACCESSION NUMBER: NM_007308
<309> DATABASE ENTRY DATE: 2002-12-05
<313> RELEVANT RESIDUES IN SEQ ID NO: (1)..(1096)

<400> SEQUENCE: 23

| | |
|---|---|
| gaauucauua gccauggaug uauucaugaa aggacuuuca aaggccaagg agggaguugu | 60 |
| ggcugcugcu gagaaaacca aacagggugu ggcagaagca gcaggaaaga caaaagaggg | 120 |
| uguucucuau guaggcucca aaaccaagga gggaguggug cauggugugg caacaguggc | 180 |
| ugagaagacc aaagagcaag ugacaaaugu uggaggagca guggugacgg gugugacagc | 240 |
| aguagcccag aagacagugg agggagcagg gagcauugca gcagccacug gcuuugucaa | 300 |
| aaaggaccag uuggcaagg aagggguauca agacuacgaa ccugaagccu aagaaauauc | 360 |
| uuugcuccca guucuugag aucugcugac agauguucca uccuguacaa gugcucaguu | 420 |
| ccaaugugcc cagucaugac auuucucaaa guuuuuacag uguaucucga agucuuccau | 480 |
| cagcagugau ugaaguaucu guaccugccc ccacucagca uuucggugcu ucccuuucac | 540 |
| ugaagugaau acaugguagc agggucuuug ugucgugugg auuugguggc uucaaucuac | 600 |
| gauguuaaaa caaauuaaaa acaccuaagu gacuaccacu uauuucuaaa uccucacuau | 660 |
| uuuuguguug cuguuguuca gaaguuguua ugauuugcu aucauauauu auaagauuuu | 720 |
| uaggugucuu uuaaugauac ugcuaagaa uaaugacgua uugugaaauu guuaauaua | 780 |
| uauaauacuu aaaaauaugu gagcaugaaa cuaugcaccu auaaauacua aaugaaau | 840 |

-continued

```
uuuaccauuu ugcgaugugu uuuauucacu uguguuugua uauaaauggu gagaauuaaa      900
auaaaacguu aucucauugc aaaaauauuu uauuuuuauc ccaucucacu uuaauaauaa      960
aaaucaugcu uauaagcaac augaauuaag aacugacaca aaggacaaaa auauaaaguu     1020
auuaauagcc auuugaagaa ggaggaauuu uagaagaggu agagaaaaug gaacauuaac     1080
ccuacacucg gaauuc                                                    1096
```

<210> SEQ ID NO 24
<211> LENGTH: 21
<212> TYPE: DNA
<213> ORGANISM: Mus musculus
<220> FEATURE:
<221> NAME/KEY: misc_feature
<222> LOCATION: (0803)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0803. The two 5' nucleotides AA are optional in MB0803.

<400> SEQUENCE: 24
aagggtgtgt atgtgcccta c                                                 21

<210> SEQ ID NO 25
<211> LENGTH: 21
<212> TYPE: DNA
<213> ORGANISM: Mus Musculus
<220> FEATURE:
<221> NAME/KEY: misc_feature
<222> LOCATION: (1663)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1663. The two 5' nucleotides AA are optional in MB1663.

<400> SEQUENCE: 25
aattggcttt gctgtcagcg c                                                 21

<210> SEQ ID NO 26
<211> LENGTH: 21
<212> TYPE: DNA
<213> ORGANISM: Mus Musculus
<220> FEATURE:
<221> NAME/KEY: misc_feature
<222> LOCATION: (1749)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1749. The two 5' nucleotides AA are optional in MB1749.

<400> SEQUENCE: 26
aagactgtgg ctacaacatt c                                                 21

<210> SEQ ID NO 27
<211> LENGTH: 21
<212> TYPE: DNA
<213> ORGANISM: Mus Musculus
<220> FEATURE:
<221> NAME/KEY: misc_feature
<222> LOCATION: (3249)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 3249.
<220> FEATURE:
<221> NAME/KEY: misc_feature
<222> LOCATION: (3249)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 3249. The two 5' nucleotides AA are optional in MB3249.

```
<400> SEQUENCE: 27
aaggctgcct ggagaaagga t                                              21

<210> SEQ ID NO 28
<211> LENGTH: 21
<212> TYPE: DNA
<213> ORGANISM: Mus Musculus
<220> FEATURE:
<221> NAME/KEY: misc_feature
<222> LOCATION: (0916)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0916. The two 5' nucleotides CA are optional in DhMB0918.

<400> SEQUENCE: 28
cactgaatcg gacaagttct t                                              21

<210> SEQ ID NO 29
<211> LENGTH: 21
<212> TYPE: DNA
<213> ORGANISM: Mus Musculus
<220> FEATURE:
<221> NAME/KEY: misc_feature
<222> LOCATION: (1129)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1129. The two 5' nucleotides CA are optional in DhMB1131.

<400> SEQUENCE: 29
catgatcatt ggtggtatcg a                                              21

<210> SEQ ID NO 30
<211> LENGTH: 21
<212> TYPE: DNA
<213> ORGANISM: Mus Musculus
<220> FEATURE:
<221> NAME/KEY: misc_feature
<222> LOCATION: (1231)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1231.
<220> FEATURE:
<221> NAME/KEY: misc_feature
<222> LOCATION: (1231)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1231. The two 5' nucleotides AA are optional in DhMB1233.

<400> SEQUENCE: 30
aatcaatggt caagatctca a                                              21

<210> SEQ ID NO 31
<211> LENGTH: 21
<212> TYPE: DNA
<213> ORGANISM: Mus Musculus
<220> FEATURE:
<221> NAME/KEY: misc_feature
<222> LOCATION: (1507)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1507. The two 5' nucleotides CA are optional in DhMB1509.

<400> SEQUENCE: 31
catccttcct cagcaatacc t                                              21
```

```
<210> SEQ ID NO 32
<211> LENGTH: 21
<212> TYPE: DNA
<213> ORGANISM: Mus musculus
<220> FEATURE:
<221> NAME/KEY: misc_feature
<222> LOCATION: (0683)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0683. The two 5' nucleotides CA are optional in SEC0683.

<400> SEQUENCE: 32
cagacgctca acatcctggt g                                              21

<210> SEQ ID NO 33
<211> LENGTH: 21
<212> TYPE: DNA
<213> ORGANISM: Mus musculus
<220> FEATURE:
<221> NAME/KEY: misc_feature
<222> LOCATION: (1722)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1722. The two 5' nucleotides AA are optional in SEC1722.

<400> SEQUENCE: 33
aaggtccgtt tgttacggca g                                              21

<210> SEQ ID NO 34
<211> LENGTH: 21
<212> TYPE: DNA
<213> ORGANISM: Mus musculus
<220> FEATURE:
<221> NAME/KEY: misc_feature
<222> LOCATION: (2163)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 2163. The two 5' nucleotides AA are optional in SEC2163.

<400> SEQUENCE: 34
aatatcctta gacaccacaa a                                              21

<210> SEQ ID NO 35
<211> LENGTH: 21
<212> TYPE: DNA
<213> ORGANISM: Mus musculus
<220> FEATURE:
<221> NAME/KEY: misc_feature
<222> LOCATION: (2466)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 2466. The two 5' nucleotides AA are optional in SEC2466.

<400> SEQUENCE: 35
aaacaagaac ctatgcgatg c                                              21

<210> SEQ ID NO 36
<211> LENGTH: 21
<212> TYPE: DNA
<213> ORGANISM: Mus musculus
<220> FEATURE:
<221> NAME/KEY: misc_feature
<222> LOCATION: (2473)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 2473. The two 5' nucleotides AA are optional in SEC2473.
```

```
<400> SEQUENCE: 36
aacctatgcg atgcgaatgt t                                              21

<210> SEQ ID NO 37
<211> LENGTH: 22
<212> TYPE: DNA
<213> ORGANISM: Mus musculus
<220> FEATURE:
<221> NAME/KEY: misc_feature
<223> OTHER INFORMATION: Oligonucleotide MB1749A to construct the DNA
      encoding for a hairpin loop of RNA corresponding to MB1749.

<400> SEQUENCE: 37
gaagactgtg gctacaacat tc                                             22

<210> SEQ ID NO 38
<211> LENGTH: 38
<212> TYPE: DNA
<213> ORGANISM: Mus musculus
<220> FEATURE:
<221> NAME/KEY: misc_feature
<223> OTHER INFORMATION: Oligonucleotide MB1749B to construct the DNA
      encoding for a hairpin loop of RNA corresponding to MB1749.

<400> SEQUENCE: 38
ttcaagagag aatgttgtag ccacagtctt cttttttg                            38

<210> SEQ ID NO 39
<211> LENGTH: 35
<212> TYPE: DNA
<213> ORGANISM: Mus musculus
<220> FEATURE:
<221> NAME/KEY: misc_feature
<223> OTHER INFORMATION: Oligonucleotide MB1749C to construct the DNA
      encoding for a hairpin loop of RNA corresponding to MB1749.

<400> SEQUENCE: 39
tctcttgaag aatgttgtag ccacagtctt cggcc                               35

<210> SEQ ID NO 40
<211> LENGTH: 33
<212> TYPE: DNA
<213> ORGANISM: Mus musculus
<220> FEATURE:
<221> NAME/KEY: misc_feature
<223> OTHER INFORMATION: Oligonucleotide MB1749D to construct the DNA
      encoding for a hairpin loop of RNA corresponding to MB1749.

<400> SEQUENCE: 40
aattcaaaaa agaagactgt ggctacaaca ttc                                 33

<210> SEQ ID NO 41
<211> LENGTH: 21
<212> TYPE: DNA
<213> ORGANISM: Homo sapiens
<220> FEATURE:
<221> NAME/KEY: misc_feature
<222> LOCATION: (0188)..()
<223> OTHER INFORMATION: Oligonucleotide MD0188 to construct the DNA
      encoding for siRNA starting at position 0188 within human
      Huntington cDNA(Genbank Accession NM_002111.3. The first two 5'
      nucleotides AA are optional in MD0188

<400> SEQUENCE: 41
aagatggacg gccgctcagg t                                              21
```

```
<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (0358)..()
<223> OTHER INFORMATION: Oligonucleotide MD0358 to construct the DNA
      encoding for siRNA starting at position 0358 within human
      Huntington cDNA(Genbank Accession NM_002111.3. The first two 5'
      nucleotides AA are optional in MD0358,

<400> SEQUENCE: 42
aagtccttcc agcagcagca g                                              21

<210> SEQ ID NO 43
<211> LENGTH: 21
<212> TYPE: DNA
<213> ORGANISM: Homo sapiens
<220> FEATURE:
<221> NAME/KEY: misc_feature
<222> LOCATION: (0813)..()
<223> OTHER INFORMATION: Oligonucleotide MD0813 to construct the DNA
      encoding for siRNA starting at position 0813 within human
      Huntington cDNA (Genbank Accession NM_002111.3.). The first two
      5' nucleotides AA are optional in MD0813.

<400> SEQUENCE: 43
aaggttacag ctcgagctct a                                              21

<210> SEQ ID NO 44
<211> LENGTH: 21
<212> TYPE: DNA
<213> ORGANISM: Homo sapiens
<220> FEATURE:
<221> NAME/KEY: misc_feature
<222> LOCATION: (1066)..()
<223> OTHER INFORMATION: Oligonucleotide M1066 to construct the DNA
      encoding for siRNA starting at position 1066 within human
      Huntington cDNA (Genbank Accession NM_002111.3.). The two 5'
      nucleotides AA are optional in M1066.

<400> SEQUENCE: 44
aaggttttgt taaaggcctt c                                              21

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (1639)..()
<223> OTHER INFORMATION: Oligonucleotide M1639 to construct the DNA
      encoding for siRNA starting at position 1639 within human
      Huntington cDNA (Genbank Accession NM_002111.3.). The two 5'
      nucleotides AA are optional in M1639.

<400> SEQUENCE: 45
aaaggcaaag tgctcttagg a                                              21

<210> SEQ ID NO 46
<211> LENGTH: 21
<212> TYPE: DNA
<213> ORGANISM: Homo sapiens
<220> FEATURE:
<221> NAME/KEY: misc_feature
<222> LOCATION: (2060)..()
<223> OTHER INFORMATION: Oligonucleotide M2060 to construct the DNA
      encoding for siRNA starting at position 2060 within human
      Huntington cDNA (Genbank Accession NM_002111.3.). The two 5'
      nucleotides AA are optional in M2060.
```

<400> SEQUENCE: 46
aaattgtgtt agacggtacc g  21

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (2714)..()
<223> OTHER INFORMATION: Oligonucleotide M2714 to construct the DNA encoding for siRNA starting at position 2714 within human Huntington cDNA (Genbank Accession NM_002111.3.). The two 5' nucleotides CA are optional in M2714.

<400> SEQUENCE: 47
caggaaatac attttctttg g  21

<210> SEQ ID NO 48
<211> LENGTH: 846
<212> TYPE: DNA
<213> ORGANISM: Ovis aries

<400> SEQUENCE: 48
atggcgaccc tggaaaagct gatgaaggcc ttcgagtccc tcaagtcctt ccagcagcag   60
cagcagcagc agcagcagca gcagcagcaa cagccgccac cgccgccacc cggcccggct  120
gtggctgagg agccgctgca ccgaccaaag aaagagctct cagccaccaa gaaagaccgc  180
gtgaaccact gtctgacaat ctgtgaaaac atcgtcgcgc agtctctcag aaattctcca  240
gaatttcaga aacttctggg catcgctatg gaactttttc tgctgtgcag tgatgacgca  300
gagtcagatg tcaggatggt ggctgacgaa tgcctcaaca aagtcataaa agctttgatg  360
gactctaatc ttccgaggtt gcagctagaa ctctacaagg aaattaaaaa gaacggcgcc  420
ccgcggagcc tgcgcgcggc cctctggagg ttcgccgagc tggctcacct ggtccggcct  480
cagaagtgca ggccgtacct ggtgaacctg ttgccctgcc tgacgcgcac aagcaagaga  540
cccgaggagt ccgtccagga gacgctggct gcagcgatcc ctaaaattat ggcttctttt  600
ggcaactttg cgaacgacaa tgagattaag gttctgttga aggctttcat cgcgaacctg  660
aagtccagtt ccccgactgt gcggcggacc gcggcgggct cagtggtcag catctgccag  720
cactccagga ggacgcagta cttttacagc tggctgctca gcgtgctcct aggttttgctg  780 gtccccgtgg aggaggagca ccccacccctg ctgatcctcg gcgtcctgct caccctgagg  840
tatctg  846

<210> SEQ ID NO 49
<211> LENGTH: 21
<212> TYPE: DNA
<213> ORGANISM: Ovis aries
<220> FEATURE:
<221> NAME/KEY: misc_feature
<222> LOCATION: (205)..()
<223> OTHER INFORMATION: Oligonucleotide EB1 to construct the DNA encoding for siRNA starting at position 205 in sheep Huntington sequence and starting position 643 of the (partially) homologous sequence in the human Huntington gene (NM_00211.3). The two 5' nucleotides GA are optional in EB1.

<400> SEQUENCE: 49
gaaaacatcg tcgcgcagtc t  21

```
<210> SEQ ID NO 50
<211> LENGTH: 21
<212> TYPE: DNA
<213> ORGANISM: Ovis aries
<220> FEATURE:
<221> NAME/KEY: misc_feature
<222> LOCATION: (328)..()
<223> OTHER INFORMATION: Oligonucleotide EB2 to construct the DNA
      encoding for siRNA starting at position 328 in sheep Huntington
      sequence and starting position 766 of the (partially) homologous
      sequence in the human Huntington gene (NM_00211.3). The two 5'
      nucleotides GA are optional in EB2.

<400> SEQUENCE: 50
gaatgcctca acaaagtcat a                                            21

<210> SEQ ID NO 51
<211> LENGTH: 21
<212> TYPE: DNA
<213> ORGANISM: Ovis aries
<220> FEATURE:
<221> NAME/KEY: misc_feature
<222> LOCATION: (603)..()
<223> OTHER INFORMATION: Oligonucleotide EB3 to construct the DNA
      encoding for siRNA starting at position 603 in sheep Huntington
      sequence and starting position 1041 of the (partially) homologous
      sequence in the human Huntington gene (NM_00211.3). The two 5'
      nucleotides CA are optional in EB3.

<400> SEQUENCE: 51
caactttgcg aacgacaatg a                                            21

<210> SEQ ID NO 52
<211> LENGTH: 21
<212> TYPE: DNA
<213> ORGANISM: Ovis aries
<220> FEATURE:
<221> NAME/KEY: misc_feature
<222> LOCATION: (628)..()
<223> OTHER INFORMATION: Oligonucleotide EB4 to construct the DNA
      encoding for siRNA starting at position 628 in sheep Huntington
      sequence and starting position 1066 of the (partially) homologous
      sequence in the human Huntington gene (NM_00211.3). The two 5'
      nucleotides AA are optional in EB4.

<400> SEQUENCE: 52
aaggttctgt tgaaggcttt c                                            21

<210> SEQ ID NO 53
<211> LENGTH: 21
<212> TYPE: DNA
<213> ORGANISM: Ovis aries
<220> FEATURE:
<221> NAME/KEY: misc_feature
<223> OTHER INFORMATION: Oligonucleotide EB5 to construct the DNA
      encoding for siRNA starting at position 367 in sheep Huntington
      sequence and starting position 805 of the (partially) homologous
      sequence in the human Huntington gene (NM_00211.3). The two 5'
      nucleotides AA are optional in EB5.

<400> SEQUENCE: 53
aatcttccga ggttgcagct a                                            21

<210> SEQ ID NO 54
<211> LENGTH: 1500
<212> TYPE: DNA
<213> ORGANISM: Homo sapiens
```

<400> SEQUENCE: 54

```
ttgctgtgtg aggcagaacc tgcggggggca ggggcgggct ggttccctgg ccagccattg      60
gcagagtccg caggctaggg ctgtcaatca tgctggccgg cgtggccccg cctccgccgg     120
cgcggccccg cctccgccgg cgcacgtctg ggacgcaagg cgccgtgggg gctgccggga     180
cgggtccaag atggacggcc gctcaggttc tgcttttacc tgcggcccag agccccattc     240
attgccccgg tgctgagcgg cgccgcgagt cggcccgagg cctccgggga ctgccgtgcc     300
gggcgggaga ccgccatggc gaccctggaa aagctgatga aggccttcga gtccctcaag     360
tccttccagc agcagcagca gcagcagcag cagcagcagc agcagcagca gcagcagcag     420
cagcagcagc aacagccgcc accgccgccg ccgccgccgc cgcctcctca gcttcctcag     480
ccgccgccgc aggcacagcc gctgctgcct cagccgcagc cgccccgcc gccgcccccg     540
ccgccacccg gcccggctgt ggctgaggag ccgctgcacc gaccaaagaa agaactttca     600
gctaccaaga aagaccgtgt gaatcattgt ctgacaatat gtgaaaacat agtggcacag     660
tctgtcagaa attctccaga atttcagaaa cttctgggca tcgctatgga actttttctg     720
ctgtgcagtg atgacgcaga gtcagatgtc aggatggtgg ctgacgaatg cctcaacaaa     780
gttatcaaag ctttgatgga ttctaatctt ccaaggttac agctcgagct ctataaggaa     840
attaaaaaga atggtgcccc tcggagtttg cgtgctgccc tgtggaggtt tgctgagctg     900
gctcacctgg ttcggcctca gaaatgcagg ccttacctgg tgaaccttct gccgtgcctg     960
actcgaacaa gcaagagacc cgaagaatca gtccaggaga ccttggctgc agctgttccc    1020
aaaattatgg cttcttttgg caattttgca aatgacaatg aaattaaggt tttgttaaag    1080
gccttcatag cgaacctgaa gtcaagctcc cccaccattc ggcggacagc ggctggatca    1140
gcagtgagca tctgccagca ctcaagaagg acacaatatt tctatagttg gctactaaat    1200
gtgctcttag gctactcgt tcctgtcgag gatgaacact ccactctgct gattcttggc    1260
gtgctgctca ccctgaggta tttggtgccc ttgctgcagc agcaggtcaa ggacacaagc    1320
ctgaaaggca gcttcggagt gacaaggaaa gaaatggaag tctctccttc tgcagagcag    1380
cttgtccagg tttatgaact gacgttacat catacacagc accaagacca caatgttgtg    1440
accggagccc tggagctgtt gcagcagctc ttcagaacgc ctccacccga gcttctgcaa    1500
```

<210> SEQ ID NO 55
<211> LENGTH: 20
<212> TYPE: DNA
<213> ORGANISM: Homo sapiens

<400> SEQUENCE: 55

```
tggtgttcaa tgcttttccc                                                  20
```

<210> SEQ ID NO 56
<211> LENGTH: 20
<212> TYPE: DNA
<213> ORGANISM: Homo sapiens

<400> SEQUENCE: 56

```
gcgtcttgta gttcccgtca                                                  20
```

<210> SEQ ID NO 57
<211> LENGTH: 60
<212> TYPE: DNA
<213> ORGANISM: Homo sapiens

```
<400> SEQUENCE: 57
gaagactgtg gctacaacat tcttcaagag agaatgttgt agccacagtc ttctttttg      60

<210> SEQ ID NO 58
<211> LENGTH: 68
<212> TYPE: DNA
<213> ORGANISM: Homo sapiens

<400> SEQUENCE: 58
aattcaaaaa agaagactgt ggctacaaca ttctctcttg aagaatgttg tagccacagt    60
cttcggcc                                                             68

<210> SEQ ID NO 59
<211> LENGTH: 22
<212> TYPE: DNA
<213> ORGANISM: Homo sapiens

<400> SEQUENCE: 59
tgacacagcc gctactacat tg                                             22

<210> SEQ ID NO 60
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 60
aagtagggca catacacacc ccctgtctc                                      29

<210> SEQ ID NO 61
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 61
aagggtgtgt atgtgcccta ccctgtctc                                      29

<210> SEQ ID NO 62
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 62
aagcgctgac agcaaagcca acctgtctc                                      29

<210> SEQ ID NO 63
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 63
aattggcttt gctgtcagcg ccctgtctc                                      29

<210> SEQ ID NO 64
<211> LENGTH: 29
<212> TYPE: DNA
<213> ORGANISM: Artificial Sequence
```

```
<220> FEATURE:
<223> OTHER INFORMATION: DNA Oligonucleotides for producing siRNA

<400> SEQUENCE: 64
aagaatgttg tagccacagt ccctgtctc                                        29

<210> SEQ ID NO 65
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 65
aagactgtgg ctacaacatt ccctgtctc                                        29

<210> SEQ ID NO 66
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 66
aaatcctttc tccaggcagc ccctgtctc                                        29

<210> SEQ ID NO 67
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 67
aaggctgcct ggagaaagga tcctgtctc                                        29

<210> SEQ ID NO 68
<211> LENGTH: 23
<212> TYPE: DNA
<213> ORGANISM: Artificial Sequence
<220> FEATURE:
<223> OTHER INFORMATION: siRNA strand

<400> SEQUENCE: 68
cugaaucgga caaguucuud tdt                                              23

<210> SEQ ID NO 69
<211> LENGTH: 23
<212> TYPE: DNA
<213> ORGANISM: Artificial Sequence
<220> FEATURE:
<223> OTHER INFORMATION: siRNA strand

<400> SEQUENCE: 69
aagaacuugu ccgauucagd tdt                                              23

<210> SEQ ID NO 70
<211> LENGTH: 23
<212> TYPE: DNA
<213> ORGANISM: Artificial Sequence
<220> FEATURE:
<223> OTHER INFORMATION: siRNA strand

<400> SEQUENCE: 70
ugaucauugg ugguaucgad tdt                                              23
```

```
<210> SEQ ID NO 71
<211> LENGTH: 23
<212> TYPE: DNA
<213> ORGANISM: Artificial Sequence
<220> FEATURE:
<223> OTHER INFORMATION: siRNA strand

<400> SEQUENCE: 71
ucgauaccac caaugaucad tdt                                              23

<210> SEQ ID NO 72
<211> LENGTH: 23
<212> TYPE: DNA
<213> ORGANISM: Artificial Sequence
<220> FEATURE:
<223> OTHER INFORMATION: siRNA strand

<400> SEQUENCE: 72
ucaaugguca agaucucaad tdt                                              23

<210> SEQ ID NO 73
<211> LENGTH: 23
<212> TYPE: DNA
<213> ORGANISM: Artificial Sequence
<220> FEATURE:
<223> OTHER INFORMATION: siRNA strand

<400> SEQUENCE: 73
uugagaucuu gaccauugad tdt                                              23

<210> SEQ ID NO 74
<211> LENGTH: 23
<212> TYPE: DNA
<213> ORGANISM: Artificial Sequence
<220> FEATURE:
<223> OTHER INFORMATION: siRNA strand

<400> SEQUENCE: 74
uccuuccuca gcaauaccud tdt                                              23

<210> SEQ ID NO 75
<211> LENGTH: 23
<212> TYPE: DNA
<213> ORGANISM: Artificial Sequence
<220> FEATURE:
<223> OTHER INFORMATION: siRNA strand

<400> SEQUENCE: 75
agguauugcu gaggaaggad tdt                                              23

<210> SEQ ID NO 76
<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 76
ggtgaagctt gaccaggatg ttgagcgtct gccggtgttt cgtcctttcc acaag          55

<210> SEQ ID NO 77
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes
```

<400> SEQUENCE: 77
cggcgaagct ttttccaaaa aacagacgct caacatcctg gtgaagcttg acca    54

<210> SEQ ID NO 78
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 78
cagctacaca aactgccgta acaaacggac ccggtgtttc gtcctttcca caag    54

<210> SEQ ID NO 79
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 79
cggcgaagct ttttccaaaa aaggtccgtt tgttacggca gctacacaaa ctgc    54

<210> SEQ ID NO 80
<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 80
aaactacaca aatttgtggt gtctaaggat accggtgttt cgtcctttcc acaag    55

<210> SEQ ID NO 81
<211> LENGTH: 55
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 81
cggcgaagct ttttccaaaa aaatatcctt agacaccaca aactacacaa atttg    55

<210> SEQ ID NO 82
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 82
tgcctacaca aagcatcgca taggttcttg tcggtgtttc gtcctttcca caag    54

<210> SEQ ID NO 83
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

```
<400> SEQUENCE: 83
cggcgaagct ttttccaaaa aaacaagaac ctatgcgatg cctacacaaa gcat              54

<210> SEQ ID NO 84
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 84
gttgaagctt gaacattcgc atcgcatagg ccggtgtttc gtcctttcca caag             54

<210> SEQ ID NO 85
<211> LENGTH: 53
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 85
cggcgaagct ttttccaaaa aacctatgcg atgcgaatgt tgaagcttga aca              53
```

DEVICES, SYSTEMS AND METHODS FOR IMPROVING MEMORY AND/OR COGNITIVE FUNCTION THROUGH BRAIN DELIVERY OF SIRNA

CROSS REFERENCE TO RELATED APPLICATIONS

This application is a continuation-in-part of U.S. application Ser. No. 11/253,393 filed on Oct. 19, 2005 now U.S. Pat. No. 7,618,948, which is a continuation-in-part of U.S. application Ser. No. 10/852,997, filed on May 25, 2004 now U.S. Pat. No. 7,829,694, which is a continuation-in-part of U.S. application Ser. No. 10/721,693, filed on Nov. 25, 2003 now U.S. Pat. No. 7,605,249, which claims priority from U.S. Provisional Patent Application No. 60/444,614, filed on Feb. 3, 2003, and U.S. Provisional Patent Application No. 60/429,387, filed on Nov. 26, 2002, which are incorporated herein by reference. U.S. Application is also a continuation-in-part of U.S. application Ser. No. 11/157,608, filed on Jun. 21, 2005, and PCT Patent Application No. US05/022156, also filed on Jun. 21, 2005 which claim the benefit of U.S. Provisional Application Ser. No. 60/581,730, filed Jun. 21, 2004, and which are also incorporated herein by reference.

FIELD OF INVENTION

This invention relates to devices, systems, and methods for improving memory and/or cognitive function by brain delivery of small interfering RNA or vectors containing the DNA encoding for small interfering RNA.

BACKGROUND OF THE INVENTION

Memory, or the function of a living organism to store information and retrieve it at a later time in a functional form, comprises multiple processes and requires the function of many different brain areas. Human memory provides declarative recall, i.e., facts and events accessible to conscious recollection, and non-declarative recall, i.e., procedural memory of skills and operations not stored regarding time and place.

The processing of information to be added to memory occurs in several stages. A newly acquired experience initially is susceptible to various forms of disruption. With time, however, the new experience becomes resistant to disruption. This observation has been interpreted to indicate that a labile, working, short-term memory is "consolidated" into a more stable, long term memory. The initial phase of memory consolidation occurs in the first few minutes after we are exposed to a new idea or learning experience. The next phase occurs over a longer period of time, such as during sleep. If a learning experience has on-going meaning to us, the next week or so serves as a further period of memory consolidation. In effect, in this phase, the memory moves from short-term to long-term storage.

Various mechanisms have been proposed for the formation of long-term memory. A wide range of observations suggest an evolutionarily conserved molecular mechanism for the formation of long-term memory. These observations include increase in release of synaptic transmitter and number of synaptic receptors as well as decrease in Km of the receptors, synthesis of new memory factors either in the pre-synaptic or post-synaptic element, new synaptic connections, and increase in the active area in the pre-synaptic membrane. Synaptic plasticity, the change in the strength of neuronal connections in the brain, is thought to underlie long-term memory storage.

On the molecular level, a series of classic studies showed that inhibition of mRNA and protein synthesis during a critical time window could disrupt the formation of long-term memory. Initial learning and recall of previously stored information was not impaired by the transient blockage of protein synthesis. This led to a hypothesis that new gene expression is necessary for the conversion or consolidation of a short-term modification of the brain into a long-term memory.

Memory consolidation, or long-term memory, is also believed to play a crucial role in a variety of neurological and mental disorders, including mental retardation, Alzheimer's disease and depression. Indeed, loss or impairment of long-term memory is a significant feature of such diseases.

For several neurodegenerative diseases, such as Parkinson's disease, Alzheimer's disease, Huntington's disease, Spinocerebellar Ataxia Type 1, Type 2, and Type 3, and dentatorubral pallidoluysian atrophy (DRLPA), proteins involved in the overall pathogenic progression of the disease have been identified. There is currently no cure for these neurodegenerative diseases. These diseases are progressively debilitating and most are ultimately fatal.

Further problematic of these neurodegenerative diseases (especially Alzheimer's disease and Parkinson's disease) is that their prevalence continues to increase, thus creating a serious public health problem. Recent studies have pointed to alpha-synuclein (Parkinson's disease), beta-amyloid-cleaving enzyme 1 (BACE1 (including variants thereof, e.g. variants A, B, C, and D)) (Alzheimer's disease), huntingtin (Huntington's disease), and ataxin 1 (Spinocerebellar Ataxia Type 1) as major factors in the pathogenesis of each of these diseases, respectively.

The neurodegenerative process in Parkinson's disease and Alzheimer's disease is characterized by extensive loss of selected neuronal cell populations accompanied by synaptic injury and astrogliosis. Pathological hallmarks of Alzheimer's disease include formation of amyloid plaques, neurofibrillary tangles and neuropil thread formation. Although the mechanisms triggering cell dysfunction and death are unclear, the prevailing view is that neurodegeneration results from toxic effects subsequent to the accumulation of specific neuronal cell proteins, such as amyloid precursor protein (APP) (Alzheimer's disease—processed into beta-amyloid by BACE1 (including variants thereof, e.g. variants A, B, C, and D)).

Alzheimer's disease is a progressive degenerative disorder of the brain characterized by mental deterioration, memory loss, confusion, and disorientation. Among the cellular mechanisms contributing to this pathology are two types of fibrillar protein deposits in the brain: intracellular neurofibrillary tangles composed of polymerized tau protein, and abundant extracellular fibrils comprised largely of beta-amyloid. Beta-amyloid, also known as Abeta, arises from the proteolytic processing of the amyloid precursor protein (APP) at the beta- and gamma-secretase cleavage sites giving rise to the cellular toxicity and amyloid-forming capacity of the two major forms of Abeta (Abeta$_{40}$ and Abeta$_{42}$). Thus, preventing APP processing into plaque-producing forms of amyloid may critically influence the formation and progression of the disease making BACE1 (including variants thereof, e.g. variants A, B, C, and D) a clinical target for inhibiting or arresting this disease. Similar reports suggest presenilins are candidate targets for redirecting aberrant processing.

The design and use of small interfering RNA complementary to mRNA targets that produce particular proteins is a recent tool employed by molecular biologists to prevent translation of specific mRNAs. Various groups have been recently studying the effectiveness of siRNAs as biologically active agents for suppressing the expression of specific proteins involved in neurological disorders. Caplen, et al. (*Human Molecular Genetics*, 11(2): 175-184 (2002)) assessed a variety of different double stranded RNAs for their ability to inhibit cell expression of mRNA transcripts of the human androgen receptor gene containing different CAG repeats. Their work found gene-specific inhibition occurred with double stranded RNAs containing CAG repeats only when flanking sequences to the CAG repeats were present in the double stranded RNAs. They were also able to show that constructed double stranded RNAs were able to rescue caspase-3 activation induced by expression of a protein with an expanded polyglutamine region. Xia, Mao, et al. (*Nature Biotechnology*, 20: 1006-1010 (2002)) demonstrated the inhibition of polyglutamine (CAG) expression in engineered neural PC12 clonal cell lines that express a fused polyglutamine-fluorescent protein using constructed recombinant adenovirus expressing siRNAs targeting the mRNA encoding green fluorescent protein.

Other tools used by molecular biologists to interfere with protein expression prior to translation involve cleavage of the mRNA sequences using ribozymes against therapeutic targets for Alzheimer's disease (see WO01/16312A2) and Parkinson's disease (see WO99/50300A1 and WO01/60794A2). However, none of the above aforementioned patents disclose methods for the specifically localized delivery of small interfering RNA vectors to targeted cells of the brain in a manner capable of local treatment of neurodegenerative diseases. The above patents do not disclose use of delivery devices or any method of delivery or infusion of small interfering RNA vectors to the brain. For example, the above patents do not disclose or suggest a method of delivery or infusion of small interfering RNA vectors to the brain by an intracranial delivery device.

The delivery of biologically active agents to the brain is an important and challenging aspect of treating a variety of neurological disorders. For treatment of some neurological disorders, it is desirable to deliver a biologically active agent (e.g., a therapeutic agent) to the brain that will cause brain cells to express DNA, for example, a missing gene (i.e., gene therapy), and/or RNA, for example, a small interfering RNA (siRNA).

Some approaches to gene therapy for neurological disorders involve surgical delivery of non-viral or viral vectors directly into the brain tissue, which is generally necessary since non-viral and viral vectors normally do not cross the blood-brain barrier (BBB). These approaches are limited by difficulty in achieving sufficient distribution and diffusion of the vector into the targeted areas of the brain, and by the potential for viral vectors to produce an immune reaction in the patient. One approach for achieving enhanced diffusion of vectors into the brain tissue is to use the technique of "convection enhanced delivery," whereby the non-viral or viral vectors are administered at a low flow rate over a long period of time with a pump providing pressure and flow volume to enhance the distribution of the vector into the tissue. While convection enhanced delivery has been shown to yield delivery of molecules and virus particles to substantial three-dimensional regions of rodent and primate brains, scale-up of this delivery approach to the three-dimensional volume of the human brain remains a technical challenge. Effective treatment of certain neurological diseases (e.g., Alzheimer's disease) using a gene or protein delivery or suppression therapy will most likely require delivery of the biologically active agents to most of the human cerebrum. In other neurological disorders, such as Parkinson's disease and Huntington's disease, even though there are circumscribed regions of the brain anatomy that are especially affected by the disease process, for example, the substantia nigra or striatum (caudate and putamen) and result in cardinal symptoms of the diseases (e.g., dyskinesias, rigidity, etc.), patients will likely benefit further from treatment of broader regions of the brain, in which the disease process causes additional symptoms (e.g., depression and cognitive deficits).

An approach of using viral vectors to deliver genes or gene suppressing agents to the brain tissue using stereotactic neurosurgery including, for example, the use of adeno-associated virus (AAV) to deliver gene therapy to the subthalamic nucleus, has shown considerable promise. However, the usefulness of stereotactic neurosurgery to deliver a viral vector carrying a gene or protein suppression therapy can be limited by one or more of the following factors. Stereotactic neurosurgery always involves a low level of surgical risk including, for example, accidental perforation of a blood vessel, which can result in cerebral hemorrhage and death. Dispersion of a viral vector to large regions of brain tissue, even using convection enhanced delivery and optimal vectors, catheter designs, and surgical technique, is likely to be limited relative to what can be attained using the blood stream as the distribution system. Manufacturing of viral particles (e.g., capsid plus DNA payload) in sufficient quantities for therapeutic use, while feasible, is costly relative to production of DNA alone. Viral particles (i.e., the capsid proteins) might be immunogenic, causing adverse reactions in sensitized individuals. While the immune response to some viruses (e.g., AAV) when administered to the brain appears minimal, it remains a potential limitation particularly for repeated therapy administrations.

It would be advantageous to administer a biologically active agent by a route that is no more invasive than a simple intravenous injection. With this approach, a biologically active agent could be delivered through the BBB by targeting the biologically active agent to the brain via endogenous BBB transport systems. Expression of a DNA or RNA in the brain requires that the biologically active agent that is injected into the blood is transported not only across the BBB by, for example, receptor-mediated transcytosis (RMT), but also across the brain cell membrane (BCM) by, for example, receptor-mediated endocytosis (RME) into the target cell in the brain. In addition, using endogenous BBB transport systems to target biologically active agents non-invasively to the brain also requires the development of a suitable formulation of the biologically active agent that is stable in the bloodstream.

An effective method for delivering gene therapy to the entire primate brain using compositions that carry plasmid DNA or antisense RNA across the blood brain barrier and into brain cells was recently disclosed in U.S. Pat. No. 6,372,250 (Pardridge). The reported ability of this method to deliver plasmid DNA to the entire primate brain constitutes an impressive technical breakthrough. However, therapeutic use of the disclosed method may be limited by one or more of the factors listed herein below. Gene expression from a plasmid or RNA is generally temporary (e.g., limited to a period of days or weeks). Intravenous delivery of the disclosed compositions can result in unintended treatment of all bodily organs, potentially resulting in adverse side-effects. Finally, intravenous delivery can result in a loss of dosing as the dose intended for the brain is delivered to other parts of the body.

Further, the foregoing prior art does not disclose any technique for delivering or infusing into the brain small interfering RNA vectors which are then capable of reducing production of at least one protein involved in the loss of memory.

The prior art describes direct systemic delivery of ribozymes. This approach for treatment of memory loss or neurodegenerative disorders would appear neither possible nor desirable. First, interfering RNAs are distinctly different than ribozymes. Second, small RNA molecules delivered systemically will not persist in vivo long enough to reach the desired target, nor are they likely to cross the blood-brain barrier. Further, the approach taken by the prior art may be impractical because of the large quantity of small interfering RNA that might have to be administered by this method to achieve an effective quantity in the brain. Even when the blood-brain barrier is temporarily opened, the vast majority of oligonucleotide delivered via the bloodstream may be lost to other organ systems in the body, especially the liver.

U.S. Pat. Nos. 5,735,814 and 6,042,579 disclose the use of drug infusion for the treatment of Huntington's disease, but the drugs specifically identified in these patents pertain to agents capable of altering the level of excitation of neurons, and do not specifically identify agents intended to enter the cell and alter protein production within cells.

Thus, new compositions and methods for delivering to the brain biologically active agents for the treatment of memory loss and cognitive dysfunction are needed.

SUMMARY OF THE INVENTION

The present invention provides devices, systems, and methods for improving memory and/or cognitive function in a normal brain, or a brain affected by a neurodegenerative disorder, by brain delivery or infusion of small interfering RNA or vectors containing the DNA encoding for small interfering RNA.

A first objective of the described therapies of the present invention is to deliver specifically tailored small interfering RNA as therapeutic agents for enhancement of cognitive function and/or memory function of a subject. In certain embodiments, the subject method can be used to treat patients who have been diagnosed as having or being at risk of developing disorders in which diminished declarative memory is a symptom, e.g., as opposed to procedural memory. As a result, the methods of the present invention may be useful for preventing memory impairment. Contemplated causes of memory impairment include toxicant exposure, brain injury, age-associated memory impairment, mild cognitive impairment, epilepsy, mental retardation in children, and dementia resulting from a disease, such as in certain cases of Parkinson's disease, Alzheimer's disease, AIDS, head trauma, Huntington's disease, Pick's disease, Creutzfeldt-Jakob disease, post cardiac surgery, Downs Syndrome, Anterior Communicating Artery Syndrome, and other symptoms of stroke. In addition, the present invention may be useful in enhancing memory in normal individuals.

A second objective of the described therapies is to deliver specifically tailored small interfering RNA as therapeutic agents for treatment of Alzheimer's disease. Specifically tailored small interfering RNA for Alzheimer's disease target the mRNA for BACE1 (including variants thereof, e.g. variants A, B, C, and D) in order to reduce the amount of BACE1 (including variants thereof, e.g. variants A, B, C, and D) protein produced in neurological cells and thereby interfere with the production of beta-amyloid. In a related embodiment the present invention provides devices that specifically access the nucleus basalis of Meynart and the cerebral cortex for delivery of anti-BACE1 (including variants thereof, e.g. variants A, B, C, and D) small interfering RNA.

The present invention provides a method of treating memory loss in a subject caused by the presence of beta amyloid produced from amyloid precursor protein by beta amyloid cleaving enzyme type 1, or BACE1 in the brain.

The present invention also provides a delivery system for a small interfering RNA vector therapy for memory loss or cognitive dysfunction that permits targeted delivery of small interfering RNA or vectors containing DNA encoding for small interfering RNA (small interfering RNA vectors) to targeted sites in the brain for brief durations of time or over an extended period of care for the patient.

In one embodiment of the present invention, small interfering RNA vectors are infused into targeted sites of the brain wherein the small interfering RNA vectors are taken up by neurons and transported to the nucleus of targeted cells. The small interfering RNA vectors are then transcribed into RNA by the host cellular machinery to produce small interfering RNA that prevent production of the targeted protein involved in memory loss or cognitive dysfunction.

In one aspect, the present invention provides a medical system for delivering DNA encoding a biologically active agent across a blood-brain barrier.

In another aspect, the present invention provides methods of using neurosurgical devices to deliver therapeutic small interfering RNA vectors to selected regions of the brain. In particular, the present invention provides methods that use surgically implanted catheters for singular, repeated, or chronic delivery of small interfering RNA vectors to the brain. The small interfering RNA vectors introduced into the affected cells have the necessary DNA sequences for transcription of the required small interfering RNA by the cells, including a promoter sequence, the small interfering RNA sequence, and optionally flanking regions allowing defined ends of the therapeutic small interfering RNA to be produced, and optionally a polyadenylation signal sequence.

In one embodiment, the system includes: a neurovascular catheter having a distal end positioned in a blood vessel supplying a patient's brain; and a means for delivering to the catheter a composition including: an artificial adeno-associated virus (AAV) vector including DNA encoding a biologically active agent; and a component to deliver at least the DNA across the blood-brain barrier.

In another embodiment, the medical system includes a neurovascular catheter having a distal end positioned in a blood vessel supplying a patient's brain; and a means for delivering to the catheter a composition including a receptor-specific nanocontainer, wherein the receptor-specific nanocontainer includes: a nanoparticle or liposome having an exterior surface and an internal compartment; an artificial adeno-associated virus (AAV) vector located within the internal compartment of the liposome, wherein the AAV vector includes DNA encoding a biologically active agent; one or more blood-brain barrier and brain cell membrane targeting agents; and one or more conjugation agents wherein each targeting agent is connected to the exterior surface of the nanocontainer via at least one of the conjugation agents.

In another aspect, the present invention provides a method for delivering DNA across a blood-brain barrier for expression in the brain. The method includes administering to a patient a composition including: an artificial adeno-associated virus (AAV) vector including DNA encoding a biologically active agent; and a component to deliver at least the DNA across the blood-brain barrier.

In another aspect, the present invention provides a method for delivering DNA across a blood-brain barrier for expression in the brain. The method includes administering to a patient a composition including a receptor-specific nanocontainer, wherein the receptor-specific nanocontainer includes: a nanoparticle or liposome having an exterior surface and an internal compartment; an artificial adeno-associated virus (AAV) vector located within the internal compartment of the nanocontainer, wherein the AAV vector includes DNA encoding a biologically active agent; one or more blood-brain barrier and brain cell membrane targeting agents; and one or more conjugation agents wherein each targeting agent is connected to the exterior surface of the nanocontainer via at least one of the conjugation agents.

In another aspect, the present invention provide artificial AAV vectors for delivering DNA encoding a biologically active agent, and methods of making and using such vectors.

In one embodiment, the present invention provides an artificial AAV vector including, in 5-prime to 3-prime order: a 5-prime AAV-ITR; a single stranded DNA encoding a biologically active agent; an internal AAV-ITR; a reverse complement of the single stranded DNA encoding the biologically active agent: and a 3-prime AAV-ITR. Methods of making such vectors are also provided.

In another embodiment, the present invention provides an artificial adeno-associated virus (AAV) vector for delivery of a linear, double stranded DNA encoding a biologically active agent, the artificial AAV vector including the linear, double stranded DNA having AAV-ITRs at the 5-prime and 3-prime ends of each strand. Preferably, the artificial AAV vector has been thermally treated in at least one heating and cooling cycle.

The present invention can offer advantages over other methods of delivering biologically active agents including, for example, conventional enhanced delivery, stereotactic neurosurgical delivery of viral or non-viral vectors, and/or intravenous delivery of a composition for carrying plasmid DNA or RNA across the blood brain barrier.

The use of an artificial AAV vector to deliver a gene or a gene-suppressing agent to a patient's brain can have many advantages over the delivery of plasmid DNA, or the delivery of actual AAV virus particles. One possible advantage of delivering the DNA of an AAV vector to the brain, rather than a plasmid DNA, is that expression of AAV-delivered gene constructs in the primate brain is known to persist for at least 3 to 4 years, whereas expression of gene constructs from plasmids is temporary. The advantages of delivering the DNA of a synthetic AAV vector over delivery of AAV virus particles can be several. First, delivery of just the DNA can circumvent the delivery of AAV viral capsids to the patient's brain. Since it is the AAV viral capsid proteins that are most likely to trigger an immune response, dispensing with the need to deliver viral particles can avoid most of the risk of adverse immune reactions to the therapy. Further, delivery of the DNA can circumvent the need to produce complete AAV particles, a difficult manufacturing step that requires the use of specially engineered and cultured cells to make the AAV capsids and package the DNA into the virus capsids. Finally, delivery of DNA rather than AAV particles can circumvent the natural limitation on the length of the DNA that can be packaged inside AAV capsids, which is about 4,700 bases of DNA. Although this size limitation is not a problem for delivery of constructs for gene suppression (e.g., DNA coding for small, interfering RNA), it can be a limitation for delivery of missing genes, if the sequence for the missing gene is longer than 4,700 bases, which has been noted as a limitation on the use of AAV as a vector for gene therapy.

DETAILED DESCRIPTION OF THE PREFERRED EMBODIMENTS

Figure 1:
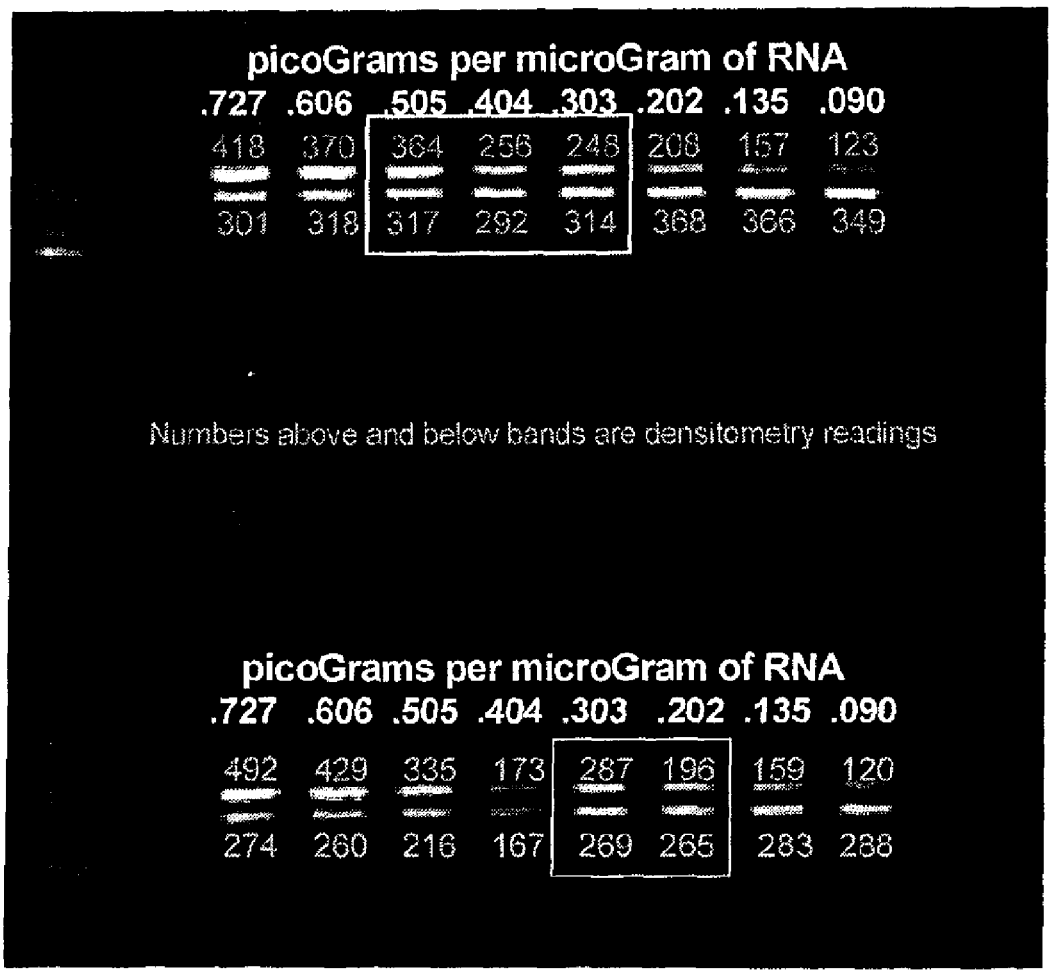
FIG. 1 shows the assay (using a quantitative RT-PCR method known to those practiced in the art) of the ataxin1 mRNA obtained from HEK293H cells that have been transfected with plasmid containing an anti-ataxin1 ribozyme (top lanes in FIG. 1) or with siRNA against ataxin1 (bottom lanes of FIG. 1).

The present invention solves two problems in the prior art at the same time: (1) the problem of how to improve impaired memory function caused by the production in neurons of a protein that has pathogenic properties and (2) the problem of delivery of therapeutic small interfering RNA to affected neurons.

In the following descriptions, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

Terminology

By "alpha-synuclein, BACE1 (including variants thereof, e.g. variants A, B, C, and D), huntingtin, ataxin-1, ataxin-3, and/or atrophin-1 proteins" is meant, a protein or a mutant protein derivative thereof, comprising the amino-acid sequence expressed and/or encoded by alpha-synuclein (Parkinson's disease), and beta-site APP-cleaving enzyme (BACE1 (including variants thereof, e.g. variants A, B, C, and D)) (Alzheimer's disease), huntingtin (Huntington's disease), and ataxin-1 (Spinocerebellar Ataxia Type 1), ataxin-3 (Spinocerebellar Ataxia Type 3 or Machado-Joseph's Disease), and/or dentatorubral-pallidoluysian atrophy (DRPLA) genes and/or the human genomic DNA respectively.

As used herein "cell" is used in its usual biological sense, and does not refer to an entire multicellular organism. The cell may be present in an organism which may be a human but is preferably of mammalian origin, e.g., such as humans, cows, sheep, apes, monkeys, swine, dogs, cats, and the like. However, several steps of producing small interfering RNA may require use of prokaryotic cells (e.g., bacterial cell) or eukaryotic cell (e.g., mammalian cell) and thereby are also included within the term "cell".

By "complementarity" it is meant that a molecule comprised of one or more nucleic acids (DNA or RNA) can form hydrogen bond(s) with another molecule comprised of one or more nucleic acids by either traditional Watson-Crick pairing or other non-traditional types.

By "equivalent" DNA to alpha-synuclein, BACE1 (including variants thereof, e.g. variants A, B, C, and D), huntingtin, ataxin-1, ataxin-3, and/or atrophin-1 it is meant to include those naturally occurring DNA molecules having homology (partial or complete) to DNA encoding for alpha-synuclein, BACE1 (including variants thereof, e.g. variants A, B, C, and D), huntingtin, ataxin-1, ataxin-3 and/or atrophin-1 proteins or encoding for proteins with similar function as alpha-synuclein, BACE1 (including variants thereof, e.g. variants A, B, C, and D), huntingtin, ataxin-1, ataxin-3 and/or atrophin-1 in various organisms, including human, rodent, primate, rabbit, pig, and microorganisms. The equivalent DNA sequence also includes regions such as the 5'-untranslated region, the 3'-untranslated region, introns, intron-exon junctions, small interfering RNA targeted site and the like, optionally incorporated into the DNA of infective viruses, such as adeno-associated virus (AAV).

The term "functional equivalent" refers to any derivative that is functionally similar to the reference sequence or protein. In particular the term "functional equivalent" includes derivatives in which the nucleotide bases(s) have been added, deleted, or replaced without a significant adverse effect on biological function.

As used herein, the term "biologically active" as used with "agent" or "siRNA" means that the agent or siRNA can modify a cell in any way including, for example, modifying the metabolism of the cell, the structure of the cell, the function of the cell, and/or permit the cell containing the agent or siRNA to be detected. Examples of biologically active agents and/or siRNAs include, for example, polynucleotides, polypeptides, and combinations thereof. A biologically active agent or siRNA may be therapeutic (i.e., able to treat or prevent a disease) or non-therapeutic (i.e., not directed to the treatment or prevention of a disease). Non-therapeutic biologically active compounds include detection or diagnostic agents including, for example, markers that can be used for detecting the presence of a particular cell, distinguishing cells, and/or detecting whether a targeting group is functioning to target a particular tissue. As used herein, the term "polynucleotide" or "nucleic acid molecule" refers to a polymeric form of nucleotides of any length, either ribonucleotides or deoxynucleotides, and includes both double- and single-stranded DNA and RNA, and combinations thereof. A polynucleotide may include nucleotide sequences having different functions including, for example, coding sequences and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, or a fragment.

A "coding sequence" or a "coding region" is a polynucleotide that encodes a polypeptide and, when placed under the control of appropriate regulatory sequences, expresses the encoded polypeptide. The boundaries of a coding region are generally determined by a translational start codon at its 5-prime end and a translational stop codon at its 3-prime end. A regulatory sequence is a nucleotide sequence that regulates expression of a coding region to which it is operably linked. Nonlimiting examples of regulatory sequences include promoters, transcriptional initiation sites, translational start sites, translational stop sites, transcriptional terminators (including, for example, polyadenylation signals), and intervening sequences (introns). "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

By "gene" it is meant a region of DNA that controls the production of RNA. In context of producing functional small interfering RNA, this definition includes the necessary DNA sequence information encompassing the DNA sequences encoding the small interfering RNA, noncoding regulatory sequence and any included introns. The term "gene" is meant to include a polynucleotide that includes a coding sequence or coding region. The present definition does not exclude the possibility that additional genes encoding proteins may function in association or in tandem with the genes encoding small interfering RNA.

The term "vector" is commonly known in the art and defines a plasmid DNA, phage DNA, viral DNA and the like, which can serve as a DNA vehicle into which DNA of the present invention can be inserted, and from which RNA can be transcribed. The term "vectors" refers to any of these nucleic acid and/or viral-based techniques used to deliver a desired nucleic acid. Numerous types of vectors exist and are well known in the art.

The term "expression" defines the process by which a gene is transcribed into RNA (transcription); the RNA may be further processed into the mature small interfering RNA.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

"Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences, which serve to initiate transcription.

By "homology" it is meant that the nucleotide sequence of two or more nucleic acid molecules is partially or completely identical.

By "highly conserved sequence region" it is meant that a nucleotide sequence of one or more regions in a target gene does not vary significantly from one generation to the other or from one biological system to the other.

By the term "inhibit" or "inhibitory" it is meant that the activity of the target genes or level of mRNAs or equivalent RNAs encoding target genes is reduced below that observed in the absence of the provided small interfering RNA. Preferably the inhibition is at least 10% less, 25% less, 50% less, or 75% less, 85% less, or 95% less than in the absence of the small interfering RNA.

By "inhibited expression" it is meant that the reduction of alpha-synuclein, BACE1 (including variants thereof, e.g. variants A, B, C, and D), huntingtin, ataxin-1, ataxin-3 and/or atrophin-1 mRNA levels and thus reduction in the level of the respective protein to relieve, to some extent, the symptoms of the disease or condition.

By "RNA" is meant ribonucleic acid, a molecule consisting of ribonucleotides connected via a phosphate-ribose (sugar) backbone. By "ribonucleotide" is meant guanine, cytosine, uracil, or adenine or some nucleotide with a hydroxyl group at the 2' position of a beta-D-ribo-furanose moiety. As is well known in the art, the genetic code uses thymidine as a base in DNA sequences and uracil in RNA. One skilled in the art knows how to replace thymidine with uracil in a written nucleic acid sequence to convert a written DNA sequence into a written RNA sequence, or vice versa.

By "patient" is meant an organism, which is a donor or recipient of explanted cells or the cells themselves. "Patient" also refers to an organism to which the nucleic acid molecules of the invention can be administered. Preferably, a patient is a mammal or mammalian cells, e.g., such as humans, cows, sheep, apes, monkeys, swine, dogs, cats, and the like, or cells of these animals used for transplantation. More preferably, a patient is a human or human cells.

The term "synuclein" may refer to alpha-synuclein (especially human or mouse) or beta-synuclein (especially human or mouse). The full nucleotide sequence encoding human alpha-synuclein is available under Accession No AF163864 (SEQ ID NO:7). Two variants of the human alpha-synuclein sequence are available under Accession No NM_000345 (SEQ ID NO:14) and Accession No NM_007308 (SEQ ID NO:23). The mouse alpha-synuclein is available under Accession No. AF163865 (SEQ ID NO:10).

The term "BACE1" may refer to beta-site amyloid precursor protein cleaving enzyme type 1 (especially human or mouse). Several variants of BACE1 have been sequenced, including variants A, B, C, and D. In some scientific literature, BACE1 is also known as ASP2 and Memapsin2. The full nucleotide sequences encoding human BACE1, and variants related thereto, are available under Accession No. NM_138971 (SEQ ID NO:20), Accession No. NM_138972 (SEQ ID NO:19), Accession No. NM_138973 (SEQ ID NO:21), and Accession No. NM_012104 (SEQ ID NO:18). The sequence for a mouse homolog is available under accession number NM_011792 (SEQ ID NO:22).

The term "huntingtin" may refer to the protein product encoded by the Huntington's Disease gene (IT-15) (especially human or mouse). The full nucleotide sequence encoding human IT-15 is available under Accession No AH003045 (SEQ ID NO:9). The mouse sequence is available under Accession No. U24233 (SEQ ID NO:12).

The term "ataxin-1" may refer to the protein product encoded by the Spinocerebellar Ataxia Type 1 gene (especially human or mouse). The full nucleotide sequence encoding human SCA1 is available under Accession No NM_000332 (SEQ ID NO:15). The mouse sca1 is available under Accession No. NM_009124 (SEQ ID NO:13).

The term "ataxin-3" may refer to the protein product encoded by the Spinocerebellar Ataxia Type 3 gene (especially human or mouse). The full nucleotide sequence encoding human SCA3 is available under Accession No NM_004993 (splice variant 1) (SEQ ID NO:16), and NM_030660 (splice variant 2) (SEQ ID NO:17).

The term "atrophin-1" may refer to the protein product encoded by the dentatorubral-pallidolysian atrophy (DRPLA) gene (especially human or mouse).

The term "modification" includes derivatives substantially similar to the reference sequence or protein.

By "nucleic acid molecule" as used herein is meant a molecule having nucleotides. The nucleic acid can be single, double, or multiple stranded and may comprise modified or unmodified nucleotides or non-nucleotides or various mixtures and combinations thereof. An example of a nucleic acid molecule according to the invention is a gene which encodes for a small interfering RNA, even though it does not necessarily have its more common meaning for encoding for the production of protein.

By "small interfering RNA" is meant a nucleic acid molecule which has complementarity in a substrate binding region to a specified gene target, and which acts to specifically guide enzymes in the host cell to cleave the target RNA. That is, the small interfering RNA by virtue of the specificity of its sequence and its homology to the RNA target, is able to cause cleavage of the RNA strand and thereby inactivate a target RNA molecule because it is no longer able to be transcribed. These complementary regions allow sufficient hybridization of the small interfering RNA to the target RNA and thus permit cleavage. One hundred percent complementarity often necessary for biological activity and therefore is preferred, but complementarity as low as 90% may also be useful in this invention. The specific small interfering RNA described in the present application are not meant to be limiting and those skilled in the art will recognize that all that is important in a small interfering RNA of this invention is that it have a specific substrate binding site which is complementary to one or more of the target nucleic acid regions.

Small interfering RNAs are double stranded RNA agents that have complementarity to (i.e., able to base-pair with) a portion of the target RNA (generally messenger RNA). Generally, such complementarity is 100%, but can be less if desired, such as 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target under physiological conditions).

A "reverse complement" of a DNA strand in a 5-prime to 3-prime direction is a DNA strand in the reverse order with the corresponding complementary bases according to Watson-Crick or other base pairing rules.

By "comprising" is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention provides devices, systems and methods for improving memory and/or cognitive function through delivery of siRNA to a subject. In this aspect of the invention the method provides for improving memory function in a subject in need thereof, comprising administering to the subject a therapeutically effective dose of a composition that decreases the expression of a beta amyloid cleaving enzyme type 1, or BACE1, in a cell of the nervous system of the subject, wherein the composition comprises a small interfering RNA molecule specific for a BACE1 gene and wherein the small interfering RNA molecule specifically suppresses BACE1 gene expression in a cell of the nervous system of the subject.

Another aspect of the invention provides a method for improving memory function in a subject in need thereof, comprising modulating the expression or production of a beta amyloid cleaving enzyme type 1, or BACE1 protein in neurons by intracranial delivery of a small interfering RNA specific for a BACE1 gene that reduces said expression of production of said BACE1 protein, in a pharmaceutically acceptable carrier.

Another aspect of the present invention provides medical systems and methods for delivering DNA to a target site (e.g., to a cell or across the blood-brain barrier). The cell may be in vivo or ex vivo. As used herein, the term "ex vivo" refers to a cell that has been removed, for example, isolated, from the body of a subject. Ex vivo cells include, for example, primary cells (e.g., cells that have recently been removed from a subject and are capable of limited growth or maintenance in tissue culture medium), and cultured cells (e.g., cells that are capable of extended growth or maintenance in tissue culture medium). As used herein, the term "in vivo" refers to a cell that is within the body of a subject.

The medical systems include a neurovascular catheter having its distal end positioned in a blood vessel supplying a patient's brain. Optionally, the system further includes an implantable pump for delivery of the composition to the patient's blood stream. The medical system further includes a means for delivering to the catheter a composition as described herein. Methods of delivering such compositions to a cell or across the blood-brain barrier for expression in the brain are also described herein.

In brief, compositions disclosed and used in the present invention include an artificial adeno-associated virus (AAV) vector (single or double stranded vector; preferably a single stranded vector), including DNA encoding a biologically active agent; and a component (e.g., a receptor-specific liposome as described herein) that delivers at least the DNA across the blood-brain barrier. In some embodiments, the artificial AAV vector includes, in 5-prime to 3-prime order: a 5-prime AAV inverted terminal repeat (AAV-ITR); a single stranded DNA encoding the biologically active agent; and a 3-prime AAV-ITR. In other embodiments, the artificial AAV vector includes, in 5-prime to 3-prime order: a 5-prime AAV-ITR; a single stranded DNA encoding a biologically active agent; an internal AAV-ITR; a reverse complement of the single stranded DNA encoding the biologically active agent: and a 3-prime AAV-ITR. In still other embodiments, the artificial AAV vector includes a linear, double stranded DNA having AAV-ITRs at the 5-prime and 3-prime ends of each strand. Preferably, the artificial AAV vector does not include a coding sequence to encode a capsid, and thus, the preferred vectors are not encapsulated in a viral capsid structure. Methods of making artificial AAV vectors are also disclosed.

For embodiments in which the DNA encodes a small interfering RNA, the compositions can be useful for treating, among other things, various neurodegenerative disorders caused by a pathogenic protein. For embodiments in which the DNA encodes a protein, the compositions can be useful for treating, among other things, various neurological diseases caused by the absence of the protein.

In some embodiments, the compositions include a receptor-specific liposome and a pharmaceutically acceptable carrier for the receptor-specific liposome, wherein the receptor-specific liposome includes: a liposome having an exterior surface and an internal compartment; the artificial adeno-associated virus (AAV) vector located within the internal compartment of the liposome; one or more blood-brain barrier and brain cell membrane targeting agents; and one or more conjugation agents, wherein each targeting agent is connected to the exterior surface of the liposome via at least one of the conjugation agents.

In other embodiments, the compositions include a receptor-specific nanocontainer (i.e., a container having at least one dimension on the order of a few nanometers or less) and a pharmaceutically acceptable carrier for the receptor-specific nanocontainer, wherein the receptor-specific nanocontainer includes: a nanocontainer having an exterior surface and an internal compartment; an artificial adeno-associated virus (AAV) vector located within the internal compartment of the nanocontainer; one or more receptor specific targeting agents that target the receptor located on the cell; and one or more conjugation agents, wherein each targeting agent is connected to the exterior surface of the nanocontainer via at least one of the conjugation agents.

Another aspect of the invention provides a method of delivering a small interfering RNA to a location in the brain of a subject suffering from memory impairment comprising the steps of: a) surgically implanting an intracranial access delivery device; and b) infusing a small interfering RNA and/or a vector encoding said small interfering RNA at a predetermined site in the brain, wherein at least one attribute of memory function is improved.

Another aspect of the invention provides a method for improving memory function in a subject comprised of modulating the expression or production of a beta amyloid cleaving enzyme type 1, or BACE1 protein in neurons by intracranial delivery of a small interfering RNA from SEQ ID NOS: 24-40 that reduces said expression of production of said BACE1 protein, in a pharmaceutically acceptable carrier.

Another aspect of the invention provides a method of delivering a small interfering RNA to a location in the brain of a subject suffering from memory impairment comprising the steps of: a) surgically implanting an intracranial access delivery device; and b) infusing a small interfering RNA and/or a vector encoding said small interfering RNA containing one or more sequences coded from SEQ ID NOS: 24-40 at a predetermined site in the brain; wherein at least one attribute of said memory impairment is improved.

Another aspect of the invention provides a medical system for improving memory function in a subject comprising: a) an intracranial access device; b) a mapping means for locating a predetermined location in the brain; c) a deliverable amount of a small interfering RNA or vector encoding said small interfering RNA selected from one or more sequences coded from SEQ ID NOS: 24-40; and d) a delivery means for delivering said small interfering RNA or vector encoding said small interfering RNA to said location of the brain from said intracranial access device.

Medical Devices

The present invention also provides medical devices that include a neurovascular catheter and an optional implantable pump for delivery of the composition into a patient's blood stream. The distal, delivery end of the neurovascular catheter is positioned in a blood vessel supplying the brain. For acute use, the proximal end of the neurovascular catheter would remain outside the patient's body at the point of introduction (e.g., the femoral artery) and used by the physician to deliver the composition in a suitable fluid solution to the patient's brain. Although the delivery in this case is acute, the therapy may nevertheless be long-lasting as described herein below.

Alternatively, the proximal end of the neurovascular catheter can be attached to the optional implantable pump, and both the pump and catheter chronically implanted in the body. In the latter case, the pump provides a "catheter access port-"through which the physician can transcutaneously make repeated bolus injections of the composition through the catheter into the blood vessel supplying the patient's brain. The pump provides a fluid reservoir used to supply heparinized saline, dilute tissue plasminogen activator (tPA), or a similar agent that is continuously pumped at a low rate through the neurovascular catheter in between uses of the catheter for bolus injections. The purpose is to prevent blood clots from forming at the distal end of the catheter, occluding the catheter lumen and posing a risk of embolic stroke to the patient.

Using the small interfering RNA vectors previously described, the present invention also provides devices, systems, and methods for delivery of small interfering RNA to target locations of the brain. The envisioned route of delivery is through the use of implanted, indwelling, intraparenchymal catheters that provide a means for injecting small volumes of fluid containing AAV or other vectors directly into local brain tissue. The proximal end of these catheters may be connected to an implanted, intracerebral access port surgically affixed to the patient's cranium, or to an implanted drug pump located in the patient's torso.

Figure 4:
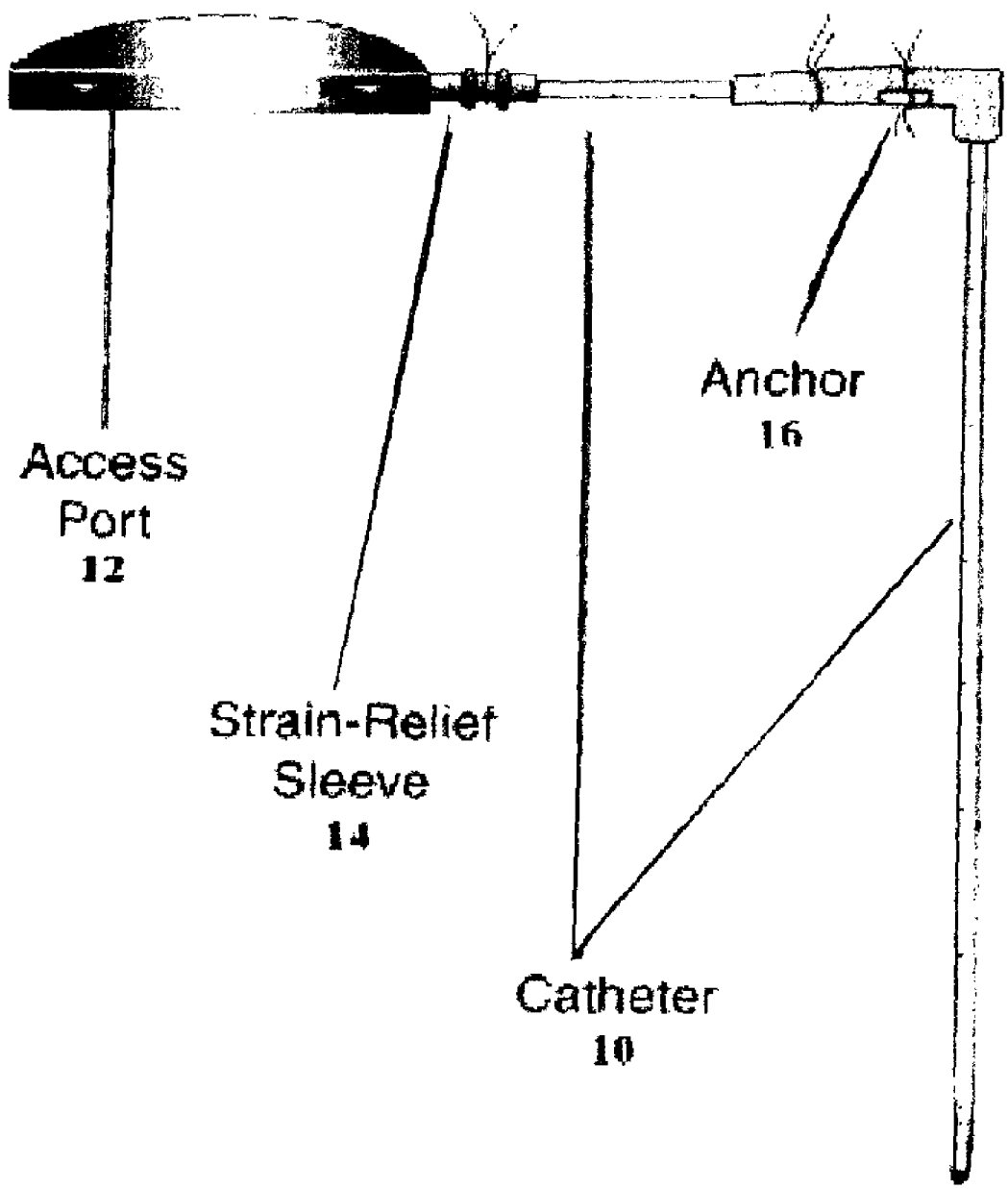
FIG. 4 illustrates an investigational device (by Medtronic, Inc. of Minneapolis, Minn. Model 8506), which can be implanted subcutaneously on the cranium, and provides an access port through which therapeutic agents may be delivered to the brain.
Figure 5:
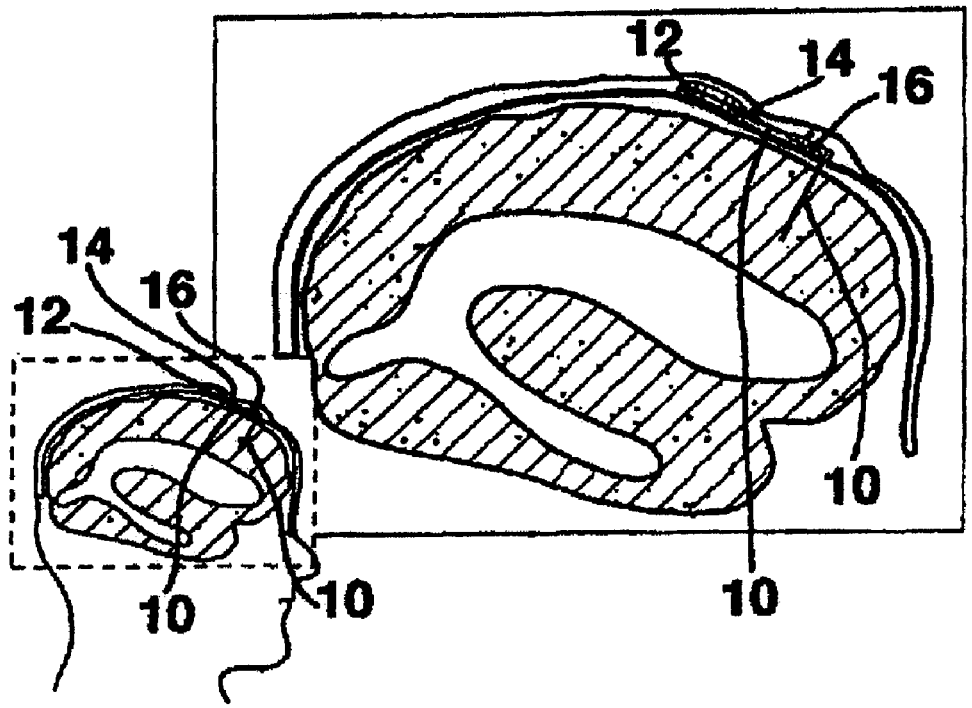
FIG. 5 illustrates a cranium of a patient with an investigational device (by Medtronic, Inc. of Minneapolis, Minn.—schematic of Model 8506), implanted subcutaneously on the cranium, and provides an access port through which therapeutic agents may be delivered to the brain.

Examples of the delivery devices within the scope of the present invention include the Model 8506 investigational device (by Medtronic, Inc. of Minneapolis, Minn.), which can be implanted subcutaneously on the cranium, and provides an access port through which therapeutic agents may be delivered to the brain. Delivery occurs through a stereotactically implanted polyurethane catheter. The Model 8506 is schematically depicted in FIGS. 4 and 5. Briefly, referring to FIG. 4, the device comprises a catheter 10. The catheter 10 is secured to the intracranial access port 12 which may optionally have strain relief 14. The catheter is also secured to the skull of the patient by anchor 16. FIG. 5 shows the device illustrated in FIG. 4 implanted into the patient, as shown by the saggital view of the patient's head 18. The intracranial access port 12 is implanted subcutaneously on the cranium of the patient. The catheter 10 extends through the relief strain 14 and is secured by the anchor 16 to the patient's skull. The distal tip of the catheter 10 is located in the predetermined location in the patient's brain. It is preferred to place some means for locating the distal end of the catheter 10 during the access and location process. This is preferably done by applying a marker, to the distal end of the catheter which is detected during the access and location process. If access and location is accomplished using some form of x-ray radiation, the marker is preferably radiopaque. Radiopaque marker renders at least a portion of distal tip opaque to x-rays, enabling the tip to be observed via fluoroscopy or via x-ray during access and location of catheter 10. In a preferred embodiment, radiopaque marker comprises tantalum powder dispersed in a matrix composed of a biocompatible adhesive, such as those discussed above. Other materials may also be suitable for radiopaque marker, such as barium or platinum materials. Alternately, the radiographic marker may be chosen of a material that has sufficient radiodensity for visualization during radiologic procedures, but in powdered form that is dispersed in the catheter tip at the time the distal tip of the catheter is molded. Alternatively, the marker may be composed of a material that is compatible to nuclear magnetic resonance imaging (MRI) to enable the distal tip of the catheter 10 to be detected during an MRI scan. Preferred material for such a marker is platinum, though barium, tantalum, and similar materials are also suitable. Regardless of whether radiography or MRI is being utilized, the goal of providing a radiographic marker is to enable the operator to accurately detect the precise location of the distal tip of the catheter to facilitate placement and later verification of the integrity and position of the distal tip of catheter 10. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. No. 09/540,444 (U.S. Pat. No. 6,551,290) and Ser. No. 09/625,751 (U.S. Pat. No. 6,945,969), which are incorporated herein by reference. The latter catheter has multiple outlets on its distal end to deliver the therapeutic agent to multiple sites along the catheter path. In addition to the aforementioned device, the delivery of the small interfering RNA vectors in accordance with the present invention can be accomplished with a wide variety of devices, including but not limited to U.S. Pat. Nos. 5,735,814, 5,814,014, and 6,042,579, all of which are incorporated herein by reference. Using the teachings of the present invention and those of skill in the art will recognize that these and other devices and systems may be suitable for delivery of small interfering RNA vectors for the treatment of neurodegenerative diseases in accordance with the present invention.

In one preferred embodiment, the method further comprises the steps of implanting a pump outside the brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said brain.

Thus, the present invention includes the delivery of small interfering RNA vectors using an implantable pump and catheter, like that taught in U.S. Pat. Nos. 5,735,814 and 6,042,579, and further using a sensor as part of the infusion system to regulate the amount of small interfering RNA vectors delivered to the brain, like that taught in U.S. Pat. No. 5,814,014. Other devices and systems can be used in accordance with the method of the present invention, for example, the devices and systems disclosed in U.S. Ser. No. 09/872,698 (filed Jun. 1, 2001) and Ser. No. 09/864,646 (filed May 23, 2001), which are incorporated herein by reference.

The design and use of small interfering RNA complementary to mRNA targets that produce particular proteins is a recent tool employed by molecular biologists to prevent translation of specific mRNAs. Other tools used by molecular biologists to interfere with protein expression prior to translation involve cleavage of the mRNA sequences using ribozymes against therapeutic targets for Alzheimer's disease (see, for example, PCT International Application Publication No. WO 01/16312 A2 (McSwiggen et al.)) and Parkinson's disease (see, for example, PCT International Application Publication Nos. WO 99/50300 A1 (Trojanowski et al.) and WO 01/60794 A2 (Eliezer)). PCT International Application Publication No. WO 2004/047872 A2 (Kaemmerer) and U.S. Patent Application Publication No. 2004/0220132 A1 (Kaemmerer) disclose devices, small interfering RNA, and methods for treating a neurodegenerative disorder including the steps of surgically implanting a catheter so that a discharge portion of the catheter lies adjacent to a predetermined infusion site in a brain, and discharging through the discharge portion of the catheter a predetermined dosage of at least one substance that inhibits production of at least one neurodegenerative protein. PCT International Application Publication No. WO 2004/047872 A2 (Kaemmerer) and U.S. Patent Application Publication No. 2004/0220132 A1 (Kaemmerer) further disclose small interfering RNA vectors, and methods for treating neurodegenerative disorders such as Alzheimer's disease, Parkinson's disease, Huntington's disease, Spinocerebellar Ataxia Type 1, Type 2, Type 3, and/or dentatorubral-pallidoluysian atrophy.

As previously indicated, the small interfering RNA (or siRNA) described herein, is a segment of double stranded RNA that is from 15 to 30 nucleotides in length. It is used to trigger a cellular reaction known as RNA interference. In RNA interference, double-stranded RNA is digested by an intracellular enzyme known as Dicer, producing siRNA duplexes. The siRNA duplexes bind to another intracellular enzyme complex which is thereby activated to target whatever mRNA molecules are homologous (or complementary) to the siRNA sequence. The activated enzyme complex cleaves the targeted mRNA, destroying it and preventing it from being used to direct the synthesis of its corresponding protein product.

Recent evidence suggests that RNA interference is an ancient, innate mechanism for not only defense against viral infection (many viruses introduce foreign RNA into cells) but also gene regulation at very fundamental levels. RNA interference has been found to occur in plants, insects, lower animals, and mammals, and has been found to be dramatically more effective than other gene silencing technologies, such as antisense or ribozymes. Used as a biotechnology, siRNA involves introducing into cells (or causing cells to produce) short, double-stranded molecules of RNA similar to those that would be produced by the Dicer enzyme from an invading double-stranded RNA virus. The artificially-triggered RNA interference process then continues from that point.

To deliver a small interfering RNA to a patient's brain, a preferred method will be to introduce the DNA encoding for the siRNA, rather than the siRNA molecules themselves, into the cells of the brain. The DNA sequence encoding for the particular therapeutic siRNA can be specified upon knowing (a) the sequence for a small and accessible portion of the target mRNA (available in public human genome databases), and (b) well-known scientific rules for how to specify DNA that will result in production of a corresponding RNA sequence when the DNA is transcribed by cells. The DNA sequence, once specified, can be constructed in the laboratory from synthetic molecules ordered from a laboratory supplier, and inserted using standard molecular biology methods into one of several alternative "vectors" for delivery of DNA to cells. Once delivered into the neurons of the patient's brain, those neurons will themselves produce the RNA that becomes the therapeutic siRNA, by transcribing the inserted DNA into RNA. The result will be that the cells themselves produce the siRNA that will silence the targeted gene. The result will be a reduction of the amount of the targeted protein produced by the cell.

Small Interfering RNA and Small Interfering RNA Vectors

In accordance with the present invention, small interfering RNA against specific mRNAs produced in the affected cells prevent the production of the disease related proteins in neurons. In accordance with the present invention is the use of specifically tailored vectors designed to deliver small interfering RNA to targeted cells. The success of the designed small interfering RNA is predicated on their successful delivery to the targeted cells of the brain to treat the neurodegenerative diseases.

Small interfering RNA have been shown to be capable of targeting specific mRNA molecules in human cells. Small interfering RNA vectors can be constructed to transfect human cells and produce small interfering RNA that cause the cleavage of the target RNA and thereby interrupt production of the encoded protein.

A small interfering RNA vector of the present invention will prevent production of the pathogenic protein by suppressing production of the neuropathogenic protein itself or by suppressing production of a protein involved in the production or processing of the neuropathogenic protein. Repeated administration of the therapeutic agent to the patient may be required to accomplish the change in a large enough number of neurons to improve the patient's quality of life. Within an individual neuron, however, the change is longstanding enough to provide a therapeutic benefit. The desperate situation of many patients suffering from neurodegenerative disorders, such as Alzheimer's disease, Parkinson's disease, Huntington's disease, or Spinocerebellar Ataxia Type 1 provides a strong likelihood that the benefit from the therapy will outweigh the risks of the therapy delivery and administration. While it may be possible to accomplish some reduction in the production of neuropathogenic proteins with other therapeutic agents and routes of administration, development of successful therapies involving direct in vivo transfection of neurons may provide the best approach based on delivery of small interfering RNA vectors to targeted cells.

The preferred vector for delivery of foreign DNA to neurons in the brain is adeno-associated virus (AAV), such as recombinant adeno-associated virus serotype 2 or recombinant adeno-associated virus serotype 5. Alternatively, other viral vectors, such as herpes simplex virus, may be used for delivery of foreign DNA to central nervous system neurons. It is also possible that non-viral vectors, such as plasmid DNA delivered alone or complexed with liposomal compounds or polyethyleneimine, may be used to deliver foreign DNA to neurons in the brain.

It is important to note that the anti-ataxin-1 small interfering RNA and the anti-BACE1 small interfering RNA illustrated here, as well as the other small interfering RNAs for treating neurodegenerative disorders, are just but some examples of the embodiment of the invention. Experimentation using neurosurgical methods with animals, known to those practiced in neuroscience, can be used to identify the candidate small interfering RNAs. The target site on the mRNA and the corresponding small interfering RNA identified by these empirical methods will be the one that will lead to the greatest therapeutic effect when administered to patients with the subject neurodegenerative disease.

In reference to the nucleic molecules of the present invention, the small interfering RNA are targeted to complementary sequences in the mRNA sequence coding for the production of the target protein, either within the actual protein coding sequence, or in the 5' untranslated region or the 3' untranslated region. After hybridization, the host enzymes guided by the siRNA are capable of cleavage of the mRNA sequence. Perfect or a very high degree of complementarity is needed for the small interfering RNA to be effective. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. However, it should be noted that single mismatches, or base-substitutions, within the siRNA sequence can substantially reduce the gene silencing activity of a small interfering RNA.

In preferred embodiments of the present invention, a small interfering RNA is 15 to 30 nucleotides in length. In particular embodiments, the nucleic acid molecule is 15, 16, 17, 18, 19, 20, 21, 22, 23, 24, 25, 26, 27, 28, 29, or 30 nucleotides in length. In preferred embodiments the length of the siRNA sequence can be between 19-30 base pairs, and more preferably between 21 and 25 base pairs, and more preferably between 21 and 23 base pairs.

In a preferred embodiment, the invention provides a method for producing a class of nucleic acid-based gene inhibiting agents that exhibit a high degree of specificity for the RNA of a desired target. For example, the small interfering RNA is preferably targeted to a highly conserved sequence region of target RNAs encoding BACE1 (including variants thereof, e.g. variants A, B, C, and D), RNA such that specific treatment of a disease or condition can be provided with either one or several nucleic acid molecules of the invention. Further, generally, interfering RNA sequences are selected by identifying regions in the target sequence that begin with a pair of adenine bases (AA) (see Examples). SiRNAs can be constructed in vitro or in vivo using appropriate transcription enzymes or expression vectors.

SiRNAs can be constructed in vitro using DNA oligonucleotides. These oligonucleotides can be constructed to include an 8 base sequence complementary to the 5' end of the T7 promoter primer included in the Silencer siRNA (Ambion Construction Kit 1620). Each gene specific oligonucleotide is annealed to a supplied T7 promoter primer, and a fill-in reaction with Klenow fragment generates a full-length DNA template for transcription into RNA. Two in vitro transcribed RNAs (one the antisense to the other) are generated by in vitro transcription reactions and then hybridized to each other to make double-stranded RNA. The double-stranded RNA product is treated with DNase (to remove the DNA transcription templates) and RNase (to polish the ends of the double-stranded RNA), and column purified to provide the siRNA that can be delivered and tested in cells.

Construction of siRNA vectors that express siRNAs within mammalian cells typically use an RNA polymerase III promoter to drive expression of a short hairpin RNA that mimics the structure of an siRNA. The insert that encodes this hairpin is designed to have two inverted repeats separated by a short spacer sequence. One inverted repeat is complementary to the mRNA to which the siRNA is targeted. A string of six consecutive thymidines added to the 3' end serves as a pol III transcription termination site. Once inside the cell, the vector constitutively expresses the hairpin RNA. The hairpin RNA is processed into an siRNA which induces silencing of the expression of the target gene, which is called RNA interference (RNAi).

In most siRNA expression vectors described to date, one of three different RNA polymerase III (pol III) promoters is used to drive the expression of a small hairpin siRNA (1-5). These promoters include the well-characterized human and mouse U6 promoters and the human H1 promoter. RNA pol III was chosen to drive siRNA expression because it expresses relatively large amounts of small RNAs in mammalian cells and it terminates transcription upon incorporating a string of 3-6 uridines.

The constructed nucleic acid molecules can be delivered exogenously to specific tissue or cellular targets as required. Alternatively, the nucleic acid molecules (e.g., small interfering RNA) can be expressed from DNA plasmid, DNA viral vectors, and/or RNA retroviral vectors that are delivered to specific cells.

The delivered small nuclear RNA sequences delivered to the targeted cells or tissues are nucleic acid-based inhibitors of BACE1 (including variants thereof, e.g. variants A, B, C, and D), that are useful for the prevention of the neurodegenerative diseases including Alzheimer's disease, memory loss or cognitive dysfunction, and any other diseases or conditions related to the level of BACE1 and/or beta-amyloid in a cell or tissue.

The nucleic acid-based inhibitors of the invention are added directly, or can be complexed with cationic lipids, packaged within liposomes, packaged within viral vectors, or otherwise delivered to target cells or tissues. The nucleic acid or nucleic acid complexes can be locally administered to relevant tissues ex vivo, or in vivo through injection, infusion pump or stent, with or without their incorporation in biopolymers. In preferred embodiments, the nucleic acid inhibitors comprise sequences which are a sufficient length and/or stably interact with their complementary substrate sequences identified in SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53. Examples of such small interfering RNA (siRNA) also are shown in SEQ ID NOS: 1, 2, 3, 4, for SEQ ID NOS: relating to siRNAs suppressing Ataxin1 mRNA (see also Examples 1-3). Examples of such small interfering RNA are shown in SEQ ID NOS: 24, 25, 26, 27, 28, 29, 30, 31, 32, 33, 34, 35, 36, 37, 38, 39, or 40 relating to suppressing BACE1 mRNA (see also all of Examples 4-6). Examples of such small interfering RNA are shown in SEQ ID NOS: 41, 42, 43, 44, 45, 46, 47, 48, 49, 50, 51, 52, and 53 relating to siRNAs suppressing Huntington mRNA.

In another aspect, the invention provides mammalian cells containing one or more nucleic acid molecules and/or expression vectors of this invention. The one or more nucleic acid molecules may independently be targeted to the same or different sites.

In another aspect of the invention, small interfering RNA molecules that interact with target RNA molecules and inhibit alpha-synuclein, BACE1 (including variants thereof, e.g. variants A, B, C, and D), huntingtin, ataxin-1, ataxin-3 and/or atrophin-1 RNA activity are expressed from transcription units inserted into DNA or RNA vectors. The recombinant vectors are preferably DNA plasmids or viral vectors. Small interfering RNA expressed from viral vectors could be constructed based on, but not limited to, the vector sequences of adeno-associated virus, retrovirus, or adenovirus. Preferably, the recombinant vectors capable of expressing the small interfering RNA are delivered as described above, and persist in target cells. Alternatively, viral vectors may be used that provide for transient expression of small interfering RNA. Such vectors might be repeatedly administered as necessary. Once expressed, the small interfering RNA bind to the target RNA and through use of the host machinery inhibit its expression and thereby its function. Delivery of small interfering RNA expressing vectors, or the small interfering RNA themselves, is by use of intracranial access devices.

The nucleic acid molecules of the instant invention, individually, or in combination or in conjunction with other drugs, can be used to treat diseases or conditions discussed above. For example, to treat a disease or condition associated with alpha-synuclein (Parkinson's Disease), and beta-site APP-cleaving enzyme (Alzheimer's Disease), huntingtin (Huntington's Disease), and Ataxin 1 (Spinocerebellar Ataxia), the patient may be treated, or other appropriate cells may be treated, as is evident to those skilled in the art, individually or in combination with one or more drugs under conditions suitable for the treatment.

In a further embodiment, the described small interfering RNA can be used in combination with other known treatments to treat conditions or diseases discussed above.

In another preferred embodiment, the invention provides nucleic acid-based inhibitors (e.g., small interfering RNA) and methods for their use to downregulate or inhibit the expression of RNA (e.g., alpha-synuclein, BACE1 (including variants thereof, e.g. variants A, B, C, and D), huntingtin, ataxin-1, ataxin-3 and/or atrophin-1) coding for proteins involved in the progression and/or maintenance of Parkinson's disease, Alzheimer's disease, Huntington's disease, Spinocerebellar Ataxia Type 1, Spinocerebellar Ataxia Type 3, and dentatorubral-pallidoluysian atrophy.

The present invention also provides nucleic acid molecules that can be expressed within cells from known eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J Virol., 66, 1432-41; Weerasinghe et al., 1991, J Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45; all of these references are hereby incorporated herein, in their totalities, by reference). Those skilled in the art realize that any nucleic acid can be expressed in eukaryotic cells from the appropriate DNA/RNA vector. The activity of such nucleic acids can be augmented by their release from the primary transcript by ribozymes (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J Biol. Chem., 269, 25856; all of these references are hereby incorporated in their totality by reference herein).

In another aspect of the invention, RNA molecules of the present invention are preferably expressed from transcription units (see, for example, Couture et al., 1996, TIG., 12, 5-10) inserted into DNA or RNA vectors. The recombinant vectors are preferably DNA plasmids or viral vectors. Small interfering RNA expressing viral vectors could be constructed based on, but not limited to, adeno-associated virus, retrovirus, adenovirus, or alphavirus.

In one aspect, the invention features an expression vector comprising a nucleic acid sequence encoding at least one functional segment of the nucleic acid molecules of the instant invention. The nucleic acid sequence encoding the nucleic acid molecule of the instant invention is operably linked in a manner which allows expression of that nucleic acid molecule.

In another aspect the invention features an expression vector comprising: a) a transcription initiation region (e.g., eukaryotic pol I, II or III initiation region); b) a nucleic acid sequence encoding at least one of the nucleic acid agents of the instant invention; and c) a transcription termination region (e.g., eukaryotic pol I, II or III termination region); wherein said sequence is operably linked to said initiation region and said termination region, in a manner which allows expression and/or delivery of said nucleic acid molecule.

Transcription of the nucleic acid molecule sequences are driven from a promoter for eukaryotic RNA polymerase I (pol 1), RNA polymerase II (pol II), or RNA polymerase III (pol III) as is known and appreciated in the art. All of these references are incorporated by reference herein. Several investigators have demonstrated that RNA molecules can be expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J, 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as small interfering RNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96118736; all of these publications are incorporated by reference herein). The above small interfering RNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

It should be noted that the exemplified methods for constructing the small interfering RNA to be used as the therapeutic agents in the invention (that is, in vitro transcription from DNA templates and assembly into double-stranded RNA, or cloning the DNA coding for a hairpin structure of RNA into an adeno-associated viral expression vector) are only two possible means for making the therapeutic small interfering RNA. Other larger scale, more efficient methods for manufacturing small interfering RNA may be used to produce the clinical grade and clinical quantities used for treating human patients, without altering the essence of the invention.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the composition comprising the siRNA agent or precursors or derivatives thereof is formulated in accordance with standard procedure as a pharmaceutical composition adapted for delivered administration to human beings and other mammals. Typically, compositions for intravenous administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing small interfering RNA or precursors or derivatives thereof can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, triethylamine, 2-ethylamino ethanol, histidine, procaine or similar.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. Suitable dose ranges for intracranial administration are generally about $10^3$ to $10^{15}$ infectious units of viral vector per microliter delivered in 1 to 3000 microliters of single injection volume. Addition amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Effective doses may be extrapolated from dose-responsive curves derived from in vitro or in vivo test systems.

For the small interfering RNA vector therapy for neurodegenerative disease of the present invention, multiple catheters having access ports can be implanted in a given patient for a complete therapy. In a preferred embodiment, there is one port and catheter system per cerebral or cerebellar hemisphere, and perhaps several. Once the implantations are performed by a neurosurgeon, the patient's neurologist can perform a course of therapy consisting of repeated bolus injections of small interfering RNA expression vectors over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned, or explanted as well. The device material should not interfere with magnetic resonance imaging, and, of course, the small interfering RNA preparations must be compatible with the access port and catheter materials and any surface coatings.

The polymerase chain reaction (PCR) used in the construction of siRNA expression plasmids and/or viral vectors is carried out in accordance with known techniques. See, e.g., U.S. Pat. Nos. 4,683,195; 4,683,202; 4,800,159; and 4,965, 188 (the disclosures of all three U.S. patent are incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques (see PCR Protocols, A Guide to Methods and Amplifications, Michael et al. Eds, Acad. Press, 1990).

Artificial AAV Vector

An artificial AAV vector includes DNA encoding a biologically active agent, and can be used to deliver a gene or a gene-suppressing agent to a patient's neurons. Thus, the artificial AAV preferably includes a cassette to deliver a gene, or a cassette to deliver a gene-suppressing agent. For example, in the case of a gene therapy intended to supply a missing gene to the patient's brain, the expression cassette can include a promoter element, the coding sequence for the missing gene, and a polyadenylation signal sequence. For another example, in the case of a gene suppression therapy intended to suppress the expression of an endogenous gene in the patient's brain, the expression cassette can include a promoter element, the coding sequence for a small, interfering RNA (siRNA), and a termination sequence.

In one embodiment, the artificial AAV vector is a double stranded vector. The double stranded vector, which may include either type of expression cassette, includes a 5-prime copy of the inverted terminal repeat (AAV-ITR) from the adeno-associated virus genome, followed by an expression cassette for a gene or gene-suppressing agent (whose identity depends upon the neurological disorder to be treated), followed at the 3-prime end by a 3-prime copy of the AAV-ITR.

In another embodiment, the artificial AAV vector, which may include either type of expression cassette, is a single stranded vector. The single stranded vector includes a single stranded DNA segment including a 5-prime copy of the inverted terminal repeat (AAV-ITR) from the adeno-associated virus genome, followed by an expression cassette for a gene or gene-suppressing agent (whose identity depends upon the neurological disorder to be treated), followed at the 3-prime end by a 3-prime copy of the AAV-ITR. Optionally and preferably, the entire DNA sequence including either type of expression cassette is repeated in reverse complement order, so that the DNA sequence includes the 5-prime AAV-ITR, the expression cassette, an internal AAV-ITR, the reverse complement of the expression cassette, and the 3-prime AAV-ITR. The 3-prime AAV-ITR is the reverse complement of the 5-prime AAV-ITR (as illustrated, for example, in Example 1 herein), and either a 3-prime or 5-prime AAV-ITR can be used as the internal AAV-ITR. The resulting "self-complementary" artificial AAV vector is preferred because it may produce more effective transfection of neurons by the DNA. See, for example, Fu et al., *Molecular Therapy* 8:911-917 (2003).

Figure 3A:
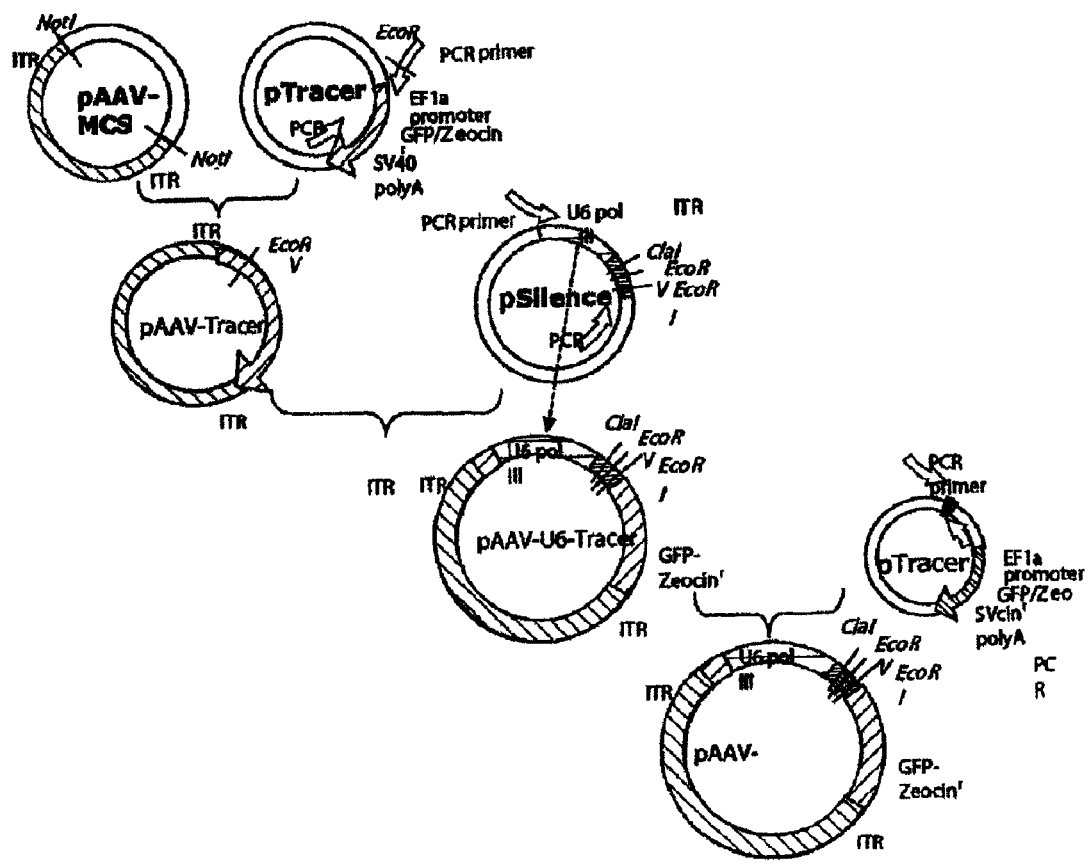
FIG. 3a shows the construction of the adeno-associated virus expression vector pAAV-siRNA as described in Example 3.
Figure 3B:
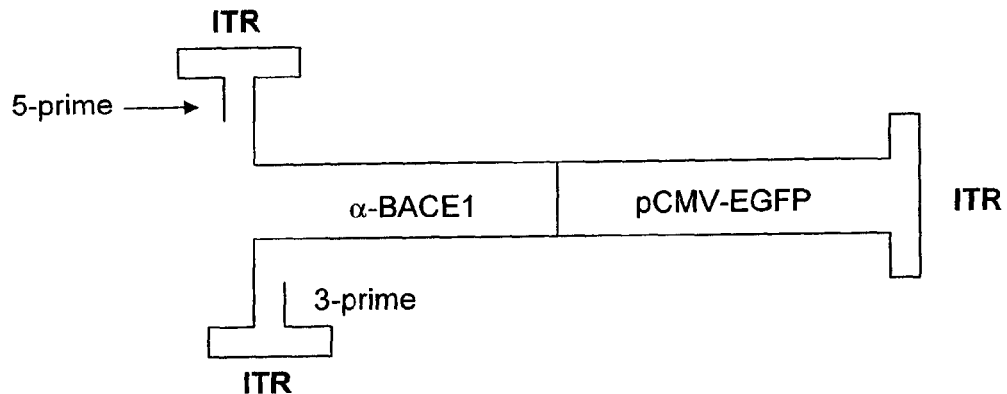
FIG. 3b is a schematic representation of one embodiment of a self-complementary artificial AAV vector for delivery of a single stranded DNA. The artificial AAV vector includes, in 5-prime to 3-prime order: a 5-prime AAV-ITR (ITR); a single stranded DNA (a-BACE1/pCMV-EGFP); an internal AAV-ITR (ITR); a reverse complement of the single stranded DNA (a-BACE1/pCMV-EGFP); and a 3-prime AAV-ITR (ITR).
Figure 3C:
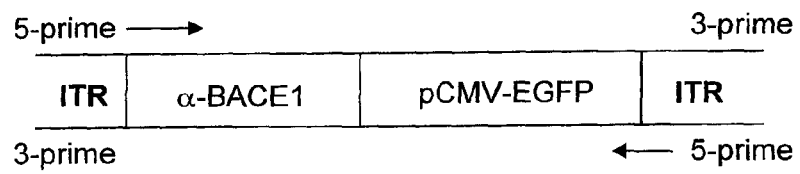
FIG. 3c is a schematic representation of one embodiment of an artificial AAV vector for delivery of a linear, double stranded DNA. The linear, double stranded DNA (a-BACE1/pCMV-EGFP) has AAV-ITRs (ITR) at the 5-prime and 3-prime ends of each strand.

It will be appreciated by those skilled in the art that the embodiment of a double-stranded artificial AAV vector and the embodiment of a single-stranded self-complementary artificial AAV vector differ only in that the single stranded self-complementary vector has a single, single-stranded AAV-ITR joining the complementary strands of the expression cassette (covalently joining the 3-prime end of one strand to the 5-prime end of the complementary strand, as shown schematically in FIG. 3b) so that the entire artificial AAV vector is one single DNA strand "folded back" on itself with hydrogen bonds between the complementary strands of the expression cassette. In the case of the double stranded artificial AAV vector, there are double-stranded AAV-ITRs at the 5-prime end and the 3-prime end of the expression cassette with no covalent bond joining strands at either end (as illustrated schematically in FIG. 3c).

Figure 3D:
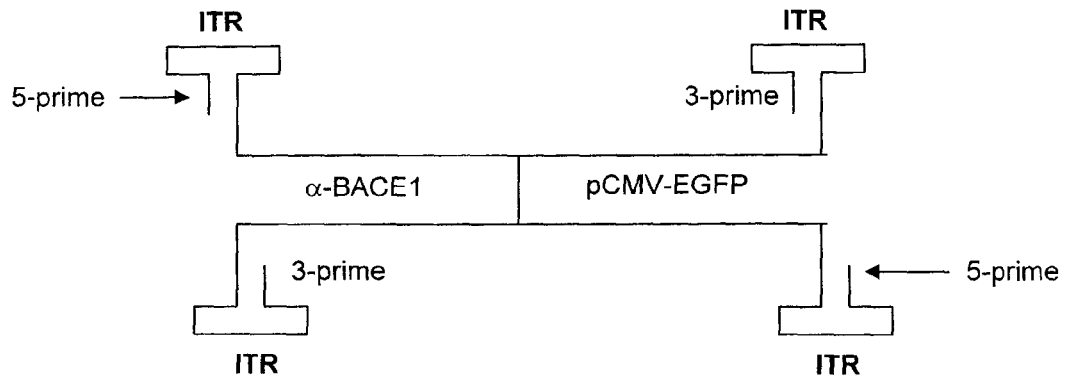
FIG. 3d is a schematic representation of one embodiment of an artificial AAV vector for delivery of a linear, double stranded DNA as illustrated in FIG. 3c that has been thermally treated in at least one heating and cooling cycle. The schematic representation illustrates a secondary structure of the ITRs in which the ITRs have folded so as to allow the self-complementary portions of each ITR to internally hybridize.

An exemplary method for preparing a double-stranded artificial AAV vector is disclosed. The method includes the steps of: assembling the 5-prime AAV-ITR, expression cassette, and 3-prime AAV-ITR in any suitable DNA plasmid using standard DNA cloning methods; liberating the 5-prime AAV-ITR, expression cassette, and 3-prime AAV-ITR from the plasmid by digesting the plasmid with a restriction enzyme that cuts the DNA at a site just 5-prime to the 5-prime AAV-ITR and just 3-prime to the 3-prime AAV-ITR; and purifying the linear DNA fragment consisting of the 5-prime AAV-ITR, expression cassette, and 3-prime AAV-ITR using standard methods. Optionally, the resulting linear double-stranded artificial AAV vector may be further processed by a thermal treatment step including, for example, heating the purified linear DNA fragment (e.g., heating to 65° C. or higher for 10 minutes or more), followed by cooling (e.g., allowing the DNA fragment to cool slowly to room temperature over a period of 10 minutes or more). These heating and cooling steps can allow the AAV ITRs to assume a secondary structure, conducive to long-term gene expression from this double-stranded artificial AAV vector, as illustrated schematically in FIG. 3d.

Exemplary methods for preparing a single-stranded DNA as described herein above are also disclosed. One method includes the steps of: assembling the 5-prime AAV-ITR, expression cassette, and 3-prime AAV-ITR in any suitable DNA plasmid using standard DNA cloning methods; generating a single-stranded RNA transcript of the desired single-stranded DNA from the DNA plasmid using standard in vitro transcription methods; generating single-stranded DNA from the RNA transcript by reverse transcription using standard reverse transcription reaction methods; removing the RNA transcript from the reaction products by digestion of the RNA using RNase enzyme; and purifying the resulting single-stranded DNA product from the reaction products by standard DNA purification methods, such as gel purification or column affinity methods.

Another method includes the steps of: assembling the 5-prime AAV-ITR, expression cassette, and 3-prime AAV-ITR in any suitable DNA plasmid using standard DNA cloning methods; linearizing the circular plasmid by digesting the plasmid with a restriction enzyme that cuts the DNA at a single, known location in the plasmid sequence just 5-prime to the 5-prime AAV-ITR; chemically conjugating an affinity tag (e.g., a biotin molecule) to the 5-prime ends of each strand of the linearized plasmid; cutting the DNA sequence with a restriction enzyme that cuts the DNA at a second single, known location in the plasmid sequence just 3-prime to the 3-prime AAV-ITR, such that the restriction digest results in two linear double-stranded DNA segments of different sizes; separating the populations of DNA molecules by size using any suitable size separation method (e.g., column filtration or gel electrophoresis) and recovering the desired double-stranded DNA; and melting the DNA to separate its two complementary strands into two single strands and passing the mixture through an affinity column for the tag (e.g., a streptavidin affinity column when a biotin molecule is used as the affinity tag) such that the strand which was tagged in step 3 is captured on the column while the non-tagged single-strand flows through as the desired final product. This method can be advantageous for not involving any DNA or RNA polymerization steps that might introduce sequence errors in the final product.

In the case of a self-complementary AAV, the method includes the steps of: assembling the 5-prime AAV-ITR, expression cassette, internal AAV-ITR, reverse complement of the same expression cassette, and 3-prime AAV-ITR into any suitable DNA plasmid using standard DNA cloning methods; linearizing the circular plasmid by digesting the plasmid with restriction enzymes that cut out the desired DNA sequence (from the 5-prime AAV-ITR through the 3-prime AAV-ITR); recovering the desired DNA sequence from step 2 by size using any suitable size separation method; melting this double-stranded DNA to separate its two complementary strands into two single strands; and lowering the temperature (preferably slowly) of the melted DNA to allow the single strands to self-anneal into a hairpin form. All of the resulting single strands ("sense" or "anti-sense" strand) would be useful as the final product, since either strand would contain a copy of the desired expression cassette in a 5-prime to 3-prime orientation.

Compositions

For embodiments in which the composition is delivered across the blood-brain barrier, the composition includes, for example, a liposome as described, for example, in U.S. Pat. No. 6,372,250 (Pardridge), and a pharmaceutically acceptable carrier. Preferably the liposome is a receptor-specific liposome, wherein the receptor-specific liposome includes: a liposome having an exterior surface and an internal compartment; an artificial adeno-associated virus (AAV) vector located within the internal compartment of the liposome; one or more blood-brain barrier and brain cell membrane targeting agents; and one or more conjugation agents (e.g., polyethylene glycol (PEG) strands), wherein each targeting agent is connected to the exterior surface of the liposome via at least one of the conjugation agents. Receptor-specific liposomes including an artificial adeno-associated virus (AAV) vector located within the internal compartment of the liposome can be prepared by the general methods described in U.S. Pat. No. 6,372,250 (Pardridge), except that the artificial adeno-associated virus (AAV) vector is used instead of the plasmid DNA.

Liposomes as described herein can deliver biologically active agents across the blood-brain barrier, followed by expression in the brain. Liposomes and nanoparticles are exemplary forms of nanocontainers that are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1%) of cationic lipid, such as didodecyldimethylammonium bromide (DDAB) to stabilize the DNA within the liposome.

Although the invention has been described using liposomes as the preferred nanocontainer, it will be recognized by those skilled in the art that other nanocontainers may be used. For example, the liposome can be replaced with a nanoparticle or any other molecular nanocontainer with a diameter <200 nm that can encapsulate the DNA and protect the nucleic acid from nucleases while the formulation is still in the blood or in transit from the blood to the intracellular compartment of the target cell. Also, instead of using conjugation agents such as PEG strands, one or more other polymeric substances, such as sphingomylein, can be attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of DNA to any group of cells or organs which have specific target receptors. The liposomes may be used to deliver DNA to organs, such as liver, lung and spleen.

The liposomes may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990).

In a preferred embodiment of the present invention, the compositions or precursors or derivatives thereof are formulated in accordance with standard procedure as a pharmaceutical composition adapted for delivered administration to human beings and other mammals. Typically, compositions for intravenous administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a composition of the present invention including encapsulation in liposomes, microparticles, microcapsules and the like.

In yet another preferred embodiment, compositions can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

The amount of a composition of the present invention which will be effective in the treatment of a particular disorder or condition will depend on the nature of the disorder or condition, and can be determined by standard clinical techniques, well established in the administration of compositions. The precise dose to be employed in the formulation will also depend on the route of administration, and the seriousness of the disease or disorder, and should be decided according to the judgment of the practitioner and the patient's needs. Suitable dose ranges for intracranial administration are generally about $10^3$ to $10^{15}$ infectious units of viral vector per microliter delivered in 1 to 3000 microliters of single injection volume. Addition amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Appropriate dosage may be extrapolated from dose-responsive curves derived from in vitro or in vivo test systems.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor. Laboratories) and Ausubel et al. (1994, Current Protocols in Molecular Biology, Wiley, New York).

To summarize, the present invention provides methods to deliver small interfering RNA vectors to the human central nervous system, and thus treat memory loss in normal human brains and neurodegenerative diseases by reducing the production of a pathogenic protein within neurons.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of a Small Interfering RNA Targeting Human Ataxin1 mRNA

As an example of the embodiments of the invention, a small interfering RNA that targets the mRNA for human ataxin1 was made. This small interfering RNA reduces the amount of mRNA for human ataxin1 in human cells, in cell cultures. As a therapy for Spinocerebellar Ataxia Type 1 (SCA1), this same small interfering RNA or a similar small interfering RNA will be delivered to the cells of the cerebellum in the patient's brain, using implanted access ports and catheters. The result will be a reduction in the amount of ataxin1 protein in these cells, thereby slowing or arresting the progression of the patient's SCA1 disease.

The small interfering RNA against human ataxin1 was been constructed from the nucleotide sequence for human ataxin1. The sequence from human ataxin 1 was retrieved from the publicly-accessible nucleotide database provided by NCBI, retrievable as NCBI accession number NM_000332 (SEQ ID NO:15). A portion of the human mRNA sequence for ataxin1 was identified as a potential site for small interfering RNA cleavage and also predicted to be single-stranded by MFOLD analysis. In accession NM_000332 (SEQ ID NO:15), three pairs of anti-ataxin1 siRNA targets were constructed:

```
1.  Antiataxin1 siRNA targeting the mRNA
    sequence at sites numbered 945 through
    965:
    SEQ ID NO: 1  5'-AACCAAGAGCGGAGCAACGAA-3'
    SEQ ID NO: 2  3'-GGTTCTCGCCTCGTTGCTTAA-5'

2.  Antiataxin1 siRNA targeting the mRNA
    sequence at sites numbered 1671-through
    1691:
    SEQ ID NO: 3  5'-AACCAAGAGCGGAGCAACGAA-3'
    SEQ ID NO: 4  3'-GGTTCTCGCCTCGTTGCTTAA-5'

3.  Antiataxin1 siRNA targeting the mRNA
    sequence at sites numbered 2750-through
    2770:
    SEQ ID NO: 5  5'-AACCAGTACGTCCACATTTCC-3'
    SEQ ID NO: 6  3'-GGTCATGCAGGTGTAAAGGAA-5'
```

A series of six deoxyoligonucleotide fragments were designed, ordered and purchased from the MWG Biotech, Inc., custom oligonucleotide synthesis service to provide the six fragments making up the three target sites. Additionally, these oligonucleotides were constructed to include an 8 base sequence complementary to the 5' end of the T7 promoter primer included in an siRNA construction kit (Ambion, Inc. catalog number 1620). Each specific oligonucleotide was annealed to the supplied T7 promoter primer, and filled-in with Klenow fragment to generate a full-length DNA template for transcription into RNA. Two in vitro transcribed RNAs (one the antisense to the other) were generated by in vitro transcription reactions then hybridized to each other to make double-stranded RNA. The double-stranded RNA product was treated with DNase (to remove the DNA transcription templates) and RNase (to polish the ends of the double-stranded RNA), and column purified to provide the three siRNAs that were delivered and tested in cells.

Example 2

Delivery Of A Small Interfering RNA Targeting Human Ataxin1 mRNA

The constructed siRNA molecules 1-3 described in Example 1 were transfected into HEK293 cells. The RNA produced by the transfected cells was harvested and assayed to measure the amount of human ataxin1 mRNA.

FIG. 1 shows the results of a quantitative reverse-transcriptase polymerase chain reaction (qRT-PCR) assay for the amount of ataxin1 messenger RNA (mRNA) per microgram of total RNA from cultures of HEK293H cells. Four cell populations were assayed. The first were 293H cells that had been transiently transfected with siRNA against GAPDH, a "housekeeping gene" with no known relationship to ataxin1 mRNA expression. (The siRNA against GAPDH was supplied as a standard control by Ambion, Inc., in their commercially-available kit for making and testing siRNA). The second were 293H cells that had been transiently transfected with siRNA against ataxin1 mRNA at location 1671 in the ataxin1 mRNA sequence. The third were 293H cells transiently transfected with a plasmid containing a ribozyme against ataxin1 mRNA (which cleaves ataxin1 mRNA at position 1364 in the ataxin1 mRNA sequence). The fourth were 293H cells transiently transfected with siRNA against ataxin1 mRNA at location 0945. All cell populations were harvested concurrently for total cellular RNA, at a time point 48 hours after transfection.

On the gels pictured, the amplified DNA products of the RT-PCR reaction were separated by molecular size, using gel electrophoresis, and are visible as bands of varying intensity. Each cell population described was assayed using a series of parallel reactions, shown as a set of lanes at the top or bottom of each gel. Each set of lanes contains two bands per lane. The top band is the DNA product amplified from a known quantity of DNA added to the reaction to compete with the endogenous cDNA reverse transcribed from the cellular mRNA. If the bands in a given lane are of the same intensity, then the amount of cellular mRNA in the original cell sample can be inferred to be equivalent to the amount of known quantity of DNA added to the reaction tube. From left to right across the lanes, the amount of known DNA standard added was decreased, in the picogram amounts shown. The assay is interpreted by looking for the set of lanes for which the intensity of the bands "crosses over"from being brightest for the DNA standard, to being brightest for the cellular product below it, indicating that the amount of DNA standard is now lower than the amount of cellular mRNA.

On the gel shown in FIG. 1, the top set of lanes is from the cells transfected with the ribozyme against ataxin1 mRNA. The comparison of the bands from this cellular sample to the bands from the DNA standards indicates that the amount of ataxin1 mRNA in these cells is between 0.505 and 0.303 picograms per microgram of total cellular RNA. The bottom set of lanes is from the cells transfected with siRNA against ataxin1 at position 0945. Analysis of these lanes indicates that the amount of ataxin1 mRNA in these cells is between 0.303 and 0.202 picograms per microgram of total cellular RNA.

Figure 2:
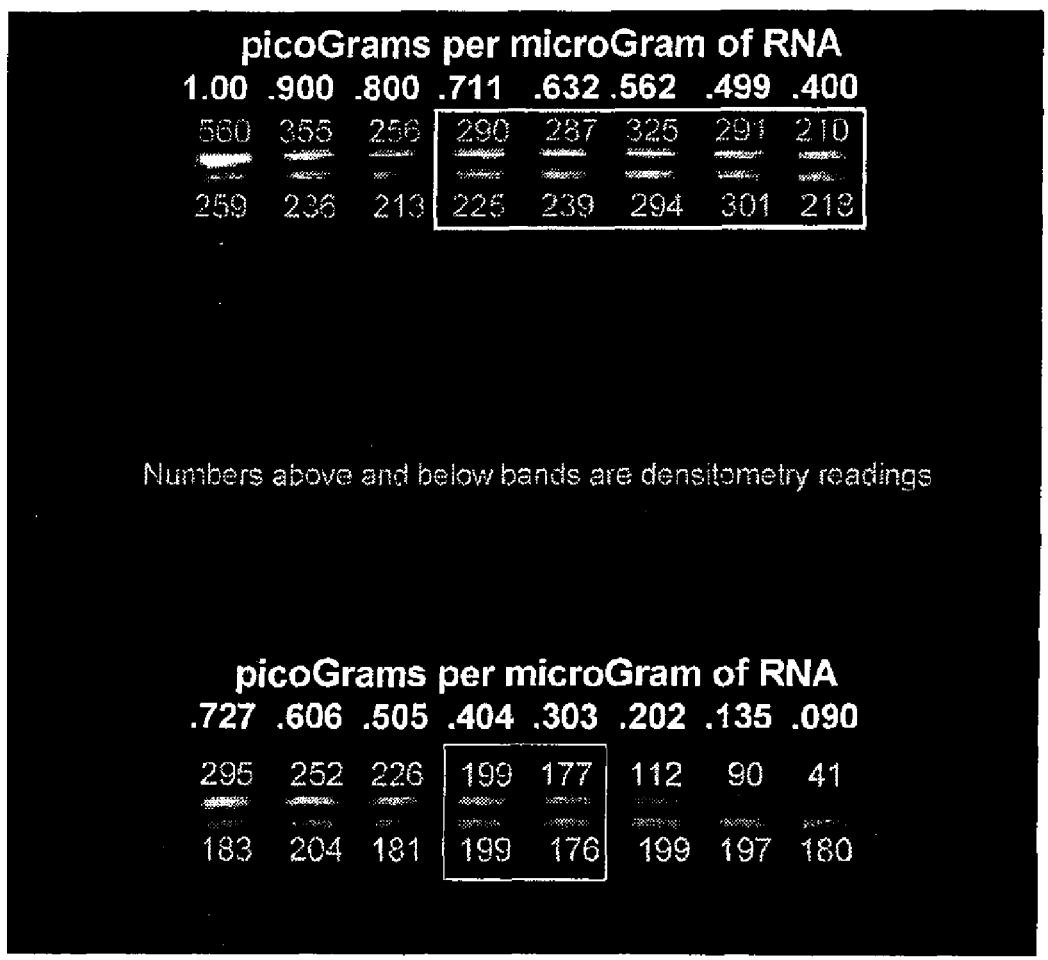
FIG. 2 shows the assay (using the same quantitative RT-PCR method known to those practiced in the art) of the ataxin-1 mRNA obtained from HEK293H cells that have been transfected with anti-ataxin-1 small interfering RNA (bottom lanes) compared to the mRNA obtained from HEK293H cells that have been transfected with a control siRNA that targets the mRNA for glyceraldehyde-3-phosphate dehydrogenase (GAPDH)

On the gel shown in FIG. 2, the top set of lanes is from the cells transfected with a control siRNA against GAPDH. Analysis of these lanes indicates that the amount of ataxin1 mRNA in these cells is between 0.711 and 0.400 picograms per microgram of total cellular RNA. Finally, the bottom set of lanes is from cells transfected with another siRNA against ataxin1, at position 1671. These lanes indicate that the amount of ataxin1 mRNA in these cells is between 0.404 and 0.303 picograms per microgram of total cellular RNA.

In summary, the results of this particular analysis were:

| Treatment | Amount of ataxin1 mRNA (picograms per microgram total cellular RNA) | | |
|---|---|---|---|
| | Lower bound | Upper bound | Midpoint Estimate |
| Control (GAPDH) | 0.400 | 0.711 | 0.555 |
| Ribozyme (A1364A) | 0.303 | 0.505 | 0.404 |
| siRNA (AT1671) SEQ ID Nos: 3 and 4 | 0.303 | 0.404 | 0.353 |
| siRNA (AT0945) SEQ ID Nos: 1 and 2 | 0.202 | 0.303 | 0.252 |

These data indicate that both the AT1671 and AT0945 siRNA against ataxin1 were effective at reducing the amount of ataxin1 mRNA in these cells within 48 hours after transfection, and that the siRNA were more effective at the reduction of ataxin1 mRNA than was this anti-ataxin1 ribozyme.

It should be noted that the exemplified method for constructing the small interfering RNA to be used as the therapeutic agents in the invention (that is, assembly from oligonucleotides using in vitro transcription and hybridization) is only one possible means for making the therapeutic small interfering RNA. Other larger scale, more efficient methods for manufacturing small interfering RNA may be used to produce the clinical grade and clinical quantities used for treating human patients, without altering the essence of the invention or departing from the spirit and scope of this invention, as set forth in the appended claims.

Example 3

Construction of Small, Interfering RNA Viral Vectors

A selectable reporter plasmid, pAAV-U6-Tracer for cloning siRNA was constructed. (See FIG. 3). The plasmid pAAV-U6-Tracer was constructed to contain the inverted terminal repeats (ITR) of adeno-associated virus, flanking the U6 RNA polymerase III promoter from pSilencer (Ambion), and the EF1a promoter, green fluorescence protein, Zeocin" resistance, and SV40 poly A from pTracer (Invitrogen). The gene segments are cloned as shown in FIG. 3. Oligonucleotides for expressing siRNA are cloned into the multiple cloning region just downstream in the 3' direction from the U6 RNA polymerase III promoter.

HEK293 Cells are cotransfected with pAAV-siRNA, pHelper, and pAAV-RC to make viral producer cells, where the pAAV-RC and pHelper plasmids are part of the three plasmid AAV production system Avigen, Inc.). The producer 293 cells are grown in culture and are used to isolate recombinant viruses which is used to transfect cells for assessment of treatment effect, such as: HeLa Cells, DAOY cells, and SK-N-SH cells.

Example 4

Treatment of Memory Dysfunction Using RNA Interference Targeting Beta-Amyloid Cleaving Enzyme Type 1 (BACE1)

One aspect of the invention provides a therapy for Alzheimer's disease. Another aspect of the invention provides a therapy for memory dysfunction. The latter therapy has been tested in normal, aged mice. This therapy uses a viral vector that encodes for a siRNA sequence that, upon uptake by a neuronal cell, reduces the amount of mRNA for beta-amyloid cleaving enzyme type 1 (BACE1) produced in that neuronal cell. Reducing the amount of BACE1 mRNA in cells results in a reduction of the amount of the enzyme produced, and subsequently the amount of beta-amyloid fragments cleaved from the amyloid-precursor protein (APP) by the BACE1 enzyme. Reduction in the amount of beta-amyloid fragments in the brain is the biological mechanism by which memory dysfunction is treated by this therapy.

The overall steps involved in this work include (1) in vitro screening of candidate anti-BACE1 siRNA sequences for efficacy, (2) construction of a viral vector for in vivo delivery of DNA encoding for the anti-BACE1 siRNA to the mammalian brain, (3) neurosurgical administration of the vector to the mice, (4) testing of the behavior of the mice to assess the effect of the treatment, and (5) examination of the brain tissue of the mice to assess the effect of the treatment. Steps 1 and 2 are described in this Example in detail below, and steps 3, 4, and 5 are described in Example 5.

(1) Screening of Anti-BACE1 siRNA Sequences for In Vitro Efficacy

Identification of candidate anti-BACE1 siRNA sequences: In order to identify an siRNA sequence that is effective at reducing the expression of BACE1 mRNA in neuronal cells, analysis of the human and mouse cDNA sequences for the BACE1 gene available in the Genbank database (National Center for Biotechnology Information, accession numbers NM_012104, NM_138971, NM_138972, and NM_138973 for human, and NM_011792 for mouse) was performed. The analysis consisted of identifying sections of the cDNA sequence beginning with two successive adenine nucleotides (AA) or with a cytosine and adenine (CA), and comprising those two nucleotides plus the nineteen successive nucleotides. These candidate sequences were tested for possible partial matches to other sequences in other genes, using the BLAST software program provided by the National Center for Biotechnology Information website and sequences with a high amount of partial matching to other genes (e.g., a match of more than 15 out of the 19 successive nucleotides following the AA or CA nucleotides) were eliminated from further consideration. Candidate sequences with an extreme percentage of guanine or cytosine (G or C) nucleotides in the sequence (e.g., greater than 65% or less than 35% of the 19 successive nucleotides were G or C rather than A or T) were also eliminated from consideration. From the remaining candidates, the following were selected for laboratory screening:

Anti-BACE1 siRNA candidates and corresponding in vitro suppression of BACE1 expression

| SEQ ID No. | Item | Name | Starting position within mouse BACE1 (Genbank) Accession NM_011792) | DNA sequence corresponding to the therapeutic siRNA | Method for production of siRNA for in vitro screening | Mean %* | SD | N trials |
|---|---|---|---|---|---|---|---|---|
| 24 | 1 | MB0803 | 0803 | AAGGGTGTGTATGTGCCCTAC | in vitro transcription | 57.0 | 1.4 | 2 |
| 25 | 2 | MB1663 | 1663 | AATTGGCTTTGCTGTCAGCGC | in vitro transcription | 42.0 | 24.0 | 2 |
| 26 | 3 | MB1749 | 1749 | AAGACTGTGGCTACAACATTC | in vitro transcription | 96.5 | 0.7 | 2 |
| 27 | 4 | MB3249 | 3249 | AAGGCTGCCTGGAGAAAGGAT | in vitro transcription | 0.0 | 11.3 | 2 |
| 28 | 5 | DhMB0918 | 0916 | CaCTGAATCGGACAAGTTCTT | chemical synthesis | 78.7 | 24.8 | 3 |
| 29 | 6 | DhMB1131 | 1129 | CaTGATCATTGGTGGTATCGA | chemical synthesis | 85.0 | 10.4 | 3 |
| 30 | 7 | DhMB1233 | 1231 | AaTCAATGGTCAAGATCTCAA | chemical synthesis | 81.7 | 13.7 | 3 |
| 31 | 8 | DhMB1509 | 1507 | CaTCCTTCCTCAGCAATACCT | chemical synthesis | 57.3 | 39.3 | 3 |
| 32 | 9 | SEC0683 | 0683 | CAGACGCTCAACATCCTGGTG | expression cassette | 54.3 | 19.0 | 4 |
| 33 | 10 | SEC1722 | 1722 | AAGGTCCGTTTGTTACGGCAG | expression cassette | 50.3 | 31.6 | 4 |
| 34 | 11 | SEC2163 | 2163 | AATATCCTTAGACACCACAAA | expression cassette | 47.5 | 19.2 | 4 |
| 35 | 12 | SEC2466 | 2466 | AAACAAGAACCTATGCGATGC | expression cassette | 41.5 | 33.3 | 4 |
| 36 | 13 | SEC2473 | 2473 | AACCTATGCGATGCGAATGTT | expression cassette | 61.0 | 18.6 | 4 |

*Percent suppression of co-transfected BACE1 in Neuro2a cell cultures.

The set screened in the laboratory were selected to include candidates from a wide range of positions within the cDNA of the mouse BACE1 sequence. For purposes of testing this therapy in mice, it was essential that the siRNA sequence be effective at suppressing the native mouse BACE1 enzyme in the mice. Therefore, priority was given to candidate siRNA sequences corresponding to mouse cDNA regardless of the amount of homology to human BACE1 cDNA. However, some of the candidate siRNA sequences correspond 100% to human as well as mouse BACE1 cDNA. For example, MB1749, targets a regions of BACE1 mRNA that is 100% identical across the human and mouse species, and thus constitutes a therapy component that is applicable to humans as well as mice.

Production of siRNA candidates for in vitro testing: Double-stranded RNA corresponding to the MB0803, MB1663, MB1749, or MB3249 siRNA candidates were made by in vitro transcription from custom DNA oligonucleotides and other reagents using the Ambion Silencer™ siRNA Construction Kit (Ambion, Inc., Austin, Tex.; catalog number 1620) following the procedure recommended by the manufacturer. The custom DNA oligonucleotides used to produce our specific siRNA were as follows. The siRNA target sequences are listed in capital letters, while other oligonucleotides for use in the in vitro transcription method are listed in lower case letters.

| SEQ ID: Sence | siRNA | Sense oligonucleotide (DNA) | Antisense oligonucleotide (DNA) | SEQ ID antisense |
|---|---|---|---|---|
| 60 | MB0803 | aaGTAGGGCACATACACACCCcct-gtctc | AAGGGTGTGTATGTGCCCTACcctgtctc | 61 |
| 62 | MB1663 | aaGCGCTGACAGCAAAGCCAAcct-gtctc | AATTGGCTTTGCTGTCAGCGCcctgtctc | 63 |
| 64 | MB1749 | aaGAATGTTGTAGCCACAGTCcct-gtctc | AAGACTGTGGCTACAACATTCcctgtctc | 65 |
| 66 | MB3249 | aaATCCTTTCTCCAGGCAGCCcct-gtctc | AAGGCTGCCTGGAGAAAGGATcctgtctc | 67 |

Chemically synthesized double-stranded RNA corresponding to the DhMB0918, DhMB1131, DhMB1233, and DhMB1509 siRNA candidates were ordered from Dharmacon, Inc. (Lafayette, Colo.). The sequences specified for the supplier to produce were as follows:

| SEQ ID: to Sense Oligonucl. | siRNA | Sense oligonucleotide (RNA) | Antisense oligonucleotide (RNA) | SEQ ID Antisense |
|---|---|---|---|---|
| 68 | DhMB0918 | CUGAAUCGGACAAGUUCUUdTdT | AAGAACUUGUCCGAUUCAGdTdT | 69 |
| 70 | DhMB1131 | UGAUCAUUGGUGGUAUCGAdTdT | UCGAUACCACCAAUGAUCAdTdT | 71 |
| 72 | DhMB1233 | UCAAUGGUCAAGAUCUCAAdTdT | UUGAGAUCUUGACCAUUGAdTdT | 73 |
| 74 | DhMB1509 | UCCUUCCUCAGCAAUACCUdTdT | AGGUAUUGCUGAGGAAGGAdTdT | 75 |

DNA expression cassettes were made from which cells transcribe RNA that forms a hairpin corresponding to the SEC0683, SEC1722, SEC2163, SEC2466, or SEC2473 siRNA candidates by polymerase chain reaction, using custom DNA oligonucleotides plus reagents from the Ambion Silencer™ Express siRNA Expression Cassette Kit (Ambion, Inc., Austin, Tex.; catalog number 1682) following the procedure recommended by the manufacturer. The custom DNA oligonucleotides used to produce specific siRNA expression cassettes were as follows. The siRNA target sequences are listed in capital letters, while other oligonucleotides needed for use in the expression cassette method are listed in lower case letters.

| siRNA | strand | oligonucleotide (DNA) | SEQ ID: |
|---|---|---|---|
| SEC0683 | sense | ggtgaagcttgACCAGGATGTTGAGCGTCTGccggtgtttcgtcctttccacaag | 76 |
|  | antisense | cggcgaagcttttccaaaaaaCAGACGCTCAACATCCTGGTGaagcttgacca |  |

-continued

| siRNA | strand | oligonucleotide (DNA) | SEQ ID: |
|---|---|---|---|
| SEC1722 | sense | cagctacacaaaCTGCCGTAACAAACGGACCcggtgtttcgtcctttccacaag | 78 |
| | antisense | cggcgaagcttttccaaaaAAGGTCCGTTTGTTACGGCAGctacacaaactgc | |
| SEC2163 | sense | aaactacacaaaTTTGTGGTGTCTAAGGATAccggtgtttcgtcctttccacaag | 80 |
| | antisense | cggcgaagcttttccaaaaAATATCCTTAGACACCACAAActacacaaatttg | |
| SEC2466 | sense | tgcctacacaaaGCATCGCATAGGTTCTTGTcggtgtttcgtcctttccacaag | 82 |
| | antisense | cggcgaagcttttccaaaaAAACAAGAACCTATGCGATGCctacacaaagcat | 83 |
| SEC2473 | sense | gttgaagcttgAACATTCGCATCGCATAGGccggtgtttcgtcctttccacaag | 84 |
| | antisense | cggcgaagcttttccaaaaAACCTATGCGATGCGAATGTTgaagcttgaaca | 85 |

Figure 6:
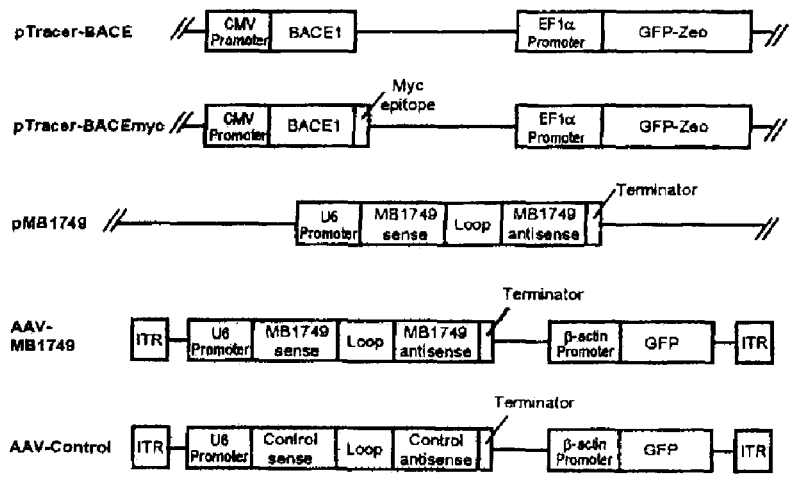
FIG. 6 illustrates diagrams of plasmids used. Plasmids pTracerBACE and pTracer-BACEmyc were used to screen for effective anti-BACE1 siRNA as described. Plasmid pMB1749 encoding for MB1749 as a shRNA was constructed as an intermediate step in the production of the viruses administered to mice as described, AAV-MB1749 and AAV-Control.

In vitro application of the siRNA candidates to neuronal cell cultures: To assess the effectiveness of each anti-BACE1 siRNA candidate in suppressing BACE1 mRNA in vitro, mouse neuronal cells of the Neuro2a cell line (American Type Culture Collection, catalog number CCL-131) were cultured using the standard cell culture conditions for these cells. Upon reaching 50-70% confluence, the cells were co-transfected with one of the siRNA candidates, and with a plasmid containing the cDNA for mouse BACE and for green fluorescent protein (GFP). This plasmid, called pTracerBace1, was constructed for this purpose by cloning the full length open reading frame of murine BACE1 cDNA (Open Biosystems, Huntsville Ala., IMAGE mouse cDNA clone 6831622) into the pTracer™-CMV2 plasmid (Invitrogen, Carlsbad Calif., #V885-20) downstream of the CMV promoter. The plasmid contains a second eukaryotic expression cassette encoding a fusion gene of green fluorescent protein and the Zeocin resistance marker (GFPzeo) whose expression is directed by the EF1a constitutive promoter (FIG. 6).

The cell transfection procedure and reagents used to conduct the in vitro testing varied as appropriate for the form (RNA or DNA) in which the siRNA candidate was applied. For transfection of cells with plasmid plus siRNA candidates produced by in vitro transcription (MB0803, MB1663, MB1749, MB3249) or by direct chemical synthesis (DhMB0918, DhMB1131, DhMB1233, DhMB1509), first a mixture of pTracerBace1 plasmid in Transit-Neural transfection reagent (Mirus, Inc. Madison, Wis.; catalog number 2144) was formed following the manufacturer's recommended procedures. Then, Transit-TKO transfection reagent (Mirus, Inc., catalog number 2154) was added dropwise to the Transit-Neural mixture, and incubated at room temperature for 10 minutes. Next, the siRNA was added to the mixture, incubated to allow the siRNA to form complexes with the Transit-TKO, then finally added dropwise to the cells. In all cases, the amount of pTracerBace1 plasmid per cell culture well was 1 microgram per well (of a six-well culture plate) across the various conditions, and the final concentration of siRNA per cell culture well is 25 nanoMolar.

For transfection of cells with plasmid plus siRNA candidates in the form of DNA (Silencer Expression Cassettes SEC0683, SEC1722, SEC2163, SEC2466, SEC2473) the method was similar, but SiPort-XP1 transfection reagent (Ambion, Inc., Austin, Tex.; catalog number 4506) was used for transfection of the cells with the double-stranded DNA PCR products constituting the expression cassettes. In these cases, SiPort-XP1 reagent was added dropwise to Opti-MEM® reduced-serum medium (Invitrogen, Carlsbad, Calif.; catalog number 22600), vortexed, and incubated at room temperature for 15 minutes following the procedure recommended by Ambion, Inc. Then, pTracerBace1 plasmid was added to one aliquot of the SiPort-XP1 mixture, and siRNA expression cassette DNA was added to a separate aliquot of SiPort-XP1 mixture. Each aliquot was incubated at room temperature for 15 minutes to allow the DNA molecules to complex with the SiPort-XP1 reagent, then the two mixtures were combined and added dropwise to cells. The amount of pTracerBace1 plasmid per cell culture well was 1 migrogram per well across the various conditions, and the amount of siRNA expression cassette DNA added per well was 500 nanograms per well.

Assay of the effect of siRNA candidates on BACE1 mRNA levels in cells: To determine the effect of siRNA candidate on BACE1 mRNA levels in cells, the cells were harvested 48 to 72 hours after transfection with the siRNA and pTracerBace1 plasmid, and total cellular RNA was recovered from the cell lysate using the Qiagen RNeasy Mini Kit (Qiagen, Inc., Valencia, Calif.; catalog number 74106). The RNA was treated with DNase during this isolation, to eliminate genomic and plasmid DNA from the samples. The RNA samples were reverse transcribed to cDNA using the StrataScript First Strand cDNA Synthesis Kit (Stratagene, Inc., La Jolla, Calif.; catalog number 200420) following the manufacturer's protocol, and using oligo-dT to prime the cDNA synthesis. Parallel samples included in the same protocol, but omitting the inclusion of the reverse transcriptase enzyme, were used to verify the lack of genomic or plasmid DNA carryover to the PCR analysis.

The cDNA samples obtained from the reverse transcription reactions were then used to conduct real-time quantitative PCR analysis of relative amounts of BACE1 cDNA, GAPDH cDNA, and GFP cDNA in the samples. The assays for the various cDNA species were conducted in parallel on aliquots of the same sample, divided just before the addition of the pertinent PCR primers and fluorescent substrates for the PCR reactions. All reactions were performed in parallel in a Rotor-Gene 3000 real-time PCR machine (Corbett Research, Inc., Sydney, Australia) using TaqMan Universal PCR Mix without Amperase UNG (Applied Biosystems Foster City, Calif.; catalog number 4324018) as the polymerase and nucleotide reagent. The PCR assay for mouse BACE1 was performed using the BACE1 Assay on Demand (Applied Biosystems; catalog number Mm00478664_ml). The assay for rodent GAPDH was the TaqMan® Rodent Gapdh Control Reagents (Applied Biosystems; catalog number 4308313). The assay for GFP (introduced into transfected cells by the pTracer-Bace1 plasmid) was the QuantiTect SYBR Green (Qiagen; catalog number 204143) and the following custom PCR primers: forward: 5'-TGGTGTTCAATGCTTTTCCC-3' (SEQ ID NO: 55) and reverse: 5'-GCGTCTTGTAGTTC-CCGTCA-3'(SEQ ID NO: 56), produce an expected PCR product size of 128 basepairs.

To quantify the relative amounts of mRNA in various cell samples, a series of dilutions of cDNA from a sample of cells that was transfected with pTracerBace1 but not treated with any siRNA candidate was used to generate a standard curve relating PCR cycle threshold to cDNA quantity, ranging from 1 to 100 nanograms of mRNA per microliter of sample. Based on the standard curve for each mRNA target (BACE1, GAPDH, or GFP), the nanograms per microliter of mRNA of each gene product was obtained for each cell sample. Finally, the amount of BACE1 mRNA in the cell sample was normalized to the amount of GFP mRNA in the same sample. From these normalized amounts of BACE1 mRNA, the percentage reduction in BACE1 mRNA resulting from a given siRNA treatment relative to the untreated cells was calculated.

The cell transfections and quantitative real-time RT-PCR assays for BACE1 mRNA levels relative to GFP mRNA levels in transfected Neuro2a cells were repeated independently by at least two persons. The resulting percentage of BACE1 mRNA suppression for each siRNA candidate, averaged over the independent assays, was determined.

Figure 7:
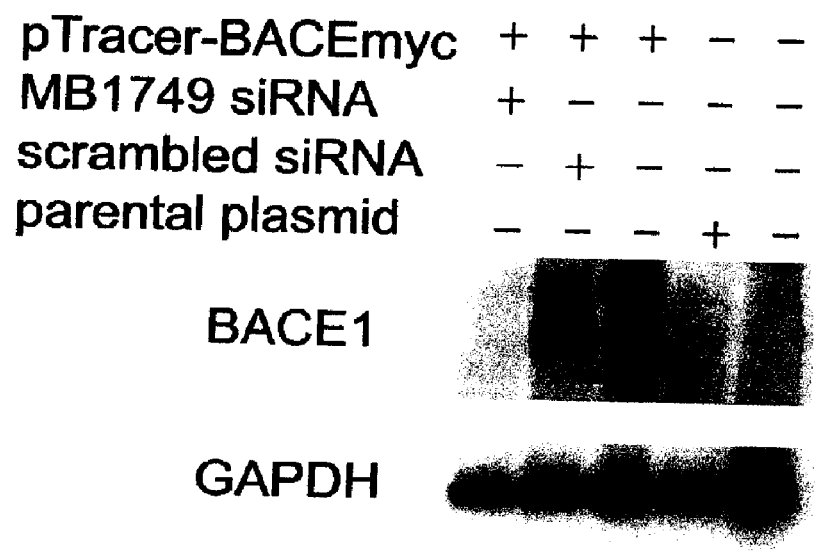
FIG. 7 illustrates western blot analysis of protein extracts from HEK293 cells transfected with a plasmid encoding a myc-tagged BACE1 or the parental myc-epitope plasmid, and optionally co-transfected with MB1749 or a scrambled control siRNA. Immunoblotting for the myc epitope shows suppression of BACE1 expression in cells co-transfected with MB1749 (leftmost lane). Re-blotting for GAPDH shows equivalent amounts of protein was loaded in each lane.

To further confirm the effectiveness of MB1749 at suppressing BACE1 expression, MB1749 siRNA or a scrambled control siRNA was co-transfected into HEK293 cells along with a variant of pTracer-BACE1 plasmid to which a myc epitope tag had been added at the carboxyl end of the BACE1 protein expression cassette (FIG. 6). A western blot of protein harvested from these cells 48 hours later showed substantial suppression of the myc-tagged BACE1 protein in cells transfected with the MB1749 siRNA compared to cells co-transfected with the scrambled siRNA or transfected with the pTracer-BACE1-myc plasmid alone (FIG. 7).

(2) Development of an AAV Vector Encoding for Anti-BACE1 siRNA:

To administer the MB1749 anti-BACE1 siRNA therapy to mice, an adeno-associated viral (AAV) vector containing DNA encoding for the MB1749 siRNA was chosen. AAV is known to transduce neuronal cells in vivo in the rodent brain following surgical injection into the brain tissue, and produce long-lasting expression of the delivered DNA within transduced neuronal cells. The expression of the MB1749 siRNA within transduced cells was driven by the mouse U6 RNA polymerase III promoter, provided by the pSilencer™ 1.0-U6 plasmid available from Ambion, Inc. (catalog number 7207). DNA was genetically engineered which encodes for a hairpin loop of RNA (consisting of the sequence for MB1749, a loop sequence, and the reverse complement of MB1749) (FIG. 6) into pSilencer™ between the ApaI and EcoRI restriction sites, using the following method.

Construction of the siRNA expression cassette using oligonucleotide condensation: In order to construct the DNA encoding for a hairpin loop of RNA corresponding to MB1749, the following four oligonucleotides were obtained from a synthesizing service:

| Oligo name | SEQ ID NO: | DNA sequence |
|---|---|---|
| MB1749A | SEQ ID NO: 37 | 5'-G<u>AAGACTGTGGCTACAACATTC</u>-3' |
| MB1749B | SEQ ID NO: 38 | 5'-TTCAAGAGAGAATGTTGTAGCCACAGTCTTCTTTTTTG-3' |
| MB1749C | SEQ ID NO: 39 | 5'-TCTCTTGAAGAATGTTGTAGCCACAGTCTTCGGCC-3' |
| MB1749D | SEQ ID NO: 40 | 5'-AATTCAAAAAAG<u>AAGACTGTGGCTACAACATTC</u>-3' |

In the above table, the portions of the oligonucleotide sequences that correspond to the effective siRNA sequence against BACE1 are underlined. Note that the reverse complement for oligonucleotide A is found within the sequence for oligonucleotide C, and all but the first four bases of oligonucleotide D is the reverse complement of the 3' end of oligonucleotide B. Thus, A and C are largely complementary to one another, and B and D are largely complementary to one another.

To construct the double-stranded DNA insert to be cloned into pSilencer™ 1.0-U6 to make pMB1749 plasmid, the four oligonucleotides were suspended in water to a concentration of 25 micromolar, then their ends were phosphorylated using T4 Polynucleotide Kinase enzyme. Next, in one tube, oligo MB1749A was mixed with oligo MB1749C, and in another tube, oligo MB1749B was mixed with oligo MB1749D. The mixtures were heated to 65° C. for 5 minutes then allowed to cool slowly to room temperature, to cause these complementary oligonucleotides to anneal into double-stranded form, with single-stranded overhangs. Next, a three-component ligation reaction was conducted by mixing oligosA/C and oligos B/D with pSilencer™ 1.0-U6 that had been linearized with ApaI and EcoRI restriction enzyme digestion, using standard molecular biology methods. The resulting ligation products were cloned into bacteria, and colonies screened to identify the desired plasmid product, which consists of the following construct inserted between the ApaI and EcoRI restrictions sites in pSilencer™ 1.0-U6 (SEQ ID NOs: 57 and 58, respectively):

SEQ ID NO: 57

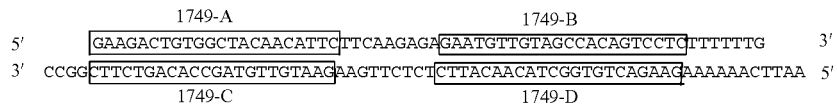

SEQ ID NO: 58

This strategy of assembling four oligonucleotides, rather than a single sense and antisense pair, was used to efficiently clone the DNA coding for the MB1749 hairpin siRNA. Use of single sense and antisense strands (such as can be obtained by concatenating the sequence for MB1749A with MB1749B, making one longer sense strand oligonucleotide, and concatenating MB1749C and MB1749D, making one longer antisense strand) results in molecular strands that tend to form intramolecular hairpins, preventing annealing into a double-stranded DNA, and ligation into the plasmid.

Verification of BACE1 mRNA expression by the MB1749 plasmid: In order to verify that the pMB1749 plasmid, coding for a hairpin loop of RNA corresponding to MB1749, does in fact produce an siRNA that reduces the amount of BACE1 mRNA in cells, mouse Neuro2a neuronal cells were co-transfected with pTracerBace1 plasmid and pMB1749 plasmid, using the SiPort-XP1 transfection reagent as described above. After 48 hours, the total cellular RNA was harvested from these cells, and used to conduct a reverse transcription quantitative real-time PCR assay, as described above. The results showed 94% suppression in BACE1 mRNA compared to cells not treated with pMB1749. A second plasmid (pControl) containing a scrambled sequence (shRNA corresponding to 5'-TGACACAGCCGCTACTACATTG-3', SEQ ID NO: 59) was constructed as a control, and confirmed not to suppress BACE1 mRNA expression in vitro.

Verification of BACE1 mRNA expression by the MB1749 viral vector: To obtain a supply of the viral vector for administration to the brains of mice in vivo, the pMB1749 plasmid was provided to GeneDetect, Ltd. (Auckland, New Zealand) for transfer of the U6 promoter, the MB1749 construct, and the RNA polymerase III termination sequence (consisting of 6 thymines in succession) into their plasmid containing AAV inverted terminal repeats and a green fluorescent protein reporter gene expressed from a chicken beta-actin enhancer and CMV promoter. The MB1749 expression cassette (U6 promoter, MB1749 construct, and termination sequence) was inserted following the 5' inverted terminal repeat for AAV, and before the GFP expression cassette. The resulting AAV plasmid was then used by GeneDetect to produce AAV-anti-BACE1-MB1749. GeneDetect was also provided with another plasmid containing a scrambled sequence for MB1749, which can be verified in vitro not to be active at suppressing BACE1 mRNA expression and not homologous to any known gene in Genbank, for production of AAV-control vector. AAV-MB1749 viral particles with a chimeric AAV1/2 capsid were produced from this plasmid using an adenovirus-free method, and were provided at a titer of 1.2-1.4×10$^{12}$ genomic particles per milliliter. Similarly, AAV-Control vector was made from the pControl plasmid, and provided at a titer of 3.8-4.1×10$^{12}$ genomic particles per milliliter.

To verify in vitro that the resulting AAV-anti-BACE1-MB1749 vector, when used to infect cells, results in suppression of BACE1 mRNA, and the AAV-control vector does not, HEK293 cells were infected with AAV-MB1749 or AAV-Control, then 24 hours later transfected with pTracerBACE1. Infection of cells by the AAV was confirmed by observation of GFP expression. In two separate cell cultures, AAV-MB1749 resulted in a 72.8% and 57.6% (average, 65.2%) reduction in BACE1 mRNA 72 hours post-viral transduction, while AAV-control vector had no significant effect (16.2% and <0% reduction in two separate cultures).

Example 5

AAV-Mediated BACE1 Gene Silencing in the Hippocampus Improves Contextual Fear Conditioning in Aging Mice The effect of reducing BACE1 levels in the hippocampus of aging, wildtype mice was determined following AAV-mediated siRNA delivery using the AAV vectors produced as described in Example 4. In this regard, behavioral freezing following contextual fear conditioning was used as an indicator of hippocampal function, as the acquisition and maintenance of a freezing response to a context previously paired with an unconditioned stimulus (foot shock) is dependent upon hippocampal function. Lesions of the dorsal hippocampus prevent the acquisition of contextual conditioning (Phillips, R. G. and LeDoux, J. E., Learn Mem., May-June (1994) 34-44) and post-training lesions attenuate contextual freezing (McNish, K. A., al., J. Neurosci., 17 (1997) 9353-9360).

It has been shown that single injections of AAV-mediated shRNA can result in persistent silencing of targeted gene expression in transduced regions of the rodent brain in vivo (Xia, H. et al., Nature Medicine, 10 (2004) 816-820). While reactive astrocytes have been shown to express BACE1 (Hartlage-Rubsamen, M., et al., Glia, 41 (2003) 169-179), the vast preponderance of BACE1 activity in the brain is in neurons (Zhao, J., et al., J. Biol. Chem., 271 (1996) 31407-31411).

Accordingly, an AAV vector (with chimeric serotype 1/2) that preferentially transduces neurons almost to the exclusion of glia was used (Burger, C., et al., Mol. Ther., 10 (2004) 302-317). Overall steps in this work include (1) in vitro screening of candidate anti-BACE1 siRNA sequences for efficacy, and (2) construction of a viral vector for in vivo delivery of DNA encoding for the anti-BACE1 siRNA to the mammalian brain, as described in Example 4, and (3) neurosurgical administration of the vector to the mice, (4) testing of the behavior of the mice to assess the effect of the treatment, and (5) examination of the brain tissue of the mice to assess the effect of the treatment.

Step 3) Neurosurgical administration of the vector to the mice: Pilot injections (to confirm stereotactic coordinates): To verify correct anatomical targeting of the mouse hippocampus in this age and strain of mouse, and to verify expression from the AAV vector, three nine-month old wildtype C57BL/6 female mice were injected with 5 microliters of a standard AAV vector (at a concentration of approximately 2.3×10$^{12}$ viral particles per milliliter) containing the GFP reporter gene (rAVE-GFP 1/2, GeneDetect, Auckland, New Zealand). The injections were at the following stereotactic coordinates, expressed in millimeters from bregma, with the incisor bar at −5 mm: AP −2.70, ML ±3.00, DV −2.25. (The details of the neurosurgical procedure used to perform the injections are further described below).

Thirteen days post-surgery, these mice were euthanized and transcardially perfused with saline followed by 4% paraformaldehyde to flush and fix their organ tissues. The brains were cut into 30 micron thick sections along the parasagittal planes, with serial sections collected from throughout the entire left and right hemispheres. These sections were numbered sequentially with the lower numbers assigned to the lateral edge of the hemisphere, and higher numbers to the more medial sections of the hemisphere. Approximate targeting of the AAV vector to the hippocampus of the mice using this method was confirmed by visual confirmation of green fluorescent protein expression in the hippocampus of these mice by fluorescence microscopy, and the stereotactic coordinates for use in the main study were refined to −2.3 mm AP, +/−2.0 mm ML, and 1.6 mm DV below dura.

Neurosurgical method: The details of the neurosurgical method for use in delivery of the therapy of the present invention to mice are as follows. After the induction of surgical anesthesia using isofluorene inhalation, the mouse is placed in the stereotaxic frame and its head is immobilized using the ear bars, incisor bar and anesthesia mask associated with the apparatus (MyNeuroLab, St. Louis, Mo.; Benchmark™ Digital Stereotaxic). The patency of the mouse's airway is verified. The fur on the head is clipped, and betadyne is used to sanitize the scalp. After the depth of the mouse's anesthesia is verified (i.e., unresponsive to tail and paw pinch), a midline incision 1.0 to 1.5 cm in length is made in the skin over the skull in the saggital plane. The skin is manually retracted and membranous tissue covering the skull is scraped away with a sterile #11 scalpel blade. A Hamilton syringe (Hamilton Company, Reno, Nev.; Model 88011) is placed in the syringe holder of the stereotaxic frame, and the tip of the syringe needle is moved to the bregma point on the mouse's skull; (the intersection of the rostral, medial-lateral bone suture and the midline suture, identifiable by visual inspection). The needle is then positioned to the following stereotaxic coordinates on the left side of the skull: AP=−2.30 mm, ML=−2.00 mm. The corresponding point on the skull is noted visually through the surgical microscope. A dental drill with a sterile burr bit is used to erode a burr hole at this site through the skull bone. The syringe needle is again positioned at the bregma point, then moved to AP=−2.30 mm, ML =+2.00 mm on the right hemisphere of the skull. The site is noted visually, and a burr hole made at this site.

Once the burr holes are made, a Hamilton syringe is loaded with 5 microliters of AAV vector (AAV-antiBACE1-MB1749 or AAV-control at 1.3 to 3.9×10$^{12}$ genomic particles per milliliter), positioned from bregma to AP −2.30, ML −2.00, then lowered until the tip of the needle pierces the dura membrane covering the brain. Next, the needle is lowered to 1.25 mm below dura and left in place for 2 minutes. Then, the 5.0 microliters of AAV solution is injected into the hippocampus via the Hamilton syringe at the rate of 0.333 microliters per minute using an automated syringe pump. At the conclusion of the 15-minute injection, the needle is left in place for 2 minutes. Finally, the needle is slowly withdrawn from the brain at the rate of about 1 mm per minute. Once the needle tip is clear of the dura, the injection to this site is complete. Injection to the site in the right hemisphere proceeds in the same manner. Following completion of both injections, the incision in the skin over the skull is approximated using forceps and the skin is closed with silk sutures. The skin is swabbed with alcohol and the mouse is removed from the stereotaxic device and placed in a clean recovery cage. Sterile saline (0.5 mL) is injected subcutaneously at a site on the back to aid in hydration, and diazepam (1-2 mg/kg) is administered to prevent the occurrence of seizures during recovery. Upon complete recovery from anesthesia, the animal is returned to standard housing.

Eleven-month old female C57B6/SJL wildtype mice were obtained from the University of Minnesota (nine mice, courtesy of Karen Hsiao-Ashe) and from Taconic Farms (six mice, Germantown, N.Y.). Mice were housed two or three mice per cage in a 12-hour light/dark cycle temperature-controlled environment with food and water available ad lib. At 12 months of age, each mouse received a single, bilateral injection of either AAV-MB1749 or AAV-Control into the hippocampus at (from bregma) −2.3 mm AP, +/−2.0 mm ML, and 1.6 mm DV below dura, while under anesthesia by isofluorene inhalation. A digital stereotactic headframe was used for precise targeting. At each injection site, 5 microliters of AAV vector was infused via Hamilton syringe and syringe pump at a rate of 0.333 microliters per minute. Following each 15-minute infusion, the syringe was left in place for an additional two minutes for pressure equalization and then removed from the brain over a period of two minutes. Upon recovery from anesthesia, the mouse was returned to its normal housing. Mice were randomly assigned to receive either the AAV-MB1749 or AAV-Control vector, with nearly equal numbers of mice from each supplier assigned to each experimental group.

Step 4) Testing of the behavior of the mice to assess the effect of the treatment: The contextual fear conditioning procedure is a well-established method in the published research literature, and it has been determined that this method provides a measurement for hippocampus-dependent brain functioning. The procedure is a behavioral test that is performed over two successive days. On the first day, the mouse receives training to associate a cage context and auditory cue with a mild electric foot shock. On the second day, the mouse is placed in the same cage context as the first day, but no shocks are administered; rather, the amount of movement (or conversely, behavioral "freezing") of the mouse is observed and quantified by instrumentation. The mouse is returned to its home cage for an hour, then placed in a novel apparatus and again its amount of movement (or "freezing") is quantified.

At 15, 16, 18, and 19 months of age, each mouse was tested using a two-day contextual fear conditioning protocol similar to that described by Dineley, et al., (J. Biol. Chem., 277 (2005) 22768-22780). On the first day ("training"), the mouse was placed in the fear conditioning apparatus (Coulbourn Instruments, Allentown Pa. #H10-11M-TC), and allowed to freely explore the chamber for 3 minutes. Next, repetitions of the following stimulus regimen were presented: an auditory cue (80 dB white noise) and visual cue (lighting of a white bulb positioned in the chamber wall) were presented for 20 seconds. During the final two seconds of the 20-second period, a 0.20 millivolt (0.5 mAmp) foot shock was administered to the mouse through the floor grid of the chamber. A 40-second interval elapsed before the next cue presentation. At 15 months of age, five repetitions of this regimen were presented; at 16, 18, and 19 months of age, two repetitions were presented. On the second day of each two-day protocol, 24 hours after "training," the mouse was placed in the fear conditioning apparatus and its behavior was videotaped for five minutes. No cues or foot shocks were presented during this "test" period. One hour later, the light bulb and speaker were removed from the apparatus, and the apparatus was altered to have different wall appearance (color pattern versus bare metal), a different floor (smooth plastic versus wire grid), and a different scent (citrus versus no scent). The mouse was placed in this "novel"environment, and its behavior was videotaped for three minutes.

Contextual fear conditioning (a hippocampus-dependent function) was assessed by comparing motor "freezing" by the mice in the "test" compared to the "novel" environment. (Cued fear learning was not assessed). Freezing behavior was scored automatically by machine using the FreezeFrame™ video system (Actimetrics, Wilmette Ill.). This system computes frame-by-frame differences in the video image (at four frames per second), and is capable of detecting movements as small as 1 mm. Freezing "bouts" exceeding 1.0 second were scored as behavioral freezing; the amount of behavioral freezing per "training" period (prior to the first cue/shock presentation), per "test" period (five minute observation) and per "novel" period (three minute observation) were expressed as percent of total time spent freezing. The data for the mice receiving the AAV-MB1749 vector (n=7) and the mice receiving the AAV-Control vector (n=8) are shown in the table below. Contextual fear conditioning for each mouse was measured as the difference between the percent of time spent freezing in the "test" environment versus the "novel" environment, on the same measurement day. A repeated measures ANOVA of these difference scores shows significantly greater contextual fear conditioning in mice receiving the AAV-MB1749 vector (F (1.11)=8.57, p<0.015), and a marginally significant increase in contextual fear conditioning across both groups of mice over months (F (3.33)=2.35, p<0.09). The profile of difference scores across months did not differ by AAV treatment group (p=0.997 for F-test of interaction effect).

Percent Behavioral Freezing in Contextual Fear Conditioning Assay

| Context | Age (mos) | AAV-MB1749 | AAV-Control | p* |
|---|---|---|---|---|
| Day 1: Training | 15 | 1.1% | 0.6% | ns |
| | 16 | 49.8 | 42.9 | ns |
| | 18 | 72.1 | 47.6 | 0.061 |
| | 19 | 66.8 | 52.8 | ns |
| Day 2: Test | 15 | 48.9 | 24.2 | 0.043 |
| | 16 | 61.8 | 36.1 | 0.062 |
| | 18 | 74.9 | 44.4 | 0.019 |
| | 19 | 60.1 | 45.2 | ns |
| Day 2: Novel context | 15 | 2.3 | 4.1 | ns |
| | 16 | 12.4 | 9.0 | ns |
| | 18 | 10.6 | 3.4 | ns |
| | 19 | 7.2 | 15.0 | ns |
| Difference (Test-Novel) | 15 | 46.6 | 20.2 | 0.016 |
| | 16 | 49.3 | 27.0 | 0.053 |
| | 18 | 64.3 | 41.0 | 0.059 |
| | 19 | 52.9 | 30.2 | 0.093 |

*p values for t-tests comparing treatment groups

Further analyses of these data on a month-by-month basis indicate that the mice receiving AAV-MB1749 exhibited more freezing than the mice receiving AAV-Control in the "test"period at ages 15, 16, and 18 months, while there was no difference among the two groups of mice in the amount of freezing exhibited in the "novel" environment at any age (see Table immediately above). In addition, there is marginally significant evidence (p=0.0613) that the mice receiving AAV-MB1749 had better long-term recall of the context in which they had received the foot shocks, in that they exhibited more freezing (72.1%) than control mice (47.6%) during the "training"period at age 18 months (prior to the first presentation of the cues and shock at that age) though they had not been exposed to the apparatus for two months. The mice receiving the AAV-Control vector did not display this enhanced long-term recall. These data are consistent with the interpretation that mice receiving hippocampal injections of the AAV-MB1749 vector at twelve months of age displayed better hippocampal-dependent learning and recall at 15 months of age, with the enhancement persisting for at least three more months (through 18 months of age).

Figure 8:
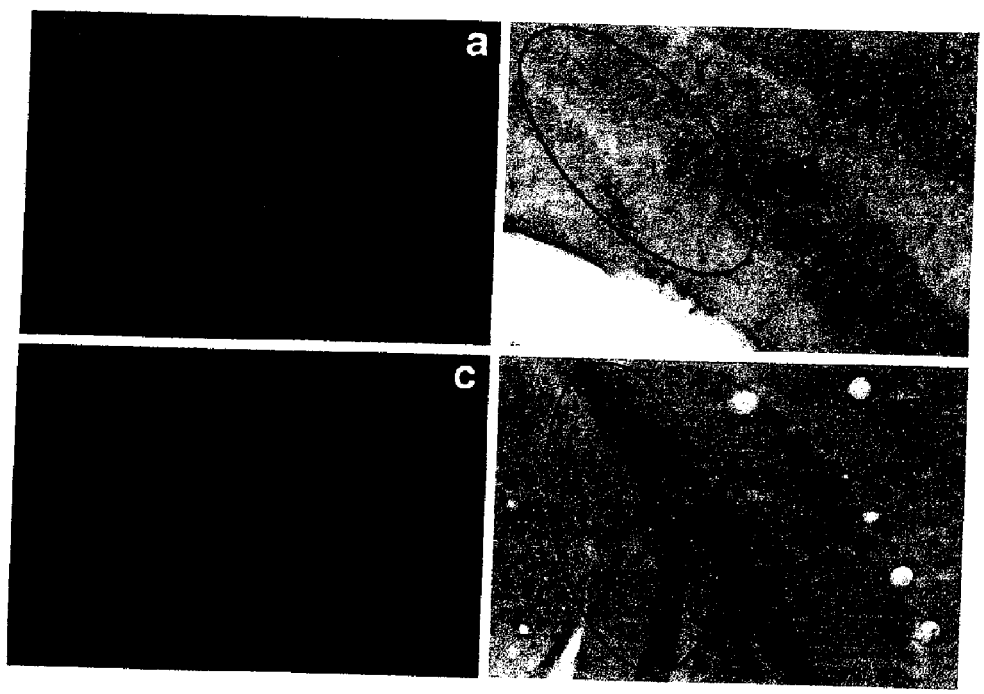
FIG. 8 illustrates fluorescence microscopy (left) and brightfield images (right, both 20× objective) showing GFP expression and BACE1 immunostaining respectively in example brain sections from a mouse treated with AAV-MB1749 (a,b) and a mouse treated with AAV-Control (c,d). The circled regions in the photographs designate regions of viral transduction (based on GFP expression). Levels of BACE1 immunoreactivity were reduced (p<0.002) in virally transduced regions in mice receiving AAV-MB1749.

5) Examination of the brain tissue of the mice to assess the effect of the treatment: To verify that the administration of AAV-MB1749 to the mice resulted in suppression of BACE1 protein expression, the brains of the mice were harvested at termination when the mice were 19.5 months old, and analyzed by immunohistochemistry. One mouse that received AAV-Control was found dead in its cage at 18.5 months of age—efforts to preserve its brain for histological analysis were unsuccessful. A blinded pathologist's examination of this mouse found a lymphosarcoma of the mesenteric lymph node, a common finding in SJL mice over 12 months of age (Katz, J. D. and Bonavida, B., Bioessays, 11 (1998) 181-185). Mice were euthanized by Nembutal overdose, then transcardially perfused with 50 mL of wash solution (137 mM NaCl, 20 mM dextrose, 23 mM sucrose, 2 mM anhydrous $CaCl_2$, and 1.6 mM anhydrous sodium cacodylate), followed by 100 mL of fixation solution (117 mM sucrose and 67 mM sodium cacodylate in 4% paraformaldehyde, pH 7.3). Brains were stored in 1.6 mM sodium cacodylate solution (pH 7.0) at 4 degrees C. until processing. All brains were then mounted in a single MultiBrain™ block (Neuroscience Associates [NSA], Knoxville Tenn.) and sectioned coronally (35 μM sections). Every fourth section throughout the hippocampus was stained for BACE1 by NSA using a polyclonal rabbit anti-BACE1 antibody (Calbiochem, San Diego Calif., #195111, 1:2000 dilution), visualized using peroxidase-conjugated secondary antibody (Vectastain™ ABC Method, Vector Laboratories #PK-6101). Adjacent sections were used to identify regions of AAV transduction, by means of fluorescence microscopy for GFP protein expression. The extent of transduction of mouse brains by the AAV-MB1749 or AAV-Control vector did not differ across treatment groups or hemispheres, with GFP-expressing cells detectable in an average of 3.5 coronal sections (spanning 490 microns rostrocaudally). Example images of hippocampal regions transduced by the AAV vectors and BACE1 immunostaining of these regions are shown in FIG. 8.

To quantify the level of expression of BACE1 in the mouse brains, scans of the brain sections immunostained for BACE1 were digitized as 24-bit color images at a resolution of 2400 pixels per inch with an Epson 4870 scanner. These images were overlaid with fluorescence microscopy images of adjacent, corresponding brain sections to identify regions that expressed GFP from the AAV transgene. Regions of pixels encompassing GFP-expressing cells in the neuronal layers of the hippocampus were identified for each hemisphere of each mouse brain section in a series of seven slides spanning 875 microns of the rostral-caudal extent of the hippocampus surrounding the AAV injection sites. The staining intensity for BACE1 in each hemisphere of each section was measured by averaging the pixel intensity value of pixels in these regions (min 3, max 16, average 10 regions per measurement). For each hemisphere and tissue section, a comparable intensity measurement was made for non-GFP expressing cells in adjacent areas of the hippocampus. Although the staining variability across sections and mice was minimal (due to the MultiBrain™ method of processing), the staining intensity of non-GFP-expressing cells was subtracted pairwise from the staining intensity of GFP-expressing cells to control for background staining levels. An ANOVA of these difference scores showed that the amount of BACE1 protein expressed by GFP-positive cells in the hippocampus of mice receiving AAV-MB1749 injections was significantly reduced compared to mice receiving AAV-Control injections (F (1.45)= 10.88, p=0.0019). When expressed as a percentage of background intensity, the pixel intensity of BACE1 stained GFP-positive cells in mice treated with AAV-MB1749 was 12.7%± 2.1% fainter than the background staining (versus 4.5%± 2.1% [mean±se] fainter in mice treated with AAV-Control). These results indicate that hippocampal injections of AAV-MB1749 resulted in reduced expression of BACE1 enzyme in the treated mice, consistent with persistent expression of the anti-BACE1 shRNA transgene.

Reduction in Abeta in AAV-MB1749 treated mice resulting from the action of the anti-BACE1 shRNA transgene was investigated by staining sections from all mouse brains for soluble Abeta and amyloid deposits. However, in these wild-type mice, levels of soluble Abeta were below detection limits throughout the brain in both treatment groups, and no amyloid deposits were detectable. Nevertheless, because BACE1 activity is required for the production of Abeta from APP (Cai, H., et al., Nat. Neurosci., 4 (2001) 233-234; Luo, Y., et al., Neurobiol. Dis., 14 (2003) 81-88), and because increased expression of beta-secretase in mouse brain results in increase steady-state levels of beta amyloid (Bodendorf, U., et al., J. Neurochem., 80 (2002) 799-806), our results showing reduced BACE1 expression in the AAV-MB1749 treated mice suggest that Abeta production and steady-state levels of Abeta in the hippocampal regions of these mice also were reduced.

In this experiment, whether or not reduced Abeta could be measured, the possibility would remain that the enhanced fear conditioning observed in the AAV-MB1749 treated mice was due to a direct effect of reduced BACE1 expression or reduction in some other product of BACE1 activity (Kitazume, S., et al., J. Biol. Chem., 280 (2005) 8589-8595) rather than an effect mediated by reduced Abeta production. It has been shown that BACE1 knock-out mice have an "anxious" behavioral phenotype that includes reduced exploratory behavior and timidity (Harrison, S. M., et al., Mol. Cell. Neurosci., 24 (2003) 646-655). However, the fear conditioning effect observed in the AAV-MB1749 treated mice was contextual, and not a reflection of an overall increase in fearful behavior. No differences were seen between these mice and control mice in behavior in the apparatus at the start of training (prior to the first shock presentation) or at any time in the "novel" context (see table immediately above). Thus, these results are more consistent with a local effect on hippocampal functioning than with a more general effect of BACE1 reduction.

Because soluble Abeta can be synaptotoxic (Mucke, L., et al., J. Neurosci., 20 (2000) 4050-4058) and intracerebroventricular administration of oligomeric forms of beta amyloid into normal rats is sufficient to produce cognitive impairment (Cleary, J. P., et al., Nat. Neurosci., 8 (2005) 79-84), these results support a beneficial effect of Abeta reduction in the hippocampus on hippocampal-dependent functioning, however it is possible that the beneficial effect of BACE1 suppression was due to some other mechanism. Notably, the effect did not require treatment of the animals at a young age, but was obtained in older adult animals. In addition, the beneficial effect was obtained in normal, aging animals, and was not dependent upon an over-expression of APP. These findings support the significance of BACE1 as a treatment target not only for Alzheimer's disease, but also for other mild cognitive impairments associated with aging.

Example 6

AAV-Mediated BACE1 Gene Silencing in the Hippocampus as a Treatment for Alzheimer's Disease in a Transgenic Mouse Model of Alzheimer's Disease The present invention can be validated for treatment of Alzheimer's disease by surgically injecting an AAV vector encoding for the MB1749 siRNA targeting murine BACE1 into the hippocampus of 12 month-old female Tg2576 mice, then assessing the mice for effects of the therapy at ages 15 months and beyond.

The Tg2576 mouse is an accepted animal model of Alzheimer's disease that overexpresses the human transgene for APP (Hsiao et al, 1996). The Tg2576 transgenic mouse line develops amyloid plaques containing beta-amyloid beginning at about 10 to 12 months of age (Gau et al, 2002). The plaques are particularly frequent in the cerebral cortex and hippocampus. They are readily detectable 15 months of age, and become more severe at 19 months of age and beyond (Kawarabayashi et al, 2001). Aged female Tg2576 mice deposit significantly more beta-amyloid in the brain than do aged male Tg2576 mice (Callahan et al, 2001). By 19 months of age, the Tg2576 mice exhibit behavioral and cognitive deficits on measures of balance, agility, and spatial memory (King and Arandash, 2002).

Experimental design for In Vivo Testing in Tg2576 Transgenic Mice: Several heterozygous transgenic and age-matched wildtype controls from Tg2576 litters (obtained from Taconic Farms, Inc.) are injected with either AAV-anti-BACE1-MB1749 or AAV-control at 12 months of age using the above procedure. Half of the mice receive bilateral injections of AAV-antiBACE1-MB1749, and the other half receive bilateral injections of AAV-control, in a 2×2 design:

| Number of mice | Treatment Administered | |
| --- | --- | --- |
| Genotype: | AAV-anti-BACE1-MB1749 | AAV-control |
| Tg2576 heterozygote | N | N |
| Wildtype | N | N |

*N equals the number of mice used in the experiment.

Overall steps in this work will include (1) in vitro screening of candidate anti-BACE1 siRNA sequences for efficacy, and (2) construction of a viral vector for in vivo delivery of DNA encoding for the anti-BACE1 siRNA to the mammalian brain, as described in Example 4, and (3) neurosurgical administration of the vector to the mice as described in Example 5, (4) testing of the behavior of the mice to assess the effect of the treatment as described in Example 5, and (5) examination of the brain tissue of the mice to assess the effect of the treatment as described below.

Step 5) Histological analysis of the effects of anti-BACE1 siRNA treatment in the Tg2576 mouse brain tissue: Once the mice that have been treated with AAV-anti-Bace1-MB1749 or AAV-control have attained the age of 19 months, they will be euthanized and their brain tissue examined to determine the effect of the treatment on level of BACE1 protein in the treated regions of the hippocampus, and the effect of the treatment on the extent of beta-amyloid plaque formation in those regions. The treated regions will be identifiable based on the expression of green fluorescent protein in the neuronal cells. The level of BACE1 protein will be identifiable based on immunohistochemical staining using standard methods, with an anti-Bace1 primary antibody, and a peroxidase-conjugated secondary antibody for visualization.

In the treated animals (heterozygous Tg2576 or wildtype mice receiving AAV-anti-BACE1-MB1749), it is expected that the amount of BACE1 protein will be reduced in the regions expressing the GFP reporter gene, and that also in these regions in the heterozygous Tg2576 mice, there will be fewer beta-amyloid plaques.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference. Further, the hard copy of the sequence listing submitted herewith and the corresponding computer readable form are both incorporated herein by reference in their entireties.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

I claim:

1. A method for improving memory or cognitive function in a subject diagnosed as having a disorder in which a diminished declarative memory is a symptom, comprising intracranially administering to the subject a therapeutically effective dose of a composition that decreases the expression of a beta amyloid cleaving enzyme type 1, or BACE1, in a cell of the nervous system of the subject, wherein the composition comprises a shRNA or a siRNA or a vector encoding said siRNA or said shRNA, wherein further said shRNA or said siRNA comprises a double-stranded portion 21 to 30 nucleotides long and wherein one strand of said double-stranded portion comprises 21 contiguous nucleotides encoded by SEQ ID NO: 29, and wherein at least one attribute of said memory or cognitive function is improved.

2. The method of claim 1 wherein the composition is delivered to the subject by intracranial delivery through an intracranial access device.

3. The method of claim 2, further comprising the step of: implanting a pump outside the brain, the pump coupled to the proximal end of an intracranial catheter.

4. The method of claim 3 comprising operating the pump to deliver a predetermined dosage of the said shRNA or said siRNA or said vector encoding said siRNA or said shRNA from the pump through a discharge portion of the said intracranial catheter.

5. The method of claim 3 further comprising the step of periodically refreshing the pump with said composition.

6. The method of claim 3 wherein the pump is an infusion pump.

7. The method of claim 6 wherein the infusion pump is an electromechanical pump.

8. The method of claim 6 wherein the infusion pump is an osmotic pump.

9. The method of claim 1, wherein said composition is delivered to the nucleus basalis of Meynert or the cerebral cortex or the hippocampus.

10. The method of claim 1, wherein the composition comprises the vector encoding said siRNA or said shRNA.

11. The method of claim 10, wherein the vector is selected from the group consisting of adeno-associated virus, adenovirus, herpes simplex virus, lentivirus and a DNA plasmid.

12. A method of delivering a small interfering RNA across a blood-brain barrier for expression in the brain of a subject diagnosed as having or being at risk of developing disorders in which diminished declarative memory is a symptom comprising administering to a blood vessel directly supplying blood to the brain of the subject a composition comprising a liposome having an exterior surface and an internal compartment containing an artificial adeno-associated virus (AAV) encoding a shRNA comprising a double-stranded portion between 21 and 30 nucleotides long, wherein one strand of said double-stranded portion is encoded by SEQ ID NO: 29.

13. The method of claim 12, wherein the artificial AAV vector is for delivery of a single stranded DNA encoding the shRNA, the artificial AAV vector comprising the single stranded DNA having AAV-ITRs at the 5-prime and 3-prime ends.

14. The method of claim 12, wherein the artificial AAV vector is for delivery of a single stranded DNA encoding the shRNA, the artificial AAV vector comprising, in 5-prime to 3-prime order:

a 5-prime AAV-ITR;

the single stranded DNA;

an internal AAV-ITR;

a reverse complement of the single stranded DNA; and a 3-prime AAV-ITR.

15. The method of claim 12, wherein the artificial AAV vector is for delivery of a linear, double stranded DNA encoding said shRNA, the artificial AAV vector comprising the linear, double stranded DNA having AAV-ITRs at the 5-prime and 3-prime ends of each strand, or wherein the artificial AAV vector is for delivery of a single stranded DNA encoding said shRNA, the artificial AAV vector comprising, in 5-prime to 3-prime order:

a 5-prime AAV-ITR;

DNA encoding one strand of said shRNA;

an internal AAV-ITR;

DNA encoding the other strand of said shRNA; and a 3-prime AAV-ITR.

16. The method of claim 12, wherein the composition is administered intra-arterially.

17. The method of claim 12, wherein the liposome comprises an exterior surface defining a sphere having a diameter of at most 200 nanometers.

18. The method of claim 12, wherein the liposome comprises one or more blood-brain barrier and brain cell membrane targeting agents and wherein at least 5 and at most 1000 blood-brain barrier or brain cell membrane targeting agents are conjugated to an exterior surface of the liposome.

19. The method of claim 18, wherein at least 25 and at most 40 blood-brain barrier or brain cell membrane targeting agents are conjugated to the surface of the liposome.

20. The method of claim 12, wherein the exterior surface of the liposome further comprises one or more conjugation agents selected from the group consisting of polyethylene glycol, sphingomyelin, biotin, streptavidin, organic polymers, and combinations thereof.

21. The method of claim 20, wherein the molecular weight of the conjugation agent is at least 1000 Daltons and at most 50,000 Daltons.

22. The method of claim 12, wherein the artificial AAV vector has been thermally treated in at least one heating and cooling cycle.

23. A medical system for delivering a small interfering RNA into a pre-determined location in a brain of a patient comprising:
 a) an intracranial access device selected from the group consisting of an intracranial catheter and an intracranial access port;
 b) a deliverable amount of a siRNA or a shRNA or a vector encoding said siRNA or said shRNA wherein said siRNA or said shRNA comprises a double-stranded portion between 21 and 30 nucleotides long, wherein one strand comprises 21 contiguous nucleotides encoded by SEQ ID NO: 29; and
 c) a delivery means for delivering said small interfering RNA or vector encoding said small interfering RNA to said location of the brain from said intracranial access device.

24. The medical system of claim 23, wherein said delivery means is selected from the group consisting of an infusion pump, an electromechanical pump, and an osmotic pump.

25. The medical system of claim 23, wherein the predetermined location is the nucleus basalis of Meynert or the cerebral cortex or the hippocampus.

26. The medical system of claim 23, wherein the delivery means is injection from an external syringe into an intracranial access port.

* * * * *